(12) United States Patent
De Maria et al.

(10) Patent No.: US 7,537,921 B2
(45) Date of Patent: May 26, 2009

(54) GALACTANASE VARIANTS

(75) Inventors: Leonardo De Maria, Frederiksberg (DK); Allan Svendsen, Hoersholm (DK); Torben Vedel Borchert, Birkeroed (DK); Lars Lehmann Hylling Christensen, Alleroed (DK); Sine Larsen, Grenoble (FR); Carsten Ryttersgaard, Los Angeles, CA (US)

(73) Assignee: Novozymes A/S, Bagsvaerd (DK)

( * ) Notice: Subject to any disclaimer, the term of this patent is extended or adjusted under 35 U.S.C. 154(b) by 278 days.

(21) Appl. No.: 10/537,746

(22) PCT Filed: Dec. 11, 2003

(86) PCT No.: PCT/DK03/00851

§ 371 (c)(1),
(2), (4) Date: Jun. 6, 2005

(87) PCT Pub. No.: WO2004/056988

PCT Pub. Date: Jul. 8, 2004

(65) Prior Publication Data

US 2007/0128180 A1    Jun. 7, 2007

Related U.S. Application Data

(60) Provisional application No. 60/437,615, filed on Jan. 2, 2003, provisional application No. 60/461,230, filed on Apr. 8, 2003.

(30) Foreign Application Priority Data

Dec. 20, 2002   (DK) ................................ 2002 01968
Apr. 8, 2003    (DK) ................................ 2003 00537

(51) Int. Cl.
C12N 9/24       (2006.01)
G01N 33/53      (2006.01)
C12Q 1/34       (2006.01)
C07H 21/04      (2006.01)
A23C 17/00      (2006.01)

(52) U.S. Cl. .................. 435/200; 435/7.6; 426/42; 536/23.2

(58) Field of Classification Search .................. 435/200, 435/7.6, 69.1; 536/23.2
See application file for complete search history.

(56) References Cited

U.S. PATENT DOCUMENTS 6,329,185 B1 * 12/2001 Kofod et al. ................ 435/201

FOREIGN PATENT DOCUMENTS

WO    WO 97/32014    9/1997
WO    WO 00/47711    8/2000

OTHER PUBLICATIONS

UniProt Accession No. Q9Y7F8, created on Nov. 1, 1999.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
Ryttersgaard et al., "Crystallization and Preliminary X-Ray Studies of beta-1,4-galactanasse from *Aspergillus aculeatus*", Acta Crystallographica, vol. D55, pp. 929-930 (1999).
Le Nours et al., "Structure of two fungal beta-1,4-galactanases: Searching for the basis for temperature and pH optimum", Protein Science, vol. 12, pp. 1195-1204 (2003).
Abstract of JP 2003174892 (Jun. 24, 2003).
Braithwaite et al., "Evidence That Galactanase from *Pseudomonas fluorescence* Subspecies *cellulosa* Is a Retaining Family 53 Glycosyl Hydrolase in Which E161 and E270 Are the Catalytic Residues", Biochemistry, vol. 36, No. 49, pp. 15489-15500 (1997).
Ryttersgaard et al., "*Aspergillus aculeatus* beta-1,4-Galactanase: Substrate Recognition and Relations to Other Glycoside Hydrolases in Clan GH-A", Biochemistry, vol. 41, No. 51, pp. 15135-15143 (2002).

* cited by examiner

*Primary Examiner*—Nashaat T Nashed
*Assistant Examiner*—Iqbal H Chowdhury
(74) *Attorney, Agent, or Firm*—Elias Lambiris

(57) ABSTRACT

Variants of Glycoside Hydrolase family 53 galactanases, e.g. variants of the galactanases from strains of *Yersinia, Aspergillus, Humicola, Meripilus, Myceliophthora, Thermomyces, Bacillus, Bifidobacterium, Cellvibrio, Clostridium, Pseudomonas, Thermotoga,* or *Xanthomonas*.

32 Claims, 174 Drawing Sheets

| HEADER | | | | | | | | | | MTGL | |
|---|---|---|---|---|---|---|---|---|---|---|---|
| ATOM | 1 | CB | ALA | 1 | 15.214 | -2.789 | 18.265 | 1.00 | 29.91 | | MTGL |
| ATOM | 2 | C | ALA | 1 | 17.670 | -3.053 | 17.823 | 1.00 | 27.24 | | MTGL |
| ATOM | 3 | O | ALA | 1 | 18.335 | -2.394 | 17.026 | 1.00 | 27.44 | | MTGL |
| ATOM | 4 | N | ALA | 1 | 16.132 | -5.006 | 17.678 | 1.00 | 29.26 | | MTGL |
| ATOM | 5 | CA | ALA | 1 | 16.268 | -3.540 | 17.450 | 1.00 | 28.32 | | MTGL |
| ATOM | 6 | N | LEU | 2 | 18.116 | -3.378 | 19.034 | 1.00 | 25.13 | | MTGL |
| ATOM | 7 | CA | LEU | 2 | 19.439 | -2.955 | 19.486 | 1.00 | 23.17 | | MTGL |
| ATOM | 8 | CB | LEU | 2 | 19.648 | -3.322 | 20.957 | 1.00 | 23.07 | | MTGL |
| ATOM | 9 | CG | LEU | 2 | 18.891 | -2.507 | 22.005 | 1.00 | 23.57 | | MTGL |
| ATOM | 10 | CD1 | LEU | 2 | 19.156 | -3.090 | 23.384 | 1.00 | 23.95 | | MTGL |
| ATOM | 11 | CD2 | LEU | 2 | 19.330 | -1.057 | 21.940 | 1.00 | 23.31 | | MTGL |
| ATOM | 12 | C | LEU | 2 | 20.560 | -3.574 | 18.664 | 1.00 | 22.07 | | MTGL |
| ATOM | 13 | O | LEU | 2 | 20.524 | -4.757 | 18.340 | 1.00 | 21.83 | | MTGL |
| ATOM | 14 | N | THR | 3 | 21.557 | -2.767 | 18.329 | 1.00 | 20.29 | | MTGL |
| ATOM | 15 | CA | THR | 3 | 22.699 | -3.257 | 17.575 | 1.00 | 19.63 | | MTGL |
| ATOM | 16 | CB | THR | 3 | 23.506 | -2.100 | 16.978 | 1.00 | 20.33 | | MTGL |
| ATOM | 17 | OG1 | THR | 3 | 22.674 | -1.360 | 16.083 | 1.00 | 20.92 | | MTGL |
| ATOM | 18 | CG2 | THR | 3 | 24.728 | -2.626 | 16.227 | 1.00 | 20.96 | | MTGL |
| ATOM | 19 | C | THR | 3 | 23.610 | -4.038 | 18.515 | 1.00 | 19.16 | | MTGL |
| ATOM | 20 | O | THR | 3 | 24.131 | -5.092 | 18.156 | 1.00 | 19.29 | | MTGL |
| ATOM | 21 | N | TYR | 4 | 23.796 | -3.514 | 19.724 | 1.00 | 18.09 | | MTGL |
| ATOM | 22 | CA | TYR | 4 | 24.652 | -4.159 | 20.715 | 1.00 | 17.42 | | MTGL |
| ATOM | 23 | CB | TYR | 4 | 25.724 | -3.180 | 21.202 | 1.00 | 17.15 | | MTGL |
| ATOM | 24 | CG | TYR | 4 | 26.514 | -2.544 | 20.082 | 1.00 | 18.02 | | MTGL |
| ATOM | 25 | CD1 | TYR | 4 | 27.516 | -3.251 | 19.412 | 1.00 | 17.43 | | MTGL |
| ATOM | 26 | CE1 | TYR | 4 | 28.210 | -2.678 | 18.348 | 1.00 | 18.07 | | MTGL |
| ATOM | 27 | CD2 | TYR | 4 | 26.229 | -1.246 | 19.661 | 1.00 | 17.07 | | MTGL |
| ATOM | 28 | CE2 | TYR | 4 | 26.916 | -0.666 | 18.598 | 1.00 | 18.55 | | MTGL |
| ATOM | 29 | CZ | TYR | 4 | 27.902 | -1.386 | 17.948 | 1.00 | 17.59 | | MTGL |
| ATOM | 30 | OH | TYR | 4 | 28.564 | -0.814 | 16.891 | 1.00 | 18.07 | | MTGL |
| ATOM | 31 | C | TYR | 4 | 23.858 | -4.657 | 21.912 | 1.00 | 16.29 | | MTGL |
| ATOM | 32 | O | TYR | 4 | 23.210 | -3.876 | 22.615 | 1.00 | 16.95 | | MTGL |
| ATOM | 33 | N | ARG | 5 | 23.907 | -5.964 | 22.125 | 1.00 | 15.87 | | MTGL |
| ATOM | 34 | CA | ARG | 5 | 23.232 | -6.611 | 23.244 | 1.00 | 16.37 | | MTGL |
| ATOM | 35 | CB | ARG | 5 | 22.281 | -7.711 | 22.746 | 1.00 | 17.04 | | MTGL |
| ATOM | 36 | CG | ARG | 5 | 21.203 | -7.235 | 21.764 | 1.00 | 18.21 | | MTGL |
| ATOM | 37 | CD | ARG | 5 | 20.189 | -8.348 | 21.482 | 1.00 | 18.30 | | MTGL |
| ATOM | 38 | NE | ARG | 5 | 20.839 | -9.547 | 20.950 | 1.00 | 19.36 | | MTGL |
| ATOM | 39 | CZ | ARG | 5 | 21.243 | -9.681 | 19.692 | 1.00 | 20.62 | | MTGL |
| ATOM | 40 | NH1 | ARG | 5 | 21.054 | -8.696 | 18.824 | 1.00 | 19.45 | | MTGL |
| ATOM | 41 | NH2 | ARG | 5 | 21.864 | -10.790 | 19.307 | 1.00 | 21.29 | | MTGL |
| ATOM | 42 | C | ARG | 5 | 24.390 | -7.238 | 24.009 | 1.00 | 16.18 | | MTGL |
| ATOM | 43 | O | ARG | 5 | 24.869 | -8.311 | 23.642 | 1.00 | 16.58 | | MTGL |
| ATOM | 44 | N | GLY | 6 | 24.853 | -6.577 | 25.064 | 1.00 | 16.16 | | MTGL |
| ATOM | 45 | CA | GLY | 6 | 25.991 | -7.135 | 25.770 | 1.00 | 16.79 | | MTGL |
| ATOM | 46 | C | GLY | 6 | 26.064 | -7.065 | 27.275 | 1.00 | 15.64 | | MTGL |
| ATOM | 47 | O | GLY | 6 | 25.129 | -6.664 | 27.968 | 1.00 | 15.46 | | MTGL |
| ATOM | 48 | N | VAL | 7 | 27.213 | -7.497 | 27.775 | 1.00 | 15.87 | | MTGL |
| ATOM | 49 | CA | VAL | 7 | 27.491 | -7.500 | 29.199 | 1.00 | 15.12 | | MTGL |
| ATOM | 50 | CB | VAL | 7 | 27.178 | -8.877 | 29.846 | 1.00 | 14.43 | | MTGL |
| ATOM | 51 | CG1 | VAL | 7 | 25.750 | -9.293 | 29.537 | 1.00 | 12.85 | | MTGL |
| ATOM | 52 | CG2 | VAL | 7 | 28.170 | -9.931 | 29.348 | 1.00 | 13.29 | | MTGL |
| ATOM | 53 | C | VAL | 7 | 28.977 | -7.238 | 29.363 | 1.00 | 16.14 | | MTGL |
| ATOM | 54 | O | VAL | 7 | 29.768 | -7.469 | 28.440 | 1.00 | 17.27 | | MTGL |
| ATOM | 55 | N | ASP | 8 | 29.354 | -6.737 | 30.531 | 1.00 | 15.62 | | MTGL |
| ATOM | 56 | CA | ASP | 8 | 30.755 | -6.514 | 30.842 | 1.00 | 15.20 | | MTGL |
| ATOM | 57 | CB | ASP | 8 | 30.920 | -5.292 | 31.751 | 1.00 | 14.35 | | MTGL |

Fig. 1

| | | | | | | | | | |
|---|---|---|---|---|---|---|---|---|---|
| ATOM | 58 | CG | ASP | 8 | 32.373 | -4.975 | 32.034 | 1.00 15.24 | MTGL |
| ATOM | 59 | OD1 | ASP | 8 | 33.105 | -5.881 | 32.486 | 1.00 14.12 | MTGL |
| ATOM | 60 | OD2 | ASP | 8 | 32.784 | -3.817 | 31.805 | 1.00 14.89 | MTGL |
| ATOM | 61 | C | ASP | 8 | 31.108 | -7.793 | 31.602 | 1.00 14.33 | MTGL |
| ATOM | 62 | O | ASP | 8 | 30.573 | -8.040 | 32.683 | 1.00 15.61 | MTGL |
| ATOM | 63 | N | TRP | 9 | 31.980 | -8.614 | 31.027 | 1.00 13.27 | MTGL |
| ATOM | 64 | CA | TRP | 9 | 32.365 | -9.872 | 31.653 | 1.00 13.40 | MTGL |
| ATOM | 65 | CB | TRP | 9 | 32.124 | -11.020 | 30.663 | 1.00 12.58 | MTGL |
| ATOM | 66 | CG | TRP | 9 | 33.183 | -11.146 | 29.585 | 1.00 13.96 | MTGL |
| ATOM | 67 | CD2 | TRP | 9 | 33.682 | -12.362 | 29.012 | 1.00 13.39 | MTGL |
| ATOM | 68 | CE2 | TRP | 9 | 34.661 | -12.008 | 28.057 | 1.00 13.29 | MTGL |
| ATOM | 69 | CE3 | TRP | 9 | 33.396 | -13.719 | 29.214 | 1.00 14.51 | MTGL |
| ATOM | 70 | CD1 | TRP | 9 | 33.860 | -10.128 | 28.964 | 1.00 14.11 | MTGL |
| ATOM | 71 | NE1 | TRP | 9 | 34.752 | -10.640 | 28.046 | 1.00 13.31 | MTGL |
| ATOM | 72 | CZ2 | TRP | 9 | 35.357 | -12.964 | 27.305 | 1.00 14.73 | MTGL |
| ATOM | 73 | CZ3 | TRP | 9 | 34.093 | -14.673 | 28.463 | 1.00 14.84 | MTGL |
| ATOM | 74 | CH2 | TRP | 9 | 35.059 | -14.287 | 27.523 | 1.00 14.12 | MTGL |
| ATOM | 75 | C | TRP | 9 | 33.832 | -9.860 | 32.102 | 1.00 13.91 | MTGL |
| ATOM | 76 | O | TRP | 9 | 34.454 | -10.915 | 32.272 | 1.00 13.71 | MTGL |
| ATOM | 77 | N | SER | 10 | 34.373 | -8.660 | 32.295 | 1.00 13.08 | MTGL |
| ATOM | 78 | CA | SER | 10 | 35.770 | -8.481 | 32.692 | 1.00 14.15 | MTGL |
| ATOM | 79 | CB | SER | 10 | 35.983 | -7.052 | 33.193 | 1.00 13.75 | MTGL |
| ATOM | 80 | OG | SER | 10 | 35.691 | -6.114 | 32.168 | 1.00 14.07 | MTGL |
| ATOM | 81 | C | SER | 10 | 36.321 | -9.460 | 33.726 | 1.00 14.36 | MTGL |
| ATOM | 82 | O | SER | 10 | 37.414 | -9.994 | 33.553 | 1.00 14.45 | MTGL |
| ATOM | 83 | N | SER | 11 | 35.561 | -9.697 | 34.789 | 1.00 14.45 | MTGL |
| ATOM | 84 | CA | SER | 11 | 35.985 | -10.588 | 35.870 | 1.00 15.55 | MTGL |
| ATOM | 85 | CB | SER | 11 | 35.053 | -10.416 | 37.069 | 1.00 15.32 | MTGL |
| ATOM | 86 | OG | SER | 11 | 33.795 | -11.014 | 36.792 | 1.00 13.85 | MTGL |
| ATOM | 87 | C | SER | 11 | 36.043 | -12.080 | 35.544 | 1.00 16.02 | MTGL |
| ATOM | 88 | O | SER | 11 | 36.438 | -12.870 | 36.401 | 1.00 16.91 | MTGL |
| ATOM | 89 | N | VAL | 12 | 35.656 | -12.472 | 34.330 | 1.00 16.04 | MTGL |
| ATOM | 90 | CA | VAL | 12 | 35.640 | -13.890 | 33.969 | 1.00 14.89 | MTGL |
| ATOM | 91 | CB | VAL | 12 | 35.367 | -14.090 | 32.448 | 1.00 14.61 | MTGL |
| ATOM | 92 | CG1 | VAL | 12 | 36.418 | -13.371 | 31.604 | 1.00 13.79 | MTGL |
| ATOM | 93 | CG2 | VAL | 12 | 35.336 | -15.583 | 32.124 | 1.00 13.78 | MTGL |
| ATOM | 94 | C | VAL | 12 | 36.861 | -14.726 | 34.373 | 1.00 15.76 | MTGL |
| ATOM | 95 | O | VAL | 12 | 36.709 | -15.751 | 35.034 | 1.00 14.51 | MTGL |
| ATOM | 96 | N | VAL | 13 | 38.065 | -14.312 | 33.990 | 1.00 16.87 | MTGL |
| ATOM | 97 | CA | VAL | 13 | 39.246 | -15.100 | 34.343 | 1.00 17.35 | MTGL |
| ATOM | 98 | CB | VAL | 13 | 40.496 | -14.656 | 33.534 | 1.00 17.20 | MTGL |
| ATOM | 99 | CG1 | VAL | 13 | 41.775 | -15.198 | 34.177 | 1.00 16.12 | MTGL |
| ATOM | 100 | CG2 | VAL | 13 | 40.391 | -15.193 | 32.109 | 1.00 15.88 | MTGL |
| ATOM | 101 | C | VAL | 13 | 39.534 | -15.043 | 35.841 | 1.00 18.53 | MTGL |
| ATOM | 102 | O | VAL | 13 | 40.002 | -16.024 | 36.430 | 1.00 19.44 | MTGL |
| ATOM | 103 | N | VAL | 14 | 39.242 | -13.907 | 36.466 | 1.00 17.79 | MTGL |
| ATOM | 104 | CA | VAL | 14 | 39.463 | -13.785 | 37.900 | 1.00 18.35 | MTGL |
| ATOM | 105 | CB | VAL | 14 | 39.106 | -12.368 | 38.411 | 1.00 18.68 | MTGL |
| ATOM | 106 | CG1 | VAL | 14 | 39.117 | -12.347 | 39.939 | 1.00 19.58 | MTGL |
| ATOM | 107 | CG2 | VAL | 14 | 40.113 | -11.352 | 37.876 | 1.00 17.40 | MTGL |
| ATOM | 108 | C | VAL | 14 | 38.588 | -14.816 | 38.620 | 1.00 17.85 | MTGL |
| ATOM | 109 | O | VAL | 14 | 39.034 | -15.495 | 39.543 | 1.00 17.72 | MTGL |
| ATOM | 110 | N | GLU | 15 | 37.341 | -14.941 | 38.181 | 1.00 17.47 | MTGL |
| ATOM | 111 | CA | GLU | 15 | 36.420 | -15.889 | 38.800 | 1.00 18.52 | MTGL |
| ATOM | 112 | CB | GLU | 15 | 34.985 | -15.585 | 38.373 | 1.00 19.09 | MTGL |
| ATOM | 113 | CG | GLU | 15 | 34.392 | -14.361 | 39.056 | 1.00 20.86 | MTGL |
| ATOM | 114 | CD | GLU | 15 | 34.147 | -14.579 | 40.542 | 1.00 22.32 | MTGL |
| ATOM | 115 | OE1 | GLU | 15 | 35.113 | -14.887 | 41.273 | 1.00 23.29 | MTGL |

Fig. 1 cont.

| ATOM | 116 | OE2 | GLU | 15 | 32.984 | -14.445 | 40.981 | 1.00 | 22.28 | MTGL |
|------|-----|-----|-----|----|--------|---------|--------|------|-------|------|
| ATOM | 117 | C | GLU | 15 | 36.753 | -17.346 | 38.502 | 1.00 | 18.21 | MTGL |
| ATOM | 118 | O | GLU | 15 | 36.640 | -18.196 | 39.377 | 1.00 | 19.29 | MTGL |
| ATOM | 119 | N | GLU | 16 | 37.151 | -17.639 | 37.272 | 1.00 | 18.79 | MTGL |
| ATOM | 120 | CA | GLU | 16 | 37.504 | -19.006 | 36.921 | 1.00 | 19.07 | MTGL |
| ATOM | 121 | CB | GLU | 16 | 37.827 | -19.103 | 35.424 | 1.00 | 19.33 | MTGL |
| ATOM | 122 | CG | GLU | 16 | 36.645 | -18.735 | 34.530 | 1.00 | 19.54 | MTGL |
| ATOM | 123 | CD | GLU | 16 | 36.970 | -18.798 | 33.049 | 1.00 | 19.73 | MTGL |
| ATOM | 124 | OE1 | GLU | 16 | 38.143 | -18.577 | 32.683 | 1.00 | 19.62 | MTGL |
| ATOM | 125 | OE2 | GLU | 16 | 36.048 | -19.048 | 32.244 | 1.00 | 20.12 | MTGL |
| ATOM | 126 | C | GLU | 16 | 38.706 | -19.425 | 37.767 | 1.00 | 18.57 | MTGL |
| ATOM | 127 | O | GLU | 16 | 38.766 | -20.557 | 38.250 | 1.00 | 17.78 | MTGL |
| ATOM | 128 | N | ARG | 17 | 39.640 | -18.492 | 37.960 | 1.00 | 17.17 | MTGL |
| ATOM | 129 | CA | ARG | 17 | 40.842 | -18.759 | 38.756 | 1.00 | 18.26 | MTGL |
| ATOM | 130 | CB | ARG | 17 | 41.872 | -17.646 | 38.568 | 1.00 | 17.11 | MTGL |
| ATOM | 131 | CG | ARG | 17 | 42.593 | -17.719 | 37.240 | 1.00 | 16.83 | MTGL |
| ATOM | 132 | CD | ARG | 17 | 43.446 | -16.496 | 37.009 | 1.00 | 15.44 | MTGL |
| ATOM | 133 | NE | ARG | 17 | 44.246 | -16.636 | 35.801 | 1.00 | 15.36 | MTGL |
| ATOM | 134 | CZ | ARG | 17 | 45.084 | -15.708 | 35.357 | 1.00 | 15.76 | MTGL |
| ATOM | 135 | NH1 | ARG | 17 | 45.225 | -14.570 | 36.025 | 1.00 | 15.62 | MTGL |
| ATOM | 136 | NH2 | ARG | 17 | 45.788 | -15.922 | 34.254 | 1.00 | 15.66 | MTGL |
| ATOM | 137 | C | ARG | 17 | 40.502 | -18.887 | 40.225 | 1.00 | 18.97 | MTGL |
| ATOM | 138 | O | ARG | 17 | 41.279 | -19.407 | 41.017 | 1.00 | 19.60 | MTGL |
| ATOM | 139 | N | ALA | 18 | 39.330 | -18.396 | 40.590 | 1.00 | 19.85 | MTGL |
| ATOM | 140 | CA | ALA | 18 | 38.890 | -18.486 | 41.967 | 1.00 | 21.00 | MTGL |
| ATOM | 141 | CB | ALA | 18 | 38.071 | -17.262 | 42.339 | 1.00 | 21.45 | MTGL |
| ATOM | 142 | C | ALA | 18 | 38.066 | -19.756 | 42.154 | 1.00 | 21.18 | MTGL |
| ATOM | 143 | O | ALA | 18 | 37.495 | -19.982 | 43.216 | 1.00 | 21.53 | MTGL |
| ATOM | 144 | N | GLY | 19 | 37.994 | -20.577 | 41.110 | 1.00 | 20.78 | MTGL |
| ATOM | 145 | CA | GLY | 19 | 37.265 | -21.827 | 41.218 | 1.00 | 21.14 | MTGL |
| ATOM | 146 | C | GLY | 19 | 35.833 | -21.845 | 40.716 | 1.00 | 21.86 | MTGL |
| ATOM | 147 | O | GLY | 19 | 35.124 | -22.833 | 40.901 | 1.00 | 20.92 | MTGL |
| ATOM | 148 | N | VAL | 20 | 35.386 | -20.769 | 40.080 | 1.00 | 21.60 | MTGL |
| ATOM | 149 | CA | VAL | 20 | 34.021 | -20.755 | 39.578 | 1.00 | 21.91 | MTGL |
| ATOM | 150 | CB | VAL | 20 | 33.533 | -19.321 | 39.264 | 1.00 | 23.06 | MTGL |
| ATOM | 151 | CG1 | VAL | 20 | 32.126 | -19.370 | 38.674 | 1.00 | 22.39 | MTGL |
| ATOM | 152 | CG2 | VAL | 20 | 33.530 | -18.475 | 40.530 | 1.00 | 22.53 | MTGL |
| ATOM | 153 | C | VAL | 20 | 33.877 | -21.589 | 38.305 | 1.00 | 21.53 | MTGL |
| ATOM | 154 | O | VAL | 20 | 34.673 | -21.473 | 37.377 | 1.00 | 21.65 | MTGL |
| ATOM | 155 | N | SER | 21 | 32.864 | -22.444 | 38.283 | 0.50 | 21.24 | MTGL |
| ATOM | 156 | CA | SER | 21 | 32.596 | -23.272 | 37.116 | 0.50 | 21.35 | MTGL |
| ATOM | 157 | CB | SER | 21 | 32.602 | -24.757 | 37.488 | 0.50 | 22.01 | MTGL |
| ATOM | 158 | OG | SER | 21 | 33.897 | -25.165 | 37.901 | 0.50 | 22.69 | MTGL |
| ATOM | 159 | C | SER | 21 | 31.227 | -22.857 | 36.605 | 0.50 | 20.74 | MTGL |
| ATOM | 160 | O | SER | 21 | 30.205 | -23.167 | 37.214 | 0.50 | 20.32 | MTGL |
| ATOM | 161 | N | TYR | 22 | 31.216 | -22.134 | 35.491 | 1.00 | 20.34 | MTGL |
| ATOM | 162 | CA | TYR | 22 | 29.972 | -21.659 | 34.914 | 1.00 | 20.72 | MTGL |
| ATOM | 163 | CB | TYR | 22 | 30.270 | -20.511 | 33.952 | 1.00 | 19.18 | MTGL |
| ATOM | 164 | CG | TYR | 22 | 30.765 | -19.280 | 34.682 | 1.00 | 18.50 | MTGL |
| ATOM | 165 | CD1 | TYR | 22 | 29.909 | -18.548 | 35.503 | 1.00 | 17.85 | MTGL |
| ATOM | 166 | CE1 | TYR | 22 | 30.357 | -17.428 | 36.202 | 1.00 | 17.95 | MTGL |
| ATOM | 167 | CD2 | TYR | 22 | 32.092 | -18.865 | 34.578 | 1.00 | 17.87 | MTGL |
| ATOM | 168 | CE2 | TYR | 22 | 32.552 | -17.744 | 35.275 | 1.00 | 17.81 | MTGL |
| ATOM | 169 | CZ | TYR | 22 | 31.676 | -17.031 | 36.083 | 1.00 | 17.46 | MTGL |
| ATOM | 170 | OH | TYR | 22 | 32.107 | -15.915 | 36.767 | 1.00 | 17.47 | MTGL |
| ATOM | 171 | C | TYR | 22 | 29.152 | -22.742 | 34.239 | 1.00 | 21.41 | MTGL |
| ATOM | 172 | O | TYR | 22 | 29.688 | -23.634 | 33.588 | 1.00 | 21.91 | MTGL |
| ATOM | 173 | N | LYS | 23 | 27.839 | -22.654 | 34.414 | 1.00 | 22.66 | MTGL |

Fig. 1 cont.

| | | | | | | | | | |
|---|---|---|---|---|---|---|---|---|---|
| ATOM | 174 | CA | LYS | 23 | 26.918 | -23.619 | 33.836 | 1.00 23.97 | MTGL |
| ATOM | 175 | CB | LYS | 23 | 26.387 | -24.537 | 34.936 | 1.00 24.47 | MTGL |
| ATOM | 176 | CG | LYS | 23 | 27.479 | -25.094 | 35.839 | 1.00 26.17 | MTGL |
| ATOM | 177 | CD | LYS | 23 | 26.894 | -25.778 | 37.066 | 1.00 28.12 | MTGL |
| ATOM | 178 | CE | LYS | 23 | 27.985 | -26.217 | 38.040 | 1.00 29.23 | MTGL |
| ATOM | 179 | NZ | LYS | 23 | 28.750 | -25.069 | 38.615 | 1.00 28.37 | MTGL |
| ATOM | 180 | C | LYS | 23 | 25.748 | -22.915 | 33.158 | 1.00 24.07 | MTGL |
| ATOM | 181 | O | LYS | 23 | 25.344 | -21.823 | 33.570 | 1.00 23.42 | MTGL |
| ATOM | 182 | N | ASN | 24 | 25.210 | -23.557 | 32.125 | 1.00 25.34 | MTGL |
| ATOM | 183 | CA | ASN | 24 | 24.074 | -23.020 | 31.390 | 1.00 26.76 | MTGL |
| ATOM | 184 | CB | ASN | 24 | 23.907 | -23.741 | 30.042 | 1.00 27.22 | MTGL |
| ATOM | 185 | CG | ASN | 24 | 23.925 | -25.258 | 30.174 | 1.00 28.00 | MTGL |
| ATOM | 186 | OD1 | ASN | 24 | 23.306 | -25.825 | 31.075 | 1.00 28.00 | MTGL |
| ATOM | 187 | ND2 | ASN | 24 | 24.626 | -25.923 | 29.258 | 1.00 28.41 | MTGL |
| ATOM | 188 | C | ASN | 24 | 22.802 | -23.171 | 32.216 | 1.00 27.53 | MTGL |
| ATOM | 189 | O | ASN | 24 | 22.830 | -23.727 | 33.315 | 1.00 26.87 | MTGL |
| ATOM | 190 | N | THR | 25 | 21.691 | -22.668 | 31.687 | 1.00 29.20 | MTGL |
| ATOM | 191 | CA | THR | 25 | 20.408 | -22.754 | 32.378 | 1.00 31.61 | MTGL |
| ATOM | 192 | CB | THR | 25 | 19.299 | -21.968 | 31.619 | 1.00 31.89 | MTGL |
| ATOM | 193 | OG1 | THR | 25 | 19.269 | -22.380 | 30.245 | 1.00 32.33 | MTGL |
| ATOM | 194 | CG2 | THR | 25 | 19.558 | -20.468 | 31.689 | 1.00 30.90 | MTGL |
| ATOM | 195 | C | THR | 25 | 19.968 | -24.209 | 32.540 | 1.00 33.20 | MTGL |
| ATOM | 196 | O | THR | 25 | 19.107 | -24.518 | 33.362 | 1.00 34.49 | MTGL |
| ATOM | 197 | N | ASN | 26 | 20.561 | -25.101 | 31.754 | 1.00 33.98 | MTGL |
| ATOM | 198 | CA | ASN | 26 | 20.229 | -26.521 | 31.831 | 1.00 34.91 | MTGL |
| ATOM | 199 | CB | ASN | 26 | 20.595 | -27.233 | 30.529 | 1.00 37.07 | MTGL |
| ATOM | 200 | CG | ASN | 26 | 19.515 | -27.114 | 29.479 | 1.00 38.98 | MTGL |
| ATOM | 201 | OD1 | ASN | 26 | 19.743 | -27.405 | 28.305 | 1.00 40.46 | MTGL |
| ATOM | 202 | ND2 | ASN | 26 | 18.325 | -26.696 | 29.898 | 1.00 39.01 | MTGL |
| ATOM | 203 | C | ASN | 26 | 21.000 | -27.153 | 32.967 | 1.00 33.95 | MTGL |
| ATOM | 204 | O | ASN | 26 | 20.752 | -28.294 | 33.356 | 1.00 34.07 | MTGL |
| ATOM | 205 | N | GLY | 27 | 21.952 | -26.402 | 33.493 | 1.00 32.34 | MTGL |
| ATOM | 206 | CA | GLY | 27 | 22.739 | -26.928 | 34.583 | 1.00 30.16 | MTGL |
| ATOM | 207 | C | GLY | 27 | 24.009 | -27.629 | 34.140 | 1.00 29.51 | MTGL |
| ATOM | 208 | O | GLY | 27 | 24.692 | -28.244 | 34.950 | 1.00 28.86 | MTGL |
| ATOM | 209 | N | ASN | 28 | 24.350 | -27.547 | 32.864 | 1.00 29.22 | MTGL |
| ATOM | 210 | CA | ASN | 28 | 25.565 | -28.205 | 32.419 | 1.00 28.62 | MTGL |
| ATOM | 211 | CB | ASN | 28 | 25.323 | -28.945 | 31.108 | 1.00 30.49 | MTGL |
| ATOM | 212 | CG | ASN | 28 | 24.313 | -30.063 | 31.258 | 1.00 31.94 | MTGL |
| ATOM | 213 | OD1 | ASN | 28 | 24.453 | -30.930 | 32.124 | 1.00 32.14 | MTGL |
| ATOM | 214 | ND2 | ASN | 28 | 23.288 | -30.049 | 30.417 | 1.00 32.11 | MTGL |
| ATOM | 215 | C | ASN | 28 | 26.714 | -27.228 | 32.264 | 1.00 27.80 | MTGL |
| ATOM | 216 | O | ASN | 28 | 26.537 | -26.085 | 31.831 | 1.00 26.86 | MTGL |
| ATOM | 217 | N | ALA | 29 | 27.897 | -27.695 | 32.629 | 1.00 26.54 | MTGL |
| ATOM | 218 | CA | ALA | 29 | 29.103 | -26.889 | 32.547 | 1.00 26.11 | MTGL |
| ATOM | 219 | CB | ALA | 29 | 30.290 | -27.687 | 33.067 | 1.00 25.81 | MTGL |
| ATOM | 220 | C | ALA | 29 | 29.351 | -26.456 | 31.110 | 1.00 25.11 | MTGL |
| ATOM | 221 | O | ALA | 29 | 29.232 | -27.254 | 30.184 | 1.00 24.31 | MTGL |
| ATOM | 222 | N | GLN | 30 | 29.713 | -25.192 | 30.932 | 1.00 23.82 | MTGL |
| ATOM | 223 | CA | GLN | 30 | 29.967 | -24.655 | 29.603 | 1.00 23.10 | MTGL |
| ATOM | 224 | CB | GLN | 30 | 28.620 | -24.424 | 28.901 | 1.00 23.68 | MTGL |
| ATOM | 225 | CG | GLN | 30 | 28.676 | -23.687 | 27.578 | 1.00 26.45 | MTGL |
| ATOM | 226 | CD | GLN | 30 | 27.335 | -23.695 | 26.858 | 1.00 27.43 | MTGL |
| ATOM | 227 | OE1 | GLN | 30 | 26.282 | -23.584 | 27.486 | 1.00 27.66 | MTGL |
| ATOM | 228 | NE2 | GLN | 30 | 27.371 | -23.815 | 25.537 | 1.00 27.00 | MTGL |
| ATOM | 229 | C | GLN | 30 | 30.748 | -23.350 | 29.740 | 1.00 21.50 | MTGL |
| ATOM | 230 | O | GLN | 30 | 30.556 | -22.609 | 30.700 | 1.00 21.61 | MTGL |
| ATOM | 231 | N | PRO | 31 | 31.661 | -23.066 | 28.797 | 1.00 20.08 | MTGL |

Fig. 1 cont.

```
ATOM    232  CD   PRO    31      32.110  -23.886   27.657  1.00 20.60      MTGL
ATOM    233  CA   PRO    31      32.432  -21.820   28.886  1.00 19.48      MTGL
ATOM    234  CB   PRO    31      33.262  -21.834   27.603  1.00 20.47      MTGL
ATOM    235  CG   PRO    31      33.489  -23.309   27.369  1.00 20.52      MTGL
ATOM    236  C    PRO    31      31.492  -20.617   28.960  1.00 18.32      MTGL
ATOM    237  O    PRO    31      30.491  -20.558   28.246  1.00 17.02      MTGL
ATOM    238  N    LEU    32      31.811  -19.664   29.828  1.00 18.30      MTGL
ATOM    239  CA   LEU    32      30.971  -18.477   29.987  1.00 18.52      MTGL
ATOM    240  CB   LEU    32      31.623  -17.476   30.954  1.00 17.22      MTGL
ATOM    241  CG   LEU    32      30.828  -16.190   31.227  1.00 17.71      MTGL
ATOM    242  CD1  LEU    32      29.443  -16.536   31.767  1.00 15.78      MTGL
ATOM    243  CD2  LEU    32      31.588  -15.319   32.235  1.00 15.40      MTGL
ATOM    244  C    LEU    32      30.655  -17.776   28.669  1.00 17.46      MTGL
ATOM    245  O    LEU    32      29.504  -17.413   28.429  1.00 18.85      MTGL
ATOM    246  N    GLU    33      31.660  -17.581   27.818  1.00 16.99      MTGL
ATOM    247  CA   GLU    33      31.421  -16.903   26.546  1.00 17.55      MTGL
ATOM    248  CB   GLU    33      32.716  -16.763   25.735  1.00 17.22      MTGL
ATOM    249  CG   GLU    33      33.426  -18.077   25.424  1.00 16.64      MTGL
ATOM    250  CD   GLU    33      34.496  -18.417   26.453  1.00 16.72      MTGL
ATOM    251  OE1  GLU    33      34.234  -18.270   27.667  1.00 14.95      MTGL
ATOM    252  OE2  GLU    33      35.597  -18.840   26.048  1.00 16.02      MTGL
ATOM    253  C    GLU    33      30.369  -17.630   25.712  1.00 18.39      MTGL
ATOM    254  O    GLU    33      29.576  -16.988   25.021  1.00 19.97      MTGL
ATOM    255  N    ASN    34      30.354  -18.959   25.779  1.00 18.00      MTGL
ATOM    256  CA   ASN    34      29.381  -19.739   25.019  1.00 19.90      MTGL
ATOM    257  CB   ASN    34      29.793  -21.214   24.955  1.00 21.66      MTGL
ATOM    258  CG   ASN    34      31.121  -21.420   24.251  1.00 24.08      MTGL
ATOM    259  OD1  ASN    34      31.355  -20.886   23.168  1.00 25.77      MTGL
ATOM    260  ND2  ASN    34      31.995  -22.207   24.861  1.00 26.27      MTGL
ATOM    261  C    ASN    34      27.991  -19.618   25.640  1.00 19.84      MTGL
ATOM    262  O    ASN    34      26.988  -19.598   24.931  1.00 19.75      MTGL
ATOM    263  N    ILE    35      27.932  -19.553   26.967  1.00 18.73      MTGL
ATOM    264  CA   ILE    35      26.656  -19.404   27.656  1.00 18.63      MTGL
ATOM    265  CB   ILE    35      26.845  -19.440   29.188  1.00 18.28      MTGL
ATOM    266  CG2  ILE    35      25.556  -19.028   29.890  1.00 17.35      MTGL
ATOM    267  CG1  ILE    35      27.270  -20.844   29.623  1.00 18.06      MTGL
ATOM    268  CD1  ILE    35      27.652  -20.946   31.091  1.00 19.14      MTGL
ATOM    269  C    ILE    35      26.048  -18.053   27.258  1.00 18.92      MTGL
ATOM    270  O    ILE    35      24.867  -17.966   26.907  1.00 18.51      MTGL
ATOM    271  N    LEU    36      26.866  -17.005   27.313  1.00 18.03      MTGL
ATOM    272  CA   LEU    36      26.416  -15.665   26.956  1.00 17.16      MTGL
ATOM    273  CB   LEU    36      27.563  -14.660   27.110  1.00 17.06      MTGL
ATOM    274  CG   LEU    36      28.076  -14.411   28.538  1.00 16.94      MTGL
ATOM    275  CD1  LEU    36      29.323  -13.516   28.504  1.00 14.36      MTGL
ATOM    276  CD2  LEU    36      26.969  -13.761   29.372  1.00 16.43      MTGL
ATOM    277  C    LEU    36      25.891  -15.636   25.522  1.00 17.26      MTGL
ATOM    278  O    LEU    36      24.795  -15.132   25.270  1.00 16.08      MTGL
ATOM    279  N    ALA    37      26.675  -16.174   24.589  1.00 17.12      MTGL
ATOM    280  CA   ALA    37      26.278  -16.203   23.187  1.00 17.86      MTGL
ATOM    281  CB   ALA    37      27.362  -16.863   22.338  1.00 16.93      MTGL
ATOM    282  C    ALA    37      24.961  -16.948   23.014  1.00 18.20      MTGL
ATOM    283  O    ALA    37      24.062  -16.480   22.314  1.00 19.46      MTGL
ATOM    284  N    ALA    38      24.850  -18.105   23.658  1.00 18.38      MTGL
ATOM    285  CA   ALA    38      23.643  -18.917   23.560  1.00 20.05      MTGL
ATOM    286  CB   ALA    38      23.809  -20.212   24.358  1.00 19.05      MTGL
ATOM    287  C    ALA    38      22.419  -18.154   24.049  1.00 20.48      MTGL
ATOM    288  O    ALA    38      21.294  -18.447   23.634  1.00 21.25      MTGL
ATOM    289  N    ASN    39      22.637  -17.173   24.923  1.00 20.10      MTGL
```

Fig. 1 cont.

| | | | | | | | | | |
|---|---|---|---|---|---|---|---|---|---|
| ATOM | 290 | CA | ASN | 39 | 21.531 | -16.390 | 25.460 | 1.00 19.15 | MTGL |
| ATOM | 291 | CB | ASN | 39 | 21.717 | -16.168 | 26.963 | 1.00 19.77 | MTGL |
| ATOM | 292 | CG | ASN | 39 | 21.416 | -17.414 | 27.774 | 1.00 19.60 | MTGL |
| ATOM | 293 | OD1 | ASN | 39 | 22.241 | -18.327 | 27.872 | 1.00 22.00 | MTGL |
| ATOM | 294 | ND2 | ASN | 39 | 20.224 | -17.467 | 28.346 | 1.00 18.25 | MTGL |
| ATOM | 295 | C | ASN | 39 | 21.253 | -15.056 | 24.768 | 1.00 18.64 | MTGL |
| ATOM | 296 | O | ASN | 39 | 20.544 | -14.213 | 25.317 | 1.00 19.42 | MTGL |
| ATOM | 297 | N | GLY | 40 | 21.803 | -14.862 | 23.572 | 1.00 17.47 | MTGL |
| ATOM | 298 | CA | GLY | 40 | 21.535 | -13.635 | 22.837 | 1.00 17.26 | MTGL |
| ATOM | 299 | C | GLY | 40 | 22.585 | -12.537 | 22.880 | 1.00 17.22 | MTGL |
| ATOM | 300 | O | GLY | 40 | 22.523 | -11.594 | 22.095 | 1.00 17.12 | MTGL |
| ATOM | 301 | N | VAL | 41 | 23.544 | -12.641 | 23.791 | 1.00 16.80 | MTGL |
| ATOM | 302 | CA | VAL | 41 | 24.589 | -11.631 | 23.893 | 1.00 15.92 | MTGL |
| ATOM | 303 | CB | VAL | 41 | 25.510 | -11.908 | 25.103 | 1.00 16.19 | MTGL |
| ATOM | 304 | CG1 | VAL | 41 | 26.630 | -10.888 | 25.144 | 1.00 14.75 | MTGL |
| ATOM | 305 | CG2 | VAL | 41 | 24.707 | -11.875 | 26.397 | 1.00 15.59 | MTGL |
| ATOM | 306 | C | VAL | 41 | 25.441 | -11.645 | 22.626 | 1.00 15.77 | MTGL |
| ATOM | 307 | O | VAL | 41 | 25.832 | -12.715 | 22.158 | 1.00 14.76 | MTGL |
| ATOM | 308 | N | ASN | 42 | 25.724 | -10.469 | 22.064 | 1.00 16.34 | MTGL |
| ATOM | 309 | CA | ASN | 42 | 26.559 | -10.406 | 20.864 | 1.00 16.57 | MTGL |
| ATOM | 310 | CB | ASN | 42 | 25.771 | -9.889 | 19.646 | 1.00 17.06 | MTGL |
| ATOM | 311 | CG | ASN | 42 | 25.299 | -8.443 | 19.798 | 1.00 18.15 | MTGL |
| ATOM | 312 | OD1 | ASN | 42 | 25.727 | -7.709 | 20.694 | 1.00 18.63 | MTGL |
| ATOM | 313 | ND2 | ASN | 42 | 24.416 | -8.028 | 18.898 | 1.00 16.75 | MTGL |
| ATOM | 314 | C | ASN | 42 | 27.812 | -9.560 | 21.048 | 1.00 16.81 | MTGL |
| ATOM | 315 | O | ASN | 42 | 28.651 | -9.478 | 20.147 | 1.00 17.52 | MTGL |
| ATOM | 316 | N | THR | 43 | 27.952 | -8.951 | 22.221 | 1.00 16.55 | MTGL |
| ATOM | 317 | CA | THR | 43 | 29.108 | -8.108 | 22.502 | 1.00 15.96 | MTGL |
| ATOM | 318 | CB | THR | 43 | 28.827 | -6.634 | 22.136 | 1.00 16.50 | MTGL |
| ATOM | 319 | OG1 | THR | 43 | 28.192 | -6.565 | 20.850 | 1.00 17.26 | MTGL |
| ATOM | 320 | CG2 | THR | 43 | 30.123 | -5.840 | 22.102 | 1.00 15.22 | MTGL |
| ATOM | 321 | C | THR | 43 | 29.487 | -8.144 | 23.976 | 1.00 15.93 | MTGL |
| ATOM | 322 | O | THR | 43 | 28.618 | -8.180 | 24.849 | 1.00 16.10 | MTGL |
| ATOM | 323 | N | VAL | 44 | 30.786 | -8.148 | 24.251 | 1.00 14.74 | MTGL |
| ATOM | 324 | CA | VAL | 44 | 31.251 | -8.136 | 25.626 | 1.00 15.41 | MTGL |
| ATOM | 325 | CB | VAL | 44 | 32.038 | -9.418 | 26.012 | 1.00 16.13 | MTGL |
| ATOM | 326 | CG1 | VAL | 44 | 31.084 | -10.603 | 26.096 | 1.00 16.11 | MTGL |
| ATOM | 327 | CG2 | VAL | 44 | 33.146 | -9.689 | 25.004 | 1.00 14.58 | MTGL |
| ATOM | 328 | C | VAL | 44 | 32.137 | -6.922 | 25.849 | 1.00 15.69 | MTGL |
| ATOM | 329 | O | VAL | 44 | 32.974 | -6.574 | 25.014 | 1.00 16.22 | MTGL |
| ATOM | 330 | N | ARG | 45 | 31.916 | -6.271 | 26.981 | 1.00 14.86 | MTGL |
| ATOM | 331 | CA | ARG | 45 | 32.662 | -5.091 | 27.383 | 1.00 15.51 | MTGL |
| ATOM | 332 | CB | ARG | 45 | 31.702 | -4.129 | 28.087 | 1.00 16.51 | MTGL |
| ATOM | 333 | CG | ARG | 45 | 32.297 | -2.828 | 28.597 | 1.00 17.41 | MTGL |
| ATOM | 334 | CD | ARG | 45 | 31.143 | -1.971 | 29.107 | 1.00 18.63 | MTGL |
| ATOM | 335 | NE | ARG | 45 | 31.519 | -0.636 | 29.554 | 1.00 19.44 | MTGL |
| ATOM | 336 | CZ | ARG | 45 | 31.756 | -0.309 | 30.820 | 1.00 19.56 | MTGL |
| ATOM | 337 | NH1 | ARG | 45 | 31.671 | -1.225 | 31.777 | 1.00 18.15 | MTGL |
| ATOM | 338 | NH2 | ARG | 45 | 32.032 | 0.949 | 31.130 | 1.00 19.68 | MTGL |
| ATOM | 339 | C | ARG | 45 | 33.752 | -5.561 | 28.342 | 1.00 15.10 | MTGL |
| ATOM | 340 | O | ARG | 45 | 33.516 | -6.446 | 29.168 | 1.00 13.85 | MTGL |
| ATOM | 341 | N | GLN | 46 | 34.938 | -4.965 | 28.232 | 1.00 14.87 | MTGL |
| ATOM | 342 | CA | GLN | 46 | 36.071 | -5.331 | 29.074 | 1.00 14.52 | MTGL |
| ATOM | 343 | CB | GLN | 46 | 37.030 | -6.246 | 28.296 | 1.00 14.23 | MTGL |
| ATOM | 344 | CG | GLN | 46 | 36.376 | -7.512 | 27.746 | 1.00 14.12 | MTGL |
| ATOM | 345 | CD | GLN | 46 | 37.310 | -8.358 | 26.902 | 1.00 13.86 | MTGL |
| ATOM | 346 | OE1 | GLN | 46 | 36.895 | -9.363 | 26.335 | 1.00 15.22 | MTGL |
| ATOM | 347 | NE2 | GLN | 46 | 38.575 | -7.958 | 26.814 | 1.00 13.21 | MTGL |

Fig. 1 cont.

| ATOM | 348 | C | GLN | 46 | 36.831 | -4.089 | 29.534 | 1.00 | 15.79 | MTGL |
|------|-----|-----|-----|----|--------|--------|--------|------|-------|------|
| ATOM | 349 | O | GLN | 46 | 37.153 | -3.211 | 28.728 | 1.00 | 15.74 | MTGL |
| ATOM | 350 | N | ARG | 47 | 37.111 | -4.005 | 30.830 | 1.00 | 15.01 | MTGL |
| ATOM | 351 | CA | ARG | 47 | 37.851 | -2.866 | 31.350 | 1.00 | 15.05 | MTGL |
| ATOM | 352 | CB | ARG | 47 | 37.524 | -2.631 | 32.828 | 1.00 | 13.91 | MTGL |
| ATOM | 353 | CG | ARG | 47 | 37.649 | -3.868 | 33.710 | 1.00 | 13.56 | MTGL |
| ATOM | 354 | CD | ARG | 47 | 37.391 | -3.520 | 35.175 | 1.00 | 13.26 | MTGL |
| ATOM | 355 | NE | ARG | 47 | 37.207 | -4.710 | 36.004 | 1.00 | 12.49 | MTGL |
| ATOM | 356 | CZ | ARG | 47 | 36.063 | -5.382 | 36.117 | 1.00 | 13.71 | MTGL |
| ATOM | 357 | NH1 | ARG | 47 | 34.983 | -4.981 | 35.457 | 1.00 | 13.79 | MTGL |
| ATOM | 358 | NH2 | ARG | 47 | 36.004 | -6.477 | 36.876 | 1.00 | 12.61 | MTGL |
| ATOM | 359 | C | ARG | 47 | 39.347 | -3.107 | 31.182 | 1.00 | 15.50 | MTGL |
| ATOM | 360 | O | ARG | 47 | 39.849 | -4.209 | 31.433 | 1.00 | 15.21 | MTGL |
| ATOM | 361 | N | VAL | 48 | 40.056 | -2.072 | 30.745 | 1.00 | 15.84 | MTGL |
| ATOM | 362 | CA | VAL | 48 | 41.496 | -2.171 | 30.557 | 1.00 | 15.53 | MTGL |
| ATOM | 363 | CB | VAL | 48 | 41.899 | -1.874 | 29.102 | 1.00 | 16.38 | MTGL |
| ATOM | 364 | CG1 | VAL | 48 | 43.418 | -1.906 | 28.975 | 1.00 | 15.45 | MTGL |
| ATOM | 365 | CG2 | VAL | 48 | 41.258 | -2.892 | 28.160 | 1.00 | 14.39 | MTGL |
| ATOM | 366 | C | VAL | 48 | 42.222 | -1.185 | 31.459 | 1.00 | 16.31 | MTGL |
| ATOM | 367 | O | VAL | 48 | 41.941 | 0.013 | 31.433 | 1.00 | 14.76 | MTGL |
| ATOM | 368 | N | TRP | 49 | 43.139 | -1.707 | 32.270 | 1.00 | 16.64 | MTGL |
| ATOM | 369 | CA | TRP | 49 | 43.938 | -0.890 | 33.172 | 1.00 | 17.13 | MTGL |
| ATOM | 370 | CB | TRP | 49 | 43.893 | -1.458 | 34.598 | 1.00 | 17.19 | MTGL |
| ATOM | 371 | CG | TRP | 49 | 42.525 | -1.365 | 35.239 | 1.00 | 17.50 | MTGL |
| ATOM | 372 | CD2 | TRP | 49 | 42.129 | -1.903 | 36.510 | 1.00 | 17.36 | MTGL |
| ATOM | 373 | CE2 | TRP | 49 | 40.773 | -1.550 | 36.710 | 1.00 | 17.08 | MTGL |
| ATOM | 374 | CE3 | TRP | 49 | 42.786 | -2.651 | 37.497 | 1.00 | 16.24 | MTGL |
| ATOM | 375 | CD1 | TRP | 49 | 41.426 | -0.728 | 34.736 | 1.00 | 17.53 | MTGL |
| ATOM | 376 | NE1 | TRP | 49 | 40.370 | -0.832 | 35.614 | 1.00 | 17.76 | MTGL |
| ATOM | 377 | CZ2 | TRP | 49 | 40.063 | -1.915 | 37.860 | 1.00 | 16.34 | MTGL |
| ATOM | 378 | CZ3 | TRP | 49 | 42.079 | -3.014 | 38.642 | 1.00 | 17.30 | MTGL |
| ATOM | 379 | CH2 | TRP | 49 | 40.729 | -2.645 | 38.812 | 1.00 | 16.66 | MTGL |
| ATOM | 380 | C | TRP | 49 | 45.369 | -0.870 | 32.632 | 1.00 | 17.96 | MTGL |
| ATOM | 381 | O | TRP | 49 | 45.819 | -1.830 | 32.007 | 1.00 | 16.92 | MTGL |
| ATOM | 382 | N | VAL | 50 | 46.078 | 0.228 | 32.874 | 1.00 | 18.74 | MTGL |
| ATOM | 383 | CA | VAL | 50 | 47.438 | 0.408 | 32.373 | 1.00 | 18.43 | MTGL |
| ATOM | 384 | CB | VAL | 50 | 47.898 | 1.865 | 32.604 | 1.00 | 17.51 | MTGL |
| ATOM | 385 | CG1 | VAL | 50 | 49.310 | 2.061 | 32.069 | 1.00 | 16.69 | MTGL |
| ATOM | 386 | CG2 | VAL | 50 | 46.931 | 2.814 | 31.912 | 1.00 | 16.38 | MTGL |
| ATOM | 387 | C | VAL | 50 | 48.492 | -0.568 | 32.910 | 1.00 | 20.17 | MTGL |
| ATOM | 388 | O | VAL | 50 | 49.035 | -1.359 | 32.141 | 1.00 | 20.17 | MTGL |
| ATOM | 389 | N | ASN | 51 | 48.809 | -0.513 | 34.203 | 1.00 | 20.54 | MTGL |
| ATOM | 390 | CA | ASN | 51 | 49.800 | -1.438 | 34.780 | 1.00 | 22.14 | MTGL |
| ATOM | 391 | CB | ASN | 51 | 51.181 | -0.778 | 34.894 | 1.00 | 22.82 | MTGL |
| ATOM | 392 | CG | ASN | 51 | 51.899 | -0.671 | 33.564 | 1.00 | 24.64 | MTGL |
| ATOM | 393 | OD1 | ASN | 51 | 52.211 | 0.430 | 33.102 | 1.00 | 25.29 | MTGL |
| ATOM | 394 | ND2 | ASN | 51 | 52.180 | -1.813 | 32.945 | 1.00 | 24.48 | MTGL |
| ATOM | 395 | C | ASN | 51 | 49.416 | -1.943 | 36.173 | 1.00 | 22.18 | MTGL |
| ATOM | 396 | O | ASN | 51 | 50.177 | -1.771 | 37.119 | 1.00 | 23.10 | MTGL |
| ATOM | 397 | N | PRO | 52 | 48.242 | -2.584 | 36.317 | 1.00 | 21.49 | MTGL |
| ATOM | 398 | CD | PRO | 52 | 47.333 | -3.089 | 35.273 | 1.00 | 20.91 | MTGL |
| ATOM | 399 | CA | PRO | 52 | 47.847 | -3.079 | 37.642 | 1.00 | 20.88 | MTGL |
| ATOM | 400 | CB | PRO | 52 | 46.509 | -3.769 | 37.370 | 1.00 | 20.37 | MTGL |
| ATOM | 401 | CG | PRO | 52 | 46.683 | -4.283 | 35.963 | 1.00 | 20.56 | MTGL |
| ATOM | 402 | C | PRO | 52 | 48.905 | -4.041 | 38.177 | 1.00 | 21.68 | MTGL |
| ATOM | 403 | O | PRO | 52 | 49.390 | -4.902 | 37.449 | 1.00 | 20.78 | MTGL |
| ATOM | 404 | N | ALA | 53 | 49.261 | -3.891 | 39.448 | 1.00 | 22.20 | MTGL |
| ATOM | 405 | CA | ALA | 53 | 50.278 | -4.739 | 40.061 | 1.00 | 23.49 | MTGL |

Fig. 1 cont.

| | | | | | | | | | | |
|---|---|---|---|---|---|---|---|---|---|---|
| ATOM | 406 | CB  | ALA | 53 | 50.409 | -4.407  | 41.549 | 1.00 | 23.83 | MTGL |
| ATOM | 407 | C   | ALA | 53 | 50.037 | -6.235  | 39.883 | 1.00 | 23.68 | MTGL |
| ATOM | 408 | O   | ALA | 53 | 50.937 | -6.960  | 39.466 | 1.00 | 23.33 | MTGL |
| ATOM | 409 | N   | ASP | 54 | 48.831 | -6.704  | 40.195 | 1.00 | 24.06 | MTGL |
| ATOM | 410 | CA  | ASP | 54 | 48.539 | -8.126  | 40.058 | 1.00 | 24.64 | MTGL |
| ATOM | 411 | CB  | ASP | 54 | 47.400 | -8.540  | 40.994 | 1.00 | 26.42 | MTGL |
| ATOM | 412 | CG  | ASP | 54 | 46.109 | -7.805  | 40.706 | 1.00 | 27.54 | MTGL |
| ATOM | 413 | OD1 | ASP | 54 | 45.834 | -7.515  | 39.522 | 1.00 | 29.32 | MTGL |
| ATOM | 414 | OD2 | ASP | 54 | 45.360 | -7.529  | 41.664 | 1.00 | 27.59 | MTGL |
| ATOM | 415 | C   | ASP | 54 | 48.207 | -8.560  | 38.631 | 1.00 | 24.00 | MTGL |
| ATOM | 416 | O   | ASP | 54 | 47.878 | -9.720  | 38.396 | 1.00 | 24.44 | MTGL |
| ATOM | 417 | N   | GLY | 55 | 48.286 | -7.630  | 37.686 | 1.00 | 22.74 | MTGL |
| ATOM | 418 | CA  | GLY | 55 | 48.013 | -7.959  | 36.296 | 1.00 | 21.74 | MTGL |
| ATOM | 419 | C   | GLY | 55 | 46.566 | -8.102  | 35.854 | 1.00 | 20.84 | MTGL |
| ATOM | 420 | O   | GLY | 55 | 46.294 | -8.150  | 34.652 | 1.00 | 20.70 | MTGL |
| ATOM | 421 | N   | ASN | 56 | 45.627 | -8.173  | 36.791 | 1.00 | 20.23 | MTGL |
| ATOM | 422 | CA  | ASN | 56 | 44.229 | -8.320  | 36.399 | 1.00 | 19.77 | MTGL |
| ATOM | 423 | CB  | ASN | 56 | 43.329 | -8.530  | 37.623 | 1.00 | 21.09 | MTGL |
| ATOM | 424 | CG  | ASN | 56 | 43.569 | -9.876  | 38.301 | 1.00 | 22.81 | MTGL |
| ATOM | 425 | OD1 | ASN | 56 | 43.921 | -10.859 | 37.647 | 1.00 | 20.74 | MTGL |
| ATOM | 426 | ND2 | ASN | 56 | 43.359 | -9.926  | 39.611 | 1.00 | 22.17 | MTGL |
| ATOM | 427 | C   | ASN | 56 | 43.751 | -7.108  | 35.612 | 1.00 | 18.30 | MTGL |
| ATOM | 428 | O   | ASN | 56 | 43.972 | -5.968  | 36.016 | 1.00 | 17.82 | MTGL |
| ATOM | 429 | N   | TYR | 57 | 43.108 | -7.376  | 34.480 | 1.00 | 16.29 | MTGL |
| ATOM | 430 | CA  | TYR | 57 | 42.570 | -6.353  | 33.591 | 1.00 | 15.51 | MTGL |
| ATOM | 431 | CB  | TYR | 57 | 41.680 | -5.376  | 34.368 | 1.00 | 15.50 | MTGL |
| ATOM | 432 | CG  | TYR | 57 | 40.756 | -6.062  | 35.348 | 1.00 | 16.25 | MTGL |
| ATOM | 433 | CD1 | TYR | 57 | 39.969 | -7.150  | 34.955 | 1.00 | 15.93 | MTGL |
| ATOM | 434 | CE1 | TYR | 57 | 39.137 | -7.799  | 35.859 | 1.00 | 16.29 | MTGL |
| ATOM | 435 | CD2 | TYR | 57 | 40.681 | -5.642  | 36.671 | 1.00 | 16.32 | MTGL |
| ATOM | 436 | CE2 | TYR | 57 | 39.847 | -6.288  | 37.585 | 1.00 | 17.00 | MTGL |
| ATOM | 437 | CZ  | TYR | 57 | 39.080 | -7.363  | 37.172 | 1.00 | 15.31 | MTGL |
| ATOM | 438 | OH  | TYR | 57 | 38.254 | -8.000  | 38.066 | 1.00 | 15.12 | MTGL |
| ATOM | 439 | C   | TYR | 57 | 43.627 | -5.579  | 32.807 | 1.00 | 15.53 | MTGL |
| ATOM | 440 | O   | TYR | 57 | 43.315 | -4.561  | 32.189 | 1.00 | 14.98 | MTGL |
| ATOM | 441 | N   | ASN | 58 | 44.877 | -6.033  | 32.825 | 1.00 | 14.46 | MTGL |
| ATOM | 442 | CA  | ASN | 58 | 45.876 | -5.327  | 32.032 | 1.00 | 15.65 | MTGL |
| ATOM | 443 | CB  | ASN | 58 | 47.314 | -5.594  | 32.522 | 1.00 | 15.44 | MTGL |
| ATOM | 444 | CG  | ASN | 58 | 47.783 | -7.030  | 32.319 | 1.00 | 16.49 | MTGL |
| ATOM | 445 | OD1 | ASN | 58 | 48.869 | -7.390  | 32.779 | 1.00 | 18.71 | MTGL |
| ATOM | 446 | ND2 | ASN | 58 | 46.995 | -7.844  | 31.640 | 1.00 | 13.70 | MTGL |
| ATOM | 447 | C   | ASN | 58 | 45.660 | -5.763  | 30.582 | 1.00 | 16.00 | MTGL |
| ATOM | 448 | O   | ASN | 58 | 44.774 | -6.579  | 30.317 | 1.00 | 14.12 | MTGL |
| ATOM | 449 | N   | LEU | 59 | 46.447 | -5.235  | 29.649 | 1.00 | 16.39 | MTGL |
| ATOM | 450 | CA  | LEU | 59 | 46.241 | -5.564  | 28.242 | 1.00 | 17.31 | MTGL |
| ATOM | 451 | CB  | LEU | 59 | 47.192 | -4.751  | 27.356 | 1.00 | 17.07 | MTGL |
| ATOM | 452 | CG  | LEU | 59 | 46.797 | -4.743  | 25.874 | 1.00 | 17.21 | MTGL |
| ATOM | 453 | CD1 | LEU | 59 | 45.367 | -4.208  | 25.722 | 1.00 | 16.29 | MTGL |
| ATOM | 454 | CD2 | LEU | 59 | 47.769 | -3.882  | 25.085 | 1.00 | 16.17 | MTGL |
| ATOM | 455 | C   | LEU | 59 | 46.333 | -7.046  | 27.880 | 1.00 | 17.51 | MTGL |
| ATOM | 456 | O   | LEU | 59 | 45.517 | -7.537  | 27.096 | 1.00 | 17.20 | MTGL |
| ATOM | 457 | N   | ASP | 60 | 47.317 | -7.754  | 28.432 | 1.00 | 17.48 | MTGL |
| ATOM | 458 | CA  | ASP | 60 | 47.460 | -9.183  | 28.152 | 1.00 | 18.05 | MTGL |
| ATOM | 459 | CB  | ASP | 60 | 48.700 | -9.768  | 28.837 | 1.00 | 20.82 | MTGL |
| ATOM | 460 | CG  | ASP | 60 | 49.995 | -9.286  | 28.217 | 1.00 | 23.01 | MTGL |
| ATOM | 461 | OD1 | ASP | 60 | 50.012 | -9.009  | 26.999 | 1.00 | 25.11 | MTGL |
| ATOM | 462 | OD2 | ASP | 60 | 51.002 | -9.204  | 28.946 | 1.00 | 25.50 | MTGL |
| ATOM | 463 | C   | ASP | 60 | 46.237 | -9.943  | 28.647 | 1.00 | 17.40 | MTGL |

Fig. 1 cont.

| | | | | | | | | | | |
|---|---|---|---|---|---|---|---|---|---|---|
| ATOM | 464 | O | ASP | 60 | 45.749 | -10.856 | 27.984 | 1.00 | 16.59 | MTGL |
| ATOM | 465 | N | TYR | 61 | 45.756 | -9.573 | 29.827 | 1.00 | 15.42 | MTGL |
| ATOM | 466 | CA | TYR | 61 | 44.580 | -10.215 | 30.398 | 1.00 | 15.67 | MTGL |
| ATOM | 467 | CB | TYR | 61 | 44.266 | -9.581 | 31.759 | 1.00 | 15.24 | MTGL |
| ATOM | 468 | CG | TYR | 61 | 43.000 | -10.071 | 32.427 | 1.00 | 15.21 | MTGL |
| ATOM | 469 | CD1 | TYR | 61 | 41.746 | -9.597 | 32.032 | 1.00 | 15.96 | MTGL |
| ATOM | 470 | CE1 | TYR | 61 | 40.578 | -10.025 | 32.670 | 1.00 | 14.87 | MTGL |
| ATOM | 471 | CD2 | TYR | 61 | 43.058 | -10.990 | 33.473 | 1.00 | 15.54 | MTGL |
| ATOM | 472 | CE2 | TYR | 61 | 41.899 | -11.428 | 34.120 | 1.00 | 14.46 | MTGL |
| ATOM | 473 | CZ | TYR | 61 | 40.662 | -10.943 | 33.714 | 1.00 | 16.75 | MTGL |
| ATOM | 474 | OH | TYR | 61 | 39.511 | -11.379 | 34.345 | 1.00 | 14.25 | MTGL |
| ATOM | 475 | C | TYR | 61 | 43.400 | -10.042 | 29.434 | 1.00 | 15.36 | MTGL |
| ATOM | 476 | O | TYR | 61 | 42.651 | -10.987 | 29.175 | 1.00 | 15.76 | MTGL |
| ATOM | 477 | N | ASN | 62 | 43.257 | -8.834 | 28.897 | 1.00 | 14.42 | MTGL |
| ATOM | 478 | CA | ASN | 62 | 42.174 | -8.509 | 27.971 | 1.00 | 16.00 | MTGL |
| ATOM | 479 | CB | ASN | 62 | 42.072 | -6.990 | 27.811 | 1.00 | 15.99 | MTGL |
| ATOM | 480 | CG | ASN | 62 | 41.231 | -6.354 | 28.895 | 1.00 | 18.27 | MTGL |
| ATOM | 481 | OD1 | ASN | 62 | 39.998 | -6.396 | 28.840 | 1.00 | 18.23 | MTGL |
| ATOM | 482 | ND2 | ASN | 62 | 41.887 | -5.780 | 29.901 | 1.00 | 16.02 | MTGL |
| ATOM | 483 | C | ASN | 62 | 42.306 | -9.172 | 26.600 | 1.00 | 16.04 | MTGL |
| ATOM | 484 | O | ASN | 62 | 41.306 | -9.546 | 25.990 | 1.00 | 15.56 | MTGL |
| ATOM | 485 | N | ILE | 63 | 43.534 | -9.311 | 26.110 | 1.00 | 16.06 | MTGL |
| ATOM | 486 | CA | ILE | 63 | 43.732 | -9.952 | 24.824 | 1.00 | 17.20 | MTGL |
| ATOM | 487 | CB | ILE | 63 | 45.202 | -9.827 | 24.350 | 1.00 | 16.83 | MTGL |
| ATOM | 488 | CG2 | ILE | 63 | 45.481 | -10.814 | 23.214 | 1.00 | 17.67 | MTGL |
| ATOM | 489 | CG1 | ILE | 63 | 45.463 | -8.391 | 23.887 | 1.00 | 17.41 | MTGL |
| ATOM | 490 | CD1 | ILE | 63 | 46.910 | -8.105 | 23.521 | 1.00 | 18.09 | MTGL |
| ATOM | 491 | C | ILE | 63 | 43.333 | -11.420 | 24.945 | 1.00 | 17.68 | MTGL |
| ATOM | 492 | O | ILE | 63 | 42.664 | -11.964 | 24.068 | 1.00 | 18.06 | MTGL |
| ATOM | 493 | N | ALA | 64 | 43.722 | -12.058 | 26.046 | 1.00 | 17.70 | MTGL |
| ATOM | 494 | CA | ALA | 64 | 43.379 | -13.463 | 26.253 | 1.00 | 17.86 | MTGL |
| ATOM | 495 | CB | ALA | 64 | 44.000 | -13.971 | 27.555 | 1.00 | 17.49 | MTGL |
| ATOM | 496 | C | ALA | 64 | 41.860 | -13.703 | 26.262 | 1.00 | 17.48 | MTGL |
| ATOM | 497 | O | ALA | 64 | 41.370 | -14.616 | 25.599 | 1.00 | 17.31 | MTGL |
| ATOM | 498 | N | ILE | 65 | 41.104 | -12.895 | 27.002 | 1.00 | 16.55 | MTGL |
| ATOM | 499 | CA | ILE | 65 | 39.665 | -13.117 | 27.030 | 1.00 | 16.75 | MTGL |
| ATOM | 500 | CB | ILE | 65 | 38.991 | -12.503 | 28.289 | 1.00 | 16.00 | MTGL |
| ATOM | 501 | CG2 | ILE | 65 | 39.574 | -13.130 | 29.536 | 1.00 | 16.34 | MTGL |
| ATOM | 502 | CG1 | ILE | 65 | 39.173 | -10.984 | 28.322 | 1.00 | 18.05 | MTGL |
| ATOM | 503 | CD1 | ILE | 65 | 38.423 | -10.321 | 29.474 | 1.00 | 15.44 | MTGL |
| ATOM | 504 | C | ILE | 65 | 38.989 | -12.598 | 25.760 | 1.00 | 16.71 | MTGL |
| ATOM | 505 | O | ILE | 65 | 37.938 | -13.101 | 25.368 | 1.00 | 16.21 | MTGL |
| ATOM | 506 | N | ALA | 66 | 39.598 | -11.609 | 25.107 | 1.00 | 16.15 | MTGL |
| ATOM | 507 | CA | ALA | 66 | 39.036 | -11.087 | 23.866 | 1.00 | 16.93 | MTGL |
| ATOM | 508 | CB | ALA | 66 | 39.806 | -9.854 | 23.404 | 1.00 | 15.85 | MTGL |
| ATOM | 509 | C | ALA | 66 | 39.106 | -12.185 | 22.802 | 1.00 | 17.72 | MTGL |
| ATOM | 510 | O | ALA | 66 | 38.189 | -12.330 | 21.989 | 1.00 | 16.94 | MTGL |
| ATOM | 511 | N | LYS | 67 | 40.188 | -12.965 | 22.817 | 1.00 | 18.09 | MTGL |
| ATOM | 512 | CA | LYS | 67 | 40.340 | -14.059 | 21.856 | 1.00 | 19.65 | MTGL |
| ATOM | 513 | CB | LYS | 67 | 41.700 | -14.748 | 22.010 | 1.00 | 21.06 | MTGL |
| ATOM | 514 | CG | LYS | 67 | 42.892 | -13.953 | 21.484 | 1.00 | 23.60 | MTGL |
| ATOM | 515 | CD | LYS | 67 | 44.159 | -14.795 | 21.550 | 1.00 | 26.88 | MTGL |
| ATOM | 516 | CE | LYS | 67 | 45.365 | -14.050 | 21.000 | 1.00 | 29.59 | MTGL |
| ATOM | 517 | NZ | LYS | 67 | 45.208 | -13.714 | 19.551 | 1.00 | 32.62 | MTGL |
| ATOM | 518 | C | LYS | 67 | 39.229 | -15.085 | 22.070 | 1.00 | 19.44 | MTGL |
| ATOM | 519 | O | LYS | 67 | 38.667 | -15.616 | 21.109 | 1.00 | 19.17 | MTGL |
| ATOM | 520 | N | ARG | 68 | 38.921 | -15.365 | 23.335 | 1.00 | 18.94 | MTGL |
| ATOM | 521 | CA | ARG | 68 | 37.866 | -16.317 | 23.672 | 1.00 | 17.61 | MTGL |

Fig. 1 cont.

| | | | | | | | | | |
|---|---|---|---|---|---|---|---|---|---|
| ATOM | 522 | CB | ARG | 68 | 37.834 | -16.567 | 25.181 | 1.00 16.99 | MTGL |
| ATOM | 523 | CG | ARG | 68 | 38.950 | -17.488 | 25.679 | 1.00 18.79 | MTGL |
| ATOM | 524 | CD | ARG | 68 | 39.015 | -17.515 | 27.199 | 1.00 17.89 | MTGL |
| ATOM | 525 | NE | ARG | 68 | 37.742 | -17.892 | 27.809 | 1.00 18.08 | MTGL |
| ATOM | 526 | CZ | ARG | 68 | 37.555 | -18.020 | 29.120 | 1.00 18.59 | MTGL |
| ATOM | 527 | NH1 | ARG | 68 | 38.561 | -17.798 | 29.961 | 1.00 18.68 | MTGL |
| ATOM | 528 | NH2 | ARG | 68 | 36.371 | -18.381 | 29.595 | 1.00 16.96 | MTGL |
| ATOM | 529 | C | ARG | 68 | 36.511 | -15.799 | 23.209 | 1.00 17.25 | MTGL |
| ATOM | 530 | O | ARG | 68 | 35.679 | -16.563 | 22.711 | 1.00 15.99 | MTGL |
| ATOM | 531 | N | ALA | 69 | 36.285 | -14.503 | 23.395 | 1.00 16.95 | MTGL |
| ATOM | 532 | CA | ALA | 69 | 35.030 | -13.886 | 22.982 | 1.00 18.21 | MTGL |
| ATOM | 533 | CB | ALA | 69 | 35.001 | -12.411 | 23.393 | 1.00 18.02 | MTGL |
| ATOM | 534 | C | ALA | 69 | 34.907 | -14.012 | 21.465 | 1.00 18.17 | MTGL |
| ATOM | 535 | O | ALA | 69 | 33.867 | -14.407 | 20.945 | 1.00 16.83 | MTGL |
| ATOM | 536 | N | LYS | 70 | 35.984 | -13.675 | 20.764 | 1.00 18.35 | MTGL |
| ATOM | 537 | CA | LYS | 70 | 36.011 | -13.764 | 19.312 | 1.00 19.84 | MTGL |
| ATOM | 538 | CB | LYS | 70 | 37.402 | -13.390 | 18.795 | 1.00 19.40 | MTGL |
| ATOM | 539 | CG | LYS | 70 | 37.548 | -13.420 | 17.284 | 1.00 21.56 | MTGL |
| ATOM | 540 | CD | LYS | 70 | 38.992 | -13.123 | 16.892 | 1.00 22.53 | MTGL |
| ATOM | 541 | CE | LYS | 70 | 39.180 | -13.123 | 15.383 | 1.00 23.66 | MTGL |
| ATOM | 542 | NZ | LYS | 70 | 40.592 | -12.852 | 15.015 | 1.00 21.95 | MTGL |
| ATOM | 543 | C | LYS | 70 | 35.648 | -15.186 | 18.861 | 1.00 20.29 | MTGL |
| ATOM | 544 | O | LYS | 70 | 34.842 | -15.365 | 17.948 | 1.00 19.93 | MTGL |
| ATOM | 545 | N | ALA | 71 | 36.235 | -16.190 | 19.511 | 1.00 19.37 | MTGL |
| ATOM | 546 | CA | ALA | 71 | 35.970 | -17.585 | 19.159 | 1.00 20.95 | MTGL |
| ATOM | 547 | CB | ALA | 71 | 36.896 | -18.514 | 19.941 | 1.00 20.90 | MTGL |
| ATOM | 548 | C | ALA | 71 | 34.514 | -17.975 | 19.405 | 1.00 21.38 | MTGL |
| ATOM | 549 | O | ALA | 71 | 34.010 | -18.929 | 18.810 | 1.00 22.34 | MTGL |
| ATOM | 550 | N | ALA | 72 | 33.839 | -17.244 | 20.282 | 1.00 20.63 | MTGL |
| ATOM | 551 | CA | ALA | 72 | 32.439 | -17.529 | 20.574 | 1.00 20.92 | MTGL |
| ATOM | 552 | CB | ALA | 72 | 32.149 | -17.284 | 22.050 | 1.00 20.20 | MTGL |
| ATOM | 553 | C | ALA | 72 | 31.523 | -16.659 | 19.710 | 1.00 20.68 | MTGL |
| ATOM | 554 | O | ALA | 72 | 30.305 | -16.644 | 19.899 | 1.00 20.23 | MTGL |
| ATOM | 555 | N | GLY | 73 | 32.116 | -15.934 | 18.768 | 1.00 20.42 | MTGL |
| ATOM | 556 | CA | GLY | 73 | 31.339 | -15.077 | 17.889 | 1.00 20.87 | MTGL |
| ATOM | 557 | C | GLY | 73 | 30.874 | -13.774 | 18.523 | 1.00 21.42 | MTGL |
| ATOM | 558 | O | GLY | 73 | 29.946 | -13.133 | 18.027 | 1.00 21.96 | MTGL |
| ATOM | 559 | N | LEU | 74 | 31.522 | -13.373 | 19.612 | 1.00 20.70 | MTGL |
| ATOM | 560 | CA | LEU | 74 | 31.160 | -12.146 | 20.315 | 1.00 19.98 | MTGL |
| ATOM | 561 | CB | LEU | 74 | 31.221 | -12.372 | 21.830 | 1.00 19.61 | MTGL |
| ATOM | 562 | CG | LEU | 74 | 30.359 | -13.491 | 22.420 | 1.00 19.97 | MTGL |
| ATOM | 563 | CD1 | LEU | 74 | 30.692 | -13.659 | 23.898 | 1.00 19.32 | MTGL |
| ATOM | 564 | CD2 | LEU | 74 | 28.881 | -13.162 | 22.232 | 1.00 18.79 | MTGL |
| ATOM | 565 | C | LEU | 74 | 32.071 | -10.978 | 19.960 | 1.00 19.91 | MTGL |
| ATOM | 566 | O | LEU | 74 | 33.292 | -11.133 | 19.882 | 1.00 20.26 | MTGL |
| ATOM | 567 | N | GLY | 75 | 31.473 | -9.809 | 19.740 | 1.00 19.06 | MTGL |
| ATOM | 568 | CA | GLY | 75 | 32.261 | -8.627 | 19.438 | 1.00 18.36 | MTGL |
| ATOM | 569 | C | GLY | 75 | 32.856 | -8.106 | 20.738 | 1.00 17.17 | MTGL |
| ATOM | 570 | O | GLY | 75 | 32.380 | -8.457 | 21.821 | 1.00 16.83 | MTGL |
| ATOM | 571 | N | VAL | 76 | 33.885 | -7.271 | 20.648 | 1.00 16.99 | MTGL |
| ATOM | 572 | CA | VAL | 76 | 34.522 | -6.748 | 21.853 | 1.00 17.15 | MTGL |
| ATOM | 573 | CB | VAL | 76 | 35.996 | -7.202 | 21.947 | 1.00 18.28 | MTGL |
| ATOM | 574 | CG1 | VAL | 76 | 36.626 | -6.682 | 23.238 | 1.00 17.92 | MTGL |
| ATOM | 575 | CG2 | VAL | 76 | 36.074 | -8.726 | 21.896 | 1.00 17.32 | MTGL |
| ATOM | 576 | C | VAL | 76 | 34.476 | -5.231 | 21.984 | 1.00 17.67 | MTGL |
| ATOM | 577 | O | VAL | 76 | 34.770 | -4.491 | 21.039 | 1.00 18.33 | MTGL |
| ATOM | 578 | N | TYR | 77 | 34.108 | -4.785 | 23.177 | 1.00 16.77 | MTGL |
| ATOM | 579 | CA | TYR | 77 | 34.013 | -3.366 | 23.517 | 1.00 16.63 | MTGL |

Fig. 1 cont.

| ATOM | 580 | CB  | TYR | 77 | 32.608 | -3.102 | 24.097 | 1.00 | 15.27 | MTGL |
|------|-----|-----|-----|----|--------|--------|--------|------|-------|------|
| ATOM | 581 | CG  | TYR | 77 | 32.335 | -1.799 | 24.840 | 1.00 | 15.55 | MTGL |
| ATOM | 582 | CD1 | TYR | 77 | 33.343 | -0.886 | 25.149 | 1.00 | 15.39 | MTGL |
| ATOM | 583 | CE1 | TYR | 77 | 33.068 | 0.257  | 25.925 | 1.00 | 16.48 | MTGL |
| ATOM | 584 | CD2 | TYR | 77 | 31.046 | -1.532 | 25.312 | 1.00 | 16.02 | MTGL |
| ATOM | 585 | CE2 | TYR | 77 | 30.766 | -0.414 | 26.075 | 1.00 | 15.87 | MTGL |
| ATOM | 586 | CZ  | TYR | 77 | 31.772 | 0.475  | 26.386 | 1.00 | 16.20 | MTGL |
| ATOM | 587 | OH  | TYR | 77 | 31.471 | 1.541  | 27.200 | 1.00 | 15.93 | MTGL |
| ATOM | 588 | C   | TYR | 77 | 35.114 | -3.128 | 24.548 | 1.00 | 16.00 | MTGL |
| ATOM | 589 | O   | TYR | 77 | 35.026 | -3.604 | 25.683 | 1.00 | 16.53 | MTGL |
| ATOM | 590 | N   | ILE | 78 | 36.163 | -2.419 | 24.142 | 1.00 | 16.29 | MTGL |
| ATOM | 591 | CA  | ILE | 78 | 37.280 | -2.121 | 25.044 | 1.00 | 17.09 | MTGL |
| ATOM | 592 | CB  | ILE | 78 | 38.611 | -2.008 | 24.261 | 1.00 | 17.14 | MTGL |
| ATOM | 593 | CG2 | ILE | 78 | 39.695 | -1.387 | 25.140 | 1.00 | 16.04 | MTGL |
| ATOM | 594 | CG1 | ILE | 78 | 39.049 | -3.394 | 23.777 | 1.00 | 16.84 | MTGL |
| ATOM | 595 | CD1 | ILE | 78 | 39.424 | -4.364 | 24.905 | 1.00 | 17.38 | MTGL |
| ATOM | 596 | C   | ILE | 78 | 37.031 | -0.818 | 25.818 | 1.00 | 17.27 | MTGL |
| ATOM | 597 | O   | ILE | 78 | 36.834 | 0.241  | 25.227 | 1.00 | 17.22 | MTGL |
| ATOM | 598 | N   | ASP | 79 | 37.046 | -0.912 | 27.142 | 1.00 | 16.43 | MTGL |
| ATOM | 599 | CA  | ASP | 79 | 36.817 | 0.234  | 28.009 | 1.00 | 16.05 | MTGL |
| ATOM | 600 | CB  | ASP | 79 | 35.738 | -0.127 | 29.039 | 1.00 | 17.34 | MTGL |
| ATOM | 601 | CG  | ASP | 79 | 35.577 | 0.920  | 30.133 | 1.00 | 19.18 | MTGL |
| ATOM | 602 | OD1 | ASP | 79 | 36.023 | 2.072  | 29.952 | 1.00 | 19.88 | MTGL |
| ATOM | 603 | OD2 | ASP | 79 | 34.986 | 0.583  | 31.181 | 1.00 | 20.19 | MTGL |
| ATOM | 604 | C   | ASP | 79 | 38.113 | 0.657  | 28.699 | 1.00 | 16.01 | MTGL |
| ATOM | 605 | O   | ASP | 79 | 38.479 | 0.102  | 29.732 | 1.00 | 15.54 | MTGL |
| ATOM | 606 | N   | PHE | 80 | 38.810 | 1.626  | 28.105 | 1.00 | 15.57 | MTGL |
| ATOM | 607 | CA  | PHE | 80 | 40.065 | 2.138  | 28.654 | 1.00 | 15.49 | MTGL |
| ATOM | 608 | CB  | PHE | 80 | 40.811 | 3.005  | 27.627 | 1.00 | 14.72 | MTGL |
| ATOM | 609 | CG  | PHE | 80 | 41.533 | 2.230  | 26.566 | 1.00 | 14.70 | MTGL |
| ATOM | 610 | CD1 | PHE | 80 | 42.548 | 1.343  | 26.899 | 1.00 | 14.82 | MTGL |
| ATOM | 611 | CD2 | PHE | 80 | 41.224 | 2.419  | 25.222 | 1.00 | 15.80 | MTGL |
| ATOM | 612 | CE1 | PHE | 80 | 43.251 | 0.649  | 25.912 | 1.00 | 15.54 | MTGL |
| ATOM | 613 | CE2 | PHE | 80 | 41.921 | 1.730  | 24.221 | 1.00 | 16.06 | MTGL |
| ATOM | 614 | CZ  | PHE | 80 | 42.938 | 0.844  | 24.568 | 1.00 | 14.92 | MTGL |
| ATOM | 615 | C   | PHE | 80 | 39.800 | 3.009  | 29.869 | 1.00 | 16.16 | MTGL |
| ATOM | 616 | O   | PHE | 80 | 39.126 | 4.036  | 29.759 | 1.00 | 15.79 | MTGL |
| ATOM | 617 | N   | HIS | 81 | 40.328 | 2.617  | 31.025 | 1.00 | 15.76 | MTGL |
| ATOM | 618 | CA  | HIS | 81 | 40.140 | 3.419  | 32.234 | 1.00 | 15.04 | MTGL |
| ATOM | 619 | CB  | HIS | 81 | 40.130 | 2.533  | 33.485 | 1.00 | 13.87 | MTGL |
| ATOM | 620 | CG  | HIS | 81 | 38.846 | 1.790  | 33.686 | 1.00 | 14.70 | MTGL |
| ATOM | 621 | CD2 | HIS | 81 | 37.971 | 1.263  | 32.795 | 1.00 | 13.78 | MTGL |
| ATOM | 622 | ND1 | HIS | 81 | 38.312 | 1.554  | 34.933 | 1.00 | 13.45 | MTGL |
| ATOM | 623 | CE1 | HIS | 81 | 37.161 | 0.918  | 34.804 | 1.00 | 15.90 | MTGL |
| ATOM | 624 | NE2 | HIS | 81 | 36.931 | 0.730  | 33.516 | 1.00 | 14.78 | MTGL |
| ATOM | 625 | C   | HIS | 81 | 41.244 | 4.466  | 32.357 | 1.00 | 15.46 | MTGL |
| ATOM | 626 | O   | HIS | 81 | 41.113 | 5.439  | 33.102 | 1.00 | 14.94 | MTGL |
| ATOM | 627 | N   | TYR | 82 | 42.326 | 4.273  | 31.609 | 1.00 | 15.09 | MTGL |
| ATOM | 628 | CA  | TYR | 82 | 43.452 | 5.199  | 31.663 | 1.00 | 16.48 | MTGL |
| ATOM | 629 | CB  | TYR | 82 | 43.092 | 6.520  | 30.974 | 1.00 | 15.74 | MTGL |
| ATOM | 630 | CG  | TYR | 82 | 42.849 | 6.384  | 29.476 | 1.00 | 15.85 | MTGL |
| ATOM | 631 | CD1 | TYR | 82 | 43.702 | 5.615  | 28.680 | 1.00 | 15.30 | MTGL |
| ATOM | 632 | CE1 | TYR | 82 | 43.527 | 5.530  | 27.307 | 1.00 | 16.13 | MTGL |
| ATOM | 633 | CD2 | TYR | 82 | 41.801 | 7.062  | 28.852 | 1.00 | 15.60 | MTGL |
| ATOM | 634 | CE2 | TYR | 82 | 41.613 | 6.985  | 27.465 | 1.00 | 16.11 | MTGL |
| ATOM | 635 | CZ  | TYR | 82 | 42.482 | 6.218  | 26.705 | 1.00 | 17.06 | MTGL |
| ATOM | 636 | OH  | TYR | 82 | 42.331 | 6.148  | 25.345 | 1.00 | 18.86 | MTGL |
| ATOM | 637 | C   | TYR | 82 | 43.866 | 5.437  | 33.122 | 1.00 | 17.11 | MTGL |

Fig. 1 cont.

| | | | | | | | | | | |
|---|---|---|---|---|---|---|---|---|---|---|
| ATOM | 638 | O | TYR | 82 | 43.987 | 6.573 | 33.593 | 1.00 | 17.37 | MTGL |
| ATOM | 639 | N | SER | 83 | 44.077 | 4.329 | 33.822 | 1.00 | 17.17 | MTGL |
| ATOM | 640 | CA | SER | 83 | 44.482 | 4.328 | 35.223 | 1.00 | 17.21 | MTGL |
| ATOM | 641 | CB | SER | 83 | 43.288 | 4.679 | 36.115 | 1.00 | 16.41 | MTGL |
| ATOM | 642 | OG | SER | 83 | 43.639 | 4.651 | 37.487 | 1.00 | 16.64 | MTGL |
| ATOM | 643 | C | SER | 83 | 44.948 | 2.904 | 35.518 | 1.00 | 17.88 | MTGL |
| ATOM | 644 | O | SER | 83 | 44.689 | 1.993 | 34.732 | 1.00 | 17.59 | MTGL |
| ATOM | 645 | N | ASP | 84 | 45.646 | 2.706 | 36.630 | 1.00 | 18.00 | MTGL |
| ATOM | 646 | CA | ASP | 84 | 46.106 | 1.369 | 36.984 | 1.00 | 17.91 | MTGL |
| ATOM | 647 | CB | ASP | 84 | 47.378 | 1.415 | 37.840 | 1.00 | 18.31 | MTGL |
| ATOM | 648 | CG | ASP | 84 | 48.570 | 1.993 | 37.105 | 1.00 | 19.40 | MTGL |
| ATOM | 649 | OD1 | ASP | 84 | 48.732 | 1.724 | 35.897 | 1.00 | 18.50 | MTGL |
| ATOM | 650 | OD2 | ASP | 84 | 49.366 | 2.705 | 37.750 | 1.00 | 20.89 | MTGL |
| ATOM | 651 | C | ASP | 84 | 45.017 | 0.665 | 37.785 | 1.00 | 17.16 | MTGL |
| ATOM | 652 | O | ASP | 84 | 45.118 | -0.525 | 38.061 | 1.00 | 16.64 | MTGL |
| ATOM | 653 | N | THR | 85 | 43.978 | 1.406 | 38.152 | 1.00 | 16.98 | MTGL |
| ATOM | 654 | CA | THR | 85 | 42.889 | 0.837 | 38.943 | 1.00 | 17.09 | MTGL |
| ATOM | 655 | CB | THR | 85 | 43.169 | 1.056 | 40.456 | 1.00 | 17.53 | MTGL |
| ATOM | 656 | OG1 | THR | 85 | 42.211 | 0.337 | 41.239 | 1.00 | 20.04 | MTGL |
| ATOM | 657 | CG2 | THR | 85 | 43.107 | 2.549 | 40.805 | 1.00 | 16.84 | MTGL |
| ATOM | 658 | C | THR | 85 | 41.543 | 1.460 | 38.546 | 1.00 | 16.53 | MTGL |
| ATOM | 659 | O | THR | 85 | 41.481 | 2.245 | 37.598 | 1.00 | 16.58 | MTGL |
| ATOM | 660 | N | TRP | 86 | 40.477 | 1.100 | 39.264 | 1.00 | 15.91 | MTGL |
| ATOM | 661 | CA | TRP | 86 | 39.130 | 1.597 | 38.982 | 1.00 | 16.71 | MTGL |
| ATOM | 662 | CB | TRP | 86 | 38.166 | 1.291 | 40.143 | 1.00 | 15.33 | MTGL |
| ATOM | 663 | CG | TRP | 86 | 38.079 | -0.151 | 40.525 | 1.00 | 17.03 | MTGL |
| ATOM | 664 | CD2 | TRP | 86 | 37.311 | -1.165 | 39.871 | 1.00 | 16.85 | MTGL |
| ATOM | 665 | CE2 | TRP | 86 | 37.548 | -2.378 | 40.560 | 1.00 | 17.49 | MTGL |
| ATOM | 666 | CE3 | TRP | 86 | 36.448 | -1.170 | 38.767 | 1.00 | 16.06 | MTGL |
| ATOM | 667 | CD1 | TRP | 86 | 38.731 | -0.768 | 41.555 | 1.00 | 16.85 | MTGL |
| ATOM | 668 | NE1 | TRP | 86 | 38.417 | -2.104 | 41.583 | 1.00 | 17.28 | MTGL |
| ATOM | 669 | CZ2 | TRP | 86 | 36.951 | -3.588 | 40.180 | 1.00 | 16.23 | MTGL |
| ATOM | 670 | CZ3 | TRP | 86 | 35.853 | -2.373 | 38.388 | 1.00 | 17.14 | MTGL |
| ATOM | 671 | CH2 | TRP | 86 | 36.110 | -3.566 | 39.095 | 1.00 | 17.46 | MTGL |
| ATOM | 672 | C | TRP | 86 | 39.044 | 3.093 | 38.703 | 1.00 | 16.71 | MTGL |
| ATOM | 673 | O | TRP | 86 | 39.500 | 3.911 | 39.500 | 1.00 | 16.21 | MTGL |
| ATOM | 674 | N | ALA | 87 | 38.440 | 3.443 | 37.574 | 1.00 | 16.31 | MTGL |
| ATOM | 675 | CA | ALA | 87 | 38.249 | 4.845 | 37.223 | 1.00 | 17.57 | MTGL |
| ATOM | 676 | CB | ALA | 87 | 38.760 | 5.124 | 35.809 | 1.00 | 16.32 | MTGL |
| ATOM | 677 | C | ALA | 87 | 36.753 | 5.119 | 37.297 | 1.00 | 18.11 | MTGL |
| ATOM | 678 | O | ALA | 87 | 35.965 | 4.409 | 36.677 | 1.00 | 18.07 | MTGL |
| ATOM | 679 | N | ASP | 88 | 36.368 | 6.125 | 38.077 | 1.00 | 18.47 | MTGL |
| ATOM | 680 | CA | ASP | 88 | 34.965 | 6.512 | 38.213 | 1.00 | 18.85 | MTGL |
| ATOM | 681 | CB | ASP | 88 | 34.287 | 5.730 | 39.354 | 1.00 | 18.63 | MTGL |
| ATOM | 682 | CG | ASP | 88 | 35.047 | 5.816 | 40.661 | 1.00 | 19.12 | MTGL |
| ATOM | 683 | OD1 | ASP | 88 | 35.352 | 6.940 | 41.109 | 1.00 | 18.34 | MTGL |
| ATOM | 684 | OD2 | ASP | 88 | 35.331 | 4.749 | 41.248 | 1.00 | 19.72 | MTGL |
| ATOM | 685 | C | ASP | 88 | 34.932 | 8.021 | 38.460 | 1.00 | 18.13 | MTGL |
| ATOM | 686 | O | ASP | 88 | 35.980 | 8.656 | 38.505 | 1.00 | 17.65 | MTGL |
| ATOM | 687 | N | PRO | 89 | 33.737 | 8.616 | 38.615 | 1.00 | 18.93 | MTGL |
| ATOM | 688 | CD | PRO | 89 | 32.382 | 8.046 | 38.501 | 1.00 | 19.94 | MTGL |
| ATOM | 689 | CA | PRO | 89 | 33.672 | 10.066 | 38.842 | 1.00 | 19.49 | MTGL |
| ATOM | 690 | CB | PRO | 89 | 32.174 | 10.327 | 39.000 | 1.00 | 19.80 | MTGL |
| ATOM | 691 | CG | PRO | 89 | 31.555 | 9.263 | 38.125 | 1.00 | 19.69 | MTGL |
| ATOM | 692 | C | PRO | 89 | 34.476 | 10.600 | 40.025 | 1.00 | 19.90 | MTGL |
| ATOM | 693 | O | PRO | 89 | 34.833 | 11.778 | 40.048 | 1.00 | 20.62 | MTGL |
| ATOM | 694 | N | ALA | 90 | 34.760 | 9.743 | 40.999 | 1.00 | 18.70 | MTGL |
| ATOM | 695 | CA | ALA | 90 | 35.519 | 10.164 | 42.175 | 1.00 | 19.35 | MTGL |

Fig. 1 cont.

| ATOM | 696 | CB  | ALA | 90 | 34.818 | 9.685  | 43.457 | 1.00 | 17.48 | MTGL |
| ATOM | 697 | C   | ALA | 90 | 36.964 | 9.674  | 42.162 | 1.00 | 18.63 | MTGL |
| ATOM | 698 | O   | ALA | 90 | 37.730 | 9.988  | 43.071 | 1.00 | 19.58 | MTGL |
| ATOM | 699 | N   | HIS | 91 | 37.333 | 8.901  | 41.145 | 1.00 | 17.84 | MTGL |
| ATOM | 700 | CA  | HIS | 91 | 38.698 | 8.391  | 41.039 | 1.00 | 17.68 | MTGL |
| ATOM | 701 | CB  | HIS | 91 | 38.833 | 7.000  | 41.679 | 1.00 | 18.34 | MTGL |
| ATOM | 702 | CG  | HIS | 91 | 38.298 | 6.910  | 43.072 | 1.00 | 20.31 | MTGL |
| ATOM | 703 | CD2 | HIS | 91 | 38.927 | 6.936  | 44.272 | 1.00 | 19.87 | MTGL |
| ATOM | 704 | ND1 | HIS | 91 | 36.953 | 6.784  | 43.344 | 1.00 | 18.50 | MTGL |
| ATOM | 705 | CE1 | HIS | 91 | 36.775 | 6.736  | 44.653 | 1.00 | 20.43 | MTGL |
| ATOM | 706 | NE2 | HIS | 91 | 37.956 | 6.826  | 45.238 | 1.00 | 21.64 | MTGL |
| ATOM | 707 | C   | HIS | 91 | 39.177 | 8.280  | 39.597 | 1.00 | 16.55 | MTGL |
| ATOM | 708 | O   | HIS | 91 | 38.661 | 7.478  | 38.823 | 1.00 | 16.39 | MTGL |
| ATOM | 709 | N   | GLN | 92 | 40.169 | 9.087  | 39.246 | 1.00 | 15.52 | MTGL |
| ATOM | 710 | CA  | GLN | 92 | 40.760 | 9.064  | 37.911 | 1.00 | 15.68 | MTGL |
| ATOM | 711 | CB  | GLN | 92 | 40.281 | 10.255 | 37.072 | 1.00 | 14.49 | MTGL |
| ATOM | 712 | CG  | GLN | 92 | 38.786 | 10.229 | 36.702 | 1.00 | 13.93 | MTGL |
| ATOM | 713 | CD  | GLN | 92 | 38.413 | 9.127  | 35.699 | 1.00 | 14.84 | MTGL |
| ATOM | 714 | OE1 | GLN | 92 | 39.173 | 8.814  | 34.779 | 1.00 | 15.41 | MTGL |
| ATOM | 715 | NE2 | GLN | 92 | 37.221 | 8.559  | 35.861 | 1.00 | 14.23 | MTGL |
| ATOM | 716 | C   | GLN | 92 | 42.254 | 9.166  | 38.190 | 1.00 | 15.81 | MTGL |
| ATOM | 717 | O   | GLN | 92 | 42.925 | 10.108 | 37.782 | 1.00 | 16.26 | MTGL |
| ATOM | 718 | N   | THR | 93 | 42.759 | 8.169  | 38.902 | 1.00 | 16.47 | MTGL |
| ATOM | 719 | CA  | THR | 93 | 44.156 | 8.136  | 39.302 | 1.00 | 17.33 | MTGL |
| ATOM | 720 | CB  | THR | 93 | 44.387 | 7.062  | 40.364 | 1.00 | 17.41 | MTGL |
| ATOM | 721 | OG1 | THR | 93 | 43.433 | 7.239  | 41.417 | 1.00 | 19.90 | MTGL |
| ATOM | 722 | CG2 | THR | 93 | 45.800 | 7.177  | 40.944 | 1.00 | 19.68 | MTGL |
| ATOM | 723 | C   | THR | 93 | 45.136 | 7.925  | 38.165 | 1.00 | 17.55 | MTGL |
| ATOM | 724 | O   | THR | 93 | 45.035 | 6.973  | 37.390 | 1.00 | 17.01 | MTGL |
| ATOM | 725 | N   | MET | 94 | 46.093 | 8.839  | 38.089 | 1.00 | 17.63 | MTGL |
| ATOM | 726 | CA  | MET | 94 | 47.131 | 8.820  | 37.079 | 1.00 | 18.68 | MTGL |
| ATOM | 727 | CB  | MET | 94 | 48.144 | 9.926  | 37.383 | 1.00 | 21.10 | MTGL |
| ATOM | 728 | CG  | MET | 94 | 49.195 | 10.133 | 36.315 | 1.00 | 23.55 | MTGL |
| ATOM | 729 | SD  | MET | 94 | 48.474 | 10.956 | 34.894 | 1.00 | 27.41 | MTGL |
| ATOM | 730 | CE  | MET | 94 | 48.342 | 12.657 | 35.533 | 1.00 | 25.13 | MTGL |
| ATOM | 731 | C   | MET | 94 | 47.854 | 7.476  | 37.064 | 1.00 | 18.43 | MTGL |
| ATOM | 732 | O   | MET | 94 | 48.179 | 6.925  | 38.113 | 1.00 | 18.13 | MTGL |
| ATOM | 733 | N   | PRO | 95 | 48.088 | 6.914  | 35.871 | 1.00 | 17.41 | MTGL |
| ATOM | 734 | CD  | PRO | 95 | 47.534 | 7.255  | 34.551 | 1.00 | 16.67 | MTGL |
| ATOM | 735 | CA  | PRO | 95 | 48.797 | 5.631  | 35.834 | 1.00 | 17.83 | MTGL |
| ATOM | 736 | CB  | PRO | 95 | 48.814 | 5.287  | 34.347 | 1.00 | 17.25 | MTGL |
| ATOM | 737 | CG  | PRO | 95 | 47.544 | 5.914  | 33.843 | 1.00 | 17.35 | MTGL |
| ATOM | 738 | C   | PRO | 95 | 50.202 | 5.903  | 36.371 | 1.00 | 18.71 | MTGL |
| ATOM | 739 | O   | PRO | 95 | 50.784 | 6.952  | 36.084 | 1.00 | 17.30 | MTGL |
| ATOM | 740 | N   | ALA | 96 | 50.746 | 4.978  | 37.152 | 1.00 | 18.59 | MTGL |
| ATOM | 741 | CA  | ALA | 96 | 52.082 | 5.177  | 37.705 | 1.00 | 20.01 | MTGL |
| ATOM | 742 | CB  | ALA | 96 | 52.470 | 3.983  | 38.587 | 1.00 | 19.66 | MTGL |
| ATOM | 743 | C   | ALA | 96 | 53.095 | 5.357  | 36.577 | 1.00 | 20.37 | MTGL |
| ATOM | 744 | O   | ALA | 96 | 53.081 | 4.617  | 35.595 | 1.00 | 20.80 | MTGL |
| ATOM | 745 | N   | GLY | 97 | 53.959 | 6.356  | 36.710 | 1.00 | 20.53 | MTGL |
| ATOM | 746 | CA  | GLY | 97 | 54.967 | 6.595  | 35.693 | 1.00 | 20.43 | MTGL |
| ATOM | 747 | C   | GLY | 97 | 54.611 | 7.644  | 34.654 | 1.00 | 20.83 | MTGL |
| ATOM | 748 | O   | GLY | 97 | 55.491 | 8.144  | 33.959 | 1.00 | 22.30 | MTGL |
| ATOM | 749 | N   | TRP | 98 | 53.332 | 7.982  | 34.537 | 1.00 | 20.23 | MTGL |
| ATOM | 750 | CA  | TRP | 98 | 52.902 | 8.978  | 33.561 | 1.00 | 19.86 | MTGL |
| ATOM | 751 | CB  | TRP | 98 | 51.415 | 8.795  | 33.249 | 1.00 | 18.17 | MTGL |
| ATOM | 752 | CG  | TRP | 98 | 51.106 | 7.576  | 32.421 | 1.00 | 17.34 | MTGL |
| ATOM | 753 | CD2 | TRP | 98 | 49.987 | 7.397  | 31.543 | 1.00 | 16.19 | MTGL |

Fig. 1 cont.

| | | | | | | | | | |
|---|---|---|---|---|---|---|---|---|---|
| ATOM | 754 | CE2 | TRP | 98 | 50.082 | 6.093 | 31.006 | 1.00 16.95 | MTGL |
| ATOM | 755 | CE3 | TRP | 98 | 48.914 | 8.213 | 31.156 | 1.00 15.48 | MTGL |
| ATOM | 756 | CD1 | TRP | 98 | 51.810 | 6.406 | 32.385 | 1.00 18.21 | MTGL |
| ATOM | 757 | NE1 | TRP | 98 | 51.202 | 5.511 | 31.538 | 1.00 17.45 | MTGL |
| ATOM | 758 | CZ2 | TRP | 98 | 49.140 | 5.580 | 30.103 | 1.00 17.12 | MTGL |
| ATOM | 759 | CZ3 | TRP | 98 | 47.974 | 7.704 | 30.257 | 1.00 15.71 | MTGL |
| ATOM | 760 | CH2 | TRP | 98 | 48.098 | 6.399 | 29.740 | 1.00 16.54 | MTGL |
| ATOM | 761 | C | TRP | 98 | 53.156 | 10.401 | 34.056 | 1.00 20.28 | MTGL |
| ATOM | 762 | O | TRP | 98 | 52.958 | 10.706 | 35.230 | 1.00 19.92 | MTGL |
| ATOM | 763 | N | PRO | 99 | 53.593 | 11.295 | 33.156 | 1.00 21.71 | MTGL |
| ATOM | 764 | CD | PRO | 99 | 53.852 | 11.048 | 31.725 | 1.00 22.15 | MTGL |
| ATOM | 765 | CA | PRO | 99 | 53.875 | 12.693 | 33.505 | 1.00 22.69 | MTGL |
| ATOM | 766 | CB | PRO | 99 | 54.610 | 13.205 | 32.269 | 1.00 22.58 | MTGL |
| ATOM | 767 | CG | PRO | 99 | 53.938 | 12.454 | 31.163 | 1.00 22.80 | MTGL |
| ATOM | 768 | C | PRO | 99 | 52.598 | 13.483 | 33.797 | 1.00 23.10 | MTGL |
| ATOM | 769 | O | PRO | 99 | 51.530 | 13.156 | 33.277 | 1.00 23.44 | MTGL |
| ATOM | 770 | N | SER | 100 | 52.716 | 14.522 | 34.621 | 1.00 22.96 | MTGL |
| ATOM | 771 | CA | SER | 100 | 51.572 | 15.353 | 34.995 | 1.00 23.06 | MTGL |
| ATOM | 772 | CB | SER | 100 | 51.714 | 15.831 | 36.445 | 1.00 24.32 | MTGL |
| ATOM | 773 | OG | SER | 100 | 51.658 | 14.746 | 37.353 | 1.00 26.38 | MTGL |
| ATOM | 774 | C | SER | 100 | 51.332 | 16.574 | 34.115 | 1.00 22.44 | MTGL |
| ATOM | 775 | O | SER | 100 | 50.202 | 17.051 | 34.032 | 1.00 22.25 | MTGL |
| ATOM | 776 | N | ASP | 101 | 52.379 | 17.098 | 33.480 | 1.00 22.38 | MTGL |
| ATOM | 777 | CA | ASP | 101 | 52.208 | 18.283 | 32.639 | 1.00 23.28 | MTGL |
| ATOM | 778 | CB | ASP | 101 | 53.565 | 18.890 | 32.254 | 1.00 24.51 | MTGL |
| ATOM | 779 | CG | ASP | 101 | 54.382 | 17.986 | 31.352 | 1.00 25.84 | MTGL |
| ATOM | 780 | OD1 | ASP | 101 | 54.886 | 16.954 | 31.842 | 1.00 26.46 | MTGL |
| ATOM | 781 | OD2 | ASP | 101 | 54.515 | 18.310 | 30.152 | 1.00 25.84 | MTGL |
| ATOM | 782 | C | ASP | 101 | 51.411 | 17.933 | 31.386 | 1.00 22.28 | MTGL |
| ATOM | 783 | O | ASP | 101 | 51.667 | 16.915 | 30.743 | 1.00 21.59 | MTGL |
| ATOM | 784 | N | ILE | 102 | 50.452 | 18.787 | 31.042 | 1.00 21.77 | MTGL |
| ATOM | 785 | CA | ILE | 102 | 49.584 | 18.548 | 29.890 | 1.00 21.42 | MTGL |
| ATOM | 786 | CB | ILE | 102 | 48.623 | 19.738 | 29.663 | 1.00 20.48 | MTGL |
| ATOM | 787 | CG2 | ILE | 102 | 49.411 | 20.998 | 29.313 | 1.00 20.99 | MTGL |
| ATOM | 788 | CG1 | ILE | 102 | 47.617 | 19.392 | 28.560 | 1.00 21.44 | MTGL |
| ATOM | 789 | CD1 | ILE | 102 | 46.730 | 18.200 | 28.879 | 1.00 19.62 | MTGL |
| ATOM | 790 | C | ILE | 102 | 50.281 | 18.196 | 28.573 | 1.00 21.71 | MTGL |
| ATOM | 791 | O | ILE | 102 | 49.861 | 17.258 | 27.896 | 1.00 20.84 | MTGL |
| ATOM | 792 | N | ASP | 103 | 51.336 | 18.918 | 28.201 | 1.00 21.01 | MTGL |
| ATOM | 793 | CA | ASP | 103 | 52.012 | 18.608 | 26.945 | 1.00 22.44 | MTGL |
| ATOM | 794 | CB | ASP | 103 | 53.219 | 19.523 | 26.716 | 1.00 24.91 | MTGL |
| ATOM | 795 | CG | ASP | 103 | 52.821 | 20.942 | 26.370 | 1.00 27.06 | MTGL |
| ATOM | 796 | OD1 | ASP | 103 | 51.633 | 21.178 | 26.070 | 1.00 27.99 | MTGL |
| ATOM | 797 | OD2 | ASP | 103 | 53.703 | 21.823 | 26.385 | 1.00 28.69 | MTGL |
| ATOM | 798 | C | ASP | 103 | 52.478 | 17.160 | 26.886 | 1.00 22.61 | MTGL |
| ATOM | 799 | O | ASP | 103 | 52.144 | 16.435 | 25.948 | 1.00 23.39 | MTGL |
| ATOM | 800 | N | ASN | 104 | 53.244 | 16.734 | 27.885 | 1.00 21.79 | MTGL |
| ATOM | 801 | CA | ASN | 104 | 53.751 | 15.366 | 27.898 | 1.00 22.22 | MTGL |
| ATOM | 802 | CB | ASN | 104 | 54.912 | 15.244 | 28.884 | 1.00 23.92 | MTGL |
| ATOM | 803 | CG | ASN | 104 | 56.149 | 15.977 | 28.406 | 1.00 26.18 | MTGL |
| ATOM | 804 | OD1 | ASN | 104 | 56.715 | 15.643 | 27.364 | 1.00 26.60 | MTGL |
| ATOM | 805 | ND2 | ASN | 104 | 56.570 | 16.989 | 29.157 | 1.00 26.07 | MTGL |
| ATOM | 806 | C | ASN | 104 | 52.699 | 14.311 | 28.191 | 1.00 21.08 | MTGL |
| ATOM | 807 | O | ASN | 104 | 52.774 | 13.210 | 27.655 | 1.00 20.89 | MTGL |
| ATOM | 808 | N | LEU | 105 | 51.722 | 14.642 | 29.032 | 1.00 20.18 | MTGL |
| ATOM | 809 | CA | LEU | 105 | 50.663 | 13.693 | 29.361 | 1.00 19.91 | MTGL |
| ATOM | 810 | CB | LEU | 105 | 49.743 | 14.249 | 30.452 | 1.00 17.16 | MTGL |
| ATOM | 811 | CG | LEU | 105 | 48.568 | 13.339 | 30.842 | 1.00 18.64 | MTGL |

Fig. 1 cont.

| ATOM | 812 | CD1 | LEU | 105 | 49.089 | 12.019 | 31.413 | 1.00 | 15.72 | MTGL |
|------|-----|-----|-----|-----|--------|--------|--------|------|-------|------|
| ATOM | 813 | CD2 | LEU | 105 | 47.690 | 14.040 | 31.860 | 1.00 | 17.06 | MTGL |
| ATOM | 814 | C   | LEU | 105 | 49.841 | 13.392 | 28.109 | 1.00 | 20.55 | MTGL |
| ATOM | 815 | O   | LEU | 105 | 49.506 | 12.237 | 27.839 | 1.00 | 20.48 | MTGL |
| ATOM | 816 | N   | SER | 106 | 49.521 | 14.435 | 27.346 | 1.00 | 20.24 | MTGL |
| ATOM | 817 | CA  | SER | 106 | 48.746 | 14.264 | 26.124 | 1.00 | 21.47 | MTGL |
| ATOM | 818 | CB  | SER | 106 | 48.514 | 15.610 | 25.437 | 1.00 | 22.23 | MTGL |
| ATOM | 819 | OG  | SER | 106 | 47.695 | 16.447 | 26.235 | 1.00 | 27.30 | MTGL |
| ATOM | 820 | C   | SER | 106 | 49.484 | 13.338 | 25.173 | 1.00 | 20.88 | MTGL |
| ATOM | 821 | O   | SER | 106 | 48.884 | 12.487 | 24.527 | 1.00 | 19.42 | MTGL |
| ATOM | 822 | N   | TRP | 107 | 50.795 | 13.513 | 25.096 | 1.00 | 22.85 | MTGL |
| ATOM | 823 | CA  | TRP | 107 | 51.623 | 12.696 | 24.223 | 1.00 | 24.06 | MTGL |
| ATOM | 824 | CB  | TRP | 107 | 53.033 | 13.282 | 24.164 | 1.00 | 27.94 | MTGL |
| ATOM | 825 | CG  | TRP | 107 | 53.780 | 12.934 | 22.924 | 1.00 | 32.46 | MTGL |
| ATOM | 826 | CD2 | TRP | 107 | 55.136 | 13.276 | 22.621 | 1.00 | 35.03 | MTGL |
| ATOM | 827 | CE2 | TRP | 107 | 55.414 | 12.776 | 21.328 | 1.00 | 36.06 | MTGL |
| ATOM | 828 | CE3 | TRP | 107 | 56.141 | 13.971 | 23.309 | 1.00 | 36.31 | MTGL |
| ATOM | 829 | CD1 | TRP | 107 | 53.303 | 12.249 | 21.839 | 1.00 | 33.32 | MTGL |
| ATOM | 830 | NE1 | TRP | 107 | 54.280 | 12.148 | 20.877 | 1.00 | 35.87 | MTGL |
| ATOM | 831 | CZ2 | TRP | 107 | 56.662 | 12.934 | 20.715 | 1.00 | 36.87 | MTGL |
| ATOM | 832 | CZ3 | TRP | 107 | 57.381 | 14.130 | 22.698 | 1.00 | 37.64 | MTGL |
| ATOM | 833 | CH2 | TRP | 107 | 57.627 | 13.617 | 21.410 | 1.00 | 37.50 | MTGL |
| ATOM | 834 | C   | TRP | 107 | 51.674 | 11.250 | 24.725 | 1.00 | 23.66 | MTGL |
| ATOM | 835 | O   | TRP | 107 | 51.632 | 10.306 | 23.929 | 1.00 | 22.42 | MTGL |
| ATOM | 836 | N   | LYS | 108 | 51.754 | 11.085 | 26.045 | 1.00 | 21.87 | MTGL |
| ATOM | 837 | CA  | LYS | 108 | 51.810 | 9.758  | 26.654 | 1.00 | 21.77 | MTGL |
| ATOM | 838 | CB  | LYS | 108 | 52.012 | 9.870  | 28.167 | 1.00 | 22.68 | MTGL |
| ATOM | 839 | CG  | LYS | 108 | 52.928 | 8.818  | 28.787 | 1.00 | 25.44 | MTGL |
| ATOM | 840 | CD  | LYS | 108 | 52.756 | 7.420  | 28.208 | 1.00 | 25.37 | MTGL |
| ATOM | 841 | CE  | LYS | 108 | 53.657 | 6.436  | 28.948 | 1.00 | 26.82 | MTGL |
| ATOM | 842 | NZ  | LYS | 108 | 53.912 | 5.168  | 28.202 | 1.00 | 25.16 | MTGL |
| ATOM | 843 | C   | LYS | 108 | 50.502 | 9.016  | 26.400 | 1.00 | 21.11 | MTGL |
| ATOM | 844 | O   | LYS | 108 | 50.499 | 7.825  | 26.082 | 1.00 | 20.02 | MTGL |
| ATOM | 845 | N   | LEU | 109 | 49.394 | 9.733  | 26.569 | 1.00 | 20.01 | MTGL |
| ATOM | 846 | CA  | LEU | 109 | 48.069 | 9.165  | 26.378 | 1.00 | 19.28 | MTGL |
| ATOM | 847 | CB  | LEU | 109 | 46.998 | 10.210 | 26.701 | 1.00 | 17.83 | MTGL |
| ATOM | 848 | CG  | LEU | 109 | 45.541 | 9.782  | 26.544 | 1.00 | 18.16 | MTGL |
| ATOM | 849 | CD1 | LEU | 109 | 45.278 | 8.500  | 27.331 | 1.00 | 16.64 | MTGL |
| ATOM | 850 | CD2 | LEU | 109 | 44.639 | 10.912 | 27.023 | 1.00 | 17.12 | MTGL |
| ATOM | 851 | C   | LEU | 109 | 47.922 | 8.689  | 24.941 | 1.00 | 19.15 | MTGL |
| ATOM | 852 | O   | LEU | 109 | 47.356 | 7.630  | 24.681 | 1.00 | 17.95 | MTGL |
| ATOM | 853 | N   | TYR | 110 | 48.439 | 9.485  | 24.013 | 1.00 | 19.31 | MTGL |
| ATOM | 854 | CA  | TYR | 110 | 48.390 | 9.141  | 22.602 | 1.00 | 20.23 | MTGL |
| ATOM | 855 | CB  | TYR | 110 | 48.928 | 10.308 | 21.765 | 1.00 | 20.77 | MTGL |
| ATOM | 856 | CG  | TYR | 110 | 49.112 | 9.988  | 20.301 | 1.00 | 22.28 | MTGL |
| ATOM | 857 | CD1 | TYR | 110 | 50.324 | 9.483  | 19.827 | 1.00 | 22.42 | MTGL |
| ATOM | 858 | CE1 | TYR | 110 | 50.500 | 9.174  | 18.478 | 1.00 | 23.01 | MTGL |
| ATOM | 859 | CD2 | TYR | 110 | 48.072 | 10.179 | 19.388 | 1.00 | 21.90 | MTGL |
| ATOM | 860 | CE2 | TYR | 110 | 48.236 | 9.873  | 18.033 | 1.00 | 22.98 | MTGL |
| ATOM | 861 | CZ  | TYR | 110 | 49.453 | 9.373  | 17.589 | 1.00 | 22.70 | MTGL |
| ATOM | 862 | OH  | TYR | 110 | 49.628 | 9.075  | 16.261 | 1.00 | 22.60 | MTGL |
| ATOM | 863 | C   | TYR | 110 | 49.209 | 7.873  | 22.351 | 1.00 | 20.36 | MTGL |
| ATOM | 864 | O   | TYR | 110 | 48.713 | 6.915  | 21.753 | 1.00 | 19.75 | MTGL |
| ATOM | 865 | N   | ASN | 111 | 50.453 | 7.864  | 22.826 | 1.00 | 19.95 | MTGL |
| ATOM | 866 | CA  | ASN | 111 | 51.333 | 6.712  | 22.650 | 1.00 | 20.79 | MTGL |
| ATOM | 867 | CB  | ASN | 111 | 52.691 | 6.944  | 23.316 | 1.00 | 22.26 | MTGL |
| ATOM | 868 | CG  | ASN | 111 | 53.496 | 8.030  | 22.642 | 1.00 | 26.38 | MTGL |
| ATOM | 869 | OD1 | ASN | 111 | 53.175 | 8.463  | 21.534 | 1.00 | 25.33 | MTGL |

Fig. 1 cont.

| | | | | | | | | | |
|---|---|---|---|---|---|---|---|---|---|
| ATOM | 870 | ND2 | ASN | 111 | 54.556 | 8.463 | 23.317 | 1.00 29.11 | MTGL |
| ATOM | 871 | C | ASN | 111 | 50.736 | 5.445 | 23.234 | 1.00 20.44 | MTGL |
| ATOM | 872 | O | ASN | 111 | 50.764 | 4.391 | 22.605 | 1.00 20.22 | MTGL |
| ATOM | 873 | N | TYR | 112 | 50.218 | 5.551 | 24.452 | 1.00 19.27 | MTGL |
| ATOM | 874 | CA | TYR | 112 | 49.622 | 4.406 | 25.123 | 1.00 18.94 | MTGL |
| ATOM | 875 | CB | TYR | 112 | 49.131 | 4.801 | 26.517 | 1.00 16.74 | MTGL |
| ATOM | 876 | CG | TYR | 112 | 48.211 | 3.770 | 27.137 | 1.00 17.22 | MTGL |
| ATOM | 877 | CD1 | TYR | 112 | 48.723 | 2.632 | 27.766 | 1.00 15.42 | MTGL |
| ATOM | 878 | CE1 | TYR | 112 | 47.876 | 1.671 | 28.311 | 1.00 17.32 | MTGL |
| ATOM | 879 | CD2 | TYR | 112 | 46.827 | 3.916 | 27.065 | 1.00 15.87 | MTGL |
| ATOM | 880 | CE2 | TYR | 112 | 45.971 | 2.960 | 27.604 | 1.00 17.72 | MTGL |
| ATOM | 881 | CZ | TYR | 112 | 46.500 | 1.844 | 28.225 | 1.00 16.39 | MTGL |
| ATOM | 882 | OH | TYR | 112 | 45.653 | 0.907 | 28.766 | 1.00 18.06 | MTGL |
| ATOM | 883 | C | TYR | 112 | 48.449 | 3.832 | 24.330 | 1.00 18.50 | MTGL |
| ATOM | 884 | O | TYR | 112 | 48.358 | 2.622 | 24.129 | 1.00 17.86 | MTGL |
| ATOM | 885 | N | THR | 113 | 47.545 | 4.709 | 23.903 | 1.00 18.56 | MTGL |
| ATOM | 886 | CA | THR | 113 | 46.372 | 4.288 | 23.152 | 1.00 18.24 | MTGL |
| ATOM | 887 | CB | THR | 113 | 45.408 | 5.474 | 22.930 | 1.00 17.98 | MTGL |
| ATOM | 888 | OG1 | THR | 113 | 45.017 | 6.014 | 24.198 | 1.00 16.20 | MTGL |
| ATOM | 889 | CG2 | THR | 113 | 44.158 | 5.021 | 22.184 | 1.00 17.01 | MTGL |
| ATOM | 890 | C | THR | 113 | 46.765 | 3.682 | 21.805 | 1.00 18.67 | MTGL |
| ATOM | 891 | O | THR | 113 | 46.272 | 2.619 | 21.423 | 1.00 18.43 | MTGL |
| ATOM | 892 | N | LEU | 114 | 47.655 | 4.360 | 21.090 | 1.00 19.14 | MTGL |
| ATOM | 893 | CA | LEU | 114 | 48.114 | 3.873 | 19.797 | 1.00 20.50 | MTGL |
| ATOM | 894 | CB | LEU | 114 | 49.133 | 4.848 | 19.197 | 1.00 20.12 | MTGL |
| ATOM | 895 | CG | LEU | 114 | 49.864 | 4.396 | 17.929 | 1.00 21.74 | MTGL |
| ATOM | 896 | CD1 | LEU | 114 | 48.866 | 4.214 | 16.794 | 1.00 21.80 | MTGL |
| ATOM | 897 | CD2 | LEU | 114 | 50.924 | 5.430 | 17.547 | 1.00 22.25 | MTGL |
| ATOM | 898 | C | LEU | 114 | 48.753 | 2.498 | 19.984 | 1.00 20.96 | MTGL |
| ATOM | 899 | O | LEU | 114 | 48.441 | 1.551 | 19.263 | 1.00 21.53 | MTGL |
| ATOM | 900 | N | ASP | 115 | 49.650 | 2.399 | 20.961 | 1.00 21.00 | MTGL |
| ATOM | 901 | CA | ASP | 115 | 50.335 | 1.148 | 21.252 | 1.00 21.18 | MTGL |
| ATOM | 902 | CB | ASP | 115 | 51.276 | 1.331 | 22.442 | 1.00 22.68 | MTGL |
| ATOM | 903 | CG | ASP | 115 | 51.957 | 0.041 | 22.843 | 1.00 24.76 | MTGL |
| ATOM | 904 | OD1 | ASP | 115 | 52.826 | -0.429 | 22.078 | 1.00 26.71 | MTGL |
| ATOM | 905 | OD2 | ASP | 115 | 51.616 | -0.509 | 23.917 | 1.00 25.94 | MTGL |
| ATOM | 906 | C | ASP | 115 | 49.351 | 0.018 | 21.561 | 1.00 21.01 | MTGL |
| ATOM | 907 | O | ASP | 115 | 49.461 | -1.078 | 21.012 | 1.00 20.38 | MTGL |
| ATOM | 908 | N | ALA | 116 | 48.404 | 0.287 | 22.456 | 1.00 19.72 | MTGL |
| ATOM | 909 | CA | ALA | 116 | 47.410 | -0.711 | 22.833 | 1.00 19.79 | MTGL |
| ATOM | 910 | CB | ALA | 116 | 46.501 | -0.163 | 23.923 | 1.00 19.04 | MTGL |
| ATOM | 911 | C | ALA | 116 | 46.578 | -1.140 | 21.627 | 1.00 18.78 | MTGL |
| ATOM | 912 | O | ALA | 116 | 46.302 | -2.323 | 21.448 | 1.00 18.71 | MTGL |
| ATOM | 913 | N | ALA | 117 | 46.184 | -0.172 | 20.806 | 1.00 18.51 | MTGL |
| ATOM | 914 | CA | ALA | 117 | 45.384 | -0.456 | 19.616 | 1.00 19.07 | MTGL |
| ATOM | 915 | CB | ALA | 117 | 45.012 | 0.840 | 18.913 | 1.00 17.76 | MTGL |
| ATOM | 916 | C | ALA | 117 | 46.144 | -1.372 | 18.662 | 1.00 19.00 | MTGL |
| ATOM | 917 | O | ALA | 117 | 45.588 | -2.344 | 18.157 | 1.00 20.94 | MTGL |
| ATOM | 918 | N | ASN | 118 | 47.414 | -1.064 | 18.421 | 1.00 19.11 | MTGL |
| ATOM | 919 | CA | ASN | 118 | 48.234 | -1.880 | 17.530 | 1.00 20.09 | MTGL |
| ATOM | 920 | CB | ASN | 118 | 49.594 | -1.214 | 17.280 | 1.00 19.53 | MTGL |
| ATOM | 921 | CG | ASN | 118 | 49.481 | 0.043 | 16.432 | 1.00 21.06 | MTGL |
| ATOM | 922 | OD1 | ASN | 118 | 48.591 | 0.158 | 15.584 | 1.00 22.85 | MTGL |
| ATOM | 923 | ND2 | ASN | 118 | 50.394 | 0.984 | 16.644 | 1.00 19.62 | MTGL |
| ATOM | 924 | C | ASN | 118 | 48.446 | -3.294 | 18.069 | 1.00 20.53 | MTGL |
| ATOM | 925 | O | ASN | 118 | 48.509 | -4.250 | 17.298 | 1.00 20.72 | MTGL |
| ATOM | 926 | N | LYS | 119 | 48.570 | -3.427 | 19.389 | 1.00 20.26 | MTGL |
| ATOM | 927 | CA | LYS | 119 | 48.755 | -4.745 | 19.992 | 1.00 19.69 | MTGL |

Fig. 1 cont.

| | | | | | | | | | | |
|---|---|---|---|---|---|---|---|---|---|---|
| ATOM | 928 | CB | LYS | 119 | 49.134 | -4.616 | 21.468 | 1.00 | 20.25 | MTGL |
| ATOM | 929 | CG | LYS | 119 | 50.589 | -4.225 | 21.668 | 1.00 | 23.15 | MTGL |
| ATOM | 930 | CD | LYS | 119 | 50.933 | -4.015 | 23.131 | 1.00 | 25.43 | MTGL |
| ATOM | 931 | CE | LYS | 119 | 52.378 | -3.533 | 23.273 | 1.00 | 26.95 | MTGL |
| ATOM | 932 | NZ | LYS | 119 | 52.701 | -3.126 | 24.666 | 1.00 | 26.48 | MTGL |
| ATOM | 933 | C | LYS | 119 | 47.482 | -5.570 | 19.843 | 1.00 | 18.61 | MTGL |
| ATOM | 934 | O | LYS | 119 | 47.533 | -6.777 | 19.615 | 1.00 | 16.84 | MTGL |
| ATOM | 935 | N | LEU | 120 | 46.339 | -4.911 | 19.975 | 1.00 | 17.54 | MTGL |
| ATOM | 936 | CA | LEU | 120 | 45.064 | -5.599 | 19.820 | 1.00 | 18.74 | MTGL |
| ATOM | 937 | CB | LEU | 120 | 43.909 | -4.643 | 20.144 | 1.00 | 17.57 | MTGL |
| ATOM | 938 | CG | LEU | 120 | 43.736 | -4.330 | 21.635 | 1.00 | 17.26 | MTGL |
| ATOM | 939 | CD1 | LEU | 120 | 42.836 | -3.117 | 21.830 | 1.00 | 17.85 | MTGL |
| ATOM | 940 | CD2 | LEU | 120 | 43.152 | -5.549 | 22.325 | 1.00 | 16.86 | MTGL |
| ATOM | 941 | C | LEU | 120 | 44.976 | -6.086 | 18.372 | 1.00 | 18.39 | MTGL |
| ATOM | 942 | O | LEU | 120 | 44.660 | -7.243 | 18.116 | 1.00 | 19.13 | MTGL |
| ATOM | 943 | N | GLN | 121 | 45.273 | -5.193 | 17.434 | 1.00 | 19.05 | MTGL |
| ATOM | 944 | CA | GLN | 121 | 45.245 | -5.524 | 16.013 | 1.00 | 20.51 | MTGL |
| ATOM | 945 | CB | GLN | 121 | 45.715 | -4.324 | 15.182 | 1.00 | 20.27 | MTGL |
| ATOM | 946 | CG | GLN | 121 | 45.927 | -4.606 | 13.694 | 1.00 | 19.88 | MTGL |
| ATOM | 947 | CD | GLN | 121 | 44.677 | -5.116 | 12.998 | 1.00 | 20.20 | MTGL |
| ATOM | 948 | OE1 | GLN | 121 | 43.565 | -4.680 | 13.291 | 1.00 | 19.32 | MTGL |
| ATOM | 949 | NE2 | GLN | 121 | 44.859 | -6.035 | 12.055 | 1.00 | 20.98 | MTGL |
| ATOM | 950 | C | GLN | 121 | 46.142 | -6.723 | 15.734 | 1.00 | 20.78 | MTGL |
| ATOM | 951 | O | GLN | 121 | 45.729 | -7.672 | 15.078 | 1.00 | 21.20 | MTGL |
| ATOM | 952 | N | ASN | 122 | 47.369 | -6.676 | 16.242 | 1.00 | 20.58 | MTGL |
| ATOM | 953 | CA | ASN | 122 | 48.322 | -7.762 | 16.037 | 1.00 | 22.39 | MTGL |
| ATOM | 954 | CB | ASN | 122 | 49.685 | -7.371 | 16.611 | 1.00 | 24.20 | MTGL |
| ATOM | 955 | CG | ASN | 122 | 50.350 | -6.260 | 15.817 | 1.00 | 26.36 | MTGL |
| ATOM | 956 | OD1 | ASN | 122 | 51.298 | -5.630 | 16.285 | 1.00 | 29.40 | MTGL |
| ATOM | 957 | ND2 | ASN | 122 | 49.863 | -6.021 | 14.605 | 1.00 | 26.25 | MTGL |
| ATOM | 958 | C | ASN | 122 | 47.859 | -9.082 | 16.646 | 1.00 | 22.40 | MTGL |
| ATOM | 959 | O | ASN | 122 | 48.312 | -10.153 | 16.243 | 1.00 | 23.25 | MTGL |
| ATOM | 960 | N | ALA | 123 | 46.957 | -9.005 | 17.616 | 1.00 | 21.34 | MTGL |
| ATOM | 961 | CA | ALA | 123 | 46.436 | -10.209 | 18.252 | 1.00 | 21.19 | MTGL |
| ATOM | 962 | CB | ALA | 123 | 46.151 | -9.939 | 19.730 | 1.00 | 21.28 | MTGL |
| ATOM | 963 | C | ALA | 123 | 45.163 | -10.669 | 17.545 | 1.00 | 20.31 | MTGL |
| ATOM | 964 | O | ALA | 123 | 44.512 | -11.621 | 17.981 | 1.00 | 21.19 | MTGL |
| ATOM | 965 | N | GLY | 124 | 44.813 | -9.985 | 16.457 | 1.00 | 20.00 | MTGL |
| ATOM | 966 | CA | GLY | 124 | 43.621 | -10.332 | 15.705 | 1.00 | 19.34 | MTGL |
| ATOM | 967 | C | GLY | 124 | 42.338 | -9.853 | 16.367 | 1.00 | 20.32 | MTGL |
| ATOM | 968 | O | GLY | 124 | 41.255 | -10.376 | 16.098 | 1.00 | 19.71 | MTGL |
| ATOM | 969 | N | ILE | 125 | 42.450 | -8.855 | 17.239 | 1.00 | 18.85 | MTGL |
| ATOM | 970 | CA | ILE | 125 | 41.281 | -8.327 | 17.928 | 1.00 | 17.97 | MTGL |
| ATOM | 971 | CB | ILE | 125 | 41.502 | -8.279 | 19.465 | 1.00 | 18.21 | MTGL |
| ATOM | 972 | CG2 | ILE | 125 | 40.264 | -7.709 | 20.149 | 1.00 | 18.39 | MTGL |
| ATOM | 973 | CG1 | ILE | 125 | 41.807 | -9.681 | 20.013 | 1.00 | 16.78 | MTGL |
| ATOM | 974 | CD1 | ILE | 125 | 40.682 | -10.694 | 19.808 | 1.00 | 15.33 | MTGL |
| ATOM | 975 | C | ILE | 125 | 40.936 | -6.908 | 17.460 | 1.00 | 18.72 | MTGL |
| ATOM | 976 | O | ILE | 125 | 41.682 | -5.959 | 17.718 | 1.00 | 18.82 | MTGL |
| ATOM | 977 | N | GLN | 126 | 39.810 | -6.771 | 16.769 | 1.00 | 17.38 | MTGL |
| ATOM | 978 | CA | GLN | 126 | 39.355 | -5.463 | 16.310 | 1.00 | 17.54 | MTGL |
| ATOM | 979 | CB | GLN | 126 | 39.059 | -5.459 | 14.810 | 1.00 | 17.95 | MTGL |
| ATOM | 980 | CG | GLN | 126 | 40.267 | -5.634 | 13.905 | 1.00 | 18.48 | MTGL |
| ATOM | 981 | CD | GLN | 126 | 40.704 | -7.082 | 13.784 | 1.00 | 19.41 | MTGL |
| ATOM | 982 | OE1 | GLN | 126 | 39.874 | -7.991 | 13.722 | 1.00 | 18.45 | MTGL |
| ATOM | 983 | NE2 | GLN | 126 | 42.014 | -7.302 | 13.731 | 1.00 | 18.37 | MTGL |
| ATOM | 984 | C | GLN | 126 | 38.078 | -5.152 | 17.073 | 1.00 | 17.01 | MTGL |
| ATOM | 985 | O | GLN | 126 | 36.990 | -5.578 | 16.686 | 1.00 | 17.42 | MTGL |

Fig. 1 cont.

| | | | | | | | | | | |
|---|---|---|---|---|---|---|---|---|---|---|
| ATOM | 986 | N | PRO | 127 | 38.196 | -4.424 | 18.189 | 1.00 | 17.14 | MTGL |
| ATOM | 987 | CD | PRO | 127 | 39.397 | -3.833 | 18.803 | 1.00 | 16.94 | MTGL |
| ATOM | 988 | CA | PRO | 127 | 36.990 | -4.103 | 18.954 | 1.00 | 17.76 | MTGL |
| ATOM | 989 | CB | PRO | 127 | 37.534 | -3.333 | 20.162 | 1.00 | 17.60 | MTGL |
| ATOM | 990 | CG | PRO | 127 | 38.806 | -2.730 | 19.644 | 1.00 | 20.07 | MTGL |
| ATOM | 991 | C | PRO | 127 | 36.004 | -3.290 | 18.130 | 1.00 | 17.06 | MTGL |
| ATOM | 992 | O | PRO | 127 | 36.400 | -2.472 | 17.303 | 1.00 | 18.03 | MTGL |
| ATOM | 993 | N | THR | 128 | 34.719 | -3.536 | 18.340 | 1.00 | 17.80 | MTGL |
| ATOM | 994 | CA | THR | 128 | 33.688 | -2.803 | 17.620 | 1.00 | 17.59 | MTGL |
| ATOM | 995 | CB | THR | 128 | 32.357 | -3.582 | 17.615 | 1.00 | 18.62 | MTGL |
| ATOM | 996 | OG1 | THR | 128 | 32.035 | -3.994 | 18.951 | 1.00 | 17.44 | MTGL |
| ATOM | 997 | CG2 | THR | 128 | 32.467 | -4.816 | 16.717 | 1.00 | 18.59 | MTGL |
| ATOM | 998 | C | THR | 128 | 33.499 | -1.451 | 18.310 | 1.00 | 17.94 | MTGL |
| ATOM | 999 | O | THR | 128 | 33.086 | -0.476 | 17.683 | 1.00 | 16.71 | MTGL |
| ATOM | 1000 | N | ILE | 129 | 33.834 | -1.397 | 19.600 | 1.00 | 16.54 | MTGL |
| ATOM | 1001 | CA | ILE | 129 | 33.701 | -0.161 | 20.373 | 1.00 | 16.74 | MTGL |
| ATOM | 1002 | CB | ILE | 129 | 32.426 | -0.166 | 21.249 | 1.00 | 17.47 | MTGL |
| ATOM | 1003 | CG2 | ILE | 129 | 32.323 | 1.138 | 22.032 | 1.00 | 16.90 | MTGL |
| ATOM | 1004 | CG1 | ILE | 129 | 31.182 | -0.340 | 20.380 | 1.00 | 18.59 | MTGL |
| ATOM | 1005 | CD1 | ILE | 129 | 29.913 | -0.501 | 21.189 | 1.00 | 18.26 | MTGL |
| ATOM | 1006 | C | ILE | 129 | 34.878 | 0.056 | 21.317 | 1.00 | 16.72 | MTGL |
| ATOM | 1007 | O | ILE | 129 | 35.361 | -0.883 | 21.949 | 1.00 | 16.12 | MTGL |
| ATOM | 1008 | N | VAL | 130 | 35.329 | 1.303 | 21.410 | 1.00 | 16.38 | MTGL |
| ATOM | 1009 | CA | VAL | 130 | 36.413 | 1.666 | 22.313 | 1.00 | 16.43 | MTGL |
| ATOM | 1010 | CB | VAL | 130 | 37.738 | 1.891 | 21.568 | 1.00 | 16.85 | MTGL |
| ATOM | 1011 | CG1 | VAL | 130 | 38.783 | 2.444 | 22.532 | 1.00 | 15.96 | MTGL |
| ATOM | 1012 | CG2 | VAL | 130 | 38.224 | 0.581 | 20.958 | 1.00 | 16.65 | MTGL |
| ATOM | 1013 | C | VAL | 130 | 36.040 | 2.965 | 23.020 | 1.00 | 16.57 | MTGL |
| ATOM | 1014 | O | VAL | 130 | 35.807 | 3.981 | 22.369 | 1.00 | 17.33 | MTGL |
| ATOM | 1015 | N | SER | 131 | 35.955 | 2.931 | 24.347 | 1.00 | 15.26 | MTGL |
| ATOM | 1016 | CA | SER | 131 | 35.640 | 4.142 | 25.088 | 1.00 | 14.32 | MTGL |
| ATOM | 1017 | CB | SER | 131 | 34.741 | 3.840 | 26.296 | 1.00 | 13.74 | MTGL |
| ATOM | 1018 | OG | SER | 131 | 35.427 | 3.100 | 27.299 | 1.00 | 14.55 | MTGL |
| ATOM | 1019 | C | SER | 131 | 36.957 | 4.737 | 25.563 | 1.00 | 13.67 | MTGL |
| ATOM | 1020 | O | SER | 131 | 37.812 | 4.024 | 26.094 | 1.00 | 14.63 | MTGL |
| ATOM | 1021 | N | ILE | 132 | 37.140 | 6.033 | 25.349 | 1.00 | 12.98 | MTGL |
| ATOM | 1022 | CA | ILE | 132 | 38.362 | 6.684 | 25.791 | 1.00 | 13.07 | MTGL |
| ATOM | 1023 | CB | ILE | 132 | 38.793 | 7.796 | 24.811 | 1.00 | 13.05 | MTGL |
| ATOM | 1024 | CG2 | ILE | 132 | 39.419 | 7.169 | 23.573 | 1.00 | 14.24 | MTGL |
| ATOM | 1025 | CG1 | ILE | 132 | 37.591 | 8.649 | 24.397 | 1.00 | 13.32 | MTGL |
| ATOM | 1026 | CD1 | ILE | 132 | 37.960 | 9.760 | 23.429 | 1.00 | 14.06 | MTGL |
| ATOM | 1027 | C | ILE | 132 | 38.103 | 7.234 | 27.188 | 1.00 | 13.33 | MTGL |
| ATOM | 1028 | O | ILE | 132 | 37.800 | 8.415 | 27.372 | 1.00 | 12.93 | MTGL |
| ATOM | 1029 | N | GLY | 133 | 38.206 | 6.339 | 28.170 | 1.00 | 12.78 | MTGL |
| ATOM | 1030 | CA | GLY | 133 | 37.957 | 6.703 | 29.552 | 1.00 | 13.26 | MTGL |
| ATOM | 1031 | C | GLY | 133 | 36.687 | 6.040 | 30.066 | 1.00 | 14.41 | MTGL |
| ATOM | 1032 | O | GLY | 133 | 35.821 | 5.638 | 29.279 | 1.00 | 14.45 | MTGL |
| ATOM | 1033 | N | ASN | 134 | 36.573 | 5.915 | 31.385 | 1.00 | 14.34 | MTGL |
| ATOM | 1034 | CA | ASN | 134 | 35.393 | 5.311 | 31.995 | 1.00 | 14.81 | MTGL |
| ATOM | 1035 | CB | ASN | 134 | 35.797 | 4.063 | 32.780 | 1.00 | 14.03 | MTGL |
| ATOM | 1036 | CG | ASN | 134 | 34.602 | 3.307 | 33.321 | 1.00 | 15.54 | MTGL |
| ATOM | 1037 | OD1 | ASN | 134 | 33.932 | 2.558 | 32.596 | 1.00 | 14.69 | MTGL |
| ATOM | 1038 | ND2 | ASN | 134 | 34.311 | 3.515 | 34.599 | 1.00 | 13.31 | MTGL |
| ATOM | 1039 | C | ASN | 134 | 34.727 | 6.328 | 32.929 | 1.00 | 15.45 | MTGL |
| ATOM | 1040 | O | ASN | 134 | 35.355 | 6.823 | 33.865 | 1.00 | 14.99 | MTGL |
| ATOM | 1041 | N | GLU | 135 | 33.458 | 6.632 | 32.672 | 1.00 | 15.32 | MTGL |
| ATOM | 1042 | CA | GLU | 135 | 32.708 | 7.600 | 33.480 | 1.00 | 16.19 | MTGL |
| ATOM | 1043 | CB | GLU | 135 | 32.225 | 6.948 | 34.780 | 1.00 | 16.84 | MTGL |

Fig. 1 cont.

| | | | | | | | | | |
|---|---|---|---|---|---|---|---|---|---|
| ATOM | 1044 | CG | GLU | 135 | 31.360 | 5.710 | 34.571 | 1.00 18.65 | MTGL |
| ATOM | 1045 | CD | GLU | 135 | 30.758 | 5.173 | 35.862 | 1.00 19.18 | MTGL |
| ATOM | 1046 | OE1 | GLU | 135 | 31.449 | 5.200 | 36.905 | 1.00 20.99 | MTGL |
| ATOM | 1047 | OE2 | GLU | 135 | 29.602 | 4.705 | 35.829 | 1.00 16.99 | MTGL |
| ATOM | 1048 | C | GLU | 135 | 33.553 | 8.834 | 33.806 | 1.00 16.49 | MTGL |
| ATOM | 1049 | O | GLU | 135 | 33.777 | 9.153 | 34.974 | 1.00 15.93 | MTGL |
| ATOM | 1050 | N | ILE | 136 | 34.004 | 9.536 | 32.770 | 1.00 15.57 | MTGL |
| ATOM | 1051 | CA | ILE | 136 | 34.846 | 10.712 | 32.957 | 1.00 16.13 | MTGL |
| ATOM | 1052 | CB | ILE | 136 | 35.802 | 10.887 | 31.756 | 1.00 16.05 | MTGL |
| ATOM | 1053 | CG2 | ILE | 136 | 36.783 | 9.719 | 31.706 | 1.00 16.66 | MTGL |
| ATOM | 1054 | CG1 | ILE | 136 | 35.001 | 10.956 | 30.451 | 1.00 16.40 | MTGL |
| ATOM | 1055 | CD1 | ILE | 136 | 35.858 | 11.171 | 29.211 | 1.00 14.50 | MTGL |
| ATOM | 1056 | C | ILE | 136 | 34.060 | 12.006 | 33.168 | 1.00 16.79 | MTGL |
| ATOM | 1057 | O | ILE | 136 | 34.457 | 13.067 | 32.697 | 1.00 16.67 | MTGL |
| ATOM | 1058 | N | ARG | 137 | 32.949 | 11.909 | 33.890 | 1.00 17.28 | MTGL |
| ATOM | 1059 | CA | ARG | 137 | 32.099 | 13.057 | 34.170 | 1.00 18.25 | MTGL |
| ATOM | 1060 | CB | ARG | 137 | 30.884 | 12.612 | 34.976 | 1.00 20.33 | MTGL |
| ATOM | 1061 | CG | ARG | 137 | 29.879 | 13.712 | 35.248 | 1.00 22.61 | MTGL |
| ATOM | 1062 | CD | ARG | 137 | 29.087 | 13.370 | 36.487 | 1.00 26.40 | MTGL |
| ATOM | 1063 | NE | ARG | 137 | 29.837 | 13.668 | 37.696 | 1.00 28.06 | MTGL |
| ATOM | 1064 | CZ | ARG | 137 | 29.643 | 13.076 | 38.869 | 1.00 28.40 | MTGL |
| ATOM | 1065 | NH1 | ARG | 137 | 28.726 | 12.132 | 39.006 | 1.00 27.39 | MTGL |
| ATOM | 1066 | NH2 | ARG | 137 | 30.355 | 13.459 | 39.918 | 1.00 30.54 | MTGL |
| ATOM | 1067 | C | ARG | 137 | 32.849 | 14.145 | 34.937 | 1.00 19.12 | MTGL |
| ATOM | 1068 | O | ARG | 137 | 32.537 | 15.327 | 34.812 | 1.00 19.19 | MTGL |
| ATOM | 1069 | N | ALA | 138 | 33.832 | 13.744 | 35.738 | 1.00 17.89 | MTGL |
| ATOM | 1070 | CA | ALA | 138 | 34.626 | 14.708 | 36.487 | 1.00 18.61 | MTGL |
| ATOM | 1071 | CB | ALA | 138 | 34.679 | 14.320 | 37.965 | 1.00 18.89 | MTGL |
| ATOM | 1072 | C | ALA | 138 | 36.028 | 14.744 | 35.888 | 1.00 18.04 | MTGL |
| ATOM | 1073 | O | ALA | 138 | 37.003 | 15.050 | 36.573 | 1.00 18.75 | MTGL |
| ATOM | 1074 | N | GLY | 139 | 36.119 | 14.415 | 34.603 | 1.00 17.60 | MTGL |
| ATOM | 1075 | CA | GLY | 139 | 37.401 | 14.424 | 33.920 | 1.00 16.74 | MTGL |
| ATOM | 1076 | C | GLY | 139 | 38.141 | 13.103 | 33.979 | 1.00 17.00 | MTGL |
| ATOM | 1077 | O | GLY | 139 | 37.558 | 12.061 | 34.303 | 1.00 15.56 | MTGL |
| ATOM | 1078 | N | LEU | 140 | 39.430 | 13.150 | 33.653 | 1.00 16.36 | MTGL |
| ATOM | 1079 | CA | LEU | 140 | 40.288 | 11.965 | 33.666 | 1.00 16.91 | MTGL |
| ATOM | 1080 | CB | LEU | 140 | 40.254 | 11.255 | 32.308 | 1.00 16.55 | MTGL |
| ATOM | 1081 | CG | LEU | 140 | 40.965 | 11.954 | 31.137 | 1.00 17.14 | MTGL |
| ATOM | 1082 | CD1 | LEU | 140 | 41.157 | 10.962 | 29.985 | 1.00 17.61 | MTGL |
| ATOM | 1083 | CD2 | LEU | 140 | 40.158 | 13.157 | 30.673 | 1.00 16.51 | MTGL |
| ATOM | 1084 | C | LEU | 140 | 41.731 | 12.366 | 33.961 | 1.00 16.82 | MTGL |
| ATOM | 1085 | O | LEU | 140 | 42.078 | 13.549 | 33.919 | 1.00 16.86 | MTGL |
| ATOM | 1086 | N | LEU | 141 | 42.566 | 11.373 | 34.254 | 1.00 16.21 | MTGL |
| ATOM | 1087 | CA | LEU | 141 | 43.979 | 11.616 | 34.521 | 1.00 16.03 | MTGL |
| ATOM | 1088 | CB | LEU | 141 | 44.711 | 11.839 | 33.191 | 1.00 14.81 | MTGL |
| ATOM | 1089 | CG | LEU | 141 | 44.626 | 10.646 | 32.220 | 1.00 15.72 | MTGL |
| ATOM | 1090 | CD1 | LEU | 141 | 45.076 | 11.054 | 30.818 | 1.00 14.73 | MTGL |
| ATOM | 1091 | CD2 | LEU | 141 | 45.494 | 9.501 | 32.752 | 1.00 14.97 | MTGL |
| ATOM | 1092 | C | LEU | 141 | 44.166 | 12.822 | 35.444 | 1.00 16.13 | MTGL |
| ATOM | 1093 | O | LEU | 141 | 44.776 | 13.819 | 35.069 | 1.00 15.77 | MTGL |
| ATOM | 1094 | N | TRP | 142 | 43.631 | 12.715 | 36.655 | 1.00 16.15 | MTGL |
| ATOM | 1095 | CA | TRP | 142 | 43.718 | 13.789 | 37.635 | 1.00 16.13 | MTGL |
| ATOM | 1096 | CB | TRP | 142 | 42.854 | 13.446 | 38.845 | 1.00 16.04 | MTGL |
| ATOM | 1097 | CG | TRP | 142 | 41.387 | 13.408 | 38.559 | 1.00 16.68 | MTGL |
| ATOM | 1098 | CD2 | TRP | 142 | 40.345 | 13.114 | 39.494 | 1.00 16.86 | MTGL |
| ATOM | 1099 | CE2 | TRP | 142 | 39.117 | 13.217 | 38.800 | 1.00 16.85 | MTGL |
| ATOM | 1100 | CE3 | TRP | 142 | 40.330 | 12.779 | 40.855 | 1.00 17.53 | MTGL |
| ATOM | 1101 | CD1 | TRP | 142 | 40.769 | 13.669 | 37.365 | 1.00 16.02 | MTGL |

Fig. 1 cont.

| | | | | | | | | | |
|---|---|---|---|---|---|---|---|---|---|
| ATOM | 1102 | NE1 | TRP | 142 | 39.404 | 13.557 | 37.503 | 1.00 16.14 | MTGL |
| ATOM | 1103 | CZ2 | TRP | 142 | 37.884 | 12.993 | 39.421 | 1.00 16.71 | MTGL |
| ATOM | 1104 | CZ3 | TRP | 142 | 39.097 | 12.557 | 41.475 | 1.00 17.85 | MTGL |
| ATOM | 1105 | CH2 | TRP | 142 | 37.894 | 12.666 | 40.755 | 1.00 17.70 | MTGL |
| ATOM | 1106 | C | TRP | 142 | 45.151 | 14.036 | 38.092 | 1.00 16.70 | MTGL |
| ATOM | 1107 | O | TRP | 142 | 45.965 | 13.116 | 38.132 | 1.00 15.98 | MTGL |
| ATOM | 1108 | N | PRO | 143 | 45.476 | 15.289 | 38.452 | 1.00 18.10 | MTGL |
| ATOM | 1109 | CD | PRO | 143 | 46.716 | 15.597 | 39.183 | 1.00 18.05 | MTGL |
| ATOM | 1110 | CA | PRO | 143 | 44.586 | 16.458 | 38.444 | 1.00 17.24 | MTGL |
| ATOM | 1111 | CB | PRO | 143 | 45.170 | 17.362 | 39.539 | 1.00 17.56 | MTGL |
| ATOM | 1112 | CG | PRO | 143 | 46.199 | 16.496 | 40.260 | 1.00 19.44 | MTGL |
| ATOM | 1113 | C | PRO | 143 | 44.599 | 17.177 | 37.096 | 1.00 17.09 | MTGL |
| ATOM | 1114 | O | PRO | 143 | 43.804 | 18.092 | 36.864 | 1.00 16.74 | MTGL |
| ATOM | 1115 | N | THR | 144 | 45.509 | 16.767 | 36.219 | 1.00 16.23 | MTGL |
| ATOM | 1116 | CA | THR | 144 | 45.651 | 17.396 | 34.910 | 1.00 17.05 | MTGL |
| ATOM | 1117 | CB | THR | 144 | 46.677 | 16.640 | 34.048 | 1.00 17.49 | MTGL |
| ATOM | 1118 | OG1 | THR | 144 | 47.864 | 16.413 | 34.817 | 1.00 18.41 | MTGL |
| ATOM | 1119 | CG2 | THR | 144 | 47.040 | 17.453 | 32.811 | 1.00 17.61 | MTGL |
| ATOM | 1120 | C | THR | 144 | 44.346 | 17.510 | 34.129 | 1.00 16.98 | MTGL |
| ATOM | 1121 | O | THR | 144 | 44.027 | 18.579 | 33.610 | 1.00 17.37 | MTGL |
| ATOM | 1122 | N | GLY | 145 | 43.594 | 16.414 | 34.052 | 1.00 17.00 | MTGL |
| ATOM | 1123 | CA | GLY | 145 | 42.336 | 16.432 | 33.322 | 1.00 16.55 | MTGL |
| ATOM | 1124 | C | GLY | 145 | 41.111 | 16.472 | 34.219 | 1.00 17.19 | MTGL |
| ATOM | 1125 | O | GLY | 145 | 40.033 | 16.013 | 33.837 | 1.00 15.11 | MTGL |
| ATOM | 1126 | N | ARG | 146 | 41.269 | 17.009 | 35.423 | 1.00 16.86 | MTGL |
| ATOM | 1127 | CA | ARG | 146 | 40.153 | 17.118 | 36.361 | 1.00 18.80 | MTGL |
| ATOM | 1128 | CB | ARG | 146 | 40.707 | 17.308 | 37.784 | 1.00 20.43 | MTGL |
| ATOM | 1129 | CG | ARG | 146 | 39.671 | 17.572 | 38.870 | 1.00 24.77 | MTGL |
| ATOM | 1130 | CD | ARG | 146 | 38.729 | 16.394 | 39.052 | 1.00 27.03 | MTGL |
| ATOM | 1131 | NE | ARG | 146 | 37.715 | 16.623 | 40.081 | 1.00 30.10 | MTGL |
| ATOM | 1132 | CZ | ARG | 146 | 37.922 | 16.516 | 41.391 | 1.00 31.39 | MTGL |
| ATOM | 1133 | NH1 | ARG | 146 | 39.122 | 16.182 | 41.861 | 1.00 31.38 | MTGL |
| ATOM | 1134 | NH2 | ARG | 146 | 36.916 | 16.729 | 42.236 | 1.00 32.17 | MTGL |
| ATOM | 1135 | C | ARG | 146 | 39.261 | 18.308 | 35.961 | 1.00 18.91 | MTGL |
| ATOM | 1136 | O | ARG | 146 | 39.763 | 19.344 | 35.534 | 1.00 17.30 | MTGL |
| ATOM | 1137 | N | THR | 147 | 37.940 | 18.147 | 36.055 | 1.00 18.95 | MTGL |
| ATOM | 1138 | CA | THR | 147 | 37.037 | 19.255 | 35.732 | 1.00 19.02 | MTGL |
| ATOM | 1139 | CB | THR | 147 | 35.550 | 18.826 | 35.731 | 1.00 18.33 | MTGL |
| ATOM | 1140 | OG1 | THR | 147 | 35.278 | 18.044 | 36.890 | 1.00 18.17 | MTGL |
| ATOM | 1141 | CG2 | THR | 147 | 35.217 | 18.016 | 34.490 | 1.00 18.17 | MTGL |
| ATOM | 1142 | C | THR | 147 | 37.278 | 20.271 | 36.858 | 1.00 19.51 | MTGL |
| ATOM | 1143 | O | THR | 147 | 37.539 | 19.861 | 37.983 | 1.00 18.48 | MTGL |
| ATOM | 1144 | N | GLU | 148 | 37.158 | 21.574 | 36.598 | 1.00 19.44 | MTGL |
| ATOM | 1145 | CA | GLU | 148 | 36.771 | 22.124 | 35.317 | 1.00 20.37 | MTGL |
| ATOM | 1146 | CB | GLU | 148 | 35.829 | 23.309 | 35.551 | 1.00 22.32 | MTGL |
| ATOM | 1147 | CG | GLU | 148 | 34.576 | 22.960 | 36.356 | 1.00 26.58 | MTGL |
| ATOM | 1148 | CD | GLU | 148 | 34.081 | 24.123 | 37.217 | 1.00 29.48 | MTGL |
| ATOM | 1149 | OE1 | GLU | 148 | 33.777 | 25.209 | 36.672 | 1.00 30.90 | MTGL |
| ATOM | 1150 | OE2 | GLU | 148 | 33.988 | 23.929 | 38.448 | 1.00 30.75 | MTGL |
| ATOM | 1151 | C | GLU | 148 | 37.858 | 22.540 | 34.312 | 1.00 20.17 | MTGL |
| ATOM | 1152 | O | GLU | 148 | 37.649 | 23.550 | 33.633 | 1.00 20.26 | MTGL |
| ATOM | 1153 | N | ASN | 149 | 39.019 | 21.853 | 34.186 | 0.50 20.18 | MTGL |
| ATOM | 1154 | CA | ASN | 149 | 40.039 | 22.216 | 33.154 | 0.50 20.26 | MTGL |
| ATOM | 1155 | CB | ASN | 149 | 41.436 | 21.616 | 33.436 | 0.50 21.36 | MTGL |
| ATOM | 1156 | CG | ASN | 149 | 42.198 | 22.423 | 34.433 | 0.50 22.41 | MTGL |
| ATOM | 1157 | OD1 | ASN | 149 | 42.651 | 23.520 | 34.132 | 0.50 23.31 | MTGL |
| ATOM | 1158 | ND2 | ASN | 149 | 42.298 | 21.917 | 35.646 | 0.50 23.40 | MTGL |
| ATOM | 1159 | C | ASN | 149 | 39.555 | 21.656 | 31.811 | 0.50 19.48 | MTGL |

Fig. 1 cont.

| ATOM | 1160 | O   | ASN | 149 | 40.152 | 20.702 | 31.289 | 0.50 | 17.94 | MTGL |
| ATOM | 1161 | N   | TRP | 150 | 38.480 | 22.230 | 31.261 | 1.00 | 19.00 | MTGL |
| ATOM | 1162 | CA  | TRP | 150 | 37.920 | 21.769 | 30.000 | 1.00 | 18.91 | MTGL |
| ATOM | 1163 | CB  | TRP | 150 | 36.777 | 22.704 | 29.605 | 1.00 | 18.17 | MTGL |
| ATOM | 1164 | CG  | TRP | 150 | 35.710 | 22.781 | 30.629 | 1.00 | 17.82 | MTGL |
| ATOM | 1165 | CD2 | TRP | 150 | 34.895 | 21.702 | 31.094 | 1.00 | 18.44 | MTGL |
| ATOM | 1166 | CE2 | TRP | 150 | 34.013 | 22.232 | 32.060 | 1.00 | 18.24 | MTGL |
| ATOM | 1167 | CE3 | TRP | 150 | 34.824 | 20.335 | 30.787 | 1.00 | 18.25 | MTGL |
| ATOM | 1168 | CD1 | TRP | 150 | 35.301 | 23.895 | 31.310 | 1.00 | 17.99 | MTGL |
| ATOM | 1169 | NE1 | TRP | 150 | 34.282 | 23.571 | 32.170 | 1.00 | 19.19 | MTGL |
| ATOM | 1170 | CZ2 | TRP | 150 | 33.066 | 21.443 | 32.725 | 1.00 | 19.86 | MTGL |
| ATOM | 1171 | CZ3 | TRP | 150 | 33.879 | 19.547 | 31.448 | 1.00 | 19.02 | MTGL |
| ATOM | 1172 | CH2 | TRP | 150 | 33.013 | 20.105 | 32.408 | 1.00 | 19.52 | MTGL |
| ATOM | 1173 | C   | TRP | 150 | 38.990 | 21.744 | 28.904 | 1.00 | 19.25 | MTGL |
| ATOM | 1174 | O   | TRP | 150 | 39.022 | 20.828 | 28.091 | 1.00 | 19.43 | MTGL |
| ATOM | 1175 | N   | ALA | 151 | 39.851 | 22.759 | 28.880 | 1.00 | 17.86 | MTGL |
| ATOM | 1176 | CA  | ALA | 151 | 40.897 | 22.822 | 27.864 | 1.00 | 18.96 | MTGL |
| ATOM | 1177 | CB  | ALA | 151 | 41.753 | 24.090 | 28.047 | 1.00 | 19.41 | MTGL |
| ATOM | 1178 | C   | ALA | 151 | 41.784 | 21.571 | 27.897 | 1.00 | 18.90 | MTGL |
| ATOM | 1179 | O   | ALA | 151 | 42.098 | 20.994 | 26.857 | 1.00 | 19.89 | MTGL |
| ATOM | 1180 | N   | ASN | 152 | 42.184 | 21.144 | 29.088 | 1.00 | 18.45 | MTGL |
| ATOM | 1181 | CA  | ASN | 152 | 43.027 | 19.954 | 29.209 | 1.00 | 18.07 | MTGL |
| ATOM | 1182 | CB  | ASN | 152 | 43.584 | 19.830 | 30.635 | 1.00 | 16.97 | MTGL |
| ATOM | 1183 | CG  | ASN | 152 | 44.767 | 20.764 | 30.886 | 1.00 | 18.19 | MTGL |
| ATOM | 1184 | OD1 | ASN | 152 | 45.095 | 21.603 | 30.054 | 1.00 | 17.89 | MTGL |
| ATOM | 1185 | ND2 | ASN | 152 | 45.407 | 20.618 | 32.043 | 1.00 | 17.33 | MTGL |
| ATOM | 1186 | C   | ASN | 152 | 42.250 | 18.686 | 28.848 | 1.00 | 17.48 | MTGL |
| ATOM | 1187 | O   | ASN | 152 | 42.762 | 17.805 | 28.155 | 1.00 | 17.16 | MTGL |
| ATOM | 1188 | N   | ILE | 153 | 41.016 | 18.598 | 29.325 | 1.00 | 17.57 | MTGL |
| ATOM | 1189 | CA  | ILE | 153 | 40.177 | 17.437 | 29.048 | 1.00 | 18.34 | MTGL |
| ATOM | 1190 | CB  | ILE | 153 | 38.801 | 17.573 | 29.741 | 1.00 | 17.84 | MTGL |
| ATOM | 1191 | CG2 | ILE | 153 | 37.836 | 16.486 | 29.243 | 1.00 | 17.51 | MTGL |
| ATOM | 1192 | CG1 | ILE | 153 | 38.987 | 17.468 | 31.255 | 1.00 | 17.49 | MTGL |
| ATOM | 1193 | CD1 | ILE | 153 | 37.761 | 17.837 | 32.060 | 1.00 | 17.26 | MTGL |
| ATOM | 1194 | C   | ILE | 153 | 39.974 | 17.246 | 27.548 | 1.00 | 17.82 | MTGL |
| ATOM | 1195 | O   | ILE | 153 | 40.174 | 16.150 | 27.027 | 1.00 | 17.52 | MTGL |
| ATOM | 1196 | N   | ALA | 154 | 39.596 | 18.318 | 26.858 | 1.00 | 17.93 | MTGL |
| ATOM | 1197 | CA  | ALA | 154 | 39.359 | 18.255 | 25.416 | 1.00 | 18.68 | MTGL |
| ATOM | 1198 | CB  | ALA | 154 | 38.884 | 19.620 | 24.896 | 1.00 | 17.82 | MTGL |
| ATOM | 1199 | C   | ALA | 154 | 40.624 | 17.834 | 24.686 | 1.00 | 18.79 | MTGL |
| ATOM | 1200 | O   | ALA | 154 | 40.584 | 17.037 | 23.744 | 1.00 | 17.95 | MTGL |
| ATOM | 1201 | N   | ARG | 155 | 41.749 | 18.375 | 25.131 | 1.00 | 18.32 | MTGL |
| ATOM | 1202 | CA  | ARG | 155 | 43.025 | 18.064 | 24.512 | 1.00 | 19.09 | MTGL |
| ATOM | 1203 | CB  | ARG | 155 | 44.098 | 18.972 | 25.094 | 1.00 | 20.03 | MTGL |
| ATOM | 1204 | CG  | ARG | 155 | 45.415 | 18.867 | 24.403 | 1.00 | 23.57 | MTGL |
| ATOM | 1205 | CD  | ARG | 155 | 46.295 | 19.990 | 24.873 | 1.00 | 26.84 | MTGL |
| ATOM | 1206 | NE  | ARG | 155 | 47.681 | 19.767 | 24.498 | 1.00 | 29.65 | MTGL |
| ATOM | 1207 | CZ  | ARG | 155 | 48.686 | 20.513 | 24.931 | 1.00 | 28.58 | MTGL |
| ATOM | 1208 | NH1 | ARG | 155 | 48.443 | 21.525 | 25.753 | 1.00 | 29.23 | MTGL |
| ATOM | 1209 | NH2 | ARG | 155 | 49.922 | 20.244 | 24.540 | 1.00 | 29.12 | MTGL |
| ATOM | 1210 | C   | ARG | 155 | 43.402 | 16.598 | 24.721 | 1.00 | 18.37 | MTGL |
| ATOM | 1211 | O   | ARG | 155 | 43.848 | 15.916 | 23.792 | 1.00 | 17.92 | MTGL |
| ATOM | 1212 | N   | LEU | 156 | 43.217 | 16.115 | 25.944 | 1.00 | 17.77 | MTGL |
| ATOM | 1213 | CA  | LEU | 156 | 43.540 | 14.731 | 26.258 | 1.00 | 17.18 | MTGL |
| ATOM | 1214 | CB  | LEU | 156 | 43.360 | 14.473 | 27.761 | 1.00 | 16.68 | MTGL |
| ATOM | 1215 | CG  | LEU | 156 | 44.375 | 15.158 | 28.689 | 1.00 | 16.04 | MTGL |
| ATOM | 1216 | CD1 | LEU | 156 | 43.921 | 15.032 | 30.139 | 1.00 | 17.64 | MTGL |
| ATOM | 1217 | CD2 | LEU | 156 | 45.745 | 14.532 | 28.504 | 1.00 | 14.11 | MTGL |

Fig. 1 cont.

```
ATOM   1218  C    LEU  156      42.660  13.777  25.447  1.00 17.29      MTGL
ATOM   1219  O    LEU  156      43.152  12.794  24.886  1.00 16.71      MTGL
ATOM   1220  N    LEU  157      41.363  14.071  25.377  1.00 16.48      MTGL
ATOM   1221  CA   LEU  157      40.438  13.219  24.639  1.00 16.71      MTGL
ATOM   1222  CB   LEU  157      38.992  13.651  24.900  1.00 15.25      MTGL
ATOM   1223  CG   LEU  157      38.509  13.425  26.339  1.00 14.15      MTGL
ATOM   1224  CD1  LEU  157      37.080  13.903  26.505  1.00 13.65      MTGL
ATOM   1225  CD2  LEU  157      38.599  11.944  26.676  1.00 13.61      MTGL
ATOM   1226  C    LEU  157      40.744  13.230  23.146  1.00 18.12      MTGL
ATOM   1227  O    LEU  157      40.549  12.224  22.456  1.00 16.85      MTGL
ATOM   1228  N    HIS  158      41.231  14.366  22.652  1.00 19.80      MTGL
ATOM   1229  CA   HIS  158      41.600  14.498  21.244  1.00 20.98      MTGL
ATOM   1230  CB   HIS  158      42.001  15.946  20.938  1.00 22.94      MTGL
ATOM   1231  CG   HIS  158      42.458  16.170  19.528  1.00 24.32      MTGL
ATOM   1232  CD2  HIS  158      43.695  16.367  19.013  1.00 23.88      MTGL
ATOM   1233  ND1  HIS  158      41.586  16.230  18.460  1.00 24.92      MTGL
ATOM   1234  CE1  HIS  158      42.266  16.460  17.350  1.00 23.22      MTGL
ATOM   1235  NE2  HIS  158      43.548  16.547  17.658  1.00 24.57      MTGL
ATOM   1236  C    HIS  158      42.783  13.567  20.973  1.00 21.01      MTGL
ATOM   1237  O    HIS  158      42.809  12.851  19.971  1.00 21.78      MTGL
ATOM   1238  N    SER  159      43.762  13.578  21.874  1.00 20.28      MTGL
ATOM   1239  CA   SER  159      44.940  12.730  21.726  1.00 20.15      MTGL
ATOM   1240  CB   SER  159      45.961  13.021  22.829  1.00 21.81      MTGL
ATOM   1241  OG   SER  159      46.476  14.333  22.721  1.00 24.73      MTGL
ATOM   1242  C    SER  159      44.570  11.253  21.774  1.00 18.92      MTGL
ATOM   1243  O    SER  159      45.095  10.453  21.004  1.00 19.31      MTGL
ATOM   1244  N    ALA  160      43.675  10.894  22.687  1.00 17.87      MTGL
ATOM   1245  CA   ALA  160      43.249   9.504  22.824  1.00 17.96      MTGL
ATOM   1246  CB   ALA  160      42.322   9.352  24.026  1.00 18.26      MTGL
ATOM   1247  C    ALA  160      42.538   9.044  21.556  1.00 18.59      MTGL
ATOM   1248  O    ALA  160      42.844   7.982  21.013  1.00 17.77      MTGL
ATOM   1249  N    ALA  161      41.593   9.852  21.083  1.00 18.03      MTGL
ATOM   1250  CA   ALA  161      40.846   9.519  19.875  1.00 18.84      MTGL
ATOM   1251  CB   ALA  161      39.851  10.623  19.547  1.00 16.85      MTGL
ATOM   1252  C    ALA  161      41.778   9.294  18.695  1.00 18.82      MTGL
ATOM   1253  O    ALA  161      41.654   8.301  17.983  1.00 19.53      MTGL
ATOM   1254  N    TRP  162      42.715  10.211  18.485  1.00 18.98      MTGL
ATOM   1255  CA   TRP  162      43.636  10.057  17.371  1.00 19.92      MTGL
ATOM   1256  CB   TRP  162      44.330  11.386  17.064  1.00 21.12      MTGL
ATOM   1257  CG   TRP  162      43.420  12.264  16.268  1.00 24.00      MTGL
ATOM   1258  CD2  TRP  162      43.215  12.212  14.851  1.00 24.55      MTGL
ATOM   1259  CE2  TRP  162      42.158  13.102  14.546  1.00 24.96      MTGL
ATOM   1260  CE3  TRP  162      43.822  11.499  13.808  1.00 25.38      MTGL
ATOM   1261  CD1  TRP  162      42.509  13.160  16.752  1.00 24.55      MTGL
ATOM   1262  NE1  TRP  162      41.743  13.665  15.724  1.00 25.20      MTGL
ATOM   1263  CZ2  TRP  162      41.691  13.293  13.241  1.00 24.56      MTGL
ATOM   1264  CZ3  TRP  162      43.355  11.689  12.507  1.00 25.72      MTGL
ATOM   1265  CH2  TRP  162      42.302  12.581  12.238  1.00 24.73      MTGL
ATOM   1266  C    TRP  162      44.643   8.927  17.556  1.00 20.10      MTGL
ATOM   1267  O    TRP  162      45.263   8.483  16.596  1.00 19.99      MTGL
ATOM   1268  N    GLY  163      44.803   8.458  18.786  1.00 20.69      MTGL
ATOM   1269  CA   GLY  163      45.703   7.343  19.016  1.00 20.86      MTGL
ATOM   1270  C    GLY  163      45.051   6.124  18.375  1.00 20.81      MTGL
ATOM   1271  O    GLY  163      45.720   5.225  17.868  1.00 20.64      MTGL
ATOM   1272  N    ILE  164      43.724   6.109  18.395  1.00 20.00      MTGL
ATOM   1273  CA   ILE  164      42.956   5.020  17.810  1.00 19.28      MTGL
ATOM   1274  CB   ILE  164      41.515   5.020  18.347  1.00 18.69      MTGL
ATOM   1275  CG2  ILE  164      40.670   3.977  17.601  1.00 17.15      MTGL
```

Fig. 1 cont.

| ATOM | 1276 | CG1 | ILE | 164 | 41.529 | 4.750 | 19.852 | 1.00 | 18.11 | MTGL |
|------|------|-----|-----|-----|--------|-------|--------|------|-------|------|
| ATOM | 1277 | CD1 | ILE | 164 | 40.155 | 4.779 | 20.489 | 1.00 | 18.52 | MTGL |
| ATOM | 1278 | C | ILE | 164 | 42.913 | 5.181 | 16.291 | 1.00 | 20.20 | MTGL |
| ATOM | 1279 | O | ILE | 164 | 43.125 | 4.219 | 15.548 | 1.00 | 18.00 | MTGL |
| ATOM | 1280 | N | LYS | 165 | 42.645 | 6.405 | 15.839 | 1.00 | 20.30 | MTGL |
| ATOM | 1281 | CA | LYS | 165 | 42.563 | 6.701 | 14.410 | 1.00 | 21.80 | MTGL |
| ATOM | 1282 | CB | LYS | 165 | 42.100 | 8.149 | 14.191 | 1.00 | 21.88 | MTGL |
| ATOM | 1283 | CG | LYS | 165 | 40.670 | 8.436 | 14.647 | 1.00 | 23.28 | MTGL |
| ATOM | 1284 | CD | LYS | 165 | 40.346 | 9.924 | 14.509 | 1.00 | 22.94 | MTGL |
| ATOM | 1285 | CE | LYS | 165 | 38.989 | 10.268 | 15.097 | 1.00 | 24.34 | MTGL |
| ATOM | 1286 | NZ | LYS | 165 | 37.857 | 9.632 | 14.363 | 1.00 | 25.77 | MTGL |
| ATOM | 1287 | C | LYS | 165 | 43.879 | 6.468 | 13.668 | 1.00 | 21.72 | MTGL |
| ATOM | 1288 | O | LYS | 165 | 43.868 | 6.086 | 12.501 | 1.00 | 21.82 | MTGL |
| ATOM | 1289 | N | ASP | 166 | 45.009 | 6.699 | 14.335 | 1.00 | 22.15 | MTGL |
| ATOM | 1290 | CA | ASP | 166 | 46.315 | 6.496 | 13.705 | 1.00 | 21.98 | MTGL |
| ATOM | 1291 | CB | ASP | 166 | 47.373 | 7.438 | 14.299 | 1.00 | 22.61 | MTGL |
| ATOM | 1292 | CG | ASP | 166 | 47.119 | 8.907 | 13.970 | 1.00 | 24.69 | MTGL |
| ATOM | 1293 | OD1 | ASP | 166 | 46.345 | 9.197 | 13.032 | 1.00 | 25.51 | MTGL |
| ATOM | 1294 | OD2 | ASP | 166 | 47.709 | 9.775 | 14.645 | 1.00 | 23.73 | MTGL |
| ATOM | 1295 | C | ASP | 166 | 46.818 | 5.063 | 13.853 | 1.00 | 21.80 | MTGL |
| ATOM | 1296 | O | ASP | 166 | 47.900 | 4.737 | 13.373 | 1.00 | 22.35 | MTGL |
| ATOM | 1297 | N | SER | 167 | 46.043 | 4.208 | 14.511 | 1.00 | 21.58 | MTGL |
| ATOM | 1298 | CA | SER | 167 | 46.460 | 2.822 | 14.722 | 1.00 | 21.57 | MTGL |
| ATOM | 1299 | CB | SER | 167 | 45.724 | 2.229 | 15.927 | 1.00 | 20.98 | MTGL |
| ATOM | 1300 | OG | SER | 167 | 44.368 | 1.952 | 15.620 | 1.00 | 20.07 | MTGL |
| ATOM | 1301 | C | SER | 167 | 46.235 | 1.920 | 13.508 | 1.00 | 21.73 | MTGL |
| ATOM | 1302 | O | SER | 167 | 45.669 | 2.347 | 12.503 | 1.00 | 21.01 | MTGL |
| ATOM | 1303 | N | SER | 168 | 46.676 | 0.668 | 13.619 | 1.00 | 21.44 | MTGL |
| ATOM | 1304 | CA | SER | 168 | 46.520 | -0.304 | 12.539 | 1.00 | 20.71 | MTGL |
| ATOM | 1305 | CB | SER | 168 | 47.711 | -1.264 | 12.519 | 1.00 | 21.31 | MTGL |
| ATOM | 1306 | OG | SER | 168 | 47.836 | -1.921 | 13.768 | 1.00 | 23.08 | MTGL |
| ATOM | 1307 | C | SER | 168 | 45.229 | -1.116 | 12.654 | 1.00 | 20.14 | MTGL |
| ATOM | 1308 | O | SER | 168 | 45.001 | -2.033 | 11.869 | 1.00 | 19.79 | MTGL |
| ATOM | 1309 | N | LEU | 169 | 44.388 | -0.792 | 13.630 | 1.00 | 19.27 | MTGL |
| ATOM | 1310 | CA | LEU | 169 | 43.132 | -1.514 | 13.791 | 1.00 | 19.92 | MTGL |
| ATOM | 1311 | CB | LEU | 169 | 42.306 | -0.921 | 14.935 | 1.00 | 19.48 | MTGL |
| ATOM | 1312 | CG | LEU | 169 | 42.758 | -1.226 | 16.365 | 1.00 | 19.56 | MTGL |
| ATOM | 1313 | CD1 | LEU | 169 | 41.918 | -0.417 | 17.342 | 1.00 | 18.93 | MTGL |
| ATOM | 1314 | CD2 | LEU | 169 | 42.612 | -2.717 | 16.650 | 1.00 | 19.30 | MTGL |
| ATOM | 1315 | C | LEU | 169 | 42.323 | -1.450 | 12.501 | 1.00 | 20.54 | MTGL |
| ATOM | 1316 | O | LEU | 169 | 42.053 | -0.365 | 11.981 | 1.00 | 20.27 | MTGL |
| ATOM | 1317 | N | SER | 170 | 41.940 | -2.614 | 11.987 | 1.00 | 20.36 | MTGL |
| ATOM | 1318 | CA | SER | 170 | 41.159 | -2.678 | 10.760 | 1.00 | 21.47 | MTGL |
| ATOM | 1319 | CB | SER | 170 | 42.088 | -2.784 | 9.545 | 1.00 | 22.54 | MTGL |
| ATOM | 1320 | OG | SER | 170 | 41.344 | -2.749 | 8.341 | 1.00 | 22.78 | MTGL |
| ATOM | 1321 | C | SER | 170 | 40.216 | -3.875 | 10.797 | 1.00 | 21.69 | MTGL |
| ATOM | 1322 | O | SER | 170 | 40.659 | -5.024 | 10.819 | 1.00 | 21.79 | MTGL |
| ATOM | 1323 | N | PRO | 171 | 38.899 | -3.621 | 10.800 | 1.00 | 21.30 | MTGL |
| ATOM | 1324 | CD | PRO | 171 | 37.874 | -4.676 | 10.884 | 1.00 | 21.70 | MTGL |
| ATOM | 1325 | CA | PRO | 171 | 38.277 | -2.294 | 10.764 | 1.00 | 21.48 | MTGL |
| ATOM | 1326 | CB | PRO | 171 | 36.806 | -2.616 | 10.530 | 1.00 | 21.60 | MTGL |
| ATOM | 1327 | CG | PRO | 171 | 36.644 | -3.901 | 11.285 | 1.00 | 22.67 | MTGL |
| ATOM | 1328 | C | PRO | 171 | 38.497 | -1.472 | 12.039 | 1.00 | 21.36 | MTGL |
| ATOM | 1329 | O | PRO | 171 | 38.790 | -2.009 | 13.109 | 1.00 | 20.24 | MTGL |
| ATOM | 1330 | N | LYS | 172 | 38.351 | -0.161 | 11.908 | 1.00 | 20.37 | MTGL |
| ATOM | 1331 | CA | LYS | 172 | 38.525 | 0.749 | 13.032 | 1.00 | 21.42 | MTGL |
| ATOM | 1332 | CB | LYS | 172 | 38.670 | 2.183 | 12.501 | 1.00 | 22.43 | MTGL |
| ATOM | 1333 | CG | LYS | 172 | 39.602 | 3.071 | 13.310 | 1.00 | 25.68 | MTGL |

Fig. 1 cont.

| | | | | | | | | | |
|---|---|---|---|---|---|---|---|---|---|
| ATOM | 1334 | CD | LYS | 172 | 41.052 | 2.616 | 13.220 | 1.00 24.85 | MTGL |
| ATOM | 1335 | CE | LYS | 172 | 41.659 | 2.946 | 11.878 | 1.00 25.80 | MTGL |
| ATOM | 1336 | NZ | LYS | 172 | 42.984 | 2.294 | 11.703 | 1.00 24.26 | MTGL |
| ATOM | 1337 | C | LYS | 172 | 37.295 | 0.626 | 13.940 | 1.00 20.16 | MTGL |
| ATOM | 1338 | O | LYS | 172 | 36.199 | 0.307 | 13.478 | 1.00 19.92 | MTGL |
| ATOM | 1339 | N | PRO | 173 | 37.465 | 0.848 | 15.248 | 1.00 19.30 | MTGL |
| ATOM | 1340 | CD | PRO | 173 | 38.722 | 1.088 | 15.980 | 1.00 19.67 | MTGL |
| ATOM | 1341 | CA | PRO | 173 | 36.335 | 0.751 | 16.177 | 1.00 19.05 | MTGL |
| ATOM | 1342 | CB | PRO | 173 | 37.018 | 0.437 | 17.497 | 1.00 19.14 | MTGL |
| ATOM | 1343 | CG | PRO | 173 | 38.237 | 1.321 | 17.412 | 1.00 18.48 | MTGL |
| ATOM | 1344 | C | PRO | 173 | 35.565 | 2.066 | 16.270 | 1.00 18.59 | MTGL |
| ATOM | 1345 | O | PRO | 173 | 36.049 | 3.110 | 15.832 | 1.00 16.92 | MTGL |
| ATOM | 1346 | N | LYS | 174 | 34.359 | 2.007 | 16.824 | 1.00 17.93 | MTGL |
| ATOM | 1347 | CA | LYS | 174 | 33.591 | 3.222 | 17.037 | 1.00 18.70 | MTGL |
| ATOM | 1348 | CB | LYS | 174 | 32.109 | 2.901 | 17.240 | 1.00 18.25 | MTGL |
| ATOM | 1349 | CG | LYS | 174 | 31.388 | 2.529 | 15.947 | 1.00 19.90 | MTGL |
| ATOM | 1350 | CD | LYS | 174 | 29.937 | 2.142 | 16.200 | 1.00 20.92 | MTGL |
| ATOM | 1351 | CE | LYS | 174 | 29.230 | 1.784 | 14.892 | 1.00 21.51 | MTGL |
| ATOM | 1352 | NZ | LYS | 174 | 27.839 | 1.317 | 15.135 | 1.00 20.89 | MTGL |
| ATOM | 1353 | C | LYS | 174 | 34.193 | 3.808 | 18.318 | 1.00 18.48 | MTGL |
| ATOM | 1354 | O | LYS | 174 | 34.452 | 3.076 | 19.281 | 1.00 18.00 | MTGL |
| ATOM | 1355 | N | ILE | 175 | 34.448 | 5.112 | 18.320 | 1.00 17.76 | MTGL |
| ATOM | 1356 | CA | ILE | 175 | 35.033 | 5.768 | 19.487 | 1.00 17.60 | MTGL |
| ATOM | 1357 | CB | ILE | 175 | 35.999 | 6.883 | 19.050 | 1.00 17.54 | MTGL |
| ATOM | 1358 | CG2 | ILE | 175 | 36.564 | 7.610 | 20.271 | 1.00 17.48 | MTGL |
| ATOM | 1359 | CG1 | ILE | 175 | 37.134 | 6.266 | 18.226 | 1.00 16.88 | MTGL |
| ATOM | 1360 | CD1 | ILE | 175 | 38.083 | 7.263 | 17.618 | 1.00 15.96 | MTGL |
| ATOM | 1361 | C | ILE | 175 | 33.945 | 6.330 | 20.393 | 1.00 17.11 | MTGL |
| ATOM | 1362 | O | ILE | 175 | 33.102 | 7.122 | 19.962 | 1.00 17.92 | MTGL |
| ATOM | 1363 | N | MET | 176 | 33.966 | 5.914 | 21.653 | 1.00 16.13 | MTGL |
| ATOM | 1364 | CA | MET | 176 | 32.955 | 6.345 | 22.615 | 1.00 16.14 | MTGL |
| ATOM | 1365 | CB | MET | 176 | 32.223 | 5.120 | 23.171 | 1.00 16.50 | MTGL |
| ATOM | 1366 | CG | MET | 176 | 31.333 | 5.410 | 24.379 | 1.00 16.70 | MTGL |
| ATOM | 1367 | SD | MET | 176 | 30.643 | 3.896 | 25.097 | 1.00 19.61 | MTGL |
| ATOM | 1368 | CE | MET | 176 | 29.473 | 3.433 | 23.769 | 1.00 15.92 | MTGL |
| ATOM | 1369 | C | MET | 176 | 33.458 | 7.163 | 23.797 | 1.00 16.18 | MTGL |
| ATOM | 1370 | O | MET | 176 | 34.562 | 6.946 | 24.299 | 1.00 15.62 | MTGL |
| ATOM | 1371 | N | ILE | 177 | 32.628 | 8.109 | 24.227 | 1.00 16.05 | MTGL |
| ATOM | 1372 | CA | ILE | 177 | 32.915 | 8.927 | 25.402 | 1.00 16.22 | MTGL |
| ATOM | 1373 | CB | ILE | 177 | 32.786 | 10.436 | 25.117 | 1.00 15.59 | MTGL |
| ATOM | 1374 | CG2 | ILE | 177 | 32.729 | 11.210 | 26.438 | 1.00 16.50 | MTGL |
| ATOM | 1375 | CG1 | ILE | 177 | 33.985 | 10.900 | 24.273 | 1.00 16.91 | MTGL |
| ATOM | 1376 | CD1 | ILE | 177 | 33.988 | 12.380 | 23.935 | 1.00 17.23 | MTGL |
| ATOM | 1377 | C | ILE | 177 | 31.847 | 8.467 | 26.383 | 1.00 15.72 | MTGL |
| ATOM | 1378 | O | ILE | 177 | 30.660 | 8.467 | 26.062 | 1.00 16.21 | MTGL |
| ATOM | 1379 | N | HIS | 178 | 32.278 | 8.061 | 27.571 | 1.00 16.15 | MTGL |
| ATOM | 1380 | CA | HIS | 178 | 31.376 | 7.518 | 28.581 | 1.00 16.02 | MTGL |
| ATOM | 1381 | CB | HIS | 178 | 31.866 | 6.112 | 28.949 | 1.00 14.76 | MTGL |
| ATOM | 1382 | CG | HIS | 178 | 31.099 | 5.461 | 30.057 | 1.00 14.66 | MTGL |
| ATOM | 1383 | CD2 | HIS | 178 | 29.850 | 5.681 | 30.534 | 1.00 13.15 | MTGL |
| ATOM | 1384 | ND1 | HIS | 178 | 31.612 | 4.415 | 30.793 | 1.00 13.39 | MTGL |
| ATOM | 1385 | CE1 | HIS | 178 | 30.714 | 4.020 | 31.679 | 1.00 14.18 | MTGL |
| ATOM | 1386 | NE2 | HIS | 178 | 29.636 | 4.770 | 31.543 | 1.00 13.19 | MTGL |
| ATOM | 1387 | C | HIS | 178 | 31.232 | 8.354 | 29.850 | 1.00 16.83 | MTGL |
| ATOM | 1388 | O | HIS | 178 | 32.210 | 8.605 | 30.553 | 1.00 16.59 | MTGL |
| ATOM | 1389 | N | LEU | 179 | 29.997 | 8.757 | 30.138 | 1.00 17.26 | MTGL |
| ATOM | 1390 | CA | LEU | 179 | 29.670 | 9.539 | 31.329 | 1.00 18.11 | MTGL |
| ATOM | 1391 | CB | LEU | 179 | 29.014 | 10.866 | 30.925 | 1.00 18.73 | MTGL |

Fig. 1 cont.

| ATOM | 1392 | CG  | LEU | 179 | 29.877 | 12.128 | 30.808 | 1.00 | 20.65 | MTGL |
| ATOM | 1393 | CD1 | LEU | 179 | 31.265 | 11.812 | 30.272 | 1.00 | 19.45 | MTGL |
| ATOM | 1394 | CD2 | LEU | 179 | 29.150 | 13.130 | 29.923 | 1.00 | 20.83 | MTGL |
| ATOM | 1395 | C   | LEU | 179 | 28.693 | 8.732  | 32.186 | 1.00 | 18.96 | MTGL |
| ATOM | 1396 | O   | LEU | 179 | 27.947 | 7.899  | 31.668 | 1.00 | 19.30 | MTGL |
| ATOM | 1397 | N   | ASP | 180 | 28.693 | 8.974  | 33.493 | 1.00 | 18.24 | MTGL |
| ATOM | 1398 | CA  | ASP | 180 | 27.780 | 8.267  | 34.385 | 1.00 | 18.02 | MTGL |
| ATOM | 1399 | CB  | ASP | 180 | 28.377 | 8.171  | 35.795 | 1.00 | 17.69 | MTGL |
| ATOM | 1400 | CG  | ASP | 180 | 28.398 | 9.505  | 36.518 | 1.00 | 19.25 | MTGL |
| ATOM | 1401 | OD1 | ASP | 180 | 28.702 | 10.538 | 35.884 | 1.00 | 19.57 | MTGL |
| ATOM | 1402 | OD2 | ASP | 180 | 28.117 | 9.512  | 37.734 | 1.00 | 20.92 | MTGL |
| ATOM | 1403 | C   | ASP | 180 | 26.453 | 9.020  | 34.430 | 1.00 | 18.13 | MTGL |
| ATOM | 1404 | O   | ASP | 180 | 26.268 | 9.995  | 33.708 | 1.00 | 17.92 | MTGL |
| ATOM | 1405 | N   | ASN | 181 | 25.533 | 8.546  | 35.266 | 1.00 | 19.02 | MTGL |
| ATOM | 1406 | CA  | ASN | 181 | 24.219 | 9.165  | 35.439 | 1.00 | 19.13 | MTGL |
| ATOM | 1407 | CB  | ASN | 181 | 24.337 | 10.360 | 36.393 | 1.00 | 19.61 | MTGL |
| ATOM | 1408 | CG  | ASN | 181 | 24.840 | 9.959  | 37.776 | 1.00 | 20.81 | MTGL |
| ATOM | 1409 | OD1 | ASN | 181 | 24.561 | 8.857  | 38.259 | 1.00 | 20.36 | MTGL |
| ATOM | 1410 | ND2 | ASN | 181 | 25.567 | 10.862 | 38.427 | 1.00 | 21.46 | MTGL |
| ATOM | 1411 | C   | ASN | 181 | 23.541 | 9.604  | 34.135 | 1.00 | 19.21 | MTGL |
| ATOM | 1412 | O   | ASN | 181 | 23.277 | 10.791 | 33.925 | 1.00 | 18.32 | MTGL |
| ATOM | 1413 | N   | GLY | 182 | 23.238 | 8.635  | 33.276 | 1.00 | 18.94 | MTGL |
| ATOM | 1414 | CA  | GLY | 182 | 22.610 | 8.937  | 32.003 | 1.00 | 18.55 | MTGL |
| ATOM | 1415 | C   | GLY | 182 | 21.309 | 9.704  | 32.101 | 1.00 | 18.91 | MTGL |
| ATOM | 1416 | O   | GLY | 182 | 20.952 | 10.428 | 31.179 | 1.00 | 18.95 | MTGL |
| ATOM | 1417 | N   | TRP | 183 | 20.609 | 9.546  | 33.219 | 1.00 | 19.65 | MTGL |
| ATOM | 1418 | CA  | TRP | 183 | 19.332 | 10.213 | 33.459 | 1.00 | 19.57 | MTGL |
| ATOM | 1419 | CB  | TRP | 183 | 18.643 | 9.588  | 34.671 | 1.00 | 20.28 | MTGL |
| ATOM | 1420 | CG  | TRP | 183 | 19.515 | 9.586  | 35.904 | 1.00 | 21.43 | MTGL |
| ATOM | 1421 | CD2 | TRP | 183 | 19.671 | 10.653 | 36.856 | 1.00 | 21.48 | MTGL |
| ATOM | 1422 | CE2 | TRP | 183 | 20.614 | 10.222 | 37.816 | 1.00 | 21.25 | MTGL |
| ATOM | 1423 | CE3 | TRP | 183 | 19.103 | 11.931 | 36.989 | 1.00 | 21.53 | MTGL |
| ATOM | 1424 | CD1 | TRP | 183 | 20.348 | 8.585  | 36.316 | 1.00 | 20.88 | MTGL |
| ATOM | 1425 | NE1 | TRP | 183 | 21.011 | 8.959  | 37.463 | 1.00 | 21.48 | MTGL |
| ATOM | 1426 | CZ2 | TRP | 183 | 21.010 | 11.024 | 38.896 | 1.00 | 22.46 | MTGL |
| ATOM | 1427 | CZ3 | TRP | 183 | 19.497 | 12.732 | 38.065 | 1.00 | 21.36 | MTGL |
| ATOM | 1428 | CH2 | TRP | 183 | 20.440 | 12.272 | 39.004 | 1.00 | 21.87 | MTGL |
| ATOM | 1429 | C   | TRP | 183 | 19.477 | 11.705 | 33.724 | 1.00 | 20.04 | MTGL |
| ATOM | 1430 | O   | TRP | 183 | 18.506 | 12.457 | 33.613 | 1.00 | 19.18 | MTGL |
| ATOM | 1431 | N   | ASP | 184 | 20.686 | 12.126 | 34.083 | 1.00 | 20.76 | MTGL |
| ATOM | 1432 | CA  | ASP | 184 | 20.957 | 13.522 | 34.417 | 1.00 | 20.14 | MTGL |
| ATOM | 1433 | CB  | ASP | 184 | 22.085 | 13.581 | 35.455 | 1.00 | 21.31 | MTGL |
| ATOM | 1434 | CG  | ASP | 184 | 22.327 | 14.986 | 35.988 | 1.00 | 24.62 | MTGL |
| ATOM | 1435 | OD1 | ASP | 184 | 21.643 | 15.936 | 35.540 | 1.00 | 24.90 | MTGL |
| ATOM | 1436 | OD2 | ASP | 184 | 23.210 | 15.138 | 36.859 | 1.00 | 25.79 | MTGL |
| ATOM | 1437 | C   | ASP | 184 | 21.312 | 14.374 | 33.201 | 1.00 | 20.22 | MTGL |
| ATOM | 1438 | O   | ASP | 184 | 22.487 | 14.584 | 32.899 | 1.00 | 19.35 | MTGL |
| ATOM | 1439 | N   | TRP | 185 | 20.289 | 14.879 | 32.518 | 1.00 | 19.30 | MTGL |
| ATOM | 1440 | CA  | TRP | 185 | 20.498 | 15.704 | 31.333 | 1.00 | 19.09 | MTGL |
| ATOM | 1441 | CB  | TRP | 185 | 19.148 | 16.149 | 30.753 | 1.00 | 18.81 | MTGL |
| ATOM | 1442 | CG  | TRP | 185 | 19.267 | 17.255 | 29.746 | 1.00 | 18.32 | MTGL |
| ATOM | 1443 | CD2 | TRP | 185 | 20.044 | 17.245 | 28.541 | 1.00 | 18.10 | MTGL |
| ATOM | 1444 | CE2 | TRP | 185 | 19.889 | 18.509 | 27.933 | 1.00 | 18.68 | MTGL |
| ATOM | 1445 | CE3 | TRP | 185 | 20.856 | 16.290 | 27.917 | 1.00 | 18.54 | MTGL |
| ATOM | 1446 | CD1 | TRP | 185 | 18.686 | 18.491 | 29.814 | 1.00 | 18.71 | MTGL |
| ATOM | 1447 | NE1 | TRP | 185 | 19.057 | 19.250 | 28.730 | 1.00 | 18.49 | MTGL |
| ATOM | 1448 | CZ2 | TRP | 185 | 20.518 | 18.845 | 26.732 | 1.00 | 19.18 | MTGL |
| ATOM | 1449 | CZ3 | TRP | 185 | 21.484 | 16.626 | 26.722 | 1.00 | 18.13 | MTGL |

Fig. 1 cont.

| ATOM | 1450 | CH2 | TRP | 185 | 21.311 | 17.891 | 26.144 | 1.00 | 19.60 | MTGL |
|------|------|-----|-----|-----|--------|--------|--------|------|-------|------|
| ATOM | 1451 | C   | TRP | 185 | 21.360 | 16.931 | 31.626 | 1.00 | 18.76 | MTGL |
| ATOM | 1452 | O   | TRP | 185 | 22.271 | 17.256 | 30.866 | 1.00 | 17.61 | MTGL |
| ATOM | 1453 | N   | GLY | 186 | 21.068 | 17.612 | 32.731 | 1.00 | 19.33 | MTGL |
| ATOM | 1454 | CA  | GLY | 186 | 21.834 | 18.797 | 33.081 | 1.00 | 19.04 | MTGL |
| ATOM | 1455 | C   | GLY | 186 | 23.336 | 18.565 | 33.066 | 1.00 | 19.17 | MTGL |
| ATOM | 1456 | O   | GLY | 186 | 24.098 | 19.353 | 32.505 | 1.00 | 19.02 | MTGL |
| ATOM | 1457 | N   | THR | 187 | 23.772 | 17.473 | 33.677 | 1.00 | 19.36 | MTGL |
| ATOM | 1458 | CA  | THR | 187 | 25.192 | 17.172 | 33.718 | 1.00 | 20.31 | MTGL |
| ATOM | 1459 | CB  | THR | 187 | 25.482 | 16.098 | 34.773 | 1.00 | 21.41 | MTGL |
| ATOM | 1460 | OG1 | THR | 187 | 25.114 | 16.609 | 36.059 | 1.00 | 21.37 | MTGL |
| ATOM | 1461 | CG2 | THR | 187 | 26.964 | 15.735 | 34.781 | 1.00 | 23.08 | MTGL |
| ATOM | 1462 | C   | THR | 187 | 25.731 | 16.745 | 32.359 | 1.00 | 19.27 | MTGL |
| ATOM | 1463 | O   | THR | 187 | 26.815 | 17.166 | 31.965 | 1.00 | 19.21 | MTGL |
| ATOM | 1464 | N   | GLN | 188 | 24.980 | 15.916 | 31.637 | 1.00 | 19.95 | MTGL |
| ATOM | 1465 | CA  | GLN | 188 | 25.420 | 15.479 | 30.312 | 1.00 | 19.24 | MTGL |
| ATOM | 1466 | CB  | GLN | 188 | 24.356 | 14.602 | 29.638 | 1.00 | 19.13 | MTGL |
| ATOM | 1467 | CG  | GLN | 188 | 24.033 | 13.278 | 30.329 | 1.00 | 18.75 | MTGL |
| ATOM | 1468 | CD  | GLN | 188 | 25.203 | 12.299 | 30.339 | 1.00 | 18.38 | MTGL |
| ATOM | 1469 | OE1 | GLN | 188 | 25.874 | 12.099 | 29.328 | 1.00 | 18.47 | MTGL |
| ATOM | 1470 | NE2 | GLN | 188 | 25.435 | 11.675 | 31.483 | 1.00 | 16.34 | MTGL |
| ATOM | 1471 | C   | GLN | 188 | 25.655 | 16.714 | 29.437 | 1.00 | 19.43 | MTGL |
| ATOM | 1472 | O   | GLN | 188 | 26.695 | 16.850 | 28.792 | 1.00 | 18.38 | MTGL |
| ATOM | 1473 | N   | ASN | 189 | 24.673 | 17.612 | 29.429 | 1.00 | 20.01 | MTGL |
| ATOM | 1474 | CA  | ASN | 189 | 24.733 | 18.830 | 28.625 | 1.00 | 20.84 | MTGL |
| ATOM | 1475 | CB  | ASN | 189 | 23.392 | 19.568 | 28.722 | 1.00 | 22.61 | MTGL |
| ATOM | 1476 | CG  | ASN | 189 | 23.323 | 20.781 | 27.813 | 1.00 | 24.36 | MTGL |
| ATOM | 1477 | OD1 | ASN | 189 | 23.788 | 20.744 | 26.674 | 1.00 | 24.74 | MTGL |
| ATOM | 1478 | ND2 | ASN | 189 | 22.725 | 21.860 | 28.310 | 1.00 | 24.46 | MTGL |
| ATOM | 1479 | C   | ASN | 189 | 25.878 | 19.746 | 29.050 | 1.00 | 21.20 | MTGL |
| ATOM | 1480 | O   | ASN | 189 | 26.622 | 20.267 | 28.214 | 1.00 | 20.76 | MTGL |
| ATOM | 1481 | N   | TRP | 190 | 26.015 | 19.935 | 30.356 | 1.00 | 21.74 | MTGL |
| ATOM | 1482 | CA  | TRP | 190 | 27.073 | 20.770 | 30.917 | 1.00 | 22.16 | MTGL |
| ATOM | 1483 | CB  | TRP | 190 | 26.959 | 20.758 | 32.442 | 1.00 | 23.20 | MTGL |
| ATOM | 1484 | CG  | TRP | 190 | 28.143 | 21.315 | 33.192 | 1.00 | 25.19 | MTGL |
| ATOM | 1485 | CD2 | TRP | 190 | 29.121 | 20.563 | 33.925 | 1.00 | 25.40 | MTGL |
| ATOM | 1486 | CE2 | TRP | 190 | 30.015 | 21.491 | 34.505 | 1.00 | 25.48 | MTGL |
| ATOM | 1487 | CE3 | TRP | 190 | 29.336 | 19.194 | 34.137 | 1.00 | 25.81 | MTGL |
| ATOM | 1488 | CD1 | TRP | 190 | 28.474 | 22.632 | 33.355 | 1.00 | 24.81 | MTGL |
| ATOM | 1489 | NE1 | TRP | 190 | 29.595 | 22.744 | 34.146 | 1.00 | 26.35 | MTGL |
| ATOM | 1490 | CZ2 | TRP | 190 | 31.098 | 21.095 | 35.298 | 1.00 | 26.43 | MTGL |
| ATOM | 1491 | CZ3 | TRP | 190 | 30.420 | 18.800 | 34.925 | 1.00 | 26.45 | MTGL |
| ATOM | 1492 | CH2 | TRP | 190 | 31.288 | 19.750 | 35.490 | 1.00 | 25.29 | MTGL |
| ATOM | 1493 | C   | TRP | 190 | 28.451 | 20.252 | 30.493 | 1.00 | 21.86 | MTGL |
| ATOM | 1494 | O   | TRP | 190 | 29.322 | 21.023 | 30.081 | 1.00 | 21.57 | MTGL |
| ATOM | 1495 | N   | TRP | 191 | 28.637 | 18.939 | 30.586 | 1.00 | 20.42 | MTGL |
| ATOM | 1496 | CA  | TRP | 191 | 29.915 | 18.325 | 30.245 | 1.00 | 19.96 | MTGL |
| ATOM | 1497 | CB  | TRP | 191 | 29.902 | 16.846 | 30.631 | 1.00 | 18.89 | MTGL |
| ATOM | 1498 | CG  | TRP | 191 | 31.272 | 16.231 | 30.703 | 1.00 | 18.14 | MTGL |
| ATOM | 1499 | CD2 | TRP | 191 | 32.017 | 15.658 | 29.621 | 1.00 | 17.74 | MTGL |
| ATOM | 1500 | CE2 | TRP | 191 | 33.244 | 15.201 | 30.154 | 1.00 | 17.14 | MTGL |
| ATOM | 1501 | CE3 | TRP | 191 | 31.767 | 15.481 | 28.253 | 1.00 | 17.05 | MTGL |
| ATOM | 1502 | CD1 | TRP | 191 | 32.058 | 16.108 | 31.815 | 1.00 | 18.47 | MTGL |
| ATOM | 1503 | NE1 | TRP | 191 | 33.241 | 15.489 | 31.494 | 1.00 | 16.67 | MTGL |
| ATOM | 1504 | CZ2 | TRP | 191 | 34.221 | 14.583 | 29.366 | 1.00 | 16.52 | MTGL |
| ATOM | 1505 | CZ3 | TRP | 191 | 32.739 | 14.862 | 27.468 | 1.00 | 15.97 | MTGL |
| ATOM | 1506 | CH2 | TRP | 191 | 33.950 | 14.420 | 28.030 | 1.00 | 16.29 | MTGL |
| ATOM | 1507 | C   | TRP | 191 | 30.293 | 18.455 | 28.770 | 1.00 | 19.44 | MTGL |

Fig. 1 cont.

```
ATOM   1508  O    TRP  191      31.342  19.019  28.436  1.00 18.48      MTGL
ATOM   1509  N    TYR  192      29.447  17.921  27.893  1.00 19.02      MTGL
ATOM   1510  CA   TYR  192      29.707  17.961  26.455  1.00 18.88      MTGL
ATOM   1511  CB   TYR  192      28.629  17.174  25.702  1.00 18.06      MTGL
ATOM   1512  CG   TYR  192      28.820  15.670  25.779  1.00 17.74      MTGL
ATOM   1513  CD1  TYR  192      29.890  15.048  25.126  1.00 17.96      MTGL
ATOM   1514  CE1  TYR  192      30.069  13.671  25.189  1.00 18.35      MTGL
ATOM   1515  CD2  TYR  192      27.935  14.870  26.502  1.00 16.89      MTGL
ATOM   1516  CE2  TYR  192      28.107  13.487  26.574  1.00 17.96      MTGL
ATOM   1517  CZ   TYR  192      29.172  12.895  25.917  1.00 18.14      MTGL
ATOM   1518  OH   TYR  192      29.340  11.530  25.986  1.00 19.50      MTGL
ATOM   1519  C    TYR  192      29.810  19.378  25.895  1.00 19.64      MTGL
ATOM   1520  O    TYR  192      30.661  19.651  25.047  1.00 17.67      MTGL
ATOM   1521  N    THR  193      28.956  20.280  26.373  1.00 20.13      MTGL
ATOM   1522  CA   THR  193      28.988  21.658  25.904  1.00 21.63      MTGL
ATOM   1523  CB   THR  193      27.884  22.504  26.569  1.00 21.95      MTGL
ATOM   1524  OG1  THR  193      26.600  21.990  26.195  1.00 23.39      MTGL
ATOM   1525  CG2  THR  193      27.978  23.956  26.114  1.00 23.15      MTGL
ATOM   1526  C    THR  193      30.346  22.306  26.189  1.00 21.54      MTGL
ATOM   1527  O    THR  193      30.978  22.863  25.291  1.00 21.18      MTGL
ATOM   1528  N    ASN  194      30.804  22.218  27.434  1.00 21.85      MTGL
ATOM   1529  CA   ASN  194      32.084  22.816  27.800  1.00 22.13      MTGL
ATOM   1530  CB   ASN  194      32.243  22.833  29.318  1.00 23.00      MTGL
ATOM   1531  CG   ASN  194      31.437  23.944  29.968  1.00 24.26      MTGL
ATOM   1532  OD1  ASN  194      31.675  25.123  29.709  1.00 25.08      MTGL
ATOM   1533  ND2  ASN  194      30.478  23.573  30.810  1.00 23.61      MTGL
ATOM   1534  C    ASN  194      33.292  22.146  27.156  1.00 21.45      MTGL
ATOM   1535  O    ASN  194      34.266  22.813  26.815  1.00 21.18      MTGL
ATOM   1536  N    VAL  195      33.236  20.831  26.986  1.00 21.36      MTGL
ATOM   1537  CA   VAL  195      34.346  20.123  26.362  1.00 20.65      MTGL
ATOM   1538  CB   VAL  195      34.187  18.590  26.503  1.00 20.76      MTGL
ATOM   1539  CG1  VAL  195      35.165  17.871  25.583  1.00 19.43      MTGL
ATOM   1540  CG2  VAL  195      34.429  18.179  27.947  1.00 20.62      MTGL
ATOM   1541  C    VAL  195      34.453  20.475  24.879  1.00 21.44      MTGL
ATOM   1542  O    VAL  195      35.540  20.792  24.385  1.00 20.78      MTGL
ATOM   1543  N    LEU  196      33.323  20.429  24.178  1.00 21.29      MTGL
ATOM   1544  CA   LEU  196      33.300  20.712  22.746  1.00 23.23      MTGL
ATOM   1545  CB   LEU  196      31.953  20.285  22.150  1.00 22.71      MTGL
ATOM   1546  CG   LEU  196      31.703  18.772  22.118  1.00 24.14      MTGL
ATOM   1547  CD1  LEU  196      30.276  18.477  21.657  1.00 22.72      MTGL
ATOM   1548  CD2  LEU  196      32.720  18.115  21.187  1.00 23.15      MTGL
ATOM   1549  C    LEU  196      33.589  22.158  22.354  1.00 24.05      MTGL
ATOM   1550  O    LEU  196      34.054  22.413  21.250  1.00 24.38      MTGL
ATOM   1551  N    LYS  197      33.326  23.104  23.248  1.00 25.84      MTGL
ATOM   1552  CA   LYS  197      33.562  24.506  22.919  1.00 27.64      MTGL
ATOM   1553  CB   LYS  197      32.753  25.413  23.850  1.00 29.58      MTGL
ATOM   1554  CG   LYS  197      33.282  25.505  25.268  1.00 32.86      MTGL
ATOM   1555  CD   LYS  197      32.239  26.101  26.207  1.00 35.16      MTGL
ATOM   1556  CE   LYS  197      31.742  27.456  25.726  1.00 37.48      MTGL
ATOM   1557  NZ   LYS  197      30.672  28.001  26.617  1.00 39.55      MTGL
ATOM   1558  C    LYS  197      35.038  24.897  22.956  1.00 27.59      MTGL
ATOM   1559  O    LYS  197      35.397  26.010  22.577  1.00 27.09      MTGL
ATOM   1560  N    GLN  198      35.896  23.980  23.395  1.00 27.10      MTGL
ATOM   1561  CA   GLN  198      37.323  24.271  23.459  1.00 26.85      MTGL
ATOM   1562  CB   GLN  198      38.053  23.202  24.274  1.00 26.22      MTGL
ATOM   1563  CG   GLN  198      37.608  23.127  25.718  1.00 24.93      MTGL
ATOM   1564  CD   GLN  198      37.637  24.480  26.400  1.00 25.72      MTGL
ATOM   1565  OE1  GLN  198      38.667  25.152  26.432  1.00 25.49      MTGL
```

Fig. 1 cont.

```
ATOM   1566  NE2  GLN  198      36.501  24.886  26.950  1.00  24.69      MTGL
ATOM   1567  C    GLN  198      37.953  24.381  22.071  1.00  27.46      MTGL
ATOM   1568  O    GLN  198      38.937  25.097  21.885  1.00  27.60      MTGL
ATOM   1569  N    GLY  199      37.401  23.664  21.101  1.00  27.40      MTGL
ATOM   1570  CA   GLY  199      37.941  23.738  19.757  1.00  28.72      MTGL
ATOM   1571  C    GLY  199      39.002  22.713  19.397  1.00  29.03      MTGL
ATOM   1572  O    GLY  199      39.487  22.711  18.269  1.00  30.82      MTGL
ATOM   1573  N    THR  200      39.382  21.852  20.337  1.00  27.35      MTGL
ATOM   1574  CA   THR  200      40.377  20.823  20.041  1.00  26.65      MTGL
ATOM   1575  CB   THR  200      41.335  20.596  21.230  1.00  26.55      MTGL
ATOM   1576  OG1  THR  200      40.579  20.447  22.438  1.00  27.05      MTGL
ATOM   1577  CG2  THR  200      42.297  21.780  21.366  1.00  26.96      MTGL
ATOM   1578  C    THR  200      39.633  19.532  19.705  1.00  25.68      MTGL
ATOM   1579  O    THR  200      39.665  19.072  18.569  1.00  25.00      MTGL
ATOM   1580  N    LEU  201      38.960  18.947  20.690  1.00  25.02      MTGL
ATOM   1581  CA   LEU  201      38.180  17.745  20.428  1.00  24.16      MTGL
ATOM   1582  CB   LEU  201      37.701  17.105  21.734  1.00  23.23      MTGL
ATOM   1583  CG   LEU  201      36.814  15.867  21.556  1.00  23.41      MTGL
ATOM   1584  CD1  LEU  201      37.674  14.680  21.136  1.00  22.70      MTGL
ATOM   1585  CD2  LEU  201      36.099  15.552  22.852  1.00  23.70      MTGL
ATOM   1586  C    LEU  201      36.967  18.221  19.628  1.00  23.81      MTGL
ATOM   1587  O    LEU  201      36.280  19.152  20.041  1.00  22.98      MTGL
ATOM   1588  N    GLU  202      36.710  17.608  18.480  1.00  23.89      MTGL
ATOM   1589  CA   GLU  202      35.554  18.002  17.672  1.00  25.20      MTGL
ATOM   1590  CB   GLU  202      35.962  18.281  16.227  1.00  26.99      MTGL
ATOM   1591  CG   GLU  202      37.142  19.208  16.054  1.00  30.89      MTGL
ATOM   1592  CD   GLU  202      37.380  19.539  14.596  1.00  33.28      MTGL
ATOM   1593  OE1  GLU  202      36.601  20.338  14.034  1.00  35.02      MTGL
ATOM   1594  OE2  GLU  202      38.333  18.989  14.004  1.00  34.29      MTGL
ATOM   1595  C    GLU  202      34.545  16.863  17.667  1.00  24.61      MTGL
ATOM   1596  O    GLU  202      34.886  15.725  17.990  1.00  23.46      MTGL
ATOM   1597  N    LEU  203      33.311  17.169  17.286  1.00  24.45      MTGL
ATOM   1598  CA   LEU  203      32.267  16.157  17.222  1.00  25.47      MTGL
ATOM   1599  CB   LEU  203      30.959  16.768  16.721  1.00  26.23      MTGL
ATOM   1600  CG   LEU  203      30.009  17.289  17.794  1.00  27.61      MTGL
ATOM   1601  CD1  LEU  203      28.830  17.970  17.126  1.00  28.79      MTGL
ATOM   1602  CD2  LEU  203      29.532  16.139  18.672  1.00  27.38      MTGL
ATOM   1603  C    LEU  203      32.666  15.007  16.305  1.00  25.18      MTGL
ATOM   1604  O    LEU  203      32.307  13.857  16.555  1.00  25.60      MTGL
ATOM   1605  N    SER  204      33.411  15.318  15.249  1.00  23.52      MTGL
ATOM   1606  CA   SER  204      33.841  14.295  14.305  1.00  23.46      MTGL
ATOM   1607  CB   SER  204      34.367  14.941  13.016  1.00  24.47      MTGL
ATOM   1608  OG   SER  204      35.559  15.677  13.253  1.00  23.17      MTGL
ATOM   1609  C    SER  204      34.918  13.379  14.877  1.00  22.84      MTGL
ATOM   1610  O    SER  204      35.235  12.353  14.278  1.00  22.80      MTGL
ATOM   1611  N    ASP  205      35.482  13.742  16.027  1.00  21.73      MTGL
ATOM   1612  CA   ASP  205      36.529  12.920  16.626  1.00  21.47      MTGL
ATOM   1613  CB   ASP  205      37.369  13.735  17.616  1.00  21.78      MTGL
ATOM   1614  CG   ASP  205      38.284  14.737  16.925  1.00  23.69      MTGL
ATOM   1615  OD1  ASP  205      38.859  14.388  15.870  1.00  23.46      MTGL
ATOM   1616  OD2  ASP  205      38.442  15.866  17.446  1.00  23.01      MTGL
ATOM   1617  C    ASP  205      36.020  11.653  17.310  1.00  20.42      MTGL
ATOM   1618  O    ASP  205      36.795  10.727  17.545  1.00  20.47      MTGL
ATOM   1619  N    PHE  206      34.736  11.609  17.650  1.00  19.52      MTGL
ATOM   1620  CA   PHE  206      34.183  10.408  18.275  1.00  20.33      MTGL
ATOM   1621  CB   PHE  206      34.060  10.565  19.801  1.00  18.69      MTGL
ATOM   1622  CG   PHE  206      33.098  11.626  20.244  1.00  18.95      MTGL
ATOM   1623  CD1  PHE  206      33.403  12.974  20.083  1.00  18.40      MTGL
```

Fig. 1 cont.

| ATOM | 1624 | CD2 | PHE | 206 | 31.899 | 11.275 | 20.861 | 1.00 | 18.16 | MTGL |
|------|------|-----|-----|-----|--------|--------|--------|------|-------|------|
| ATOM | 1625 | CE1 | PHE | 206 | 32.529 | 13.959 | 20.534 | 1.00 | 19.01 | MTGL |
| ATOM | 1626 | CE2 | PHE | 206 | 31.015 | 12.253 | 21.316 | 1.00 | 19.53 | MTGL |
| ATOM | 1627 | CZ | PHE | 206 | 31.331 | 13.601 | 21.153 | 1.00 | 18.89 | MTGL |
| ATOM | 1628 | C | PHE | 206 | 32.850 | 10.031 | 17.642 | 1.00 | 20.83 | MTGL |
| ATOM | 1629 | O | PHE | 206 | 32.267 | 10.825 | 16.901 | 1.00 | 20.91 | MTGL |
| ATOM | 1630 | N | ASP | 207 | 32.365 | 8.827 | 17.937 | 1.00 | 20.94 | MTGL |
| ATOM | 1631 | CA | ASP | 207 | 31.134 | 8.331 | 17.322 | 1.00 | 21.05 | MTGL |
| ATOM | 1632 | CB | ASP | 207 | 31.470 | 7.084 | 16.500 | 1.00 | 21.79 | MTGL |
| ATOM | 1633 | CG | ASP | 207 | 32.766 | 7.235 | 15.730 | 1.00 | 22.83 | MTGL |
| ATOM | 1634 | OD1 | ASP | 207 | 32.811 | 8.093 | 14.826 | 1.00 | 22.13 | MTGL |
| ATOM | 1635 | OD2 | ASP | 207 | 33.739 | 6.506 | 16.036 | 1.00 | 21.38 | MTGL |
| ATOM | 1636 | C | ASP | 207 | 29.978 | 7.990 | 18.256 | 1.00 | 20.40 | MTGL |
| ATOM | 1637 | O | ASP | 207 | 28.813 | 8.022 | 17.847 | 1.00 | 20.09 | MTGL |
| ATOM | 1638 | N | MET | 208 | 30.286 | 7.660 | 19.502 | 1.00 | 19.17 | MTGL |
| ATOM | 1639 | CA | MET | 208 | 29.236 | 7.281 | 20.431 | 1.00 | 17.84 | MTGL |
| ATOM | 1640 | CB | MET | 208 | 29.282 | 5.771 | 20.688 | 1.00 | 17.36 | MTGL |
| ATOM | 1641 | CG | MET | 208 | 29.319 | 4.900 | 19.455 | 1.00 | 17.72 | MTGL |
| ATOM | 1642 | SD | MET | 208 | 29.434 | 3.141 | 19.906 | 1.00 | 19.72 | MTGL |
| ATOM | 1643 | CE | MET | 208 | 27.745 | 2.786 | 20.301 | 1.00 | 18.67 | MTGL |
| ATOM | 1644 | C | MET | 208 | 29.293 | 7.979 | 21.775 | 1.00 | 17.33 | MTGL |
| ATOM | 1645 | O | MET | 208 | 30.351 | 8.410 | 22.232 | 1.00 | 16.75 | MTGL |
| ATOM | 1646 | N | MET | 209 | 28.125 | 8.080 | 22.397 | 1.00 | 16.30 | MTGL |
| ATOM | 1647 | CA | MET | 209 | 27.991 | 8.653 | 23.722 | 1.00 | 17.25 | MTGL |
| ATOM | 1648 | CB | MET | 209 | 27.037 | 9.852 | 23.730 | 1.00 | 16.86 | MTGL |
| ATOM | 1649 | CG | MET | 209 | 27.525 | 11.048 | 22.926 | 1.00 | 17.20 | MTGL |
| ATOM | 1650 | SD | MET | 209 | 26.439 | 12.511 | 23.096 | 1.00 | 15.98 | MTGL |
| ATOM | 1651 | CE | MET | 209 | 27.636 | 13.808 | 22.762 | 1.00 | 17.32 | MTGL |
| ATOM | 1652 | C | MET | 209 | 27.405 | 7.529 | 24.557 | 1.00 | 16.92 | MTGL |
| ATOM | 1653 | O | MET | 209 | 26.311 | 7.033 | 24.273 | 1.00 | 16.52 | MTGL |
| ATOM | 1654 | N | GLY | 210 | 28.153 | 7.103 | 25.565 | 1.00 | 16.49 | MTGL |
| ATOM | 1655 | CA | GLY | 210 | 27.675 | 6.038 | 26.423 | 1.00 | 16.81 | MTGL |
| ATOM | 1656 | C | GLY | 210 | 27.361 | 6.585 | 27.797 | 1.00 | 16.14 | MTGL |
| ATOM | 1657 | O | GLY | 210 | 27.991 | 7.537 | 28.257 | 1.00 | 15.66 | MTGL |
| ATOM | 1658 | N | VAL | 211 | 26.370 | 5.998 | 28.450 | 1.00 | 16.46 | MTGL |
| ATOM | 1659 | CA | VAL | 211 | 25.999 | 6.431 | 29.784 | 1.00 | 15.55 | MTGL |
| ATOM | 1660 | CB | VAL | 211 | 24.691 | 7.247 | 29.773 | 1.00 | 15.54 | MTGL |
| ATOM | 1661 | CG1 | VAL | 211 | 24.824 | 8.449 | 28.839 | 1.00 | 16.27 | MTGL |
| ATOM | 1662 | CG2 | VAL | 211 | 23.525 | 6.354 | 29.353 | 1.00 | 14.06 | MTGL |
| ATOM | 1663 | C | VAL | 211 | 25.781 | 5.236 | 30.700 | 1.00 | 16.00 | MTGL |
| ATOM | 1664 | O | VAL | 211 | 25.418 | 4.148 | 30.243 | 1.00 | 15.69 | MTGL |
| ATOM | 1665 | N | SER | 212 | 26.013 | 5.445 | 31.991 | 1.00 | 15.22 | MTGL |
| ATOM | 1666 | CA | SER | 212 | 25.766 | 4.414 | 32.983 | 1.00 | 15.39 | MTGL |
| ATOM | 1667 | CB | SER | 212 | 26.741 | 4.537 | 34.158 | 1.00 | 15.48 | MTGL |
| ATOM | 1668 | OG | SER | 212 | 28.083 | 4.327 | 33.748 | 1.00 | 16.02 | MTGL |
| ATOM | 1669 | C | SER | 212 | 24.346 | 4.707 | 33.469 | 1.00 | 15.93 | MTGL |
| ATOM | 1670 | O | SER | 212 | 23.922 | 5.863 | 33.498 | 1.00 | 16.20 | MTGL |
| ATOM | 1671 | N | PHE | 213 | 23.599 | 3.670 | 33.821 | 1.00 | 15.04 | MTGL |
| ATOM | 1672 | CA | PHE | 213 | 22.248 | 3.866 | 34.323 | 1.00 | 15.18 | MTGL |
| ATOM | 1673 | CB | PHE | 213 | 21.218 | 3.762 | 33.191 | 1.00 | 14.75 | MTGL |
| ATOM | 1674 | CG | PHE | 213 | 19.801 | 3.982 | 33.647 | 1.00 | 14.40 | MTGL |
| ATOM | 1675 | CD1 | PHE | 213 | 19.383 | 5.238 | 34.071 | 1.00 | 15.35 | MTGL |
| ATOM | 1676 | CD2 | PHE | 213 | 18.897 | 2.924 | 33.694 | 1.00 | 14.80 | MTGL |
| ATOM | 1677 | CE1 | PHE | 213 | 18.079 | 5.441 | 34.542 | 1.00 | 15.59 | MTGL |
| ATOM | 1678 | CE2 | PHE | 213 | 17.594 | 3.113 | 34.160 | 1.00 | 15.14 | MTGL |
| ATOM | 1679 | CZ | PHE | 213 | 17.185 | 4.376 | 34.586 | 1.00 | 15.11 | MTGL |
| ATOM | 1680 | C | PHE | 213 | 21.956 | 2.821 | 35.388 | 1.00 | 16.01 | MTGL |
| ATOM | 1681 | O | PHE | 213 | 21.757 | 1.646 | 35.078 | 1.00 | 16.44 | MTGL |

Fig. 1 cont.

| | | | | | | | | | | |
|---|---|---|---|---|---|---|---|---|---|---|
| ATOM | 1682 | N   | TYR | 214 | 21.954 |  3.258 | 36.644 | 1.00 | 16.44 | MTGL |
| ATOM | 1683 | CA  | TYR | 214 | 21.691 |  2.382 | 37.782 | 1.00 | 16.37 | MTGL |
| ATOM | 1684 | CB  | TYR | 214 | 22.917 |  2.332 | 38.700 | 1.00 | 16.76 | MTGL |
| ATOM | 1685 | CG  | TYR | 214 | 24.097 |  1.562 | 38.131 | 1.00 | 16.18 | MTGL |
| ATOM | 1686 | CD1 | TYR | 214 | 24.114 |  0.168 | 38.139 | 1.00 | 16.62 | MTGL |
| ATOM | 1687 | CE1 | TYR | 214 | 25.201 | -0.544 | 37.637 | 1.00 | 17.99 | MTGL |
| ATOM | 1688 | CD2 | TYR | 214 | 25.199 |  2.228 | 37.599 | 1.00 | 16.40 | MTGL |
| ATOM | 1689 | CE2 | TYR | 214 | 26.295 |  1.524 | 37.093 | 1.00 | 16.27 | MTGL |
| ATOM | 1690 | CZ  | TYR | 214 | 26.288 |  0.142 | 37.118 | 1.00 | 16.37 | MTGL |
| ATOM | 1691 | OH  | TYR | 214 | 27.375 | -0.556 | 36.648 | 1.00 | 17.15 | MTGL |
| ATOM | 1692 | C   | TYR | 214 | 20.479 |  2.904 | 38.554 | 1.00 | 17.45 | MTGL |
| ATOM | 1693 | O   | TYR | 214 | 20.246 |  4.111 | 38.632 | 1.00 | 17.08 | MTGL |
| ATOM | 1694 | N   | PRO | 215 | 19.691 |  1.997 | 39.140 | 1.00 | 17.07 | MTGL |
| ATOM | 1695 | CD  | PRO | 215 | 19.704 |  0.537 | 38.916 | 1.00 | 17.36 | MTGL |
| ATOM | 1696 | CA  | PRO | 215 | 18.506 |  2.395 | 39.896 | 1.00 | 17.11 | MTGL |
| ATOM | 1697 | CB  | PRO | 215 | 17.547 |  1.247 | 39.619 | 1.00 | 17.64 | MTGL |
| ATOM | 1698 | CG  | PRO | 215 | 18.481 |  0.060 | 39.693 | 1.00 | 17.35 | MTGL |
| ATOM | 1699 | C   | PRO | 215 | 18.728 |  2.576 | 41.395 | 1.00 | 18.08 | MTGL |
| ATOM | 1700 | O   | PRO | 215 | 17.847 |  3.078 | 42.092 | 1.00 | 17.47 | MTGL |
| ATOM | 1701 | N   | PHE | 216 | 19.896 |  2.180 | 41.891 | 1.00 | 18.78 | MTGL |
| ATOM | 1702 | CA  | PHE | 216 | 20.152 |  2.251 | 43.328 | 1.00 | 19.20 | MTGL |
| ATOM | 1703 | CB  | PHE | 216 | 20.530 |  0.851 | 43.836 | 1.00 | 17.80 | MTGL |
| ATOM | 1704 | CG  | PHE | 216 | 21.456 |  0.095 | 42.915 | 1.00 | 18.00 | MTGL |
| ATOM | 1705 | CD1 | PHE | 216 | 22.673 |  0.641 | 42.522 | 1.00 | 18.05 | MTGL |
| ATOM | 1706 | CD2 | PHE | 216 | 21.117 | -1.172 | 42.456 | 1.00 | 17.34 | MTGL |
| ATOM | 1707 | CE1 | PHE | 216 | 23.543 | -0.064 | 41.680 | 1.00 | 17.92 | MTGL |
| ATOM | 1708 | CE2 | PHE | 216 | 21.981 | -1.887 | 41.614 | 1.00 | 17.55 | MTGL |
| ATOM | 1709 | CZ  | PHE | 216 | 23.194 | -1.331 | 41.228 | 1.00 | 16.80 | MTGL |
| ATOM | 1710 | C   | PHE | 216 | 21.145 |  3.276 | 43.872 | 1.00 | 19.84 | MTGL |
| ATOM | 1711 | O   | PHE | 216 | 21.726 |  3.068 | 44.940 | 1.00 | 21.57 | MTGL |
| ATOM | 1712 | N   | TYR | 217 | 21.346 |  4.379 | 43.161 | 1.00 | 19.60 | MTGL |
| ATOM | 1713 | CA  | TYR | 217 | 22.251 |  5.419 | 43.647 | 1.00 | 20.50 | MTGL |
| ATOM | 1714 | CB  | TYR | 217 | 23.468 |  5.575 | 42.732 | 1.00 | 20.09 | MTGL |
| ATOM | 1715 | CG  | TYR | 217 | 24.398 |  4.382 | 42.724 | 1.00 | 21.44 | MTGL |
| ATOM | 1716 | CD1 | TYR | 217 | 24.956 |  3.895 | 43.909 | 1.00 | 21.17 | MTGL |
| ATOM | 1717 | CE1 | TYR | 217 | 25.815 |  2.797 | 43.902 | 1.00 | 21.86 | MTGL |
| ATOM | 1718 | CD2 | TYR | 217 | 24.721 |  3.739 | 41.529 | 1.00 | 20.83 | MTGL |
| ATOM | 1719 | CE2 | TYR | 217 | 25.577 |  2.642 | 41.511 | 1.00 | 21.46 | MTGL |
| ATOM | 1720 | CZ  | TYR | 217 | 26.120 |  2.174 | 42.697 | 1.00 | 21.33 | MTGL |
| ATOM | 1721 | OH  | TYR | 217 | 26.960 |  1.087 | 42.672 | 1.00 | 20.10 | MTGL |
| ATOM | 1722 | C   | TYR | 217 | 21.520 |  6.752 | 43.727 | 1.00 | 21.29 | MTGL |
| ATOM | 1723 | O   | TYR | 217 | 22.127 |  7.778 | 44.026 | 1.00 | 21.40 | MTGL |
| ATOM | 1724 | N   | SER | 218 | 20.218 |  6.725 | 43.450 | 1.00 | 21.47 | MTGL |
| ATOM | 1725 | CA  | SER | 218 | 19.387 |  7.926 | 43.475 | 1.00 | 22.44 | MTGL |
| ATOM | 1726 | CB  | SER | 218 | 20.043 |  9.050 | 42.677 | 1.00 | 23.02 | MTGL |
| ATOM | 1727 | OG  | SER | 218 | 19.128 | 10.108 | 42.463 | 1.00 | 23.85 | MTGL |
| ATOM | 1728 | C   | SER | 218 | 18.012 |  7.661 | 42.888 | 1.00 | 22.12 | MTGL |
| ATOM | 1729 | O   | SER | 218 | 17.888 |  7.058 | 41.821 | 1.00 | 22.86 | MTGL |
| ATOM | 1730 | N   | SER | 219 | 16.980 |  8.128 | 43.577 | 1.00 | 21.77 | MTGL |
| ATOM | 1731 | CA  | SER | 219 | 15.615 |  7.938 | 43.111 | 1.00 | 22.44 | MTGL |
| ATOM | 1732 | CB  | SER | 219 | 14.624 |  8.308 | 44.216 | 1.00 | 22.46 | MTGL |
| ATOM | 1733 | OG  | SER | 219 | 14.793 |  9.658 | 44.607 | 1.00 | 22.44 | MTGL |
| ATOM | 1734 | C   | SER | 219 | 15.333 |  8.782 | 41.867 | 1.00 | 22.56 | MTGL |
| ATOM | 1735 | O   | SER | 219 | 14.282 |  8.646 | 41.247 | 1.00 | 23.34 | MTGL |
| ATOM | 1736 | N   | SER | 220 | 16.267 |  9.653 | 41.503 | 1.00 | 22.13 | MTGL |
| ATOM | 1737 | CA  | SER | 220 | 16.088 | 10.488 | 40.319 | 1.00 | 22.61 | MTGL |
| ATOM | 1738 | CB  | SER | 220 | 17.037 | 11.691 | 40.358 | 1.00 | 23.25 | MTGL |
| ATOM | 1739 | OG  | SER | 220 | 16.688 | 12.584 | 41.403 | 1.00 | 25.72 | MTGL |

Fig. 1 cont.

| | | | | | | | | | | |
|---|---|---|---|---|---|---|---|---|---|---|
| ATOM | 1740 | C | SER | 220 | 16.330 | 9.704 | 39.032 | 1.00 | 22.26 | MTGL |
| ATOM | 1741 | O | SER | 220 | 16.025 | 10.187 | 37.942 | 1.00 | 22.75 | MTGL |
| ATOM | 1742 | N | ALA | 221 | 16.872 | 8.495 | 39.160 | 1.00 | 20.89 | MTGL |
| ATOM | 1743 | CA | ALA | 221 | 17.164 | 7.667 | 37.996 | 1.00 | 20.44 | MTGL |
| ATOM | 1744 | CB | ALA | 221 | 18.266 | 6.644 | 38.343 | 1.00 | 19.75 | MTGL |
| ATOM | 1745 | C | ALA | 221 | 15.933 | 6.949 | 37.439 | 1.00 | 20.80 | MTGL |
| ATOM | 1746 | O | ALA | 221 | 15.941 | 5.731 | 37.265 | 1.00 | 20.53 | MTGL |
| ATOM | 1747 | N | THR | 222 | 14.875 | 7.705 | 37.163 | 1.00 | 20.53 | MTGL |
| ATOM | 1748 | CA | THR | 222 | 13.651 | 7.134 | 36.607 | 1.00 | 20.82 | MTGL |
| ATOM | 1749 | CB | THR | 222 | 12.464 | 8.120 | 36.690 | 1.00 | 20.95 | MTGL |
| ATOM | 1750 | OG1 | THR | 222 | 12.792 | 9.310 | 35.966 | 1.00 | 21.38 | MTGL |
| ATOM | 1751 | CG2 | THR | 222 | 12.152 | 8.483 | 38.137 | 1.00 | 21.55 | MTGL |
| ATOM | 1752 | C | THR | 222 | 13.848 | 6.809 | 35.129 | 1.00 | 20.30 | MTGL |
| ATOM | 1753 | O | THR | 222 | 14.754 | 7.334 | 34.479 | 1.00 | 20.05 | MTGL |
| ATOM | 1754 | N | LEU | 223 | 12.990 | 5.947 | 34.598 | 1.00 | 20.97 | MTGL |
| ATOM | 1755 | CA | LEU | 223 | 13.060 | 5.583 | 33.190 | 1.00 | 20.57 | MTGL |
| ATOM | 1756 | CB | LEU | 223 | 12.116 | 4.412 | 32.894 | 1.00 | 21.05 | MTGL |
| ATOM | 1757 | CG | LEU | 223 | 12.455 | 3.097 | 33.612 | 1.00 | 22.20 | MTGL |
| ATOM | 1758 | CD1 | LEU | 223 | 11.415 | 2.039 | 33.276 | 1.00 | 22.93 | MTGL |
| ATOM | 1759 | CD2 | LEU | 223 | 13.841 | 2.629 | 33.195 | 1.00 | 21.13 | MTGL |
| ATOM | 1760 | C | LEU | 223 | 12.674 | 6.800 | 32.346 | 1.00 | 20.76 | MTGL |
| ATOM | 1761 | O | LEU | 223 | 13.214 | 7.009 | 31.258 | 1.00 | 19.94 | MTGL |
| ATOM | 1762 | N | SER | 224 | 11.741 | 7.607 | 32.852 | 1.00 | 20.13 | MTGL |
| ATOM | 1763 | CA | SER | 224 | 11.311 | 8.804 | 32.128 | 1.00 | 20.71 | MTGL |
| ATOM | 1764 | CB | SER | 224 | 10.096 | 9.448 | 32.812 | 1.00 | 21.29 | MTGL |
| ATOM | 1765 | OG | SER | 224 | 10.392 | 9.812 | 34.149 | 1.00 | 26.36 | MTGL |
| ATOM | 1766 | C | SER | 224 | 12.452 | 9.815 | 32.036 | 1.00 | 18.99 | MTGL |
| ATOM | 1767 | O | SER | 224 | 12.641 | 10.450 | 30.999 | 1.00 | 19.23 | MTGL |
| ATOM | 1768 | N | ALA | 225 | 13.214 | 9.967 | 33.115 | 1.00 | 18.09 | MTGL |
| ATOM | 1769 | CA | ALA | 225 | 14.333 | 10.901 | 33.093 | 1.00 | 17.82 | MTGL |
| ATOM | 1770 | CB | ALA | 225 | 14.928 | 11.057 | 34.492 | 1.00 | 17.28 | MTGL |
| ATOM | 1771 | C | ALA | 225 | 15.395 | 10.410 | 32.108 | 1.00 | 17.15 | MTGL |
| ATOM | 1772 | O | ALA | 225 | 16.018 | 11.208 | 31.410 | 1.00 | 18.25 | MTGL |
| ATOM | 1773 | N | LEU | 226 | 15.598 | 9.097 | 32.048 | 1.00 | 16.97 | MTGL |
| ATOM | 1774 | CA | LEU | 226 | 16.580 | 8.534 | 31.122 | 1.00 | 17.41 | MTGL |
| ATOM | 1775 | CB | LEU | 226 | 16.693 | 7.017 | 31.303 | 1.00 | 17.39 | MTGL |
| ATOM | 1776 | CG | LEU | 226 | 17.711 | 6.325 | 30.389 | 1.00 | 17.54 | MTGL |
| ATOM | 1777 | CD1 | LEU | 226 | 19.109 | 6.852 | 30.679 | 1.00 | 17.23 | MTGL |
| ATOM | 1778 | CD2 | LEU | 226 | 17.658 | 4.824 | 30.606 | 1.00 | 17.56 | MTGL |
| ATOM | 1779 | C | LEU | 226 | 16.126 | 8.839 | 29.696 | 1.00 | 17.60 | MTGL |
| ATOM | 1780 | O | LEU | 226 | 16.909 | 9.311 | 28.868 | 1.00 | 17.24 | MTGL |
| ATOM | 1781 | N | LYS | 227 | 14.854 | 8.566 | 29.423 | 1.00 | 17.18 | MTGL |
| ATOM | 1782 | CA | LYS | 227 | 14.277 | 8.811 | 28.105 | 1.00 | 18.16 | MTGL |
| ATOM | 1783 | CB | LYS | 227 | 12.780 | 8.488 | 28.120 | 1.00 | 18.24 | MTGL |
| ATOM | 1784 | CG | LYS | 227 | 12.007 | 8.984 | 26.890 | 1.00 | 18.81 | MTGL |
| ATOM | 1785 | CD | LYS | 227 | 12.540 | 8.394 | 25.590 | 1.00 | 17.63 | MTGL |
| ATOM | 1786 | CE | LYS | 227 | 11.629 | 8.737 | 24.411 | 1.00 | 18.20 | MTGL |
| ATOM | 1787 | NZ | LYS | 227 | 12.191 | 8.269 | 23.111 | 1.00 | 17.92 | MTGL |
| ATOM | 1788 | C | LYS | 227 | 14.476 | 10.258 | 27.668 | 1.00 | 18.40 | MTGL |
| ATOM | 1789 | O | LYS | 227 | 14.978 | 10.526 | 26.576 | 1.00 | 18.56 | MTGL |
| ATOM | 1790 | N | SER | 228 | 14.078 | 11.190 | 28.529 | 1.00 | 18.71 | MTGL |
| ATOM | 1791 | CA | SER | 228 | 14.209 | 12.610 | 28.225 | 1.00 | 18.63 | MTGL |
| ATOM | 1792 | CB | SER | 228 | 13.584 | 13.449 | 29.344 | 1.00 | 19.90 | MTGL |
| ATOM | 1793 | OG | SER | 228 | 13.763 | 14.835 | 29.096 | 1.00 | 20.80 | MTGL |
| ATOM | 1794 | C | SER | 228 | 15.662 | 13.022 | 28.024 | 1.00 | 18.30 | MTGL |
| ATOM | 1795 | O | SER | 228 | 15.973 | 13.778 | 27.106 | 1.00 | 18.71 | MTGL |
| ATOM | 1796 | N | SER | 229 | 16.553 | 12.525 | 28.880 | 1.00 | 17.99 | MTGL |
| ATOM | 1797 | CA | SER | 229 | 17.969 | 12.862 | 28.768 | 1.00 | 18.28 | MTGL |

Fig. 1 cont.

| ATOM | 1798 | CB  | SER | 229 | 18.752 | 12.299 | 29.962 | 1.00 | 18.83 | MTGL |
|------|------|-----|-----|-----|--------|--------|--------|------|-------|------|
| ATOM | 1799 | OG  | SER | 229 | 20.127 | 12.641 | 29.867 | 1.00 | 17.92 | MTGL |
| ATOM | 1800 | C   | SER | 229 | 18.577 | 12.339 | 27.463 | 1.00 | 18.05 | MTGL |
| ATOM | 1801 | O   | SER | 229 | 19.251 | 13.076 | 26.744 | 1.00 | 18.70 | MTGL |
| ATOM | 1802 | N   | LEU | 230 | 18.338 | 11.070 | 27.149 | 1.00 | 17.87 | MTGL |
| ATOM | 1803 | CA  | LEU | 230 | 18.884 | 10.503 | 25.920 | 1.00 | 17.26 | MTGL |
| ATOM | 1804 | CB  | LEU | 230 | 18.620 | 8.994  | 25.860 | 1.00 | 16.24 | MTGL |
| ATOM | 1805 | CG  | LEU | 230 | 19.265 | 8.162  | 26.976 | 1.00 | 16.12 | MTGL |
| ATOM | 1806 | CD1 | LEU | 230 | 19.069 | 6.676  | 26.671 | 1.00 | 16.29 | MTGL |
| ATOM | 1807 | CD2 | LEU | 230 | 20.749 | 8.473  | 27.084 | 1.00 | 12.97 | MTGL |
| ATOM | 1808 | C   | LEU | 230 | 18.299 | 11.204 | 24.689 | 1.00 | 17.08 | MTGL |
| ATOM | 1809 | O   | LEU | 230 | 19.014 | 11.458 | 23.721 | 1.00 | 15.52 | MTGL |
| ATOM | 1810 | N   | ASP | 231 | 17.006 | 11.525 | 24.728 | 1.00 | 18.20 | MTGL |
| ATOM | 1811 | CA  | ASP | 231 | 16.380 | 12.223 | 23.604 | 1.00 | 18.97 | MTGL |
| ATOM | 1812 | CB  | ASP | 231 | 14.896 | 12.494 | 23.878 | 1.00 | 20.35 | MTGL |
| ATOM | 1813 | CG  | ASP | 231 | 13.985 | 11.337 | 23.455 | 1.00 | 20.69 | MTGL |
| ATOM | 1814 | OD1 | ASP | 231 | 14.460 | 10.361 | 22.838 | 1.00 | 21.48 | MTGL |
| ATOM | 1815 | OD2 | ASP | 231 | 12.775 | 11.418 | 23.738 | 1.00 | 20.71 | MTGL |
| ATOM | 1816 | C   | ASP | 231 | 17.102 | 13.553 | 23.393 | 1.00 | 19.05 | MTGL |
| ATOM | 1817 | O   | ASP | 231 | 17.423 | 13.927 | 22.265 | 1.00 | 20.05 | MTGL |
| ATOM | 1818 | N   | ASN | 232 | 17.369 | 14.260 | 24.486 | 1.00 | 18.97 | MTGL |
| ATOM | 1819 | CA  | ASN | 232 | 18.057 | 15.546 | 24.403 | 1.00 | 19.27 | MTGL |
| ATOM | 1820 | CB  | ASN | 232 | 18.126 | 16.219 | 25.781 | 1.00 | 19.34 | MTGL |
| ATOM | 1821 | CG  | ASN | 232 | 16.775 | 16.752 | 26.238 | 1.00 | 21.88 | MTGL |
| ATOM | 1822 | OD1 | ASN | 232 | 15.911 | 17.054 | 25.420 | 1.00 | 23.78 | MTGL |
| ATOM | 1823 | ND2 | ASN | 232 | 16.595 | 16.882 | 27.545 | 1.00 | 21.09 | MTGL |
| ATOM | 1824 | C   | ASN | 232 | 19.459 | 15.397 | 23.834 | 1.00 | 19.42 | MTGL |
| ATOM | 1825 | O   | ASN | 232 | 19.887 | 16.205 | 23.003 | 1.00 | 19.51 | MTGL |
| ATOM | 1826 | N   | MET | 233 | 20.174 | 14.368 | 24.280 | 1.00 | 19.18 | MTGL |
| ATOM | 1827 | CA  | MET | 233 | 21.533 | 14.124 | 23.803 | 1.00 | 19.15 | MTGL |
| ATOM | 1828 | CB  | MET | 233 | 22.151 | 12.936 | 24.551 | 1.00 | 18.27 | MTGL |
| ATOM | 1829 | CG  | MET | 233 | 22.433 | 13.191 | 26.029 | 1.00 | 19.33 | MTGL |
| ATOM | 1830 | SD  | MET | 233 | 22.806 | 11.662 | 26.940 | 1.00 | 19.17 | MTGL |
| ATOM | 1831 | CE  | MET | 233 | 24.330 | 11.165 | 26.125 | 1.00 | 17.20 | MTGL |
| ATOM | 1832 | C   | MET | 233 | 21.510 | 13.833 | 22.305 | 1.00 | 19.80 | MTGL |
| ATOM | 1833 | O   | MET | 233 | 22.356 | 14.314 | 21.547 | 1.00 | 19.41 | MTGL |
| ATOM | 1834 | N   | ALA | 234 | 20.529 | 13.043 | 21.885 | 1.00 | 20.01 | MTGL |
| ATOM | 1835 | CA  | ALA | 234 | 20.390 | 12.673 | 20.480 | 1.00 | 21.04 | MTGL |
| ATOM | 1836 | CB  | ALA | 234 | 19.274 | 11.633 | 20.324 | 1.00 | 19.66 | MTGL |
| ATOM | 1837 | C   | ALA | 234 | 20.111 | 13.879 | 19.583 | 1.00 | 21.48 | MTGL |
| ATOM | 1838 | O   | ALA | 234 | 20.761 | 14.055 | 18.549 | 1.00 | 20.87 | MTGL |
| ATOM | 1839 | N   | LYS | 235 | 19.156 | 14.715 | 19.985 | 1.00 | 22.48 | MTGL |
| ATOM | 1840 | CA  | LYS | 235 | 18.804 | 15.881 | 19.176 | 1.00 | 24.12 | MTGL |
| ATOM | 1841 | CB  | LYS | 235 | 17.507 | 16.515 | 19.681 | 1.00 | 26.52 | MTGL |
| ATOM | 1842 | CG  | LYS | 235 | 17.053 | 17.695 | 18.835 | 1.00 | 33.00 | MTGL |
| ATOM | 1843 | CD  | LYS | 235 | 15.744 | 18.274 | 19.331 | 1.00 | 36.39 | MTGL |
| ATOM | 1844 | CE  | LYS | 235 | 15.288 | 19.436 | 18.451 | 1.00 | 40.33 | MTGL |
| ATOM | 1845 | NZ  | LYS | 235 | 13.979 | 19.997 | 18.912 | 1.00 | 42.05 | MTGL |
| ATOM | 1846 | C   | LYS | 235 | 19.900 | 16.937 | 19.145 | 1.00 | 22.78 | MTGL |
| ATOM | 1847 | O   | LYS | 235 | 20.041 | 17.660 | 18.169 | 1.00 | 21.57 | MTGL |
| ATOM | 1848 | N   | THR | 236 | 20.688 | 17.014 | 20.209 | 1.00 | 23.01 | MTGL |
| ATOM | 1849 | CA  | THR | 236 | 21.753 | 18.004 | 20.280 | 1.00 | 22.42 | MTGL |
| ATOM | 1850 | CB  | THR | 236 | 22.146 | 18.289 | 21.744 | 1.00 | 22.63 | MTGL |
| ATOM | 1851 | OG1 | THR | 236 | 20.973 | 18.616 | 22.495 | 1.00 | 23.14 | MTGL |
| ATOM | 1852 | CG2 | THR | 236 | 23.118 | 19.459 | 21.818 | 1.00 | 22.49 | MTGL |
| ATOM | 1853 | C   | THR | 236 | 23.020 | 17.635 | 19.506 | 1.00 | 22.72 | MTGL |
| ATOM | 1854 | O   | THR | 236 | 23.556 | 18.468 | 18.773 | 1.00 | 22.41 | MTGL |
| ATOM | 1855 | N   | TRP | 237 | 23.495 | 16.398 | 19.655 | 1.00 | 21.45 | MTGL |

Fig. 1 cont.

| | | | | | | | | | |
|---|---|---|---|---|---|---|---|---|---|
| ATOM | 1856 | CA | TRP | 237 | 24.728 | 15.984 | 18.984 | 1.00 21.17 | MTGL |
| ATOM | 1857 | CB | TRP | 237 | 25.773 | 15.621 | 20.041 | 1.00 21.53 | MTGL |
| ATOM | 1858 | CG | TRP | 237 | 26.103 | 16.796 | 20.916 | 1.00 21.36 | MTGL |
| ATOM | 1859 | CD2 | TRP | 237 | 25.684 | 17.004 | 22.270 | 1.00 20.90 | MTGL |
| ATOM | 1860 | CE2 | TRP | 237 | 26.156 | 18.274 | 22.662 | 1.00 20.29 | MTGL |
| ATOM | 1861 | CE3 | TRP | 237 | 24.957 | 16.237 | 23.191 | 1.00 20.64 | MTGL |
| ATOM | 1862 | CD1 | TRP | 237 | 26.795 | 17.920 | 20.554 | 1.00 21.20 | MTGL |
| ATOM | 1863 | NE1 | TRP | 237 | 26.827 | 18.811 | 21.595 | 1.00 19.36 | MTGL |
| ATOM | 1864 | CZ2 | TRP | 237 | 25.919 | 18.799 | 23.935 | 1.00 20.39 | MTGL |
| ATOM | 1865 | CZ3 | TRP | 237 | 24.724 | 16.760 | 24.458 | 1.00 20.25 | MTGL |
| ATOM | 1866 | CH2 | TRP | 237 | 25.205 | 18.028 | 24.817 | 1.00 20.45 | MTGL |
| ATOM | 1867 | C | TRP | 237 | 24.600 | 14.868 | 17.941 | 1.00 21.19 | MTGL |
| ATOM | 1868 | O | TRP | 237 | 25.561 | 14.555 | 17.238 | 1.00 20.33 | MTGL |
| ATOM | 1869 | N | ASN | 238 | 23.414 | 14.274 | 17.865 | 0.50 21.58 | MTGL |
| ATOM | 1870 | CA | ASN | 238 | 23.119 | 13.212 | 16.908 | 0.50 21.97 | MTGL |
| ATOM | 1871 | CB | ASN | 238 | 22.847 | 13.829 | 15.534 | 0.50 23.20 | MTGL |
| ATOM | 1872 | CG | ASN | 238 | 21.696 | 14.822 | 15.560 | 0.50 24.82 | MTGL |
| ATOM | 1873 | OD1 | ASN | 238 | 20.631 | 14.540 | 16.107 | 0.50 25.88 | MTGL |
| ATOM | 1874 | ND2 | ASN | 238 | 21.904 | 15.989 | 14.960 | 0.50 26.50 | MTGL |
| ATOM | 1875 | C | ASN | 238 | 24.179 | 12.113 | 16.782 | 0.50 21.69 | MTGL |
| ATOM | 1876 | O | ASN | 238 | 24.564 | 11.730 | 15.678 | 0.50 21.51 | MTGL |
| ATOM | 1877 | N | LYS | 239 | 24.644 | 11.607 | 17.919 | 1.00 21.56 | MTGL |
| ATOM | 1878 | CA | LYS | 239 | 25.639 | 10.534 | 17.938 | 1.00 20.81 | MTGL |
| ATOM | 1879 | CB | LYS | 239 | 26.732 | 10.832 | 18.971 | 1.00 21.93 | MTGL |
| ATOM | 1880 | CG | LYS | 239 | 27.684 | 11.957 | 18.598 | 1.00 21.60 | MTGL |
| ATOM | 1881 | CD | LYS | 239 | 28.521 | 11.569 | 17.396 | 1.00 23.06 | MTGL |
| ATOM | 1882 | CE | LYS | 239 | 29.543 | 12.633 | 17.053 | 1.00 23.30 | MTGL |
| ATOM | 1883 | NZ | LYS | 239 | 30.266 | 12.280 | 15.800 | 1.00 22.03 | MTGL |
| ATOM | 1884 | C | LYS | 239 | 24.927 | 9.243 | 18.331 | 1.00 20.23 | MTGL |
| ATOM | 1885 | O | LYS | 239 | 23.814 | 9.287 | 18.856 | 1.00 19.43 | MTGL |
| ATOM | 1886 | N | GLU | 240 | 25.548 | 8.096 | 18.072 | 1.00 19.70 | MTGL |
| ATOM | 1887 | CA | GLU | 240 | 24.933 | 6.835 | 18.467 | 1.00 19.84 | MTGL |
| ATOM | 1888 | CB | GLU | 240 | 25.702 | 5.633 | 17.912 | 1.00 21.53 | MTGL |
| ATOM | 1889 | CG | GLU | 240 | 25.612 | 5.485 | 16.402 | 1.00 24.54 | MTGL |
| ATOM | 1890 | CD | GLU | 240 | 25.950 | 4.081 | 15.930 | 1.00 26.26 | MTGL |
| ATOM | 1891 | OE1 | GLU | 240 | 26.984 | 3.532 | 16.366 | 1.00 27.61 | MTGL |
| ATOM | 1892 | OE2 | GLU | 240 | 25.179 | 3.527 | 15.118 | 1.00 28.35 | MTGL |
| ATOM | 1893 | C | GLU | 240 | 24.972 | 6.823 | 19.985 | 1.00 18.12 | MTGL |
| ATOM | 1894 | O | GLU | 240 | 25.945 | 7.269 | 20.589 | 1.00 16.94 | MTGL |
| ATOM | 1895 | N | ILE | 241 | 23.910 | 6.320 | 20.598 | 1.00 17.17 | MTGL |
| ATOM | 1896 | CA | ILE | 241 | 23.816 | 6.290 | 22.049 | 1.00 17.75 | MTGL |
| ATOM | 1897 | CB | ILE | 241 | 22.639 | 7.161 | 22.509 | 1.00 18.47 | MTGL |
| ATOM | 1898 | CG2 | ILE | 241 | 22.411 | 6.997 | 24.013 | 1.00 19.08 | MTGL |
| ATOM | 1899 | CG1 | ILE | 241 | 22.918 | 8.617 | 22.126 | 1.00 17.74 | MTGL |
| ATOM | 1900 | CD1 | ILE | 241 | 21.732 | 9.539 | 22.297 | 1.00 18.08 | MTGL |
| ATOM | 1901 | C | ILE | 241 | 23.651 | 4.894 | 22.625 | 1.00 17.68 | MTGL |
| ATOM | 1902 | O | ILE | 241 | 23.020 | 4.026 | 22.015 | 1.00 16.98 | MTGL |
| ATOM | 1903 | N | ALA | 242 | 24.219 | 4.683 | 23.809 | 1.00 17.80 | MTGL |
| ATOM | 1904 | CA | ALA | 242 | 24.115 | 3.389 | 24.465 | 1.00 17.48 | MTGL |
| ATOM | 1905 | CB | ALA | 242 | 25.170 | 2.433 | 23.906 | 1.00 16.79 | MTGL |
| ATOM | 1906 | C | ALA | 242 | 24.244 | 3.457 | 25.977 | 1.00 16.97 | MTGL |
| ATOM | 1907 | O | ALA | 242 | 24.966 | 4.291 | 26.520 | 1.00 16.47 | MTGL |
| ATOM | 1908 | N | VAL | 243 | 23.505 | 2.586 | 26.654 | 1.00 16.88 | MTGL |
| ATOM | 1909 | CA | VAL | 243 | 23.594 | 2.478 | 28.098 | 1.00 16.35 | MTGL |
| ATOM | 1910 | CB | VAL | 243 | 22.261 | 2.003 | 28.715 | 1.00 15.54 | MTGL |
| ATOM | 1911 | CG1 | VAL | 243 | 22.470 | 1.580 | 30.159 | 1.00 16.43 | MTGL |
| ATOM | 1912 | CG2 | VAL | 243 | 21.238 | 3.133 | 28.655 | 1.00 15.23 | MTGL |
| ATOM | 1913 | C | VAL | 243 | 24.667 | 1.396 | 28.212 | 1.00 16.01 | MTGL |

Fig. 1 cont.

| | | | | | | | | | | |
|---|---|---|---|---|---|---|---|---|---|---|
| ATOM | 1914 | O | VAL | 243 | 24.424 | 0.243 | 27.856 | 1.00 | 16.07 | MTGL |
| ATOM | 1915 | N | VAL | 244 | 25.860 | 1.774 | 28.665 | 1.00 | 15.48 | MTGL |
| ATOM | 1916 | CA | VAL | 244 | 26.971 | 0.822 | 28.758 | 1.00 | 15.55 | MTGL |
| ATOM | 1917 | CB | VAL | 244 | 28.292 | 1.501 | 28.345 | 1.00 | 15.25 | MTGL |
| ATOM | 1918 | CG1 | VAL | 244 | 28.167 | 2.024 | 26.922 | 1.00 | 15.71 | MTGL |
| ATOM | 1919 | CG2 | VAL | 244 | 28.618 | 2.646 | 29.294 | 1.00 | 14.98 | MTGL |
| ATOM | 1920 | C | VAL | 244 | 27.163 | 0.125 | 30.097 | 1.00 | 15.27 | MTGL |
| ATOM | 1921 | O | VAL | 244 | 28.052 | -0.710 | 30.244 | 1.00 | 16.53 | MTGL |
| ATOM | 1922 | N | GLU | 245 | 26.326 | 0.464 | 31.068 | 1.00 | 15.31 | MTGL |
| ATOM | 1923 | CA | GLU | 245 | 26.387 | -0.145 | 32.391 | 1.00 | 15.54 | MTGL |
| ATOM | 1924 | CB | GLU | 245 | 27.390 | 0.581 | 33.301 | 1.00 | 15.71 | MTGL |
| ATOM | 1925 | CG | GLU | 245 | 28.833 | 0.193 | 33.105 | 1.00 | 17.89 | MTGL |
| ATOM | 1926 | CD | GLU | 245 | 29.738 | 0.777 | 34.177 | 1.00 | 19.37 | MTGL |
| ATOM | 1927 | OE1 | GLU | 245 | 29.322 | 0.824 | 35.359 | 1.00 | 18.55 | MTGL |
| ATOM | 1928 | OE2 | GLU | 245 | 30.867 | 1.174 | 33.827 | 1.00 | 20.37 | MTGL |
| ATOM | 1929 | C | GLU | 245 | 25.024 | -0.053 | 33.043 | 1.00 | 15.41 | MTGL |
| ATOM | 1930 | O | GLU | 245 | 24.421 | 1.014 | 33.060 | 1.00 | 16.55 | MTGL |
| ATOM | 1931 | N | THR | 246 | 24.533 | -1.174 | 33.563 | 1.00 | 15.11 | MTGL |
| ATOM | 1932 | CA | THR | 246 | 23.266 | -1.185 | 34.280 | 1.00 | 14.75 | MTGL |
| ATOM | 1933 | CB | THR | 246 | 22.053 | -1.052 | 33.322 | 1.00 | 15.60 | MTGL |
| ATOM | 1934 | OG1 | THR | 246 | 20.884 | -0.721 | 34.085 | 1.00 | 14.95 | MTGL |
| ATOM | 1935 | CG2 | THR | 246 | 21.809 | -2.352 | 32.564 | 1.00 | 14.91 | MTGL |
| ATOM | 1936 | C | THR | 246 | 23.168 | -2.467 | 35.100 | 1.00 | 14.67 | MTGL |
| ATOM | 1937 | O | THR | 246 | 23.853 | -3.451 | 34.807 | 1.00 | 15.70 | MTGL |
| ATOM | 1938 | N | ASN | 247 | 22.331 | -2.441 | 36.134 | 1.00 | 14.38 | MTGL |
| ATOM | 1939 | CA | ASN | 247 | 22.128 | -3.579 | 37.035 | 1.00 | 14.91 | MTGL |
| ATOM | 1940 | CB | ASN | 247 | 23.012 | -3.462 | 38.294 | 1.00 | 15.25 | MTGL |
| ATOM | 1941 | CG | ASN | 247 | 24.397 | -4.085 | 38.150 | 1.00 | 16.92 | MTGL |
| ATOM | 1942 | OD1 | ASN | 247 | 25.212 | -3.972 | 39.068 | 1.00 | 16.53 | MTGL |
| ATOM | 1943 | ND2 | ASN | 247 | 24.668 | -4.746 | 37.024 | 1.00 | 14.82 | MTGL |
| ATOM | 1944 | C | ASN | 247 | 20.693 | -3.554 | 37.560 | 1.00 | 15.99 | MTGL |
| ATOM | 1945 | O | ASN | 247 | 20.057 | -2.496 | 37.609 | 1.00 | 15.64 | MTGL |
| ATOM | 1946 | N | TRP | 248 | 20.194 | -4.723 | 37.946 | 1.00 | 15.53 | MTGL |
| ATOM | 1947 | CA | TRP | 248 | 18.893 | -4.830 | 38.600 | 1.00 | 16.36 | MTGL |
| ATOM | 1948 | CB | TRP | 248 | 17.732 | -5.127 | 37.657 | 1.00 | 14.84 | MTGL |
| ATOM | 1949 | CG | TRP | 248 | 16.455 | -5.135 | 38.445 | 1.00 | 13.73 | MTGL |
| ATOM | 1950 | CD2 | TRP | 248 | 15.743 | -3.989 | 38.940 | 1.00 | 14.11 | MTGL |
| ATOM | 1951 | CE2 | TRP | 248 | 14.684 | -4.467 | 39.739 | 1.00 | 12.13 | MTGL |
| ATOM | 1952 | CE3 | TRP | 248 | 15.902 | -2.603 | 38.786 | 1.00 | 14.57 | MTGL |
| ATOM | 1953 | CD1 | TRP | 248 | 15.812 | -6.224 | 38.949 | 1.00 | 13.26 | MTGL |
| ATOM | 1954 | NE1 | TRP | 248 | 14.751 | -5.833 | 39.728 | 1.00 | 13.69 | MTGL |
| ATOM | 1955 | CZ2 | TRP | 248 | 13.784 | -3.613 | 40.384 | 1.00 | 14.00 | MTGL |
| ATOM | 1956 | CZ3 | TRP | 248 | 15.008 | -1.751 | 39.427 | 1.00 | 13.98 | MTGL |
| ATOM | 1957 | CH2 | TRP | 248 | 13.962 | -2.260 | 40.218 | 1.00 | 14.50 | MTGL |
| ATOM | 1958 | C | TRP | 248 | 19.080 | -5.972 | 39.576 | 1.00 | 16.41 | MTGL |
| ATOM | 1959 | O | TRP | 248 | 19.507 | -7.060 | 39.200 | 1.00 | 17.70 | MTGL |
| ATOM | 1960 | N | PRO | 249 | 18.765 | -5.739 | 40.850 | 1.00 | 17.62 | MTGL |
| ATOM | 1961 | CD | PRO | 249 | 18.316 | -4.468 | 41.449 | 1.00 | 17.41 | MTGL |
| ATOM | 1962 | CA | PRO | 249 | 18.933 | -6.774 | 41.868 | 1.00 | 17.81 | MTGL |
| ATOM | 1963 | CB | PRO | 249 | 19.010 | -5.961 | 43.156 | 1.00 | 18.08 | MTGL |
| ATOM | 1964 | CG | PRO | 249 | 18.056 | -4.857 | 42.892 | 1.00 | 20.03 | MTGL |
| ATOM | 1965 | C | PRO | 249 | 17.922 | -7.898 | 41.972 | 1.00 | 18.16 | MTGL |
| ATOM | 1966 | O | PRO | 249 | 16.729 | -7.722 | 41.728 | 1.00 | 18.74 | MTGL |
| ATOM | 1967 | N | ILE | 250 | 18.426 | -9.074 | 42.322 | 1.00 | 18.86 | MTGL |
| ATOM | 1968 | CA | ILE | 250 | 17.561 | -10.215 | 42.549 | 1.00 | 20.06 | MTGL |
| ATOM | 1969 | CB | ILE | 250 | 18.189 | -11.544 | 42.040 | 1.00 | 20.52 | MTGL |
| ATOM | 1970 | CG2 | ILE | 250 | 18.230 | -11.553 | 40.518 | 1.00 | 19.08 | MTGL |
| ATOM | 1971 | CG1 | ILE | 250 | 19.590 | -11.734 | 42.614 | 1.00 | 20.81 | MTGL |

Fig. 1 cont.

| | | | | | | | | | |
|---|---|---|---|---|---|---|---|---|---|
| ATOM | 1972 | CD1 | ILE | 250 | 20.222 | -13.061 | 42.216 | 1.00 21.09 | MTGL |
| ATOM | 1973 | C | ILE | 250 | 17.408 | -10.234 | 44.075 | 1.00 19.97 | MTGL |
| ATOM | 1974 | O | ILE | 250 | 16.659 | -11.028 | 44.637 | 1.00 20.48 | MTGL |
| ATOM | 1975 | N | SER | 251 | 18.127 | -9.327 | 44.735 | 1.00 20.21 | MTGL |
| ATOM | 1976 | CA | SER | 251 | 18.072 | -9.206 | 46.188 | 1.00 21.30 | MTGL |
| ATOM | 1977 | CB | SER | 251 | 18.878 | -10.331 | 46.843 | 1.00 22.63 | MTGL |
| ATOM | 1978 | OG | SER | 251 | 18.757 | -10.273 | 48.253 | 1.00 24.04 | MTGL |
| ATOM | 1979 | C | SER | 251 | 18.603 | -7.855 | 46.658 | 1.00 21.50 | MTGL |
| ATOM | 1980 | O | SER | 251 | 19.735 | -7.485 | 46.343 | 1.00 21.25 | MTGL |
| ATOM | 1981 | N | CYS | 252 | 17.784 | -7.112 | 47.400 | 1.00 21.87 | MTGL |
| ATOM | 1982 | CA | CYS | 252 | 18.194 | -5.806 | 47.918 | 1.00 23.27 | MTGL |
| ATOM | 1983 | C | CYS | 252 | 17.529 | -5.505 | 49.263 | 1.00 24.17 | MTGL |
| ATOM | 1984 | O | CYS | 252 | 16.654 | -4.647 | 49.340 | 1.00 24.61 | MTGL |
| ATOM | 1985 | CB | CYS | 252 | 17.840 | -4.684 | 46.927 | 1.00 23.57 | MTGL |
| ATOM | 1986 | SG | CYS | 252 | 18.756 | -3.154 | 47.311 | 1.00 23.83 | MTGL |
| ATOM | 1987 | N | PRO | 253 | 17.951 | -6.199 | 50.340 | 1.00 25.34 | MTGL |
| ATOM | 1988 | CD | PRO | 253 | 18.950 | -7.281 | 50.290 | 1.00 26.08 | MTGL |
| ATOM | 1989 | CA | PRO | 253 | 17.428 | -6.052 | 51.707 | 1.00 25.93 | MTGL |
| ATOM | 1990 | CB | PRO | 253 | 18.308 | -7.001 | 52.518 | 1.00 26.63 | MTGL |
| ATOM | 1991 | CG | PRO | 253 | 18.627 | -8.068 | 51.539 | 1.00 27.12 | MTGL |
| ATOM | 1992 | C | PRO | 253 | 17.416 | -4.645 | 52.294 | 1.00 26.16 | MTGL |
| ATOM | 1993 | O | PRO | 253 | 16.415 | -4.223 | 52.865 | 1.00 26.46 | MTGL |
| ATOM | 1994 | N | ASN | 254 | 18.526 | -3.922 | 52.178 | 1.00 26.96 | MTGL |
| ATOM | 1995 | CA | ASN | 254 | 18.574 | -2.560 | 52.713 | 1.00 27.76 | MTGL |
| ATOM | 1996 | CB | ASN | 254 | 19.145 | -2.538 | 54.137 | 1.00 29.54 | MTGL |
| ATOM | 1997 | CG | ASN | 254 | 20.541 | -3.097 | 54.220 | 1.00 31.33 | MTGL |
| ATOM | 1998 | OD1 | ASN | 254 | 20.854 | -4.102 | 53.587 | 1.00 34.28 | MTGL |
| ATOM | 1999 | ND2 | ASN | 254 | 21.388 | -2.465 | 55.028 | 1.00 30.87 | MTGL |
| ATOM | 2000 | C | ASN | 254 | 19.329 | -1.580 | 51.834 | 1.00 26.98 | MTGL |
| ATOM | 2001 | O | ASN | 254 | 20.525 | -1.355 | 51.990 | 1.00 26.72 | MTGL |
| ATOM | 2002 | N | PRO | 255 | 18.623 | -0.993 | 50.873 | 1.00 26.12 | MTGL |
| ATOM | 2003 | CD | PRO | 255 | 17.274 | -1.385 | 50.443 | 1.00 25.65 | MTGL |
| ATOM | 2004 | CA | PRO | 255 | 19.222 | -0.023 | 49.957 | 1.00 25.15 | MTGL |
| ATOM | 2005 | CB | PRO | 255 | 18.128 | 0.211 | 48.913 | 1.00 25.50 | MTGL |
| ATOM | 2006 | CG | PRO | 255 | 16.895 | -0.262 | 49.550 | 1.00 25.88 | MTGL |
| ATOM | 2007 | C | PRO | 255 | 19.638 | 1.279 | 50.637 | 1.00 25.08 | MTGL |
| ATOM | 2008 | O | PRO | 255 | 18.993 | 1.735 | 51.586 | 1.00 24.66 | MTGL |
| ATOM | 2009 | N | ARG | 256 | 20.717 | 1.869 | 50.128 | 1.00 23.54 | MTGL |
| ATOM | 2010 | CA | ARG | 256 | 21.219 | 3.131 | 50.653 | 1.00 24.56 | MTGL |
| ATOM | 2011 | CB | ARG | 256 | 22.679 | 3.345 | 50.230 | 1.00 26.20 | MTGL |
| ATOM | 2012 | CG | ARG | 256 | 23.290 | 4.673 | 50.685 | 1.00 29.88 | MTGL |
| ATOM | 2013 | CD | ARG | 256 | 23.244 | 4.843 | 52.205 | 1.00 33.75 | MTGL |
| ATOM | 2014 | NE | ARG | 256 | 24.112 | 3.900 | 52.913 | 1.00 36.98 | MTGL |
| ATOM | 2015 | CZ | ARG | 256 | 24.215 | 3.826 | 54.241 | 1.00 38.13 | MTGL |
| ATOM | 2016 | NH1 | ARG | 256 | 23.503 | 4.638 | 55.016 | 1.00 37.96 | MTGL |
| ATOM | 2017 | NH2 | ARG | 256 | 25.034 | 2.942 | 54.796 | 1.00 38.27 | MTGL |
| ATOM | 2018 | C | ARG | 256 | 20.346 | 4.291 | 50.152 | 1.00 24.09 | MTGL |
| ATOM | 2019 | O | ARG | 256 | 20.223 | 5.312 | 50.820 | 1.00 22.82 | MTGL |
| ATOM | 2020 | N | TYR | 257 | 19.740 | 4.129 | 48.978 | 1.00 23.76 | MTGL |
| ATOM | 2021 | CA | TYR | 257 | 18.869 | 5.162 | 48.417 | 1.00 24.47 | MTGL |
| ATOM | 2022 | CB | TYR | 257 | 19.506 | 5.829 | 47.197 | 1.00 25.66 | MTGL |
| ATOM | 2023 | CG | TYR | 257 | 20.889 | 6.365 | 47.430 | 1.00 27.18 | MTGL |
| ATOM | 2024 | CD1 | TYR | 257 | 22.003 | 5.538 | 47.316 | 1.00 27.30 | MTGL |
| ATOM | 2025 | CE1 | TYR | 257 | 23.283 | 6.020 | 47.567 | 1.00 28.24 | MTGL |
| ATOM | 2026 | CD2 | TYR | 257 | 21.086 | 7.693 | 47.802 | 1.00 28.37 | MTGL |
| ATOM | 2027 | CE2 | TYR | 257 | 22.363 | 8.184 | 48.058 | 1.00 28.50 | MTGL |
| ATOM | 2028 | CZ | TYR | 257 | 23.455 | 7.341 | 47.940 | 1.00 29.46 | MTGL |
| ATOM | 2029 | OH | TYR | 257 | 24.720 | 7.814 | 48.215 | 1.00 30.61 | MTGL |

Fig. 1 cont.

| | | | | | | | | | |
|---|---|---|---|---|---|---|---|---|---|
| ATOM | 2030 | C | TYR | 257 | 17.539 | 4.578 | 47.986 | 1.00 24.30 | MTGL |
| ATOM | 2031 | O | TYR | 257 | 17.450 | 3.408 | 47.619 | 1.00 24.04 | MTGL |
| ATOM | 2032 | N | SER | 258 | 16.507 | 5.411 | 48.018 | 1.00 24.57 | MTGL |
| ATOM | 2033 | CA | SER | 258 | 15.178 | 4.984 | 47.607 | 1.00 24.95 | MTGL |
| ATOM | 2034 | CB | SER | 258 | 14.162 | 6.084 | 47.930 | 1.00 25.55 | MTGL |
| ATOM | 2035 | OG | SER | 258 | 14.261 | 6.471 | 49.292 | 1.00 27.69 | MTGL |
| ATOM | 2036 | C | SER | 258 | 15.230 | 4.746 | 46.102 | 1.00 23.31 | MTGL |
| ATOM | 2037 | O | SER | 258 | 15.949 | 5.449 | 45.392 | 1.00 23.48 | MTGL |
| ATOM | 2038 | N | PHE | 259 | 14.488 | 3.754 | 45.619 | 1.00 22.69 | MTGL |
| ATOM | 2039 | CA | PHE | 259 | 14.459 | 3.452 | 44.190 | 1.00 23.46 | MTGL |
| ATOM | 2040 | CB | PHE | 259 | 13.961 | 2.022 | 43.958 | 1.00 22.78 | MTGL |
| ATOM | 2041 | CG | PHE | 259 | 15.051 | 0.990 | 43.984 | 1.00 22.99 | MTGL |
| ATOM | 2042 | CD1 | PHE | 259 | 15.923 | 0.904 | 45.066 | 1.00 24.03 | MTGL |
| ATOM | 2043 | CD2 | PHE | 259 | 15.218 | 0.112 | 42.919 | 1.00 22.03 | MTGL |
| ATOM | 2044 | CE1 | PHE | 259 | 16.945 | -0.046 | 45.089 | 1.00 24.16 | MTGL |
| ATOM | 2045 | CE2 | PHE | 259 | 16.233 | -0.839 | 42.929 | 1.00 22.81 | MTGL |
| ATOM | 2046 | CZ | PHE | 259 | 17.103 | -0.918 | 44.019 | 1.00 23.26 | MTGL |
| ATOM | 2047 | C | PHE | 259 | 13.580 | 4.429 | 43.411 | 1.00 23.33 | MTGL |
| ATOM | 2048 | O | PHE | 259 | 12.681 | 5.048 | 43.975 | 1.00 23.29 | MTGL |
| ATOM | 2049 | N | PRO | 260 | 13.840 | 4.581 | 42.100 | 1.00 23.87 | MTGL |
| ATOM | 2050 | CD | PRO | 260 | 14.959 | 4.002 | 41.338 | 1.00 23.34 | MTGL |
| ATOM | 2051 | CA | PRO | 260 | 13.057 | 5.492 | 41.259 | 1.00 23.83 | MTGL |
| ATOM | 2052 | CB | PRO | 260 | 13.711 | 5.346 | 39.888 | 1.00 23.96 | MTGL |
| ATOM | 2053 | CG | PRO | 260 | 15.138 | 5.012 | 40.229 | 1.00 23.75 | MTGL |
| ATOM | 2054 | C | PRO | 260 | 11.594 | 5.062 | 41.255 | 1.00 24.68 | MTGL |
| ATOM | 2055 | O | PRO | 260 | 11.287 | 3.867 | 41.233 | 1.00 22.71 | MTGL |
| ATOM | 2056 | N | SER | 261 | 10.700 | 6.042 | 41.274 | 1.00 24.81 | MTGL |
| ATOM | 2057 | CA | SER | 261 | 9.267 | 5.783 | 41.298 | 1.00 25.73 | MTGL |
| ATOM | 2058 | CB | SER | 261 | 8.494 | 7.107 | 41.254 | 1.00 26.69 | MTGL |
| ATOM | 2059 | OG | SER | 261 | 8.667 | 7.757 | 40.003 | 1.00 27.65 | MTGL |
| ATOM | 2060 | C | SER | 261 | 8.725 | 4.862 | 40.207 | 1.00 25.31 | MTGL |
| ATOM | 2061 | O | SER | 261 | 7.853 | 4.048 | 40.488 | 1.00 25.28 | MTGL |
| ATOM | 2062 | N | ASP | 262 | 9.214 | 4.979 | 38.973 | 1.00 26.49 | MTGL |
| ATOM | 2063 | CA | ASP | 262 | 8.678 | 4.131 | 37.909 | 1.00 27.78 | MTGL |
| ATOM | 2064 | CB | ASP | 262 | 8.762 | 4.824 | 36.535 | 1.00 27.44 | MTGL |
| ATOM | 2065 | CG | ASP | 262 | 10.166 | 5.267 | 36.170 | 1.00 29.75 | MTGL |
| ATOM | 2066 | OD1 | ASP | 262 | 11.138 | 4.673 | 36.681 | 1.00 29.62 | MTGL |
| ATOM | 2067 | OD2 | ASP | 262 | 10.289 | 6.207 | 35.349 | 1.00 29.82 | MTGL |
| ATOM | 2068 | C | ASP | 262 | 9.259 | 2.724 | 37.816 | 1.00 28.89 | MTGL |
| ATOM | 2069 | O | ASP | 262 | 9.063 | 2.037 | 36.812 | 1.00 29.03 | MTGL |
| ATOM | 2070 | N | VAL | 263 | 9.968 | 2.291 | 38.857 | 1.00 29.21 | MTGL |
| ATOM | 2071 | CA | VAL | 263 | 10.529 | 0.941 | 38.878 | 1.00 29.98 | MTGL |
| ATOM | 2072 | CB | VAL | 263 | 12.063 | 0.930 | 38.613 | 1.00 29.51 | MTGL |
| ATOM | 2073 | CG1 | VAL | 263 | 12.355 | 1.468 | 37.226 | 1.00 28.86 | MTGL |
| ATOM | 2074 | CG2 | VAL | 263 | 12.788 | 1.751 | 39.669 | 1.00 29.09 | MTGL |
| ATOM | 2075 | C | VAL | 263 | 10.254 | 0.257 | 40.218 | 1.00 30.76 | MTGL |
| ATOM | 2076 | O | VAL | 263 | 10.672 | -0.879 | 40.434 | 1.00 30.49 | MTGL |
| ATOM | 2077 | N | LYS | 264 | 9.534 | 0.941 | 41.108 | 1.00 31.82 | MTGL |
| ATOM | 2078 | CA | LYS | 264 | 9.215 | 0.394 | 42.432 | 1.00 33.07 | MTGL |
| ATOM | 2079 | CB | LYS | 264 | 8.570 | 1.464 | 43.317 | 1.00 34.40 | MTGL |
| ATOM | 2080 | CG | LYS | 264 | 9.566 | 2.391 | 44.002 | 1.00 36.45 | MTGL |
| ATOM | 2081 | CD | LYS | 264 | 8.859 | 3.344 | 44.961 | 1.00 38.24 | MTGL |
| ATOM | 2082 | CE | LYS | 264 | 9.844 | 4.281 | 45.655 | 1.00 40.37 | MTGL |
| ATOM | 2083 | NZ | LYS | 264 | 9.148 | 5.291 | 46.508 | 1.00 40.59 | MTGL |
| ATOM | 2084 | C | LYS | 264 | 8.321 | -0.842 | 42.415 | 1.00 33.40 | MTGL |
| ATOM | 2085 | O | LYS | 264 | 8.267 | -1.595 | 43.394 | 1.00 33.28 | MTGL |
| ATOM | 2086 | N | ASN | 265 | 7.612 | -1.049 | 41.313 | 1.00 32.77 | MTGL |
| ATOM | 2087 | CA | ASN | 265 | 6.738 | -2.208 | 41.194 | 1.00 32.23 | MTGL |

Fig. 1 cont.

| | | | | | | | | | |
|---|---|---|---|---|---|---|---|---|---|
| ATOM | 2088 | CB | ASN | 265 | 5.587 | -1.898 | 40.236 | 1.00 34.35 | MTGL |
| ATOM | 2089 | CG | ASN | 265 | 6.074 | -1.544 | 38.845 | 1.00 36.81 | MTGL |
| ATOM | 2090 | OD1 | ASN | 265 | 6.837 | -0.593 | 38.667 | 1.00 37.33 | MTGL |
| ATOM | 2091 | ND2 | ASN | 265 | 5.638 | -2.311 | 37.848 | 1.00 38.71 | MTGL |
| ATOM | 2092 | C | ASN | 265 | 7.504 | -3.436 | 40.689 | 1.00 30.70 | MTGL |
| ATOM | 2093 | O | ASN | 265 | 6.998 | -4.555 | 40.744 | 1.00 30.83 | MTGL |
| ATOM | 2094 | N | ILE | 266 | 8.719 | -3.226 | 40.192 | 1.00 28.28 | MTGL |
| ATOM | 2095 | CA | ILE | 266 | 9.517 | -4.336 | 39.687 | 1.00 25.48 | MTGL |
| ATOM | 2096 | CB | ILE | 266 | 10.651 | -3.848 | 38.767 | 1.00 23.96 | MTGL |
| ATOM | 2097 | CG2 | ILE | 266 | 11.449 | -5.046 | 38.257 | 1.00 23.40 | MTGL |
| ATOM | 2098 | CG1 | ILE | 266 | 10.067 | -3.054 | 37.594 | 1.00 23.38 | MTGL |
| ATOM | 2099 | CD1 | ILE | 266 | 11.114 | -2.516 | 36.627 | 1.00 22.30 | MTGL |
| ATOM | 2100 | C | ILE | 266 | 10.122 | -5.094 | 40.867 | 1.00 24.88 | MTGL |
| ATOM | 2101 | O | ILE | 266 | 10.825 | -4.520 | 41.691 | 1.00 22.68 | MTGL |
| ATOM | 2102 | N | PRO | 267 | 9.850 | -6.404 | 40.960 | 1.00 24.25 | MTGL |
| ATOM | 2103 | CD | PRO | 267 | 9.012 | -7.212 | 40.051 | 1.00 23.79 | MTGL |
| ATOM | 2104 | CA | PRO | 267 | 10.374 | -7.225 | 42.052 | 1.00 23.72 | MTGL |
| ATOM | 2105 | CB | PRO | 267 | 9.542 | -8.497 | 41.946 | 1.00 24.48 | MTGL |
| ATOM | 2106 | CG | PRO | 267 | 9.373 | -8.633 | 40.455 | 1.00 24.22 | MTGL |
| ATOM | 2107 | C | PRO | 267 | 11.865 | -7.526 | 41.943 | 1.00 23.20 | MTGL |
| ATOM | 2108 | O | PRO | 267 | 12.437 | -7.515 | 40.851 | 1.00 22.29 | MTGL |
| ATOM | 2109 | N | PHE | 268 | 12.487 | -7.781 | 43.090 | 1.00 22.29 | MTGL |
| ATOM | 2110 | CA | PHE | 268 | 13.898 | -8.134 | 43.119 | 1.00 22.67 | MTGL |
| ATOM | 2111 | CB | PHE | 268 | 14.533 | -7.757 | 44.462 | 1.00 22.68 | MTGL |
| ATOM | 2112 | CG | PHE | 268 | 14.493 | -6.285 | 44.754 | 1.00 22.93 | MTGL |
| ATOM | 2113 | CD1 | PHE | 268 | 14.838 | -5.360 | 43.773 | 1.00 22.68 | MTGL |
| ATOM | 2114 | CD2 | PHE | 268 | 14.115 | -5.821 | 46.008 | 1.00 23.18 | MTGL |
| ATOM | 2115 | CE1 | PHE | 268 | 14.806 | -3.993 | 44.037 | 1.00 23.40 | MTGL |
| ATOM | 2116 | CE2 | PHE | 268 | 14.079 | -4.454 | 46.283 | 1.00 23.36 | MTGL |
| ATOM | 2117 | CZ | PHE | 268 | 14.425 | -3.539 | 45.298 | 1.00 23.35 | MTGL |
| ATOM | 2118 | C | PHE | 268 | 13.925 | -9.643 | 42.921 | 1.00 21.88 | MTGL |
| ATOM | 2119 | O | PHE | 268 | 13.780 | -10.414 | 43.873 | 1.00 21.02 | MTGL |
| ATOM | 2120 | N | SER | 269 | 14.088 | -10.049 | 41.667 | 1.00 21.08 | MTGL |
| ATOM | 2121 | CA | SER | 269 | 14.110 | -11.457 | 41.294 | 1.00 20.72 | MTGL |
| ATOM | 2122 | CB | SER | 269 | 12.702 | -12.052 | 41.417 | 1.00 19.79 | MTGL |
| ATOM | 2123 | OG | SER | 269 | 11.814 | -11.416 | 40.509 | 1.00 19.06 | MTGL |
| ATOM | 2124 | C | SER | 269 | 14.554 | -11.546 | 39.844 | 1.00 20.32 | MTGL |
| ATOM | 2125 | O | SER | 269 | 14.670 | -10.530 | 39.161 | 1.00 19.97 | MTGL |
| ATOM | 2126 | N | PRO | 270 | 14.814 | -12.767 | 39.354 | 1.00 21.15 | MTGL |
| ATOM | 2127 | CD | PRO | 270 | 14.896 | -14.054 | 40.075 | 1.00 20.43 | MTGL |
| ATOM | 2128 | CA | PRO | 270 | 15.237 | -12.915 | 37.958 | 1.00 20.91 | MTGL |
| ATOM | 2129 | CB | PRO | 270 | 15.407 | -14.426 | 37.809 | 1.00 20.78 | MTGL |
| ATOM | 2130 | CG | PRO | 270 | 15.832 | -14.852 | 39.196 | 1.00 20.58 | MTGL |
| ATOM | 2131 | C | PRO | 270 | 14.169 | -12.348 | 37.016 | 1.00 20.97 | MTGL |
| ATOM | 2132 | O | PRO | 270 | 14.489 | -11.688 | 36.028 | 1.00 20.64 | MTGL |
| ATOM | 2133 | N | GLU | 271 | 12.900 | -12.605 | 37.331 | 1.00 21.15 | MTGL |
| ATOM | 2134 | CA | GLU | 271 | 11.797 | -12.102 | 36.508 | 1.00 21.55 | MTGL |
| ATOM | 2135 | CB | GLU | 271 | 10.446 | -12.538 | 37.082 | 1.00 22.38 | MTGL |
| ATOM | 2136 | CG | GLU | 271 | 10.155 | -14.036 | 37.003 | 1.00 25.49 | MTGL |
| ATOM | 2137 | CD | GLU | 271 | 11.082 | -14.873 | 37.870 | 1.00 26.37 | MTGL |
| ATOM | 2138 | OE1 | GLU | 271 | 11.447 | -14.415 | 38.970 | 1.00 26.39 | MTGL |
| ATOM | 2139 | OE2 | GLU | 271 | 11.433 | -15.997 | 37.457 | 1.00 27.82 | MTGL |
| ATOM | 2140 | C | GLU | 271 | 11.861 | -10.577 | 36.476 | 1.00 20.84 | MTGL |
| ATOM | 2141 | O | GLU | 271 | 11.640 | -9.949 | 35.434 | 1.00 20.80 | MTGL |
| ATOM | 2142 | N | GLY | 272 | 12.166 | -9.993 | 37.631 | 1.00 19.71 | MTGL |
| ATOM | 2143 | CA | GLY | 272 | 12.271 | -8.550 | 37.734 | 1.00 18.93 | MTGL |
| ATOM | 2144 | C | GLY | 272 | 13.415 | -8.008 | 36.897 | 1.00 18.95 | MTGL |
| ATOM | 2145 | O | GLY | 272 | 13.284 | -6.941 | 36.289 | 1.00 19.13 | MTGL |

Fig. 1 cont.

| ATOM | 2146 | N   | GLN | 273 | 14.534 | -8.734  | 36.859 | 1.00 | 17.61 | MTGL |
|------|------|-----|-----|-----|--------|---------|--------|------|-------|------|
| ATOM | 2147 | CA  | GLN | 273 | 15.687 | -8.299  | 36.074 | 1.00 | 18.43 | MTGL |
| ATOM | 2148 | CB  | GLN | 273 | 16.864 | -9.260  | 36.230 | 1.00 | 17.76 | MTGL |
| ATOM | 2149 | CG  | GLN | 273 | 17.467 | -9.345  | 37.610 | 1.00 | 19.26 | MTGL |
| ATOM | 2150 | CD  | GLN | 273 | 18.720 | -10.190 | 37.607 | 1.00 | 19.87 | MTGL |
| ATOM | 2151 | OE1 | GLN | 273 | 18.726 | -11.304 | 37.073 | 1.00 | 18.60 | MTGL |
| ATOM | 2152 | NE2 | GLN | 273 | 19.793 | -9.667  | 38.198 | 1.00 | 19.12 | MTGL |
| ATOM | 2153 | C   | GLN | 273 | 15.300 | -8.270  | 34.607 | 1.00 | 18.09 | MTGL |
| ATOM | 2154 | O   | GLN | 273 | 15.660 | -7.353  | 33.869 | 1.00 | 17.98 | MTGL |
| ATOM | 2155 | N   | THR | 274 | 14.579 | -9.305  | 34.193 | 1.00 | 17.84 | MTGL |
| ATOM | 2156 | CA  | THR | 274 | 14.131 | -9.433  | 32.815 | 1.00 | 17.91 | MTGL |
| ATOM | 2157 | CB  | THR | 274 | 13.293 | -10.712 | 32.637 | 1.00 | 18.13 | MTGL |
| ATOM | 2158 | OG1 | THR | 274 | 14.128 | -11.857 | 32.859 | 1.00 | 19.81 | MTGL |
| ATOM | 2159 | CG2 | THR | 274 | 12.695 | -10.777 | 31.231 | 1.00 | 19.04 | MTGL |
| ATOM | 2160 | C   | THR | 274 | 13.293 | -8.219  | 32.428 | 1.00 | 17.34 | MTGL |
| ATOM | 2161 | O   | THR | 274 | 13.504 | -7.619  | 31.376 | 1.00 | 16.72 | MTGL |
| ATOM | 2162 | N   | THR | 275 | 12.351 | -7.859  | 33.294 | 1.00 | 16.98 | MTGL |
| ATOM | 2163 | CA  | THR | 275 | 11.483 | -6.712  | 33.056 | 1.00 | 17.24 | MTGL |
| ATOM | 2164 | CB  | THR | 275 | 10.425 | -6.574  | 34.169 | 1.00 | 17.29 | MTGL |
| ATOM | 2165 | OG1 | THR | 275 | 9.587  | -7.735  | 34.181 | 1.00 | 17.49 | MTGL |
| ATOM | 2166 | CG2 | THR | 275 | 9.563  | -5.331  | 33.937 | 1.00 | 16.88 | MTGL |
| ATOM | 2167 | C   | THR | 275 | 12.270 | -5.405  | 32.982 | 1.00 | 17.05 | MTGL |
| ATOM | 2168 | O   | THR | 275 | 12.090 | -4.618  | 32.052 | 1.00 | 17.86 | MTGL |
| ATOM | 2169 | N   | PHE | 276 | 13.139 | -5.174  | 33.963 | 1.00 | 16.71 | MTGL |
| ATOM | 2170 | CA  | PHE | 276 | 13.937 | -3.949  | 34.000 | 1.00 | 15.62 | MTGL |
| ATOM | 2171 | CB  | PHE | 276 | 14.781 | -3.890  | 35.278 | 1.00 | 15.45 | MTGL |
| ATOM | 2172 | CG  | PHE | 276 | 15.621 | -2.646  | 35.389 | 1.00 | 16.62 | MTGL |
| ATOM | 2173 | CD1 | PHE | 276 | 15.048 | -1.437  | 35.777 | 1.00 | 17.56 | MTGL |
| ATOM | 2174 | CD2 | PHE | 276 | 16.976 | -2.675  | 35.077 | 1.00 | 17.00 | MTGL |
| ATOM | 2175 | CE1 | PHE | 276 | 15.817 | -0.272  | 35.860 | 1.00 | 18.40 | MTGL |
| ATOM | 2176 | CE2 | PHE | 276 | 17.757 | -1.518  | 35.155 | 1.00 | 18.28 | MTGL |
| ATOM | 2177 | CZ  | PHE | 276 | 17.176 | -0.314  | 35.546 | 1.00 | 17.73 | MTGL |
| ATOM | 2178 | C   | PHE | 276 | 14.866 | -3.825  | 32.796 | 1.00 | 16.42 | MTGL |
| ATOM | 2179 | O   | PHE | 276 | 14.907 | -2.785  | 32.136 | 1.00 | 17.18 | MTGL |
| ATOM | 2180 | N   | ILE | 277 | 15.627 | -4.881  | 32.520 | 1.00 | 15.71 | MTGL |
| ATOM | 2181 | CA  | ILE | 277 | 16.558 | -4.864  | 31.399 | 1.00 | 14.72 | MTGL |
| ATOM | 2182 | CB  | ILE | 277 | 17.364 | -6.181  | 31.330 | 1.00 | 14.70 | MTGL |
| ATOM | 2183 | CG2 | ILE | 277 | 18.227 | -6.209  | 30.063 | 1.00 | 14.44 | MTGL |
| ATOM | 2184 | CG1 | ILE | 277 | 18.238 | -6.305  | 32.587 | 1.00 | 14.86 | MTGL |
| ATOM | 2185 | CD1 | ILE | 277 | 18.945 | -7.635  | 32.727 | 1.00 | 14.36 | MTGL |
| ATOM | 2186 | C   | ILE | 277 | 15.832 | -4.643  | 30.081 | 1.00 | 14.58 | MTGL |
| ATOM | 2187 | O   | ILE | 277 | 16.286 | -3.868  | 29.250 | 1.00 | 14.01 | MTGL |
| ATOM | 2188 | N   | THR | 278 | 14.708 | -5.330  | 29.890 | 1.00 | 14.56 | MTGL |
| ATOM | 2189 | CA  | THR | 278 | 13.930 | -5.182  | 28.663 | 1.00 | 15.56 | MTGL |
| ATOM | 2190 | CB  | THR | 278 | 12.724 | -6.159  | 28.635 | 1.00 | 15.82 | MTGL |
| ATOM | 2191 | OG1 | THR | 278 | 13.203 | -7.505  | 28.742 | 1.00 | 16.63 | MTGL |
| ATOM | 2192 | CG2 | THR | 278 | 11.942 | -6.017  | 27.329 | 1.00 | 15.47 | MTGL |
| ATOM | 2193 | C   | THR | 278 | 13.411 | -3.747  | 28.530 | 1.00 | 15.31 | MTGL |
| ATOM | 2194 | O   | THR | 278 | 13.435 | -3.168  | 27.446 | 1.00 | 16.65 | MTGL |
| ATOM | 2195 | N   | ASN | 279 | 12.946 | -3.174  | 29.634 | 1.00 | 15.85 | MTGL |
| ATOM | 2196 | CA  | ASN | 279 | 12.430 | -1.808  | 29.609 | 1.00 | 16.36 | MTGL |
| ATOM | 2197 | CB  | ASN | 279 | 11.743 | -1.475  | 30.939 | 1.00 | 15.56 | MTGL |
| ATOM | 2198 | CG  | ASN | 279 | 10.388 | -2.159  | 31.077 | 1.00 | 17.29 | MTGL |
| ATOM | 2199 | OD1 | ASN | 279 | 9.939  | -2.848  | 30.167 | 1.00 | 15.98 | MTGL |
| ATOM | 2200 | ND2 | ASN | 279 | 9.736  | -1.966  | 32.215 | 1.00 | 17.61 | MTGL |
| ATOM | 2201 | C   | ASN | 279 | 13.520 | -0.783  | 29.304 | 1.00 | 16.68 | MTGL |
| ATOM | 2202 | O   | ASN | 279 | 13.300 | 0.155   | 28.533 | 1.00 | 16.98 | MTGL |
| ATOM | 2203 | N   | VAL | 280 | 14.695 | -0.950  | 29.904 | 1.00 | 16.27 | MTGL |

Fig. 1 cont.

```
ATOM   2204  CA   VAL   280      15.782   -0.013   29.641  1.00 15.63           MTGL
ATOM   2205  CB   VAL   280      17.005   -0.283   30.545  1.00 15.75           MTGL
ATOM   2206  CG1  VAL   280      18.171    0.623   30.126  1.00 14.59           MTGL
ATOM   2207  CG2  VAL   280      16.634   -0.023   32.007  1.00 14.29           MTGL
ATOM   2208  C    VAL   280      16.203   -0.144   28.183  1.00 15.42           MTGL
ATOM   2209  O    VAL   280      16.483    0.852   27.512  1.00 14.80           MTGL
ATOM   2210  N    ALA   281      16.236   -1.381   27.697  1.00 14.47           MTGL
ATOM   2211  CA   ALA   281      16.614   -1.645   26.315  1.00 15.95           MTGL
ATOM   2212  CB   ALA   281      16.573   -3.147   26.035  1.00 15.85           MTGL
ATOM   2213  C    ALA   281      15.662   -0.922   25.369  1.00 16.21           MTGL
ATOM   2214  O    ALA   281      16.087   -0.290   24.403  1.00 15.33           MTGL
ATOM   2215  N    ASN   282      14.369   -1.018   25.653  1.00 16.95           MTGL
ATOM   2216  CA   ASN   282      13.383   -0.386   24.792  1.00 17.84           MTGL
ATOM   2217  CB   ASN   282      12.015   -1.013   25.021  1.00 19.13           MTGL
ATOM   2218  CG   ASN   282      11.924   -2.398   24.400  1.00 20.19           MTGL
ATOM   2219  OD1  ASN   282      12.393   -2.605   23.289  1.00 23.04           MTGL
ATOM   2220  ND2  ASN   282      11.328   -3.341   25.108  1.00 19.74           MTGL
ATOM   2221  C    ASN   282      13.337    1.124   24.910  1.00 18.52           MTGL
ATOM   2222  O    ASN   282      12.841    1.806   24.011  1.00 17.57           MTGL
ATOM   2223  N    ILE   283      13.851    1.651   26.015  1.00 18.29           MTGL
ATOM   2224  CA   ILE   283      13.902    3.095   26.168  1.00 18.86           MTGL
ATOM   2225  CB   ILE   283      14.254    3.496   27.603  1.00 19.57           MTGL
ATOM   2226  CG2  ILE   283      14.818    4.917   27.636  1.00 20.74           MTGL
ATOM   2227  CG1  ILE   283      13.003    3.365   28.471  1.00 21.83           MTGL
ATOM   2228  CD1  ILE   283      13.214    3.728   29.909  1.00 25.75           MTGL
ATOM   2229  C    ILE   283      14.994    3.566   25.209  1.00 17.96           MTGL
ATOM   2230  O    ILE   283      14.816    4.543   24.483  1.00 17.19           MTGL
ATOM   2231  N    VAL   284      16.114    2.844   25.200  1.00 17.16           MTGL
ATOM   2232  CA   VAL   284      17.236    3.164   24.321  1.00 15.86           MTGL
ATOM   2233  CB   VAL   284      18.420    2.194   24.554  1.00 16.05           MTGL
ATOM   2234  CG1  VAL   284      19.491    2.409   23.491  1.00 14.09           MTGL
ATOM   2235  CG2  VAL   284      19.006    2.416   25.956  1.00 14.93           MTGL
ATOM   2236  C    VAL   284      16.797    3.075   22.861  1.00 16.21           MTGL
ATOM   2237  O    VAL   284      17.089    3.963   22.059  1.00 15.26           MTGL
ATOM   2238  N    SER   285      16.086    2.004   22.519  1.00 16.71           MTGL
ATOM   2239  CA   SER   285      15.618    1.813   21.145  1.00 18.87           MTGL
ATOM   2240  CB   SER   285      14.977    0.429   20.979  1.00 18.71           MTGL
ATOM   2241  OG   SER   285      15.954   -0.595   21.082  1.00 25.57           MTGL
ATOM   2242  C    SER   285      14.622    2.882   20.697  1.00 18.52           MTGL
ATOM   2243  O    SER   285      14.453    3.101   19.507  1.00 19.96           MTGL
ATOM   2244  N    SER   286      13.964    3.544   21.644  1.00 17.61           MTGL
ATOM   2245  CA   SER   286      12.993    4.574   21.295  1.00 18.49           MTGL
ATOM   2246  CB   SER   286      11.970    4.754   22.421  1.00 18.70           MTGL
ATOM   2247  OG   SER   286      12.505    5.533   23.483  1.00 18.21           MTGL
ATOM   2248  C    SER   286      13.686    5.909   21.040  1.00 18.76           MTGL
ATOM   2249  O    SER   286      13.043    6.892   20.676  1.00 17.84           MTGL
ATOM   2250  N    VAL   287      15.000    5.931   21.235  1.00 18.85           MTGL
ATOM   2251  CA   VAL   287      15.793    7.138   21.048  1.00 17.18           MTGL
ATOM   2252  CB   VAL   287      16.866    7.267   22.158  1.00 17.69           MTGL
ATOM   2253  CG1  VAL   287      17.764    8.477   21.890  1.00 17.29           MTGL
ATOM   2254  CG2  VAL   287      16.189    7.399   23.512  1.00 17.29           MTGL
ATOM   2255  C    VAL   287      16.493    7.144   19.702  1.00 17.44           MTGL
ATOM   2256  O    VAL   287      16.979    6.112   19.241  1.00 16.36           MTGL
ATOM   2257  N    SER   288      16.546    8.313   19.073  1.00 18.07           MTGL
ATOM   2258  CA   SER   288      17.215    8.442   17.787  1.00 18.93           MTGL
ATOM   2259  CB   SER   288      17.202    9.900   17.329  1.00 19.03           MTGL
ATOM   2260  OG   SER   288      17.858   10.045   16.082  1.00 21.05           MTGL
ATOM   2261  C    SER   288      18.657    7.950   17.911  1.00 18.73           MTGL
```

Fig. 1 cont.

| | | | | | | | | | | |
|---|---|---|---|---|---|---|---|---|---|---|
| ATOM | 2262 | O | SER | 288 | 19.444 | 8.498 | 18.682 | 1.00 | 18.95 | MTGL |
| ATOM | 2263 | N | ARG | 289 | 18.984 | 6.915 | 17.145 | 1.00 | 17.81 | MTGL |
| ATOM | 2264 | CA | ARG | 289 | 20.313 | 6.311 | 17.137 | 1.00 | 18.49 | MTGL |
| ATOM | 2265 | CB | ARG | 289 | 21.387 | 7.347 | 16.760 | 1.00 | 20.78 | MTGL |
| ATOM | 2266 | CG | ARG | 289 | 21.128 | 8.067 | 15.429 | 1.00 | 24.72 | MTGL |
| ATOM | 2267 | CD | ARG | 289 | 22.378 | 8.761 | 14.890 | 1.00 | 26.86 | MTGL |
| ATOM | 2268 | NE | ARG | 289 | 23.269 | 7.812 | 14.225 | 1.00 | 31.29 | MTGL |
| ATOM | 2269 | CZ | ARG | 289 | 24.483 | 8.101 | 13.758 | 1.00 | 32.57 | MTGL |
| ATOM | 2270 | NH1 | ARG | 289 | 24.981 | 9.327 | 13.880 | 1.00 | 33.06 | MTGL |
| ATOM | 2271 | NH2 | ARG | 289 | 25.200 | 7.159 | 13.159 | 1.00 | 32.56 | MTGL |
| ATOM | 2272 | C | ARG | 289 | 20.687 | 5.616 | 18.456 | 1.00 | 17.41 | MTGL |
| ATOM | 2273 | O | ARG | 289 | 21.865 | 5.493 | 18.785 | 1.00 | 16.35 | MTGL |
| ATOM | 2274 | N | GLY | 290 | 19.681 | 5.173 | 19.207 | 1.00 | 16.31 | MTGL |
| ATOM | 2275 | CA | GLY | 290 | 19.944 | 4.449 | 20.442 | 1.00 | 16.82 | MTGL |
| ATOM | 2276 | C | GLY | 290 | 20.267 | 3.042 | 19.970 | 1.00 | 17.04 | MTGL |
| ATOM | 2277 | O | GLY | 290 | 19.393 | 2.353 | 19.450 | 1.00 | 16.17 | MTGL |
| ATOM | 2278 | N | VAL | 291 | 21.502 | 2.595 | 20.159 | 1.00 | 17.31 | MTGL |
| ATOM | 2279 | CA | VAL | 291 | 21.893 | 1.290 | 19.644 | 1.00 | 17.47 | MTGL |
| ATOM | 2280 | CB | VAL | 291 | 22.951 | 1.475 | 18.534 | 1.00 | 17.89 | MTGL |
| ATOM | 2281 | CG1 | VAL | 291 | 22.387 | 2.347 | 17.419 | 1.00 | 18.32 | MTGL |
| ATOM | 2282 | CG2 | VAL | 291 | 24.204 | 2.125 | 19.112 | 1.00 | 16.95 | MTGL |
| ATOM | 2283 | C | VAL | 291 | 22.403 | 0.194 | 20.581 | 1.00 | 18.18 | MTGL |
| ATOM | 2284 | O | VAL | 291 | 22.610 | -0.933 | 20.133 | 1.00 | 17.39 | MTGL |
| ATOM | 2285 | N | GLY | 292 | 22.608 | 0.489 | 21.861 | 1.00 | 18.56 | MTGL |
| ATOM | 2286 | CA | GLY | 292 | 23.117 | -0.559 | 22.730 | 1.00 | 17.86 | MTGL |
| ATOM | 2287 | C | GLY | 292 | 22.774 | -0.538 | 24.205 | 1.00 | 18.08 | MTGL |
| ATOM | 2288 | O | GLY | 292 | 22.404 | 0.493 | 24.766 | 1.00 | 17.12 | MTGL |
| ATOM | 2289 | N | LEU | 293 | 22.913 | -1.708 | 24.824 | 1.00 | 18.07 | MTGL |
| ATOM | 2290 | CA | LEU | 293 | 22.653 | -1.902 | 26.246 | 1.00 | 18.28 | MTGL |
| ATOM | 2291 | CB | LEU | 293 | 21.223 | -2.404 | 26.474 | 1.00 | 19.14 | MTGL |
| ATOM | 2292 | CG | LEU | 293 | 20.858 | -2.808 | 27.910 | 1.00 | 22.33 | MTGL |
| ATOM | 2293 | CD1 | LEU | 293 | 21.047 | -1.625 | 28.842 | 1.00 | 23.17 | MTGL |
| ATOM | 2294 | CD2 | LEU | 293 | 19.410 | -3.278 | 27.965 | 1.00 | 23.54 | MTGL |
| ATOM | 2295 | C | LEU | 293 | 23.634 | -2.952 | 26.744 | 1.00 | 17.77 | MTGL |
| ATOM | 2296 | O | LEU | 293 | 23.763 | -4.009 | 26.130 | 1.00 | 17.95 | MTGL |
| ATOM | 2297 | N | PHE | 294 | 24.322 | -2.658 | 27.847 | 1.00 | 16.70 | MTGL |
| ATOM | 2298 | CA | PHE | 294 | 25.288 | -3.586 | 28.431 | 1.00 | 16.53 | MTGL |
| ATOM | 2299 | CB | PHE | 294 | 26.726 | -3.097 | 28.229 | 1.00 | 16.07 | MTGL |
| ATOM | 2300 | CG | PHE | 294 | 27.199 | -3.136 | 26.800 | 1.00 | 16.47 | MTGL |
| ATOM | 2301 | CD1 | PHE | 294 | 26.792 | -2.164 | 25.890 | 1.00 | 16.58 | MTGL |
| ATOM | 2302 | CD2 | PHE | 294 | 28.069 | -4.137 | 26.368 | 1.00 | 15.29 | MTGL |
| ATOM | 2303 | CE1 | PHE | 294 | 27.241 | -2.188 | 24.571 | 1.00 | 16.35 | MTGL |
| ATOM | 2304 | CE2 | PHE | 294 | 28.523 | -4.170 | 25.050 | 1.00 | 15.62 | MTGL |
| ATOM | 2305 | CZ | PHE | 294 | 28.110 | -3.192 | 24.150 | 1.00 | 15.75 | MTGL |
| ATOM | 2306 | C | PHE | 294 | 25.046 | -3.739 | 29.930 | 1.00 | 16.96 | MTGL |
| ATOM | 2307 | O | PHE | 294 | 25.032 | -2.752 | 30.667 | 1.00 | 17.04 | MTGL |
| ATOM | 2308 | N | TYR | 295 | 24.855 | -4.977 | 30.374 | 1.00 | 16.03 | MTGL |
| ATOM | 2309 | CA | TYR | 295 | 24.639 | -5.253 | 31.789 | 1.00 | 15.26 | MTGL |
| ATOM | 2310 | CB | TYR | 295 | 23.905 | -6.582 | 31.963 | 1.00 | 14.47 | MTGL |
| ATOM | 2311 | CG | TYR | 295 | 23.323 | -6.755 | 33.344 | 1.00 | 14.21 | MTGL |
| ATOM | 2312 | CD1 | TYR | 295 | 22.033 | -6.312 | 33.637 | 1.00 | 12.09 | MTGL |
| ATOM | 2313 | CE1 | TYR | 295 | 21.512 | -6.421 | 34.918 | 1.00 | 13.83 | MTGL |
| ATOM | 2314 | CD2 | TYR | 295 | 24.080 | -7.316 | 34.372 | 1.00 | 13.69 | MTGL |
| ATOM | 2315 | CE2 | TYR | 295 | 23.566 | -7.431 | 35.662 | 1.00 | 13.74 | MTGL |
| ATOM | 2316 | CZ | TYR | 295 | 22.284 | -6.979 | 35.930 | 1.00 | 14.39 | MTGL |
| ATOM | 2317 | OH | TYR | 295 | 21.784 | -7.058 | 37.211 | 1.00 | 15.39 | MTGL |
| ATOM | 2318 | C | TYR | 295 | 26.033 | -5.346 | 32.410 | 1.00 | 15.23 | MTGL |
| ATOM | 2319 | O | TYR | 295 | 26.932 | -5.933 | 31.814 | 1.00 | 15.00 | MTGL |

Fig. 1 cont.

```
ATOM  2320  N    TRP  296    26.228  -4.778  33.594  1.00  14.56    MTGL
ATOM  2321  CA   TRP  296    27.559  -4.829  34.195  1.00  15.23    MTGL
ATOM  2322  CB   TRP  296    27.847  -3.541  34.984  1.00  14.28    MTGL
ATOM  2323  CG   TRP  296    29.306  -3.370  35.309  1.00  15.53    MTGL
ATOM  2324  CD2  TRP  296    29.918  -3.408  36.611  1.00  16.19    MTGL
ATOM  2325  CE2  TRP  296    31.309  -3.221  36.424  1.00  15.45    MTGL
ATOM  2326  CE3  TRP  296    29.428  -3.583  37.916  1.00  16.72    MTGL
ATOM  2327  CD1  TRP  296    30.321  -3.168  34.418  1.00  15.37    MTGL
ATOM  2328  NE1  TRP  296    31.526  -3.077  35.079  1.00  15.66    MTGL
ATOM  2329  CZ2  TRP  296    32.219  -3.201  37.495  1.00  15.21    MTGL
ATOM  2330  CZ3  TRP  296    30.334  -3.564  38.985  1.00  16.55    MTGL
ATOM  2331  CH2  TRP  296    31.715  -3.375  38.763  1.00  16.36    MTGL
ATOM  2332  C    TRP  296    27.842  -6.029  35.097  1.00  14.61    MTGL
ATOM  2333  O    TRP  296    27.174  -6.224  36.114  1.00  15.45    MTGL
ATOM  2334  N    GLU  297    28.835  -6.826  34.702  1.00  14.69    MTGL
ATOM  2335  CA   GLU  297    29.298  -7.977  35.479  1.00  14.59    MTGL
ATOM  2336  CB   GLU  297    30.125  -7.465  36.661  1.00  13.64    MTGL
ATOM  2337  CG   GLU  297    31.453  -6.849  36.261  1.00  14.27    MTGL
ATOM  2338  CD   GLU  297    32.506  -7.896  35.947  1.00  13.45    MTGL
ATOM  2339  OE1  GLU  297    32.176  -9.102  35.991  1.00  12.29    MTGL
ATOM  2340  OE2  GLU  297    33.661  -7.510  35.660  1.00  14.90    MTGL
ATOM  2341  C    GLU  297    28.245  -8.952  36.000  1.00  15.16    MTGL
ATOM  2342  O    GLU  297    28.177  -9.219  37.205  1.00  15.61    MTGL
ATOM  2343  N    PRO  298    27.436  -9.529  35.100  1.00  14.59    MTGL
ATOM  2344  CD   PRO  298    27.545  -9.487  33.631  1.00  12.84    MTGL
ATOM  2345  CA   PRO  298    26.395 -10.474  35.517  1.00  14.70    MTGL
ATOM  2346  CB   PRO  298    25.651 -10.750  34.217  1.00  13.52    MTGL
ATOM  2347  CG   PRO  298    26.765 -10.716  33.213  1.00  12.86    MTGL
ATOM  2348  C    PRO  298    26.897 -11.774  36.158  1.00  14.86    MTGL
ATOM  2349  O    PRO  298    26.159 -12.424  36.901  1.00  14.01    MTGL
ATOM  2350  N    ALA  299    28.143 -12.147  35.875  1.00  15.30    MTGL
ATOM  2351  CA   ALA  299    28.689 -13.397  36.396  1.00  16.12    MTGL
ATOM  2352  CB   ALA  299    29.321 -14.184  35.245  1.00  16.45    MTGL
ATOM  2353  C    ALA  299    29.684 -13.297  37.551  1.00  16.40    MTGL
ATOM  2354  O    ALA  299    30.281 -14.303  37.934  1.00  16.31    MTGL
ATOM  2355  N    TRP  300    29.861 -12.104  38.111  1.00  16.53    MTGL
ATOM  2356  CA   TRP  300    30.804 -11.911  39.218  1.00  16.99    MTGL
ATOM  2357  CB   TRP  300    31.205 -10.438  39.300  1.00  15.26    MTGL
ATOM  2358  CG   TRP  300    32.518 -10.195  39.960  1.00  16.30    MTGL
ATOM  2359  CD2  TRP  300    33.248  -8.960  39.982  1.00  14.96    MTGL
ATOM  2360  CE2  TRP  300    34.440  -9.195  40.697  1.00  14.93    MTGL
ATOM  2361  CE3  TRP  300    33.007  -7.679  39.463  1.00  15.40    MTGL
ATOM  2362  CD1  TRP  300    33.274 -11.099  40.648  1.00  14.90    MTGL
ATOM  2363  NE1  TRP  300    34.429 -10.508  41.092  1.00  16.48    MTGL
ATOM  2364  CZ2  TRP  300    35.398  -8.195  40.912  1.00  13.85    MTGL
ATOM  2365  CZ3  TRP  300    33.960  -6.678  39.678  1.00  13.88    MTGL
ATOM  2366  CH2  TRP  300    35.143  -6.949  40.398  1.00  15.26    MTGL
ATOM  2367  C    TRP  300    30.159 -12.347  40.536  1.00  17.14    MTGL
ATOM  2368  O    TRP  300    29.909 -11.522  41.423  1.00  16.66    MTGL
ATOM  2369  N    ILE  301    29.907 -13.645  40.670  1.00  17.69    MTGL
ATOM  2370  CA   ILE  301    29.255 -14.168  41.866  1.00  19.29    MTGL
ATOM  2371  CB   ILE  301    28.893 -15.655  41.695  1.00  20.95    MTGL
ATOM  2372  CG2  ILE  301    27.937 -15.812  40.517  1.00  19.88    MTGL
ATOM  2373  CG1  ILE  301    30.153 -16.496  41.479  1.00  22.04    MTGL
ATOM  2374  CD1  ILE  301    29.858 -17.985  41.366  1.00  23.83    MTGL
ATOM  2375  C    ILE  301    29.973 -13.980  43.205  1.00  19.82    MTGL
ATOM  2376  O    ILE  301    29.325 -14.022  44.249  1.00  19.53    MTGL
ATOM  2377  N    HIS  302    31.287 -13.768  43.189  1.00  19.79    MTGL
```

Fig. 1 cont.

```
ATOM   2378  CA  HIS   302      32.016 -13.555  44.441  1.00 21.73      MTGL
ATOM   2379  CB  HIS   302      33.464 -14.042  44.317  1.00 22.38      MTGL
ATOM   2380  CG  HIS   302      33.603 -15.529  44.396  1.00 24.09      MTGL
ATOM   2381  CD2 HIS   302      33.254 -16.405  45.368  1.00 25.41      MTGL
ATOM   2382  ND1 HIS   302      34.154 -16.282  43.382  1.00 25.82      MTGL
ATOM   2383  CE1 HIS   302      34.137 -17.558  43.724  1.00 26.05      MTGL
ATOM   2384  NE2 HIS   302      33.596 -17.659  44.924  1.00 26.28      MTGL
ATOM   2385  C   HIS   302      32.002 -12.085  44.857  1.00 21.31      MTGL
ATOM   2386  O   HIS   302      32.609 -11.707  45.854  1.00 22.67      MTGL
ATOM   2387  N   ASN   303      31.303 -11.265  44.079  1.00 20.90      MTGL
ATOM   2388  CA  ASN   303      31.183  -9.831  44.337  1.00 20.21      MTGL
ATOM   2389  CB  ASN   303      32.200  -9.074  43.473  1.00 20.27      MTGL
ATOM   2390  CG  ASN   303      32.170  -7.573  43.706  1.00 21.40      MTGL
ATOM   2391  OD1 ASN   303      31.977  -7.118  44.828  1.00 22.04      MTGL
ATOM   2392  ND2 ASN   303      32.380  -6.799  42.643  1.00 19.16      MTGL
ATOM   2393  C   ASN   303      29.752  -9.467  43.946  1.00 20.34      MTGL
ATOM   2394  O   ASN   303      29.508  -8.488  43.233  1.00 18.25      MTGL
ATOM   2395  N   ALA   304      28.820 -10.284  44.432  1.00 19.57      MTGL
ATOM   2396  CA  ALA   304      27.395 -10.180  44.134  1.00 19.48      MTGL
ATOM   2397  CB  ALA   304      26.612 -11.157  45.017  1.00 18.17      MTGL
ATOM   2398  C   ALA   304      26.731  -8.813  44.182  1.00 19.61      MTGL
ATOM   2399  O   ALA   304      25.909  -8.505  43.323  1.00 20.70      MTGL
ATOM   2400  N   ASN   305      27.050  -7.999  45.181  1.00 18.88      MTGL
ATOM   2401  CA  ASN   305      26.424  -6.685  45.271  1.00 19.31      MTGL
ATOM   2402  CB  ASN   305      26.580  -6.114  46.683  1.00 19.61      MTGL
ATOM   2403  CG  ASN   305      28.024  -5.847  47.048  1.00 20.60      MTGL
ATOM   2404  OD1 ASN   305      28.868  -6.747  47.014  1.00 21.53      MTGL
ATOM   2405  ND2 ASN   305      28.318  -4.606  47.403  1.00 21.29      MTGL
ATOM   2406  C   ASN   305      27.018  -5.723  44.240  1.00 19.61      MTGL
ATOM   2407  O   ASN   305      26.522  -4.611  44.041  1.00 19.33      MTGL
ATOM   2408  N   LEU   306      28.088  -6.160  43.587  1.00 18.26      MTGL
ATOM   2409  CA  LEU   306      28.747  -5.359  42.563  1.00 18.47      MTGL
ATOM   2410  CB  LEU   306      27.919  -5.384  41.270  1.00 17.67      MTGL
ATOM   2411  CG  LEU   306      27.771  -6.764  40.612  1.00 18.35      MTGL
ATOM   2412  CD1 LEU   306      26.888  -6.670  39.372  1.00 16.49      MTGL
ATOM   2413  CD2 LEU   306      29.144  -7.300  40.238  1.00 16.40      MTGL
ATOM   2414  C   LEU   306      28.994  -3.915  42.990  1.00 19.28      MTGL
ATOM   2415  O   LEU   306      28.698  -2.981  42.241  1.00 19.04      MTGL
ATOM   2416  N   GLY   307      29.529  -3.740  44.196  1.00 18.62      MTGL
ATOM   2417  CA  GLY   307      29.828  -2.414  44.700  1.00 18.44      MTGL
ATOM   2418  C   GLY   307      28.657  -1.530  45.092  1.00 18.36      MTGL
ATOM   2419  O   GLY   307      28.866  -0.379  45.466  1.00 18.04      MTGL
ATOM   2420  N   SER   308      27.435  -2.047  45.020  1.00 17.93      MTGL
ATOM   2421  CA  SER   308      26.256  -1.256  45.380  1.00 17.81      MTGL
ATOM   2422  CB  SER   308      25.134  -1.480  44.361  1.00 16.84      MTGL
ATOM   2423  OG  SER   308      24.555  -2.759  44.528  1.00 15.76      MTGL
ATOM   2424  C   SER   308      25.756  -1.651  46.762  1.00 18.10      MTGL
ATOM   2425  O   SER   308      26.282  -2.585  47.361  1.00 18.30      MTGL
ATOM   2426  N   SER   309      24.735  -0.947  47.250  1.00 18.76      MTGL
ATOM   2427  CA  SER   309      24.157  -1.220  48.560  1.00 20.76      MTGL
ATOM   2428  CB  SER   309      23.424   0.022  49.092  1.00 21.48      MTGL
ATOM   2429  OG  SER   309      22.304   0.358  48.283  1.00 22.88      MTGL
ATOM   2430  C   SER   309      23.193  -2.404  48.517  1.00 22.16      MTGL
ATOM   2431  O   SER   309      22.754  -2.899  49.560  1.00 23.34      MTGL
ATOM   2432  N   CYS   310      22.852  -2.846  47.312  1.00 22.36      MTGL
ATOM   2433  CA  CYS   310      21.954  -3.987  47.159  1.00 23.23      MTGL
ATOM   2434  C   CYS   310      22.784  -5.265  47.300  1.00 23.23      MTGL
ATOM   2435  O   CYS   310      23.935  -5.300  46.877  1.00 25.45      MTGL
```

Fig. 1 cont.

```
ATOM  2436  CB   CYS  310     21.275   -3.945  45.793  1.00 23.30      MTGL
ATOM  2437  SG   CYS  310     19.871   -2.792  45.648  1.00 24.32      MTGL
ATOM  2438  N    ALA  311     22.197   -6.309  47.877  1.00 21.14      MTGL
ATOM  2439  CA   ALA  311     22.903   -7.564  48.110  1.00 20.13      MTGL
ATOM  2440  CB   ALA  311     22.076   -8.449  49.052  1.00 20.15      MTGL
ATOM  2441  C    ALA  311     23.335   -8.383  46.894  1.00 19.87      MTGL
ATOM  2442  O    ALA  311     24.442   -8.915  46.875  1.00 18.96      MTGL
ATOM  2443  N    ASP  312     22.482   -8.502  45.882  1.00 18.99      MTGL
ATOM  2444  CA   ASP  312     22.849   -9.313  44.723  1.00 19.21      MTGL
ATOM  2445  CB   ASP  312     22.346  -10.747  44.931  1.00 19.01      MTGL
ATOM  2446  CG   ASP  312     22.949  -11.733  43.946  1.00 19.92      MTGL
ATOM  2447  OD1  ASP  312     23.450  -11.305  42.884  1.00 19.68      MTGL
ATOM  2448  OD2  ASP  312     22.908  -12.948  44.230  1.00 20.69      MTGL
ATOM  2449  C    ASP  312     22.310   -8.772  43.403  1.00 18.27      MTGL
ATOM  2450  O    ASP  312     21.098   -8.692  43.205  1.00 18.94      MTGL
ATOM  2451  N    ASN  313     23.222   -8.418  42.500  1.00 17.28      MTGL
ATOM  2452  CA   ASN  313     22.855   -7.892  41.187  1.00 17.18      MTGL
ATOM  2453  CB   ASN  313     23.478   -6.507  40.962  1.00 16.90      MTGL
ATOM  2454  CG   ASN  313     22.860   -5.440  41.835  1.00 17.53      MTGL
ATOM  2455  OD1  ASN  313     21.636   -5.293  41.879  1.00 20.07      MTGL
ATOM  2456  ND2  ASN  313     23.704   -4.677  42.529  1.00 16.34      MTGL
ATOM  2457  C    ASN  313     23.305   -8.809  40.053  1.00 17.15      MTGL
ATOM  2458  O    ASN  313     23.190   -8.452  38.881  1.00 17.24      MTGL
ATOM  2459  N    THR  314     23.826   -9.982  40.391  1.00 15.74      MTGL
ATOM  2460  CA   THR  314     24.289  -10.903  39.365  1.00 15.54      MTGL
ATOM  2461  CB   THR  314     25.226  -11.977  39.953  1.00 15.83      MTGL
ATOM  2462  OG1  THR  314     24.502  -12.779  40.894  1.00 16.12      MTGL
ATOM  2463  CG2  THR  314     26.418  -11.322  40.651  1.00 14.76      MTGL
ATOM  2464  C    THR  314     23.130  -11.604  38.657  1.00 16.42      MTGL
ATOM  2465  O    THR  314     21.972  -11.525  39.087  1.00 15.23      MTGL
ATOM  2466  N    MET  315     23.453  -12.273  37.555  1.00 16.30      MTGL
ATOM  2467  CA   MET  315     22.458  -13.006  36.776  1.00 17.57      MTGL
ATOM  2468  CB   MET  315     22.390  -12.447  35.350  1.00 16.92      MTGL
ATOM  2469  CG   MET  315     21.934  -10.997  35.281  1.00 16.10      MTGL
ATOM  2470  SD   MET  315     21.871  -10.343  33.592  1.00 18.97      MTGL
ATOM  2471  CE   MET  315     20.232  -10.916  33.083  1.00 14.39      MTGL
ATOM  2472  C    MET  315     22.820  -14.492  36.753  1.00 17.49      MTGL
ATOM  2473  O    MET  315     22.404  -15.234  35.871  1.00 17.40      MTGL
ATOM  2474  N    PHE  316     23.614  -14.905  37.736  1.00 17.70      MTGL
ATOM  2475  CA   PHE  316     24.050  -16.291  37.879  1.00 18.51      MTGL
ATOM  2476  CB   PHE  316     25.521  -16.451  37.482  1.00 16.98      MTGL
ATOM  2477  CG   PHE  316     25.760  -16.485  35.995  1.00 17.56      MTGL
ATOM  2478  CD1  PHE  316     25.616  -15.337  35.220  1.00 17.13      MTGL
ATOM  2479  CD2  PHE  316     26.124  -17.671  35.370  1.00 16.95      MTGL
ATOM  2480  CE1  PHE  316     25.845  -15.370  33.845  1.00 17.76      MTGL
ATOM  2481  CE2  PHE  316     26.355  -17.717  33.993  1.00 17.39      MTGL
ATOM  2482  CZ   PHE  316     26.212  -16.566  33.227  1.00 16.28      MTGL
ATOM  2483  C    PHE  316     23.891  -16.679  39.344  1.00 19.70      MTGL
ATOM  2484  O    PHE  316     23.980  -15.825  40.229  1.00 19.34      MTGL
ATOM  2485  N    SER  317     23.659  -17.963  39.598  1.00 19.30      MTGL
ATOM  2486  CA   SER  317     23.495  -18.444  40.963  1.00 20.50      MTGL
ATOM  2487  CB   SER  317     22.894  -19.853  40.972  1.00 19.80      MTGL
ATOM  2488  OG   SER  317     23.832  -20.798  40.484  1.00 18.89      MTGL
ATOM  2489  C    SER  317     24.860  -18.479  41.633  1.00 20.89      MTGL
ATOM  2490  O    SER  317     25.895  -18.352  40.973  1.00 19.59      MTGL
ATOM  2491  N    GLN  318     24.857  -18.659  42.946  1.00 21.68      MTGL
ATOM  2492  CA   GLN  318     26.104  -18.711  43.685  1.00 22.69      MTGL
ATOM  2493  CB   GLN  318     25.813  -18.649  45.186  1.00 23.06      MTGL
```

Fig. 1 cont.

```
ATOM   2494  CG  GLN 318      25.363 -17.254  45.625  1.00 24.34           MTGL
ATOM   2495  CD  GLN 318      26.459 -16.209  45.445  1.00 25.12           MTGL
ATOM   2496  OE1 GLN 318      27.473 -16.241  46.142  1.00 27.51           MTGL
ATOM   2497  NE2 GLN 318      26.266 -15.287  44.503  1.00 23.16           MTGL
ATOM   2498  C   GLN 318      26.920 -19.947  43.315  1.00 22.71           MTGL
ATOM   2499  O   GLN 318      28.095 -20.052  43.662  1.00 24.10           MTGL
ATOM   2500  N   SER 319      26.307 -20.875  42.588  1.00 22.97           MTGL
ATOM   2501  CA  SER 319      27.022 -22.074  42.160  1.00 23.61           MTGL
ATOM   2502  CB  SER 319      26.112 -23.306  42.235  1.00 24.83           MTGL
ATOM   2503  OG  SER 319      24.914 -23.111  41.500  1.00 28.30           MTGL
ATOM   2504  C   SER 319      27.553 -21.900  40.737  1.00 23.21           MTGL
ATOM   2505  O   SER 319      28.158 -22.814  40.180  1.00 23.75           MTGL
ATOM   2506  N   GLY 320      27.315 -20.726  40.153  1.00 22.56           MTGL
ATOM   2507  CA  GLY 320      27.798 -20.439  38.811  1.00 22.10           MTGL
ATOM   2508  C   GLY 320      26.851 -20.771  37.670  1.00 22.30           MTGL
ATOM   2509  O   GLY 320      27.262 -20.809  36.504  1.00 22.30           MTGL
ATOM   2510  N   GLN 321      25.582 -21.009  37.984  1.00 21.21           MTGL
ATOM   2511  CA  GLN 321      24.618 -21.337  36.941  1.00 21.36           MTGL
ATOM   2512  CB  GLN 321      23.652 -22.415  37.426  1.00 23.27           MTGL
ATOM   2513  CG  GLN 321      22.649 -22.855  36.371  1.00 24.43           MTGL
ATOM   2514  CD  GLN 321      21.803 -24.021  36.833  1.00 26.48           MTGL
ATOM   2515  OE1 GLN 321      22.320 -25.009  37.347  1.00 27.39           MTGL
ATOM   2516  NE2 GLN 321      20.497 -23.920  36.641  1.00 27.02           MTGL
ATOM   2517  C   GLN 321      23.826 -20.121  36.483  1.00 20.04           MTGL
ATOM   2518  O   GLN 321      23.289 -19.371  37.291  1.00 19.56           MTGL
ATOM   2519  N   ALA 322      23.755 -19.939  35.172  1.00 20.60           MTGL
ATOM   2520  CA  ALA 322      23.028 -18.817  34.596  1.00 20.07           MTGL
ATOM   2521  CB  ALA 322      23.129 -18.864  33.079  1.00 18.41           MTGL
ATOM   2522  C   ALA 322      21.565 -18.855  35.017  1.00 20.05           MTGL
ATOM   2523  O   ALA 322      20.921 -19.901  34.945  1.00 19.07           MTGL
ATOM   2524  N   LEU 323      21.052 -17.713  35.464  0.50 19.28           MTGL
ATOM   2525  CA  LEU 323      19.658 -17.611  35.878  0.50 19.33           MTGL
ATOM   2526  CB  LEU 323      19.470 -16.426  36.830  0.50 18.12           MTGL
ATOM   2527  CG  LEU 323      20.241 -16.493  38.152  0.50 17.16           MTGL
ATOM   2528  CD1 LEU 323      19.944 -15.244  38.979  0.50 16.83           MTGL
ATOM   2529  CD2 LEU 323      19.844 -17.758  38.920  0.50 16.13           MTGL
ATOM   2530  C   LEU 323      18.779 -17.431  34.645  0.50 19.86           MTGL
ATOM   2531  O   LEU 323      19.270 -17.113  33.561  0.50 19.75           MTGL
ATOM   2532  N   SER 324      17.477 -17.630  34.817  1.00 21.01           MTGL
ATOM   2533  CA  SER 324      16.524 -17.511  33.719  1.00 21.34           MTGL
ATOM   2534  CB  SER 324      15.114 -17.827  34.220  1.00 21.65           MTGL
ATOM   2535  OG  SER 324      14.713 -16.887  35.202  1.00 22.41           MTGL
ATOM   2536  C   SER 324      16.529 -16.130  33.075  1.00 21.33           MTGL
ATOM   2537  O   SER 324      16.159 -15.980  31.913  1.00 20.59           MTGL
ATOM   2538  N   SER 325      16.955 -15.123  33.830  1.00 20.04           MTGL
ATOM   2539  CA  SER 325      16.984 -13.759  33.321  1.00 20.07           MTGL
ATOM   2540  CB  SER 325      17.227 -12.780  34.476  1.00 19.69           MTGL
ATOM   2541  OG  SER 325      18.417 -13.106  35.172  1.00 17.73           MTGL
ATOM   2542  C   SER 325      18.012 -13.515  32.213  1.00 20.16           MTGL
ATOM   2543  O   SER 325      17.892 -12.549  31.460  1.00 19.87           MTGL
ATOM   2544  N   LEU 326      19.010 -14.388  32.104  1.00 19.54           MTGL
ATOM   2545  CA  LEU 326      20.048 -14.230  31.085  1.00 19.73           MTGL
ATOM   2546  CB  LEU 326      21.126 -15.314  31.236  1.00 20.49           MTGL
ATOM   2547  CG  LEU 326      22.606 -14.910  31.307  1.00 22.10           MTGL
ATOM   2548  CD1 LEU 326      23.433 -15.966  30.587  1.00 21.95           MTGL
ATOM   2549  CD2 LEU 326      22.848 -13.551  30.678  1.00 22.81           MTGL
ATOM   2550  C   LEU 326      19.519 -14.274  29.646  1.00 19.72           MTGL
ATOM   2551  O   LEU 326      20.094 -13.655  28.754  1.00 19.08           MTGL
```

Fig. 1 cont.

```
ATOM   2552  N   SER  327      18.439  -15.015  29.412  1.00  18.98       MTGL
ATOM   2553  CA  SER  327      17.875  -15.133  28.067  1.00  18.71       MTGL
ATOM   2554  CB  SER  327      16.861  -16.271  28.023  1.00  17.52       MTGL
ATOM   2555  OG  SER  327      15.740  -15.947  28.825  1.00  16.77       MTGL
ATOM   2556  C   SER  327      17.191  -13.851  27.585  1.00  18.81       MTGL
ATOM   2557  O   SER  327      16.698  -13.795  26.459  1.00  18.63       MTGL
ATOM   2558  N   VAL  328      17.140  -12.836  28.440  1.00  18.22       MTGL
ATOM   2559  CA  VAL  328      16.517  -11.573  28.066  1.00  18.51       MTGL
ATOM   2560  CB  VAL  328      16.590  -10.545  29.223  1.00  19.11       MTGL
ATOM   2561  CG1 VAL  328      18.046  -10.177  29.509  1.00  17.14       MTGL
ATOM   2562  CG2 VAL  328      15.777   -9.304  28.868  1.00  19.04       MTGL
ATOM   2563  C   VAL  328      17.210  -10.983  26.839  1.00  19.25       MTGL
ATOM   2564  O   VAL  328      16.589  -10.285  26.039  1.00  18.81       MTGL
ATOM   2565  N   PHE  329      18.498  -11.273  26.685  1.00  20.22       MTGL
ATOM   2566  CA  PHE  329      19.258  -10.752  25.550  1.00  22.10       MTGL
ATOM   2567  CB  PHE  329      20.752  -10.989  25.774  1.00  21.20       MTGL
ATOM   2568  CG  PHE  329      21.307  -10.211  26.929  1.00  21.71       MTGL
ATOM   2569  CD1 PHE  329      21.525   -8.842  26.814  1.00  21.66       MTGL
ATOM   2570  CD2 PHE  329      21.551  -10.831  28.151  1.00  20.67       MTGL
ATOM   2571  CE1 PHE  329      21.979   -8.099  27.901  1.00  22.16       MTGL
ATOM   2572  CE2 PHE  329      22.003  -10.098  29.240  1.00  22.03       MTGL
ATOM   2573  CZ  PHE  329      22.215   -8.728  29.114  1.00  22.57       MTGL
ATOM   2574  C   PHE  329      18.815  -11.340  24.212  1.00  23.27       MTGL
ATOM   2575  O   PHE  329      19.267  -10.904  23.152  1.00  23.56       MTGL
ATOM   2576  N   GLN  330      17.927  -12.326  24.267  1.00  23.16       MTGL
ATOM   2577  CA  GLN  330      17.402  -12.950  23.058  1.00  24.83       MTGL
ATOM   2578  CB  GLN  330      16.994  -14.403  23.333  1.00  25.48       MTGL
ATOM   2579  CG  GLN  330      18.138  -15.371  23.573  1.00  25.89       MTGL
ATOM   2580  CD  GLN  330      17.648  -16.773  23.894  1.00  27.09       MTGL
ATOM   2581  OE1 GLN  330      18.390  -17.748  23.750  1.00  29.08       MTGL
ATOM   2582  NE2 GLN  330      16.400  -16.882  24.343  1.00  24.64       MTGL
ATOM   2583  C   GLN  330      16.157  -12.198  22.596  1.00  25.46       MTGL
ATOM   2584  O   GLN  330      15.651  -12.439  21.502  1.00  25.45       MTGL
ATOM   2585  N   ARG  331      15.669  -11.282  23.426  1.00  25.05       MTGL
ATOM   2586  CA  ARG  331      14.443  -10.573  23.094  1.00  25.37       MTGL
ATOM   2587  CB  ARG  331      13.356  -10.991  24.087  1.00  24.60       MTGL
ATOM   2588  CG  ARG  331      13.223  -12.507  24.246  1.00  25.96       MTGL
ATOM   2589  CD  ARG  331      12.110  -12.882  25.220  1.00  26.44       MTGL
ATOM   2590  NE  ARG  331      12.400  -12.493  26.600  1.00  27.25       MTGL
ATOM   2591  CZ  ARG  331      13.123  -13.218  27.451  1.00  27.98       MTGL
ATOM   2592  NH1 ARG  331      13.637  -14.383  27.073  1.00  26.83       MTGL
ATOM   2593  NH2 ARG  331      13.329  -12.777  28.683  1.00  26.92       MTGL
ATOM   2594  C   ARG  331      14.506   -9.049  23.017  1.00  25.38       MTGL
ATOM   2595  O   ARG  331      13.468   -8.391  23.085  1.00  25.25       MTGL
ATOM   2596  N   ILE  332      15.703   -8.487  22.863  1.00  25.52       MTGL
ATOM   2597  CA  ILE  332      15.847   -7.035  22.779  1.00  26.69       MTGL
ATOM   2598  CB  ILE  332      16.510   -6.459  24.049  1.00  26.08       MTGL
ATOM   2599  CG2 ILE  332      15.646   -6.765  25.269  1.00  25.81       MTGL
ATOM   2600  CG1 ILE  332      17.912   -7.047  24.224  1.00  25.06       MTGL
ATOM   2601  CD1 ILE  332      18.663   -6.506  25.425  1.00  23.51       MTGL
ATOM   2602  C   ILE  332      16.664   -6.599  21.567  1.00  27.88       MTGL
ATOM   2603  O   ILE  332      17.171   -7.485  20.855  1.00  28.65       MTGL
ATOM   2604  OXT ILE  332      16.787   -5.372  21.344  1.00  30.38       MTGL
END
```

Fig. 1 cont.

```
HEADER                                                          HIGL
ATOM     1 CB   ALA    1       6.247  74.348 114.849  1.00 27.43      HIGL
ATOM     2 C    ALA    1       7.283  72.458 113.617  1.00 26.21      HIGL
ATOM     3 O    ALA    1       6.683  72.007 112.638  1.00 26.69      HIGL
ATOM     4 N    ALA    1       7.237  74.771 112.633  1.00 26.59      HIGL
ATOM     5 CA   ALA    1       7.343  73.961 113.883  1.00 26.86      HIGL
ATOM     6 N    LEU    2       7.883  71.693 114.524  1.00 24.15      HIGL
ATOM     7 CA   LEU    2       7.971  70.244 114.405  1.00 22.16      HIGL
ATOM     8 CB   LEU    2       8.883  69.700 115.498  1.00 21.06      HIGL
ATOM     9 CG   LEU    2      10.274  70.334 115.565  1.00 20.32      HIGL
ATOM    10 CD1  LEU    2      10.966  69.921 116.848  1.00 19.78      HIGL
ATOM    11 CD2  LEU    2      11.076  69.921 114.346  1.00 20.05      HIGL
ATOM    12 C    LEU    2       6.663  69.471 114.429  1.00 22.53      HIGL
ATOM    13 O    LEU    2       5.748  69.767 115.202  1.00 23.10      HIGL
ATOM    14 N    GLN    3       6.597  68.456 113.576  1.00 21.51      HIGL
ATOM    15 CA   GLN    3       5.430  67.601 113.493  1.00 20.06      HIGL
ATOM    16 CB   GLN    3       5.435  66.837 112.175  1.00 18.80      HIGL
ATOM    17 CG   GLN    3       4.157  66.084 111.909  1.00 19.14      HIGL
ATOM    18 CD   GLN    3       4.246  65.213 110.680  1.00 19.73      HIGL
ATOM    19 OE1  GLN    3       4.884  65.577 109.689  1.00 21.27      HIGL
ATOM    20 NE2  GLN    3       3.594  64.062 110.728  1.00 18.71      HIGL
ATOM    21 C    GLN    3       5.504  66.609 114.644  1.00 19.78      HIGL
ATOM    22 O    GLN    3       4.513  66.342 115.324  1.00 20.14      HIGL
ATOM    23 N    TYR    4       6.696  66.060 114.849  1.00 19.50      HIGL
ATOM    24 CA   TYR    4       6.920  65.083 115.902  1.00 19.32      HIGL
ATOM    25 CB   TYR    4       7.614  63.849 115.328  1.00 18.96      HIGL
ATOM    26 CG   TYR    4       6.913  63.222 114.145  1.00 19.19      HIGL
ATOM    27 CD1  TYR    4       5.639  62.669 114.271  1.00 19.50      HIGL
ATOM    28 CE1  TYR    4       5.019  62.033 113.199  1.00 18.39      HIGL
ATOM    29 CD2  TYR    4       7.546  63.131 112.909  1.00 19.30      HIGL
ATOM    30 CE2  TYR    4       6.935  62.497 111.831  1.00 19.42      HIGL
ATOM    31 CZ   TYR    4       5.672  61.947 111.984  1.00 19.38      HIGL
ATOM    32 OH   TYR    4       5.083  61.288 110.922  1.00 18.91      HIGL
ATOM    33 C    TYR    4       7.790  65.686 117.000  1.00 19.57      HIGL
ATOM    34 O    TYR    4       8.954  66.022 116.776  1.00 19.37      HIGL
ATOM    35 N    LYS    5       7.220  65.845 118.185  1.00 19.13      HIGL
ATOM    36 CA   LYS    5       7.980  66.388 119.293  1.00 19.83      HIGL
ATOM    37 CB   LYS    5       7.666  67.874 119.495  1.00 21.28      HIGL
ATOM    38 CG   LYS    5       6.198  68.219 119.599  1.00 23.14      HIGL
ATOM    39 CD   LYS    5       6.031  69.730 119.695  1.00 25.10      HIGL
ATOM    40 CE   LYS    5       4.563  70.143 119.714  1.00 25.68      HIGL
ATOM    41 NZ   LYS    5       4.438  71.621 119.884  1.00 27.35      HIGL
ATOM    42 C    LYS    5       7.661  65.589 120.539  1.00 19.09      HIGL
ATOM    43 O    LYS    5       6.537  65.616 121.043  1.00 20.34      HIGL
ATOM    44 N    GLY    6       8.653  64.858 121.027  1.00 17.54      HIGL
ATOM    45 CA   GLY    6       8.428  64.050 122.203  1.00 16.41      HIGL
ATOM    46 C    GLY    6       9.685  63.574 122.897  1.00 15.75      HIGL
ATOM    47 O    GLY    6      10.779  64.112 122.698  1.00 15.49      HIGL
ATOM    48 N    VAL    7       9.518  62.548 123.721  1.00 14.73      HIGL
ATOM    49 CA   VAL    7      10.623  61.996 124.470  1.00 14.42      HIGL
ATOM    50 CB   VAL    7      10.518  62.373 125.963  1.00 15.12      HIGL
ATOM    51 CG1  VAL    7      10.337  63.879 126.121  1.00 15.55      HIGL
ATOM    52 CG2  VAL    7       9.361  61.620 126.605  1.00 14.47      HIGL
ATOM    53 C    VAL    7      10.629  60.481 124.392  1.00 13.95      HIGL
ATOM    54 O    VAL    7       9.650  59.863 123.979  1.00 13.25      HIGL
ATOM    55 N    ASP    8      11.753  59.895 124.784  1.00 13.51      HIGL
ATOM    56 CA   ASP    8      11.863  58.452 124.844  1.00 13.71      HIGL
ATOM    57 CB   ASP    8      13.263  57.981 124.473  1.00 13.57      HIGL
ATOM    58 CG   ASP    8      13.354  56.480 124.393  1.00 13.68      HIGL
ATOM    59 OD1  ASP    8      12.912  55.814 125.353  1.00 13.24      HIGL
ATOM    60 OD2  ASP    8      13.861  55.967 123.373  1.00 14.72      HIGL
ATOM    61 C    ASP    8      11.626  58.233 126.324  1.00 13.84      HIGL
ATOM    62 O    ASP    8      12.391  58.735 127.156  1.00 13.94      HIGL
ATOM    63 N    TRP    9      10.562  57.510 126.658  1.00 13.89      HIGL
ATOM    64 CA   TRP    9      10.207  57.280 128.059  1.00 13.87      HIGL
```

Fig. 2

| | | | | | | | | | |
|---|---|---|---|---|---|---|---|---|---|
| ATOM | 65 | CB | TRP | 9 | 8.822 | 57.889 | 128.324 | 1.00 11.91 | HIGL |
| ATOM | 66 | CG | TRP | 9 | 7.684 | 57.044 | 127.823 | 1.00 12.26 | HIGL |
| ATOM | 67 | CD2 | TRP | 9 | 6.406 | 56.867 | 128.448 | 1.00 12.11 | HIGL |
| ATOM | 68 | CE2 | TRP | 9 | 5.670 | 55.963 | 127.647 | 1.00 12.19 | HIGL |
| ATOM | 69 | CE3 | TRP | 9 | 5.809 | 57.383 | 129.609 | 1.00 11.70 | HIGL |
| ATOM | 70 | CD1 | TRP | 9 | 7.668 | 56.268 | 126.696 | 1.00 11.92 | HIGL |
| ATOM | 71 | NE1 | TRP | 9 | 6.466 | 55.614 | 126.586 | 1.00 11.76 | HIGL |
| ATOM | 72 | CZ2 | TRP | 9 | 4.365 | 55.562 | 127.968 | 1.00 11.52 | HIGL |
| ATOM | 73 | CZ3 | TRP | 9 | 4.510 | 56.986 | 129.930 | 1.00 11.57 | HIGL |
| ATOM | 74 | CH2 | TRP | 9 | 3.804 | 56.085 | 129.111 | 1.00 11.64 | HIGL |
| ATOM | 75 | C | TRP | 9 | 10.212 | 55.798 | 128.440 | 1.00 14.10 | HIGL |
| ATOM | 76 | O | TRP | 9 | 9.551 | 55.392 | 129.392 | 1.00 15.49 | HIGL |
| ATOM | 77 | N | SER | 10 | 10.984 | 55.002 | 127.713 | 1.00 14.17 | HIGL |
| ATOM | 78 | CA | SER | 10 | 11.051 | 53.561 | 127.939 | 1.00 14.00 | HIGL |
| ATOM | 79 | CB | SER | 10 | 12.154 | 52.958 | 127.056 | 1.00 14.22 | HIGL |
| ATOM | 80 | OG | SER | 10 | 11.946 | 53.282 | 125.685 | 1.00 12.67 | HIGL |
| ATOM | 81 | C | SER | 10 | 11.232 | 53.095 | 129.385 | 1.00 13.46 | HIGL |
| ATOM | 82 | O | SER | 10 | 10.652 | 52.096 | 129.794 | 1.00 13.12 | HIGL |
| ATOM | 83 | N | SER | 11 | 12.021 | 53.821 | 130.162 | 1.00 13.49 | HIGL |
| ATOM | 84 | CA | SER | 11 | 12.281 | 53.437 | 131.542 | 1.00 13.65 | HIGL |
| ATOM | 85 | CB | SER | 11 | 13.490 | 54.200 | 132.051 | 1.00 12.96 | HIGL |
| ATOM | 86 | OG | SER | 11 | 13.175 | 55.576 | 132.142 | 1.00 11.73 | HIGL |
| ATOM | 87 | C | SER | 11 | 11.134 | 53.664 | 132.524 | 1.00 15.06 | HIGL |
| ATOM | 88 | O | SER | 11 | 11.192 | 53.198 | 133.667 | 1.00 15.59 | HIGL |
| ATOM | 89 | N | VAL | 12 | 10.090 | 54.357 | 132.089 | 1.00 15.52 | HIGL |
| ATOM | 90 | CA | VAL | 12 | 8.987 | 54.682 | 132.983 | 1.00 16.34 | HIGL |
| ATOM | 91 | CB | VAL | 12 | 7.793 | 55.248 | 132.197 | 1.00 16.01 | HIGL |
| ATOM | 92 | CG1 | VAL | 12 | 7.264 | 54.205 | 131.248 | 1.00 16.29 | HIGL |
| ATOM | 93 | CG2 | VAL | 12 | 6.714 | 55.720 | 133.159 | 1.00 15.28 | HIGL |
| ATOM | 94 | C | VAL | 12 | 8.485 | 53.594 | 133.945 | 1.00 17.29 | HIGL |
| ATOM | 95 | O | VAL | 12 | 8.361 | 53.855 | 135.143 | 1.00 18.04 | HIGL |
| ATOM | 96 | N | MET | 13 | 8.197 | 52.390 | 133.457 | 1.00 17.84 | HIGL |
| ATOM | 97 | CA | MET | 13 | 7.695 | 51.346 | 134.355 | 1.00 17.96 | HIGL |
| ATOM | 98 | CB | MET | 13 | 7.044 | 50.203 | 133.568 | 1.00 17.95 | HIGL |
| ATOM | 99 | CG | MET | 13 | 5.703 | 50.579 | 132.968 | 1.00 19.53 | HIGL |
| ATOM | 100 | SD | MET | 13 | 4.678 | 49.147 | 132.593 | 1.00 23.13 | HIGL |
| ATOM | 101 | CE | MET | 13 | 5.559 | 48.452 | 131.185 | 1.00 23.08 | HIGL |
| ATOM | 102 | C | MET | 13 | 8.756 | 50.788 | 135.290 | 1.00 17.76 | HIGL |
| ATOM | 103 | O | MET | 13 | 8.456 | 50.415 | 136.420 | 1.00 17.26 | HIGL |
| ATOM | 104 | N | VAL | 14 | 9.994 | 50.723 | 134.817 | 1.00 17.91 | HIGL |
| ATOM | 105 | CA | VAL | 14 | 11.082 | 50.225 | 135.640 | 1.00 17.21 | HIGL |
| ATOM | 106 | CB | VAL | 14 | 12.413 | 50.169 | 134.845 | 1.00 16.85 | HIGL |
| ATOM | 107 | CG1 | VAL | 14 | 13.559 | 49.837 | 135.761 | 1.00 13.37 | HIGL |
| ATOM | 108 | CG2 | VAL | 14 | 12.311 | 49.128 | 133.741 | 1.00 15.66 | HIGL |
| ATOM | 109 | C | VAL | 14 | 11.212 | 51.187 | 136.809 | 1.00 17.76 | HIGL |
| ATOM | 110 | O | VAL | 14 | 11.455 | 50.774 | 137.945 | 1.00 18.17 | HIGL |
| ATOM | 111 | N | GLU | 15 | 11.031 | 52.473 | 136.533 | 1.00 18.10 | HIGL |
| ATOM | 112 | CA | GLU | 15 | 11.120 | 53.476 | 137.586 | 1.00 19.10 | HIGL |
| ATOM | 113 | CB | GLU | 15 | 11.207 | 54.881 | 136.991 | 1.00 19.32 | HIGL |
| ATOM | 114 | CG | GLU | 15 | 12.554 | 55.178 | 136.365 | 1.00 20.08 | HIGL |
| ATOM | 115 | CD | GLU | 15 | 13.676 | 55.158 | 137.383 | 1.00 21.57 | HIGL |
| ATOM | 116 | OE1 | GLU | 15 | 13.838 | 54.131 | 138.076 | 1.00 22.32 | HIGL |
| ATOM | 117 | OE2 | GLU | 15 | 14.398 | 56.171 | 137.492 | 1.00 22.71 | HIGL |
| ATOM | 118 | C | GLU | 15 | 9.937 | 53.387 | 138.539 | 1.00 19.39 | HIGL |
| ATOM | 119 | O | GLU | 15 | 10.107 | 53.492 | 139.757 | 1.00 19.72 | HIGL |
| ATOM | 120 | N | GLU | 16 | 8.740 | 53.196 | 137.992 | 1.00 19.13 | HIGL |
| ATOM | 121 | CA | GLU | 16 | 7.562 | 53.084 | 138.839 | 1.00 19.39 | HIGL |
| ATOM | 122 | CB | GLU | 16 | 6.289 | 52.932 | 137.996 | 1.00 18.72 | HIGL |
| ATOM | 123 | CG | GLU | 16 | 5.945 | 54.180 | 137.193 | 1.00 19.94 | HIGL |
| ATOM | 124 | CD | GLU | 16 | 4.840 | 53.959 | 136.159 | 1.00 21.79 | HIGL |
| ATOM | 125 | OE1 | GLU | 16 | 4.817 | 52.881 | 135.521 | 1.00 22.23 | HIGL |
| ATOM | 126 | OE2 | GLU | 16 | 4.003 | 54.874 | 135.966 | 1.00 21.65 | HIGL |
| ATOM | 127 | C | GLU | 16 | 7.759 | 51.885 | 139.761 | 1.00 19.47 | HIGL |
| ATOM | 128 | O | GLU | 16 | 7.547 | 51.989 | 140.969 | 1.00 19.63 | HIGL |
| ATOM | 129 | N | ARG | 17 | 8.190 | 50.756 | 139.202 | 1.00 19.74 | HIGL |

Fig. 2 cont.

| | | | | | | | | |
|---|---|---|---|---|---|---|---|---|
| ATOM | 130 | CA | ARG | 17 | 8.416 | 49.562 | 140.014 | 1.00 20.25 | HIGL |
| ATOM | 131 | CB | ARG | 17 | 8.911 | 48.392 | 139.164 | 1.00 21.03 | HIGL |
| ATOM | 132 | CG | ARG | 17 | 7.873 | 47.765 | 138.257 | 1.00 23.68 | HIGL |
| ATOM | 133 | CD | ARG | 17 | 8.178 | 46.286 | 138.053 | 1.00 27.08 | HIGL |
| ATOM | 134 | NE | ARG | 17 | 7.410 | 45.701 | 136.956 | 1.00 31.03 | HIGL |
| ATOM | 135 | CZ | ARG | 17 | 7.660 | 45.919 | 135.664 | 1.00 32.87 | HIGL |
| ATOM | 136 | NH1 | ARG | 17 | 8.666 | 46.709 | 135.299 | 1.00 32.97 | HIGL |
| ATOM | 137 | NH2 | ARG | 17 | 6.902 | 45.352 | 134.731 | 1.00 33.75 | HIGL |
| ATOM | 138 | C | ARG | 17 | 9.445 | 49.840 | 141.104 | 1.00 19.92 | HIGL |
| ATOM | 139 | O | ARG | 17 | 9.443 | 49.198 | 142.151 | 1.00 20.42 | HIGL |
| ATOM | 140 | N | ALA | 18 | 10.325 | 50.801 | 140.850 | 1.00 19.29 | HIGL |
| ATOM | 141 | CA | ALA | 18 | 11.357 | 51.153 | 141.811 | 1.00 17.90 | HIGL |
| ATOM | 142 | CB | ALA | 18 | 12.584 | 51.698 | 141.086 | 1.00 17.12 | HIGL |
| ATOM | 143 | C | ALA | 18 | 10.846 | 52.168 | 142.830 | 1.00 17.59 | HIGL |
| ATOM | 144 | O | ALA | 18 | 11.611 | 52.653 | 143.669 | 1.00 16.93 | HIGL |
| ATOM | 145 | N | GLY | 19 | 9.557 | 52.494 | 142.745 | 1.00 16.98 | HIGL |
| ATOM | 146 | CA | GLY | 19 | 8.963 | 53.424 | 143.687 | 1.00 16.15 | HIGL |
| ATOM | 147 | C | GLY | 19 | 8.935 | 54.890 | 143.298 | 1.00 16.93 | HIGL |
| ATOM | 148 | O | GLY | 19 | 8.543 | 55.734 | 144.104 | 1.00 17.33 | HIGL |
| ATOM | 149 | N | VAL | 20 | 9.333 | 55.209 | 142.072 | 1.00 17.17 | HIGL |
| ATOM | 150 | CA | VAL | 20 | 9.336 | 56.598 | 141.626 | 1.00 17.58 | HIGL |
| ATOM | 151 | CB | VAL | 20 | 10.148 | 56.764 | 140.330 | 1.00 17.22 | HIGL |
| ATOM | 152 | CG1 | VAL | 20 | 10.013 | 58.190 | 139.814 | 1.00 16.00 | HIGL |
| ATOM | 153 | CG2 | VAL | 20 | 11.609 | 56.419 | 140.584 | 1.00 17.68 | HIGL |
| ATOM | 154 | C | VAL | 20 | 7.945 | 57.167 | 141.370 | 1.00 17.79 | HIGL |
| ATOM | 155 | O | VAL | 20 | 7.084 | 56.490 | 140.826 | 1.00 18.75 | HIGL |
| ATOM | 156 | N | ARG | 21 | 7.740 | 58.420 | 141.760 | 1.00 17.99 | HIGL |
| ATOM | 157 | CA | ARG | 21 | 6.470 | 59.106 | 141.537 | 1.00 18.92 | HIGL |
| ATOM | 158 | CB | ARG | 21 | 5.775 | 59.399 | 142.862 | 1.00 19.66 | HIGL |
| ATOM | 159 | CG | ARG | 21 | 5.367 | 58.155 | 143.617 | 1.00 20.84 | HIGL |
| ATOM | 160 | CD | ARG | 21 | 4.245 | 57.425 | 142.917 | 1.00 21.60 | HIGL |
| ATOM | 161 | NE | ARG | 21 | 3.389 | 56.783 | 143.906 | 1.00 23.75 | HIGL |
| ATOM | 162 | CZ | ARG | 21 | 3.734 | 55.707 | 144.598 | 1.00 23.89 | HIGL |
| ATOM | 163 | NH1 | ARG | 21 | 4.920 | 55.148 | 144.389 | 1.00 25.67 | HIGL |
| ATOM | 164 | NH2 | ARG | 21 | 2.911 | 55.215 | 145.516 | 1.00 22.10 | HIGL |
| ATOM | 165 | C | ARG | 21 | 6.749 | 60.412 | 140.809 | 1.00 18.45 | HIGL |
| ATOM | 166 | O | ARG | 21 | 7.598 | 61.198 | 141.231 | 1.00 18.88 | HIGL |
| ATOM | 167 | N | TYR | 22 | 6.032 | 60.640 | 139.717 | 1.00 17.66 | HIGL |
| ATOM | 168 | CA | TYR | 22 | 6.221 | 61.846 | 138.920 | 1.00 16.70 | HIGL |
| ATOM | 169 | CB | TYR | 22 | 6.236 | 61.480 | 137.438 | 1.00 15.81 | HIGL |
| ATOM | 170 | CG | TYR | 22 | 7.402 | 60.608 | 137.038 | 1.00 16.16 | HIGL |
| ATOM | 171 | CD1 | TYR | 22 | 8.706 | 61.124 | 136.998 | 1.00 14.69 | HIGL |
| ATOM | 172 | CE1 | TYR | 22 | 9.790 | 60.322 | 136.647 | 1.00 14.60 | HIGL |
| ATOM | 173 | CD2 | TYR | 22 | 7.211 | 59.260 | 136.715 | 1.00 15.58 | HIGL |
| ATOM | 174 | CE2 | TYR | 22 | 8.294 | 58.442 | 136.361 | 1.00 16.20 | HIGL |
| ATOM | 175 | CZ | TYR | 22 | 9.582 | 58.980 | 136.330 | 1.00 15.43 | HIGL |
| ATOM | 176 | OH | TYR | 22 | 10.648 | 58.178 | 135.994 | 1.00 12.55 | HIGL |
| ATOM | 177 | C | TYR | 22 | 5.156 | 62.903 | 139.166 | 1.00 17.06 | HIGL |
| ATOM | 178 | O | TYR | 22 | 4.008 | 62.591 | 139.482 | 1.00 17.73 | HIGL |
| ATOM | 179 | N | LYS | 23 | 5.545 | 64.160 | 139.011 | 1.00 17.11 | HIGL |
| ATOM | 180 | CA | LYS | 23 | 4.631 | 65.279 | 139.191 | 1.00 17.49 | HIGL |
| ATOM | 181 | CB | LYS | 23 | 4.813 | 65.913 | 140.575 | 1.00 18.19 | HIGL |
| ATOM | 182 | CG | LYS | 23 | 4.800 | 64.938 | 141.748 | 1.00 19.57 | HIGL |
| ATOM | 183 | CD | LYS | 23 | 6.141 | 64.239 | 141.933 | 1.00 18.82 | HIGL |
| ATOM | 184 | CE | LYS | 23 | 6.061 | 63.255 | 143.085 | 1.00 18.77 | HIGL |
| ATOM | 185 | NZ | LYS | 23 | 7.366 | 62.602 | 143.352 | 1.00 19.04 | HIGL |
| ATOM | 186 | C | LYS | 23 | 4.975 | 66.318 | 138.137 | 1.00 17.45 | HIGL |
| ATOM | 187 | O | LYS | 23 | 6.098 | 66.342 | 137.640 | 1.00 17.10 | HIGL |
| ATOM | 188 | N | ASN | 24 | 4.021 | 67.171 | 137.786 | 1.00 17.71 | HIGL |
| ATOM | 189 | CA | ASN | 24 | 4.315 | 68.221 | 136.823 | 1.00 17.61 | HIGL |
| ATOM | 190 | CB | ASN | 24 | 3.029 | 68.792 | 136.210 | 1.00 17.78 | HIGL |
| ATOM | 191 | CG | ASN | 24 | 1.986 | 69.174 | 137.252 | 1.00 17.86 | HIGL |
| ATOM | 192 | OD1 | ASN | 24 | 2.314 | 69.585 | 138.368 | 1.00 18.49 | HIGL |
| ATOM | 193 | ND2 | ASN | 24 | 0.717 | 69.061 | 136.876 | 1.00 17.05 | HIGL |
| ATOM | 194 | C | ASN | 24 | 5.081 | 69.294 | 137.597 | 1.00 17.97 | HIGL |

Fig. 2 cont.

```
ATOM   195  O    ASN   24     5.481  69.060 138.739  1.00 16.84      HIGL
ATOM   196  N    VAL   25     5.285  70.462 136.994  1.00 19.12      HIGL
ATOM   197  CA   VAL   25     6.033  71.537 137.660  1.00 20.42      HIGL
ATOM   198  CB   VAL   25     6.164  72.813 136.789  1.00 20.47      HIGL
ATOM   199  CG1  VAL   25     7.591  73.345 136.856  1.00 18.59      HIGL
ATOM   200  CG2  VAL   25     5.749  72.534 135.377  1.00 21.79      HIGL
ATOM   201  C    VAL   25     5.399  72.009 138.957  1.00 20.49      HIGL
ATOM   202  O    VAL   25     6.071  72.577 139.812  1.00 19.69      HIGL
ATOM   203  N    ASN   26     4.101  71.782 139.094  1.00 21.96      HIGL
ATOM   204  CA   ASN   26     3.375  72.242 140.271  1.00 22.88      HIGL
ATOM   205  CB   ASN   26     1.979  72.686 139.841  1.00 23.37      HIGL
ATOM   206  CG   ASN   26     2.026  73.861 138.879  1.00 24.96      HIGL
ATOM   207  OD1  ASN   26     1.188  73.986 137.980  1.00 26.06      HIGL
ATOM   208  ND2  ASN   26     3.009  74.739 139.071  1.00 24.54      HIGL
ATOM   209  C    ASN   26     3.295  71.249 141.418  1.00 22.79      HIGL
ATOM   210  O    ASN   26     2.669  71.529 142.441  1.00 23.56      HIGL
ATOM   211  N    GLY   27     3.933  70.095 141.250  1.00 22.15      HIGL
ATOM   212  CA   GLY   27     3.932  69.094 142.299  1.00 20.67      HIGL
ATOM   213  C    GLY   27     2.743  68.157 142.290  1.00 19.93      HIGL
ATOM   214  O    GLY   27     2.574  67.357 143.214  1.00 20.18      HIGL
ATOM   215  N    GLN   28     1.912  68.247 141.258  1.00 19.35      HIGL
ATOM   216  CA   GLN   28     0.748  67.376 141.164  1.00 19.04      HIGL
ATOM   217  CB   GLN   28    -0.314  68.025 140.274  1.00 19.46      HIGL
ATOM   218  CG   GLN   28    -1.579  67.207 140.102  1.00 19.85      HIGL
ATOM   219  CD   GLN   28    -2.666  67.970 139.363  1.00 21.15      HIGL
ATOM   220  OE1  GLN   28    -2.425  68.547 138.299  1.00 21.73      HIGL
ATOM   221  NE2  GLN   28    -3.871  67.971 139.921  1.00 20.85      HIGL
ATOM   222  C    GLN   28     1.164  66.009 140.607  1.00 18.84      HIGL
ATOM   223  O    GLN   28     1.602  65.901 139.464  1.00 18.45      HIGL
ATOM   224  N    GLU   29     1.038  64.973 141.432  1.00 18.66      HIGL
ATOM   225  CA   GLU   29     1.402  63.619 141.042  1.00 18.76      HIGL
ATOM   226  CB   GLU   29     1.487  62.730 142.287  1.00 18.41      HIGL
ATOM   227  CG   GLU   29     1.966  61.316 141.998  1.00 19.70      HIGL
ATOM   228  CD   GLU   29     2.223  60.504 143.252  1.00 21.17      HIGL
ATOM   229  OE1  GLU   29     2.828  61.042 144.204  1.00 22.90      HIGL
ATOM   230  OE2  GLU   29     1.836  59.318 143.285  1.00 21.00      HIGL
ATOM   231  C    GLU   29     0.412  63.005 140.045  1.00 18.74      HIGL
ATOM   232  O    GLU   29    -0.793  63.133 140.205  1.00 20.35      HIGL
ATOM   233  N    LYS   30     0.929  62.357 139.007  1.00 18.03      HIGL
ATOM   234  CA   LYS   30     0.096  61.696 137.997  1.00 18.21      HIGL
ATOM   235  CB   LYS   30    -0.563  62.702 137.038  1.00 18.37      HIGL
ATOM   236  CG   LYS   30    -0.511  64.151 137.467  1.00 19.45      HIGL
ATOM   237  CD   LYS   30    -0.017  65.012 136.323  1.00 19.01      HIGL
ATOM   238  CE   LYS   30    -1.150  65.659 135.558  1.00 19.86      HIGL
ATOM   239  NZ   LYS   30    -1.471  67.014 136.095  1.00 19.22      HIGL
ATOM   240  C    LYS   30     0.999  60.777 137.179  1.00 17.33      HIGL
ATOM   241  O    LYS   30     2.227  60.837 137.297  1.00 18.02      HIGL
ATOM   242  N    PRO   31     0.404  59.905 136.353  1.00 16.17      HIGL
ATOM   243  CD   PRO   31    -1.032  59.580 136.274  1.00 16.56      HIGL
ATOM   244  CA   PRO   31     1.201  58.991 135.525  1.00 15.20      HIGL
ATOM   245  CB   PRO   31     0.147  58.122 134.854  1.00 15.51      HIGL
ATOM   246  CG   PRO   31    -1.001  58.135 135.843  1.00 16.29      HIGL
ATOM   247  C    PRO   31     1.992  59.830 134.521  1.00 15.68      HIGL
ATOM   248  O    PRO   31     1.455  60.782 133.943  1.00 16.00      HIGL
ATOM   249  N    LEU   32     3.258  59.478 134.313  1.00 14.62      HIGL
ATOM   250  CA   LEU   32     4.139  60.224 133.416  1.00 13.57      HIGL
ATOM   251  CB   LEU   32     5.433  59.437 133.198  1.00 12.66      HIGL
ATOM   252  CG   LEU   32     6.592  60.142 132.490  1.00 12.44      HIGL
ATOM   253  CD1  LEU   32     6.934  61.428 133.209  1.00 11.76      HIGL
ATOM   254  CD2  LEU   32     7.805  59.218 132.455  1.00 12.43      HIGL
ATOM   255  C    LEU   32     3.546  60.628 132.062  1.00 13.85      HIGL
ATOM   256  O    LEU   32     3.684  61.781 131.641  1.00 13.20      HIGL
ATOM   257  N    GLU   33     2.881  59.698 131.379  1.00 14.00      HIGL
ATOM   258  CA   GLU   33     2.316  60.020 130.073  1.00 14.95      HIGL
ATOM   259  CB   GLU   33     1.486  58.847 129.510  1.00 15.36      HIGL
```

Fig. 2 cont.

| | | | | | | | | | | |
|---|---|---|---|---|---|---|---|---|---|---|
| ATOM | 260 | CG | GLU | 33 | 0.259 | 58.440 | 130.324 | 1.00 | 16.87 | HIGL |
| ATOM | 261 | CD | GLU | 33 | 0.560 | 57.350 | 131.339 | 1.00 | 18.43 | HIGL |
| ATOM | 262 | OE1 | GLU | 33 | 1.586 | 57.459 | 132.049 | 1.00 | 19.77 | HIGL |
| ATOM | 263 | OE2 | GLU | 33 | -0.234 | 56.387 | 131.433 | 1.00 | 18.45 | HIGL |
| ATOM | 264 | C | GLU | 33 | 1.476 | 61.300 | 130.102 | 1.00 | 15.90 | HIGL |
| ATOM | 265 | O | GLU | 33 | 1.429 | 62.032 | 129.113 | 1.00 | 17.16 | HIGL |
| ATOM | 266 | N | TYR | 34 | 0.824 | 61.584 | 131.228 | 1.00 | 16.05 | HIGL |
| ATOM | 267 | CA | TYR | 34 | 0.005 | 62.787 | 131.325 | 1.00 | 15.44 | HIGL |
| ATOM | 268 | CB | TYR | 34 | -1.104 | 62.593 | 132.358 | 1.00 | 16.32 | HIGL |
| ATOM | 269 | CG | TYR | 34 | -2.087 | 61.551 | 131.901 | 1.00 | 16.99 | HIGL |
| ATOM | 270 | CD1 | TYR | 34 | -2.063 | 60.257 | 132.426 | 1.00 | 17.20 | HIGL |
| ATOM | 271 | CE1 | TYR | 34 | -2.915 | 59.267 | 131.937 | 1.00 | 17.14 | HIGL |
| ATOM | 272 | CD2 | TYR | 34 | -2.992 | 61.832 | 130.875 | 1.00 | 17.08 | HIGL |
| ATOM | 273 | CE2 | TYR | 34 | -3.845 | 60.851 | 130.378 | 1.00 | 17.17 | HIGL |
| ATOM | 274 | CZ | TYR | 34 | -3.801 | 59.572 | 130.913 | 1.00 | 17.87 | HIGL |
| ATOM | 275 | OH | TYR | 34 | -4.647 | 58.603 | 130.425 | 1.00 | 19.84 | HIGL |
| ATOM | 276 | C | TYR | 34 | 0.828 | 64.030 | 131.617 | 1.00 | 14.61 | HIGL |
| ATOM | 277 | O | TYR | 34 | 0.512 | 65.115 | 131.126 | 1.00 | 13.80 | HIGL |
| ATOM | 278 | N | ILE | 35 | 1.889 | 63.880 | 132.399 | 1.00 | 14.26 | HIGL |
| ATOM | 279 | CA | ILE | 35 | 2.763 | 65.014 | 132.672 | 1.00 | 14.92 | HIGL |
| ATOM | 280 | CB | ILE | 35 | 3.865 | 64.662 | 133.679 | 1.00 | 15.08 | HIGL |
| ATOM | 281 | CG2 | ILE | 35 | 4.882 | 65.794 | 133.753 | 1.00 | 14.72 | HIGL |
| ATOM | 282 | CG1 | ILE | 35 | 3.243 | 64.398 | 135.051 | 1.00 | 15.03 | HIGL |
| ATOM | 283 | CD1 | ILE | 35 | 4.219 | 63.877 | 136.067 | 1.00 | 15.01 | HIGL |
| ATOM | 284 | C | ILE | 35 | 3.424 | 65.404 | 131.352 | 1.00 | 14.91 | HIGL |
| ATOM | 285 | O | ILE | 35 | 3.656 | 66.584 | 131.092 | 1.00 | 15.44 | HIGL |
| ATOM | 286 | N | LEU | 36 | 3.715 | 64.403 | 130.518 | 1.00 | 14.83 | HIGL |
| ATOM | 287 | CA | LEU | 36 | 4.332 | 64.649 | 129.215 | 1.00 | 14.44 | HIGL |
| ATOM | 288 | CB | LEU | 36 | 4.765 | 63.340 | 128.557 | 1.00 | 14.34 | HIGL |
| ATOM | 289 | CG | LEU | 36 | 5.806 | 62.491 | 129.280 | 1.00 | 15.12 | HIGL |
| ATOM | 290 | CD1 | LEU | 36 | 6.153 | 61.306 | 128.385 | 1.00 | 15.81 | HIGL |
| ATOM | 291 | CD2 | LEU | 36 | 7.050 | 63.320 | 129.595 | 1.00 | 13.46 | HIGL |
| ATOM | 292 | C | LEU | 36 | 3.385 | 65.375 | 128.267 | 1.00 | 14.40 | HIGL |
| ATOM | 293 | O | LEU | 36 | 3.761 | 66.376 | 127.659 | 1.00 | 13.88 | HIGL |
| ATOM | 294 | N | ALA | 37 | 2.162 | 64.864 | 128.131 | 1.00 | 14.45 | HIGL |
| ATOM | 295 | CA | ALA | 37 | 1.173 | 65.482 | 127.247 | 1.00 | 15.05 | HIGL |
| ATOM | 296 | CB | ALA | 37 | -0.121 | 64.677 | 127.269 | 1.00 | 14.89 | HIGL |
| ATOM | 297 | C | ALA | 37 | 0.918 | 66.915 | 127.711 | 1.00 | 15.47 | HIGL |
| ATOM | 298 | O | ALA | 37 | 0.757 | 67.832 | 126.907 | 1.00 | 14.62 | HIGL |
| ATOM | 299 | N | GLU | 38 | 0.910 | 67.081 | 129.028 | 1.00 | 16.62 | HIGL |
| ATOM | 300 | CA | GLU | 38 | 0.693 | 68.362 | 129.689 | 1.00 | 17.33 | HIGL |
| ATOM | 301 | CB | GLU | 38 | 0.784 | 68.145 | 131.200 | 1.00 | 19.24 | HIGL |
| ATOM | 302 | CG | GLU | 38 | 0.365 | 69.311 | 132.054 | 1.00 | 21.29 | HIGL |
| ATOM | 303 | CD | GLU | 38 | 0.550 | 69.028 | 133.529 | 1.00 | 22.16 | HIGL |
| ATOM | 304 | OE1 | GLU | 38 | 0.222 | 67.905 | 133.972 | 1.00 | 21.31 | HIGL |
| ATOM | 305 | OE2 | GLU | 38 | 1.018 | 69.939 | 134.244 | 1.00 | 23.91 | HIGL |
| ATOM | 306 | C | GLU | 38 | 1.727 | 69.402 | 129.262 | 1.00 | 16.88 | HIGL |
| ATOM | 307 | O | GLU | 38 | 1.441 | 70.597 | 129.205 | 1.00 | 16.84 | HIGL |
| ATOM | 308 | N | ASN | 39 | 2.934 | 68.942 | 128.960 | 1.00 | 16.61 | HIGL |
| ATOM | 309 | CA | ASN | 39 | 4.010 | 69.841 | 128.569 | 1.00 | 16.17 | HIGL |
| ATOM | 310 | CB | ASN | 39 | 5.311 | 69.379 | 129.218 | 1.00 | 16.22 | HIGL |
| ATOM | 311 | CG | ASN | 39 | 5.441 | 69.846 | 130.650 | 1.00 | 16.62 | HIGL |
| ATOM | 312 | OD1 | ASN | 39 | 5.928 | 70.948 | 130.907 | 1.00 | 16.26 | HIGL |
| ATOM | 313 | ND2 | ASN | 39 | 4.991 | 69.017 | 131.594 | 1.00 | 15.54 | HIGL |
| ATOM | 314 | C | ASN | 39 | 4.218 | 70.024 | 127.067 | 1.00 | 16.04 | HIGL |
| ATOM | 315 | O | ASN | 39 | 5.226 | 70.597 | 126.649 | 1.00 | 16.85 | HIGL |
| ATOM | 316 | N | GLY | 40 | 3.279 | 69.535 | 126.259 | 1.00 | 15.42 | HIGL |
| ATOM | 317 | CA | GLY | 40 | 3.392 | 69.694 | 124.821 | 1.00 | 14.77 | HIGL |
| ATOM | 318 | C | GLY | 40 | 3.895 | 68.494 | 124.037 | 1.00 | 15.22 | HIGL |
| ATOM | 319 | O | GLY | 40 | 3.890 | 68.517 | 122.810 | 1.00 | 15.07 | HIGL |
| ATOM | 320 | N | VAL | 41 | 4.342 | 67.451 | 124.725 | 1.00 | 15.28 | HIGL |
| ATOM | 321 | CA | VAL | 41 | 4.822 | 66.257 | 124.038 | 1.00 | 15.01 | HIGL |
| ATOM | 322 | CB | VAL | 41 | 5.357 | 65.212 | 125.047 | 1.00 | 15.77 | HIGL |
| ATOM | 323 | CG1 | VAL | 41 | 5.682 | 63.896 | 124.328 | 1.00 | 14.74 | HIGL |
| ATOM | 324 | CG2 | VAL | 41 | 6.596 | 65.760 | 125.751 | 1.00 | 15.28 | HIGL |

Fig. 2 cont.

| ATOM | 325 | C   | VAL | 41 | 3.668  | 65.643 | 123.259 | 1.00 | 14.29 | HIGL |
|------|-----|-----|-----|----|--------|--------|---------|------|-------|------|
| ATOM | 326 | O   | VAL | 41 | 2.560  | 65.558 | 123.776 | 1.00 | 14.34 | HIGL |
| ATOM | 327 | N   | ASN | 42 | 3.913  | 65.230 | 122.017 | 1.00 | 14.20 | HIGL |
| ATOM | 328 | CA  | ASN | 42 | 2.846  | 64.611 | 121.217 | 1.00 | 14.11 | HIGL |
| ATOM | 329 | CB  | ASN | 42 | 2.451  | 65.488 | 120.008 | 1.00 | 13.09 | HIGL |
| ATOM | 330 | CG  | ASN | 42 | 3.588  | 65.683 | 119.003 | 1.00 | 15.29 | HIGL |
| ATOM | 331 | OD1 | ASN | 42 | 4.632  | 65.030 | 119.077 | 1.00 | 14.89 | HIGL |
| ATOM | 332 | ND2 | ASN | 42 | 3.376  | 66.587 | 118.044 | 1.00 | 13.72 | HIGL |
| ATOM | 333 | C   | ASN | 42 | 3.220  | 63.215 | 120.734 | 1.00 | 13.63 | HIGL |
| ATOM | 334 | O   | ASN | 42 | 2.523  | 62.628 | 119.907 | 1.00 | 13.90 | HIGL |
| ATOM | 335 | N   | MET | 43 | 4.319  | 62.683 | 121.259 | 1.00 | 13.09 | HIGL |
| ATOM | 336 | CA  | MET | 43 | 4.776  | 61.355 | 120.865 | 1.00 | 12.43 | HIGL |
| ATOM | 337 | CB  | MET | 43 | 5.290  | 61.373 | 119.421 | 1.00 | 12.54 | HIGL |
| ATOM | 338 | CG  | MET | 43 | 5.833  | 60.029 | 118.943 | 1.00 | 13.16 | HIGL |
| ATOM | 339 | SD  | MET | 43 | 6.153  | 59.988 | 117.164 | 1.00 | 15.39 | HIGL |
| ATOM | 340 | CE  | MET | 43 | 4.461  | 60.024 | 116.523 | 1.00 | 14.86 | HIGL |
| ATOM | 341 | C   | MET | 43 | 5.870  | 60.820 | 121.774 | 1.00 | 11.00 | HIGL |
| ATOM | 342 | O   | MET | 43 | 6.730  | 61.563 | 122.229 | 1.00 | 9.98  | HIGL |
| ATOM | 343 | N   | VAL | 44 | 5.824  | 59.522 | 122.041 | 1.00 | 10.40 | HIGL |
| ATOM | 344 | CA  | VAL | 44 | 6.837  | 58.900 | 122.872 | 1.00 | 10.47 | HIGL |
| ATOM | 345 | CB  | VAL | 44 | 6.218  | 58.213 | 124.113 | 1.00 | 10.16 | HIGL |
| ATOM | 346 | CG1 | VAL | 44 | 5.663  | 59.259 | 125.057 | 1.00 | 10.97 | HIGL |
| ATOM | 347 | CG2 | VAL | 44 | 5.120  | 57.251 | 123.696 | 1.00 | 10.36 | HIGL |
| ATOM | 348 | C   | VAL | 44 | 7.607  | 57.868 | 122.051 | 1.00 | 10.89 | HIGL |
| ATOM | 349 | O   | VAL | 44 | 7.060  | 57.241 | 121.140 | 1.00 | 9.61  | HIGL |
| ATOM | 350 | N   | ARG | 45 | 8.889  | 57.721 | 122.368 | 1.00 | 11.52 | HIGL |
| ATOM | 351 | CA  | ARG | 45 | 9.758  | 56.765 | 121.696 | 1.00 | 12.77 | HIGL |
| ATOM | 352 | CB  | ARG | 45 | 11.085 | 57.442 | 121.351 | 1.00 | 14.01 | HIGL |
| ATOM | 353 | CG  | ARG | 45 | 12.129 | 56.570 | 120.667 | 1.00 | 15.59 | HIGL |
| ATOM | 354 | CD  | ARG | 45 | 13.326 | 57.430 | 120.305 | 1.00 | 16.97 | HIGL |
| ATOM | 355 | NE  | ARG | 45 | 14.418 | 56.694 | 119.679 | 1.00 | 17.87 | HIGL |
| ATOM | 356 | CZ  | ARG | 45 | 15.496 | 56.254 | 120.320 | 1.00 | 17.82 | HIGL |
| ATOM | 357 | NH1 | ARG | 45 | 15.642 | 56.466 | 121.620 | 1.00 | 17.90 | HIGL |
| ATOM | 358 | NH2 | ARG | 45 | 16.439 | 55.610 | 119.653 | 1.00 | 18.55 | HIGL |
| ATOM | 359 | C   | ARG | 45 | 9.970  | 55.628 | 122.687 | 1.00 | 13.22 | HIGL |
| ATOM | 360 | O   | ARG | 45 | 10.244 | 55.870 | 123.859 | 1.00 | 13.66 | HIGL |
| ATOM | 361 | N   | GLN | 46 | 9.821  | 54.390 | 122.232 | 1.00 | 13.78 | HIGL |
| ATOM | 362 | CA  | GLN | 46 | 9.996  | 53.243 | 123.118 | 1.00 | 14.54 | HIGL |
| ATOM | 363 | CB  | GLN | 46 | 8.639  | 52.573 | 123.394 | 1.00 | 15.20 | HIGL |
| ATOM | 364 | CG  | GLN | 46 | 7.582  | 53.492 | 124.043 | 1.00 | 16.94 | HIGL |
| ATOM | 365 | CD  | GLN | 46 | 6.298  | 52.748 | 124.403 | 1.00 | 18.02 | HIGL |
| ATOM | 366 | OE1 | GLN | 46 | 5.361  | 53.328 | 124.944 | 1.00 | 17.27 | HIGL |
| ATOM | 367 | NE2 | GLN | 46 | 6.257  | 51.454 | 124.097 | 1.00 | 19.40 | HIGL |
| ATOM | 368 | C   | GLN | 46 | 10.960 | 52.228 | 122.512 | 1.00 | 14.27 | HIGL |
| ATOM | 369 | O   | GLN | 46 | 10.808 | 51.829 | 121.360 | 1.00 | 15.12 | HIGL |
| ATOM | 370 | N   | ARG | 47 | 11.962 | 51.821 | 123.280 | 1.00 | 14.18 | HIGL |
| ATOM | 371 | CA  | ARG | 47 | 12.923 | 50.847 | 122.787 | 1.00 | 14.34 | HIGL |
| ATOM | 372 | CB  | ARG | 47 | 14.264 | 51.008 | 123.510 | 1.00 | 14.68 | HIGL |
| ATOM | 373 | CG  | ARG | 47 | 14.172 | 51.059 | 125.026 | 1.00 | 14.19 | HIGL |
| ATOM | 374 | CD  | ARG | 47 | 15.555 | 50.900 | 125.661 | 1.00 | 14.01 | HIGL |
| ATOM | 375 | NE  | ARG | 47 | 15.530 | 51.133 | 127.101 | 1.00 | 13.64 | HIGL |
| ATOM | 376 | CZ  | ARG | 47 | 15.463 | 52.341 | 127.651 | 1.00 | 13.65 | HIGL |
| ATOM | 377 | NH1 | ARG | 47 | 15.422 | 53.415 | 126.872 | 1.00 | 12.61 | HIGL |
| ATOM | 378 | NH2 | ARG | 47 | 15.436 | 52.479 | 128.969 | 1.00 | 12.29 | HIGL |
| ATOM | 379 | C   | ARG | 47 | 12.375 | 49.434 | 122.979 | 1.00 | 14.38 | HIGL |
| ATOM | 380 | O   | ARG | 47 | 11.742 | 49.139 | 123.990 | 1.00 | 14.26 | HIGL |
| ATOM | 381 | N   | VAL | 48 | 12.616 | 48.567 | 121.999 | 1.00 | 14.13 | HIGL |
| ATOM | 382 | CA  | VAL | 48 | 12.136 | 47.194 | 122.054 | 1.00 | 14.66 | HIGL |
| ATOM | 383 | CB  | VAL | 48 | 11.108 | 46.931 | 120.946 | 1.00 | 14.30 | HIGL |
| ATOM | 384 | CG1 | VAL | 48 | 10.497 | 45.549 | 121.109 | 1.00 | 12.51 | HIGL |
| ATOM | 385 | CG2 | VAL | 48 | 10.044 | 48.001 | 120.977 | 1.00 | 14.44 | HIGL |
| ATOM | 386 | C   | VAL | 48 | 13.266 | 46.185 | 121.901 | 1.00 | 15.87 | HIGL |
| ATOM | 387 | O   | VAL | 48 | 13.987 | 46.200 | 120.903 | 1.00 | 16.88 | HIGL |
| ATOM | 388 | N   | TRP | 49 | 13.420 | 45.319 | 122.901 | 1.00 | 16.25 | HIGL |
| ATOM | 389 | CA  | TRP | 49 | 14.449 | 44.283 | 122.881 | 1.00 | 16.07 | HIGL |

Fig. 2 cont.

| | | | | | | | | | |
|---|---|---|---|---|---|---|---|---|---|
| ATOM | 390 | CB | TRP | 49 | 15.243 | 44.280 | 124.194 | 1.00 15.19 | HIGL |
| ATOM | 391 | CG | TRP | 49 | 16.039 | 45.533 | 124.422 | 1.00 15.37 | HIGL |
| ATOM | 392 | CD2 | TRP | 49 | 16.745 | 45.898 | 125.613 | 1.00 15.05 | HIGL |
| ATOM | 393 | CE2 | TRP | 49 | 17.359 | 47.146 | 125.370 | 1.00 14.69 | HIGL |
| ATOM | 394 | CE3 | TRP | 49 | 16.922 | 45.290 | 126.864 | 1.00 15.17 | HIGL |
| ATOM | 395 | CD1 | TRP | 49 | 16.247 | 46.550 | 123.529 | 1.00 15.47 | HIGL |
| ATOM | 396 | NE1 | TRP | 49 | 17.037 | 47.521 | 124.093 | 1.00 14.49 | HIGL |
| ATOM | 397 | CZ2 | TRP | 49 | 18.138 | 47.798 | 126.332 | 1.00 15.16 | HIGL |
| ATOM | 398 | CZ3 | TRP | 49 | 17.696 | 45.939 | 127.819 | 1.00 14.43 | HIGL |
| ATOM | 399 | CH2 | TRP | 49 | 18.294 | 47.179 | 127.547 | 1.00 14.14 | HIGL |
| ATOM | 400 | C | TRP | 49 | 13.793 | 42.924 | 122.665 | 1.00 16.51 | HIGL |
| ATOM | 401 | O | TRP | 49 | 12.657 | 42.695 | 123.100 | 1.00 16.05 | HIGL |
| ATOM | 402 | N | VAL | 50 | 14.517 | 42.031 | 121.990 | 1.00 16.88 | HIGL |
| ATOM | 403 | CA | VAL | 50 | 14.031 | 40.690 | 121.675 | 1.00 17.15 | HIGL |
| ATOM | 404 | CB | VAL | 50 | 15.039 | 39.953 | 120.754 | 1.00 17.71 | HIGL |
| ATOM | 405 | CG1 | VAL | 50 | 14.449 | 38.639 | 120.260 | 1.00 17.30 | HIGL |
| ATOM | 406 | CG2 | VAL | 50 | 15.402 | 40.841 | 119.571 | 1.00 17.23 | HIGL |
| ATOM | 407 | C | VAL | 50 | 13.763 | 39.843 | 122.923 | 1.00 17.92 | HIGL |
| ATOM | 408 | O | VAL | 50 | 12.617 | 39.724 | 123.362 | 1.00 18.11 | HIGL |
| ATOM | 409 | N | ASN | 51 | 14.812 | 39.258 | 123.495 | 1.00 18.58 | HIGL |
| ATOM | 410 | CA | ASN | 51 | 14.660 | 38.430 | 124.690 | 1.00 18.99 | HIGL |
| ATOM | 411 | CB | ASN | 51 | 15.126 | 37.010 | 124.410 | 1.00 21.64 | HIGL |
| ATOM | 412 | CG | ASN | 51 | 14.602 | 36.480 | 123.093 | 1.00 24.95 | HIGL |
| ATOM | 413 | OD1 | ASN | 51 | 13.388 | 36.364 | 122.892 | 1.00 27.18 | HIGL |
| ATOM | 414 | ND2 | ASN | 51 | 15.517 | 36.156 | 122.180 | 1.00 25.56 | HIGL |
| ATOM | 415 | C | ASN | 51 | 15.443 | 38.978 | 125.875 | 1.00 18.38 | HIGL |
| ATOM | 416 | O | ASN | 51 | 16.417 | 38.368 | 126.319 | 1.00 17.35 | HIGL |
| ATOM | 417 | N | PRO | 52 | 15.032 | 40.144 | 126.401 | 1.00 17.80 | HIGL |
| ATOM | 418 | CD | PRO | 52 | 13.867 | 40.972 | 126.053 | 1.00 17.12 | HIGL |
| ATOM | 419 | CA | PRO | 52 | 15.747 | 40.712 | 127.543 | 1.00 17.06 | HIGL |
| ATOM | 420 | CB | PRO | 52 | 14.949 | 41.971 | 127.861 | 1.00 16.91 | HIGL |
| ATOM | 421 | CG | PRO | 52 | 13.579 | 41.650 | 127.364 | 1.00 17.23 | HIGL |
| ATOM | 422 | C | PRO | 52 | 15.776 | 39.716 | 128.688 | 1.00 17.60 | HIGL |
| ATOM | 423 | O | PRO | 52 | 14.828 | 38.954 | 128.891 | 1.00 17.99 | HIGL |
| ATOM | 424 | N | TRP | 53 | 16.877 | 39.723 | 129.428 | 1.00 17.96 | HIGL |
| ATOM | 425 | CA | TRP | 53 | 17.068 | 38.801 | 130.536 | 1.00 17.77 | HIGL |
| ATOM | 426 | CB | TRP | 53 | 18.448 | 39.013 | 131.156 | 1.00 18.06 | HIGL |
| ATOM | 427 | CG | TRP | 53 | 18.543 | 40.298 | 131.917 | 1.00 18.50 | HIGL |
| ATOM | 428 | CD2 | TRP | 53 | 18.389 | 40.459 | 133.328 | 1.00 18.71 | HIGL |
| ATOM | 429 | CE2 | TRP | 53 | 18.452 | 41.844 | 133.600 | 1.00 17.92 | HIGL |
| ATOM | 430 | CE3 | TRP | 53 | 18.198 | 39.565 | 134.390 | 1.00 18.46 | HIGL |
| ATOM | 431 | CD1 | TRP | 53 | 18.698 | 41.553 | 131.404 | 1.00 18.32 | HIGL |
| ATOM | 432 | NE1 | TRP | 53 | 18.642 | 42.489 | 132.409 | 1.00 17.61 | HIGL |
| ATOM | 433 | CZ2 | TRP | 53 | 18.331 | 42.357 | 134.888 | 1.00 19.23 | HIGL |
| ATOM | 434 | CZ3 | TRP | 53 | 18.077 | 40.074 | 135.674 | 1.00 19.45 | HIGL |
| ATOM | 435 | CH2 | TRP | 53 | 18.143 | 41.460 | 135.912 | 1.00 19.83 | HIGL |
| ATOM | 436 | C | TRP | 53 | 16.017 | 38.919 | 131.631 | 1.00 17.78 | HIGL |
| ATOM | 437 | O | TRP | 53 | 15.726 | 37.944 | 132.324 | 1.00 18.33 | HIGL |
| ATOM | 438 | N | ASP | 54 | 15.447 | 40.106 | 131.793 | 1.00 17.42 | HIGL |
| ATOM | 439 | CA | ASP | 54 | 14.455 | 40.307 | 132.845 | 1.00 17.12 | HIGL |
| ATOM | 440 | CB | ASP | 54 | 14.976 | 41.352 | 133.830 | 1.00 16.85 | HIGL |
| ATOM | 441 | CG | ASP | 54 | 15.139 | 42.705 | 133.189 | 1.00 17.98 | HIGL |
| ATOM | 442 | OD1 | ASP | 54 | 15.083 | 42.779 | 131.938 | 1.00 19.62 | HIGL |
| ATOM | 443 | OD2 | ASP | 54 | 15.325 | 43.690 | 133.927 | 1.00 17.75 | HIGL |
| ATOM | 444 | C | ASP | 54 | 13.080 | 40.718 | 132.320 | 1.00 16.46 | HIGL |
| ATOM | 445 | O | ASP | 54 | 12.196 | 41.080 | 133.094 | 1.00 16.77 | HIGL |
| ATOM | 446 | N | GLY | 55 | 12.907 | 40.666 | 131.003 | 1.00 16.49 | HIGL |
| ATOM | 447 | CA | GLY | 55 | 11.629 | 41.019 | 130.406 | 1.00 15.10 | HIGL |
| ATOM | 448 | C | GLY | 55 | 11.396 | 42.494 | 130.120 | 1.00 14.82 | HIGL |
| ATOM | 449 | O | GLY | 55 | 10.461 | 42.844 | 129.401 | 1.00 14.82 | HIGL |
| ATOM | 450 | N | ASN | 56 | 12.225 | 43.375 | 130.667 | 1.00 14.46 | HIGL |
| ATOM | 451 | CA | ASN | 56 | 12.010 | 44.792 | 130.418 | 1.00 14.01 | HIGL |
| ATOM | 452 | CB | ASN | 56 | 12.784 | 45.649 | 131.417 | 1.00 14.38 | HIGL |
| ATOM | 453 | CG | ASN | 56 | 12.130 | 45.660 | 132.785 | 1.00 15.79 | HIGL |
| ATOM | 454 | OD1 | ASN | 56 | 10.901 | 45.606 | 132.902 | 1.00 15.70 | HIGL |

Fig. 2 cont.

| | | | | | | | | |
|---|---|---|---|---|---|---|---|---|
| ATOM | 455 | ND2 | ASN | 56 | 12.941 | 45.743 | 133.826 | 1.00 16.95 | HIGL |
| ATOM | 456 | C | ASN | 56 | 12.341 | 45.204 | 128.999 | 1.00 13.31 | HIGL |
| ATOM | 457 | O | ASN | 56 | 13.366 | 44.817 | 128.442 | 1.00 12.12 | HIGL |
| ATOM | 458 | N | TYR | 57 | 11.439 | 45.991 | 128.424 | 1.00 13.34 | HIGL |
| ATOM | 459 | CA | TYR | 57 | 11.558 | 46.499 | 127.065 | 1.00 13.09 | HIGL |
| ATOM | 460 | CB | TYR | 57 | 12.968 | 47.049 | 126.789 | 1.00 12.20 | HIGL |
| ATOM | 461 | CG | TYR | 57 | 13.466 | 47.989 | 127.865 | 1.00 11.14 | HIGL |
| ATOM | 462 | CD1 | TYR | 57 | 12.666 | 49.030 | 128.330 | 1.00 10.28 | HIGL |
| ATOM | 463 | CE1 | TYR | 57 | 13.095 | 49.859 | 129.353 | 1.00  9.79 | HIGL |
| ATOM | 464 | CD2 | TYR | 57 | 14.716 | 47.808 | 128.450 | 1.00 10.12 | HIGL |
| ATOM | 465 | CE2 | TYR | 57 | 15.152 | 48.630 | 129.471 | 1.00  9.28 | HIGL |
| ATOM | 466 | CZ | TYR | 57 | 14.333 | 49.654 | 129.922 | 1.00  9.42 | HIGL |
| ATOM | 467 | OH | TYR | 57 | 14.737 | 50.450 | 130.973 | 1.00 10.17 | HIGL |
| ATOM | 468 | C | TYR | 57 | 11.214 | 45.426 | 126.052 | 1.00 13.71 | HIGL |
| ATOM | 469 | O | TYR | 57 | 11.460 | 45.591 | 124.854 | 1.00 13.96 | HIGL |
| ATOM | 470 | N | ASN | 58 | 10.657 | 44.313 | 126.515 | 1.00 13.75 | HIGL |
| ATOM | 471 | CA | ASN | 58 | 10.276 | 43.298 | 125.553 | 1.00 14.27 | HIGL |
| ATOM | 472 | CB | ASN | 58 | 10.325 | 41.874 | 126.147 | 1.00 12.09 | HIGL |
| ATOM | 473 | CG | ASN | 58 |  9.216 | 41.576 | 127.140 | 1.00  9.87 | HIGL |
| ATOM | 474 | OD1 | ASN | 58 |  8.278 | 42.353 | 127.323 | 1.00 11.38 | HIGL |
| ATOM | 475 | ND2 | ASN | 58 |  9.316 | 40.416 | 127.777 | 1.00  5.89 | HIGL |
| ATOM | 476 | C | ASN | 58 |  8.892 | 43.669 | 125.039 | 1.00 15.29 | HIGL |
| ATOM | 477 | O | ASN | 58 |  8.301 | 44.651 | 125.490 | 1.00 14.81 | HIGL |
| ATOM | 478 | N | LEU | 59 |  8.389 | 42.901 | 124.085 | 1.00 17.30 | HIGL |
| ATOM | 479 | CA | LEU | 59 |  7.096 | 43.188 | 123.482 | 1.00 19.48 | HIGL |
| ATOM | 480 | CB | LEU | 59 |  6.692 | 42.037 | 122.565 | 1.00 21.08 | HIGL |
| ATOM | 481 | CG | LEU | 59 |  5.709 | 42.447 | 121.470 | 1.00 23.34 | HIGL |
| ATOM | 482 | CD1 | LEU | 59 |  6.296 | 43.624 | 120.673 | 1.00 23.05 | HIGL |
| ATOM | 483 | CD2 | LEU | 59 |  5.436 | 41.247 | 120.561 | 1.00 23.47 | HIGL |
| ATOM | 484 | C | LEU | 59 |  5.970 | 43.488 | 124.471 | 1.00 19.90 | HIGL |
| ATOM | 485 | O | LEU | 59 |  5.367 | 44.557 | 124.415 | 1.00 21.04 | HIGL |
| ATOM | 486 | N | ASP | 60 |  5.683 | 42.555 | 125.372 | 1.00 20.10 | HIGL |
| ATOM | 487 | CA | ASP | 60 |  4.619 | 42.756 | 126.348 | 1.00 20.50 | HIGL |
| ATOM | 488 | CB | ASP | 60 |  4.599 | 41.613 | 127.369 | 1.00 21.74 | HIGL |
| ATOM | 489 | CG | ASP | 60 |  4.436 | 40.250 | 126.720 | 1.00 23.55 | HIGL |
| ATOM | 490 | OD1 | ASP | 60 |  3.553 | 40.100 | 125.844 | 1.00 23.00 | HIGL |
| ATOM | 491 | OD2 | ASP | 60 |  5.190 | 39.324 | 127.094 | 1.00 24.89 | HIGL |
| ATOM | 492 | C | ASP | 60 |  4.810 | 44.078 | 127.078 | 1.00 20.77 | HIGL |
| ATOM | 493 | O | ASP | 60 |  3.869 | 44.860 | 127.231 | 1.00 21.37 | HIGL |
| ATOM | 494 | N | TYR | 61 |  6.038 | 44.315 | 127.529 | 1.00 20.29 | HIGL |
| ATOM | 495 | CA | TYR | 61 |  6.393 | 45.533 | 128.241 | 1.00 19.19 | HIGL |
| ATOM | 496 | CB | TYR | 61 |  7.896 | 45.526 | 128.574 | 1.00 19.77 | HIGL |
| ATOM | 497 | CG | TYR | 61 |  8.400 | 46.776 | 129.274 | 1.00 19.20 | HIGL |
| ATOM | 498 | CD1 | TYR | 61 |  8.572 | 47.975 | 128.580 | 1.00 19.12 | HIGL |
| ATOM | 499 | CE1 | TYR | 61 |  8.998 | 49.132 | 129.229 | 1.00 19.60 | HIGL |
| ATOM | 500 | CD2 | TYR | 61 |  8.675 | 46.766 | 130.638 | 1.00 19.18 | HIGL |
| ATOM | 501 | CE2 | TYR | 61 |  9.101 | 47.916 | 131.297 | 1.00 20.13 | HIGL |
| ATOM | 502 | CZ | TYR | 61 |  9.259 | 49.096 | 130.589 | 1.00 20.45 | HIGL |
| ATOM | 503 | OH | TYR | 61 |  9.663 | 50.239 | 131.250 | 1.00 21.00 | HIGL |
| ATOM | 504 | C | TYR | 61 |  6.059 | 46.767 | 127.414 | 1.00 19.25 | HIGL |
| ATOM | 505 | O | TYR | 61 |  5.506 | 47.738 | 127.930 | 1.00 19.40 | HIGL |
| ATOM | 506 | N | ASN | 62 |  6.390 | 46.733 | 126.129 | 1.00 19.00 | HIGL |
| ATOM | 507 | CA | ASN | 62 |  6.128 | 47.878 | 125.271 | 1.00 19.77 | HIGL |
| ATOM | 508 | CB | ASN | 62 |  6.971 | 47.789 | 123.999 | 1.00 20.44 | HIGL |
| ATOM | 509 | CG | ASN | 62 |  8.403 | 48.223 | 124.229 | 1.00 21.08 | HIGL |
| ATOM | 510 | OD1 | ASN | 62 |  8.685 | 49.415 | 124.376 | 1.00 21.94 | HIGL |
| ATOM | 511 | ND2 | ASN | 62 |  9.315 | 47.259 | 124.284 | 1.00 20.37 | HIGL |
| ATOM | 512 | C | ASN | 62 |  4.664 | 48.053 | 124.925 | 1.00 19.75 | HIGL |
| ATOM | 513 | O | ASN | 62 |  4.235 | 49.156 | 124.588 | 1.00 20.46 | HIGL |
| ATOM | 514 | N | ILE | 63 |  3.892 | 46.977 | 125.009 | 1.00 19.62 | HIGL |
| ATOM | 515 | CA | ILE | 63 |  2.472 | 47.073 | 124.717 | 1.00 20.26 | HIGL |
| ATOM | 516 | CB | ILE | 63 |  1.856 | 45.693 | 124.478 | 1.00 20.11 | HIGL |
| ATOM | 517 | CG2 | ILE | 63 |  0.336 | 45.761 | 124.598 | 1.00 19.41 | HIGL |
| ATOM | 518 | CG1 | ILE | 63 |  2.293 | 45.198 | 123.101 | 1.00 20.67 | HIGL |
| ATOM | 519 | CD1 | ILE | 63 |  1.599 | 43.952 | 122.648 | 1.00 23.84 | HIGL |

Fig. 2 cont.

| | | | | | | | | | |
|---|---|---|---|---|---|---|---|---|---|
| ATOM | 520 | C | ILE | 63 | 1.742 | 47.775 | 125.852 | 1.00 21.15 | HIGL |
| ATOM | 521 | O | ILE | 63 | 0.807 | 48.535 | 125.617 | 1.00 20.59 | HIGL |
| ATOM | 522 | N | GLN | 64 | 2.172 | 47.528 | 127.086 | 1.00 22.72 | HIGL |
| ATOM | 523 | CA | GLN | 64 | 1.547 | 48.177 | 128.235 | 1.00 23.28 | HIGL |
| ATOM | 524 | CB | GLN | 64 | 2.117 | 47.626 | 129.544 | 1.00 24.62 | HIGL |
| ATOM | 525 | CG | GLN | 64 | 1.064 | 47.428 | 130.630 | 1.00 27.22 | HIGL |
| ATOM | 526 | CD | GLN | 64 | 1.641 | 46.837 | 131.906 | 1.00 29.98 | HIGL |
| ATOM | 527 | OE1 | GLN | 64 | 2.314 | 45.798 | 131.877 | 1.00 31.39 | HIGL |
| ATOM | 528 | NE2 | GLN | 64 | 1.380 | 47.493 | 133.037 | 1.00 29.60 | HIGL |
| ATOM | 529 | C | GLN | 64 | 1.827 | 49.675 | 128.130 | 1.00 22.91 | HIGL |
| ATOM | 530 | O | GLN | 64 | 0.952 | 50.501 | 128.400 | 1.00 23.24 | HIGL |
| ATOM | 531 | N | LEU | 65 | 3.045 | 50.018 | 127.717 | 1.00 21.90 | HIGL |
| ATOM | 532 | CA | LEU | 65 | 3.436 | 51.415 | 127.559 | 1.00 21.80 | HIGL |
| ATOM | 533 | CB | LEU | 65 | 4.925 | 51.524 | 127.241 | 1.00 21.78 | HIGL |
| ATOM | 534 | CG | LEU | 65 | 5.863 | 51.436 | 128.439 | 1.00 22.02 | HIGL |
| ATOM | 535 | CD1 | LEU | 65 | 7.300 | 51.702 | 128.006 | 1.00 21.72 | HIGL |
| ATOM | 536 | CD2 | LEU | 65 | 5.424 | 52.459 | 129.459 | 1.00 22.32 | HIGL |
| ATOM | 537 | C | LEU | 65 | 2.650 | 52.104 | 126.458 | 1.00 21.48 | HIGL |
| ATOM | 538 | O | LEU | 65 | 2.107 | 53.191 | 126.651 | 1.00 20.27 | HIGL |
| ATOM | 539 | N | ALA | 66 | 2.604 | 51.467 | 125.297 | 1.00 21.88 | HIGL |
| ATOM | 540 | CA | ALA | 66 | 1.884 | 52.017 | 124.157 | 1.00 22.71 | HIGL |
| ATOM | 541 | CB | ALA | 66 | 1.908 | 51.026 | 123.006 | 1.00 21.67 | HIGL |
| ATOM | 542 | C | ALA | 66 | 0.447 | 52.340 | 124.546 | 1.00 22.91 | HIGL |
| ATOM | 543 | O | ALA | 66 | -0.013 | 53.471 | 124.395 | 1.00 23.72 | HIGL |
| ATOM | 544 | N | ARG | 67 | -0.256 | 51.340 | 125.059 | 1.00 23.00 | HIGL |
| ATOM | 545 | CA | ARG | 67 | -1.635 | 51.517 | 125.457 | 1.00 22.83 | HIGL |
| ATOM | 546 | CB | ARG | 67 | -2.121 | 50.260 | 126.173 | 1.00 24.13 | HIGL |
| ATOM | 547 | CG | ARG | 67 | -3.621 | 50.147 | 126.305 | 1.00 26.38 | HIGL |
| ATOM | 548 | CD | ARG | 67 | -3.993 | 48.774 | 126.824 | 1.00 29.10 | HIGL |
| ATOM | 549 | NE | ARG | 67 | -3.810 | 47.732 | 125.815 | 1.00 30.83 | HIGL |
| ATOM | 550 | CZ | ARG | 67 | -3.501 | 46.469 | 126.098 | 1.00 32.31 | HIGL |
| ATOM | 551 | NH1 | ARG | 67 | -3.333 | 46.096 | 127.361 | 1.00 33.65 | HIGL |
| ATOM | 552 | NH2 | ARG | 67 | -3.369 | 45.576 | 125.126 | 1.00 32.30 | HIGL |
| ATOM | 553 | C | ARG | 67 | -1.747 | 52.749 | 126.351 | 1.00 22.02 | HIGL |
| ATOM | 554 | O | ARG | 67 | -2.627 | 53.587 | 126.158 | 1.00 22.49 | HIGL |
| ATOM | 555 | N | ARG | 68 | -0.843 | 52.876 | 127.313 | 1.00 21.00 | HIGL |
| ATOM | 556 | CA | ARG | 68 | -0.860 | 54.031 | 128.207 | 1.00 20.10 | HIGL |
| ATOM | 557 | CB | ARG | 68 | 0.183 | 53.867 | 129.321 | 1.00 19.58 | HIGL |
| ATOM | 558 | CG | ARG | 68 | -0.247 | 52.927 | 130.442 | 1.00 18.60 | HIGL |
| ATOM | 559 | CD | ARG | 68 | 0.858 | 52.723 | 131.475 | 1.00 17.98 | HIGL |
| ATOM | 560 | NE | ARG | 68 | 1.319 | 53.986 | 132.048 | 1.00 17.78 | HIGL |
| ATOM | 561 | CZ | ARG | 68 | 2.210 | 54.078 | 133.030 | 1.00 16.65 | HIGL |
| ATOM | 562 | NH1 | ARG | 68 | 2.735 | 52.975 | 133.550 | 1.00 15.08 | HIGL |
| ATOM | 563 | NH2 | ARG | 68 | 2.574 | 55.272 | 133.490 | 1.00 15.87 | HIGL |
| ATOM | 564 | C | ARG | 68 | -0.588 | 55.322 | 127.441 | 1.00 20.06 | HIGL |
| ATOM | 565 | O | ARG | 68 | -1.287 | 56.312 | 127.613 | 1.00 19.99 | HIGL |
| ATOM | 566 | N | ALA | 69 | 0.437 | 55.306 | 126.597 | 1.00 20.75 | HIGL |
| ATOM | 567 | CA | ALA | 69 | 0.800 | 56.477 | 125.808 | 1.00 21.00 | HIGL |
| ATOM | 568 | CB | ALA | 69 | 1.979 | 56.144 | 124.913 | 1.00 21.37 | HIGL |
| ATOM | 569 | C | ALA | 69 | -0.379 | 56.960 | 124.965 | 1.00 21.40 | HIGL |
| ATOM | 570 | O | ALA | 69 | -0.610 | 58.164 | 124.829 | 1.00 20.93 | HIGL |
| ATOM | 571 | N | LYS | 70 | -1.114 | 56.007 | 124.402 | 1.00 21.23 | HIGL |
| ATOM | 572 | CA | LYS | 70 | -2.273 | 56.295 | 123.574 | 1.00 22.04 | HIGL |
| ATOM | 573 | CB | LYS | 70 | -2.770 | 54.991 | 122.941 | 1.00 24.06 | HIGL |
| ATOM | 574 | CG | LYS | 70 | -4.006 | 55.118 | 122.060 | 1.00 26.72 | HIGL |
| ATOM | 575 | CD | LYS | 70 | -4.553 | 53.734 | 121.710 | 1.00 29.26 | HIGL |
| ATOM | 576 | CE | LYS | 70 | -5.785 | 53.811 | 120.813 | 1.00 30.47 | HIGL |
| ATOM | 577 | NZ | LYS | 70 | -6.349 | 52.451 | 120.547 | 1.00 31.87 | HIGL |
| ATOM | 578 | C | LYS | 70 | -3.394 | 56.946 | 124.403 | 1.00 21.81 | HIGL |
| ATOM | 579 | O | LYS | 70 | -4.034 | 57.901 | 123.958 | 1.00 21.40 | HIGL |
| ATOM | 580 | N | ALA | 71 | -3.631 | 56.439 | 125.609 | 1.00 20.36 | HIGL |
| ATOM | 581 | CA | ALA | 71 | -4.682 | 57.000 | 126.448 | 1.00 19.90 | HIGL |
| ATOM | 582 | CB | ALA | 71 | -4.770 | 56.242 | 127.767 | 1.00 19.16 | HIGL |
| ATOM | 583 | C | ALA | 71 | -4.432 | 58.485 | 126.708 | 1.00 19.54 | HIGL |
| ATOM | 584 | O | ALA | 71 | -5.371 | 59.259 | 126.862 | 1.00 20.19 | HIGL |

Fig. 2 cont.

```
ATOM    585  N    ALA    72     -3.166   58.881  126.754  1.00  18.45           HIGL
ATOM    586  CA   ALA    72     -2.822   60.276  126.987  1.00  17.24           HIGL
ATOM    587  CB   ALA    72     -1.507   60.374  127.753  1.00  16.31           HIGL
ATOM    588  C    ALA    72     -2.722   61.035  125.667  1.00  16.70           HIGL
ATOM    589  O    ALA    72     -2.210   62.147  125.628  1.00  17.88           HIGL
ATOM    590  N    GLY    73     -3.200   60.421  124.589  1.00  15.95           HIGL
ATOM    591  CA   GLY    73     -3.176   61.058  123.284  1.00  15.41           HIGL
ATOM    592  C    GLY    73     -1.809   61.236  122.647  1.00  16.92           HIGL
ATOM    593  O    GLY    73     -1.638   62.056  121.739  1.00  16.80           HIGL
ATOM    594  N    LEU    74     -0.826   60.470  123.107  1.00  16.80           HIGL
ATOM    595  CA   LEU    74      0.516   60.577  122.554  1.00  16.41           HIGL
ATOM    596  CB   LEU    74      1.545   60.366  123.663  1.00  15.23           HIGL
ATOM    597  CG   LEU    74      1.311   61.253  124.884  1.00  14.82           HIGL
ATOM    598  CD1  LEU    74      2.265   60.875  125.994  1.00  13.72           HIGL
ATOM    599  CD2  LEU    74      1.486   62.706  124.492  1.00  14.41           HIGL
ATOM    600  C    LEU    74      0.762   59.577  121.424  1.00  17.36           HIGL
ATOM    601  O    LEU    74      0.319   58.430  121.482  1.00  16.67           HIGL
ATOM    602  N    GLY    75      1.470   60.027  120.392  1.00  18.17           HIGL
ATOM    603  CA   GLY    75      1.785   59.155  119.278  1.00  17.81           HIGL
ATOM    604  C    GLY    75      2.846   58.153  119.695  1.00  18.44           HIGL
ATOM    605  O    GLY    75      3.486   58.299  120.748  1.00  18.86           HIGL
ATOM    606  N    LEU    76      3.058   57.147  118.858  1.00  17.36           HIGL
ATOM    607  CA   LEU    76      4.014   56.103  119.163  1.00  16.84           HIGL
ATOM    608  CB   LEU    76      3.262   54.777  119.306  1.00  16.53           HIGL
ATOM    609  CG   LEU    76      4.075   53.527  119.631  1.00  17.06           HIGL
ATOM    610  CD1  LEU    76      4.742   53.691  120.997  1.00  16.56           HIGL
ATOM    611  CD2  LEU    76      3.161   52.318  119.620  1.00  15.85           HIGL
ATOM    612  C    LEU    76      5.143   55.949  118.139  1.00  16.79           HIGL
ATOM    613  O    LEU    76      4.914   55.918  116.932  1.00  17.69           HIGL
ATOM    614  N    TYR    77      6.364   55.844  118.648  1.00  15.89           HIGL
ATOM    615  CA   TYR    77      7.560   55.664  117.835  1.00  15.08           HIGL
ATOM    616  CB   TYR    77      8.420   56.938  117.927  1.00  14.34           HIGL
ATOM    617  CG   TYR    77      9.866   56.872  117.435  1.00  14.79           HIGL
ATOM    618  CD1  TYR    77     10.428   55.695  116.925  1.00  13.89           HIGL
ATOM    619  CE1  TYR    77     11.774   55.644  116.552  1.00  14.56           HIGL
ATOM    620  CD2  TYR    77     10.693   57.994  117.547  1.00  15.32           HIGL
ATOM    621  CE2  TYR    77     12.039   57.955  117.179  1.00  14.67           HIGL
ATOM    622  CZ   TYR    77     12.577   56.783  116.688  1.00  15.26           HIGL
ATOM    623  OH   TYR    77     13.920   56.753  116.367  1.00  14.00           HIGL
ATOM    624  C    TYR    77      8.261   54.436  118.440  1.00  15.55           HIGL
ATOM    625  O    TYR    77      8.853   54.507  119.530  1.00  15.30           HIGL
ATOM    626  N    ILE    78      8.147   53.306  117.743  1.00  14.24           HIGL
ATOM    627  CA   ILE    78      8.751   52.051  118.183  1.00  14.13           HIGL
ATOM    628  CB   ILE    78      7.970   50.824  117.639  1.00  14.46           HIGL
ATOM    629  CG2  ILE    78      8.742   49.534  117.930  1.00  14.89           HIGL
ATOM    630  CG1  ILE    78      6.575   50.766  118.276  1.00  14.25           HIGL
ATOM    631  CD1  ILE    78      6.567   50.420  119.761  1.00  12.73           HIGL
ATOM    632  C    ILE    78     10.193   51.991  117.701  1.00  13.40           HIGL
ATOM    633  O    ILE    78     10.467   52.112  116.512  1.00  13.27           HIGL
ATOM    634  N    ASN    79     11.104   51.797  118.646  1.00  13.08           HIGL
ATOM    635  CA   ASN    79     12.533   51.753  118.378  1.00  12.27           HIGL
ATOM    636  CB   ASN    79     13.209   52.771  119.304  1.00  12.87           HIGL
ATOM    637  CG   ASN    79     14.714   52.607  119.393  1.00  12.44           HIGL
ATOM    638  OD1  ASN    79     15.291   52.886  120.435  1.00  12.93           HIGL
ATOM    639  ND2  ASN    79     15.353   52.175  118.311  1.00  12.14           HIGL
ATOM    640  C    ASN    79     13.111   50.354  118.587  1.00  12.54           HIGL
ATOM    641  O    ASN    79     13.453   49.979  119.708  1.00  12.54           HIGL
ATOM    642  N    PHE    80     13.209   49.590  117.501  1.00  12.76           HIGL
ATOM    643  CA   PHE    80     13.752   48.232  117.534  1.00  13.01           HIGL
ATOM    644  CB   PHE    80     13.453   47.486  116.228  1.00  12.75           HIGL
ATOM    645  CG   PHE    80     12.076   46.901  116.154  1.00  13.87           HIGL
ATOM    646  CD1  PHE    80     11.636   45.998  117.120  1.00  13.28           HIGL
ATOM    647  CD2  PHE    80     11.218   47.241  115.114  1.00  12.89           HIGL
ATOM    648  CE1  PHE    80     10.363   45.446  117.054  1.00  11.74           HIGL
ATOM    649  CE2  PHE    80      9.943   46.692  115.043  1.00  13.92           HIGL
```

Fig. 2 cont.

| ATOM | 650 | CZ  | PHE | 80 | 9.517  | 45.792 | 116.019 | 1.00 | 13.02 | HIGL |
| ATOM | 651 | C   | PHE | 80 | 15.259 | 48.253 | 117.690 | 1.00 | 13.33 | HIGL |
| ATOM | 652 | O   | PHE | 80 | 15.937 | 48.944 | 116.940 | 1.00 | 14.29 | HIGL |
| ATOM | 653 | N   | HIS | 81 | 15.784 | 47.499 | 118.649 | 1.00 | 12.98 | HIGL |
| ATOM | 654 | CA  | HIS | 81 | 17.227 | 47.426 | 118.823 | 1.00 | 13.87 | HIGL |
| ATOM | 655 | CB  | HIS | 81 | 17.626 | 47.425 | 120.304 | 1.00 | 13.89 | HIGL |
| ATOM | 656 | CG  | HIS | 81 | 17.633 | 48.782 | 120.933 | 1.00 | 15.21 | HIGL |
| ATOM | 657 | CD2 | HIS | 81 | 16.749 | 49.805 | 120.860 | 1.00 | 15.13 | HIGL |
| ATOM | 658 | ND1 | HIS | 81 | 18.639 | 49.204 | 121.777 | 1.00 | 15.56 | HIGL |
| ATOM | 659 | CE1 | HIS | 81 | 18.375 | 50.429 | 122.196 | 1.00 | 14.49 | HIGL |
| ATOM | 660 | NE2 | HIS | 81 | 17.234 | 50.816 | 121.655 | 1.00 | 15.27 | HIGL |
| ATOM | 661 | C   | HIS | 81 | 17.717 | 46.137 | 118.176 | 1.00 | 13.69 | HIGL |
| ATOM | 662 | O   | HIS | 81 | 18.911 | 45.971 | 117.928 | 1.00 | 14.21 | HIGL |
| ATOM | 663 | N   | TYR | 82 | 16.784 | 45.231 | 117.902 | 1.00 | 13.26 | HIGL |
| ATOM | 664 | CA  | TYR | 82 | 17.105 | 43.939 | 117.299 | 1.00 | 13.09 | HIGL |
| ATOM | 665 | CB  | TYR | 82 | 17.449 | 44.102 | 115.819 | 1.00 | 13.22 | HIGL |
| ATOM | 666 | CG  | TYR | 82 | 16.277 | 44.556 | 114.986 | 1.00 | 13.70 | HIGL |
| ATOM | 667 | CD1 | TYR | 82 | 15.014 | 43.977 | 115.161 | 1.00 | 13.38 | HIGL |
| ATOM | 668 | CE1 | TYR | 82 | 13.939 | 44.348 | 114.378 | 1.00 | 12.96 | HIGL |
| ATOM | 669 | CD2 | TYR | 82 | 16.429 | 45.529 | 114.002 | 1.00 | 12.39 | HIGL |
| ATOM | 670 | CE2 | TYR | 82 | 15.359 | 45.908 | 113.209 | 1.00 | 13.19 | HIGL |
| ATOM | 671 | CZ  | TYR | 82 | 14.114 | 45.310 | 113.400 | 1.00 | 14.02 | HIGL |
| ATOM | 672 | OH  | TYR | 82 | 13.046 | 45.652 | 112.595 | 1.00 | 15.86 | HIGL |
| ATOM | 673 | C   | TYR | 82 | 18.257 | 43.278 | 118.030 | 1.00 | 13.08 | HIGL |
| ATOM | 674 | O   | TYR | 82 | 19.217 | 42.804 | 117.421 | 1.00 | 12.93 | HIGL |
| ATOM | 675 | N   | SER | 83 | 18.137 | 43.256 | 119.352 | 1.00 | 13.03 | HIGL |
| ATOM | 676 | CA  | SER | 83 | 19.132 | 42.668 | 120.227 | 1.00 | 13.56 | HIGL |
| ATOM | 677 | CB  | SER | 83 | 20.266 | 43.671 | 120.439 | 1.00 | 13.70 | HIGL |
| ATOM | 678 | OG  | SER | 83 | 21.309 | 43.114 | 121.210 | 1.00 | 15.51 | HIGL |
| ATOM | 679 | C   | SER | 83 | 18.440 | 42.348 | 121.557 | 1.00 | 14.03 | HIGL |
| ATOM | 680 | O   | SER | 83 | 17.332 | 42.827 | 121.805 | 1.00 | 13.59 | HIGL |
| ATOM | 681 | N   | ASP | 84 | 19.066 | 41.532 | 122.405 | 1.00 | 14.12 | HIGL |
| ATOM | 682 | CA  | ASP | 84 | 18.453 | 41.215 | 123.694 | 1.00 | 14.35 | HIGL |
| ATOM | 683 | CB  | ASP | 84 | 19.025 | 39.927 | 124.294 | 1.00 | 15.38 | HIGL |
| ATOM | 684 | CG  | ASP | 84 | 18.577 | 38.682 | 123.558 | 1.00 | 16.47 | HIGL |
| ATOM | 685 | OD1 | ASP | 84 | 17.543 | 38.736 | 122.856 | 1.00 | 16.36 | HIGL |
| ATOM | 686 | OD2 | ASP | 84 | 19.259 | 37.643 | 123.704 | 1.00 | 17.16 | HIGL |
| ATOM | 687 | C   | ASP | 84 | 18.760 | 42.357 | 124.640 | 1.00 | 13.54 | HIGL |
| ATOM | 688 | O   | ASP | 84 | 18.066 | 42.571 | 125.629 | 1.00 | 12.95 | HIGL |
| ATOM | 689 | N   | THR | 85 | 19.806 | 43.100 | 124.308 | 1.00 | 12.90 | HIGL |
| ATOM | 690 | CA  | THR | 85 | 20.240 | 44.199 | 125.141 | 1.00 | 12.85 | HIGL |
| ATOM | 691 | CB  | THR | 85 | 21.471 | 43.771 | 125.920 | 1.00 | 12.51 | HIGL |
| ATOM | 692 | OG1 | THR | 85 | 21.661 | 44.642 | 127.038 | 1.00 | 14.10 | HIGL |
| ATOM | 693 | CG2 | THR | 85 | 22.685 | 43.810 | 125.013 | 1.00 | 12.87 | HIGL |
| ATOM | 694 | C   | THR | 85 | 20.555 | 45.453 | 124.314 | 1.00 | 12.72 | HIGL |
| ATOM | 695 | O   | THR | 85 | 20.377 | 45.463 | 123.095 | 1.00 | 12.75 | HIGL |
| ATOM | 696 | N   | TRP | 86 | 21.038 | 46.495 | 124.989 | 1.00 | 11.76 | HIGL |
| ATOM | 697 | CA  | TRP | 86 | 21.358 | 47.772 | 124.354 | 1.00 | 10.89 | HIGL |
| ATOM | 698 | CB  | TRP | 86 | 22.198 | 48.651 | 125.276 | 1.00 | 9.89  | HIGL |
| ATOM | 699 | CG  | TRP | 86 | 21.597 | 48.938 | 126.604 | 1.00 | 10.03 | HIGL |
| ATOM | 700 | CD2 | TRP | 86 | 20.629 | 49.947 | 126.908 | 1.00 | 9.39  | HIGL |
| ATOM | 701 | CE2 | TRP | 86 | 20.363 | 49.865 | 128.292 | 1.00 | 8.31  | HIGL |
| ATOM | 702 | CE3 | TRP | 86 | 19.959 | 50.913 | 126.147 | 1.00 | 9.93  | HIGL |
| ATOM | 703 | CD1 | TRP | 86 | 21.870 | 48.302 | 127.781 | 1.00 | 8.33  | HIGL |
| ATOM | 704 | NE1 | TRP | 86 | 21.135 | 48.852 | 128.796 | 1.00 | 7.98  | HIGL |
| ATOM | 705 | CZ2 | TRP | 86 | 19.457 | 50.711 | 128.932 | 1.00 | 7.91  | HIGL |
| ATOM | 706 | CZ3 | TRP | 86 | 19.051 | 51.760 | 126.788 | 1.00 | 9.09  | HIGL |
| ATOM | 707 | CH2 | TRP | 86 | 18.812 | 51.649 | 128.166 | 1.00 | 9.37  | HIGL |
| ATOM | 708 | C   | TRP | 86 | 22.111 | 47.668 | 123.048 | 1.00 | 11.73 | HIGL |
| ATOM | 709 | O   | TRP | 86 | 23.216 | 47.141 | 123.008 | 1.00 | 11.69 | HIGL |
| ATOM | 710 | N   | ALA | 87 | 21.524 | 48.193 | 121.980 | 1.00 | 12.59 | HIGL |
| ATOM | 711 | CA  | ALA | 87 | 22.189 | 48.180 | 120.685 | 1.00 | 12.82 | HIGL |
| ATOM | 712 | CB  | ALA | 87 | 21.246 | 47.706 | 119.603 | 1.00 | 12.18 | HIGL |
| ATOM | 713 | C   | ALA | 87 | 22.665 | 49.594 | 120.381 | 1.00 | 13.67 | HIGL |
| ATOM | 714 | O   | ALA | 87 | 21.912 | 50.553 | 120.532 | 1.00 | 13.58 | HIGL |

Fig. 2 cont.

```
ATOM    715  N    ASP    88      23.929  49.710 119.984  1.00 14.42      HIGL
ATOM    716  CA   ASP    88      24.538  50.984 119.628  1.00 14.58      HIGL
ATOM    717  CB   ASP    88      24.990  51.744 120.889  1.00 14.68      HIGL
ATOM    718  CG   ASP    88      25.901  50.925 121.783  1.00 16.21      HIGL
ATOM    719  OD1  ASP    88      26.827  50.268 121.263  1.00 18.18      HIGL
ATOM    720  OD2  ASP    88      25.701  50.949 123.014  1.00 16.03      HIGL
ATOM    721  C    ASP    88      25.721  50.691 118.690  1.00 15.64      HIGL
ATOM    722  O    ASP    88      26.023  49.529 118.416  1.00 15.14      HIGL
ATOM    723  N    PRO    89      26.408  51.734 118.192  1.00 16.24      HIGL
ATOM    724  CD   PRO    89      26.232  53.163 118.505  1.00 16.14      HIGL
ATOM    725  CA   PRO    89      27.545  51.549 117.280  1.00 16.34      HIGL
ATOM    726  CB   PRO    89      28.119  52.954 117.159  1.00 16.73      HIGL
ATOM    727  CG   PRO    89      26.918  53.823 117.343  1.00 17.24      HIGL
ATOM    728  C    PRO    89      28.607  50.541 117.708  1.00 16.16      HIGL
ATOM    729  O    PRO    89      29.283  49.961 116.871  1.00 15.63      HIGL
ATOM    730  N    ALA    90      28.760  50.326 119.006  1.00 16.46      HIGL
ATOM    731  CA   ALA    90      29.773  49.387 119.462  1.00 16.48      HIGL
ATOM    732  CB   ALA    90      30.596  50.003 120.598  1.00 14.72      HIGL
ATOM    733  C    ALA    90      29.191  48.054 119.899  1.00 16.00      HIGL
ATOM    734  O    ALA    90      29.939  47.143 120.241  1.00 17.19      HIGL
ATOM    735  N    HIS    91      27.867  47.933 119.889  1.00 15.05      HIGL
ATOM    736  CA   HIS    91      27.230  46.680 120.288  1.00 14.58      HIGL
ATOM    737  CB   HIS    91      26.897  46.673 121.785  1.00 15.34      HIGL
ATOM    738  CG   HIS    91      27.967  47.242 122.662  1.00 14.94      HIGL
ATOM    739  CD2  HIS    91      28.755  46.663 123.599  1.00 15.42      HIGL
ATOM    740  ND1  HIS    91      28.296  48.582 122.660  1.00 15.37      HIGL
ATOM    741  CE1  HIS    91      29.237  48.803 123.561  1.00 16.41      HIGL
ATOM    742  NE2  HIS    91      29.534  47.654 124.146  1.00 15.75      HIGL
ATOM    743  C    HIS    91      25.939  46.414 119.518  1.00 14.68      HIGL
ATOM    744  O    HIS    91      24.944  47.123 119.679  1.00 14.01      HIGL
ATOM    745  N    GLN    92      25.968  45.385 118.680  1.00 14.89      HIGL
ATOM    746  CA   GLN    92      24.818  44.974 117.885  1.00 14.67      HIGL
ATOM    747  CB   GLN    92      25.000  45.394 116.421  1.00 13.95      HIGL
ATOM    748  CG   GLN    92      24.928  46.904 116.159  1.00 13.75      HIGL
ATOM    749  CD   GLN    92      23.529  47.497 116.368  1.00 13.63      HIGL
ATOM    750  OE1  GLN    92      22.517  46.899 115.985  1.00 12.06      HIGL
ATOM    751  NE2  GLN    92      23.475  48.685 116.958  1.00 11.96      HIGL
ATOM    752  C    GLN    92      24.786  43.451 118.005  1.00 15.14      HIGL
ATOM    753  O    GLN    92      24.994  42.721 117.033  1.00 14.92      HIGL
ATOM    754  N    THR    93      24.530  42.984 119.222  1.00 15.07      HIGL
ATOM    755  CA   THR    93      24.510  41.561 119.520  1.00 14.27      HIGL
ATOM    756  CB   THR    93      24.672  41.329 121.023  1.00 14.39      HIGL
ATOM    757  OG1  THR    93      25.783  42.100 121.497  1.00 13.20      HIGL
ATOM    758  CG2  THR    93      24.906  39.842 121.315  1.00 12.37      HIGL
ATOM    759  C    THR    93      23.259  40.838 119.070  1.00 15.03      HIGL
ATOM    760  O    THR    93      22.169  41.066 119.600  1.00 15.53      HIGL
ATOM    761  N    THR    94      23.428  39.951 118.097  1.00 14.94      HIGL
ATOM    762  CA   THR    94      22.323  39.162 117.576  1.00 15.30      HIGL
ATOM    763  CB   THR    94      22.818  38.169 116.503  1.00 15.55      HIGL
ATOM    764  OG1  THR    94      23.376  38.893 115.399  1.00 15.22      HIGL
ATOM    765  CG2  THR    94      21.677  37.302 116.013  1.00 15.52      HIGL
ATOM    766  C    THR    94      21.720  38.373 118.732  1.00 15.67      HIGL
ATOM    767  O    THR    94      22.447  37.830 119.563  1.00 15.25      HIGL
ATOM    768  N    PRO    95      20.381  38.309 118.806  1.00 16.47      HIGL
ATOM    769  CD   PRO    95      19.409  38.946 117.901  1.00 16.88      HIGL
ATOM    770  CA   PRO    95      19.695  37.573 119.878  1.00 16.79      HIGL
ATOM    771  CB   PRO    95      18.220  37.690 119.490  1.00 16.02      HIGL
ATOM    772  CG   PRO    95      18.161  38.991 118.754  1.00 16.42      HIGL
ATOM    773  C    PRO    95      20.156  36.119 119.896  1.00 17.32      HIGL
ATOM    774  O    PRO    95      20.230  35.480 118.845  1.00 18.48      HIGL
ATOM    775  N    ALA    96      20.472  35.590 121.073  1.00 17.31      HIGL
ATOM    776  CA   ALA    96      20.903  34.196 121.149  1.00 17.43      HIGL
ATOM    777  CB   ALA    96      21.086  33.769 122.598  1.00 17.13      HIGL
ATOM    778  C    ALA    96      19.821  33.356 120.495  1.00 16.72      HIGL
ATOM    779  O    ALA    96      18.636  33.612 120.693  1.00 15.96      HIGL
```

Fig. 2 cont.

```
ATOM    780  N    GLY    97      20.229  32.371 119.700  1.00 17.32           HIGL
ATOM    781  CA   GLY    97      19.263  31.515 119.031  1.00 17.04           HIGL
ATOM    782  C    GLY    97      19.001  31.856 117.573  1.00 17.23           HIGL
ATOM    783  O    GLY    97      18.675  30.976 116.783  1.00 17.90           HIGL
ATOM    784  N    TRP    98      19.135  33.124 117.205  1.00 16.99           HIGL
ATOM    785  CA   TRP    98      18.907  33.524 115.820  1.00 17.97           HIGL
ATOM    786  CB   TRP    98      18.901  35.051 115.726  1.00 18.18           HIGL
ATOM    787  CG   TRP    98      17.627  35.621 116.258  1.00 18.37           HIGL
ATOM    788  CD2  TRP    98      17.022  36.870 115.907  1.00 18.66           HIGL
ATOM    789  CE2  TRP    98      15.824  36.978 116.650  1.00 18.98           HIGL
ATOM    790  CE3  TRP    98      17.372  37.909 115.036  1.00 18.95           HIGL
ATOM    791  CD1  TRP    98      16.798  35.041 117.175  1.00 18.96           HIGL
ATOM    792  NE1  TRP    98      15.714  35.846 117.415  1.00 19.48           HIGL
ATOM    793  CZ2  TRP    98      14.973  38.083 116.550  1.00 18.24           HIGL
ATOM    794  CZ3  TRP    98      16.521  39.011 114.936  1.00 18.88           HIGL
ATOM    795  CH2  TRP    98      15.336  39.085 115.690  1.00 18.43           HIGL
ATOM    796  C    TRP    98      19.939  32.897 114.877  1.00 17.57           HIGL
ATOM    797  O    TRP    98      21.042  32.569 115.285  1.00 17.56           HIGL
ATOM    798  N    PRO    99      19.577  32.707 113.601  1.00 17.79           HIGL
ATOM    799  CD   PRO    99      18.219  32.889 113.063  1.00 17.38           HIGL
ATOM    800  CA   PRO    99      20.459  32.106 112.594  1.00 17.62           HIGL
ATOM    801  CB   PRO    99      19.578  32.055 111.342  1.00 17.40           HIGL
ATOM    802  CG   PRO    99      18.491  33.041 111.616  1.00 18.07           HIGL
ATOM    803  C    PRO    99      21.842  32.693 112.326  1.00 17.38           HIGL
ATOM    804  O    PRO    99      22.147  33.820 112.709  1.00 17.86           HIGL
ATOM    805  N    SER   100      22.670  31.887 111.660  1.00 17.52           HIGL
ATOM    806  CA   SER   100      24.045  32.240 111.323  1.00 16.92           HIGL
ATOM    807  CB   SER   100      24.992  31.142 111.793  1.00 16.67           HIGL
ATOM    808  OG   SER   100      24.564  30.601 113.025  1.00 20.79           HIGL
ATOM    809  C    SER   100      24.283  32.452 109.833  1.00 16.73           HIGL
ATOM    810  O    SER   100      25.419  32.675 109.423  1.00 17.27           HIGL
ATOM    811  N    ASP   101      23.247  32.336 109.012  1.00 16.22           HIGL
ATOM    812  CA   ASP   101      23.422  32.564 107.579  1.00 16.38           HIGL
ATOM    813  CB   ASP   101      23.121  31.303 106.751  1.00 16.22           HIGL
ATOM    814  CG   ASP   101      21.708  30.805 106.929  1.00 15.46           HIGL
ATOM    815  OD1  ASP   101      21.423  30.151 107.950  1.00 16.82           HIGL
ATOM    816  OD2  ASP   101      20.877  31.073 106.047  1.00 16.15           HIGL
ATOM    817  C    ASP   101      22.494  33.707 107.201  1.00 16.52           HIGL
ATOM    818  O    ASP   101      21.387  33.825 107.736  1.00 16.54           HIGL
ATOM    819  N    ILE   102      22.957  34.545 106.280  1.00 15.85           HIGL
ATOM    820  CA   ILE   102      22.220  35.727 105.871  1.00 15.30           HIGL
ATOM    821  CB   ILE   102      22.958  36.484 104.746  1.00 14.62           HIGL
ATOM    822  CG2  ILE   102      22.862  35.709 103.433  1.00 14.59           HIGL
ATOM    823  CG1  ILE   102      22.361  37.884 104.594  1.00 13.26           HIGL
ATOM    824  CD1  ILE   102      22.438  38.731 105.856  1.00 10.57           HIGL
ATOM    825  C    ILE   102      20.779  35.519 105.452  1.00 16.31           HIGL
ATOM    826  O    ILE   102      19.929  36.365 105.739  1.00 17.53           HIGL
ATOM    827  N    ASN   103      20.486  34.409 104.784  1.00 15.84           HIGL
ATOM    828  CA   ASN   103      19.118  34.174 104.347  1.00 15.26           HIGL
ATOM    829  CB   ASN   103      19.056  33.026 103.345  1.00 16.44           HIGL
ATOM    830  CG   ASN   103      17.643  32.754 102.881  1.00 17.90           HIGL
ATOM    831  OD1  ASN   103      17.012  33.606 102.251  1.00 17.31           HIGL
ATOM    832  ND2  ASN   103      17.128  31.568 103.207  1.00 18.73           HIGL
ATOM    833  C    ASN   103      18.195  33.872 105.520  1.00 14.76           HIGL
ATOM    834  O    ASN   103      17.081  34.390 105.592  1.00 14.43           HIGL
ATOM    835  N    ASN   104      18.655  33.029 106.437  1.00 14.10           HIGL
ATOM    836  CA   ASN   104      17.849  32.684 107.598  1.00 13.79           HIGL
ATOM    837  CB   ASN   104      18.391  31.424 108.277  1.00 13.76           HIGL
ATOM    838  CG   ASN   104      17.923  30.149 107.594  1.00 14.35           HIGL
ATOM    839  OD1  ASN   104      16.738  30.006 107.264  1.00 13.83           HIGL
ATOM    840  ND2  ASN   104      18.843  29.212 107.392  1.00 11.49           HIGL
ATOM    841  C    ASN   104      17.766  33.822 108.603  1.00 13.46           HIGL
ATOM    842  O    ASN   104      16.706  34.066 109.169  1.00 13.67           HIGL
ATOM    843  N    LEU   105      18.875  34.522 108.824  1.00 13.84           HIGL
ATOM    844  CA   LEU   105      18.885  35.640 109.762  1.00 14.45           HIGL
```

Fig. 2 cont.

| | | | | | | | | |
|---|---|---|---|---|---|---|---|---|
| ATOM | 845 | CB | LEU | 105 | 20.282 | 36.256 | 109.855 | 1.00 14.35 | HIGL |
| ATOM | 846 | CG | LEU | 105 | 20.373 | 37.492 | 110.754 | 1.00 15.28 | HIGL |
| ATOM | 847 | CD1 | LEU | 105 | 19.941 | 37.133 | 112.168 | 1.00 14.98 | HIGL |
| ATOM | 848 | CD2 | LEU | 105 | 21.791 | 38.025 | 110.756 | 1.00 15.43 | HIGL |
| ATOM | 849 | C | LEU | 105 | 17.891 | 36.694 | 109.291 | 1.00 15.25 | HIGL |
| ATOM | 850 | O | LEU | 105 | 17.087 | 37.204 | 110.074 | 1.00 14.19 | HIGL |
| ATOM | 851 | N | ALA | 106 | 17.956 | 37.009 | 108.000 | 1.00 15.85 | HIGL |
| ATOM | 852 | CA | ALA | 106 | 17.067 | 37.990 | 107.399 | 1.00 17.40 | HIGL |
| ATOM | 853 | CB | ALA | 106 | 17.417 | 38.177 | 105.916 | 1.00 15.61 | HIGL |
| ATOM | 854 | C | ALA | 106 | 15.618 | 37.532 | 107.548 | 1.00 18.34 | HIGL |
| ATOM | 855 | O | ALA | 106 | 14.730 | 38.326 | 107.859 | 1.00 19.25 | HIGL |
| ATOM | 856 | N | TRP | 107 | 15.390 | 36.245 | 107.320 | 1.00 19.52 | HIGL |
| ATOM | 857 | CA | TRP | 107 | 14.060 | 35.663 | 107.430 | 1.00 20.70 | HIGL |
| ATOM | 858 | CB | TRP | 107 | 14.140 | 34.177 | 107.104 | 1.00 22.69 | HIGL |
| ATOM | 859 | CG | TRP | 107 | 12.847 | 33.566 | 106.709 | 1.00 26.10 | HIGL |
| ATOM | 860 | CD2 | TRP | 107 | 12.607 | 32.179 | 106.453 | 1.00 27.36 | HIGL |
| ATOM | 861 | CE2 | TRP | 107 | 11.256 | 32.056 | 106.055 | 1.00 28.11 | HIGL |
| ATOM | 862 | CE3 | TRP | 107 | 13.404 | 31.028 | 106.517 | 1.00 27.84 | HIGL |
| ATOM | 863 | CD1 | TRP | 107 | 11.665 | 34.212 | 106.466 | 1.00 26.98 | HIGL |
| ATOM | 864 | NE1 | TRP | 107 | 10.705 | 33.310 | 106.072 | 1.00 27.36 | HIGL |
| ATOM | 865 | CZ2 | TRP | 107 | 10.683 | 30.821 | 105.720 | 1.00 28.94 | HIGL |
| ATOM | 866 | CZ3 | TRP | 107 | 12.836 | 29.804 | 106.184 | 1.00 28.94 | HIGL |
| ATOM | 867 | CH2 | TRP | 107 | 11.487 | 29.711 | 105.790 | 1.00 28.79 | HIGL |
| ATOM | 868 | C | TRP | 107 | 13.567 | 35.862 | 108.862 | 1.00 20.80 | HIGL |
| ATOM | 869 | O | TRP | 107 | 12.428 | 36.280 | 109.097 | 1.00 19.49 | HIGL |
| ATOM | 870 | N | LYS | 108 | 14.453 | 35.567 | 109.812 | 1.00 20.81 | HIGL |
| ATOM | 871 | CA | LYS | 108 | 14.158 | 35.707 | 111.231 | 1.00 20.77 | HIGL |
| ATOM | 872 | CB | LYS | 108 | 15.358 | 35.255 | 112.070 | 1.00 21.15 | HIGL |
| ATOM | 873 | CG | LYS | 108 | 15.018 | 34.250 | 113.161 | 1.00 22.88 | HIGL |
| ATOM | 874 | CD | LYS | 108 | 13.942 | 34.770 | 114.100 | 1.00 23.37 | HIGL |
| ATOM | 875 | CE | LYS | 108 | 13.525 | 33.698 | 115.088 | 1.00 23.83 | HIGL |
| ATOM | 876 | NZ | LYS | 108 | 12.322 | 34.107 | 115.853 | 1.00 24.90 | HIGL |
| ATOM | 877 | C | LYS | 108 | 13.830 | 37.161 | 111.554 | 1.00 19.90 | HIGL |
| ATOM | 878 | O | LYS | 108 | 12.836 | 37.450 | 112.214 | 1.00 20.08 | HIGL |
| ATOM | 879 | N | LEU | 109 | 14.674 | 38.074 | 111.094 | 1.00 19.75 | HIGL |
| ATOM | 880 | CA | LEU | 109 | 14.445 | 39.488 | 111.344 | 1.00 19.93 | HIGL |
| ATOM | 881 | CB | LEU | 109 | 15.508 | 40.337 | 110.654 | 1.00 17.82 | HIGL |
| ATOM | 882 | CG | LEU | 109 | 15.390 | 41.827 | 110.968 | 1.00 17.82 | HIGL |
| ATOM | 883 | CD1 | LEU | 109 | 15.672 | 42.054 | 112.449 | 1.00 16.38 | HIGL |
| ATOM | 884 | CD2 | LEU | 109 | 16.368 | 42.620 | 110.103 | 1.00 16.81 | HIGL |
| ATOM | 885 | C | LEU | 109 | 13.063 | 39.861 | 110.822 | 1.00 20.34 | HIGL |
| ATOM | 886 | O | LEU | 109 | 12.362 | 40.679 | 111.423 | 1.00 20.28 | HIGL |
| ATOM | 887 | N | TYR | 110 | 12.679 | 39.247 | 109.704 | 1.00 20.51 | HIGL |
| ATOM | 888 | CA | TYR | 110 | 11.377 | 39.489 | 109.100 | 1.00 20.92 | HIGL |
| ATOM | 889 | CB | TYR | 110 | 11.309 | 38.862 | 107.704 | 1.00 21.24 | HIGL |
| ATOM | 890 | CG | TYR | 110 | 9.918 | 38.842 | 107.101 | 1.00 21.40 | HIGL |
| ATOM | 891 | CD1 | TYR | 110 | 9.064 | 37.757 | 107.292 | 1.00 22.61 | HIGL |
| ATOM | 892 | CE1 | TYR | 110 | 7.771 | 37.748 | 106.754 | 1.00 22.76 | HIGL |
| ATOM | 893 | CD2 | TYR | 110 | 9.445 | 39.922 | 106.358 | 1.00 23.16 | HIGL |
| ATOM | 894 | CE2 | TYR | 110 | 8.155 | 39.926 | 105.817 | 1.00 22.90 | HIGL |
| ATOM | 895 | CZ | TYR | 110 | 7.325 | 38.838 | 106.018 | 1.00 23.09 | HIGL |
| ATOM | 896 | OH | TYR | 110 | 6.056 | 38.849 | 105.482 | 1.00 22.70 | HIGL |
| ATOM | 897 | C | TYR | 110 | 10.249 | 38.938 | 109.972 | 1.00 21.45 | HIGL |
| ATOM | 898 | O | TYR | 110 | 9.312 | 39.671 | 110.303 | 1.00 22.10 | HIGL |
| ATOM | 899 | N | ASN | 111 | 10.326 | 37.659 | 110.344 | 1.00 20.73 | HIGL |
| ATOM | 900 | CA | ASN | 111 | 9.281 | 37.073 | 111.182 | 1.00 20.87 | HIGL |
| ATOM | 901 | CB | ASN | 111 | 9.589 | 35.619 | 111.546 | 1.00 23.22 | HIGL |
| ATOM | 902 | CG | ASN | 111 | 9.612 | 34.699 | 110.348 | 1.00 26.49 | HIGL |
| ATOM | 903 | OD1 | ASN | 111 | 9.040 | 35.005 | 109.301 | 1.00 27.21 | HIGL |
| ATOM | 904 | ND2 | ASN | 111 | 10.265 | 33.552 | 110.516 | 1.00 29.16 | HIGL |
| ATOM | 905 | C | ASN | 111 | 9.147 | 37.864 | 112.474 | 1.00 19.60 | HIGL |
| ATOM | 906 | O | ASN | 111 | 8.039 | 38.190 | 112.905 | 1.00 19.02 | HIGL |
| ATOM | 907 | N | TYR | 112 | 10.288 | 38.169 | 113.084 | 1.00 18.21 | HIGL |
| ATOM | 908 | CA | TYR | 112 | 10.310 | 38.905 | 114.337 | 1.00 16.83 | HIGL |
| ATOM | 909 | CB | TYR | 112 | 11.751 | 39.129 | 114.810 | 1.00 16.36 | HIGL |

Fig. 2 cont.

```
ATOM    910  CG   TYR   112      11.839  40.071 115.991  1.00 14.95      HIGL
ATOM    911  CD1  TYR   112      11.369  39.691 117.245  1.00 15.11      HIGL
ATOM    912  CE1  TYR   112      11.369  40.581 118.316  1.00 14.94      HIGL
ATOM    913  CD2  TYR   112      12.319  41.366 115.836  1.00 14.45      HIGL
ATOM    914  CE2  TYR   112      12.323  42.264 116.897  1.00 14.83      HIGL
ATOM    915  CZ   TYR   112      11.847  41.866 118.133  1.00 14.96      HIGL
ATOM    916  OH   TYR   112      11.848  42.754 119.182  1.00 15.27      HIGL
ATOM    917  C    TYR   112       9.601  40.243 114.224  1.00 16.36      HIGL
ATOM    918  O    TYR   112       8.686  40.534 114.999  1.00 15.41      HIGL
ATOM    919  N    THR   113      10.034  41.056 113.265  1.00 16.21      HIGL
ATOM    920  CA   THR   113       9.443  42.369 113.058  1.00 15.87      HIGL
ATOM    921  CB   THR   113      10.142  43.125 111.922  1.00 16.16      HIGL
ATOM    922  OG1  THR   113      11.537  43.252 112.221  1.00 15.12      HIGL
ATOM    923  CG2  THR   113       9.537  44.515 111.758  1.00 15.98      HIGL
ATOM    924  C    THR   113       7.973  42.216 112.717  1.00 16.24      HIGL
ATOM    925  O    THR   113       7.124  42.896 113.290  1.00 16.57      HIGL
ATOM    926  N    LEU   114       7.678  41.307 111.790  1.00 16.92      HIGL
ATOM    927  CA   LEU   114       6.304  41.043 111.366  1.00 16.65      HIGL
ATOM    928  CB   LEU   114       6.264  39.849 110.411  1.00 15.97      HIGL
ATOM    929  CG   LEU   114       4.861  39.423 109.964  1.00 16.54      HIGL
ATOM    930  CD1  LEU   114       4.220  40.543 109.154  1.00 15.93      HIGL
ATOM    931  CD2  LEU   114       4.948  38.144 109.146  1.00 14.91      HIGL
ATOM    932  C    LEU   114       5.404  40.754 112.565  1.00 16.56      HIGL
ATOM    933  O    LEU   114       4.420  41.450 112.799  1.00 16.01      HIGL
ATOM    934  N    ASP   115       5.749  39.720 113.320  1.00 16.95      HIGL
ATOM    935  CA   ASP   115       4.967  39.347 114.484  1.00 17.44      HIGL
ATOM    936  CB   ASP   115       5.562  38.104 115.139  1.00 18.68      HIGL
ATOM    937  CG   ASP   115       5.489  36.884 114.235  1.00 20.91      HIGL
ATOM    938  OD1  ASP   115       4.994  37.019 113.095  1.00 20.18      HIGL
ATOM    939  OD2  ASP   115       5.928  35.789 114.658  1.00 22.87      HIGL
ATOM    940  C    ASP   115       4.879  40.481 115.491  1.00 17.05      HIGL
ATOM    941  O    ASP   115       3.813  40.732 116.048  1.00 16.42      HIGL
ATOM    942  N    SER   116       5.990  41.174 115.713  1.00 16.71      HIGL
ATOM    943  CA   SER   116       6.005  42.279 116.660  1.00 17.19      HIGL
ATOM    944  CB   SER   116       7.409  42.869 116.774  1.00 17.37      HIGL
ATOM    945  OG   SER   116       8.307  41.969 117.391  1.00 17.53      HIGL
ATOM    946  C    SER   116       5.023  43.381 116.262  1.00 18.12      HIGL
ATOM    947  O    SER   116       4.231  43.847 117.084  1.00 17.59      HIGL
ATOM    948  N    MET   117       5.080  43.812 115.008  1.00 18.86      HIGL
ATOM    949  CA   MET   117       4.176  44.856 114.552  1.00 19.77      HIGL
ATOM    950  CB   MET   117       4.525  45.262 113.125  1.00 19.25      HIGL
ATOM    951  CG   MET   117       5.862  45.989 113.006  1.00 18.96      HIGL
ATOM    952  SD   MET   117       5.846  47.687 113.654  1.00 20.56      HIGL
ATOM    953  CE   MET   117       6.173  47.395 115.398  1.00 20.80      HIGL
ATOM    954  C    MET   117       2.729  44.384 114.641  1.00 20.69      HIGL
ATOM    955  O    MET   117       1.843  45.134 115.056  1.00 19.86      HIGL
ATOM    956  N    ASN   118       2.488  43.132 114.266  1.00 22.17      HIGL
ATOM    957  CA   ASN   118       1.137  42.589 114.327  1.00 23.55      HIGL
ATOM    958  CB   ASN   118       1.081  41.192 113.704  1.00 22.99      HIGL
ATOM    959  CG   ASN   118       0.966  41.236 112.197  1.00 24.24      HIGL
ATOM    960  OD1  ASN   118       0.231  42.054 111.648  1.00 24.38      HIGL
ATOM    961  ND2  ASN   118       1.680  40.345 111.516  1.00 25.71      HIGL
ATOM    962  C    ASN   118       0.665  42.536 115.772  1.00 24.12      HIGL
ATOM    963  O    ASN   118      -0.532  42.535 116.054  1.00 24.65      HIGL
ATOM    964  N    ARG   119       1.617  42.501 116.691  1.00 25.04      HIGL
ATOM    965  CA   ARG   119       1.289  42.457 118.104  1.00 25.97      HIGL
ATOM    966  CB   ARG   119       2.564  42.289 118.916  1.00 27.25      HIGL
ATOM    967  CG   ARG   119       2.324  41.905 120.343  1.00 30.86      HIGL
ATOM    968  CD   ARG   119       1.727  40.518 120.464  1.00 32.19      HIGL
ATOM    969  NE   ARG   119       1.381  40.252 121.856  1.00 35.20      HIGL
ATOM    970  CZ   ARG   119       2.266  40.036 122.826  1.00 35.79      HIGL
ATOM    971  NH1  ARG   119       3.566  40.038 122.564  1.00 35.68      HIGL
ATOM    972  NH2  ARG   119       1.845  39.846 124.070  1.00 37.32      HIGL
ATOM    973  C    ARG   119       0.572  43.755 118.483  1.00 26.06      HIGL
ATOM    974  O    ARG   119      -0.406  43.744 119.234  1.00 26.17      HIGL
```

Fig. 2 cont.

```
ATOM    975  N    PHE 120      1.058  44.874 117.952  1.00 25.97      HIGL
ATOM    976  CA   PHE 120      0.438  46.166 118.218  1.00 25.91      HIGL
ATOM    977  CB   PHE 120      1.369  47.312 117.811  1.00 24.71      HIGL
ATOM    978  CG   PHE 120      2.516  47.519 118.748  1.00 23.82      HIGL
ATOM    979  CD1  PHE 120      3.748  46.923 118.508  1.00 24.05      HIGL
ATOM    980  CD2  PHE 120      2.356  48.289 119.892  1.00 23.49      HIGL
ATOM    981  CE1  PHE 120      4.806  47.088 119.396  1.00 23.14      HIGL
ATOM    982  CE2  PHE 120      3.407  48.461 120.788  1.00 23.31      HIGL
ATOM    983  CZ   PHE 120      4.632  47.860 120.540  1.00 23.49      HIGL
ATOM    984  C    PHE 120     -0.879  46.283 117.452  1.00 26.35      HIGL
ATOM    985  O    PHE 120     -1.879  46.758 117.988  1.00 26.78      HIGL
ATOM    986  N    ALA 121     -0.870  45.844 116.198  1.00 26.40      HIGL
ATOM    987  CA   ALA 121     -2.058  45.891 115.357  1.00 26.80      HIGL
ATOM    988  CB   ALA 121     -1.755  45.280 114.003  1.00 27.18      HIGL
ATOM    989  C    ALA 121     -3.211  45.143 116.016  1.00 27.34      HIGL
ATOM    990  O    ALA 121     -4.314  45.674 116.152  1.00 27.77      HIGL
ATOM    991  N    ASP 122     -2.948  43.905 116.423  1.00 26.89      HIGL
ATOM    992  CA   ASP 122     -3.965  43.084 117.063  1.00 26.21      HIGL
ATOM    993  CB   ASP 122     -3.436  41.665 117.303  1.00 25.67      HIGL
ATOM    994  CG   ASP 122     -3.074  40.950 116.012  1.00 25.38      HIGL
ATOM    995  OD1  ASP 122     -3.544  41.379 114.929  1.00 24.57      HIGL
ATOM    996  OD2  ASP 122     -2.328  39.950 116.089  1.00 24.15      HIGL
ATOM    997  C    ASP 122     -4.414  43.686 118.389  1.00 26.13      HIGL
ATOM    998  O    ASP 122     -5.549  43.478 118.822  1.00 26.95      HIGL
ATOM    999  N    ALA 123     -3.517  44.427 119.033  1.00 24.90      HIGL
ATOM   1000  CA   ALA 123     -3.821  45.053 120.308  1.00 22.75      HIGL
ATOM   1001  CB   ALA 123     -2.548  45.330 121.058  1.00 23.23      HIGL
ATOM   1002  C    ALA 123     -4.595  46.344 120.102  1.00 22.12      HIGL
ATOM   1003  O    ALA 123     -5.085  46.935 121.058  1.00 22.33      HIGL
ATOM   1004  N    GLY 124     -4.704  46.778 118.850  1.00 21.85      HIGL
ATOM   1005  CA   GLY 124     -5.424  48.002 118.548  1.00 21.93      HIGL
ATOM   1006  C    GLY 124     -4.604  49.253 118.809  1.00 22.90      HIGL
ATOM   1007  O    GLY 124     -5.150  50.350 118.957  1.00 22.21      HIGL
ATOM   1008  N    ILE 125     -3.286  49.078 118.876  1.00 23.51      HIGL
ATOM   1009  CA   ILE 125     -2.352  50.174 119.113  1.00 23.71      HIGL
ATOM   1010  CB   ILE 125     -1.132  49.706 119.949  1.00 24.28      HIGL
ATOM   1011  CG2  ILE 125     -0.171  50.871 120.153  1.00 22.68      HIGL
ATOM   1012  CG1  ILE 125     -1.587  49.094 121.283  1.00 24.08      HIGL
ATOM   1013  CD1  ILE 125     -2.168  50.078 122.258  1.00 24.75      HIGL
ATOM   1014  C    ILE 125     -1.817  50.648 117.765  1.00 24.07      HIGL
ATOM   1015  O    ILE 125     -1.416  49.837 116.939  1.00 24.23      HIGL
ATOM   1016  N    GLN 126     -1.805  51.952 117.533  1.00 24.42      HIGL
ATOM   1017  CA   GLN 126     -1.282  52.451 116.274  1.00 25.40      HIGL
ATOM   1018  CB   GLN 126     -2.112  53.631 115.766  1.00 26.92      HIGL
ATOM   1019  CG   GLN 126     -1.591  54.243 114.464  1.00 29.76      HIGL
ATOM   1020  CD   GLN 126     -1.473  53.223 113.329  1.00 32.33      HIGL
ATOM   1021  OE1  GLN 126     -2.456  52.570 112.953  1.00 33.86      HIGL
ATOM   1022  NE2  GLN 126     -0.267  53.086 112.777  1.00 31.82      HIGL
ATOM   1023  C    GLN 126      0.174  52.883 116.424  1.00 25.09      HIGL
ATOM   1024  O    GLN 126      0.494  53.731 117.260  1.00 25.29      HIGL
ATOM   1025  N    VAL 127      1.046  52.280 115.617  1.00 23.64      HIGL
ATOM   1026  CA   VAL 127      2.465  52.605 115.614  1.00 21.87      HIGL
ATOM   1027  CB   VAL 127      3.329  51.373 115.255  1.00 21.30      HIGL
ATOM   1028  CG1  VAL 127      4.800  51.730 115.338  1.00 20.09      HIGL
ATOM   1029  CG2  VAL 127      3.010  50.217 116.184  1.00 20.69      HIGL
ATOM   1030  C    VAL 127      2.635  53.658 114.526  1.00 21.93      HIGL
ATOM   1031  O    VAL 127      2.268  53.427 113.378  1.00 22.89      HIGL
ATOM   1032  N    ASP 128      3.192  54.809 114.882  1.00 21.66      HIGL
ATOM   1033  CA   ASP 128      3.378  55.896 113.927  1.00 21.09      HIGL
ATOM   1034  CB   ASP 128      3.080  57.211 114.628  1.00 21.65      HIGL
ATOM   1035  CG   ASP 128      1.662  57.260 115.145  1.00 22.08      HIGL
ATOM   1036  OD1  ASP 128      0.744  57.299 114.301  1.00 23.35      HIGL
ATOM   1037  OD2  ASP 128      1.458  57.231 116.380  1.00 22.69      HIGL
ATOM   1038  C    ASP 128      4.746  55.932 113.256  1.00 21.00      HIGL
ATOM   1039  O    ASP 128      4.854  56.276 112.077  1.00 20.64      HIGL
```

Fig. 2 cont.

| | | | | | | | | | |
|---|---|---|---|---|---|---|---|---|---|
| ATOM | 1040 | N | ILE | 129 | 5.786 | 55.587 | 114.010 | 1.00 19.93 | HIGL |
| ATOM | 1041 | CA | ILE | 129 | 7.139 | 55.535 | 113.472 | 1.00 18.94 | HIGL |
| ATOM | 1042 | CB | ILE | 129 | 7.999 | 56.721 | 113.927 | 1.00 17.89 | HIGL |
| ATOM | 1043 | CG2 | ILE | 129 | 9.425 | 56.533 | 113.444 | 1.00 16.07 | HIGL |
| ATOM | 1044 | CG1 | ILE | 129 | 7.440 | 58.027 | 113.375 | 1.00 17.25 | HIGL |
| ATOM | 1045 | CD1 | ILE | 129 | 8.207 | 59.241 | 113.843 | 1.00 16.76 | HIGL |
| ATOM | 1046 | C | ILE | 129 | 7.808 | 54.267 | 113.985 | 1.00 19.57 | HIGL |
| ATOM | 1047 | O | ILE | 129 | 7.591 | 53.867 | 115.130 | 1.00 20.12 | HIGL |
| ATOM | 1048 | N | VAL | 130 | 8.614 | 53.640 | 113.133 | 1.00 19.09 | HIGL |
| ATOM | 1049 | CA | VAL | 130 | 9.343 | 52.430 | 113.497 | 1.00 18.61 | HIGL |
| ATOM | 1050 | CB | VAL | 130 | 8.734 | 51.154 | 112.868 | 1.00 19.46 | HIGL |
| ATOM | 1051 | CG1 | VAL | 130 | 9.424 | 49.923 | 113.431 | 1.00 18.88 | HIGL |
| ATOM | 1052 | CG2 | VAL | 130 | 7.255 | 51.087 | 113.133 | 1.00 21.50 | HIGL |
| ATOM | 1053 | C | VAL | 130 | 10.762 | 52.531 | 112.962 | 1.00 17.57 | HIGL |
| ATOM | 1054 | O | VAL | 130 | 10.962 | 52.707 | 111.759 | 1.00 17.98 | HIGL |
| ATOM | 1055 | N | SER | 131 | 11.749 | 52.439 | 113.843 | 1.00 15.84 | HIGL |
| ATOM | 1056 | CA | SER | 131 | 13.127 | 52.470 | 113.377 | 1.00 14.70 | HIGL |
| ATOM | 1057 | CB | SER | 131 | 14.038 | 53.282 | 114.314 | 1.00 15.28 | HIGL |
| ATOM | 1058 | OG | SER | 131 | 14.319 | 52.589 | 115.514 | 1.00 18.11 | HIGL |
| ATOM | 1059 | C | SER | 131 | 13.565 | 51.018 | 113.345 | 1.00 12.96 | HIGL |
| ATOM | 1060 | O | SER | 131 | 13.436 | 50.299 | 114.335 | 1.00 11.68 | HIGL |
| ATOM | 1061 | N | ILE | 132 | 14.039 | 50.572 | 112.191 | 1.00 10.75 | HIGL |
| ATOM | 1062 | CA | ILE | 132 | 14.492 | 49.207 | 112.073 | 1.00 10.19 | HIGL |
| ATOM | 1063 | CB | ILE | 132 | 14.319 | 48.707 | 110.632 | 1.00 10.00 | HIGL |
| ATOM | 1064 | CG2 | ILE | 132 | 12.858 | 48.371 | 110.380 | 1.00 9.71 | HIGL |
| ATOM | 1065 | CG1 | ILE | 132 | 14.785 | 49.781 | 109.646 | 1.00 10.09 | HIGL |
| ATOM | 1066 | CD1 | ILE | 132 | 14.716 | 49.350 | 108.198 | 1.00 10.00 | HIGL |
| ATOM | 1067 | C | ILE | 132 | 15.954 | 49.155 | 112.508 | 1.00 10.16 | HIGL |
| ATOM | 1068 | O | ILE | 132 | 16.869 | 49.045 | 111.693 | 1.00 9.89 | HIGL |
| ATOM | 1069 | N | GLY | 133 | 16.160 | 49.253 | 113.814 | 1.00 9.99 | HIGL |
| ATOM | 1070 | CA | GLY | 133 | 17.500 | 49.230 | 114.364 | 1.00 10.91 | HIGL |
| ATOM | 1071 | C | GLY | 133 | 17.711 | 50.461 | 115.220 | 1.00 11.73 | HIGL |
| ATOM | 1072 | O | GLY | 133 | 16.885 | 51.378 | 115.193 | 1.00 11.22 | HIGL |
| ATOM | 1073 | N | ASN | 134 | 18.804 | 50.482 | 115.983 | 1.00 11.81 | HIGL |
| ATOM | 1074 | CA | ASN | 134 | 19.119 | 51.621 | 116.843 | 1.00 11.67 | HIGL |
| ATOM | 1075 | CB | ASN | 134 | 18.878 | 51.271 | 118.307 | 1.00 11.03 | HIGL |
| ATOM | 1076 | CG | ASN | 134 | 19.010 | 52.481 | 119.217 | 1.00 11.61 | HIGL |
| ATOM | 1077 | OD1 | ASN | 134 | 18.116 | 53.328 | 119.269 | 1.00 9.26 | HIGL |
| ATOM | 1078 | ND2 | ASN | 134 | 20.140 | 52.579 | 119.923 | 1.00 10.03 | HIGL |
| ATOM | 1079 | C | ASN | 134 | 20.578 | 52.041 | 116.673 | 1.00 12.23 | HIGL |
| ATOM | 1080 | O | ASN | 134 | 21.488 | 51.299 | 117.047 | 1.00 12.50 | HIGL |
| ATOM | 1081 | N | GLU | 135 | 20.796 | 53.237 | 116.130 | 1.00 12.34 | HIGL |
| ATOM | 1082 | CA | GLU | 135 | 22.148 | 53.745 | 115.905 | 1.00 12.34 | HIGL |
| ATOM | 1083 | CB | GLU | 135 | 22.819 | 54.137 | 117.233 | 1.00 12.86 | HIGL |
| ATOM | 1084 | CG | GLU | 135 | 22.107 | 55.229 | 118.021 | 1.00 13.57 | HIGL |
| ATOM | 1085 | CD | GLU | 135 | 22.988 | 55.855 | 119.109 | 1.00 14.70 | HIGL |
| ATOM | 1086 | OE1 | GLU | 135 | 23.605 | 55.107 | 119.895 | 1.00 13.98 | HIGL |
| ATOM | 1087 | OE2 | GLU | 135 | 23.059 | 57.100 | 119.186 | 1.00 14.17 | HIGL |
| ATOM | 1088 | C | GLU | 135 | 22.980 | 52.662 | 115.217 | 1.00 11.83 | HIGL |
| ATOM | 1089 | O | GLU | 135 | 24.062 | 52.307 | 115.689 | 1.00 11.40 | HIGL |
| ATOM | 1090 | N | ILE | 136 | 22.464 | 52.139 | 114.107 | 1.00 11.55 | HIGL |
| ATOM | 1091 | CA | ILE | 136 | 23.145 | 51.086 | 113.366 | 1.00 12.33 | HIGL |
| ATOM | 1092 | CB | ILE | 136 | 22.134 | 50.255 | 112.537 | 1.00 11.21 | HIGL |
| ATOM | 1093 | CG2 | ILE | 136 | 21.187 | 49.523 | 113.478 | 1.00 11.90 | HIGL |
| ATOM | 1094 | CG1 | ILE | 136 | 21.346 | 51.166 | 111.583 | 1.00 10.88 | HIGL |
| ATOM | 1095 | CD1 | ILE | 136 | 20.307 | 50.439 | 110.712 | 1.00 5.41 | HIGL |
| ATOM | 1096 | C | ILE | 136 | 24.272 | 51.570 | 112.446 | 1.00 13.31 | HIGL |
| ATOM | 1097 | O | ILE | 136 | 24.512 | 50.981 | 111.397 | 1.00 13.57 | HIGL |
| ATOM | 1098 | N | THR | 137 | 24.978 | 52.621 | 112.860 | 1.00 14.02 | HIGL |
| ATOM | 1099 | CA | THR | 137 | 26.076 | 53.177 | 112.073 | 1.00 15.42 | HIGL |
| ATOM | 1100 | CB | THR | 137 | 26.796 | 54.290 | 112.828 | 1.00 15.31 | HIGL |
| ATOM | 1101 | OG1 | THR | 137 | 25.835 | 55.190 | 113.390 | 1.00 15.48 | HIGL |
| ATOM | 1102 | CG2 | THR | 137 | 27.705 | 55.043 | 111.887 | 1.00 13.55 | HIGL |
| ATOM | 1103 | C | THR | 137 | 27.128 | 52.139 | 111.688 | 1.00 16.83 | HIGL |
| ATOM | 1104 | O | THR | 137 | 27.690 | 52.197 | 110.595 | 1.00 17.91 | HIGL |

Fig. 2 cont.

```
ATOM   1105  N    GLN   138      27.421  51.214 112.596  1.00 17.23      HIGL
ATOM   1106  CA   GLN   138      28.396  50.166 112.308  1.00 17.23      HIGL
ATOM   1107  CB   GLN   138      29.328  49.926 113.503  1.00 18.55      HIGL
ATOM   1108  CG   GLN   138      30.240  51.101 113.856  1.00 22.06      HIGL
ATOM   1109  CD   GLN   138      30.963  51.687 112.642  1.00 24.27      HIGL
ATOM   1110  OE1  GLN   138      31.641  50.975 111.897  1.00 24.26      HIGL
ATOM   1111  NE2  GLN   138      30.821  52.997 112.445  1.00 24.87      HIGL
ATOM   1112  C    GLN   138      27.633  48.886 111.985  1.00 16.30      HIGL
ATOM   1113  O    GLN   138      28.133  47.774 112.187  1.00 15.80      HIGL
ATOM   1114  N    GLY   139      26.411  49.059 111.490  1.00 14.43      HIGL
ATOM   1115  CA   GLY   139      25.590  47.917 111.138  1.00 14.15      HIGL
ATOM   1116  C    GLY   139      24.778  47.376 112.304  1.00 13.48      HIGL
ATOM   1117  O    GLY   139      24.703  48.001 113.363  1.00 11.76      HIGL
ATOM   1118  N    LEU   140      24.175  46.207 112.098  1.00 12.77      HIGL
ATOM   1119  CA   LEU   140      23.353  45.562 113.114  1.00 12.79      HIGL
ATOM   1120  CB   LEU   140      21.878  45.922 112.917  1.00 12.46      HIGL
ATOM   1121  CG   LEU   140      21.162  45.335 111.695  1.00 12.85      HIGL
ATOM   1122  CD1  LEU   140      19.672  45.582 111.817  1.00 13.35      HIGL
ATOM   1123  CD2  LEU   140      21.687  45.954 110.416  1.00 12.87      HIGL
ATOM   1124  C    LEU   140      23.504  44.055 113.010  1.00 13.36      HIGL
ATOM   1125  O    LEU   140      24.120  43.554 112.072  1.00 13.25      HIGL
ATOM   1126  N    LEU   141      22.937  43.342 113.980  1.00 13.28      HIGL
ATOM   1127  CA   LEU   141      22.975  41.883 114.008  1.00 12.60      HIGL
ATOM   1128  CB   LEU   141      21.895  41.340 113.069  1.00 10.91      HIGL
ATOM   1129  CG   LEU   141      20.481  41.627 113.587  1.00 10.89      HIGL
ATOM   1130  CD1  LEU   141      19.432  41.270 112.543  1.00  9.50      HIGL
ATOM   1131  CD2  LEU   141      20.264  40.846 114.880  1.00  8.29      HIGL
ATOM   1132  C    LEU   141      24.337  41.284 113.656  1.00 13.21      HIGL
ATOM   1133  O    LEU   141      24.462  40.504 112.708  1.00 14.64      HIGL
ATOM   1134  N    TRP   142      25.353  41.644 114.432  1.00 13.26      HIGL
ATOM   1135  CA   TRP   142      26.705  41.149 114.204  1.00 13.14      HIGL
ATOM   1136  CB   TRP   142      27.686  41.859 115.130  1.00 11.33      HIGL
ATOM   1137  CG   TRP   142      27.757  43.330 114.910  1.00 10.90      HIGL
ATOM   1138  CD2  TRP   142      28.488  44.272 115.695  1.00 11.10      HIGL
ATOM   1139  CE2  TRP   142      28.289  45.545 115.113  1.00 11.19      HIGL
ATOM   1140  CE3  TRP   142      29.290  44.167 116.835  1.00 10.40      HIGL
ATOM   1141  CD1  TRP   142      27.158  44.046 113.911  1.00 10.69      HIGL
ATOM   1142  NE1  TRP   142      27.474  45.379 114.025  1.00 10.00      HIGL
ATOM   1143  CZ2  TRP   142      28.869  46.705 115.635  1.00 11.44      HIGL
ATOM   1144  CZ3  TRP   142      29.863  45.319 117.353  1.00 11.67      HIGL
ATOM   1145  CH2  TRP   142      29.650  46.573 116.750  1.00 11.55      HIGL
ATOM   1146  C    TRP   142      26.768  39.652 114.442  1.00 13.84      HIGL
ATOM   1147  O    TRP   142      26.046  39.126 115.286  1.00 14.95      HIGL
ATOM   1148  N    PRO   143      27.680  38.952 113.751  1.00 13.87      HIGL
ATOM   1149  CD   PRO   143      27.900  37.534 114.052  1.00 13.74      HIGL
ATOM   1150  CA   PRO   143      28.675  39.417 112.776  1.00 14.76      HIGL
ATOM   1151  CB   PRO   143      29.669  38.253 112.701  1.00 13.49      HIGL
ATOM   1152  CG   PRO   143      29.386  37.438 113.918  1.00 13.80      HIGL
ATOM   1153  C    PRO   143      28.174  39.778 111.381  1.00 15.67      HIGL
ATOM   1154  O    PRO   143      28.703  40.693 110.755  1.00 16.90      HIGL
ATOM   1155  N    LEU   144      27.182  39.044 110.887  1.00 15.74      HIGL
ATOM   1156  CA   LEU   144      26.648  39.272 109.549  1.00 16.05      HIGL
ATOM   1157  CB   LEU   144      25.366  38.459 109.358  1.00 15.16      HIGL
ATOM   1158  CG   LEU   144      25.558  36.942 109.467  1.00 14.79      HIGL
ATOM   1159  CD1  LEU   144      24.214  36.248 109.414  1.00 14.16      HIGL
ATOM   1160  CD2  LEU   144      26.455  36.449 108.331  1.00 14.04      HIGL
ATOM   1161  C    LEU   144      26.397  40.727 109.159  1.00 17.32      HIGL
ATOM   1162  O    LEU   144      26.911  41.191 108.144  1.00 17.71      HIGL
ATOM   1163  N    GLY   145      25.617  41.451 109.956  1.00 17.84      HIGL
ATOM   1164  CA   GLY   145      25.325  42.835 109.617  1.00 17.98      HIGL
ATOM   1165  C    GLY   145      26.335  43.888 110.051  1.00 18.71      HIGL
ATOM   1166  O    GLY   145      26.008  45.077 110.123  1.00 19.15      HIGL
ATOM   1167  N    LYS   146      27.560  43.477 110.341  1.00 18.29      HIGL
ATOM   1168  CA   LYS   146      28.575  44.428 110.762  1.00 19.30      HIGL
ATOM   1169  CB   LYS   146      29.733  43.687 111.423  1.00 18.95      HIGL
```

Fig. 2 cont.

| ATOM | 1170 | CG  | LYS | 146 | 30.533 | 44.508 | 112.414 | 1.00 | 18.69 | HIGL |
|------|------|-----|-----|-----|--------|--------|---------|------|-------|------|
| ATOM | 1171 | CD  | LYS | 146 | 31.624 | 43.643 | 113.039 | 1.00 | 20.37 | HIGL |
| ATOM | 1172 | CE  | LYS | 146 | 32.528 | 44.430 | 113.984 | 1.00 | 20.86 | HIGL |
| ATOM | 1173 | NZ  | LYS | 146 | 31.799 | 44.955 | 115.162 | 1.00 | 21.63 | HIGL |
| ATOM | 1174 | C   | LYS | 146 | 29.062 | 45.228 | 109.550 | 1.00 | 20.47 | HIGL |
| ATOM | 1175 | O   | LYS | 146 | 29.211 | 44.685 | 108.453 | 1.00 | 19.27 | HIGL |
| ATOM | 1176 | N   | THR | 147 | 29.312 | 46.519 | 109.752 | 1.00 | 21.74 | HIGL |
| ATOM | 1177 | CA  | THR | 147 | 29.746 | 47.374 | 108.659 | 1.00 | 23.27 | HIGL |
| ATOM | 1178 | CB  | THR | 147 | 30.212 | 48.734 | 109.130 | 1.00 | 22.61 | HIGL |
| ATOM | 1179 | OG1 | THR | 147 | 30.794 | 48.619 | 110.430 | 1.00 | 23.56 | HIGL |
| ATOM | 1180 | CG2 | THR | 147 | 29.050 | 49.703 | 109.127 | 1.00 | 23.05 | HIGL |
| ATOM | 1181 | C   | THR | 147 | 30.817 | 46.833 | 107.747 | 1.00 | 24.76 | HIGL |
| ATOM | 1182 | O   | THR | 147 | 31.763 | 46.161 | 108.173 | 1.00 | 24.27 | HIGL |
| ATOM | 1183 | N   | ASN | 148 | 30.631 | 47.193 | 106.478 | 1.00 | 26.25 | HIGL |
| ATOM | 1184 | CA  | ASN | 148 | 31.456 | 46.818 | 105.346 | 1.00 | 26.20 | HIGL |
| ATOM | 1185 | CB  | ASN | 148 | 32.917 | 46.692 | 105.763 | 1.00 | 26.56 | HIGL |
| ATOM | 1186 | CG  | ASN | 148 | 33.560 | 48.057 | 105.998 | 1.00 | 26.62 | HIGL |
| ATOM | 1187 | OD1 | ASN | 148 | 32.903 | 48.985 | 106.472 | 1.00 | 26.28 | HIGL |
| ATOM | 1188 | ND2 | ASN | 148 | 34.842 | 48.183 | 105.670 | 1.00 | 25.69 | HIGL |
| ATOM | 1189 | C   | ASN | 148 | 30.865 | 45.542 | 104.762 | 1.00 | 26.28 | HIGL |
| ATOM | 1190 | O   | ASN | 148 | 31.279 | 45.076 | 103.707 | 1.00 | 28.00 | HIGL |
| ATOM | 1191 | N   | ASN | 149 | 29.873 | 44.998 | 105.464 | 1.00 | 25.38 | HIGL |
| ATOM | 1192 | CA  | ASN | 149 | 29.127 | 43.826 | 105.007 | 1.00 | 24.20 | HIGL |
| ATOM | 1193 | CB  | ASN | 149 | 28.733 | 42.927 | 106.177 | 1.00 | 24.04 | HIGL |
| ATOM | 1194 | CG  | ASN | 149 | 29.858 | 42.016 | 106.615 | 1.00 | 24.57 | HIGL |
| ATOM | 1195 | OD1 | ASN | 149 | 31.033 | 42.309 | 106.391 | 1.00 | 25.70 | HIGL |
| ATOM | 1196 | ND2 | ASN | 149 | 29.505 | 40.910 | 107.260 | 1.00 | 23.86 | HIGL |
| ATOM | 1197 | C   | ASN | 149 | 27.877 | 44.466 | 104.421 | 1.00 | 23.50 | HIGL |
| ATOM | 1198 | O   | ASN | 149 | 26.753 | 44.012 | 104.637 | 1.00 | 24.05 | HIGL |
| ATOM | 1199 | N   | TRP | 150 | 28.101 | 45.554 | 103.698 | 1.00 | 21.67 | HIGL |
| ATOM | 1200 | CA  | TRP | 150 | 27.039 | 46.323 | 103.079 | 1.00 | 20.87 | HIGL |
| ATOM | 1201 | CB  | TRP | 150 | 27.649 | 47.265 | 102.045 | 1.00 | 19.65 | HIGL |
| ATOM | 1202 | CG  | TRP | 150 | 28.654 | 48.200 | 102.653 | 1.00 | 19.10 | HIGL |
| ATOM | 1203 | CD2 | TRP | 150 | 28.411 | 49.153 | 103.697 | 1.00 | 19.28 | HIGL |
| ATOM | 1204 | CE2 | TRP | 150 | 29.631 | 49.828 | 103.938 | 1.00 | 18.98 | HIGL |
| ATOM | 1205 | CE3 | TRP | 150 | 27.278 | 49.506 | 104.452 | 1.00 | 18.67 | HIGL |
| ATOM | 1206 | CD1 | TRP | 150 | 29.976 | 48.329 | 102.315 | 1.00 | 18.26 | HIGL |
| ATOM | 1207 | NE1 | TRP | 150 | 30.567 | 49.306 | 103.080 | 1.00 | 17.94 | HIGL |
| ATOM | 1208 | CZ2 | TRP | 150 | 29.751 | 50.837 | 104.902 | 1.00 | 19.36 | HIGL |
| ATOM | 1209 | CZ3 | TRP | 150 | 27.395 | 50.506 | 105.409 | 1.00 | 19.12 | HIGL |
| ATOM | 1210 | CH2 | TRP | 150 | 28.627 | 51.162 | 105.626 | 1.00 | 19.64 | HIGL |
| ATOM | 1211 | C   | TRP | 150 | 25.939 | 45.479 | 102.451 | 1.00 | 20.95 | HIGL |
| ATOM | 1212 | O   | TRP | 150 | 24.757 | 45.801 | 102.583 | 1.00 | 21.08 | HIGL |
| ATOM | 1213 | N   | TYR | 151 | 26.315 | 44.400 | 101.769 | 1.00 | 20.56 | HIGL |
| ATOM | 1214 | CA  | TYR | 151 | 25.312 | 43.551 | 101.146 | 1.00 | 19.67 | HIGL |
| ATOM | 1215 | CB  | TYR | 151 | 25.949 | 42.403 | 100.362 | 1.00 | 19.65 | HIGL |
| ATOM | 1216 | CG  | TYR | 151 | 24.910 | 41.515 | 99.711  | 1.00 | 20.60 | HIGL |
| ATOM | 1217 | CD1 | TYR | 151 | 24.183 | 41.962 | 98.610  | 1.00 | 20.83 | HIGL |
| ATOM | 1218 | CE1 | TYR | 151 | 23.180 | 41.179 | 98.036  | 1.00 | 20.50 | HIGL |
| ATOM | 1219 | CD2 | TYR | 151 | 24.609 | 40.249 | 100.228 | 1.00 | 20.51 | HIGL |
| ATOM | 1220 | CE2 | TYR | 151 | 23.601 | 39.457 | 99.656  | 1.00 | 20.06 | HIGL |
| ATOM | 1221 | CZ  | TYR | 151 | 22.894 | 39.933 | 98.559  | 1.00 | 20.06 | HIGL |
| ATOM | 1222 | OH  | TYR | 151 | 21.904 | 39.171 | 97.972  | 1.00 | 19.92 | HIGL |
| ATOM | 1223 | C   | TYR | 151 | 24.389 | 42.972 | 102.204 | 1.00 | 19.26 | HIGL |
| ATOM | 1224 | O   | TYR | 151 | 23.176 | 43.114 | 102.113 | 1.00 | 18.33 | HIGL |
| ATOM | 1225 | N   | ASN | 152 | 24.966 | 42.317 | 103.209 | 1.00 | 19.42 | HIGL |
| ATOM | 1226 | CA  | ASN | 152 | 24.158 | 41.722 | 104.267 | 1.00 | 19.11 | HIGL |
| ATOM | 1227 | CB  | ASN | 152 | 25.040 | 41.046 | 105.326 | 1.00 | 19.23 | HIGL |
| ATOM | 1228 | CG  | ASN | 152 | 25.663 | 39.739 | 104.835 | 1.00 | 20.56 | HIGL |
| ATOM | 1229 | OD1 | ASN | 152 | 25.221 | 39.154 | 103.839 | 1.00 | 19.15 | HIGL |
| ATOM | 1230 | ND2 | ASN | 152 | 26.687 | 39.267 | 105.549 | 1.00 | 19.90 | HIGL |
| ATOM | 1231 | C   | ASN | 152 | 23.265 | 42.756 | 104.937 | 1.00 | 18.86 | HIGL |
| ATOM | 1232 | O   | ASN | 152 | 22.111 | 42.469 | 105.248 | 1.00 | 19.25 | HIGL |
| ATOM | 1233 | N   | ILE | 153 | 23.792 | 43.958 | 105.154 | 1.00 | 18.55 | HIGL |
| ATOM | 1234 | CA  | ILE | 153 | 23.024 | 45.020 | 105.804 | 1.00 | 18.75 | HIGL |

Fig. 2 cont.

```
ATOM  1235 CB   ILE 153    23.891 46.283 106.033 1.00 17.77      HIGL
ATOM  1236 CG2  ILE 153    23.053 47.395 106.623 1.00 16.52      HIGL
ATOM  1237 CG1  ILE 153    25.046 45.949 106.982 1.00 17.36      HIGL
ATOM  1238 CD1  ILE 153    26.068 47.050 107.128 1.00 16.15      HIGL
ATOM  1239 C    ILE 153    21.770 45.414 105.021 1.00 19.29      HIGL
ATOM  1240 O    ILE 153    20.653 45.369 105.557 1.00 18.88      HIGL
ATOM  1241 N    ALA 154    21.950 45.791 103.758 1.00 18.63      HIGL
ATOM  1242 CA   ALA 154    20.814 46.198 102.936 1.00 19.02      HIGL
ATOM  1243 CB   ALA 154    21.280 46.567 101.536 1.00 17.23      HIGL
ATOM  1244 C    ALA 154    19.828 45.043 102.880 1.00 19.18      HIGL
ATOM  1245 O    ALA 154    18.609 45.227 102.823 1.00 19.09      HIGL
ATOM  1246 N    ARG 155    20.393 43.846 102.908 1.00 19.15      HIGL
ATOM  1247 CA   ARG 155    19.646 42.602 102.864 1.00 18.74      HIGL
ATOM  1248 CB   ARG 155    20.661 41.461 102.775 1.00 18.99      HIGL
ATOM  1249 CG   ARG 155    20.110 40.111 102.485 1.00 19.95      HIGL
ATOM  1250 CD   ARG 155    19.495 39.997 101.104 1.00 20.00      HIGL
ATOM  1251 NE   ARG 155    18.768 38.740 101.065 1.00 21.33      HIGL
ATOM  1252 CZ   ARG 155    19.341 37.554 100.901 1.00 22.66      HIGL
ATOM  1253 NH1  ARG 155    20.655 37.462 100.728 1.00 22.62      HIGL
ATOM  1254 NH2  ARG 155    18.607 36.454 100.981 1.00 24.41      HIGL
ATOM  1255 C    ARG 155    18.798 42.509 104.142 1.00 18.62      HIGL
ATOM  1256 O    ARG 155    17.593 42.257 104.105 1.00 18.01      HIGL
ATOM  1257 N    LEU 156    19.432 42.748 105.280 1.00 18.71      HIGL
ATOM  1258 CA   LEU 156    18.725 42.688 106.548 1.00 17.91      HIGL
ATOM  1259 CB   LEU 156    19.720 42.796 107.707 1.00 16.34      HIGL
ATOM  1260 CG   LEU 156    20.507 41.507 107.927 1.00 16.27      HIGL
ATOM  1261 CD1  LEU 156    21.555 41.716 109.000 1.00 15.19      HIGL
ATOM  1262 CD2  LEU 156    19.547 40.384 108.310 1.00 15.70      HIGL
ATOM  1263 C    LEU 156    17.651 43.757 106.680 1.00 17.08      HIGL
ATOM  1264 O    LEU 156    16.531 43.472 107.097 1.00 18.08      HIGL
ATOM  1265 N    LEU 157    17.984 44.987 106.323 1.00 16.61      HIGL
ATOM  1266 CA   LEU 157    17.025 46.069 106.448 1.00 16.27      HIGL
ATOM  1267 CB   LEU 157    17.710 47.405 106.169 1.00 15.39      HIGL
ATOM  1268 CG   LEU 157    18.901 47.674 107.103 1.00 15.27      HIGL
ATOM  1269 CD1  LEU 157    19.582 48.989 106.730 1.00 14.68      HIGL
ATOM  1270 CD2  LEU 157    18.425 47.688 108.546 1.00 13.43      HIGL
ATOM  1271 C    LEU 157    15.819 45.870 105.543 1.00 16.79      HIGL
ATOM  1272 O    LEU 157    14.686 46.120 105.950 1.00 17.48      HIGL
ATOM  1273 N    HIS 158    16.050 45.403 104.321 1.00 17.58      HIGL
ATOM  1274 CA   HIS 158    14.944 45.174 103.401 1.00 17.25      HIGL
ATOM  1275 CB   HIS 158    15.439 44.552 102.099 1.00 17.36      HIGL
ATOM  1276 CG   HIS 158    14.335 44.187 101.159 1.00 18.88      HIGL
ATOM  1277 CD2  HIS 158    13.798 42.986 100.834 1.00 18.45      HIGL
ATOM  1278 ND1  HIS 158    13.587 45.133 100.484 1.00 19.56      HIGL
ATOM  1279 CE1  HIS 158    12.641 44.530  99.790 1.00 18.81      HIGL
ATOM  1280 NE2  HIS 158    12.746 43.225  99.985 1.00 19.02      HIGL
ATOM  1281 C    HIS 158    13.920 44.242 104.051 1.00 17.47      HIGL
ATOM  1282 O    HIS 158    12.723 44.531 104.066 1.00 16.46      HIGL
ATOM  1283 N    SER 159    14.402 43.127 104.592 1.00 17.53      HIGL
ATOM  1284 CA   SER 159    13.535 42.157 105.244 1.00 17.96      HIGL
ATOM  1285 CB   SER 159    14.353 40.973 105.753 1.00 18.70      HIGL
ATOM  1286 OG   SER 159    14.963 40.280 104.684 1.00 20.45      HIGL
ATOM  1287 C    SER 159    12.778 42.782 106.409 1.00 18.11      HIGL
ATOM  1288 O    SER 159    11.577 42.549 106.577 1.00 17.79      HIGL
ATOM  1289 N    ALA 160    13.483 43.573 107.214 1.00 17.67      HIGL
ATOM  1290 CA   ALA 160    12.871 44.231 108.363 1.00 17.44      HIGL
ATOM  1291 CB   ALA 160    13.929 44.922 109.187 1.00 16.81      HIGL
ATOM  1292 C    ALA 160    11.824 45.239 107.918 1.00 17.59      HIGL
ATOM  1293 O    ALA 160    10.737 45.322 108.492 1.00 17.41      HIGL
ATOM  1294 N    ALA 161    12.157 46.012 106.892 1.00 18.14      HIGL
ATOM  1295 CA   ALA 161    11.230 47.011 106.377 1.00 18.38      HIGL
ATOM  1296 CB   ALA 161    11.831 47.714 105.189 1.00 16.08      HIGL
ATOM  1297 C    ALA 161     9.931 46.337 105.974 1.00 19.43      HIGL
ATOM  1298 O    ALA 161     8.844 46.848 106.244 1.00 20.06      HIGL
ATOM  1299 N    TRP 162    10.045 45.176 105.335 1.00 19.98      HIGL
```

Fig. 2 cont.

```
ATOM  1300 CA   TRP 162    8.864 44.463 104.889  1.00 20.45      HIGL
ATOM  1301 CB   TRP 162    9.215 43.511 103.746  1.00 21.00      HIGL
ATOM  1302 CG   TRP 162    9.298 44.267 102.482  1.00 21.58      HIGL
ATOM  1303 CD2  TRP 162    8.222 44.516 101.575  1.00 21.96      HIGL
ATOM  1304 CE2  TRP 162    8.691 45.440 100.612  1.00 21.86      HIGL
ATOM  1305 CE3  TRP 162    6.902 44.056 101.487  1.00 22.03      HIGL
ATOM  1306 CD1  TRP 162   10.354 45.019 102.040  1.00 21.86      HIGL
ATOM  1307 NE1  TRP 162    9.995 45.729 100.919  1.00 21.88      HIGL
ATOM  1308 CZ2  TRP 162    7.884 45.913  99.572  1.00 21.45      HIGL
ATOM  1309 CZ3  TRP 162    6.096 44.530 100.448  1.00 22.27      HIGL
ATOM  1310 CH2  TRP 162    6.594 45.449  99.506  1.00 21.62      HIGL
ATOM  1311 C    TRP 162    8.108 43.746 105.982  1.00 20.46      HIGL
ATOM  1312 O    TRP 162    6.919 43.463 105.829  1.00 21.30      HIGL
ATOM  1313 N    GLY 163    8.783 43.453 107.085  1.00 19.69      HIGL
ATOM  1314 CA   GLY 163    8.089 42.816 108.182  1.00 19.99      HIGL
ATOM  1315 C    GLY 163    7.048 43.833 108.622  1.00 20.35      HIGL
ATOM  1316 O    GLY 163    5.954 43.491 109.075  1.00 20.66      HIGL
ATOM  1317 N    VAL 164    7.398 45.106 108.469  1.00 19.87      HIGL
ATOM  1318 CA   VAL 164    6.504 46.194 108.832  1.00 18.68      HIGL
ATOM  1319 CB   VAL 164    7.266 47.534 108.946  1.00 18.24      HIGL
ATOM  1320 CG1  VAL 164    6.305 48.650 109.336  1.00 17.70      HIGL
ATOM  1321 CG2  VAL 164    8.391 47.409 109.959  1.00 17.30      HIGL
ATOM  1322 C    VAL 164    5.447 46.336 107.748  1.00 18.61      HIGL
ATOM  1323 O    VAL 164    4.254 46.415 108.027  1.00 18.31      HIGL
ATOM  1324 N    LYS 165    5.891 46.356 106.502  1.00 18.63      HIGL
ATOM  1325 CA   LYS 165    4.965 46.516 105.403  1.00 19.93      HIGL
ATOM  1326 CB   LYS 165    5.728 46.615 104.087  1.00 19.36      HIGL
ATOM  1327 CG   LYS 165    6.589 47.869 103.981  1.00 18.36      HIGL
ATOM  1328 CD   LYS 165    7.335 47.923 102.644  1.00 18.25      HIGL
ATOM  1329 CE   LYS 165    8.175 49.182 102.534  1.00 17.76      HIGL
ATOM  1330 NZ   LYS 165    7.317 50.401 102.629  1.00 18.31      HIGL
ATOM  1331 C    LYS 165    3.904 45.428 105.325  1.00 20.82      HIGL
ATOM  1332 O    LYS 165    2.746 45.727 105.049  1.00 21.60      HIGL
ATOM  1333 N    ASP 166    4.283 44.179 105.581  1.00 21.39      HIGL
ATOM  1334 CA   ASP 166    3.327 43.073 105.522  1.00 22.03      HIGL
ATOM  1335 CB   ASP 166    4.039 41.749 105.219  1.00 22.56      HIGL
ATOM  1336 CG   ASP 166    4.642 41.702 103.833  1.00 23.22      HIGL
ATOM  1337 OD1  ASP 166    4.195 42.463 102.951  1.00 23.72      HIGL
ATOM  1338 OD2  ASP 166    5.560 40.879 103.623  1.00 23.83      HIGL
ATOM  1339 C    ASP 166    2.481 42.860 106.782  1.00 22.48      HIGL
ATOM  1340 O    ASP 166    1.724 41.896 106.852  1.00 22.92      HIGL
ATOM  1341 N    SER 167    2.596 43.732 107.777  1.00 22.71      HIGL
ATOM  1342 CA   SER 167    1.825 43.554 109.006  1.00 22.64      HIGL
ATOM  1343 CB   SER 167    2.519 44.259 110.169  1.00 22.61      HIGL
ATOM  1344 OG   SER 167    2.442 45.667 110.023  1.00 23.18      HIGL
ATOM  1345 C    SER 167    0.396 44.081 108.886  1.00 23.16      HIGL
ATOM  1346 O    SER 167    0.040 44.722 107.903  1.00 22.85      HIGL
ATOM  1347 N    ARG 168   -0.418 43.798 109.898  1.00 23.80      HIGL
ATOM  1348 CA   ARG 168   -1.805 44.250 109.933  1.00 23.78      HIGL
ATOM  1349 CB   ARG 168   -2.601 43.465 110.978  1.00 23.09      HIGL
ATOM  1350 CG   ARG 168   -3.597 42.463 110.420  1.00 22.15      HIGL
ATOM  1351 CD   ARG 168   -3.088 41.049 110.571  1.00 21.65      HIGL
ATOM  1352 NE   ARG 168   -2.910 40.664 111.971  1.00 18.91      HIGL
ATOM  1353 CZ   ARG 168   -2.272 39.564 112.348  1.00 18.78      HIGL
ATOM  1354 NH1  ARG 168   -1.763 38.753 111.430  1.00 18.16      HIGL
ATOM  1355 NH2  ARG 168   -2.127 39.278 113.633  1.00 19.17      HIGL
ATOM  1356 C    ARG 168   -1.890 45.734 110.284  1.00 24.65      HIGL
ATOM  1357 O    ARG 168   -2.980 46.299 110.348  1.00 25.72      HIGL
ATOM  1358 N    LEU 169   -0.751 46.366 110.534  1.00 24.93      HIGL
ATOM  1359 CA   LEU 169   -0.767 47.779 110.873  1.00 25.57      HIGL
ATOM  1360 CB   LEU 169    0.642 48.300 111.135  1.00 24.39      HIGL
ATOM  1361 CG   LEU 169    1.239 47.981 112.501  1.00 23.91      HIGL
ATOM  1362 CD1  LEU 169    2.643 48.570 112.579  1.00 23.28      HIGL
ATOM  1363 CD2  LEU 169    0.350 48.545 113.595  1.00 21.07      HIGL
ATOM  1364 C    LEU 169   -1.395 48.596 109.768  1.00 26.78      HIGL
```

Fig. 2 cont.

```
ATOM   1365 O    LEU  169    -1.086  48.421 108.591  1.00 26.61      HIGL
ATOM   1366 N    ASN  170    -2.292  49.485 110.160  1.00 28.98      HIGL
ATOM   1367 CA   ASN  170    -2.962  50.356 109.216  1.00 31.16      HIGL
ATOM   1368 CB   ASN  170    -4.126  49.638 108.536  1.00 34.31      HIGL
ATOM   1369 CG   ASN  170    -4.532  50.301 107.223  1.00 37.73      HIGL
ATOM   1370 OD1  ASN  170    -5.637  50.087 106.717  1.00 39.55      HIGL
ATOM   1371 ND2  ASN  170    -3.628  51.098 106.657  1.00 38.83      HIGL
ATOM   1372 C    ASN  170    -3.482  51.560 109.989  1.00 31.18      HIGL
ATOM   1373 O    ASN  170    -4.227  51.411 110.965  1.00 31.87      HIGL
ATOM   1374 N    PRO  171    -3.044  52.767 109.599  1.00 29.94      HIGL
ATOM   1375 CD   PRO  171    -3.373  54.060 110.227  1.00 29.80      HIGL
ATOM   1376 CA   PRO  171    -2.101  52.949 108.492  1.00 28.18      HIGL
ATOM   1377 CB   PRO  171    -2.094  54.459 108.295  1.00 28.38      HIGL
ATOM   1378 CG   PRO  171    -2.269  54.960 109.698  1.00 29.83      HIGL
ATOM   1379 C    PRO  171    -0.728  52.413 108.889  1.00 26.71      HIGL
ATOM   1380 O    PRO  171    -0.472  52.183 110.068  1.00 25.16      HIGL
ATOM   1381 N    LYS  172     0.139  52.204 107.900  1.00 25.19      HIGL
ATOM   1382 CA   LYS  172     1.482  51.709 108.155  1.00 24.35      HIGL
ATOM   1383 CB   LYS  172     2.119  51.187 106.867  1.00 25.60      HIGL
ATOM   1384 CG   LYS  172     1.274  50.201 106.093  1.00 27.94      HIGL
ATOM   1385 CD   LYS  172     1.253  48.826 106.725  1.00 29.37      HIGL
ATOM   1386 CE   LYS  172     0.451  47.875 105.848  1.00 30.03      HIGL
ATOM   1387 NZ   LYS  172     0.492  46.469 106.329  1.00 30.93      HIGL
ATOM   1388 C    LYS  172     2.332  52.858 108.686  1.00 22.94      HIGL
ATOM   1389 O    LYS  172     2.212  53.992 108.220  1.00 22.83      HIGL
ATOM   1390 N    PRO  173     3.200  52.580 109.671  1.00 21.18      HIGL
ATOM   1391 CD   PRO  173     3.396  51.290 110.354  1.00 21.36      HIGL
ATOM   1392 CA   PRO  173     4.069  53.599 110.254  1.00 20.28      HIGL
ATOM   1393 CB   PRO  173     4.595  52.915 111.508  1.00 20.26      HIGL
ATOM   1394 CG   PRO  173     4.718  51.502 111.059  1.00 20.58      HIGL
ATOM   1395 C    PRO  173     5.197  53.947 109.297  1.00 19.51      HIGL
ATOM   1396 O    PRO  173     5.525  53.172 108.407  1.00 19.40      HIGL
ATOM   1397 N    LYS  174     5.778  55.123 109.482  1.00 18.84      HIGL
ATOM   1398 CA   LYS  174     6.887  55.548 108.655  1.00 18.05      HIGL
ATOM   1399 CB   LYS  174     7.168  57.032 108.875  1.00 18.15      HIGL
ATOM   1400 CG   LYS  174     5.984  57.905 108.527  1.00 18.80      HIGL
ATOM   1401 CD   LYS  174     6.308  59.380 108.602  1.00 19.52      HIGL
ATOM   1402 CE   LYS  174     5.140  60.200 108.085  1.00 18.38      HIGL
ATOM   1403 NZ   LYS  174     5.521  61.622 107.893  1.00 19.70      HIGL
ATOM   1404 C    LYS  174     8.073  54.712 109.097  1.00 17.68      HIGL
ATOM   1405 O    LYS  174     8.348  54.586 110.288  1.00 18.33      HIGL
ATOM   1406 N    ILE  175     8.764  54.119 108.139  1.00 17.03      HIGL
ATOM   1407 CA   ILE  175     9.909  53.291 108.461  1.00 16.37      HIGL
ATOM   1408 CB   ILE  175    10.071  52.178 107.420  1.00 15.88      HIGL
ATOM   1409 CG2  ILE  175    11.276  51.317 107.767  1.00 14.85      HIGL
ATOM   1410 CG1  ILE  175     8.785  51.342 107.387  1.00 14.92      HIGL
ATOM   1411 CD1  ILE  175     8.694  50.358 106.232  1.00 16.47      HIGL
ATOM   1412 C    ILE  175    11.142  54.176 108.517  1.00 15.73      HIGL
ATOM   1413 O    ILE  175    11.417  54.933 107.588  1.00 15.78      HIGL
ATOM   1414 N    MET  176    11.874  54.075 109.620  1.00 14.73      HIGL
ATOM   1415 CA   MET  176    13.054  54.896 109.836  1.00 14.35      HIGL
ATOM   1416 CB   MET  176    12.830  55.786 111.070  1.00 13.52      HIGL
ATOM   1417 CG   MET  176    14.060  56.557 111.518  1.00 13.16      HIGL
ATOM   1418 SD   MET  176    13.928  57.167 113.201  1.00 14.72      HIGL
ATOM   1419 CE   MET  176    12.695  58.477 112.999  1.00 14.08      HIGL
ATOM   1420 C    MET  176    14.358  54.122 110.024  1.00 14.18      HIGL
ATOM   1421 O    MET  176    14.376  53.040 110.603  1.00 14.19      HIGL
ATOM   1422 N    VAL  177    15.444  54.693 109.511  1.00 14.60      HIGL
ATOM   1423 CA   VAL  177    16.777  54.123 109.664  1.00 13.89      HIGL
ATOM   1424 CB   VAL  177    17.532  54.024 108.319  1.00 13.58      HIGL
ATOM   1425 CG1  VAL  177    19.004  53.680 108.573  1.00 12.32      HIGL
ATOM   1426 CG2  VAL  177    16.892  52.940 107.454  1.00 12.15      HIGL
ATOM   1427 C    VAL  177    17.461  55.113 110.597  1.00 13.92      HIGL
ATOM   1428 O    VAL  177    17.503  56.314 110.326  1.00 13.57      HIGL
ATOM   1429 N    HIS  178    17.966  54.595 111.710  1.00 14.28      HIGL
```

Fig. 2 cont.

```
ATOM   1430  CA   HIS   178      18.591  55.407 112.743  1.00 14.37      HIGL
ATOM   1431  CB   HIS   178      17.910  55.083 114.083  1.00 14.38      HIGL
ATOM   1432  CG   HIS   178      18.522  55.762 115.268  1.00 14.85      HIGL
ATOM   1433  CD2  HIS   178      18.456  55.471 116.589  1.00 14.94      HIGL
ATOM   1434  ND1  HIS   178      19.287  56.903 115.163  1.00 15.06      HIGL
ATOM   1435  CE1  HIS   178      19.670  57.285 116.369  1.00 14.39      HIGL
ATOM   1436  NE2  HIS   178      19.179  56.434 117.251  1.00 15.19      HIGL
ATOM   1437  C    HIS   178      20.102  55.235 112.850  1.00 14.74      HIGL
ATOM   1438  O    HIS   178      20.605  54.132 113.072  1.00 14.60      HIGL
ATOM   1439  N    LEU   179      20.812  56.346 112.685  1.00 14.68      HIGL
ATOM   1440  CA   LEU   179      22.269  56.381 112.769  1.00 14.88      HIGL
ATOM   1441  CB   LEU   179      22.866  56.817 111.430  1.00 14.85      HIGL
ATOM   1442  CG   LEU   179      23.217  55.794 110.349  1.00 15.01      HIGL
ATOM   1443  CD1  LEU   179      22.120  54.786 110.177  1.00 15.16      HIGL
ATOM   1444  CD2  LEU   179      23.476  56.536 109.049  1.00 14.52      HIGL
ATOM   1445  C    LEU   179      22.632  57.406 113.830  1.00 14.77      HIGL
ATOM   1446  O    LEU   179      21.867  58.336 114.070  1.00 16.15      HIGL
ATOM   1447  N    ASP   180      23.786  57.244 114.468  1.00 14.56      HIGL
ATOM   1448  CA   ASP   180      24.217  58.200 115.483  1.00 15.13      HIGL
ATOM   1449  CB   ASP   180      25.040  57.491 116.576  1.00 15.21      HIGL
ATOM   1450  CG   ASP   180      26.496  57.238 116.171  1.00 16.64      HIGL
ATOM   1451  OD1  ASP   180      26.744  56.712 115.060  1.00 15.02      HIGL
ATOM   1452  OD2  ASP   180      27.393  57.560 116.987  1.00 16.16      HIGL
ATOM   1453  C    ASP   180      25.039  59.279 114.776  1.00 15.95      HIGL
ATOM   1454  O    ASP   180      25.185  59.233 113.555  1.00 17.25      HIGL
ATOM   1455  N    ASN   181      25.556  60.249 115.525  1.00 15.91      HIGL
ATOM   1456  CA   ASN   181      26.362  61.334 114.960  1.00 15.67      HIGL
ATOM   1457  CB   ASN   181      27.754  60.824 114.594  1.00 16.57      HIGL
ATOM   1458  CG   ASN   181      28.573  60.449 115.807  1.00 17.66      HIGL
ATOM   1459  OD1  ASN   181      28.418  61.031 116.881  1.00 19.18      HIGL
ATOM   1460  ND2  ASN   181      29.464  59.487 115.641  1.00 18.44      HIGL
ATOM   1461  C    ASN   181      25.763  62.034 113.742  1.00 15.63      HIGL
ATOM   1462  O    ASN   181      26.433  62.200 112.731  1.00 15.55      HIGL
ATOM   1463  N    GLY   182      24.508  62.455 113.847  1.00 15.79      HIGL
ATOM   1464  CA   GLY   182      23.853  63.129 112.744  1.00 15.12      HIGL
ATOM   1465  C    GLY   182      24.575  64.373 112.287  1.00 15.79      HIGL
ATOM   1466  O    GLY   182      24.331  64.857 111.184  1.00 16.16      HIGL
ATOM   1467  N    TRP   183      25.459  64.902 113.130  1.00 16.94      HIGL
ATOM   1468  CA   TRP   183      26.227  66.100 112.784  1.00 16.80      HIGL
ATOM   1469  CB   TRP   183      26.854  66.746 114.034  1.00 16.19      HIGL
ATOM   1470  CG   TRP   183      27.735  65.829 114.837  1.00 14.99      HIGL
ATOM   1471  CD2  TRP   183      29.108  65.506 114.577  1.00 14.85      HIGL
ATOM   1472  CE2  TRP   183      29.505  64.558 115.547  1.00 14.72      HIGL
ATOM   1473  CE3  TRP   183      30.041  65.922 113.616  1.00 15.26      HIGL
ATOM   1474  CD1  TRP   183      27.369  65.091 115.919  1.00 15.04      HIGL
ATOM   1475  NE1  TRP   183      28.424  64.324 116.353  1.00 14.56      HIGL
ATOM   1476  CZ2  TRP   183      30.798  64.015 115.586  1.00 13.96      HIGL
ATOM   1477  CZ3  TRP   183      31.332  65.379 113.654  1.00 14.45      HIGL
ATOM   1478  CH2  TRP   183      31.693  64.436 114.634  1.00 13.99      HIGL
ATOM   1479  C    TRP   183      27.333  65.755 111.797  1.00 17.18      HIGL
ATOM   1480  O    TRP   183      27.780  66.606 111.040  1.00 18.90      HIGL
ATOM   1481  N    ASN   184      27.780  64.508 111.807  1.00 17.37      HIGL
ATOM   1482  CA   ASN   184      28.838  64.087 110.901  1.00 18.52      HIGL
ATOM   1483  CB   ASN   184      29.623  62.936 111.514  1.00 18.43      HIGL
ATOM   1484  CG   ASN   184      30.892  62.651 110.760  1.00 18.15      HIGL
ATOM   1485  OD1  ASN   184      30.904  62.652 109.528  1.00 17.65      HIGL
ATOM   1486  ND2  ASN   184      31.972  62.403 111.490  1.00 16.66      HIGL
ATOM   1487  C    ASN   184      28.265  63.647 109.551  1.00 19.20      HIGL
ATOM   1488  O    ASN   184      27.800  62.515 109.406  1.00 19.59      HIGL
ATOM   1489  N    TRP   185      28.318  64.536 108.563  1.00 18.87      HIGL
ATOM   1490  CA   TRP   185      27.780  64.239 107.246  1.00 18.50      HIGL
ATOM   1491  CB   TRP   185      27.752  65.517 106.404  1.00 19.66      HIGL
ATOM   1492  CG   TRP   185      27.658  65.269 104.923  1.00 20.74      HIGL
ATOM   1493  CD2  TRP   185      26.584  64.623 104.224  1.00 21.65      HIGL
ATOM   1494  CE2  TRP   185      26.952  64.564 102.857  1.00 21.97      HIGL
```

Fig. 2 cont.

| | | | | | | | | | |
|---|---|---|---|---|---|---|---|---|---|
| ATOM | 1495 | CE3 | TRP | 185 | 25.349 | 64.085 | 104.618 | 1.00 21.22 | HIGL |
| ATOM | 1496 | CD1 | TRP | 185 | 28.601 | 65.570 | 103.982 | 1.00 20.45 | HIGL |
| ATOM | 1497 | NE1 | TRP | 185 | 28.184 | 65.151 | 102.740 | 1.00 21.70 | HIGL |
| ATOM | 1498 | CZ2 | TRP | 185 | 26.127 | 63.985 | 101.880 | 1.00 21.82 | HIGL |
| ATOM | 1499 | CZ3 | TRP | 185 | 24.526 | 63.509 | 103.645 | 1.00 21.31 | HIGL |
| ATOM | 1500 | CH2 | TRP | 185 | 24.921 | 63.465 | 102.292 | 1.00 21.28 | HIGL |
| ATOM | 1501 | C | TRP | 185 | 28.510 | 63.126 | 106.489 | 1.00 18.87 | HIGL |
| ATOM | 1502 | O | TRP | 185 | 27.873 | 62.328 | 105.796 | 1.00 18.21 | HIGL |
| ATOM | 1503 | N | ASP | 186 | 29.835 | 63.074 | 106.606 | 1.00 18.26 | HIGL |
| ATOM | 1504 | CA | ASP | 186 | 30.595 | 62.042 | 105.918 | 1.00 18.41 | HIGL |
| ATOM | 1505 | CB | ASP | 186 | 32.094 | 62.185 | 106.181 | 1.00 19.07 | HIGL |
| ATOM | 1506 | CG | ASP | 186 | 32.662 | 63.492 | 105.644 | 1.00 19.86 | HIGL |
| ATOM | 1507 | OD1 | ASP | 186 | 32.235 | 63.922 | 104.546 | 1.00 18.31 | HIGL |
| ATOM | 1508 | OD2 | ASP | 186 | 33.539 | 64.082 | 106.321 | 1.00 20.67 | HIGL |
| ATOM | 1509 | C | ASP | 186 | 30.127 | 60.669 | 106.375 | 1.00 18.79 | HIGL |
| ATOM | 1510 | O | ASP | 186 | 30.057 | 59.738 | 105.569 | 1.00 19.44 | HIGL |
| ATOM | 1511 | N | THR | 187 | 29.804 | 60.541 | 107.662 | 1.00 18.54 | HIGL |
| ATOM | 1512 | CA | THR | 187 | 29.326 | 59.267 | 108.185 | 1.00 18.36 | HIGL |
| ATOM | 1513 | CB | THR | 187 | 29.144 | 59.303 | 109.717 | 1.00 18.81 | HIGL |
| ATOM | 1514 | OG1 | THR | 187 | 30.334 | 59.779 | 110.359 | 1.00 17.18 | HIGL |
| ATOM | 1515 | CG2 | THR | 187 | 28.841 | 57.898 | 110.229 | 1.00 17.29 | HIGL |
| ATOM | 1516 | C | THR | 187 | 27.955 | 58.970 | 107.554 | 1.00 18.81 | HIGL |
| ATOM | 1517 | O | THR | 187 | 27.749 | 57.924 | 106.953 | 1.00 18.82 | HIGL |
| ATOM | 1518 | N | GLN | 188 | 27.028 | 59.912 | 107.690 | 1.00 18.92 | HIGL |
| ATOM | 1519 | CA | GLN | 188 | 25.678 | 59.756 | 107.123 | 1.00 18.70 | HIGL |
| ATOM | 1520 | CB | GLN | 188 | 24.868 | 61.025 | 107.278 | 1.00 18.92 | HIGL |
| ATOM | 1521 | CG | GLN | 188 | 24.691 | 61.548 | 108.719 | 1.00 20.75 | HIGL |
| ATOM | 1522 | CD | GLN | 188 | 24.217 | 60.494 | 109.715 | 1.00 21.45 | HIGL |
| ATOM | 1523 | OE1 | GLN | 188 | 23.340 | 59.658 | 109.425 | 1.00 21.55 | HIGL |
| ATOM | 1524 | NE2 | GLN | 188 | 24.775 | 60.558 | 110.916 | 1.00 20.88 | HIGL |
| ATOM | 1525 | C | GLN | 188 | 25.693 | 59.419 | 105.628 | 1.00 18.27 | HIGL |
| ATOM | 1526 | O | GLN | 188 | 24.854 | 58.643 | 105.144 | 1.00 19.06 | HIGL |
| ATOM | 1527 | N | ASN | 189 | 26.652 | 60.019 | 104.912 | 1.00 18.01 | HIGL |
| ATOM | 1528 | CA | ASN | 189 | 26.837 | 59.855 | 103.466 | 1.00 17.83 | HIGL |
| ATOM | 1529 | CB | ASN | 189 | 27.713 | 61.007 | 102.897 | 1.00 18.12 | HIGL |
| ATOM | 1530 | CG | ASN | 189 | 27.816 | 60.975 | 101.367 | 1.00 18.97 | HIGL |
| ATOM | 1531 | OD1 | ASN | 189 | 27.022 | 60.302 | 100.708 | 1.00 18.06 | HIGL |
| ATOM | 1532 | ND2 | ASN | 189 | 28.776 | 61.718 | 100.800 | 1.00 19.12 | HIGL |
| ATOM | 1533 | C | ASN | 189 | 27.460 | 58.493 | 103.165 | 1.00 17.73 | HIGL |
| ATOM | 1534 | O | ASN | 189 | 26.935 | 57.760 | 102.331 | 1.00 17.69 | HIGL |
| ATOM | 1535 | N | TRP | 190 | 28.583 | 58.180 | 103.812 | 1.00 17.17 | HIGL |
| ATOM | 1536 | CA | TRP | 190 | 29.272 | 56.895 | 103.656 | 1.00 16.53 | HIGL |
| ATOM | 1537 | CB | TRP | 190 | 30.409 | 56.855 | 104.679 | 1.00 16.92 | HIGL |
| ATOM | 1538 | CG | TRP | 190 | 30.943 | 55.516 | 105.033 | 1.00 17.78 | HIGL |
| ATOM | 1539 | CD2 | TRP | 190 | 30.714 | 54.794 | 106.253 | 1.00 17.06 | HIGL |
| ATOM | 1540 | CE2 | TRP | 190 | 31.490 | 53.620 | 106.192 | 1.00 18.29 | HIGL |
| ATOM | 1541 | CE3 | TRP | 190 | 29.931 | 55.028 | 107.392 | 1.00 17.68 | HIGL |
| ATOM | 1542 | CD1 | TRP | 190 | 31.811 | 54.770 | 104.303 | 1.00 18.04 | HIGL |
| ATOM | 1543 | NE1 | TRP | 190 | 32.150 | 53.630 | 104.991 | 1.00 18.09 | HIGL |
| ATOM | 1544 | CZ2 | TRP | 190 | 31.511 | 52.675 | 107.230 | 1.00 18.43 | HIGL |
| ATOM | 1545 | CZ3 | TRP | 190 | 29.951 | 54.083 | 108.431 | 1.00 18.02 | HIGL |
| ATOM | 1546 | CH2 | TRP | 190 | 30.738 | 52.925 | 108.336 | 1.00 17.37 | HIGL |
| ATOM | 1547 | C | TRP | 190 | 28.307 | 55.715 | 103.874 | 1.00 15.60 | HIGL |
| ATOM | 1548 | O | TRP | 190 | 28.193 | 54.800 | 103.053 | 1.00 16.16 | HIGL |
| ATOM | 1549 | N | TRP | 191 | 27.609 | 55.744 | 104.997 | 1.00 14.48 | HIGL |
| ATOM | 1550 | CA | TRP | 191 | 26.674 | 54.686 | 105.327 | 1.00 14.21 | HIGL |
| ATOM | 1551 | CB | TRP | 191 | 26.028 | 54.956 | 106.681 | 1.00 12.41 | HIGL |
| ATOM | 1552 | CG | TRP | 191 | 25.437 | 53.729 | 107.273 | 1.00 11.51 | HIGL |
| ATOM | 1553 | CD2 | TRP | 191 | 24.101 | 53.250 | 107.097 | 1.00 10.28 | HIGL |
| ATOM | 1554 | CE2 | TRP | 191 | 23.990 | 52.044 | 107.827 | 1.00 10.64 | HIGL |
| ATOM | 1555 | CE3 | TRP | 191 | 22.986 | 53.720 | 106.393 | 1.00 7.88 | HIGL |
| ATOM | 1556 | CD1 | TRP | 191 | 26.068 | 52.820 | 108.074 | 1.00 12.10 | HIGL |
| ATOM | 1557 | NE1 | TRP | 191 | 25.208 | 51.805 | 108.413 | 1.00 10.86 | HIGL |
| ATOM | 1558 | CZ2 | TRP | 191 | 22.808 | 51.304 | 107.876 | 1.00 9.13 | HIGL |
| ATOM | 1559 | CZ3 | TRP | 191 | 21.818 | 52.988 | 106.440 | 1.00 8.78 | HIGL |

Fig. 2 cont.

```
ATOM   1560  CH2  TRP  191      21.735  51.790 107.178  1.00  9.52      HIGL
ATOM   1561  C    TRP  191      25.566  54.471 104.292  1.00 14.99      HIGL
ATOM   1562  O    TRP  191      25.485  53.409 103.664  1.00 14.62      HIGL
ATOM   1563  N    TYR  192      24.703  55.468 104.121  1.00 15.56      HIGL
ATOM   1564  CA   TYR  192      23.595  55.341 103.178  1.00 16.00      HIGL
ATOM   1565  CB   TYR  192      22.739  56.615 103.195  1.00 15.03      HIGL
ATOM   1566  CG   TYR  192      21.859  56.737 104.428  1.00 14.42      HIGL
ATOM   1567  CD1  TYR  192      20.759  55.886 104.617  1.00 14.00      HIGL
ATOM   1568  CE1  TYR  192      19.954  55.987 105.746  1.00 13.21      HIGL
ATOM   1569  CD2  TYR  192      22.128  57.691 105.408  1.00 13.33      HIGL
ATOM   1570  CE2  TYR  192      21.332  57.804 106.544  1.00 13.35      HIGL
ATOM   1571  CZ   TYR  192      20.244  56.950 106.709  1.00 13.89      HIGL
ATOM   1572  OH   TYR  192      19.442  57.073 107.826  1.00 12.40      HIGL
ATOM   1573  C    TYR  192      24.052  55.015 101.760  1.00 17.04      HIGL
ATOM   1574  O    TYR  192      23.433  54.199 101.071  1.00 17.52      HIGL
ATOM   1575  N    THR  193      25.137  55.643 101.325  1.00 17.90      HIGL
ATOM   1576  CA   THR  193      25.654  55.388  99.993  1.00 18.57      HIGL
ATOM   1577  CB   THR  193      26.949  56.186  99.738  1.00 19.70      HIGL
ATOM   1578  OG1  THR  193      26.634  57.582  99.645  1.00 20.25      HIGL
ATOM   1579  CG2  THR  193      27.629  55.716  98.441  1.00 17.66      HIGL
ATOM   1580  C    THR  193      25.950  53.897  99.842  1.00 18.55      HIGL
ATOM   1581  O    THR  193      25.442  53.230  98.937  1.00 18.73      HIGL
ATOM   1582  N    ASN  194      26.772  53.377 100.742  1.00 17.82      HIGL
ATOM   1583  CA   ASN  194      27.127  51.972 100.693  1.00 18.02      HIGL
ATOM   1584  CB   ASN  194      28.166  51.663 101.762  1.00 17.18      HIGL
ATOM   1585  CG   ASN  194      29.546  52.148 101.381  1.00 16.79      HIGL
ATOM   1586  OD1  ASN  194      30.135  51.668 100.411  1.00 17.28      HIGL
ATOM   1587  ND2  ASN  194      30.073  53.102 102.137  1.00 16.49      HIGL
ATOM   1588  C    ASN  194      25.934  51.031 100.830  1.00 18.35      HIGL
ATOM   1589  O    ASN  194      25.860  50.029 100.123  1.00 20.21      HIGL
ATOM   1590  N    VAL  195      25.003  51.345 101.724  1.00 17.31      HIGL
ATOM   1591  CA   VAL  195      23.838  50.495 101.908  1.00 17.12      HIGL
ATOM   1592  CB   VAL  195      23.052  50.887 103.185  1.00 17.17      HIGL
ATOM   1593  CG1  VAL  195      21.789  50.062 103.290  1.00 16.39      HIGL
ATOM   1594  CG2  VAL  195      23.906  50.675 104.411  1.00 16.35      HIGL
ATOM   1595  C    VAL  195      22.882  50.550 100.711  1.00 17.84      HIGL
ATOM   1596  O    VAL  195      22.414  49.514 100.223  1.00 17.57      HIGL
ATOM   1597  N    LEU  196      22.591  51.755 100.234  1.00 17.80      HIGL
ATOM   1598  CA   LEU  196      21.672  51.906  99.114  1.00 18.71      HIGL
ATOM   1599  CB   LEU  196      21.164  53.346  99.049  1.00 19.05      HIGL
ATOM   1600  CG   LEU  196      20.389  53.814 100.284  1.00 19.84      HIGL
ATOM   1601  CD1  LEU  196      19.935  55.255 100.071  1.00 19.18      HIGL
ATOM   1602  CD2  LEU  196      19.188  52.901 100.532  1.00 18.91      HIGL
ATOM   1603  C    LEU  196      22.219  51.490  97.745  1.00 18.86      HIGL
ATOM   1604  O    LEU  196      21.446  51.326  96.798  1.00 18.34      HIGL
ATOM   1605  N    SER  197      23.537  51.316  97.631  1.00 18.55      HIGL
ATOM   1606  CA   SER  197      24.126  50.913  96.355  1.00 18.26      HIGL
ATOM   1607  CB   SER  197      25.561  51.426  96.232  1.00 17.73      HIGL
ATOM   1608  OG   SER  197      26.436  50.722  97.091  1.00 18.32      HIGL
ATOM   1609  C    SER  197      24.113  49.397  96.184  1.00 18.38      HIGL
ATOM   1610  O    SER  197      24.322  48.884  95.088  1.00 18.24      HIGL
ATOM   1611  N    GLN  198      23.859  48.677  97.269  1.00 18.80      HIGL
ATOM   1612  CA   GLN  198      23.822  47.223  97.212  1.00 18.22      HIGL
ATOM   1613  CB   GLN  198      23.686  46.653  98.620  1.00 19.28      HIGL
ATOM   1614  CG   GLN  198      24.836  46.994  99.518  1.00 19.81      HIGL
ATOM   1615  CD   GLN  198      26.161  46.734  98.847  1.00 21.32      HIGL
ATOM   1616  OE1  GLN  198      26.353  45.693  98.210  1.00 21.68      HIGL
ATOM   1617  NE2  GLN  198      27.091  47.679  98.984  1.00 21.99      HIGL
ATOM   1618  C    GLN  198      22.682  46.707  96.340  1.00 17.65      HIGL
ATOM   1619  O    GLN  198      22.877  45.821  95.514  1.00 17.50      HIGL
ATOM   1620  N    GLY  199      21.486  47.253  96.536  1.00 17.03      HIGL
ATOM   1621  CA   GLY  199      20.347  46.821  95.745  1.00 15.62      HIGL
ATOM   1622  C    GLY  199      19.181  46.278  96.560  1.00 15.72      HIGL
ATOM   1623  O    GLY  199      18.045  46.710  96.364  1.00 15.60      HIGL
ATOM   1624  N    PRO  200      19.422  45.336  97.488  1.00 15.34      HIGL
```

Fig. 2 cont.

| | | | | | | | | | |
|---|---|---|---|---|---|---|---|---|---|
| ATOM | 1625 | CD | PRO | 200 | 20.704 | 44.672 | 97.783 | 1.00 14.88 | HIGL |
| ATOM | 1626 | CA | PRO | 200 | 18.350 | 44.764 | 98.306 | 1.00 14.92 | HIGL |
| ATOM | 1627 | CB | PRO | 200 | 19.104 | 43.814 | 99.225 | 1.00 16.05 | HIGL |
| ATOM | 1628 | CG | PRO | 200 | 20.245 | 43.367 | 98.366 | 1.00 14.92 | HIGL |
| ATOM | 1629 | C | PRO | 200 | 17.518 | 45.794 | 99.076 | 1.00 15.90 | HIGL |
| ATOM | 1630 | O | PRO | 200 | 16.288 | 45.699 | 99.112 | 1.00 14.94 | HIGL |
| ATOM | 1631 | N | PHE | 201 | 18.178 | 46.771 | 99.698 | 1.00 16.66 | HIGL |
| ATOM | 1632 | CA | PHE | 201 | 17.457 | 47.806 | 100.439 | 1.00 17.91 | HIGL |
| ATOM | 1633 | CB | PHE | 201 | 18.296 | 48.317 | 101.607 | 1.00 17.39 | HIGL |
| ATOM | 1634 | CG | PHE | 201 | 17.523 | 49.154 | 102.585 | 1.00 16.03 | HIGL |
| ATOM | 1635 | CD1 | PHE | 201 | 16.320 | 48.696 | 103.108 | 1.00 15.39 | HIGL |
| ATOM | 1636 | CD2 | PHE | 201 | 18.019 | 50.376 | 103.019 | 1.00 16.33 | HIGL |
| ATOM | 1637 | CE1 | PHE | 201 | 15.627 | 49.436 | 104.049 | 1.00 16.04 | HIGL |
| ATOM | 1638 | CE2 | PHE | 201 | 17.331 | 51.130 | 103.967 | 1.00 16.47 | HIGL |
| ATOM | 1639 | CZ | PHE | 201 | 16.133 | 50.658 | 104.484 | 1.00 16.02 | HIGL |
| ATOM | 1640 | C | PHE | 201 | 17.160 | 48.947 | 99.481 | 1.00 19.32 | HIGL |
| ATOM | 1641 | O | PHE | 201 | 18.052 | 49.707 | 99.113 | 1.00 19.83 | HIGL |
| ATOM | 1642 | N | GLU | 202 | 15.899 | 49.066 | 99.088 | 1.00 20.88 | HIGL |
| ATOM | 1643 | CA | GLU | 202 | 15.492 | 50.079 | 98.130 | 1.00 22.59 | HIGL |
| ATOM | 1644 | CB | GLU | 202 | 14.381 | 49.527 | 97.248 | 1.00 25.23 | HIGL |
| ATOM | 1645 | CG | GLU | 202 | 14.646 | 48.127 | 96.733 | 1.00 29.70 | HIGL |
| ATOM | 1646 | CD | GLU | 202 | 13.649 | 47.709 | 95.670 | 1.00 31.92 | HIGL |
| ATOM | 1647 | OE1 | GLU | 202 | 13.642 | 48.342 | 94.588 | 1.00 33.85 | HIGL |
| ATOM | 1648 | OE2 | GLU | 202 | 12.876 | 46.758 | 95.916 | 1.00 32.65 | HIGL |
| ATOM | 1649 | C | GLU | 202 | 15.033 | 51.394 | 98.724 | 1.00 22.89 | HIGL |
| ATOM | 1650 | O | GLU | 202 | 14.660 | 51.473 | 99.892 | 1.00 23.53 | HIGL |
| ATOM | 1651 | N | MET | 203 | 15.046 | 52.426 | 97.891 | 1.00 23.12 | HIGL |
| ATOM | 1652 | CA | MET | 203 | 14.624 | 53.748 | 98.309 | 1.00 23.40 | HIGL |
| ATOM | 1653 | CB | MET | 203 | 14.768 | 54.734 | 97.153 | 1.00 24.47 | HIGL |
| ATOM | 1654 | CG | MET | 203 | 16.202 | 55.007 | 96.767 | 1.00 27.52 | HIGL |
| ATOM | 1655 | SD | MET | 203 | 17.161 | 55.583 | 98.175 | 1.00 30.04 | HIGL |
| ATOM | 1656 | CE | MET | 203 | 16.411 | 57.199 | 98.411 | 1.00 29.30 | HIGL |
| ATOM | 1657 | C | MET | 203 | 13.185 | 53.748 | 98.808 | 1.00 22.78 | HIGL |
| ATOM | 1658 | O | MET | 203 | 12.835 | 54.522 | 99.696 | 1.00 22.95 | HIGL |
| ATOM | 1659 | N | SER | 204 | 12.352 | 52.878 | 98.251 | 1.00 21.87 | HIGL |
| ATOM | 1660 | CA | SER | 204 | 10.956 | 52.823 | 98.668 | 1.00 21.55 | HIGL |
| ATOM | 1661 | CB | SER | 204 | 10.077 | 52.307 | 97.521 | 1.00 21.02 | HIGL |
| ATOM | 1662 | OG | SER | 204 | 10.458 | 51.006 | 97.107 | 1.00 20.98 | HIGL |
| ATOM | 1663 | C | SER | 204 | 10.741 | 51.961 | 99.913 | 1.00 21.58 | HIGL |
| ATOM | 1664 | O | SER | 204 | 9.610 | 51.822 | 100.379 | 1.00 21.09 | HIGL |
| ATOM | 1665 | N | ASP | 205 | 11.821 | 51.388 | 100.448 | 1.00 20.89 | HIGL |
| ATOM | 1666 | CA | ASP | 205 | 11.723 | 50.545 | 101.640 | 1.00 20.32 | HIGL |
| ATOM | 1667 | CB | ASP | 205 | 12.882 | 49.539 | 101.716 | 1.00 20.48 | HIGL |
| ATOM | 1668 | CG | ASP | 205 | 12.750 | 48.411 | 100.710 | 1.00 19.95 | HIGL |
| ATOM | 1669 | OD1 | ASP | 205 | 11.607 | 47.992 | 100.424 | 1.00 20.12 | HIGL |
| ATOM | 1670 | OD2 | ASP | 205 | 13.792 | 47.933 | 100.220 | 1.00 19.93 | HIGL |
| ATOM | 1671 | C | ASP | 205 | 11.681 | 51.325 | 102.944 | 1.00 19.69 | HIGL |
| ATOM | 1672 | O | ASP | 205 | 11.284 | 50.780 | 103.971 | 1.00 19.83 | HIGL |
| ATOM | 1673 | N | PHE | 206 | 12.109 | 52.584 | 102.927 | 1.00 19.32 | HIGL |
| ATOM | 1674 | CA | PHE | 206 | 12.062 | 53.377 | 104.149 | 1.00 19.43 | HIGL |
| ATOM | 1675 | CB | PHE | 206 | 13.413 | 53.376 | 104.877 | 1.00 19.75 | HIGL |
| ATOM | 1676 | CG | PHE | 206 | 14.492 | 54.155 | 104.194 | 1.00 20.11 | HIGL |
| ATOM | 1677 | CD1 | PHE | 206 | 14.975 | 53.768 | 102.951 | 1.00 20.98 | HIGL |
| ATOM | 1678 | CD2 | PHE | 206 | 15.090 | 55.233 | 104.839 | 1.00 19.93 | HIGL |
| ATOM | 1679 | CE1 | PHE | 206 | 16.048 | 54.442 | 102.364 | 1.00 20.58 | HIGL |
| ATOM | 1680 | CE2 | PHE | 206 | 16.154 | 55.908 | 104.264 | 1.00 19.23 | HIGL |
| ATOM | 1681 | CZ | PHE | 206 | 16.636 | 55.509 | 103.025 | 1.00 19.95 | HIGL |
| ATOM | 1682 | C | PHE | 206 | 11.588 | 54.791 | 103.900 | 1.00 19.04 | HIGL |
| ATOM | 1683 | O | PHE | 206 | 11.597 | 55.267 | 102.773 | 1.00 19.32 | HIGL |
| ATOM | 1684 | N | ASP | 207 | 11.173 | 55.462 | 104.965 | 1.00 19.22 | HIGL |
| ATOM | 1685 | CA | ASP | 207 | 10.636 | 56.810 | 104.841 | 1.00 19.23 | HIGL |
| ATOM | 1686 | CB | ASP | 207 | 9.175 | 56.802 | 105.286 | 1.00 19.16 | HIGL |
| ATOM | 1687 | CG | ASP | 207 | 8.407 | 55.625 | 104.718 | 1.00 19.38 | HIGL |
| ATOM | 1688 | OD1 | ASP | 207 | 8.277 | 55.543 | 103.480 | 1.00 20.06 | HIGL |
| ATOM | 1689 | OD2 | ASP | 207 | 7.942 | 54.778 | 105.507 | 1.00 18.36 | HIGL |

Fig. 2 cont.

```
ATOM   1690 C    ASP  207      11.381  57.871 105.629  1.00 18.86           HIGL
ATOM   1691 O    ASP  207      11.381  59.045 105.260  1.00 19.26           HIGL
ATOM   1692 N    MET  208      12.015  57.466 106.716  1.00 18.21           HIGL
ATOM   1693 CA   MET  208      12.714  58.433 107.540  1.00 18.11           HIGL
ATOM   1694 CB   MET  208      12.006  58.596 108.894  1.00 18.41           HIGL
ATOM   1695 CG   MET  208      10.534  58.987 108.820  1.00 20.52           HIGL
ATOM   1696 SD   MET  208       9.808  59.310 110.452  1.00 22.01           HIGL
ATOM   1697 CE   MET  208      10.379  60.977 110.731  1.00 20.87           HIGL
ATOM   1698 C    MET  208      14.161  58.083 107.804  1.00 17.69           HIGL
ATOM   1699 O    MET  208      14.579  56.928 107.707  1.00 17.61           HIGL
ATOM   1700 N    MET  209      14.918  59.119 108.129  1.00 16.92           HIGL
ATOM   1701 CA   MET  209      16.308  58.994 108.488  1.00 16.07           HIGL
ATOM   1702 CB   MET  209      17.213  59.645 107.443  1.00 16.00           HIGL
ATOM   1703 CG   MET  209      17.373  58.828 106.170  1.00 16.81           HIGL
ATOM   1704 SD   MET  209      18.554  59.575 105.009  1.00 19.85           HIGL
ATOM   1705 CE   MET  209      18.496  58.407 103.621  1.00 17.63           HIGL
ATOM   1706 C    MET  209      16.374  59.747 109.809  1.00 16.16           HIGL
ATOM   1707 O    MET  209      16.174  60.969 109.850  1.00 15.45           HIGL
ATOM   1708 N    GLY  210      16.600  59.001 110.891  1.00 15.65           HIGL
ATOM   1709 CA   GLY  210      16.695  59.603 112.210  1.00 14.42           HIGL
ATOM   1710 C    GLY  210      18.150  59.686 112.629  1.00 14.08           HIGL
ATOM   1711 O    GLY  210      18.961  58.883 112.175  1.00 13.68           HIGL
ATOM   1712 N    VAL  211      18.490  60.651 113.484  1.00 13.61           HIGL
ATOM   1713 CA   VAL  211      19.869  60.802 113.936  1.00 13.15           HIGL
ATOM   1714 CB   VAL  211      20.627  61.892 113.141  1.00 12.33           HIGL
ATOM   1715 CG1  VAL  211      20.537  61.611 111.663  1.00 13.18           HIGL
ATOM   1716 CG2  VAL  211      20.067  63.271 113.465  1.00 11.20           HIGL
ATOM   1717 C    VAL  211      19.984  61.175 115.400  1.00 13.77           HIGL
ATOM   1718 O    VAL  211      19.118  61.837 115.958  1.00 13.69           HIGL
ATOM   1719 N    SER  212      21.069  60.741 116.022  1.00 15.09           HIGL
ATOM   1720 CA   SER  212      21.313  61.079 117.411  1.00 15.93           HIGL
ATOM   1721 CB   SER  212      22.016  59.929 118.130  1.00 16.46           HIGL
ATOM   1722 OG   SER  212      21.185  58.781 118.176  1.00 17.21           HIGL
ATOM   1723 C    SER  212      22.208  62.315 117.376  1.00 16.32           HIGL
ATOM   1724 O    SER  212      23.149  62.395 116.582  1.00 16.25           HIGL
ATOM   1725 N    PHE  213      21.890  63.289 118.214  1.00 15.47           HIGL
ATOM   1726 CA   PHE  213      22.666  64.512 118.267  1.00 15.45           HIGL
ATOM   1727 CB   PHE  213      21.923  65.634 117.528  1.00 15.73           HIGL
ATOM   1728 CG   PHE  213      22.673  66.936 117.484  1.00 16.40           HIGL
ATOM   1729 CD1  PHE  213      23.883  67.036 116.799  1.00 16.45           HIGL
ATOM   1730 CD2  PHE  213      22.183  68.057 118.146  1.00 16.56           HIGL
ATOM   1731 CE1  PHE  213      24.596  68.231 116.777  1.00 15.36           HIGL
ATOM   1732 CE2  PHE  213      22.889  69.257 118.130  1.00 16.74           HIGL
ATOM   1733 CZ   PHE  213      24.100  69.340 117.443  1.00 16.06           HIGL
ATOM   1734 C    PHE  213      22.849  64.850 119.738  1.00 14.96           HIGL
ATOM   1735 O    PHE  213      21.888  65.175 120.436  1.00 15.30           HIGL
ATOM   1736 N    TYR  214      24.085  64.742 120.208  1.00 14.20           HIGL
ATOM   1737 CA   TYR  214      24.420  65.016 121.600  1.00 13.58           HIGL
ATOM   1738 CB   TYR  214      24.875  63.736 122.298  1.00 12.69           HIGL
ATOM   1739 CG   TYR  214      23.775  62.742 122.558  1.00 11.90           HIGL
ATOM   1740 CD1  TYR  214      22.902  62.906 123.631  1.00 11.71           HIGL
ATOM   1741 CE1  TYR  214      21.885  61.989 123.874  1.00 11.65           HIGL
ATOM   1742 CD2  TYR  214      23.602  61.635 121.731  1.00 10.99           HIGL
ATOM   1743 CE2  TYR  214      22.591  60.717 121.962  1.00 11.61           HIGL
ATOM   1744 CZ   TYR  214      21.735  60.899 123.035  1.00 11.76           HIGL
ATOM   1745 OH   TYR  214      20.722  59.997 123.259  1.00 12.70           HIGL
ATOM   1746 C    TYR  214      25.541  66.035 121.660  1.00 14.26           HIGL
ATOM   1747 O    TYR  214      26.346  66.141 120.742  1.00 15.11           HIGL
ATOM   1748 N    PRO  215      25.619  66.794 122.755  1.00 14.63           HIGL
ATOM   1749 CD   PRO  215      24.581  67.036 123.775  1.00 14.17           HIGL
ATOM   1750 CA   PRO  215      26.682  67.790 122.847  1.00 14.95           HIGL
ATOM   1751 CB   PRO  215      25.990  68.930 123.572  1.00 14.94           HIGL
ATOM   1752 CG   PRO  215      25.175  68.176 124.596  1.00 14.41           HIGL
ATOM   1753 C    PRO  215      27.924  67.322 123.598  1.00 15.93           HIGL
ATOM   1754 O    PRO  215      28.999  67.898 123.437  1.00 16.94           HIGL
```

Fig. 2 cont.

```
ATOM   1755  N    PHE  216      27.778  66.276 124.405  1.00 16.00      HIGL
ATOM   1756  CA   PHE  216      28.878  65.791 125.231  1.00 16.24      HIGL
ATOM   1757  CB   PHE  216      28.350  65.520 126.644  1.00 16.24      HIGL
ATOM   1758  CG   PHE  216      27.018  64.792 126.677  1.00 16.08      HIGL
ATOM   1759  CD1  PHE  216      26.861  63.555 126.055  1.00 15.04      HIGL
ATOM   1760  CD2  PHE  216      25.924  65.347 127.343  1.00 15.16      HIGL
ATOM   1761  CE1  PHE  216      25.638  62.889 126.095  1.00 15.26      HIGL
ATOM   1762  CE2  PHE  216      24.703  64.686 127.386  1.00 14.85      HIGL
ATOM   1763  CZ   PHE  216      24.560  63.453 126.759  1.00 14.72      HIGL
ATOM   1764  C    PHE  216      29.709  64.595 124.763  1.00 16.64      HIGL
ATOM   1765  O    PHE  216      30.291  63.882 125.580  1.00 16.43      HIGL
ATOM   1766  N    TYR  217      29.789  64.377 123.459  1.00 17.14      HIGL
ATOM   1767  CA   TYR  217      30.582  63.260 122.947  1.00 17.62      HIGL
ATOM   1768  CB   TYR  217      29.675  62.193 122.323  1.00 16.27      HIGL
ATOM   1769  CG   TYR  217      28.847  61.399 123.315  1.00 16.34      HIGL
ATOM   1770  CD1  TYR  217      29.440  60.785 124.421  1.00 16.29      HIGL
ATOM   1771  CE1  TYR  217      28.687  60.024 125.312  1.00 15.97      HIGL
ATOM   1772  CD2  TYR  217      27.477  61.232 123.131  1.00 15.38      HIGL
ATOM   1773  CE2  TYR  217      26.717  60.477 124.016  1.00 14.99      HIGL
ATOM   1774  CZ   TYR  217      27.324  59.875 125.102  1.00 16.23      HIGL
ATOM   1775  OH   TYR  217      26.566  59.120 125.977  1.00 17.30      HIGL
ATOM   1776  C    TYR  217      31.605  63.723 121.909  1.00 18.43      HIGL
ATOM   1777  O    TYR  217      32.308  62.908 121.317  1.00 19.53      HIGL
ATOM   1778  N    SER  218      31.693  65.034 121.703  1.00 18.33      HIGL
ATOM   1779  CA   SER  218      32.616  65.598 120.724  1.00 17.79      HIGL
ATOM   1780  CB   SER  218      32.501  64.839 119.403  1.00 17.69      HIGL
ATOM   1781  OG   SER  218      33.128  65.542 118.347  1.00 18.59      HIGL
ATOM   1782  C    SER  218      32.298  67.070 120.485  1.00 17.69      HIGL
ATOM   1783  O    SER  218      31.141  67.438 120.306  1.00 18.71      HIGL
ATOM   1784  N    ALA  219      33.321  67.912 120.476  1.00 17.22      HIGL
ATOM   1785  CA   ALA  219      33.104  69.337 120.252  1.00 17.23      HIGL
ATOM   1786  CB   ALA  219      34.382  70.118 120.554  1.00 16.44      HIGL
ATOM   1787  C    ALA  219      32.661  69.589 118.816  1.00 16.60      HIGL
ATOM   1788  O    ALA  219      32.258  70.696 118.467  1.00 17.34      HIGL
ATOM   1789  N    SER  220      32.730  68.550 117.991  1.00 16.51      HIGL
ATOM   1790  CA   SER  220      32.355  68.641 116.581  1.00 16.08      HIGL
ATOM   1791  CB   SER  220      32.954  67.466 115.809  1.00 15.86      HIGL
ATOM   1792  OG   SER  220      34.364  67.460 115.917  1.00 16.86      HIGL
ATOM   1793  C    SER  220      30.857  68.682 116.317  1.00 15.46      HIGL
ATOM   1794  O    SER  220      30.432  69.049 115.229  1.00 14.91      HIGL
ATOM   1795  N    ALA  221      30.061  68.300 117.309  1.00 15.99      HIGL
ATOM   1796  CA   ALA  221      28.606  68.279 117.164  1.00 16.78      HIGL
ATOM   1797  CB   ALA  221      27.995  67.427 118.271  1.00 16.23      HIGL
ATOM   1798  C    ALA  221      27.969  69.673 117.164  1.00 17.33      HIGL
ATOM   1799  O    ALA  221      27.074  69.959 117.963  1.00 17.73      HIGL
ATOM   1800  N    THR  222      28.422  70.534 116.260  1.00 17.34      HIGL
ATOM   1801  CA   THR  222      27.889  71.888 116.168  1.00 17.44      HIGL
ATOM   1802  CB   THR  222      28.805  72.788 115.326  1.00 16.76      HIGL
ATOM   1803  OG1  THR  222      28.859  72.290 113.988  1.00 16.54      HIGL
ATOM   1804  CG2  THR  222      30.211  72.801 115.899  1.00 17.46      HIGL
ATOM   1805  C    THR  222      26.505  71.891 115.531  1.00 18.33      HIGL
ATOM   1806  O    THR  222      26.189  71.044 114.692  1.00 19.58      HIGL
ATOM   1807  N    LEU  223      25.675  72.842 115.933  1.00 18.21      HIGL
ATOM   1808  CA   LEU  223      24.338  72.949 115.374  1.00 18.34      HIGL
ATOM   1809  CB   LEU  223      23.611  74.143 115.991  1.00 18.27      HIGL
ATOM   1810  CG   LEU  223      23.370  74.045 117.500  1.00 19.89      HIGL
ATOM   1811  CD1  LEU  223      22.888  75.388 118.034  1.00 19.53      HIGL
ATOM   1812  CD2  LEU  223      22.340  72.943 117.786  1.00 19.06      HIGL
ATOM   1813  C    LEU  223      24.437  73.122 113.860  1.00 18.82      HIGL
ATOM   1814  O    LEU  223      23.605  72.608 113.120  1.00 20.15      HIGL
ATOM   1815  N    ASP  224      25.457  73.846 113.406  1.00 18.59      HIGL
ATOM   1816  CA   ASP  224      25.669  74.086 111.982  1.00 19.10      HIGL
ATOM   1817  CB   ASP  224      26.858  75.026 111.769  1.00 18.84      HIGL
ATOM   1818  CG   ASP  224      26.468  76.494 111.816  1.00 18.91      HIGL
ATOM   1819  OD1  ASP  224      25.286  76.812 112.069  1.00 19.14      HIGL
```

Fig. 2 cont.

```
ATOM   1820 OD2 ASP 224     27.355 77.341 111.593  1.00 19.90      HIGL
ATOM   1821 C   ASP 224     25.915 72.793 111.214  1.00 19.58      HIGL
ATOM   1822 O   ASP 224     25.341 72.583 110.146  1.00 20.23      HIGL
ATOM   1823 N   SER 225     26.785 71.939 111.750  1.00 19.67      HIGL
ATOM   1824 CA  SER 225     27.095 70.664 111.112  1.00 19.06      HIGL
ATOM   1825 CB  SER 225     28.155 69.908 111.907  1.00 18.84      HIGL
ATOM   1826 OG  SER 225     29.403 70.567 111.840  1.00 18.91      HIGL
ATOM   1827 C   SER 225     25.838 69.811 110.997  1.00 19.40      HIGL
ATOM   1828 O   SER 225     25.601 69.186 109.968  1.00 19.64      HIGL
ATOM   1829 N   LEU 226     25.039 69.774 112.058  1.00 19.24      HIGL
ATOM   1830 CA  LEU 226     23.799 69.009 112.026  1.00 19.90      HIGL
ATOM   1831 CB  LEU 226     23.069 69.103 113.372  1.00 18.41      HIGL
ATOM   1832 CG  LEU 226     21.655 68.517 113.419  1.00 18.06      HIGL
ATOM   1833 CD1 LEU 226     21.698 67.027 113.124  1.00 17.29      HIGL
ATOM   1834 CD2 LEU 226     21.042 68.768 114.786  1.00 18.51      HIGL
ATOM   1835 C   LEU 226     22.943 69.628 110.925  1.00 20.05      HIGL
ATOM   1836 O   LEU 226     22.369 68.932 110.086  1.00 19.89      HIGL
ATOM   1837 N   ARG 227     22.883 70.951 110.941  1.00 20.56      HIGL
ATOM   1838 CA  ARG 227     22.127 71.717 109.965  1.00 22.15      HIGL
ATOM   1839 CB  ARG 227     22.374 73.203 110.200  1.00 23.23      HIGL
ATOM   1840 CG  ARG 227     21.847 74.113 109.125  1.00 23.67      HIGL
ATOM   1841 CD  ARG 227     20.585 74.801 109.561  1.00 25.35      HIGL
ATOM   1842 NE  ARG 227     20.264 75.881 108.636  1.00 27.51      HIGL
ATOM   1843 CZ  ARG 227     20.963 77.007 108.534  1.00 27.97      HIGL
ATOM   1844 NH1 ARG 227     22.025 77.213 109.308  1.00 27.24      HIGL
ATOM   1845 NH2 ARG 227     20.609 77.919 107.639  1.00 28.04      HIGL
ATOM   1846 C   ARG 227     22.532 71.349 108.541  1.00 22.77      HIGL
ATOM   1847 O   ARG 227     21.682 71.091 107.685  1.00 23.17      HIGL
ATOM   1848 N   ARG 228     23.835 71.337 108.292  1.00 22.62      HIGL
ATOM   1849 CA  ARG 228     24.351 71.005 106.974  1.00 23.23      HIGL
ATOM   1850 CB  ARG 228     25.854 71.275 106.907  1.00 25.19      HIGL
ATOM   1851 CG  ARG 228     26.497 70.808 105.611  1.00 27.85      HIGL
ATOM   1852 CD  ARG 228     27.951 71.218 105.576  1.00 31.64      HIGL
ATOM   1853 NE  ARG 228     28.217 72.426 104.784  1.00 34.16      HIGL
ATOM   1854 CZ  ARG 228     27.482 73.539 104.787  1.00 34.92      HIGL
ATOM   1855 NH1 ARG 228     26.385 73.644 105.537  1.00 34.00      HIGL
ATOM   1856 NH2 ARG 228     27.869 74.572 104.049  1.00 34.79      HIGL
ATOM   1857 C   ARG 228     24.106 69.553 106.623  1.00 21.71      HIGL
ATOM   1858 O   ARG 228     23.697 69.233 105.511  1.00 21.40      HIGL
ATOM   1859 N   SER 229     24.372 68.677 107.583  1.00 20.74      HIGL
ATOM   1860 CA  SER 229     24.209 67.248 107.385  1.00 19.19      HIGL
ATOM   1861 CB  SER 229     24.596 66.499 108.657  1.00 17.46      HIGL
ATOM   1862 OG  SER 229     24.667 65.112 108.415  1.00 16.03      HIGL
ATOM   1863 C   SER 229     22.778 66.920 106.985  1.00 19.19      HIGL
ATOM   1864 O   SER 229     22.551 66.215 106.001  1.00 19.76      HIGL
ATOM   1865 N   LEU 230     21.816 67.443 107.738  1.00 18.51      HIGL
ATOM   1866 CA  LEU 230     20.414 67.200 107.437  1.00 18.83      HIGL
ATOM   1867 CB  LEU 230     19.513 67.904 108.459  1.00 18.57      HIGL
ATOM   1868 CG  LEU 230     19.748 67.471 109.906  1.00 18.99      HIGL
ATOM   1869 CD1 LEU 230     18.765 68.159 110.830  1.00 18.90      HIGL
ATOM   1870 CD2 LEU 230     19.611 65.966 110.011  1.00 19.09      HIGL
ATOM   1871 C   LEU 230     20.072 67.673 106.025  1.00 18.43      HIGL
ATOM   1872 O   LEU 230     19.440 66.944 105.261  1.00 18.80      HIGL
ATOM   1873 N   ASN 231     20.492 68.887 105.678  1.00 17.99      HIGL
ATOM   1874 CA  ASN 231     20.222 69.418 104.348  1.00 18.50      HIGL
ATOM   1875 CB  ASN 231     20.775 70.832 104.203  1.00 20.27      HIGL
ATOM   1876 CG  ASN 231     19.831 71.884 104.755  1.00 21.88      HIGL
ATOM   1877 OD1 ASN 231     18.703 72.029 104.276  1.00 23.81      HIGL
ATOM   1878 ND2 ASN 231     20.284 72.624 105.763  1.00 21.50      HIGL
ATOM   1879 C   ASN 231     20.815 68.529 103.271  1.00 18.28      HIGL
ATOM   1880 O   ASN 231     20.164 68.262 102.256  1.00 17.76      HIGL
ATOM   1881 N   ASN 232     22.042 68.064 103.497  1.00 17.66      HIGL
ATOM   1882 CA  ASN 232     22.703 67.190 102.534  1.00 17.99      HIGL
ATOM   1883 CB  ASN 232     24.141 66.893 102.963  1.00 17.29      HIGL
ATOM   1884 CG  ASN 232     25.037 68.116 102.915  1.00 16.38      HIGL
```

Fig. 2 cont.

| | | | | | | | | | |
|---|---|---|---|---|---|---|---|---|---|
| ATOM | 1885 | OD1 | ASN | 232 | 24.686 | 69.141 | 102.334 | 1.00 15.50 | HIGL |
| ATOM | 1886 | ND2 | ASN | 232 | 26.213 | 68.005 | 103.521 | 1.00 16.64 | HIGL |
| ATOM | 1887 | C | ASN | 232 | 21.948 | 65.872 | 102.375 | 1.00 18.25 | HIGL |
| ATOM | 1888 | O | ASN | 232 | 21.748 | 65.387 | 101.259 | 1.00 17.98 | HIGL |
| ATOM | 1889 | N | MET | 233 | 21.536 | 65.298 | 103.501 | 1.00 18.52 | HIGL |
| ATOM | 1890 | CA | MET | 233 | 20.805 | 64.033 | 103.507 | 1.00 18.43 | HIGL |
| ATOM | 1891 | CB | MET | 233 | 20.538 | 63.589 | 104.951 | 1.00 18.18 | HIGL |
| ATOM | 1892 | CG | MET | 233 | 21.795 | 63.269 | 105.754 | 1.00 18.25 | HIGL |
| ATOM | 1893 | SD | MET | 233 | 21.474 | 63.063 | 107.531 | 1.00 19.43 | HIGL |
| ATOM | 1894 | CE | MET | 233 | 20.199 | 61.766 | 107.504 | 1.00 17.54 | HIGL |
| ATOM | 1895 | C | MET | 233 | 19.485 | 64.177 | 102.758 | 1.00 18.12 | HIGL |
| ATOM | 1896 | O | MET | 233 | 19.183 | 63.394 | 101.851 | 1.00 18.23 | HIGL |
| ATOM | 1897 | N | VAL | 234 | 18.707 | 65.186 | 103.146 | 1.00 17.24 | HIGL |
| ATOM | 1898 | CA | VAL | 234 | 17.411 | 65.455 | 102.530 | 1.00 16.91 | HIGL |
| ATOM | 1899 | CB | VAL | 234 | 16.744 | 66.687 | 103.179 | 1.00 15.88 | HIGL |
| ATOM | 1900 | CG1 | VAL | 234 | 15.486 | 67.056 | 102.420 | 1.00 15.35 | HIGL |
| ATOM | 1901 | CG2 | VAL | 234 | 16.413 | 66.390 | 104.638 | 1.00 15.47 | HIGL |
| ATOM | 1902 | C | VAL | 234 | 17.502 | 65.678 | 101.017 | 1.00 16.63 | HIGL |
| ATOM | 1903 | O | VAL | 234 | 16.784 | 65.045 | 100.245 | 1.00 16.27 | HIGL |
| ATOM | 1904 | N | SER | 235 | 18.391 | 66.575 | 100.603 | 1.00 16.80 | HIGL |
| ATOM | 1905 | CA | SER | 235 | 18.573 | 66.882 | 99.190 | 1.00 17.13 | HIGL |
| ATOM | 1906 | CB | SER | 235 | 19.578 | 68.023 | 99.024 | 1.00 17.78 | HIGL |
| ATOM | 1907 | OG | SER | 235 | 19.784 | 68.317 | 97.656 | 1.00 17.56 | HIGL |
| ATOM | 1908 | C | SER | 235 | 19.049 | 65.677 | 98.384 | 1.00 16.92 | HIGL |
| ATOM | 1909 | O | SER | 235 | 18.768 | 65.562 | 97.190 | 1.00 17.15 | HIGL |
| ATOM | 1910 | N | ARG | 236 | 19.759 | 64.774 | 99.045 | 1.00 16.40 | HIGL |
| ATOM | 1911 | CA | ARG | 236 | 20.290 | 63.595 | 98.384 | 1.00 16.55 | HIGL |
| ATOM | 1912 | CB | ARG | 236 | 21.568 | 63.161 | 99.084 | 1.00 17.11 | HIGL |
| ATOM | 1913 | CG | ARG | 236 | 22.156 | 61.872 | 98.562 | 1.00 18.73 | HIGL |
| ATOM | 1914 | CD | ARG | 236 | 22.995 | 62.074 | 97.321 | 1.00 19.62 | HIGL |
| ATOM | 1915 | NE | ARG | 236 | 23.973 | 60.997 | 97.231 | 1.00 24.11 | HIGL |
| ATOM | 1916 | CZ | ARG | 236 | 23.732 | 59.794 | 96.710 | 1.00 25.92 | HIGL |
| ATOM | 1917 | NH1 | ARG | 236 | 22.532 | 59.505 | 96.205 | 1.00 24.62 | HIGL |
| ATOM | 1918 | NH2 | ARG | 236 | 24.691 | 58.867 | 96.725 | 1.00 25.67 | HIGL |
| ATOM | 1919 | C | ARG | 236 | 19.343 | 62.400 | 98.298 | 1.00 16.75 | HIGL |
| ATOM | 1920 | O | ARG | 236 | 19.259 | 61.740 | 97.259 | 1.00 15.62 | HIGL |
| ATOM | 1921 | N | TRP | 237 | 18.637 | 62.111 | 99.385 | 1.00 16.82 | HIGL |
| ATOM | 1922 | CA | TRP | 237 | 17.745 | 60.961 | 99.390 | 1.00 16.41 | HIGL |
| ATOM | 1923 | CB | TRP | 237 | 18.224 | 59.966 | 100.453 | 1.00 16.05 | HIGL |
| ATOM | 1924 | CG | TRP | 237 | 19.505 | 59.294 | 100.040 | 1.00 14.89 | HIGL |
| ATOM | 1925 | CD2 | TRP | 237 | 20.817 | 59.526 | 100.571 | 1.00 14.04 | HIGL |
| ATOM | 1926 | CE2 | TRP | 237 | 21.717 | 58.738 | 99.817 | 1.00 14.30 | HIGL |
| ATOM | 1927 | CE3 | TRP | 237 | 21.322 | 60.327 | 101.604 | 1.00 13.86 | HIGL |
| ATOM | 1928 | CD1 | TRP | 237 | 19.659 | 58.398 | 99.023 | 1.00 15.03 | HIGL |
| ATOM | 1929 | NE1 | TRP | 237 | 20.983 | 58.060 | 98.882 | 1.00 14.90 | HIGL |
| ATOM | 1930 | CZ2 | TRP | 237 | 23.097 | 58.727 | 100.061 | 1.00 13.70 | HIGL |
| ATOM | 1931 | CZ3 | TRP | 237 | 22.695 | 60.319 | 101.847 | 1.00 13.61 | HIGL |
| ATOM | 1932 | CH2 | TRP | 237 | 23.566 | 59.522 | 101.074 | 1.00 14.26 | HIGL |
| ATOM | 1933 | C | TRP | 237 | 16.266 | 61.281 | 99.557 | 1.00 16.86 | HIGL |
| ATOM | 1934 | O | TRP | 237 | 15.430 | 60.383 | 99.522 | 1.00 18.12 | HIGL |
| ATOM | 1935 | N | GLY | 238 | 15.953 | 62.562 | 99.732 | 1.00 16.74 | HIGL |
| ATOM | 1936 | CA | GLY | 238 | 14.574 | 62.995 | 99.869 | 1.00 16.56 | HIGL |
| ATOM | 1937 | C | GLY | 238 | 13.714 | 62.388 | 100.966 | 1.00 17.47 | HIGL |
| ATOM | 1938 | O | GLY | 238 | 12.486 | 62.346 | 100.836 | 1.00 17.51 | HIGL |
| ATOM | 1939 | N | LYS | 239 | 14.330 | 61.933 | 102.053 | 1.00 16.96 | HIGL |
| ATOM | 1940 | CA | LYS | 239 | 13.564 | 61.339 | 103.146 | 1.00 16.74 | HIGL |
| ATOM | 1941 | CB | LYS | 239 | 14.327 | 60.152 | 103.724 | 1.00 16.66 | HIGL |
| ATOM | 1942 | CG | LYS | 239 | 14.606 | 59.053 | 102.730 | 1.00 17.05 | HIGL |
| ATOM | 1943 | CD | LYS | 239 | 13.312 | 58.511 | 102.175 | 1.00 15.57 | HIGL |
| ATOM | 1944 | CE | LYS | 239 | 13.561 | 57.342 | 101.262 | 1.00 14.83 | HIGL |
| ATOM | 1945 | NZ | LYS | 239 | 12.275 | 56.925 | 100.661 | 1.00 14.06 | HIGL |
| ATOM | 1946 | C | LYS | 239 | 13.302 | 62.344 | 104.261 | 1.00 16.96 | HIGL |
| ATOM | 1947 | O | LYS | 239 | 14.036 | 63.323 | 104.398 | 1.00 17.61 | HIGL |
| ATOM | 1948 | N | GLU | 240 | 12.257 | 62.118 | 105.056 | 1.00 17.26 | HIGL |
| ATOM | 1949 | CA | GLU | 240 | 11.985 | 63.016 | 106.181 | 1.00 16.82 | HIGL |

Fig. 2 cont.

| | | | | | | | | | |
|---|---|---|---|---|---|---|---|---|---|
| ATOM | 1950 | CB  | GLU | 240 | 10.615 | 62.743 | 106.808 | 1.00 17.65 | HIGL |
| ATOM | 1951 | CG  | GLU | 240 | 9.430  | 63.085 | 105.923 | 1.00 18.86 | HIGL |
| ATOM | 1952 | CD  | GLU | 240 | 8.116  | 63.080 | 106.690 | 1.00 20.65 | HIGL |
| ATOM | 1953 | OE1 | GLU | 240 | 7.818  | 62.067 | 107.353 | 1.00 21.31 | HIGL |
| ATOM | 1954 | OE2 | GLU | 240 | 7.381  | 64.091 | 106.634 | 1.00 21.43 | HIGL |
| ATOM | 1955 | C   | GLU | 240 | 13.088 | 62.751 | 107.209 | 1.00 16.31 | HIGL |
| ATOM | 1956 | O   | GLU | 240 | 13.562 | 61.621 | 107.360 | 1.00 15.76 | HIGL |
| ATOM | 1957 | N   | VAL | 241 | 13.493 | 63.793 | 107.917 | 1.00 15.69 | HIGL |
| ATOM | 1958 | CA  | VAL | 241 | 14.571 | 63.666 | 108.883 | 1.00 15.54 | HIGL |
| ATOM | 1959 | CB  | VAL | 241 | 15.754 | 64.547 | 108.432 | 1.00 14.72 | HIGL |
| ATOM | 1960 | CG1 | VAL | 241 | 16.789 | 64.623 | 109.501 | 1.00 17.13 | HIGL |
| ATOM | 1961 | CG2 | VAL | 241 | 16.361 | 63.974 | 107.178 | 1.00 15.36 | HIGL |
| ATOM | 1962 | C   | VAL | 241 | 14.149 | 64.045 | 110.299 | 1.00 15.60 | HIGL |
| ATOM | 1963 | O   | VAL | 241 | 13.161 | 64.758 | 110.495 | 1.00 16.76 | HIGL |
| ATOM | 1964 | N   | ALA | 242 | 14.900 | 63.573 | 111.290 | 1.00 14.40 | HIGL |
| ATOM | 1965 | CA  | ALA | 242 | 14.577 | 63.888 | 112.673 | 1.00 13.72 | HIGL |
| ATOM | 1966 | CB  | ALA | 242 | 13.286 | 63.177 | 113.082 | 1.00 12.95 | HIGL |
| ATOM | 1967 | C   | ALA | 242 | 15.681 | 63.519 | 113.645 | 1.00 13.47 | HIGL |
| ATOM | 1968 | O   | ALA | 242 | 16.428 | 62.561 | 113.429 | 1.00 13.51 | HIGL |
| ATOM | 1969 | N   | VAL | 243 | 15.791 | 64.303 | 114.711 | 1.00 13.04 | HIGL |
| ATOM | 1970 | CA  | VAL | 243 | 16.760 | 64.023 | 115.758 | 1.00 13.08 | HIGL |
| ATOM | 1971 | CB  | VAL | 243 | 17.192 | 65.294 | 116.497 | 1.00 12.64 | HIGL |
| ATOM | 1972 | CG1 | VAL | 243 | 17.918 | 64.924 | 117.771 | 1.00 12.23 | HIGL |
| ATOM | 1973 | CG2 | VAL | 243 | 18.088 | 66.125 | 115.604 | 1.00 12.08 | HIGL |
| ATOM | 1974 | C   | VAL | 243 | 15.964 | 63.139 | 116.701 | 1.00 13.56 | HIGL |
| ATOM | 1975 | O   | VAL | 243 | 15.014 | 63.593 | 117.346 | 1.00 13.37 | HIGL |
| ATOM | 1976 | N   | VAL | 244 | 16.328 | 61.866 | 116.754 | 1.00 14.00 | HIGL |
| ATOM | 1977 | CA  | VAL | 244 | 15.608 | 60.927 | 117.593 | 1.00 14.42 | HIGL |
| ATOM | 1978 | CB  | VAL | 244 | 15.476 | 59.569 | 116.877 | 1.00 13.73 | HIGL |
| ATOM | 1979 | CG1 | VAL | 244 | 14.782 | 59.774 | 115.548 | 1.00 13.75 | HIGL |
| ATOM | 1980 | CG2 | VAL | 244 | 16.831 | 58.955 | 116.653 | 1.00 12.09 | HIGL |
| ATOM | 1981 | C   | VAL | 244 | 16.242 | 60.742 | 118.965 | 1.00 15.18 | HIGL |
| ATOM | 1982 | O   | VAL | 244 | 15.748 | 59.965 | 119.783 | 1.00 14.93 | HIGL |
| ATOM | 1983 | N   | GLU | 245 | 17.320 | 61.479 | 119.218 | 1.00 15.57 | HIGL |
| ATOM | 1984 | CA  | GLU | 245 | 18.023 | 61.397 | 120.490 | 1.00 16.66 | HIGL |
| ATOM | 1985 | CB  | GLU | 245 | 18.933 | 60.176 | 120.517 | 1.00 17.90 | HIGL |
| ATOM | 1986 | CG  | GLU | 245 | 18.295 | 58.883 | 120.921 | 1.00 19.86 | HIGL |
| ATOM | 1987 | CD  | GLU | 245 | 19.325 | 57.778 | 121.021 | 1.00 21.19 | HIGL |
| ATOM | 1988 | OE1 | GLU | 245 | 20.395 | 58.018 | 121.624 | 1.00 22.19 | HIGL |
| ATOM | 1989 | OE2 | GLU | 245 | 19.071 | 56.673 | 120.502 | 1.00 22.22 | HIGL |
| ATOM | 1990 | C   | GLU | 245 | 18.892 | 62.616 | 120.780 | 1.00 17.25 | HIGL |
| ATOM | 1991 | O   | GLU | 245 | 19.756 | 62.984 | 119.979 | 1.00 17.63 | HIGL |
| ATOM | 1992 | N   | THR | 246 | 18.675 | 63.226 | 121.938 | 1.00 16.70 | HIGL |
| ATOM | 1993 | CA  | THR | 246 | 19.468 | 64.372 | 122.350 | 1.00 16.24 | HIGL |
| ATOM | 1994 | CB  | THR | 246 | 19.133 | 65.632 | 121.534 | 1.00 16.24 | HIGL |
| ATOM | 1995 | OG1 | THR | 246 | 20.097 | 66.649 | 121.831 | 1.00 16.02 | HIGL |
| ATOM | 1996 | CG2 | THR | 246 | 17.737 | 66.146 | 121.872 | 1.00 14.97 | HIGL |
| ATOM | 1997 | C   | THR | 246 | 19.221 | 64.650 | 123.824 | 1.00 16.42 | HIGL |
| ATOM | 1998 | O   | THR | 246 | 18.165 | 64.315 | 124.356 | 1.00 16.91 | HIGL |
| ATOM | 1999 | N   | ASN | 247 | 20.206 | 65.256 | 124.475 | 1.00 16.16 | HIGL |
| ATOM | 2000 | CA  | ASN | 247 | 20.125 | 65.586 | 125.891 | 1.00 16.42 | HIGL |
| ATOM | 2001 | CB  | ASN | 247 | 20.753 | 64.482 | 126.754 | 1.00 18.32 | HIGL |
| ATOM | 2002 | CG  | ASN | 247 | 19.876 | 63.247 | 126.900 | 1.00 19.99 | HIGL |
| ATOM | 2003 | OD1 | ASN | 247 | 20.357 | 62.190 | 127.311 | 1.00 20.70 | HIGL |
| ATOM | 2004 | ND2 | ASN | 247 | 18.593 | 63.374 | 126.587 | 1.00 19.85 | HIGL |
| ATOM | 2005 | C   | ASN | 247 | 20.931 | 66.850 | 126.139 | 1.00 16.21 | HIGL |
| ATOM | 2006 | O   | ASN | 247 | 21.769 | 67.235 | 125.329 | 1.00 16.56 | HIGL |
| ATOM | 2007 | N   | TRP | 248 | 20.664 | 67.491 | 127.267 | 1.00 15.12 | HIGL |
| ATOM | 2008 | CA  | TRP | 248 | 21.407 | 68.666 | 127.680 | 1.00 14.40 | HIGL |
| ATOM | 2009 | CB  | TRP | 248 | 20.750 | 69.965 | 127.235 | 1.00 14.05 | HIGL |
| ATOM | 2010 | CG  | TRP | 248 | 21.582 | 71.144 | 127.642 | 1.00 13.41 | HIGL |
| ATOM | 2011 | CD2 | TRP | 248 | 22.789 | 71.592 | 127.020 | 1.00 12.55 | HIGL |
| ATOM | 2012 | CE2 | TRP | 248 | 23.279 | 72.674 | 127.787 | 1.00 13.08 | HIGL |
| ATOM | 2013 | CE3 | TRP | 248 | 23.508 | 71.183 | 125.890 | 1.00 12.85 | HIGL |
| ATOM | 2014 | CD1 | TRP | 248 | 21.391 | 71.950 | 128.728 | 1.00 13.60 | HIGL |

Fig. 2 cont.

```
ATOM   2015  NE1  TRP  248      22.408  72.870 128.824  1.00 12.73           HIGL
ATOM   2016  CZ2  TRP  248      24.457  73.352 127.458  1.00 12.54           HIGL
ATOM   2017  CZ3  TRP  248      24.679  71.857 125.564  1.00 11.70           HIGL
ATOM   2018  CH2  TRP  248      25.141  72.929 126.347  1.00 12.92           HIGL
ATOM   2019  C    TRP  248      21.404  68.570 129.188  1.00 14.62           HIGL
ATOM   2020  O    TRP  248      20.351  68.434 129.802  1.00 15.22           HIGL
ATOM   2021  N    PRO  249      22.585  68.633 129.808  1.00 14.33           HIGL
ATOM   2022  CD   PRO  249      23.925  68.623 129.197  1.00 14.04           HIGL
ATOM   2023  CA   PRO  249      22.673  68.532 131.260  1.00 14.94           HIGL
ATOM   2024  CB   PRO  249      24.099  68.041 131.468  1.00 14.74           HIGL
ATOM   2025  CG   PRO  249      24.836  68.752 130.390  1.00 13.70           HIGL
ATOM   2026  C    PRO  249      22.381  69.783 132.066  1.00 15.82           HIGL
ATOM   2027  O    PRO  249      22.594  70.895 131.604  1.00 16.63           HIGL
ATOM   2028  N    THR  250      21.882  69.578 133.282  1.00 17.24           HIGL
ATOM   2029  CA   THR  250      21.603  70.672 134.207  1.00 17.83           HIGL
ATOM   2030  CB   THR  250      20.308  70.451 134.975  1.00 16.40           HIGL
ATOM   2031  OG1  THR  250      20.478  69.353 135.875  1.00 16.53           HIGL
ATOM   2032  CG2  THR  250      19.174  70.153 134.014  1.00 17.51           HIGL
ATOM   2033  C    THR  250      22.758  70.645 135.206  1.00 18.49           HIGL
ATOM   2034  O    THR  250      22.875  71.509 136.078  1.00 19.82           HIGL
ATOM   2035  N    SER  251      23.601  69.627 135.057  1.00 18.20           HIGL
ATOM   2036  CA   SER  251      24.769  69.426 135.897  1.00 17.27           HIGL
ATOM   2037  CB   SER  251      24.373  68.700 137.181  1.00 16.80           HIGL
ATOM   2038  OG   SER  251      25.486  68.537 138.046  1.00 16.67           HIGL
ATOM   2039  C    SER  251      25.769  68.579 135.122  1.00 17.65           HIGL
ATOM   2040  O    SER  251      25.444  67.476 134.682  1.00 17.82           HIGL
ATOM   2041  N    CYS  252      26.975  69.099 134.936  1.00 17.77           HIGL
ATOM   2042  CA   CYS  252      28.012  68.359 134.218  1.00 19.00           HIGL
ATOM   2043  C    CYS  252      29.375  68.791 134.751  1.00 18.46           HIGL
ATOM   2044  O    CYS  252      30.142  69.460 134.069  1.00 18.37           HIGL
ATOM   2045  CB   CYS  252      27.940  68.611 132.703  1.00 19.48           HIGL
ATOM   2046  SG   CYS  252      28.860  67.349 131.755  1.00 21.91           HIGL
ATOM   2047  N    PRO  253      29.687  68.402 135.992  1.00 18.43           HIGL
ATOM   2048  CD   PRO  253      28.822  67.630 136.898  1.00 17.81           HIGL
ATOM   2049  CA   PRO  253      30.950  68.739 136.650  1.00 18.32           HIGL
ATOM   2050  CB   PRO  253      30.789  68.130 138.038  1.00 17.88           HIGL
ATOM   2051  CG   PRO  253      29.313  68.078 138.228  1.00 18.40           HIGL
ATOM   2052  C    PRO  253      32.191  68.204 135.952  1.00 18.83           HIGL
ATOM   2053  O    PRO  253      33.213  68.887 135.900  1.00 18.49           HIGL
ATOM   2054  N    TYR  254      32.102  66.989 135.414  1.00 19.26           HIGL
ATOM   2055  CA   TYR  254      33.256  66.378 134.766  1.00 19.93           HIGL
ATOM   2056  CB   TYR  254      33.782  65.223 135.616  1.00 19.85           HIGL
ATOM   2057  CG   TYR  254      33.909  65.574 137.076  1.00 19.85           HIGL
ATOM   2058  CD1  TYR  254      32.816  65.468 137.934  1.00 18.49           HIGL
ATOM   2059  CE1  TYR  254      32.915  65.836 139.268  1.00 18.20           HIGL
ATOM   2060  CD2  TYR  254      35.112  66.060 137.594  1.00 19.80           HIGL
ATOM   2061  CE2  TYR  254      35.218  66.434 138.930  1.00 18.50           HIGL
ATOM   2062  CZ   TYR  254      34.115  66.319 139.755  1.00 18.08           HIGL
ATOM   2063  OH   TYR  254      34.207  66.697 141.065  1.00 18.79           HIGL
ATOM   2064  C    TYR  254      33.031  65.873 133.357  1.00 21.05           HIGL
ATOM   2065  O    TYR  254      32.995  64.667 133.128  1.00 22.11           HIGL
ATOM   2066  N    PRO  255      32.898  66.789 132.387  1.00 21.11           HIGL
ATOM   2067  CD   PRO  255      33.042  68.251 132.488  1.00 20.35           HIGL
ATOM   2068  CA   PRO  255      32.684  66.391 130.999  1.00 21.28           HIGL
ATOM   2069  CB   PRO  255      32.472  67.724 130.299  1.00 21.29           HIGL
ATOM   2070  CG   PRO  255      33.369  68.632 131.075  1.00 20.00           HIGL
ATOM   2071  C    PRO  255      33.910  65.667 130.469  1.00 22.18           HIGL
ATOM   2072  O    PRO  255      35.034  66.059 130.767  1.00 22.28           HIGL
ATOM   2073  N    ARG  256      33.698  64.613 129.686  1.00 23.41           HIGL
ATOM   2074  CA   ARG  256      34.817  63.872 129.118  1.00 24.09           HIGL
ATOM   2075  CB   ARG  256      34.386  62.462 128.702  1.00 25.18           HIGL
ATOM   2076  CG   ARG  256      35.537  61.602 128.198  1.00 28.36           HIGL
ATOM   2077  CD   ARG  256      35.062  60.254 127.676  1.00 31.88           HIGL
ATOM   2078  NE   ARG  256      36.176  59.403 127.254  1.00 35.40           HIGL
ATOM   2079  CZ   ARG  256      36.043  58.228 126.636  1.00 36.69           HIGL
```

Fig. 2 cont.

```
ATOM   2080  NH1 ARG   256      34.837  57.744 126.353  1.00 36.99      HIGL
ATOM   2081  NH2 ARG   256      37.122  57.528 126.305  1.00 37.44      HIGL
ATOM   2082  C   ARG   256      35.354  64.625 127.905  1.00 23.61      HIGL
ATOM   2083  O   ARG   256      36.538  64.553 127.593  1.00 23.73      HIGL
ATOM   2084  N   TYR   257      34.481  65.357 127.226  1.00 22.94      HIGL
ATOM   2085  CA  TYR   257      34.893  66.107 126.054  1.00 23.27      HIGL
ATOM   2086  CB  TYR   257      34.287  65.502 124.788  1.00 23.86      HIGL
ATOM   2087  CG  TYR   257      34.485  64.018 124.653  1.00 24.59      HIGL
ATOM   2088  CD1 TYR   257      33.570  63.124 125.204  1.00 25.20      HIGL
ATOM   2089  CE1 TYR   257      33.742  61.747 125.077  1.00 26.62      HIGL
ATOM   2090  CD2 TYR   257      35.585  63.502 123.970  1.00 24.88      HIGL
ATOM   2091  CE2 TYR   257      35.771  62.128 123.838  1.00 26.37      HIGL
ATOM   2092  CZ  TYR   257      34.843  61.255 124.395  1.00 27.15      HIGL
ATOM   2093  OH  TYR   257      35.018  59.895 124.276  1.00 27.95      HIGL
ATOM   2094  C   TYR   257      34.480  67.567 126.127  1.00 23.40      HIGL
ATOM   2095  O   TYR   257      33.530  67.929 126.813  1.00 23.44      HIGL
ATOM   2096  N   GLN   258      35.204  68.406 125.404  1.00 23.33      HIGL
ATOM   2097  CA  GLN   258      34.886  69.816 125.367  1.00 23.32      HIGL
ATOM   2098  CB  GLN   258      35.998  70.566 124.641  1.00 25.30      HIGL
ATOM   2099  CG  GLN   258      35.814  72.063 124.549  1.00 29.69      HIGL
ATOM   2100  CD  GLN   258      37.146  72.781 124.380  1.00 33.22      HIGL
ATOM   2101  OE1 GLN   258      37.199  73.936 123.943  1.00 34.85      HIGL
ATOM   2102  NE2 GLN   258      38.234  72.099 124.741  1.00 33.71      HIGL
ATOM   2103  C   GLN   258      33.573  69.922 124.608  1.00 21.85      HIGL
ATOM   2104  O   GLN   258      33.359  69.209 123.632  1.00 21.62      HIGL
ATOM   2105  N   PHE   259      32.680  70.784 125.067  1.00 20.74      HIGL
ATOM   2106  CA  PHE   259      31.405  70.954 124.390  1.00 20.36      HIGL
ATOM   2107  CB  PHE   259      30.415  71.652 125.318  1.00 20.17      HIGL
ATOM   2108  CG  PHE   259      29.691  70.718 126.243  1.00 20.50      HIGL
ATOM   2109  CD1 PHE   259      30.383  69.756 126.969  1.00 20.48      HIGL
ATOM   2110  CD2 PHE   259      28.310  70.803 126.391  1.00 19.48      HIGL
ATOM   2111  CE1 PHE   259      29.707  68.887 127.830  1.00 21.21      HIGL
ATOM   2112  CE2 PHE   259      27.629  69.943 127.246  1.00 19.74      HIGL
ATOM   2113  CZ  PHE   259      28.328  68.982 127.968  1.00 20.03      HIGL
ATOM   2114  C   PHE   259      31.578  71.769 123.110  1.00 20.28      HIGL
ATOM   2115  O   PHE   259      32.557  72.486 122.953  1.00 19.93      HIGL
ATOM   2116  N   PRO   260      30.637  71.651 122.165  1.00 20.85      HIGL
ATOM   2117  CD  PRO   260      29.527  70.687 122.073  1.00 20.21      HIGL
ATOM   2118  CA  PRO   260      30.766  72.427 120.924  1.00 21.17      HIGL
ATOM   2119  CB  PRO   260      29.506  72.048 120.156  1.00 21.01      HIGL
ATOM   2120  CG  PRO   260      29.291  70.617 120.584  1.00 20.56      HIGL
ATOM   2121  C   PRO   260      30.837  73.928 121.239  1.00 21.74      HIGL
ATOM   2122  O   PRO   260      30.163  74.414 122.150  1.00 21.19      HIGL
ATOM   2123  N   ALA   261      31.657  74.654 120.487  1.00 21.93      HIGL
ATOM   2124  CA  ALA   261      31.830  76.089 120.697  1.00 22.38      HIGL
ATOM   2125  CB  ALA   261      32.836  76.636 119.697  1.00 21.76      HIGL
ATOM   2126  C   ALA   261      30.540  76.901 120.621  1.00 22.55      HIGL
ATOM   2127  O   ALA   261      30.411  77.929 121.290  1.00 23.31      HIGL
ATOM   2128  N   ASP   262      29.586  76.449 119.814  1.00 22.59      HIGL
ATOM   2129  CA  ASP   262      28.331  77.173 119.674  1.00 23.66      HIGL
ATOM   2130  CB  ASP   262      27.570  76.715 118.426  1.00 24.06      HIGL
ATOM   2131  CG  ASP   262      27.368  75.206 118.369  1.00 25.82      HIGL
ATOM   2132  OD1 ASP   262      27.333  74.550 119.435  1.00 26.18      HIGL
ATOM   2133  OD2 ASP   262      27.224  74.677 117.243  1.00 26.76      HIGL
ATOM   2134  C   ASP   262      27.401  77.095 120.878  1.00 24.22      HIGL
ATOM   2135  O   ASP   262      26.449  77.866 120.965  1.00 24.88      HIGL
ATOM   2136  N   VAL   263      27.661  76.174 121.802  1.00 25.01      HIGL
ATOM   2137  CA  VAL   263      26.803  76.042 122.976  1.00 26.27      HIGL
ATOM   2138  CB  VAL   263      26.062  74.680 122.990  1.00 25.93      HIGL
ATOM   2139  CG1 VAL   263      25.179  74.554 121.757  1.00 24.73      HIGL
ATOM   2140  CG2 VAL   263      27.056  73.540 123.063  1.00 25.19      HIGL
ATOM   2141  C   VAL   263      27.525  76.211 124.309  1.00 27.53      HIGL
ATOM   2142  O   VAL   263      26.931  76.014 125.365  1.00 27.35      HIGL
ATOM   2143  N   ARG   264      28.799  76.590 124.257  1.00 29.44      HIGL
ATOM   2144  CA  ARG   264      29.595  76.782 125.466  1.00 31.50      HIGL
```

Fig. 2 cont.

| | | | | | | | | | |
|---|---|---|---|---|---|---|---|---|---|
| ATOM | 2145 | CB  | ARG | 264 | 31.066 | 76.969 | 125.092 | 1.00 32.75 | HIGL |
| ATOM | 2146 | CG  | ARG | 264 | 31.645 | 75.755 | 124.389 | 1.00 35.35 | HIGL |
| ATOM | 2147 | CD  | ARG | 264 | 33.075 | 75.968 | 123.917 | 1.00 37.11 | HIGL |
| ATOM | 2148 | NE  | ARG | 264 | 33.550 | 74.810 | 123.161 | 1.00 38.51 | HIGL |
| ATOM | 2149 | CZ  | ARG | 264 | 34.738 | 74.727 | 122.571 | 1.00 38.26 | HIGL |
| ATOM | 2150 | NH1 | ARG | 264 | 35.590 | 75.742 | 122.646 | 1.00 38.84 | HIGL |
| ATOM | 2151 | NH2 | ARG | 264 | 35.072 | 73.629 | 121.903 | 1.00 37.21 | HIGL |
| ATOM | 2152 | C   | ARG | 264 | 29.110 | 77.968 | 126.294 | 1.00 31.82 | HIGL |
| ATOM | 2153 | O   | ARG | 264 | 29.649 | 78.256 | 127.360 | 1.00 32.57 | HIGL |
| ATOM | 2154 | N   | ASN | 265 | 28.086 | 78.648 | 125.796 | 1.00 31.94 | HIGL |
| ATOM | 2155 | CA  | ASN | 265 | 27.508 | 79.801 | 126.480 | 1.00 31.74 | HIGL |
| ATOM | 2156 | CB  | ASN | 265 | 27.189 | 80.893 | 125.464 | 1.00 33.87 | HIGL |
| ATOM | 2157 | CG  | ASN | 265 | 26.419 | 80.357 | 124.264 | 1.00 35.62 | HIGL |
| ATOM | 2158 | OD1 | ASN | 265 | 25.213 | 80.600 | 124.115 | 1.00 36.81 | HIGL |
| ATOM | 2159 | ND2 | ASN | 265 | 27.113 | 79.608 | 123.407 | 1.00 35.24 | HIGL |
| ATOM | 2160 | C   | ASN | 265 | 26.227 | 79.376 | 127.175 | 1.00 30.26 | HIGL |
| ATOM | 2161 | O   | ASN | 265 | 25.738 | 80.064 | 128.067 | 1.00 31.10 | HIGL |
| ATOM | 2162 | N   | VAL | 266 | 25.685 | 78.240 | 126.746 | 1.00 28.31 | HIGL |
| ATOM | 2163 | CA  | VAL | 266 | 24.455 | 77.701 | 127.307 | 1.00 25.56 | HIGL |
| ATOM | 2164 | CB  | VAL | 266 | 23.844 | 76.635 | 126.374 | 1.00 25.88 | HIGL |
| ATOM | 2165 | CG1 | VAL | 266 | 22.547 | 76.096 | 126.970 | 1.00 25.25 | HIGL |
| ATOM | 2166 | CG2 | VAL | 266 | 23.594 | 77.241 | 124.992 | 1.00 24.06 | HIGL |
| ATOM | 2167 | C   | VAL | 266 | 24.755 | 77.087 | 128.668 | 1.00 23.91 | HIGL |
| ATOM | 2168 | O   | VAL | 266 | 25.624 | 76.228 | 128.798 | 1.00 23.76 | HIGL |
| ATOM | 2169 | N   | PRO | 267 | 24.038 | 77.534 | 129.706 | 1.00 21.98 | HIGL |
| ATOM | 2170 | CD  | PRO | 267 | 23.034 | 78.615 | 129.662 | 1.00 20.37 | HIGL |
| ATOM | 2171 | CA  | PRO | 267 | 24.216 | 77.047 | 131.075 | 1.00 20.98 | HIGL |
| ATOM | 2172 | CB  | PRO | 267 | 23.483 | 78.099 | 131.899 | 1.00 20.76 | HIGL |
| ATOM | 2173 | CG  | PRO | 267 | 22.349 | 78.475 | 130.996 | 1.00 20.01 | HIGL |
| ATOM | 2174 | C   | PRO | 267 | 23.670 | 75.655 | 131.340 | 1.00 20.67 | HIGL |
| ATOM | 2175 | O   | PRO | 267 | 22.759 | 75.190 | 130.652 | 1.00 20.51 | HIGL |
| ATOM | 2176 | N   | PHE | 268 | 24.239 | 74.985 | 132.338 | 1.00 20.18 | HIGL |
| ATOM | 2177 | CA  | PHE | 268 | 23.755 | 73.668 | 132.713 | 1.00 19.81 | HIGL |
| ATOM | 2178 | CB  | PHE | 268 | 24.863 | 72.819 | 133.338 | 1.00 19.33 | HIGL |
| ATOM | 2179 | CG  | PHE | 268 | 26.001 | 72.540 | 132.405 | 1.00 18.57 | HIGL |
| ATOM | 2180 | CD1 | PHE | 268 | 25.755 | 72.175 | 131.079 | 1.00 18.00 | HIGL |
| ATOM | 2181 | CD2 | PHE | 268 | 27.320 | 72.663 | 132.837 | 1.00 17.98 | HIGL |
| ATOM | 2182 | CE1 | PHE | 268 | 26.802 | 71.941 | 130.196 | 1.00 17.94 | HIGL |
| ATOM | 2183 | CE2 | PHE | 268 | 28.382 | 72.431 | 131.961 | 1.00 17.83 | HIGL |
| ATOM | 2184 | CZ  | PHE | 268 | 28.121 | 72.070 | 130.635 | 1.00 18.17 | HIGL |
| ATOM | 2185 | C   | PHE | 268 | 22.667 | 73.953 | 133.727 | 1.00 19.80 | HIGL |
| ATOM | 2186 | O   | PHE | 268 | 22.942 | 74.140 | 134.916 | 1.00 19.98 | HIGL |
| ATOM | 2187 | N   | SER | 269 | 21.434 | 74.020 | 133.234 | 1.00 18.90 | HIGL |
| ATOM | 2188 | CA  | SER | 269 | 20.281 | 74.310 | 134.066 | 1.00 18.82 | HIGL |
| ATOM | 2189 | CB  | SER | 269 | 20.339 | 75.752 | 134.567 | 1.00 19.28 | HIGL |
| ATOM | 2190 | OG  | SER | 269 | 20.163 | 76.667 | 133.494 | 1.00 20.35 | HIGL |
| ATOM | 2191 | C   | SER | 269 | 19.021 | 74.133 | 133.243 | 1.00 18.90 | HIGL |
| ATOM | 2192 | O   | SER | 269 | 19.080 | 73.972 | 132.022 | 1.00 19.79 | HIGL |
| ATOM | 2193 | N   | ALA | 270 | 17.880 | 74.169 | 133.917 | 1.00 17.92 | HIGL |
| ATOM | 2194 | CA  | ALA | 270 | 16.604 | 74.030 | 133.245 | 1.00 17.69 | HIGL |
| ATOM | 2195 | CB  | ALA | 270 | 15.478 | 74.256 | 134.230 | 1.00 17.34 | HIGL |
| ATOM | 2196 | C   | ALA | 270 | 16.526 | 75.050 | 132.111 | 1.00 18.21 | HIGL |
| ATOM | 2197 | O   | ALA | 270 | 16.018 | 74.752 | 131.028 | 1.00 19.17 | HIGL |
| ATOM | 2198 | N   | ALA | 271 | 17.033 | 76.254 | 132.359 | 1.00 17.66 | HIGL |
| ATOM | 2199 | CA  | ALA | 271 | 17.008 | 77.307 | 131.346 | 1.00 16.71 | HIGL |
| ATOM | 2200 | CB  | ALA | 271 | 17.545 | 78.605 | 131.926 | 1.00 16.21 | HIGL |
| ATOM | 2201 | C   | ALA | 271 | 17.838 | 76.886 | 130.145 | 1.00 16.17 | HIGL |
| ATOM | 2202 | O   | ALA | 271 | 17.407 | 77.035 | 129.006 | 1.00 15.94 | HIGL |
| ATOM | 2203 | N   | GLY | 272 | 19.024 | 76.348 | 130.415 | 1.00 16.09 | HIGL |
| ATOM | 2204 | CA  | GLY | 272 | 19.906 | 75.900 | 129.353 | 1.00 16.02 | HIGL |
| ATOM | 2205 | C   | GLY | 272 | 19.321 | 74.768 | 128.528 | 1.00 16.50 | HIGL |
| ATOM | 2206 | O   | GLY | 272 | 19.527 | 74.700 | 127.316 | 1.00 16.42 | HIGL |
| ATOM | 2207 | N   | GLN | 273 | 18.593 | 73.867 | 129.177 | 1.00 16.88 | HIGL |
| ATOM | 2208 | CA  | GLN | 273 | 17.985 | 72.762 | 128.454 | 1.00 17.26 | HIGL |
| ATOM | 2209 | CB  | GLN | 273 | 17.267 | 71.809 | 129.414 | 1.00 16.57 | HIGL |

Fig. 2 cont.

```
ATOM   2210  CG   GLN   273      18.186  71.041 130.354  1.00 16.40           HIGL
ATOM   2211  CD   GLN   273      17.438  70.007 131.175  1.00 15.47           HIGL
ATOM   2212  OE1  GLN   273      16.479  70.330 131.868  1.00 15.89           HIGL
ATOM   2213  NE2  GLN   273      17.877  68.758 131.101  1.00 15.09           HIGL
ATOM   2214  C    GLN   273      16.986  73.323 127.452  1.00 18.10           HIGL
ATOM   2215  O    GLN   273      16.955  72.903 126.297  1.00 19.02           HIGL
ATOM   2216  N    THR   274      16.172  74.275 127.901  1.00 18.71           HIGL
ATOM   2217  CA   THR   274      15.161  74.899 127.058  1.00 19.11           HIGL
ATOM   2218  CB   THR   274      14.419  76.016 127.826  1.00 20.20           HIGL
ATOM   2219  OG1  THR   274      13.856  75.469 129.026  1.00 21.70           HIGL
ATOM   2220  CG2  THR   274      13.293  76.603 126.978  1.00 20.14           HIGL
ATOM   2221  C    THR   274      15.840  75.498 125.842  1.00 19.34           HIGL
ATOM   2222  O    THR   274      15.485  75.213 124.700  1.00 18.39           HIGL
ATOM   2223  N    GLN   275      16.838  76.325 126.115  1.00 20.37           HIGL
ATOM   2224  CA   GLN   275      17.613  76.999 125.087  1.00 21.17           HIGL
ATOM   2225  CB   GLN   275      18.747  77.761 125.766  1.00 22.42           HIGL
ATOM   2226  CG   GLN   275      19.418  78.828 124.942  1.00 25.01           HIGL
ATOM   2227  CD   GLN   275      20.454  79.578 125.759  1.00 28.13           HIGL
ATOM   2228  OE1  GLN   275      20.205  79.943 126.918  1.00 28.91           HIGL
ATOM   2229  NE2  GLN   275      21.621  79.817 125.166  1.00 29.71           HIGL
ATOM   2230  C    GLN   275      18.180  75.997 124.077  1.00 21.54           HIGL
ATOM   2231  O    GLN   275      18.022  76.167 122.866  1.00 21.25           HIGL
ATOM   2232  N    TYR   276      18.831  74.948 124.579  1.00 20.83           HIGL
ATOM   2233  CA   TYR   276      19.431  73.941 123.712  1.00 20.67           HIGL
ATOM   2234  CB   TYR   276      20.283  72.961 124.528  1.00 19.62           HIGL
ATOM   2235  CG   TYR   276      20.995  71.923 123.681  1.00 18.90           HIGL
ATOM   2236  CD1  TYR   276      22.193  72.222 123.020  1.00 18.90           HIGL
ATOM   2237  CE1  TYR   276      22.854  71.260 122.245  1.00 18.33           HIGL
ATOM   2238  CD2  TYR   276      20.471  70.641 123.540  1.00 18.85           HIGL
ATOM   2239  CE2  TYR   276      21.114  69.677 122.769  1.00 18.77           HIGL
ATOM   2240  CZ   TYR   276      22.304  69.986 122.127  1.00 19.64           HIGL
ATOM   2241  OH   TYR   276      22.938  69.006 121.391  1.00 19.63           HIGL
ATOM   2242  C    TYR   276      18.406  73.150 122.907  1.00 20.77           HIGL
ATOM   2243  O    TYR   276      18.547  72.992 121.695  1.00 20.48           HIGL
ATOM   2244  N    ILE   277      17.386  72.639 123.584  1.00 21.04           HIGL
ATOM   2245  CA   ILE   277      16.361  71.857 122.912  1.00 21.46           HIGL
ATOM   2246  CB   ILE   277      15.303  71.345 123.913  1.00 21.68           HIGL
ATOM   2247  CG2  ILE   277      14.172  70.635 123.167  1.00 21.01           HIGL
ATOM   2248  CG1  ILE   277      15.965  70.393 124.912  1.00 20.42           HIGL
ATOM   2249  CD1  ILE   277      15.058  69.950 126.033  1.00 21.50           HIGL
ATOM   2250  C    ILE   277      15.685  72.690 121.841  1.00 21.85           HIGL
ATOM   2251  O    ILE   277      15.334  72.185 120.780  1.00 21.88           HIGL
ATOM   2252  N    GLN   278      15.520  73.975 122.114  1.00 22.68           HIGL
ATOM   2253  CA   GLN   278      14.881  74.863 121.159  1.00 23.40           HIGL
ATOM   2254  CB   GLN   278      14.468  76.164 121.856  1.00 25.27           HIGL
ATOM   2255  CG   GLN   278      13.664  77.127 120.993  1.00 28.71           HIGL
ATOM   2256  CD   GLN   278      12.524  77.786 121.759  1.00 31.37           HIGL
ATOM   2257  OE1  GLN   278      12.699  78.244 122.900  1.00 32.36           HIGL
ATOM   2258  NE2  GLN   278      11.347  77.845 121.132  1.00 31.74           HIGL
ATOM   2259  C    GLN   278      15.789  75.145 119.963  1.00 22.37           HIGL
ATOM   2260  O    GLN   278      15.319  75.205 118.829  1.00 22.41           HIGL
ATOM   2261  N    SER   279      17.085  75.311 120.213  1.00 21.36           HIGL
ATOM   2262  CA   SER   279      18.042  75.563 119.137  1.00 20.77           HIGL
ATOM   2263  CB   SER   279      19.445  75.775 119.697  1.00 20.20           HIGL
ATOM   2264  OG   SER   279      19.492  76.892 120.554  1.00 21.57           HIGL
ATOM   2265  C    SER   279      18.083  74.372 118.185  1.00 20.98           HIGL
ATOM   2266  O    SER   279      18.103  74.536 116.962  1.00 21.23           HIGL
ATOM   2267  N    VAL   280      18.102  73.172 118.762  1.00 20.27           HIGL
ATOM   2268  CA   VAL   280      18.141  71.945 117.983  1.00 19.59           HIGL
ATOM   2269  CB   VAL   280      18.294  70.721 118.905  1.00 18.93           HIGL
ATOM   2270  CG1  VAL   280      18.277  69.436 118.088  1.00 18.16           HIGL
ATOM   2271  CG2  VAL   280      19.586  70.837 119.686  1.00 17.85           HIGL
ATOM   2272  C    VAL   280      16.865  71.821 117.161  1.00 19.71           HIGL
ATOM   2273  O    VAL   280      16.895  71.371 116.015  1.00 19.74           HIGL
ATOM   2274  N    ALA   281      15.744  72.229 117.746  1.00 19.63           HIGL
```

Fig. 2 cont.

| | | | | | | | | | |
|---|---|---|---|---|---|---|---|---|---|
| ATOM | 2275 | CA | ALA | 281 | 14.467 | 72.176 | 117.044 | 1.00 19.86 | HIGL |
| ATOM | 2276 | CB | ALA | 281 | 13.324 | 72.570 | 117.982 | 1.00 19.49 | HIGL |
| ATOM | 2277 | C | ALA | 281 | 14.519 | 73.123 | 115.847 | 1.00 19.99 | HIGL |
| ATOM | 2278 | O | ALA | 281 | 14.070 | 72.782 | 114.751 | 1.00 19.99 | HIGL |
| ATOM | 2279 | N | ASN | 282 | 15.080 | 74.309 | 116.056 | 1.00 20.40 | HIGL |
| ATOM | 2280 | CA | ASN | 282 | 15.189 | 75.283 | 114.979 | 1.00 21.01 | HIGL |
| ATOM | 2281 | CB | ASN | 282 | 15.867 | 76.562 | 115.463 | 1.00 22.58 | HIGL |
| ATOM | 2282 | CG | ASN | 282 | 15.081 | 77.253 | 116.555 | 1.00 25.95 | HIGL |
| ATOM | 2283 | OD1 | ASN | 282 | 13.850 | 77.335 | 116.489 | 1.00 27.58 | HIGL |
| ATOM | 2284 | ND2 | ASN | 282 | 15.786 | 77.765 | 117.567 | 1.00 25.99 | HIGL |
| ATOM | 2285 | C | ASN | 282 | 15.976 | 74.709 | 113.818 | 1.00 20.44 | HIGL |
| ATOM | 2286 | O | ASN | 282 | 15.608 | 74.915 | 112.662 | 1.00 21.36 | HIGL |
| ATOM | 2287 | N | VAL | 283 | 17.058 | 73.995 | 114.118 | 1.00 18.69 | HIGL |
| ATOM | 2288 | CA | VAL | 283 | 17.868 | 73.396 | 113.064 | 1.00 18.11 | HIGL |
| ATOM | 2289 | CB | VAL | 283 | 19.105 | 72.668 | 113.639 | 1.00 17.40 | HIGL |
| ATOM | 2290 | CG1 | VAL | 283 | 19.738 | 71.771 | 112.581 | 1.00 15.51 | HIGL |
| ATOM | 2291 | CG2 | VAL | 283 | 20.117 | 73.692 | 114.128 | 1.00 15.34 | HIGL |
| ATOM | 2292 | C | VAL | 283 | 17.028 | 72.418 | 112.256 | 1.00 18.82 | HIGL |
| ATOM | 2293 | O | VAL | 283 | 16.972 | 72.504 | 111.034 | 1.00 19.69 | HIGL |
| ATOM | 2294 | N | VAL | 284 | 16.365 | 71.497 | 112.942 | 1.00 19.82 | HIGL |
| ATOM | 2295 | CA | VAL | 284 | 15.518 | 70.514 | 112.277 | 1.00 20.48 | HIGL |
| ATOM | 2296 | CB | VAL | 284 | 14.874 | 69.570 | 113.304 | 1.00 19.52 | HIGL |
| ATOM | 2297 | CG1 | VAL | 284 | 14.015 | 68.549 | 112.595 | 1.00 17.63 | HIGL |
| ATOM | 2298 | CG2 | VAL | 284 | 15.956 | 68.896 | 114.132 | 1.00 18.42 | HIGL |
| ATOM | 2299 | C | VAL | 284 | 14.405 | 71.185 | 111.452 | 1.00 21.90 | HIGL |
| ATOM | 2300 | O | VAL | 284 | 14.205 | 70.863 | 110.279 | 1.00 22.17 | HIGL |
| ATOM | 2301 | N | SER | 285 | 13.685 | 72.117 | 112.068 | 1.00 22.19 | HIGL |
| ATOM | 2302 | CA | SER | 285 | 12.609 | 72.820 | 111.380 | 1.00 22.67 | HIGL |
| ATOM | 2303 | CB | SER | 285 | 11.936 | 73.817 | 112.317 | 1.00 22.73 | HIGL |
| ATOM | 2304 | OG | SER | 285 | 11.369 | 73.153 | 113.426 | 1.00 26.28 | HIGL |
| ATOM | 2305 | C | SER | 285 | 13.112 | 73.571 | 110.160 | 1.00 23.02 | HIGL |
| ATOM | 2306 | O | SER | 285 | 12.447 | 73.585 | 109.126 | 1.00 23.75 | HIGL |
| ATOM | 2307 | N | SER | 286 | 14.279 | 74.203 | 110.282 | 1.00 23.31 | HIGL |
| ATOM | 2308 | CA | SER | 286 | 14.848 | 74.975 | 109.177 | 1.00 23.26 | HIGL |
| ATOM | 2309 | CB | SER | 286 | 16.231 | 75.524 | 109.545 | 1.00 22.79 | HIGL |
| ATOM | 2310 | OG | SER | 286 | 17.224 | 74.513 | 109.479 | 1.00 22.57 | HIGL |
| ATOM | 2311 | C | SER | 286 | 14.969 | 74.104 | 107.937 | 1.00 23.61 | HIGL |
| ATOM | 2312 | O | SER | 286 | 14.824 | 74.586 | 106.812 | 1.00 24.61 | HIGL |
| ATOM | 2313 | N | VAL | 287 | 15.227 | 72.817 | 108.150 | 1.00 22.94 | HIGL |
| ATOM | 2314 | CA | VAL | 287 | 15.371 | 71.876 | 107.051 | 1.00 22.39 | HIGL |
| ATOM | 2315 | CB | VAL | 287 | 16.126 | 70.596 | 107.494 | 1.00 21.12 | HIGL |
| ATOM | 2316 | CG1 | VAL | 287 | 16.217 | 69.617 | 106.341 | 1.00 19.58 | HIGL |
| ATOM | 2317 | CG2 | VAL | 287 | 17.500 | 70.952 | 107.989 | 1.00 19.96 | HIGL |
| ATOM | 2318 | C | VAL | 287 | 14.020 | 71.452 | 106.510 | 1.00 22.70 | HIGL |
| ATOM | 2319 | O | VAL | 287 | 13.129 | 71.075 | 107.266 | 1.00 22.82 | HIGL |
| ATOM | 2320 | N | SER | 288 | 13.857 | 71.530 | 105.197 | 1.00 23.99 | HIGL |
| ATOM | 2321 | CA | SER | 288 | 12.609 | 71.083 | 104.598 | 1.00 25.42 | HIGL |
| ATOM | 2322 | CB | SER | 288 | 12.661 | 71.204 | 103.077 | 1.00 25.83 | HIGL |
| ATOM | 2323 | OG | SER | 288 | 13.511 | 70.204 | 102.537 | 1.00 26.10 | HIGL |
| ATOM | 2324 | C | SER | 288 | 12.606 | 69.606 | 104.969 | 1.00 25.73 | HIGL |
| ATOM | 2325 | O | SER | 288 | 13.655 | 68.951 | 104.917 | 1.00 27.44 | HIGL |
| ATOM | 2326 | N | LYS | 289 | 11.456 | 69.073 | 105.342 | 1.00 24.12 | HIGL |
| ATOM | 2327 | CA | LYS | 289 | 11.400 | 67.668 | 105.716 | 1.00 23.58 | HIGL |
| ATOM | 2328 | CB | LYS | 289 | 12.074 | 66.790 | 104.657 | 1.00 23.46 | HIGL |
| ATOM | 2329 | CG | LYS | 289 | 11.229 | 66.659 | 103.407 | 1.00 24.42 | HIGL |
| ATOM | 2330 | CD | LYS | 289 | 11.870 | 65.809 | 102.341 | 1.00 24.82 | HIGL |
| ATOM | 2331 | CE | LYS | 289 | 10.907 | 65.640 | 101.180 | 1.00 25.59 | HIGL |
| ATOM | 2332 | NZ | LYS | 289 | 9.680 | 64.915 | 101.624 | 1.00 27.30 | HIGL |
| ATOM | 2333 | C | LYS | 289 | 12.010 | 67.422 | 107.085 | 1.00 22.49 | HIGL |
| ATOM | 2334 | O | LYS | 289 | 12.135 | 66.281 | 107.524 | 1.00 22.48 | HIGL |
| ATOM | 2335 | N | GLY | 290 | 12.415 | 68.498 | 107.749 | 1.00 21.72 | HIGL |
| ATOM | 2336 | CA | GLY | 290 | 12.913 | 68.353 | 109.102 | 1.00 21.35 | HIGL |
| ATOM | 2337 | C | GLY | 290 | 11.587 | 68.203 | 109.830 | 1.00 20.86 | HIGL |
| ATOM | 2338 | O | GLY | 290 | 10.805 | 69.154 | 109.888 | 1.00 21.50 | HIGL |
| ATOM | 2339 | N | VAL | 291 | 11.305 | 67.029 | 110.379 | 1.00 19.98 | HIGL |

Fig. 2 cont.

| | | | | | | | | | |
|---|---|---|---|---|---|---|---|---|---|
| ATOM | 2340 | CA | VAL | 291 | 10.008 | 66.845 | 111.013 | 1.00 19.00 | HIGL |
| ATOM | 2341 | CB | VAL | 291 | 9.168 | 65.836 | 110.206 | 1.00 18.98 | HIGL |
| ATOM | 2342 | CG1 | VAL | 291 | 9.040 | 66.301 | 108.764 | 1.00 18.95 | HIGL |
| ATOM | 2343 | CG2 | VAL | 291 | 9.816 | 64.471 | 110.258 | 1.00 19.17 | HIGL |
| ATOM | 2344 | C | VAL | 291 | 9.927 | 66.441 | 112.479 | 1.00 18.36 | HIGL |
| ATOM | 2345 | O | VAL | 291 | 8.834 | 66.482 | 113.055 | 1.00 18.16 | HIGL |
| ATOM | 2346 | N | GLY | 292 | 11.043 | 66.061 | 113.098 | 1.00 16.75 | HIGL |
| ATOM | 2347 | CA | GLY | 292 | 10.943 | 65.657 | 114.489 | 1.00 15.82 | HIGL |
| ATOM | 2348 | C | GLY | 292 | 12.114 | 65.858 | 115.421 | 1.00 15.38 | HIGL |
| ATOM | 2349 | O | GLY | 292 | 13.248 | 66.043 | 114.990 | 1.00 15.70 | HIGL |
| ATOM | 2350 | N | LEU | 293 | 11.822 | 65.825 | 116.719 | 1.00 15.28 | HIGL |
| ATOM | 2351 | CA | LEU | 293 | 12.842 | 65.963 | 117.757 | 1.00 14.98 | HIGL |
| ATOM | 2352 | CB | LEU | 293 | 13.059 | 67.436 | 118.131 | 1.00 14.38 | HIGL |
| ATOM | 2353 | CG | LEU | 293 | 14.200 | 67.697 | 119.131 | 1.00 14.97 | HIGL |
| ATOM | 2354 | CD1 | LEU | 293 | 14.507 | 69.175 | 119.180 | 1.00 16.01 | HIGL |
| ATOM | 2355 | CD2 | LEU | 293 | 13.824 | 67.197 | 120.524 | 1.00 15.85 | HIGL |
| ATOM | 2356 | C | LEU | 293 | 12.450 | 65.168 | 119.006 | 1.00 14.59 | HIGL |
| ATOM | 2357 | O | LEU | 293 | 11.367 | 65.356 | 119.559 | 1.00 14.50 | HIGL |
| ATOM | 2358 | N | PHE | 294 | 13.334 | 64.281 | 119.454 | 1.00 14.69 | HIGL |
| ATOM | 2359 | CA | PHE | 294 | 13.047 | 63.487 | 120.644 | 1.00 14.76 | HIGL |
| ATOM | 2360 | CB | PHE | 294 | 12.807 | 62.023 | 120.288 | 1.00 13.63 | HIGL |
| ATOM | 2361 | CG | PHE | 294 | 11.566 | 61.788 | 119.496 | 1.00 14.32 | HIGL |
| ATOM | 2362 | CD1 | PHE | 294 | 11.557 | 61.983 | 118.116 | 1.00 14.42 | HIGL |
| ATOM | 2363 | CD2 | PHE | 294 | 10.394 | 61.372 | 120.127 | 1.00 14.49 | HIGL |
| ATOM | 2364 | CE1 | PHE | 294 | 10.395 | 61.763 | 117.372 | 1.00 14.13 | HIGL |
| ATOM | 2365 | CE2 | PHE | 294 | 9.225 | 61.149 | 119.397 | 1.00 14.10 | HIGL |
| ATOM | 2366 | CZ | PHE | 294 | 9.224 | 61.344 | 118.017 | 1.00 14.44 | HIGL |
| ATOM | 2367 | C | PHE | 294 | 14.152 | 63.552 | 121.684 | 1.00 14.75 | HIGL |
| ATOM | 2368 | O | PHE | 294 | 15.312 | 63.249 | 121.394 | 1.00 15.47 | HIGL |
| ATOM | 2369 | N | TYR | 295 | 13.778 | 63.947 | 122.897 | 1.00 14.13 | HIGL |
| ATOM | 2370 | CA | TYR | 295 | 14.716 | 64.024 | 124.006 | 1.00 13.77 | HIGL |
| ATOM | 2371 | CB | TYR | 295 | 14.199 | 64.993 | 125.065 | 1.00 13.42 | HIGL |
| ATOM | 2372 | CG | TYR | 295 | 15.267 | 65.439 | 126.031 | 1.00 12.18 | HIGL |
| ATOM | 2373 | CD1 | TYR | 295 | 15.972 | 66.628 | 125.825 | 1.00 11.42 | HIGL |
| ATOM | 2374 | CE1 | TYR | 295 | 16.991 | 67.020 | 126.696 | 1.00 11.09 | HIGL |
| ATOM | 2375 | CD2 | TYR | 295 | 15.602 | 64.656 | 127.131 | 1.00 10.29 | HIGL |
| ATOM | 2376 | CE2 | TYR | 295 | 16.612 | 65.040 | 128.004 | 1.00 10.79 | HIGL |
| ATOM | 2377 | CZ | TYR | 295 | 17.304 | 66.217 | 127.782 | 1.00 10.57 | HIGL |
| ATOM | 2378 | OH | TYR | 295 | 18.317 | 66.569 | 128.640 | 1.00 9.73 | HIGL |
| ATOM | 2379 | C | TYR | 295 | 14.783 | 62.609 | 124.586 | 1.00 13.63 | HIGL |
| ATOM | 2380 | O | TYR | 295 | 13.747 | 61.970 | 124.793 | 1.00 13.59 | HIGL |
| ATOM | 2381 | N | TRP | 296 | 15.990 | 62.120 | 124.854 | 1.00 12.80 | HIGL |
| ATOM | 2382 | CA | TRP | 296 | 16.138 | 60.764 | 125.369 | 1.00 12.83 | HIGL |
| ATOM | 2383 | CB | TRP | 296 | 17.412 | 60.119 | 124.809 | 1.00 13.03 | HIGL |
| ATOM | 2384 | CG | TRP | 296 | 17.448 | 58.640 | 125.023 | 1.00 13.14 | HIGL |
| ATOM | 2385 | CD2 | TRP | 296 | 18.316 | 57.918 | 125.900 | 1.00 13.55 | HIGL |
| ATOM | 2386 | CE2 | TRP | 296 | 17.949 | 56.555 | 125.825 | 1.00 13.63 | HIGL |
| ATOM | 2387 | CE3 | TRP | 296 | 19.369 | 58.289 | 126.747 | 1.00 14.63 | HIGL |
| ATOM | 2388 | CD1 | TRP | 296 | 16.615 | 57.711 | 124.460 | 1.00 14.08 | HIGL |
| ATOM | 2389 | NE1 | TRP | 296 | 16.909 | 56.456 | 124.939 | 1.00 13.47 | HIGL |
| ATOM | 2390 | CZ2 | TRP | 296 | 18.596 | 55.562 | 126.567 | 1.00 13.78 | HIGL |
| ATOM | 2391 | CZ3 | TRP | 296 | 20.017 | 57.297 | 127.487 | 1.00 13.79 | HIGL |
| ATOM | 2392 | CH2 | TRP | 296 | 19.624 | 55.953 | 127.390 | 1.00 14.10 | HIGL |
| ATOM | 2393 | C | TRP | 296 | 16.135 | 60.615 | 126.887 | 1.00 12.44 | HIGL |
| ATOM | 2394 | O | TRP | 296 | 16.964 | 61.202 | 127.582 | 1.00 11.79 | HIGL |
| ATOM | 2395 | N | GLU | 297 | 15.190 | 59.811 | 127.376 | 1.00 12.90 | HIGL |
| ATOM | 2396 | CA | GLU | 297 | 15.029 | 59.502 | 128.797 | 1.00 12.94 | HIGL |
| ATOM | 2397 | CB | GLU | 297 | 16.061 | 58.455 | 129.199 | 1.00 13.78 | HIGL |
| ATOM | 2398 | CG | GLU | 297 | 15.780 | 57.087 | 128.595 | 1.00 14.60 | HIGL |
| ATOM | 2399 | CD | GLU | 297 | 14.616 | 56.394 | 129.271 | 1.00 14.61 | HIGL |
| ATOM | 2400 | OE1 | GLU | 297 | 13.947 | 57.031 | 130.112 | 1.00 13.68 | HIGL |
| ATOM | 2401 | OE2 | GLU | 297 | 14.370 | 55.211 | 128.962 | 1.00 15.38 | HIGL |
| ATOM | 2402 | C | GLU | 297 | 15.089 | 60.687 | 129.749 | 1.00 13.20 | HIGL |
| ATOM | 2403 | O | GLU | 297 | 15.911 | 60.728 | 130.665 | 1.00 11.51 | HIGL |
| ATOM | 2404 | N | PRO | 298 | 14.185 | 61.659 | 129.563 | 1.00 14.35 | HIGL |

Fig. 2 cont.

| | | | | | | | | | |
|---|---|---|---|---|---|---|---|---|---|
| ATOM | 2405 | CD | PRO | 298 | 13.050 | 61.665 | 128.618 | 1.00 14.17 | HIGL |
| ATOM | 2406 | CA | PRO | 298 | 14.150 | 62.846 | 130.416 | 1.00 14.61 | HIGL |
| ATOM | 2407 | CB | PRO | 298 | 13.123 | 63.733 | 129.719 | 1.00 14.43 | HIGL |
| ATOM | 2408 | CG | PRO | 298 | 12.143 | 62.727 | 129.206 | 1.00 14.48 | HIGL |
| ATOM | 2409 | C | PRO | 298 | 13.750 | 62.555 | 131.857 | 1.00 14.61 | HIGL |
| ATOM | 2410 | O | PRO | 298 | 14.058 | 63.339 | 132.754 | 1.00 15.09 | HIGL |
| ATOM | 2411 | N | ALA | 299 | 13.082 | 61.427 | 132.080 | 1.00 14.64 | HIGL |
| ATOM | 2412 | CA | ALA | 299 | 12.601 | 61.093 | 133.419 | 1.00 15.80 | HIGL |
| ATOM | 2413 | CB | ALA | 299 | 11.089 | 60.869 | 133.372 | 1.00 15.02 | HIGL |
| ATOM | 2414 | C | ALA | 299 | 13.264 | 59.930 | 134.140 | 1.00 16.15 | HIGL |
| ATOM | 2415 | O | ALA | 299 | 12.746 | 59.459 | 135.148 | 1.00 15.99 | HIGL |
| ATOM | 2416 | N | TRP | 300 | 14.410 | 59.479 | 133.646 | 1.00 17.81 | HIGL |
| ATOM | 2417 | CA | TRP | 300 | 15.115 | 58.361 | 134.269 | 1.00 18.35 | HIGL |
| ATOM | 2418 | CB | TRP | 300 | 16.003 | 57.672 | 133.238 | 1.00 17.62 | HIGL |
| ATOM | 2419 | CG | TRP | 300 | 16.304 | 56.260 | 133.577 | 1.00 17.58 | HIGL |
| ATOM | 2420 | CD2 | TRP | 300 | 16.887 | 55.281 | 132.714 | 1.00 18.60 | HIGL |
| ATOM | 2421 | CE2 | TRP | 300 | 17.067 | 54.105 | 133.479 | 1.00 19.31 | HIGL |
| ATOM | 2422 | CE3 | TRP | 300 | 17.281 | 55.283 | 131.369 | 1.00 17.87 | HIGL |
| ATOM | 2423 | CD1 | TRP | 300 | 16.151 | 55.659 | 134.790 | 1.00 18.39 | HIGL |
| ATOM | 2424 | NE1 | TRP | 300 | 16.608 | 54.365 | 134.743 | 1.00 18.74 | HIGL |
| ATOM | 2425 | CZ2 | TRP | 300 | 17.630 | 52.938 | 132.942 | 1.00 19.15 | HIGL |
| ATOM | 2426 | CZ3 | TRP | 300 | 17.843 | 54.123 | 130.835 | 1.00 18.15 | HIGL |
| ATOM | 2427 | CH2 | TRP | 300 | 18.011 | 52.969 | 131.621 | 1.00 18.86 | HIGL |
| ATOM | 2428 | C | TRP | 300 | 15.967 | 58.852 | 135.441 | 1.00 19.00 | HIGL |
| ATOM | 2429 | O | TRP | 300 | 17.197 | 58.757 | 135.418 | 1.00 19.92 | HIGL |
| ATOM | 2430 | N | ILE | 301 | 15.299 | 59.358 | 136.473 | 1.00 18.81 | HIGL |
| ATOM | 2431 | CA | ILE | 301 | 15.975 | 59.908 | 137.637 | 1.00 18.49 | HIGL |
| ATOM | 2432 | CB | ILE | 301 | 14.955 | 60.382 | 138.686 | 1.00 18.53 | HIGL |
| ATOM | 2433 | CG2 | ILE | 301 | 14.008 | 61.385 | 138.058 | 1.00 17.80 | HIGL |
| ATOM | 2434 | CG1 | ILE | 301 | 14.161 | 59.196 | 139.226 | 1.00 20.04 | HIGL |
| ATOM | 2435 | CD1 | ILE | 301 | 13.109 | 59.586 | 140.250 | 1.00 21.03 | HIGL |
| ATOM | 2436 | C | ILE | 301 | 17.002 | 59.006 | 138.311 | 1.00 18.58 | HIGL |
| ATOM | 2437 | O | ILE | 301 | 17.991 | 59.499 | 138.851 | 1.00 18.75 | HIGL |
| ATOM | 2438 | N | HIS | 302 | 16.786 | 57.696 | 138.286 | 1.00 18.55 | HIGL |
| ATOM | 2439 | CA | HIS | 302 | 17.741 | 56.781 | 138.907 | 1.00 18.79 | HIGL |
| ATOM | 2440 | CB | HIS | 302 | 17.041 | 55.490 | 139.329 | 1.00 18.93 | HIGL |
| ATOM | 2441 | CG | HIS | 302 | 16.222 | 55.629 | 140.573 | 1.00 18.69 | HIGL |
| ATOM | 2442 | CD2 | HIS | 302 | 16.287 | 56.523 | 141.587 | 1.00 17.82 | HIGL |
| ATOM | 2443 | ND1 | HIS | 302 | 15.191 | 54.769 | 140.884 | 1.00 18.89 | HIGL |
| ATOM | 2444 | CE1 | HIS | 302 | 14.653 | 55.129 | 142.036 | 1.00 17.89 | HIGL |
| ATOM | 2445 | NE2 | HIS | 302 | 15.300 | 56.191 | 142.483 | 1.00 17.70 | HIGL |
| ATOM | 2446 | C | HIS | 302 | 18.925 | 56.453 | 137.997 | 1.00 19.20 | HIGL |
| ATOM | 2447 | O | HIS | 302 | 19.703 | 55.542 | 138.289 | 1.00 19.21 | HIGL |
| ATOM | 2448 | N | ASN | 303 | 19.057 | 57.203 | 136.904 | 1.00 19.05 | HIGL |
| ATOM | 2449 | CA | ASN | 303 | 20.140 | 57.013 | 135.944 | 1.00 19.03 | HIGL |
| ATOM | 2450 | CB | ASN | 303 | 19.737 | 55.956 | 134.909 | 1.00 19.73 | HIGL |
| ATOM | 2451 | CG | ASN | 303 | 20.845 | 55.653 | 133.920 | 1.00 20.38 | HIGL |
| ATOM | 2452 | OD1 | ASN | 303 | 22.026 | 55.600 | 134.286 | 1.00 20.50 | HIGL |
| ATOM | 2453 | ND2 | ASN | 303 | 20.474 | 55.436 | 132.662 | 1.00 19.58 | HIGL |
| ATOM | 2454 | C | ASN | 303 | 20.425 | 58.352 | 135.265 | 1.00 19.33 | HIGL |
| ATOM | 2455 | O | ASN | 303 | 20.706 | 58.413 | 134.068 | 1.00 19.13 | HIGL |
| ATOM | 2456 | N | ALA | 304 | 20.360 | 59.414 | 136.071 | 1.00 19.41 | HIGL |
| ATOM | 2457 | CA | ALA | 304 | 20.562 | 60.804 | 135.654 | 1.00 18.77 | HIGL |
| ATOM | 2458 | CB | ALA | 304 | 20.840 | 61.662 | 136.876 | 1.00 17.04 | HIGL |
| ATOM | 2459 | C | ALA | 304 | 21.603 | 61.102 | 134.584 | 1.00 18.84 | HIGL |
| ATOM | 2460 | O | ALA | 304 | 21.340 | 61.883 | 133.671 | 1.00 19.33 | HIGL |
| ATOM | 2461 | N | ASN | 305 | 22.784 | 60.508 | 134.692 | 1.00 19.13 | HIGL |
| ATOM | 2462 | CA | ASN | 305 | 23.826 | 60.761 | 133.704 | 1.00 18.89 | HIGL |
| ATOM | 2463 | CB | ASN | 305 | 25.162 | 60.163 | 134.158 | 1.00 20.60 | HIGL |
| ATOM | 2464 | CG | ASN | 305 | 25.115 | 58.665 | 134.292 | 1.00 21.86 | HIGL |
| ATOM | 2465 | OD1 | ASN | 305 | 24.345 | 58.119 | 135.085 | 1.00 23.48 | HIGL |
| ATOM | 2466 | ND2 | ASN | 305 | 25.945 | 57.984 | 133.516 | 1.00 23.52 | HIGL |
| ATOM | 2467 | C | ASN | 305 | 23.448 | 60.207 | 132.343 | 1.00 18.26 | HIGL |
| ATOM | 2468 | O | ASN | 305 | 23.993 | 60.628 | 131.331 | 1.00 19.25 | HIGL |
| ATOM | 2469 | N | LEU | 306 | 22.507 | 59.269 | 132.323 | 1.00 17.83 | HIGL |

Fig. 2 cont.

| | | | | | | | | | |
|---|---|---|---|---|---|---|---|---|---|
| ATOM | 2470 | CA | LEU | 306 | 22.035 | 58.657 | 131.080 | 1.00 17.26 | HIGL |
| ATOM | 2471 | CB | LEU | 306 | 21.217 | 59.670 | 130.270 | 1.00 16.18 | HIGL |
| ATOM | 2472 | CG | LEU | 306 | 19.907 | 60.128 | 130.937 | 1.00 16.97 | HIGL |
| ATOM | 2473 | CD1 | LEU | 306 | 19.284 | 61.278 | 130.161 | 1.00 15.17 | HIGL |
| ATOM | 2474 | CD2 | LEU | 306 | 18.937 | 58.954 | 131.024 | 1.00 16.01 | HIGL |
| ATOM | 2475 | C | LEU | 306 | 23.156 | 58.076 | 130.216 | 1.00 17.50 | HIGL |
| ATOM | 2476 | O | LEU | 306 | 23.137 | 58.195 | 128.988 | 1.00 17.52 | HIGL |
| ATOM | 2477 | N | GLY | 307 | 24.131 | 57.450 | 130.870 | 1.00 17.26 | HIGL |
| ATOM | 2478 | CA | GLY | 307 | 25.235 | 56.836 | 130.159 | 1.00 16.70 | HIGL |
| ATOM | 2479 | C | GLY | 307 | 26.294 | 57.773 | 129.616 | 1.00 16.64 | HIGL |
| ATOM | 2480 | O | GLY | 307 | 27.191 | 57.333 | 128.901 | 1.00 16.25 | HIGL |
| ATOM | 2481 | N | SER | 308 | 26.204 | 59.056 | 129.950 | 1.00 16.62 | HIGL |
| ATOM | 2482 | CA | SER | 308 | 27.181 | 60.032 | 129.471 | 1.00 17.50 | HIGL |
| ATOM | 2483 | CB | SER | 308 | 26.477 | 61.300 | 128.987 | 1.00 17.40 | HIGL |
| ATOM | 2484 | OG | SER | 308 | 26.026 | 62.065 | 130.091 | 1.00 18.14 | HIGL |
| ATOM | 2485 | C | SER | 308 | 28.159 | 60.402 | 130.582 | 1.00 17.77 | HIGL |
| ATOM | 2486 | O | SER | 308 | 28.059 | 59.905 | 131.712 | 1.00 18.46 | HIGL |
| ATOM | 2487 | N | SER | 309 | 29.104 | 61.278 | 130.265 | 1.00 17.09 | HIGL |
| ATOM | 2488 | CA | SER | 309 | 30.074 | 61.693 | 131.263 | 1.00 17.48 | HIGL |
| ATOM | 2489 | CB | SER | 309 | 31.384 | 62.138 | 130.599 | 1.00 15.98 | HIGL |
| ATOM | 2490 | OG | SER | 309 | 31.196 | 63.287 | 129.794 | 1.00 15.84 | HIGL |
| ATOM | 2491 | C | SER | 309 | 29.485 | 62.818 | 132.118 | 1.00 17.77 | HIGL |
| ATOM | 2492 | O | SER | 309 | 30.100 | 63.268 | 133.084 | 1.00 17.93 | HIGL |
| ATOM | 2493 | N | CYS | 310 | 28.289 | 63.273 | 131.763 | 1.00 18.10 | HIGL |
| ATOM | 2494 | CA | CYS | 310 | 27.641 | 64.323 | 132.541 | 1.00 18.95 | HIGL |
| ATOM | 2495 | C | CYS | 310 | 26.881 | 63.668 | 133.695 | 1.00 18.10 | HIGL |
| ATOM | 2496 | O | CYS | 310 | 26.437 | 62.528 | 133.583 | 1.00 18.94 | HIGL |
| ATOM | 2497 | CB | CYS | 310 | 26.686 | 65.139 | 131.670 | 1.00 19.41 | HIGL |
| ATOM | 2498 | SG | CYS | 310 | 27.452 | 66.412 | 130.600 | 1.00 24.23 | HIGL |
| ATOM | 2499 | N | ALA | 311 | 26.733 | 64.392 | 134.798 | 1.00 16.72 | HIGL |
| ATOM | 2500 | CA | ALA | 311 | 26.061 | 63.873 | 135.986 | 1.00 15.09 | HIGL |
| ATOM | 2501 | CB | ALA | 311 | 26.451 | 64.713 | 137.187 | 1.00 13.34 | HIGL |
| ATOM | 2502 | C | ALA | 311 | 24.539 | 63.768 | 135.917 | 1.00 14.53 | HIGL |
| ATOM | 2503 | O | ALA | 311 | 23.959 | 62.805 | 136.416 | 1.00 14.36 | HIGL |
| ATOM | 2504 | N | ASP | 312 | 23.893 | 64.755 | 135.308 | 1.00 14.02 | HIGL |
| ATOM | 2505 | CA | ASP | 312 | 22.437 | 64.767 | 135.233 | 1.00 14.14 | HIGL |
| ATOM | 2506 | CB | ASP | 312 | 21.888 | 65.569 | 136.414 | 1.00 13.88 | HIGL |
| ATOM | 2507 | CG | ASP | 312 | 20.417 | 65.338 | 136.647 | 1.00 15.05 | HIGL |
| ATOM | 2508 | OD1 | ASP | 312 | 19.703 | 64.943 | 135.692 | 1.00 16.00 | HIGL |
| ATOM | 2509 | OD2 | ASP | 312 | 19.973 | 65.562 | 137.795 | 1.00 14.74 | HIGL |
| ATOM | 2510 | C | ASP | 312 | 21.910 | 65.376 | 133.932 | 1.00 14.14 | HIGL |
| ATOM | 2511 | O | ASP | 312 | 22.085 | 66.571 | 133.690 | 1.00 13.77 | HIGL |
| ATOM | 2512 | N | ASN | 313 | 21.260 | 64.555 | 133.108 | 1.00 14.50 | HIGL |
| ATOM | 2513 | CA | ASN | 313 | 20.684 | 65.016 | 131.845 | 1.00 15.03 | HIGL |
| ATOM | 2514 | CB | ASN | 313 | 21.177 | 64.160 | 130.672 | 1.00 16.08 | HIGL |
| ATOM | 2515 | CG | ASN | 313 | 22.633 | 64.403 | 130.337 | 1.00 18.13 | HIGL |
| ATOM | 2516 | OD1 | ASN | 313 | 23.069 | 65.544 | 130.228 | 1.00 19.71 | HIGL |
| ATOM | 2517 | ND2 | ASN | 313 | 23.391 | 63.326 | 130.159 | 1.00 17.96 | HIGL |
| ATOM | 2518 | C | ASN | 313 | 19.159 | 64.947 | 131.889 | 1.00 14.73 | HIGL |
| ATOM | 2519 | O | ASN | 313 | 18.491 | 65.155 | 130.881 | 1.00 14.78 | HIGL |
| ATOM | 2520 | N | THR | 314 | 18.608 | 64.649 | 133.057 | 1.00 15.17 | HIGL |
| ATOM | 2521 | CA | THR | 314 | 17.160 | 64.535 | 133.207 | 1.00 16.32 | HIGL |
| ATOM | 2522 | CB | THR | 314 | 16.794 | 63.799 | 134.499 | 1.00 16.08 | HIGL |
| ATOM | 2523 | OG1 | THR | 314 | 17.198 | 64.596 | 135.619 | 1.00 16.57 | HIGL |
| ATOM | 2524 | CG2 | THR | 314 | 17.497 | 62.452 | 134.563 | 1.00 15.34 | HIGL |
| ATOM | 2525 | C | THR | 314 | 16.444 | 65.878 | 133.237 | 1.00 16.22 | HIGL |
| ATOM | 2526 | O | THR | 314 | 17.033 | 66.908 | 133.551 | 1.00 17.07 | HIGL |
| ATOM | 2527 | N | MET | 315 | 15.161 | 65.851 | 132.911 | 1.00 16.05 | HIGL |
| ATOM | 2528 | CA | MET | 315 | 14.352 | 67.055 | 132.929 | 1.00 17.30 | HIGL |
| ATOM | 2529 | CB | MET | 315 | 13.588 | 67.205 | 131.613 | 1.00 17.97 | HIGL |
| ATOM | 2530 | CG | MET | 315 | 14.505 | 67.282 | 130.405 | 1.00 18.13 | HIGL |
| ATOM | 2531 | SD | MET | 315 | 13.637 | 67.606 | 128.894 | 1.00 18.76 | HIGL |
| ATOM | 2532 | CE | MET | 315 | 13.387 | 69.339 | 129.091 | 1.00 19.34 | HIGL |
| ATOM | 2533 | C | MET | 315 | 13.393 | 66.933 | 134.104 | 1.00 18.03 | HIGL |
| ATOM | 2534 | O | MET | 315 | 12.283 | 67.467 | 134.103 | 1.00 17.72 | HIGL |

Fig. 2 cont.

```
ATOM   2535  N    PHE  316      13.844  66.195 135.108  1.00 18.72           HIGL
ATOM   2536  CA   PHE  316      13.075  66.002 136.316  1.00 19.71           HIGL
ATOM   2537  CB   PHE  316      12.431  64.619 136.349  1.00 20.13           HIGL
ATOM   2538  CG   PHE  316      11.179  64.517 135.541  1.00 20.75           HIGL
ATOM   2539  CD1  PHE  316      11.232  64.450 134.153  1.00 21.09           HIGL
ATOM   2540  CD2  PHE  316       9.942  64.492 136.167  1.00 19.49           HIGL
ATOM   2541  CE1  PHE  316      10.065  64.359 133.402  1.00 20.74           HIGL
ATOM   2542  CE2  PHE  316       8.776  64.401 135.429  1.00 19.68           HIGL
ATOM   2543  CZ   PHE  316       8.836  64.335 134.041  1.00 20.74           HIGL
ATOM   2544  C    PHE  316      13.926  66.175 137.561  1.00 20.14           HIGL
ATOM   2545  O    PHE  316      15.155  66.134 137.528  1.00 21.09           HIGL
ATOM   2546  N    THR  317      13.232  66.386 138.662  1.00 20.18           HIGL
ATOM   2547  CA   THR  317      13.836  66.550 139.960  1.00 20.01           HIGL
ATOM   2548  CB   THR  317      12.783  67.140 140.933  1.00 19.47           HIGL
ATOM   2549  OG1  THR  317      13.102  68.508 141.196  1.00 20.10           HIGL
ATOM   2550  CG2  THR  317      12.710  66.363 142.215  1.00 18.19           HIGL
ATOM   2551  C    THR  317      14.271  65.161 140.408  1.00 20.33           HIGL
ATOM   2552  O    THR  317      13.739  64.155 139.939  1.00 20.58           HIGL
ATOM   2553  N    PRO  318      15.265  65.087 141.299  1.00 20.32           HIGL
ATOM   2554  CD   PRO  318      16.162  66.175 141.728  1.00 20.23           HIGL
ATOM   2555  CA   PRO  318      15.740  63.793 141.791  1.00 19.64           HIGL
ATOM   2556  CB   PRO  318      16.859  64.187 142.743  1.00 19.58           HIGL
ATOM   2557  CG   PRO  318      17.416  65.425 142.093  1.00 19.55           HIGL
ATOM   2558  C    PRO  318      14.615  63.044 142.498  1.00 19.76           HIGL
ATOM   2559  O    PRO  318      14.709  61.841 142.739  1.00 19.67           HIGL
ATOM   2560  N    SER  319      13.551  63.772 142.827  1.00 19.98           HIGL
ATOM   2561  CA   SER  319      12.403  63.195 143.504  1.00 20.20           HIGL
ATOM   2562  CB   SER  319      11.887  64.147 144.578  1.00 20.64           HIGL
ATOM   2563  OG   SER  319      11.025  65.119 144.016  1.00 23.02           HIGL
ATOM   2564  C    SER  319      11.291  62.889 142.504  1.00 20.42           HIGL
ATOM   2565  O    SER  319      10.263  62.305 142.861  1.00 20.64           HIGL
ATOM   2566  N    GLY  320      11.489  63.298 141.254  1.00 20.38           HIGL
ATOM   2567  CA   GLY  320      10.505  63.006 140.225  1.00 19.64           HIGL
ATOM   2568  C    GLY  320       9.585  64.119 139.765  1.00 19.52           HIGL
ATOM   2569  O    GLY  320       8.657  63.862 138.996  1.00 19.02           HIGL
ATOM   2570  N    GLN  321       9.833  65.347 140.213  1.00 18.90           HIGL
ATOM   2571  CA   GLN  321       8.991  66.475 139.824  1.00 19.06           HIGL
ATOM   2572  CB   GLN  321       8.940  67.520 140.948  1.00 20.13           HIGL
ATOM   2573  CG   GLN  321       8.219  68.811 140.564  1.00 22.26           HIGL
ATOM   2574  CD   GLN  321       7.946  69.703 141.762  1.00 23.01           HIGL
ATOM   2575  OE1  GLN  321       7.346  69.264 142.748  1.00 25.05           HIGL
ATOM   2576  NE2  GLN  321       8.377  70.958 141.682  1.00 20.98           HIGL
ATOM   2577  C    GLN  321       9.477  67.129 138.540  1.00 18.11           HIGL
ATOM   2578  O    GLN  321      10.639  67.520 138.428  1.00 17.69           HIGL
ATOM   2579  N    ALA  322       8.578  67.263 137.574  1.00 17.71           HIGL
ATOM   2580  CA   ALA  322       8.938  67.857 136.293  1.00 17.37           HIGL
ATOM   2581  CB   ALA  322       7.725  67.942 135.387  1.00 16.48           HIGL
ATOM   2582  C    ALA  322       9.546  69.231 136.466  1.00 17.45           HIGL
ATOM   2583  O    ALA  322       9.078  70.041 137.268  1.00 19.09           HIGL
ATOM   2584  N    LEU  323      10.601  69.476 135.706  1.00 17.15           HIGL
ATOM   2585  CA   LEU  323      11.305  70.743 135.720  1.00 16.94           HIGL
ATOM   2586  CB   LEU  323      12.755  70.512 135.299  1.00 16.28           HIGL
ATOM   2587  CG   LEU  323      13.901  70.773 136.279  1.00 15.82           HIGL
ATOM   2588  CD1  LEU  323      13.500  70.423 137.707  1.00 14.61           HIGL
ATOM   2589  CD2  LEU  323      15.113  69.964 135.823  1.00 14.44           HIGL
ATOM   2590  C    LEU  323      10.603  71.677 134.731  1.00 17.93           HIGL
ATOM   2591  O    LEU  323       9.883  71.225 133.838  1.00 16.70           HIGL
ATOM   2592  N    SER  324      10.811  72.980 134.893  1.00 18.92           HIGL
ATOM   2593  CA   SER  324      10.186  73.966 134.018  1.00 19.03           HIGL
ATOM   2594  CB   SER  324      10.663  75.370 134.383  1.00 19.54           HIGL
ATOM   2595  OG   SER  324      12.069  75.478 134.241  1.00 20.56           HIGL
ATOM   2596  C    SER  324      10.496  73.707 132.555  1.00 19.19           HIGL
ATOM   2597  O    SER  324       9.628  73.843 131.697  1.00 20.39           HIGL
ATOM   2598  N    SER  325      11.743  73.338 132.282  1.00 19.12           HIGL
ATOM   2599  CA   SER  325      12.217  73.073 130.927  1.00 18.61           HIGL
```

Fig. 2 cont.

```
ATOM   2600  CB   SER   325      13.681  72.639 130.980  1.00 18.82      HIGL
ATOM   2601  OG   SER   325      13.838  71.516 131.828  1.00 18.06      HIGL
ATOM   2602  C    SER   325      11.414  72.047 130.132  1.00 18.61      HIGL
ATOM   2603  O    SER   325      11.458  72.036 128.905  1.00 18.45      HIGL
ATOM   2604  N    LEU   326      10.680  71.184 130.820  1.00 19.28      HIGL
ATOM   2605  CA   LEU   326       9.893  70.167 130.132  1.00 19.85      HIGL
ATOM   2606  CB   LEU   326       9.212  69.243 131.145  1.00 20.13      HIGL
ATOM   2607  CG   LEU   326       9.112  67.733 130.862  1.00 22.13      HIGL
ATOM   2608  CD1  LEU   326       7.849  67.179 131.542  1.00 20.56      HIGL
ATOM   2609  CD2  LEU   326       9.063  67.453 129.364  1.00 21.71      HIGL
ATOM   2610  C    LEU   326       8.822  70.787 129.230  1.00 20.36      HIGL
ATOM   2611  O    LEU   326       8.415  70.187 128.233  1.00 19.41      HIGL
ATOM   2612  N    SER   327       8.363  71.986 129.580  1.00 20.97      HIGL
ATOM   2613  CA   SER   327       7.317  72.642 128.803  1.00 21.71      HIGL
ATOM   2614  CB   SER   327       6.595  73.684 129.653  1.00 21.54      HIGL
ATOM   2615  OG   SER   327       7.439  74.785 129.921  1.00 23.10      HIGL
ATOM   2616  C    SER   327       7.829  73.301 127.533  1.00 22.18      HIGL
ATOM   2617  O    SER   327       7.100  74.056 126.887  1.00 23.13      HIGL
ATOM   2618  N    VAL   328       9.080  73.032 127.180  1.00 21.90      HIGL
ATOM   2619  CA   VAL   328       9.651  73.588 125.959  1.00 22.31      HIGL
ATOM   2620  CB   VAL   328      11.188  73.333 125.873  1.00 22.21      HIGL
ATOM   2621  CG1  VAL   328      11.483  71.843 125.809  1.00 21.74      HIGL
ATOM   2622  CG2  VAL   328      11.759  74.026 124.657  1.00 21.78      HIGL
ATOM   2623  C    VAL   328       8.958  72.917 124.764  1.00 22.65      HIGL
ATOM   2624  O    VAL   328       8.973  73.429 123.645  1.00 22.63      HIGL
ATOM   2625  N    PHE   329       8.338  71.771 125.013  1.00 22.73      HIGL
ATOM   2626  CA   PHE   329       7.654  71.048 123.959  1.00 23.91      HIGL
ATOM   2627  CB   PHE   329       7.268  69.658 124.454  1.00 23.67      HIGL
ATOM   2628  CG   PHE   329       8.440  68.723 124.557  1.00 24.39      HIGL
ATOM   2629  CD1  PHE   329       9.067  68.252 123.409  1.00 24.10      HIGL
ATOM   2630  CD2  PHE   329       8.949  68.349 125.796  1.00 23.95      HIGL
ATOM   2631  CE1  PHE   329      10.185  67.424 123.491  1.00 24.86      HIGL
ATOM   2632  CE2  PHE   329      10.063  67.524 125.887  1.00 24.79      HIGL
ATOM   2633  CZ   PHE   329      10.686  67.060 124.729  1.00 24.99      HIGL
ATOM   2634  C    PHE   329       6.446  71.806 123.420  1.00 24.94      HIGL
ATOM   2635  O    PHE   329       5.885  71.438 122.384  1.00 24.54      HIGL
ATOM   2636  N    HIS   330       6.053  72.867 124.123  1.00 25.53      HIGL
ATOM   2637  CA   HIS   330       4.944  73.706 123.677  1.00 25.92      HIGL
ATOM   2638  CB   HIS   330       4.376  74.554 124.828  1.00 25.05      HIGL
ATOM   2639  CG   HIS   330       3.507  73.795 125.786  1.00 23.98      HIGL
ATOM   2640  CD2  HIS   330       3.511  73.739 127.139  1.00 23.72      HIGL
ATOM   2641  ND1  HIS   330       2.451  73.010 125.377  1.00 23.63      HIGL
ATOM   2642  CE1  HIS   330       1.843  72.503 126.434  1.00 22.96      HIGL
ATOM   2643  NE2  HIS   330       2.467  72.931 127.517  1.00 23.30      HIGL
ATOM   2644  C    HIS   330       5.488  74.650 122.601  1.00 26.65      HIGL
ATOM   2645  O    HIS   330       4.891  74.806 121.540  1.00 27.30      HIGL
ATOM   2646  N    ARG   331       6.632  75.267 122.888  1.00 27.80      HIGL
ATOM   2647  CA   ARG   331       7.273  76.214 121.976  1.00 28.68      HIGL
ATOM   2648  CB   ARG   331       8.405  76.953 122.698  1.00 31.32      HIGL
ATOM   2649  CG   ARG   331       7.935  78.120 123.555  1.00 35.13      HIGL
ATOM   2650  CD   ARG   331       9.101  78.976 124.057  1.00 37.60      HIGL
ATOM   2651  NE   ARG   331       9.862  78.322 125.116  1.00 39.32      HIGL
ATOM   2652  CZ   ARG   331       9.311  77.800 126.208  1.00 41.08      HIGL
ATOM   2653  NH1  ARG   331       7.994  77.854 126.382  1.00 41.70      HIGL
ATOM   2654  NH2  ARG   331      10.075  77.233 127.133  1.00 41.35      HIGL
ATOM   2655  C    ARG   331       7.821  75.668 120.661  1.00 28.01      HIGL
ATOM   2656  O    ARG   331       8.119  76.440 119.753  1.00 28.33      HIGL
ATOM   2657  N    ILE   332       7.966  74.355 120.545  1.00 27.15      HIGL
ATOM   2658  CA   ILE   332       8.503  73.790 119.313  1.00 25.82      HIGL
ATOM   2659  CB   ILE   332       9.717  72.876 119.596  1.00 24.07      HIGL
ATOM   2660  CG2  ILE   332      10.747  73.636 120.419  1.00 22.61      HIGL
ATOM   2661  CG1  ILE   332       9.262  71.611 120.331  1.00 23.55      HIGL
ATOM   2662  CD1  ILE   332      10.328  70.559 120.487  1.00 21.73      HIGL
ATOM   2663  C    ILE   332       7.463  72.999 118.534  1.00 26.35      HIGL
ATOM   2664  O    ILE   332       7.659  72.716 117.351  1.00 27.46      HIGL
END
```

Fig. 2 cont.

| | | | | | | | | | | |
|---|---|---|---|---|---|---|---|---|---|---|
| HEADER | | | | | | | | | AAGL | |
| ATOM | 1 | CB | ALA | 1 | 30.233 | 36.166 | 100.975 | 1.00 | 33.89 | AAGL |
| ATOM | 2 | C | ALA | 1 | 30.173 | 35.826 | 103.455 | 1.00 | 33.23 | AAGL |
| ATOM | 3 | O | ALA | 1 | 30.978 | 35.045 | 103.960 | 1.00 | 32.69 | AAGL |
| ATOM | 4 | N | ALA | 1 | 32.066 | 36.993 | 102.404 | 1.00 | 32.99 | AAGL |
| ATOM | 5 | CA | ALA | 1 | 30.595 | 36.767 | 102.330 | 1.00 | 33.73 | AAGL |
| ATOM | 6 | N | LEU | 2 | 28.909 | 35.906 | 103.856 | 1.00 | 31.18 | AAGL |
| ATOM | 7 | CA | LEU | 2 | 28.412 | 35.052 | 104.926 | 1.00 | 29.30 | AAGL |
| ATOM | 8 | CB | LEU | 2 | 27.023 | 35.510 | 105.362 | 1.00 | 29.79 | AAGL |
| ATOM | 9 | CG | LEU | 2 | 26.868 | 36.944 | 105.864 | 1.00 | 30.10 | AAGL |
| ATOM | 10 | CD1 | LEU | 2 | 25.382 | 37.292 | 105.912 | 1.00 | 32.47 | AAGL |
| ATOM | 11 | CD2 | LEU | 2 | 27.511 | 37.098 | 107.236 | 1.00 | 30.25 | AAGL |
| ATOM | 12 | C | LEU | 2 | 28.340 | 33.612 | 104.451 | 1.00 | 28.19 | AAGL |
| ATOM | 13 | O | LEU | 2 | 28.258 | 33.351 | 103.250 | 1.00 | 28.93 | AAGL |
| ATOM | 14 | N | THR | 3 | 28.370 | 32.679 | 105.396 | 1.00 | 27.70 | AAGL |
| ATOM | 15 | CA | THR | 3 | 28.304 | 31.267 | 105.071 | 1.00 | 27.25 | AAGL |
| ATOM | 16 | CB | THR | 3 | 28.401 | 30.410 | 106.349 | 1.00 | 28.42 | AAGL |
| ATOM | 17 | OG1 | THR | 3 | 29.650 | 30.681 | 107.001 | 1.00 | 28.17 | AAGL |
| ATOM | 18 | CG2 | THR | 3 | 28.327 | 28.920 | 106.010 | 1.00 | 27.90 | AAGL |
| ATOM | 19 | C | THR | 3 | 27.000 | 30.971 | 104.343 | 1.00 | 26.98 | AAGL |
| ATOM | 20 | O | THR | 3 | 26.965 | 30.159 | 103.416 | 1.00 | 26.10 | AAGL |
| ATOM | 21 | N | TYR | 4 | 25.931 | 31.650 | 104.756 | 1.00 | 26.84 | AAGL |
| ATOM | 22 | CA | TYR | 4 | 24.623 | 31.465 | 104.137 | 1.00 | 24.81 | AAGL |
| ATOM | 23 | CB | TYR | 4 | 23.665 | 30.721 | 105.079 | 1.00 | 25.74 | AAGL |
| ATOM | 24 | CG | TYR | 4 | 24.137 | 29.377 | 105.602 | 1.00 | 25.74 | AAGL |
| ATOM | 25 | CD1 | TYR | 4 | 24.318 | 28.288 | 104.746 | 1.00 | 26.33 | AAGL |
| ATOM | 26 | CE1 | TYR | 4 | 24.692 | 27.034 | 105.247 | 1.00 | 27.71 | AAGL |
| ATOM | 27 | CD2 | TYR | 4 | 24.349 | 29.182 | 106.965 | 1.00 | 25.74 | AAGL |
| ATOM | 28 | CE2 | TYR | 4 | 24.724 | 27.940 | 107.473 | 1.00 | 26.87 | AAGL |
| ATOM | 29 | CZ | TYR | 4 | 24.891 | 26.870 | 106.609 | 1.00 | 26.22 | AAGL |
| ATOM | 30 | OH | TYR | 4 | 25.248 | 25.646 | 107.118 | 1.00 | 29.24 | AAGL |
| ATOM | 31 | C | TYR | 4 | 23.977 | 32.803 | 103.787 | 1.00 | 24.69 | AAGL |
| ATOM | 32 | O | TYR | 4 | 23.914 | 33.712 | 104.619 | 1.00 | 24.65 | AAGL |
| ATOM | 33 | N | ARG | 5 | 23.515 | 32.919 | 102.549 | 1.00 | 23.45 | AAGL |
| ATOM | 34 | CA | ARG | 5 | 22.801 | 34.103 | 102.069 | 1.00 | 25.24 | AAGL |
| ATOM | 35 | CB | ARG | 5 | 23.551 | 34.823 | 100.939 | 1.00 | 29.22 | AAGL |
| ATOM | 36 | CG | ARG | 5 | 24.781 | 35.609 | 101.366 | 1.00 | 29.88 | AAGL |
| ATOM | 37 | CD | ARG | 5 | 26.042 | 34.797 | 101.168 | 1.00 | 29.48 | AAGL |
| ATOM | 38 | NE | ARG | 5 | 26.159 | 34.336 | 99.792 | 1.00 | 29.78 | AAGL |
| ATOM | 39 | CZ | ARG | 5 | 27.061 | 33.454 | 99.373 | 1.00 | 27.81 | AAGL |
| ATOM | 40 | NH1 | ARG | 5 | 27.934 | 32.940 | 100.225 | 1.00 | 27.49 | AAGL |
| ATOM | 41 | NH2 | ARG | 5 | 27.068 | 33.068 | 98.104 | 1.00 | 29.30 | AAGL |
| ATOM | 42 | C | ARG | 5 | 21.554 | 33.439 | 101.507 | 1.00 | 25.34 | AAGL |
| ATOM | 43 | O | ARG | 5 | 21.547 | 32.962 | 100.371 | 1.00 | 23.77 | AAGL |
| ATOM | 44 | N | GLY | 6 | 20.502 | 33.381 | 102.308 | 1.00 | 24.34 | AAGL |
| ATOM | 45 | CA | GLY | 6 | 19.321 | 32.694 | 101.837 | 1.00 | 21.41 | AAGL |
| ATOM | 46 | C | GLY | 6 | 18.031 | 33.457 | 101.755 | 1.00 | 22.93 | AAGL |
| ATOM | 47 | O | GLY | 6 | 17.957 | 34.649 | 102.053 | 1.00 | 21.36 | AAGL |
| ATOM | 48 | N | ALA | 7 | 17.008 | 32.727 | 101.330 | 1.00 | 21.72 | AAGL |
| ATOM | 49 | CA | ALA | 7 | 15.669 | 33.248 | 101.182 | 1.00 | 22.02 | AAGL |
| ATOM | 50 | CB | ALA | 7 | 15.481 | 33.797 | 99.780 | 1.00 | 22.89 | AAGL |
| ATOM | 51 | C | ALA | 7 | 14.689 | 32.110 | 101.422 | 1.00 | 21.79 | AAGL |
| ATOM | 52 | O | ALA | 7 | 14.973 | 30.956 | 101.101 | 1.00 | 23.27 | AAGL |
| ATOM | 53 | N | ASP | 8 | 13.548 | 32.435 | 102.014 | 1.00 | 20.87 | AAGL |
| ATOM | 54 | CA | ASP | 8 | 12.501 | 31.448 | 102.247 | 1.00 | 21.47 | AAGL |
| ATOM | 55 | CB | ASP | 8 | 11.854 | 31.650 | 103.625 | 1.00 | 20.38 | AAGL |
| ATOM | 56 | CG | ASP | 8 | 10.772 | 30.617 | 103.923 | 1.00 | 20.93 | AAGL |
| ATOM | 57 | OD1 | ASP | 8 | 9.920 | 30.363 | 103.044 | 1.00 | 20.43 | AAGL |
| ATOM | 58 | OD2 | ASP | 8 | 10.768 | 30.069 | 105.048 | 1.00 | 19.51 | AAGL |
| ATOM | 59 | C | ASP | 8 | 11.482 | 31.736 | 101.153 | 1.00 | 19.96 | AAGL |
| ATOM | 60 | O | ASP | 8 | 10.773 | 32.738 | 101.205 | 1.00 | 21.04 | AAGL |
| ATOM | 61 | N | ILE | 9 | 11.424 | 30.870 | 100.149 | 1.00 | 20.91 | AAGL |
| ATOM | 62 | CA | ILE | 9 | 10.490 | 31.065 | 99.049 | 1.00 | 21.73 | AAGL |
| ATOM | 63 | CB | ILE | 9 | 11.234 | 31.102 | 97.689 | 1.00 | 21.80 | AAGL |
| ATOM | 64 | CG2 | ILE | 9 | 12.174 | 32.300 | 97.648 | 1.00 | 23.18 | AAGL |
| ATOM | 65 | CG1 | ILE | 9 | 12.015 | 29.807 | 97.479 | 1.00 | 22.70 | AAGL |

Fig. 3

```
ATOM     66  CD1 ILE     9      12.626  29.683  96.085  1.00 25.10      AAGL
ATOM     67  C   ILE     9       9.452  29.945  99.038  1.00 23.69      AAGL
ATOM     68  O   ILE     9       9.018  29.490  97.984  1.00 22.97      AAGL
ATOM     69  N   SER    10       9.059  29.511 100.232  1.00 22.26      AAGL
ATOM     70  CA  SER    10       8.080  28.441 100.377  1.00 22.83      AAGL
ATOM     71  CB  SER    10       7.658  28.325 101.840  1.00 20.03      AAGL
ATOM     72  OG  SER    10       8.782  28.078 102.658  1.00 21.43      AAGL
ATOM     73  C   SER    10       6.833  28.617  99.508  1.00 22.20      AAGL
ATOM     74  O   SER    10       6.286  27.649  98.995  1.00 24.50      AAGL
ATOM     75  N   SER    11       6.388  29.855  99.347  1.00 23.05      AAGL
ATOM     76  CA  SER    11       5.198  30.148  98.563  1.00 24.59      AAGL
ATOM     77  CB  SER    11       4.784  31.598  98.792  1.00 26.58      AAGL
ATOM     78  OG  SER    11       5.775  32.473  98.275  1.00 26.05      AAGL
ATOM     79  C   SER    11       5.347  29.935  97.057  1.00 25.49      AAGL
ATOM     80  O   SER    11       4.351  29.913  96.338  1.00 25.69      AAGL
ATOM     81  N   LEU    12       6.578  29.781  96.583  1.00 26.51      AAGL
ATOM     82  CA  LEU    12       6.817  29.637  95.149  1.00 25.87      AAGL
ATOM     83  CB  LEU    12       8.237  29.143  94.884  1.00 26.84      AAGL
ATOM     84  CG  LEU    12       8.609  29.025  93.398  1.00 26.26      AAGL
ATOM     85  CD1 LEU    12       8.307  30.324  92.665  1.00 26.19      AAGL
ATOM     86  CD2 LEU    12      10.078  28.685  93.273  1.00 28.47      AAGL
ATOM     87  C   LEU    12       5.844  28.768  94.362  1.00 28.42      AAGL
ATOM     88  O   LEU    12       5.181  29.257  93.447  1.00 28.84      AAGL
ATOM     89  N   LEU    13       5.758  27.487  94.701  1.00 28.60      AAGL
ATOM     90  CA  LEU    13       4.879  26.590  93.963  1.00 30.83      AAGL
ATOM     91  CB  LEU    13       4.997  25.164  94.514  1.00 30.59      AAGL
ATOM     92  CG  LEU    13       6.443  24.657  94.640  1.00 29.90      AAGL
ATOM     93  CD1 LEU    13       6.441  23.200  95.044  1.00 30.84      AAGL
ATOM     94  CD2 LEU    13       7.179  24.821  93.315  1.00 31.95      AAGL
ATOM     95  C   LEU    13       3.430  27.062  93.967  1.00 31.99      AAGL
ATOM     96  O   LEU    13       2.703  26.844  93.001  1.00 33.62      AAGL
ATOM     97  N   LEU    14       3.008  27.725  95.038  1.00 33.18      AAGL
ATOM     98  CA  LEU    14       1.639  28.226  95.106  1.00 33.64      AAGL
ATOM     99  CB  LEU    14       1.289  28.683  96.523  1.00 34.87      AAGL
ATOM    100  CG  LEU    14       0.959  27.561  97.502  1.00 35.78      AAGL
ATOM    101  CD1 LEU    14       0.492  28.145  98.828  1.00 36.41      AAGL
ATOM    102  CD2 LEU    14      -0.137  26.693  96.895  1.00 37.20      AAGL
ATOM    103  C   LEU    14       1.423  29.385  94.141  1.00 34.86      AAGL
ATOM    104  O   LEU    14       0.352  29.522  93.551  1.00 33.97      AAGL
ATOM    105  N   LEU    15       2.443  30.218  93.978  1.00 34.48      AAGL
ATOM    106  CA  LEU    15       2.344  31.359  93.080  1.00 35.10      AAGL
ATOM    107  CB  LEU    15       3.428  32.390  93.415  1.00 35.52      AAGL
ATOM    108  CG  LEU    15       3.232  33.227  94.696  1.00 37.21      AAGL
ATOM    109  CD1 LEU    15       2.912  32.357  95.879  1.00 37.69      AAGL
ATOM    110  CD2 LEU    15       4.496  34.018  94.975  1.00 35.91      AAGL
ATOM    111  C   LEU    15       2.458  30.904  91.624  1.00 35.48      AAGL
ATOM    112  O   LEU    15       1.647  31.306  90.782  1.00 35.67      AAGL
ATOM    113  N   GLU    16       3.449  30.065  91.329  1.00 35.68      AAGL
ATOM    114  CA  GLU    16       3.619  29.561  89.966  1.00 37.14      AAGL
ATOM    115  CB  GLU    16       4.747  28.527  89.890  1.00 35.01      AAGL
ATOM    116  CG  GLU    16       6.159  29.083  90.020  1.00 34.68      AAGL
ATOM    117  CD  GLU    16       7.214  27.993  89.905  1.00 35.45      AAGL
ATOM    118  OE1 GLU    16       6.928  26.849  90.317  1.00 35.57      AAGL
ATOM    119  OE2 GLU    16       8.336  28.271  89.419  1.00 35.12      AAGL
ATOM    120  C   GLU    16       2.317  28.913  89.527  1.00 39.70      AAGL
ATOM    121  O   GLU    16       1.846  29.139  88.411  1.00 40.81      AAGL
ATOM    122  N   ASP    17       1.727  28.112  90.411  1.00 41.41      AAGL
ATOM    123  CA  ASP    17       0.470  27.444  90.099  1.00 44.13      AAGL
ATOM    124  CB  ASP    17       0.029  26.557  91.262  1.00 44.94      AAGL
ATOM    125  CG  ASP    17       0.510  25.127  91.117  1.00 47.20      AAGL
ATOM    126  OD1 ASP    17       0.423  24.359  92.103  1.00 47.97      AAGL
ATOM    127  OD2 ASP    17       0.959  24.757  90.006  1.00 50.11      AAGL
ATOM    128  C   ASP    17      -0.625  28.447  89.771  1.00 45.54      AAGL
ATOM    129  O   ASP    17      -1.458  28.195  88.896  1.00 47.39      AAGL
ATOM    130  N   GLU    18      -0.629  29.581  90.471  1.00 45.43      AAGL
ATOM    131  CA  GLU    18      -1.625  30.617  90.234  1.00 47.08      AAGL
```

Fig. 3 cont.

```
ATOM    132  CB   GLU    18      -1.762   31.537   91.458  1.00 49.00      AAGL
ATOM    133  CG   GLU    18      -2.526   30.900   92.622  1.00 52.65      AAGL
ATOM    134  CD   GLU    18      -2.530   31.755   93.890  1.00 55.02      AAGL
ATOM    135  OE1  GLU    18      -3.112   31.305   94.911  1.00 55.65      AAGL
ATOM    136  OE2  GLU    18      -1.953   32.870   93.870  1.00 56.34      AAGL
ATOM    137  C    GLU    18      -1.267   31.432   88.994  1.00 46.48      AAGL
ATOM    138  O    GLU    18      -1.845   32.492   88.743  1.00 46.57      AAGL
ATOM    139  N    GLY    19      -0.307   30.929   88.223  1.00 45.75      AAGL
ATOM    140  CA   GLY    19       0.091   31.609   87.006  1.00 45.53      AAGL
ATOM    141  C    GLY    19       1.245   32.588   87.113  1.00 45.29      AAGL
ATOM    142  O    GLY    19       1.636   33.185   86.113  1.00 44.87      AAGL
ATOM    143  N    TYR    20       1.802   32.758   88.309  1.00 44.55      AAGL
ATOM    144  CA   TYR    20       2.911   33.685   88.497  1.00 44.04      AAGL
ATOM    145  CB   TYR    20       3.098   33.987   89.985  1.00 46.33      AAGL
ATOM    146  CG   TYR    20       2.199   35.092   90.475  1.00 46.92      AAGL
ATOM    147  CD1  TYR    20       1.174   34.837   91.384  1.00 47.92      AAGL
ATOM    148  CE1  TYR    20       0.317   35.856   91.804  1.00 48.81      AAGL
ATOM    149  CD2  TYR    20       2.351   36.388   89.995  1.00 48.25      AAGL
ATOM    150  CE2  TYR    20       1.509   37.406   90.399  1.00 48.75      AAGL
ATOM    151  CZ   TYR    20       0.494   37.135   91.301  1.00 49.08      AAGL
ATOM    152  OH   TYR    20      -0.350   38.146   91.676  1.00 50.05      AAGL
ATOM    153  C    TYR    20       4.243   33.232   87.916  1.00 42.70      AAGL
ATOM    154  O    TYR    20       4.541   32.043   87.857  1.00 41.19      AAGL
ATOM    155  N    SER    21       5.040   34.211   87.494  1.00 42.54      AAGL
ATOM    156  CA   SER    21       6.360   33.981   86.918  1.00 42.59      AAGL
ATOM    157  CB   SER    21       6.255   33.775   85.402  1.00 43.78      AAGL
ATOM    158  OG   SER    21       5.527   34.835   84.790  1.00 44.41      AAGL
ATOM    159  C    SER    21       7.191   35.224   87.221  1.00 41.81      AAGL
ATOM    160  O    SER    21       6.639   36.307   87.421  1.00 42.15      AAGL
ATOM    161  N    TYR    22       8.510   35.075   87.260  1.00 40.81      AAGL
ATOM    162  CA   TYR    22       9.382   36.205   87.558  1.00 40.63      AAGL
ATOM    163  CB   TYR    22      10.143   35.955   88.855  1.00 39.48      AAGL
ATOM    164  CG   TYR    22       9.248   35.579   90.010  1.00 37.92      AAGL
ATOM    165  CD1  TYR    22       8.820   34.261   90.186  1.00 35.93      AAGL
ATOM    166  CE1  TYR    22       7.987   33.913   91.246  1.00 35.62      AAGL
ATOM    167  CD2  TYR    22       8.820   36.540   90.921  1.00 37.21      AAGL
ATOM    168  CE2  TYR    22       7.982   36.204   91.982  1.00 35.75      AAGL
ATOM    169  CZ   TYR    22       7.574   34.897   92.140  1.00 36.41      AAGL
ATOM    170  OH   TYR    22       6.761   34.573   93.196  1.00 34.78      AAGL
ATOM    171  C    TYR    22      10.385   36.498   86.455  1.00 41.14      AAGL
ATOM    172  O    TYR    22      10.607   35.672   85.568  1.00 40.90      AAGL
ATOM    173  N    LYS    23      10.990   37.684   86.532  1.00 40.98      AAGL
ATOM    174  CA   LYS    23      11.987   38.131   85.565  1.00 41.42      AAGL
ATOM    175  CB   LYS    23      11.430   39.257   84.690  1.00 44.58      AAGL
ATOM    176  CG   LYS    23      10.779   38.781   83.398  1.00 49.11      AAGL
ATOM    177  CD   LYS    23       9.379   38.262   83.633  1.00 51.49      AAGL
ATOM    178  CE   LYS    23       8.453   39.401   84.042  1.00 52.49      AAGL
ATOM    179  NZ   LYS    23       8.461   40.487   83.021  1.00 51.35      AAGL
ATOM    180  C    LYS    23      13.248   38.634   86.243  1.00 40.33      AAGL
ATOM    181  O    LYS    23      13.184   39.363   87.241  1.00 39.11      AAGL
ATOM    182  N    ASN    24      14.396   38.246   85.693  1.00 38.79      AAGL
ATOM    183  CA   ASN    24      15.682   38.672   86.226  1.00 40.03      AAGL
ATOM    184  CB   ASN    24      16.807   37.935   85.509  1.00 42.29      AAGL
ATOM    185  CG   ASN    24      16.738   38.104   84.004  1.00 42.84      AAGL
ATOM    186  OD1  ASN    24      16.732   39.224   83.497  1.00 43.55      AAGL
ATOM    187  ND2  ASN    24      16.675   36.993   83.282  1.00 45.13      AAGL
ATOM    188  C    ASN    24      15.840   40.178   86.018  1.00 40.98      AAGL
ATOM    189  O    ASN    24      14.938   40.837   85.494  1.00 38.96      AAGL
ATOM    190  N    LEU    25      16.987   40.720   86.423  1.00 42.28      AAGL
ATOM    191  CA   LEU    25      17.246   42.149   86.283  1.00 44.49      AAGL
ATOM    192  CB   LEU    25      18.528   42.543   87.032  1.00 44.66      AAGL
ATOM    193  CG   LEU    25      18.549   42.643   88.563  1.00 45.79      AAGL
ATOM    194  CD1  LEU    25      17.376   43.494   89.037  1.00 45.23      AAGL
ATOM    195  CD2  LEU    25      18.493   41.252   89.189  1.00 46.13      AAGL
ATOM    196  C    LEU    25      17.345   42.614   84.824  1.00 45.76      AAGL
ATOM    197  O    LEU    25      17.454   43.814   84.562  1.00 46.23      AAGL
```

Fig. 3 cont.

| | | | | | | | | | | |
|---|---|---|---|---|---|---|---|---|---|---|
| ATOM | 198 | N | ASN | 26 | 17.311 | 41.675 | 83.880 | 1.00 | 46.41 | AAGL |
| ATOM | 199 | CA | ASN | 26 | 17.365 | 42.021 | 82.455 | 1.00 | 47.05 | AAGL |
| ATOM | 200 | CB | ASN | 26 | 18.288 | 41.066 | 81.676 | 1.00 | 47.42 | AAGL |
| ATOM | 201 | CG | ASN | 26 | 19.747 | 41.198 | 82.074 | 1.00 | 49.18 | AAGL |
| ATOM | 202 | OD1 | ASN | 26 | 20.207 | 42.276 | 82.459 | 1.00 | 49.93 | AAGL |
| ATOM | 203 | ND2 | ASN | 26 | 20.492 | 40.100 | 81.961 | 1.00 | 49.97 | AAGL |
| ATOM | 204 | C | ASN | 26 | 15.966 | 41.947 | 81.848 | 1.00 | 47.00 | AAGL |
| ATOM | 205 | O | ASN | 26 | 15.796 | 42.082 | 80.634 | 1.00 | 47.34 | AAGL |
| ATOM | 206 | N | GLY | 27 | 14.961 | 41.712 | 82.684 | 1.00 | 45.83 | AAGL |
| ATOM | 207 | CA | GLY | 27 | 13.602 | 41.628 | 82.176 | 1.00 | 45.48 | AAGL |
| ATOM | 208 | C | GLY | 27 | 13.343 | 40.327 | 81.436 | 1.00 | 45.43 | AAGL |
| ATOM | 209 | O | GLY | 27 | 12.388 | 40.225 | 80.669 | 1.00 | 46.84 | AAGL |
| ATOM | 210 | N | GLN | 28 | 14.198 | 39.332 | 81.648 | 1.00 | 45.03 | AAGL |
| ATOM | 211 | CA | GLN | 28 | 14.023 | 38.037 | 81.002 | 1.00 | 44.89 | AAGL |
| ATOM | 212 | CB | GLN | 28 | 15.385 | 37.428 | 80.633 | 1.00 | 46.09 | AAGL |
| ATOM | 213 | CG | GLN | 28 | 16.346 | 38.371 | 79.909 | 1.00 | 48.72 | AAGL |
| ATOM | 214 | CD | GLN | 28 | 17.649 | 37.684 | 79.531 | 1.00 | 49.91 | AAGL |
| ATOM | 215 | OE1 | GLN | 28 | 17.674 | 36.802 | 78.668 | 1.00 | 51.23 | AAGL |
| ATOM | 216 | NE2 | GLN | 28 | 18.740 | 38.075 | 80.187 | 1.00 | 51.05 | AAGL |
| ATOM | 217 | C | GLN | 28 | 13.312 | 37.093 | 81.980 | 1.00 | 43.57 | AAGL |
| ATOM | 218 | O | GLN | 28 | 13.800 | 36.871 | 83.088 | 1.00 | 40.72 | AAGL |
| ATOM | 219 | N | THR | 29 | 12.166 | 36.542 | 81.580 | 1.00 | 42.64 | AAGL |
| ATOM | 220 | CA | THR | 29 | 11.441 | 35.610 | 82.445 | 1.00 | 42.01 | AAGL |
| ATOM | 221 | CB | THR | 29 | 10.201 | 35.022 | 81.746 | 1.00 | 42.12 | AAGL |
| ATOM | 222 | OG1 | THR | 29 | 9.191 | 36.030 | 81.626 | 1.00 | 42.02 | AAGL |
| ATOM | 223 | CG2 | THR | 29 | 9.639 | 33.857 | 82.552 | 1.00 | 41.97 | AAGL |
| ATOM | 224 | C | THR | 29 | 12.393 | 34.472 | 82.787 | 1.00 | 41.90 | AAGL |
| ATOM | 225 | O | THR | 29 | 13.233 | 34.095 | 81.966 | 1.00 | 41.33 | AAGL |
| ATOM | 226 | N | GLN | 30 | 12.261 | 33.909 | 83.984 | 1.00 | 40.58 | AAGL |
| ATOM | 227 | CA | GLN | 30 | 13.158 | 32.835 | 84.392 | 1.00 | 39.49 | AAGL |
| ATOM | 228 | CB | GLN | 30 | 14.585 | 33.383 | 84.396 | 1.00 | 40.50 | AAGL |
| ATOM | 229 | CG | GLN | 30 | 15.604 | 32.528 | 85.100 | 1.00 | 43.69 | AAGL |
| ATOM | 230 | CD | GLN | 30 | 17.014 | 33.031 | 84.892 | 1.00 | 46.36 | AAGL |
| ATOM | 231 | OE1 | GLN | 30 | 17.325 | 34.200 | 85.159 | 1.00 | 45.16 | AAGL |
| ATOM | 232 | NE2 | GLN | 30 | 17.888 | 32.145 | 84.409 | 1.00 | 47.79 | AAGL |
| ATOM | 233 | C | GLN | 30 | 12.790 | 32.268 | 85.763 | 1.00 | 38.44 | AAGL |
| ATOM | 234 | O | GLN | 30 | 12.368 | 33.004 | 86.656 | 1.00 | 38.87 | AAGL |
| ATOM | 235 | N | ALA | 31 | 12.946 | 30.958 | 85.929 | 1.00 | 36.80 | AAGL |
| ATOM | 236 | CA | ALA | 31 | 12.617 | 30.314 | 87.202 | 1.00 | 34.49 | AAGL |
| ATOM | 237 | CB | ALA | 31 | 13.079 | 28.855 | 87.186 | 1.00 | 34.38 | AAGL |
| ATOM | 238 | C | ALA | 31 | 13.261 | 31.059 | 88.371 | 1.00 | 32.91 | AAGL |
| ATOM | 239 | O | ALA | 31 | 14.474 | 31.278 | 88.392 | 1.00 | 32.07 | AAGL |
| ATOM | 240 | N | LEU | 32 | 12.441 | 31.432 | 89.352 | 1.00 | 33.31 | AAGL |
| ATOM | 241 | CA | LEU | 32 | 12.914 | 32.180 | 90.522 | 1.00 | 29.54 | AAGL |
| ATOM | 242 | CB | LEU | 32 | 11.809 | 32.294 | 91.574 | 1.00 | 28.70 | AAGL |
| ATOM | 243 | CG | LEU | 32 | 12.229 | 33.100 | 92.815 | 1.00 | 26.84 | AAGL |
| ATOM | 244 | CD1 | LEU | 32 | 12.430 | 34.545 | 92.422 | 1.00 | 26.55 | AAGL |
| ATOM | 245 | CD2 | LEU | 32 | 11.173 | 32.985 | 93.916 | 1.00 | 26.84 | AAGL |
| ATOM | 246 | C | LEU | 32 | 14.160 | 31.618 | 91.192 | 1.00 | 30.30 | AAGL |
| ATOM | 247 | O | LEU | 32 | 15.068 | 32.375 | 91.545 | 1.00 | 29.24 | AAGL |
| ATOM | 248 | N | GLU | 33 | 14.205 | 30.304 | 91.387 | 1.00 | 29.20 | AAGL |
| ATOM | 249 | CA | GLU | 33 | 15.360 | 29.698 | 92.036 | 1.00 | 29.33 | AAGL |
| ATOM | 250 | CB | GLU | 33 | 15.164 | 28.184 | 92.223 | 1.00 | 30.11 | AAGL |
| ATOM | 251 | CG | GLU | 33 | 15.225 | 27.380 | 90.934 | 1.00 | 32.96 | AAGL |
| ATOM | 252 | CD | GLU | 33 | 13.872 | 27.167 | 90.294 | 1.00 | 32.82 | AAGL |
| ATOM | 253 | OE1 | GLU | 33 | 12.979 | 28.030 | 90.451 | 1.00 | 32.32 | AAGL |
| ATOM | 254 | OE2 | GLU | 33 | 13.706 | 26.126 | 89.609 | 1.00 | 34.46 | AAGL |
| ATOM | 255 | C | GLU | 33 | 16.641 | 29.949 | 91.242 | 1.00 | 30.20 | AAGL |
| ATOM | 256 | O | GLU | 33 | 17.708 | 30.125 | 91.828 | 1.00 | 30.32 | AAGL |
| ATOM | 257 | N | THR | 34 | 16.544 | 29.967 | 89.912 | 1.00 | 31.16 | AAGL |
| ATOM | 258 | CA | THR | 34 | 17.734 | 30.197 | 89.102 | 1.00 | 32.16 | AAGL |
| ATOM | 259 | CB | THR | 34 | 17.545 | 29.703 | 87.636 | 1.00 | 34.39 | AAGL |
| ATOM | 260 | OG1 | THR | 34 | 16.690 | 30.598 | 86.916 | 1.00 | 39.01 | AAGL |
| ATOM | 261 | CG2 | THR | 34 | 16.915 | 28.315 | 87.628 | 1.00 | 33.29 | AAGL |
| ATOM | 262 | C | THR | 34 | 18.100 | 31.677 | 89.120 | 1.00 | 30.19 | AAGL |
| ATOM | 263 | O | THR | 34 | 19.269 | 32.027 | 89.031 | 1.00 | 32.36 | AAGL |

Fig. 3 cont.

| ATOM | 264 | N   | ILE | 35 | 17.101 | 32.542 | 89.254  | 1.00 | 29.48 | AAGL |
| ATOM | 265 | CA  | ILE | 35 | 17.343 | 33.982 | 89.318  | 1.00 | 29.20 | AAGL |
| ATOM | 266 | CB  | ILE | 35 | 16.030 | 34.783 | 89.364  | 1.00 | 29.36 | AAGL |
| ATOM | 267 | CG2 | ILE | 35 | 16.329 | 36.253 | 89.647  | 1.00 | 32.47 | AAGL |
| ATOM | 268 | CG1 | ILE | 35 | 15.265 | 34.620 | 88.052  | 1.00 | 30.39 | AAGL |
| ATOM | 269 | CD1 | ILE | 35 | 13.998 | 35.456 | 87.981  | 1.00 | 32.09 | AAGL |
| ATOM | 270 | C   | ILE | 35 | 18.103 | 34.276 | 90.605  | 1.00 | 29.48 | AAGL |
| ATOM | 271 | O   | ILE | 35 | 19.039 | 35.068 | 90.627  | 1.00 | 28.30 | AAGL |
| ATOM | 272 | N   | LEU | 36 | 17.676 | 33.631 | 91.684  | 1.00 | 28.93 | AAGL |
| ATOM | 273 | CA  | LEU | 36 | 18.297 | 33.809 | 92.989  | 1.00 | 27.40 | AAGL |
| ATOM | 274 | CB  | LEU | 36 | 17.420 | 33.142 | 94.050  | 1.00 | 29.01 | AAGL |
| ATOM | 275 | CG  | LEU | 36 | 16.067 | 33.824 | 94.220  | 1.00 | 29.41 | AAGL |
| ATOM | 276 | CD1 | LEU | 36 | 15.139 | 32.993 | 95.105  | 1.00 | 32.23 | AAGL |
| ATOM | 277 | CD2 | LEU | 36 | 16.318 | 35.198 | 94.831  | 1.00 | 29.88 | AAGL |
| ATOM | 278 | C   | LEU | 36 | 19.693 | 33.220 | 93.036  | 1.00 | 26.84 | AAGL |
| ATOM | 279 | O   | LEU | 36 | 20.630 | 33.840 | 93.542  | 1.00 | 26.88 | AAGL |
| ATOM | 280 | N   | ALA | 37 | 19.829 | 32.005 | 92.515  | 1.00 | 28.77 | AAGL |
| ATOM | 281 | CA  | ALA | 37 | 21.118 | 31.325 | 92.509  | 1.00 | 30.25 | AAGL |
| ATOM | 282 | CB  | ALA | 37 | 20.988 | 29.971 | 91.805  | 1.00 | 29.94 | AAGL |
| ATOM | 283 | C   | ALA | 37 | 22.185 | 32.180 | 91.827  | 1.00 | 29.84 | AAGL |
| ATOM | 284 | O   | ALA | 37 | 23.274 | 32.373 | 92.365  | 1.00 | 30.61 | AAGL |
| ATOM | 285 | N   | ASP | 38 | 21.856 | 32.706 | 90.652  | 1.00 | 30.68 | AAGL |
| ATOM | 286 | CA  | ASP | 38 | 22.798 | 33.524 | 89.894  | 1.00 | 31.88 | AAGL |
| ATOM | 287 | CB  | ASP | 38 | 22.240 | 33.843 | 88.508  | 1.00 | 32.57 | AAGL |
| ATOM | 288 | CG  | ASP | 38 | 22.007 | 32.603 | 87.673  | 1.00 | 36.25 | AAGL |
| ATOM | 289 | OD1 | ASP | 38 | 22.749 | 31.610 | 87.859  | 1.00 | 36.97 | AAGL |
| ATOM | 290 | OD2 | ASP | 38 | 21.085 | 32.621 | 86.830  | 1.00 | 37.38 | AAGL |
| ATOM | 291 | C   | ASP | 38 | 23.127 | 34.824 | 90.601  | 1.00 | 31.89 | AAGL |
| ATOM | 292 | O   | ASP | 38 | 24.174 | 35.423 | 90.353  | 1.00 | 33.41 | AAGL |
| ATOM | 293 | N   | ALA | 39 | 22.226 | 35.265 | 91.476  | 1.00 | 31.50 | AAGL |
| ATOM | 294 | CA  | ALA | 39 | 22.433 | 36.503 | 92.207  | 1.00 | 29.58 | AAGL |
| ATOM | 295 | CB  | ALA | 39 | 21.088 | 37.099 | 92.626  | 1.00 | 29.62 | AAGL |
| ATOM | 296 | C   | ALA | 39 | 23.319 | 36.300 | 93.423  | 1.00 | 29.11 | AAGL |
| ATOM | 297 | O   | ALA | 39 | 23.739 | 37.268 | 94.053  | 1.00 | 28.08 | AAGL |
| ATOM | 298 | N   | GLY | 40 | 23.603 | 35.047 | 93.769  | 1.00 | 28.38 | AAGL |
| ATOM | 299 | CA  | GLY | 40 | 24.462 | 34.804 | 94.915  | 1.00 | 28.68 | AAGL |
| ATOM | 300 | C   | GLY | 40 | 23.804 | 34.079 | 96.077  | 1.00 | 27.30 | AAGL |
| ATOM | 301 | O   | GLY | 40 | 24.489 | 33.628 | 96.994  | 1.00 | 28.21 | AAGL |
| ATOM | 302 | N   | ILE | 41 | 22.480 | 33.973 | 96.046  | 1.00 | 27.82 | AAGL |
| ATOM | 303 | CA  | ILE | 41 | 21.754 | 33.271 | 97.105  | 1.00 | 28.31 | AAGL |
| ATOM | 304 | CB  | ILE | 41 | 20.231 | 33.267 | 96.841  | 1.00 | 28.86 | AAGL |
| ATOM | 305 | CG2 | ILE | 41 | 19.502 | 32.678 | 98.047  | 1.00 | 26.11 | AAGL |
| ATOM | 306 | CG1 | ILE | 41 | 19.741 | 34.680 | 96.490  | 1.00 | 32.71 | AAGL |
| ATOM | 307 | CD1 | ILE | 41 | 20.041 | 35.739 | 97.526  | 1.00 | 34.86 | AAGL |
| ATOM | 308 | C   | ILE | 41 | 22.262 | 31.830 | 97.055  | 1.00 | 29.05 | AAGL |
| ATOM | 309 | O   | ILE | 41 | 22.275 | 31.223 | 95.982  | 1.00 | 28.58 | AAGL |
| ATOM | 310 | N   | ASN | 42 | 22.694 | 31.283 | 98.192  | 1.00 | 27.24 | AAGL |
| ATOM | 311 | CA  | ASN | 42 | 23.209 | 29.921 | 98.192  | 1.00 | 27.38 | AAGL |
| ATOM | 312 | CB  | ASN | 42 | 24.715 | 29.897 | 98.547  | 1.00 | 26.67 | AAGL |
| ATOM | 313 | CG  | ASN | 42 | 25.014 | 30.267 | 99.999  | 1.00 | 29.27 | AAGL |
| ATOM | 314 | OD1 | ASN | 42 | 26.177 | 30.238 | 100.422 | 1.00 | 30.70 | AAGL |
| ATOM | 315 | ND2 | ASN | 42 | 23.984 | 30.620 | 100.767 | 1.00 | 28.35 | AAGL |
| ATOM | 316 | C   | ASN | 42 | 22.449 | 28.945 | 99.077  | 1.00 | 27.09 | AAGL |
| ATOM | 317 | O   | ASN | 42 | 22.873 | 27.801 | 99.244  | 1.00 | 25.65 | AAGL |
| ATOM | 318 | N   | SER | 43 | 21.324 | 29.390 | 99.633  | 1.00 | 25.87 | AAGL |
| ATOM | 319 | CA  | SER | 43 | 20.525 | 28.520 | 100.481 | 1.00 | 25.56 | AAGL |
| ATOM | 320 | CB  | SER | 43 | 21.049 | 28.551 | 101.913 | 1.00 | 26.01 | AAGL |
| ATOM | 321 | OG  | SER | 43 | 20.497 | 27.483 | 102.665 | 1.00 | 25.97 | AAGL |
| ATOM | 322 | C   | SER | 43 | 19.051 | 28.914 | 100.462 | 1.00 | 25.21 | AAGL |
| ATOM | 323 | O   | SER | 43 | 18.714 | 30.096 | 100.411 | 1.00 | 22.67 | AAGL |
| ATOM | 324 | N   | ILE | 44 | 18.177 | 27.910 | 100.494 | 1.00 | 24.04 | AAGL |
| ATOM | 325 | CA  | ILE | 44 | 16.737 | 28.146 | 100.475 | 1.00 | 23.25 | AAGL |
| ATOM | 326 | CB  | ILE | 44 | 16.105 | 27.603 | 99.166  | 1.00 | 25.17 | AAGL |
| ATOM | 327 | CG2 | ILE | 44 | 14.599 | 27.796 | 99.185  | 1.00 | 23.06 | AAGL |
| ATOM | 328 | CG1 | ILE | 44 | 16.698 | 28.333 | 97.953  | 1.00 | 25.29 | AAGL |
| ATOM | 329 | CD1 | ILE | 44 | 16.327 | 29.795 | 97.867  | 1.00 | 26.67 | AAGL |

Fig. 3 cont.

```
ATOM    330  C   ILE    44      16.057  27.481 101.677  1.00 23.88      AAGL
ATOM    331  O   ILE    44      16.273  26.305 101.953  1.00 22.19      AAGL
ATOM    332  N   ARG    45      15.244  28.262 102.384  1.00 21.15      AAGL
ATOM    333  CA  ARG    45      14.512  27.796 103.558  1.00 20.84      AAGL
ATOM    334  CB  ARG    45      14.497  28.905 104.607  1.00 19.60      AAGL
ATOM    335  CG  ARG    45      13.815  28.594 105.927  1.00 22.30      AAGL
ATOM    336  CD  ARG    45      13.941  29.840 106.803  1.00 22.44      AAGL
ATOM    337  NE  ARG    45      13.442  29.713 108.172  1.00 21.57      AAGL
ATOM    338  CZ  ARG    45      12.253  30.147 108.580  1.00 21.21      AAGL
ATOM    339  NH1 ARG    45      11.420  30.721 107.726  1.00 19.38      AAGL
ATOM    340  NH2 ARG    45      11.924  30.071 109.864  1.00 18.87      AAGL
ATOM    341  C   ARG    45      13.091  27.456 103.120  1.00 18.60      AAGL
ATOM    342  O   ARG    45      12.471  28.214 102.376  1.00 19.88      AAGL
ATOM    343  N   GLN    46      12.582  26.314 103.574  1.00 19.69      AAGL
ATOM    344  CA  GLN    46      11.235  25.881 103.212  1.00 18.26      AAGL
ATOM    345  CB  GLN    46      11.311  24.701 102.234  1.00 19.90      AAGL
ATOM    346  CG  GLN    46      12.070  25.027 100.949  1.00 19.68      AAGL
ATOM    347  CD  GLN    46      12.093  23.880  99.946  1.00 23.43      AAGL
ATOM    348  OE1 GLN    46      12.705  23.992  98.882  1.00 26.77      AAGL
ATOM    349  NE2 GLN    46      11.429  22.777 100.278  1.00 21.73      AAGL
ATOM    350  C   GLN    46      10.432  25.467 104.445  1.00 17.71      AAGL
ATOM    351  O   GLN    46      10.896  24.649 105.238  1.00 18.22      AAGL
ATOM    352  N   ARG    47       9.233  26.023 104.601  1.00 18.28      AAGL
ATOM    353  CA  ARG    47       8.409  25.670 105.751  1.00 18.38      AAGL
ATOM    354  CB  ARG    47       7.414  26.792 106.095  1.00 18.50      AAGL
ATOM    355  CG  ARG    47       6.542  27.319 104.954  1.00 21.41      AAGL
ATOM    356  CD  ARG    47       5.455  28.254 105.503  1.00 20.07      AAGL
ATOM    357  NE  ARG    47       4.735  28.978 104.453  1.00 18.68      AAGL
ATOM    358  CZ  ARG    47       5.228  30.016 103.783  1.00 19.34      AAGL
ATOM    359  NH1 ARG    47       6.448  30.472 104.054  1.00 20.84      AAGL
ATOM    360  NH2 ARG    47       4.513  30.582 102.819  1.00 19.53      AAGL
ATOM    361  C   ARG    47       7.677  24.365 105.472  1.00 18.74      AAGL
ATOM    362  O   ARG    47       7.101  24.183 104.403  1.00 18.19      AAGL
ATOM    363  N   VAL    48       7.710  23.458 106.445  1.00 19.24      AAGL
ATOM    364  CA  VAL    48       7.074  22.155 106.301  1.00 20.17      AAGL
ATOM    365  CB  VAL    48       8.109  21.023 106.490  1.00 20.89      AAGL
ATOM    366  CG1 VAL    48       7.488  19.677 106.130  1.00 20.76      AAGL
ATOM    367  CG2 VAL    48       9.350  21.301 105.644  1.00 21.80      AAGL
ATOM    368  C   VAL    48       5.947  21.932 107.311  1.00 20.72      AAGL
ATOM    369  O   VAL    48       6.166  22.027 108.517  1.00 19.48      AAGL
ATOM    370  N   TRP    49       4.748  21.647 106.805  1.00 18.93      AAGL
ATOM    371  CA  TRP    49       3.590  21.371 107.646  1.00 19.06      AAGL
ATOM    372  CB  TRP    49       2.382  22.168 107.167  1.00 19.85      AAGL
ATOM    373  CG  TRP    49       2.525  23.645 107.414  1.00 19.05      AAGL
ATOM    374  CD2 TRP    49       1.608  24.673 107.024  1.00 18.82      AAGL
ATOM    375  CE2 TRP    49       2.125  25.897 107.504  1.00 19.73      AAGL
ATOM    376  CE3 TRP    49       0.396  24.678 106.316  1.00 20.02      AAGL
ATOM    377  CD1 TRP    49       3.535  24.271 108.090  1.00 17.67      AAGL
ATOM    378  NE1 TRP    49       3.300  25.620 108.149  1.00 18.03      AAGL
ATOM    379  CZ2 TRP    49       1.475  27.117 107.301  1.00 20.25      AAGL
ATOM    380  CZ3 TRP    49      -0.253  25.899 106.112  1.00 22.82      AAGL
ATOM    381  CH2 TRP    49       0.291  27.100 106.606  1.00 22.06      AAGL
ATOM    382  C   TRP    49       3.306  19.873 107.587  1.00 19.52      AAGL
ATOM    383  O   TRP    49       3.553  19.231 106.563  1.00 19.96      AAGL
ATOM    384  N   VAL    50       2.778  19.322 108.677  1.00 18.80      AAGL
ATOM    385  CA  VAL    50       2.522  17.886 108.756  1.00 20.11      AAGL
ATOM    386  CB  VAL    50       2.398  17.443 110.231  1.00 18.82      AAGL
ATOM    387  CG1 VAL    50       2.120  15.954 110.316  1.00 21.34      AAGL
ATOM    388  CG2 VAL    50       3.695  17.768 110.966  1.00 21.13      AAGL
ATOM    389  C   VAL    50       1.340  17.362 107.947  1.00 22.22      AAGL
ATOM    390  O   VAL    50       1.538  16.629 106.973  1.00 23.75      AAGL
ATOM    391  N   ASN    51       0.119  17.721 108.329  1.00 22.74      AAGL
ATOM    392  CA  ASN    51      -1.044  17.251 107.585  1.00 25.51      AAGL
ATOM    393  CB  ASN    51      -1.765  16.133 108.354  1.00 26.96      AAGL
ATOM    394  CG  ASN    51      -0.879  14.932 108.619  0.50 27.07      AAGL
ATOM    395  OD1 ASN    51      -0.265  14.387 107.707  0.50 29.27      AAGL
```

Fig. 3 cont.

| | | | | | | | | | |
|---|---|---|---|---|---|---|---|---|---|
| ATOM | 396 | ND2 | ASN | 51 | -0.821 | 14.505 | 109.878 | 0.50 28.87 | AAGL |
| ATOM | 397 | C | ASN | 51 | -2.055 | 18.350 | 107.238 | 1.00 26.72 | AAGL |
| ATOM | 398 | O | ASN | 51 | -3.204 | 18.305 | 107.668 | 1.00 27.90 | AAGL |
| ATOM | 399 | N | PRO | 52 | -1.638 | 19.358 | 106.459 | 1.00 26.25 | AAGL |
| ATOM | 400 | CD | PRO | 52 | -0.337 | 19.594 | 105.814 | 1.00 25.34 | AAGL |
| ATOM | 401 | CA | PRO | 52 | -2.599 | 20.410 | 106.113 | 1.00 26.62 | AAGL |
| ATOM | 402 | CB | PRO | 52 | -1.735 | 21.431 | 105.389 | 1.00 25.68 | AAGL |
| ATOM | 403 | CG | PRO | 52 | -0.697 | 20.582 | 104.735 | 1.00 25.47 | AAGL |
| ATOM | 404 | C | PRO | 52 | -3.690 | 19.816 | 105.215 | 1.00 28.63 | AAGL |
| ATOM | 405 | O | PRO | 52 | -3.391 | 19.112 | 104.254 | 1.00 27.01 | AAGL |
| ATOM | 406 | N | SER | 53 | -4.949 | 20.086 | 105.543 | 1.00 29.82 | AAGL |
| ATOM | 407 | CA | SER | 53 | -6.062 | 19.554 | 104.760 | 1.00 33.18 | AAGL |
| ATOM | 408 | CB | SER | 53 | -7.394 | 20.100 | 105.281 | 1.00 35.65 | AAGL |
| ATOM | 409 | OG | SER | 53 | -7.728 | 19.496 | 106.515 | 1.00 38.67 | AAGL |
| ATOM | 410 | C | SER | 53 | -5.948 | 19.859 | 103.274 | 1.00 32.30 | AAGL |
| ATOM | 411 | O | SER | 53 | -6.284 | 19.019 | 102.434 | 1.00 32.67 | AAGL |
| ATOM | 412 | N | ASP | 54 | -5.469 | 21.053 | 102.949 | 1.00 31.58 | AAGL |
| ATOM | 413 | CA | ASP | 54 | -5.343 | 21.444 | 101.555 | 1.00 31.37 | AAGL |
| ATOM | 414 | CB | ASP | 54 | -5.736 | 22.922 | 101.389 | 1.00 33.51 | AAGL |
| ATOM | 415 | CG | ASP | 54 | -4.616 | 23.878 | 101.754 | 1.00 35.96 | AAGL |
| ATOM | 416 | OD1 | ASP | 54 | -3.796 | 23.537 | 102.630 | 1.00 35.79 | AAGL |
| ATOM | 417 | OD2 | ASP | 54 | -4.569 | 24.986 | 101.166 | 1.00 38.48 | AAGL |
| ATOM | 418 | C | ASP | 54 | -3.974 | 21.164 | 100.937 | 1.00 30.51 | AAGL |
| ATOM | 419 | O | ASP | 54 | -3.715 | 21.572 | 99.812 | 1.00 30.89 | AAGL |
| ATOM | 420 | N | GLY | 55 | -3.110 | 20.460 | 101.670 | 1.00 31.08 | AAGL |
| ATOM | 421 | CA | GLY | 55 | -1.790 | 20.102 | 101.161 | 1.00 29.00 | AAGL |
| ATOM | 422 | C | GLY | 55 | -0.684 | 21.149 | 101.119 | 1.00 28.85 | AAGL |
| ATOM | 423 | O | GLY | 55 | 0.475 | 20.829 | 100.834 | 1.00 27.57 | AAGL |
| ATOM | 424 | N | SER | 56 | -1.028 | 22.399 | 101.398 | 1.00 29.06 | AAGL |
| ATOM | 425 | CA | SER | 56 | -0.036 | 23.468 | 101.362 | 1.00 29.25 | AAGL |
| ATOM | 426 | CB | SER | 56 | -0.685 | 24.799 | 101.747 | 1.00 33.01 | AAGL |
| ATOM | 427 | OG | SER | 56 | -1.603 | 25.222 | 100.746 | 1.00 35.28 | AAGL |
| ATOM | 428 | C | SER | 56 | 1.163 | 23.211 | 102.266 | 1.00 27.16 | AAGL |
| ATOM | 429 | O | SER | 56 | 1.013 | 22.944 | 103.462 | 1.00 26.75 | AAGL |
| ATOM | 430 | N | TYR | 57 | 2.350 | 23.282 | 101.673 | 1.00 24.25 | AAGL |
| ATOM | 431 | CA | TYR | 57 | 3.611 | 23.102 | 102.379 | 1.00 23.39 | AAGL |
| ATOM | 432 | CB | TYR | 57 | 3.773 | 24.192 | 103.455 | 1.00 21.44 | AAGL |
| ATOM | 433 | CG | TYR | 57 | 3.411 | 25.586 | 102.983 | 1.00 18.93 | AAGL |
| ATOM | 434 | CD1 | TYR | 57 | 4.090 | 26.183 | 101.927 | 1.00 20.85 | AAGL |
| ATOM | 435 | CE1 | TYR | 57 | 3.733 | 27.448 | 101.457 | 1.00 20.55 | AAGL |
| ATOM | 436 | CD2 | TYR | 57 | 2.363 | 26.291 | 103.575 | 1.00 20.42 | AAGL |
| ATOM | 437 | CE2 | TYR | 57 | 1.992 | 27.555 | 103.119 | 1.00 23.25 | AAGL |
| ATOM | 438 | CZ | TYR | 57 | 2.687 | 28.130 | 102.049 | 1.00 22.03 | AAGL |
| ATOM | 439 | OH | TYR | 57 | 2.323 | 29.367 | 101.572 | 1.00 24.57 | AAGL |
| ATOM | 440 | C | TYR | 57 | 3.809 | 21.736 | 103.024 | 1.00 24.63 | AAGL |
| ATOM | 441 | O | TYR | 57 | 4.583 | 21.619 | 103.972 | 1.00 22.67 | AAGL |
| ATOM | 442 | N | ASP | 58 | 3.121 | 20.701 | 102.540 | 1.00 25.81 | AAGL |
| ATOM | 443 | CA | ASP | 58 | 3.319 | 19.376 | 103.128 | 1.00 27.04 | AAGL |
| ATOM | 444 | CB | ASP | 58 | 2.084 | 18.473 | 102.946 | 1.00 27.80 | AAGL |
| ATOM | 445 | CG | ASP | 58 | 1.763 | 18.160 | 101.491 | 1.00 32.21 | AAGL |
| ATOM | 446 | OD1 | ASP | 58 | 2.652 | 18.279 | 100.623 | 1.00 30.26 | AAGL |
| ATOM | 447 | OD2 | ASP | 58 | 0.597 | 17.768 | 101.228 | 1.00 32.38 | AAGL |
| ATOM | 448 | C | ASP | 58 | 4.574 | 18.724 | 102.542 | 1.00 28.05 | AAGL |
| ATOM | 449 | O | ASP | 58 | 5.320 | 19.367 | 101.793 | 1.00 27.53 | AAGL |
| ATOM | 450 | N | LEU | 59 | 4.820 | 17.462 | 102.883 | 1.00 26.92 | AAGL |
| ATOM | 451 | CA | LEU | 59 | 6.018 | 16.786 | 102.403 | 1.00 28.31 | AAGL |
| ATOM | 452 | CB | LEU | 59 | 6.116 | 15.377 | 103.001 | 1.00 30.14 | AAGL |
| ATOM | 453 | CG | LEU | 59 | 7.435 | 14.620 | 102.784 | 1.00 29.84 | AAGL |
| ATOM | 454 | CD1 | LEU | 59 | 8.609 | 15.430 | 103.323 | 1.00 31.61 | AAGL |
| ATOM | 455 | CD2 | LEU | 59 | 7.355 | 13.265 | 103.479 | 1.00 31.80 | AAGL |
| ATOM | 456 | C | LEU | 59 | 6.145 | 16.714 | 100.885 | 1.00 26.89 | AAGL |
| ATOM | 457 | O | LEU | 59 | 7.220 | 16.952 | 100.342 | 1.00 24.30 | AAGL |
| ATOM | 458 | N | ASP | 60 | 5.061 | 16.401 | 100.188 | 1.00 28.43 | AAGL |
| ATOM | 459 | CA | ASP | 60 | 5.145 | 16.315 | 98.736 | 1.00 29.43 | AAGL |
| ATOM | 460 | CB | ASP | 60 | 3.850 | 15.740 | 98.149 | 1.00 32.44 | AAGL |
| ATOM | 461 | CG | ASP | 60 | 3.557 | 14.332 | 98.651 | 1.00 37.53 | AAGL |

Fig. 3 cont.

```
ATOM    462  OD1 ASP    60       4.518  13.547  98.833  1.00 40.66       AAGL
ATOM    463  OD2 ASP    60       2.365  14.000  98.858  1.00 42.65       AAGL
ATOM    464  C   ASP    60       5.439  17.689  98.137  1.00 30.40       AAGL
ATOM    465  O   ASP    60       6.266  17.816  97.237  1.00 28.80       AAGL
ATOM    466  N   TYR    61       4.761  18.710  98.651  1.00 28.48       AAGL
ATOM    467  CA  TYR    61       4.944  20.088  98.203  1.00 25.60       AAGL
ATOM    468  CB  TYR    61       4.100  21.031  99.080  1.00 25.21       AAGL
ATOM    469  CG  TYR    61       4.182  22.508  98.723  1.00 25.14       AAGL
ATOM    470  CD1 TYR    61       5.283  23.286  99.095  1.00 23.80       AAGL
ATOM    471  CE1 TYR    61       5.360  24.639  98.759  1.00 24.64       AAGL
ATOM    472  CD2 TYR    61       3.154  23.125  98.006  1.00 25.32       AAGL
ATOM    473  CE2 TYR    61       3.220  24.481  97.664  1.00 26.31       AAGL
ATOM    474  CZ  TYR    61       4.327  25.231  98.043  1.00 25.45       AAGL
ATOM    475  OH  TYR    61       4.403  26.565  97.687  1.00 24.80       AAGL
ATOM    476  C   TYR    61       6.422  20.444  98.330  1.00 26.83       AAGL
ATOM    477  O   TYR    61       7.039  20.948  97.393  1.00 25.72       AAGL
ATOM    478  N   ASN    62       6.992  20.159  99.493  1.00 24.55       AAGL
ATOM    479  CA  ASN    62       8.388  20.458  99.733  1.00 25.46       AAGL
ATOM    480  CB  ASN    62       8.695  20.315 101.225  1.00 25.35       AAGL
ATOM    481  CG  ASN    62       8.316  21.568 102.009  1.00 25.66       AAGL
ATOM    482  OD1 ASN    62       9.047  22.556 101.998  1.00 23.45       AAGL
ATOM    483  ND2 ASN    62       7.159  21.539 102.666  1.00 21.77       AAGL
ATOM    484  C   ASN    62       9.355  19.629  98.899  1.00 25.81       AAGL
ATOM    485  O   ASN    62      10.450  20.090  98.596  1.00 23.79       AAGL
ATOM    486  N   LEU    63       8.969  18.411  98.528  1.00 25.79       AAGL
ATOM    487  CA  LEU    63       9.856  17.589  97.708  1.00 27.44       AAGL
ATOM    488  CB  LEU    63       9.320  16.153  97.581  1.00 29.01       AAGL
ATOM    489  CG  LEU    63       9.673  15.225  98.743  1.00 31.95       AAGL
ATOM    490  CD1 LEU    63       9.041  13.851  98.508  1.00 32.91       AAGL
ATOM    491  CD2 LEU    63      11.199  15.114  98.872  1.00 32.19       AAGL
ATOM    492  C   LEU    63      10.001  18.207  96.322  1.00 27.90       AAGL
ATOM    493  O   LEU    63      11.102  18.275  95.772  1.00 29.37       AAGL
ATOM    494  N   GLU    64       8.882  18.662  95.768  1.00 28.38       AAGL
ATOM    495  CA  GLU    64       8.859  19.280  94.447  1.00 30.60       AAGL
ATOM    496  CB  GLU    64       7.414  19.642  94.078  1.00 32.03       AAGL
ATOM    497  CG  GLU    64       7.198  20.124  92.639  1.00 36.66       AAGL
ATOM    498  CD  GLU    64       5.747  20.468  92.364  1.00 38.83       AAGL
ATOM    499  OE1 GLU    64       4.874  19.637  92.688  1.00 41.75       AAGL
ATOM    500  OE2 GLU    64       5.464  21.565  91.822  1.00 41.60       AAGL
ATOM    501  C   GLU    64       9.727  20.536  94.454  1.00 29.58       AAGL
ATOM    502  O   GLU    64      10.525  20.769  93.541  1.00 27.18       AAGL
ATOM    503  N   LEU    65       9.578  21.343  95.497  1.00 27.01       AAGL
ATOM    504  CA  LEU    65      10.344  22.576  95.611  1.00 25.95       AAGL
ATOM    505  CB  LEU    65       9.754  23.455  96.721  1.00 27.05       AAGL
ATOM    506  CG  LEU    65      10.420  24.806  97.018  1.00 25.59       AAGL
ATOM    507  CD1 LEU    65      10.528  25.628  95.760  1.00 24.36       AAGL
ATOM    508  CD2 LEU    65       9.600  25.544  98.074  1.00 25.15       AAGL
ATOM    509  C   LEU    65      11.824  22.329  95.877  1.00 26.00       AAGL
ATOM    510  O   LEU    65      12.677  23.029  95.329  1.00 27.12       AAGL
ATOM    511  N   ALA    66      12.131  21.330  96.699  1.00 23.38       AAGL
ATOM    512  CA  ALA    66      13.517  21.025  97.038  1.00 25.19       AAGL
ATOM    513  CB  ALA    66      13.572  20.017  98.203  1.00 25.90       AAGL
ATOM    514  C   ALA    66      14.278  20.481  95.833  1.00 27.46       AAGL
ATOM    515  O   ALA    66      15.479  20.714  95.697  1.00 28.22       AAGL
ATOM    516  N   LYS    67      13.578  19.752  94.969  1.00 28.70       AAGL
ATOM    517  CA  LYS    67      14.201  19.188  93.768  1.00 32.17       AAGL
ATOM    518  CB  LYS    67      13.164  18.444  92.924  1.00 32.68       AAGL
ATOM    519  CG  LYS    67      12.902  17.003  93.358  1.00 36.34       AAGL
ATOM    520  CD  LYS    67      11.676  16.443  92.655  1.00 38.14       AAGL
ATOM    521  CE  LYS    67      11.447  14.989  93.012  1.00 41.38       AAGL
ATOM    522  NZ  LYS    67      10.184  14.468  92.407  1.00 43.11       AAGL
ATOM    523  C   LYS    67      14.813  20.303  92.931  1.00 32.63       AAGL
ATOM    524  O   LYS    67      15.943  20.192  92.453  1.00 32.89       AAGL
ATOM    525  N   ARG    68      14.053  21.376  92.763  1.00 31.49       AAGL
ATOM    526  CA  ARG    68      14.497  22.523  91.988  1.00 31.44       AAGL
ATOM    527  CB  ARG    68      13.300  23.419  91.683  1.00 31.14       AAGL
```

Fig. 3 cont.

```
ATOM  528  CG   ARG  68   12.313  22.760  90.730  1.00 33.54      AAGL
ATOM  529  CD   ARG  68   11.016  23.518  90.619  1.00 32.13      AAGL
ATOM  530  NE   ARG  68   11.222  24.924  90.303  1.00 31.17      AAGL
ATOM  531  CZ   ARG  68   10.238  25.763  90.002  1.00 32.92      AAGL
ATOM  532  NH1  ARG  68    8.985  25.327  89.970  1.00 33.31      AAGL
ATOM  533  NH2  ARG  68   10.498  27.040  89.755  1.00 31.47      AAGL
ATOM  534  C    ARG  68   15.595  23.311  92.691  1.00 31.54      AAGL
ATOM  535  O    ARG  68   16.459  23.905  92.040  1.00 31.76      AAGL
ATOM  536  N    VAL  69   15.570  23.319  94.021  1.00 28.62      AAGL
ATOM  537  CA   VAL  69   16.584  24.025  94.794  1.00 27.79      AAGL
ATOM  538  CB   VAL  69   16.204  24.061  96.281  1.00 24.83      AAGL
ATOM  539  CG1  VAL  69   17.294  24.735  97.092  1.00 27.63      AAGL
ATOM  540  CG2  VAL  69   14.886  24.781  96.442  1.00 26.08      AAGL
ATOM  541  C    VAL  69   17.934  23.325  94.635  1.00 29.09      AAGL
ATOM  542  O    VAL  69   18.968  23.970  94.458  1.00 28.64      AAGL
ATOM  543  N    LYS  70   17.908  21.998  94.711  1.00 29.15      AAGL
ATOM  544  CA   LYS  70   19.108  21.187  94.561  1.00 31.30      AAGL
ATOM  545  CB   LYS  70   18.756  19.707  94.743  1.00 34.31      AAGL
ATOM  546  CG   LYS  70   19.889  18.752  94.422  1.00 36.20      AAGL
ATOM  547  CD   LYS  70   19.399  17.319  94.271  1.00 40.57      AAGL
ATOM  548  CE   LYS  70   18.290  17.224  93.229  1.00 41.78      AAGL
ATOM  549  NZ   LYS  70   18.666  17.932  91.966  1.00 42.36      AAGL
ATOM  550  C    LYS  70   19.693  21.403  93.159  1.00 31.39      AAGL
ATOM  551  O    LYS  70   20.903  21.592  92.997  1.00 31.53      AAGL
ATOM  552  N    ALA  71   18.813  21.386  92.165  1.00 30.10      AAGL
ATOM  553  CA   ALA  71   19.196  21.564  90.771  1.00 31.78      AAGL
ATOM  554  CB   ALA  71   17.957  21.525  89.879  1.00 30.31      AAGL
ATOM  555  C    ALA  71   19.949  22.870  90.570  1.00 33.02      AAGL
ATOM  556  O    ALA  71   20.975  22.900  89.888  1.00 32.79      AAGL
ATOM  557  N    ALA  72   19.442  23.940  91.179  1.00 32.06      AAGL
ATOM  558  CA   ALA  72   20.054  25.257  91.071  1.00 30.23      AAGL
ATOM  559  CB   ALA  72   19.048  26.323  91.463  1.00 31.29      AAGL
ATOM  560  C    ALA  72   21.316  25.389  91.915  1.00 29.83      AAGL
ATOM  561  O    ALA  72   21.908  26.463  91.990  1.00 29.82      AAGL
ATOM  562  N    GLY  73   21.714  24.298  92.561  1.00 28.89      AAGL
ATOM  563  CA   GLY  73   22.926  24.304  93.360  1.00 30.91      AAGL
ATOM  564  C    GLY  73   22.909  25.064  94.675  1.00 32.00      AAGL
ATOM  565  O    GLY  73   23.939  25.589  95.111  1.00 30.50      AAGL
ATOM  566  N    MET  74   21.748  25.121  95.316  1.00 31.23      AAGL
ATOM  567  CA   MET  74   21.641  25.814  96.593  1.00 31.02      AAGL
ATOM  568  CB   MET  74   20.500  26.840  96.537  1.00 29.51      AAGL
ATOM  569  CG   MET  74   20.676  27.893  95.434  1.00 29.42      AAGL
ATOM  570  SD   MET  74   19.481  29.259  95.503  1.00 28.77      AAGL
ATOM  571  CE   MET  74   18.129  28.654  94.532  1.00 26.24      AAGL
ATOM  572  C    MET  74   21.388  24.768  97.681  1.00 29.72      AAGL
ATOM  573  O    MET  74   20.893  23.682  97.385  1.00 30.60      AAGL
ATOM  574  N    SER  75   21.750  25.075  98.925  1.00 28.06      AAGL
ATOM  575  CA   SER  75   21.534  24.125 100.011  1.00 25.93      AAGL
ATOM  576  CB   SER  75   22.454  24.426 101.202  1.00 25.27      AAGL
ATOM  577  OG   SER  75   22.281  25.752 101.671  1.00 24.77      AAGL
ATOM  578  C    SER  75   20.075  24.203 100.439  1.00 27.57      AAGL
ATOM  579  O    SER  75   19.343  25.089  99.997  1.00 26.04      AAGL
ATOM  580  N    LEU  76   19.655  23.268 101.286  1.00 25.74      AAGL
ATOM  581  CA   LEU  76   18.273  23.227 101.747  1.00 27.05      AAGL
ATOM  582  CB   LEU  76   17.602  21.941 101.268  1.00 28.62      AAGL
ATOM  583  CG   LEU  76   16.130  21.726 101.615  1.00 31.64      AAGL
ATOM  584  CD1  LEU  76   15.268  22.677 100.772  1.00 29.51      AAGL
ATOM  585  CD2  LEU  76   15.748  20.268 101.346  1.00 32.16      AAGL
ATOM  586  C    LEU  76   18.177  23.309 103.264  1.00 24.07      AAGL
ATOM  587  O    LEU  76   18.890  22.619 103.985  1.00 24.81      AAGL
ATOM  588  N    TYR  77   17.293  24.179 103.732  1.00 24.59      AAGL
ATOM  589  CA   TYR  77   17.044  24.375 105.162  1.00 21.21      AAGL
ATOM  590  CB   TYR  77   17.441  25.812 105.550  1.00 21.04      AAGL
ATOM  591  CG   TYR  77   16.903  26.417 106.849  1.00 22.71      AAGL
ATOM  592  CD1  TYR  77   16.207  25.664 107.800  1.00 20.07      AAGL
ATOM  593  CE1  TYR  77   15.681  26.276 108.959  1.00 21.30      AAGL
```

Fig. 3 cont.

| | | | | | | | | | |
|---|---|---|---|---|---|---|---|---|---|
| ATOM | 594 | CD2 | TYR | 77 | 17.069 | 27.784 | 107.091 | 1.00 20.07 | AAGL |
| ATOM | 595 | CE2 | TYR | 77 | 16.558 | 28.394 | 108.232 | 1.00 22.16 | AAGL |
| ATOM | 596 | CZ | TYR | 77 | 15.863 | 27.646 | 109.159 | 1.00 22.47 | AAGL |
| ATOM | 597 | OH | TYR | 77 | 15.331 | 28.312 | 110.248 | 1.00 21.22 | AAGL |
| ATOM | 598 | C | TYR | 77 | 15.553 | 24.121 | 105.318 | 1.00 19.67 | AAGL |
| ATOM | 599 | O | TYR | 77 | 14.730 | 24.875 | 104.804 | 1.00 21.16 | AAGL |
| ATOM | 600 | N | LEU | 78 | 15.217 | 23.021 | 105.989 | 1.00 19.73 | AAGL |
| ATOM | 601 | CA | LEU | 78 | 13.826 | 22.662 | 106.216 | 1.00 20.07 | AAGL |
| ATOM | 602 | CB | LEU | 78 | 13.645 | 21.140 | 106.164 | 1.00 20.48 | AAGL |
| ATOM | 603 | CG | LEU | 78 | 13.793 | 20.485 | 104.784 | 1.00 24.57 | AAGL |
| ATOM | 604 | CD1 | LEU | 78 | 13.633 | 18.969 | 104.898 | 1.00 25.27 | AAGL |
| ATOM | 605 | CD2 | LEU | 78 | 12.750 | 21.067 | 103.833 | 1.00 23.90 | AAGL |
| ATOM | 606 | C | LEU | 78 | 13.379 | 23.199 | 107.568 | 1.00 17.57 | AAGL |
| ATOM | 607 | O | LEU | 78 | 13.980 | 22.891 | 108.599 | 1.00 18.99 | AAGL |
| ATOM | 608 | N | ASP | 79 | 12.332 | 24.018 | 107.534 | 1.00 18.03 | AAGL |
| ATOM | 609 | CA | ASP | 79 | 11.754 | 24.642 | 108.721 | 1.00 18.85 | AAGL |
| ATOM | 610 | CB | ASP | 79 | 11.386 | 26.098 | 108.389 | 1.00 19.55 | AAGL |
| ATOM | 611 | CG | ASP | 79 | 10.593 | 26.785 | 109.493 | 1.00 25.39 | AAGL |
| ATOM | 612 | OD1 | ASP | 79 | 10.682 | 26.370 | 110.662 | 1.00 22.47 | AAGL |
| ATOM | 613 | OD2 | ASP | 79 | 9.885 | 27.761 | 109.180 | 1.00 27.84 | AAGL |
| ATOM | 614 | C | ASP | 79 | 10.514 | 23.848 | 109.116 | 1.00 16.61 | AAGL |
| ATOM | 615 | O | ASP | 79 | 9.427 | 24.105 | 108.608 | 1.00 16.77 | AAGL |
| ATOM | 616 | N | LEU | 80 | 10.686 | 22.881 | 110.014 | 1.00 16.76 | AAGL |
| ATOM | 617 | CA | LEU | 80 | 9.573 | 22.051 | 110.452 | 1.00 17.99 | AAGL |
| ATOM | 618 | CB | LEU | 80 | 10.077 | 20.777 | 111.132 | 1.00 18.64 | AAGL |
| ATOM | 619 | CG | LEU | 80 | 11.103 | 19.918 | 110.385 | 1.00 19.36 | AAGL |
| ATOM | 620 | CD1 | LEU | 80 | 11.345 | 18.636 | 111.166 | 1.00 20.62 | AAGL |
| ATOM | 621 | CD2 | LEU | 80 | 10.603 | 19.605 | 108.986 | 1.00 18.29 | AAGL |
| ATOM | 622 | C | LEU | 80 | 8.708 | 22.802 | 111.441 | 1.00 18.46 | AAGL |
| ATOM | 623 | O | LEU | 80 | 9.162 | 23.121 | 112.529 | 1.00 20.06 | AAGL |
| ATOM | 624 | N | HIS | 81 | 7.464 | 23.086 | 111.071 | 1.00 17.32 | AAGL |
| ATOM | 625 | CA | HIS | 81 | 6.572 | 23.780 | 111.987 | 1.00 16.30 | AAGL |
| ATOM | 626 | CB | HIS | 81 | 5.475 | 24.525 | 111.223 | 1.00 15.62 | AAGL |
| ATOM | 627 | CG | HIS | 81 | 5.939 | 25.810 | 110.612 | 1.00 19.94 | AAGL |
| ATOM | 628 | CD2 | HIS | 81 | 7.137 | 26.167 | 110.093 | 1.00 19.51 | AAGL |
| ATOM | 629 | ND1 | HIS | 81 | 5.129 | 26.921 | 110.507 | 1.00 20.10 | AAGL |
| ATOM | 630 | CE1 | HIS | 81 | 5.811 | 27.909 | 109.952 | 1.00 20.61 | AAGL |
| ATOM | 631 | NE2 | HIS | 81 | 7.031 | 27.477 | 109.693 | 1.00 20.38 | AAGL |
| ATOM | 632 | C | HIS | 81 | 5.939 | 22.811 | 112.984 | 1.00 17.32 | AAGL |
| ATOM | 633 | O | HIS | 81 | 5.368 | 23.240 | 113.987 | 1.00 18.88 | AAGL |
| ATOM | 634 | N | LEU | 82 | 6.045 | 21.513 | 112.709 | 1.00 16.02 | AAGL |
| ATOM | 635 | CA | LEU | 82 | 5.484 | 20.480 | 113.588 | 1.00 17.14 | AAGL |
| ATOM | 636 | CB | LEU | 82 | 6.339 | 20.342 | 114.850 | 1.00 16.85 | AAGL |
| ATOM | 637 | CG | LEU | 82 | 7.813 | 20.007 | 114.595 | 1.00 20.75 | AAGL |
| ATOM | 638 | CD1 | LEU | 82 | 8.537 | 19.890 | 115.923 | 1.00 18.12 | AAGL |
| ATOM | 639 | CD2 | LEU | 82 | 7.935 | 18.712 | 113.812 | 1.00 18.95 | AAGL |
| ATOM | 640 | C | LEU | 82 | 4.048 | 20.826 | 113.965 | 1.00 18.59 | AAGL |
| ATOM | 641 | O | LEU | 82 | 3.664 | 20.829 | 115.146 | 1.00 18.40 | AAGL |
| ATOM | 642 | N | SER | 83 | 3.268 | 21.109 | 112.930 | 1.00 16.93 | AAGL |
| ATOM | 643 | CA | SER | 83 | 1.868 | 21.475 | 113.052 | 1.00 16.95 | AAGL |
| ATOM | 644 | CB | SER | 83 | 1.757 | 22.914 | 113.569 | 1.00 17.01 | AAGL |
| ATOM | 645 | OG | SER | 83 | 0.415 | 23.351 | 113.629 | 1.00 17.93 | AAGL |
| ATOM | 646 | C | SER | 83 | 1.276 | 21.367 | 111.649 | 1.00 18.89 | AAGL |
| ATOM | 647 | O | SER | 83 | 2.011 | 21.239 | 110.664 | 1.00 19.84 | AAGL |
| ATOM | 648 | N | ASP | 84 | -0.046 | 21.404 | 111.561 | 1.00 19.63 | AAGL |
| ATOM | 649 | CA | ASP | 84 | -0.715 | 21.317 | 110.275 | 1.00 20.59 | AAGL |
| ATOM | 650 | CB | ASP | 84 | -2.107 | 20.695 | 110.421 | 1.00 22.19 | AAGL |
| ATOM | 651 | CG | ASP | 84 | -2.062 | 19.246 | 110.817 | 1.00 21.52 | AAGL |
| ATOM | 652 | OD1 | ASP | 84 | -1.025 | 18.597 | 110.572 | 1.00 23.10 | AAGL |
| ATOM | 653 | OD2 | ASP | 84 | -3.079 | 18.755 | 111.360 | 1.00 23.55 | AAGL |
| ATOM | 654 | C | ASP | 84 | -0.866 | 22.706 | 109.689 | 1.00 21.71 | AAGL |
| ATOM | 655 | O | ASP | 84 | -1.340 | 22.854 | 108.563 | 1.00 21.81 | AAGL |
| ATOM | 656 | N | THR | 85 | -0.461 | 23.717 | 110.453 | 1.00 21.01 | AAGL |
| ATOM | 657 | CA | THR | 85 | -0.573 | 25.102 | 110.012 | 1.00 19.92 | AAGL |
| ATOM | 658 | CB | THR | 85 | -1.971 | 25.670 | 110.370 | 1.00 22.17 | AAGL |
| ATOM | 659 | OG1 | THR | 85 | -2.144 | 26.952 | 109.763 | 1.00 22.62 | AAGL |

Fig. 3 cont.

```
ATOM    660  CG2 THR    85      -2.134  25.800 111.874  1.00 23.94        AAGL
ATOM    661  C   THR    85       0.527  25.958 110.646  1.00 19.33        AAGL
ATOM    662  O   THR    85       1.429  25.425 111.298  1.00 18.85        AAGL
ATOM    663  N   TRP    86       0.454  27.276 110.450  1.00 18.81        AAGL
ATOM    664  CA  TRP    86       1.455  28.199 110.988  1.00 17.88        AAGL
ATOM    665  CB  TRP    86       1.011  29.654 110.800  1.00 17.85        AAGL
ATOM    666  CG  TRP    86       0.672  30.016 109.399  1.00 18.75        AAGL
ATOM    667  CD2 TRP    86       1.587  30.427 108.382  1.00 18.96        AAGL
ATOM    668  CE2 TRP    86       0.832  30.649 107.209  1.00 21.98        AAGL
ATOM    669  CE3 TRP    86       2.975  30.628 108.345  1.00 18.78        AAGL
ATOM    670  CD1 TRP    86      -0.563  30.004 108.826  1.00 21.00        AAGL
ATOM    671  NE1 TRP    86      -0.478  30.386 107.508  1.00 21.68        AAGL
ATOM    672  CZ2 TRP    86       1.418  31.065 106.007  1.00 19.73        AAGL
ATOM    673  CZ3 TRP    86       3.556  31.041 107.151  1.00 20.30        AAGL
ATOM    674  CH2 TRP    86       2.775  31.255 105.998  1.00 18.40        AAGL
ATOM    675  C   TRP    86       1.757  27.994 112.467  1.00 18.54        AAGL
ATOM    676  O   TRP    86       0.847  27.998 113.302  1.00 17.68        AAGL
ATOM    677  N   ALA    87       3.035  27.830 112.793  1.00 15.65        AAGL
ATOM    678  CA  ALA    87       3.440  27.669 114.182  1.00 19.55        AAGL
ATOM    679  CB  ALA    87       4.263  26.393 114.355  1.00 17.55        AAGL
ATOM    680  C   ALA    87       4.266  28.880 114.613  1.00 17.89        AAGL
ATOM    681  O   ALA    87       5.179  29.303 113.896  1.00 18.09        AAGL
ATOM    682  N   ASP    88       3.933  29.441 115.772  1.00 18.18        AAGL
ATOM    683  CA  ASP    88       4.655  30.585 116.325  1.00 18.94        AAGL
ATOM    684  CB  ASP    88       4.276  31.885 115.604  1.00 21.76        AAGL
ATOM    685  CG  ASP    88       2.798  32.205 115.699  1.00 26.60        AAGL
ATOM    686  OD1 ASP    88       2.221  32.074 116.789  1.00 24.49        AAGL
ATOM    687  OD2 ASP    88       2.216  32.599 114.673  1.00 30.64        AAGL
ATOM    688  C   ASP    88       4.349  30.674 117.826  1.00 20.25        AAGL
ATOM    689  O   ASP    88       3.617  29.838 118.354  1.00 18.36        AAGL
ATOM    690  N   PRO    89       4.900  31.681 118.528  1.00 19.03        AAGL
ATOM    691  CD  PRO    89       5.879  32.685 118.078  1.00 20.41        AAGL
ATOM    692  CA  PRO    89       4.656  31.813 119.969  1.00 19.78        AAGL
ATOM    693  CB  PRO    89       5.435  33.071 120.339  1.00 22.34        AAGL
ATOM    694  CG  PRO    89       6.561  33.059 119.354  1.00 20.37        AAGL
ATOM    695  C   PRO    89       3.206  31.882 120.421  1.00 21.51        AAGL
ATOM    696  O   PRO    89       2.909  31.593 121.578  1.00 22.07        AAGL
ATOM    697  N   SER    90       2.297  32.251 119.527  1.00 20.56        AAGL
ATOM    698  CA  SER    90       0.904  32.335 119.924  1.00 21.51        AAGL
ATOM    699  CB  SER    90       0.283  33.644 119.425  1.00 24.67        AAGL
ATOM    700  OG  SER    90       0.139  33.643 118.023  1.00 29.17        AAGL
ATOM    701  C   SER    90       0.086  31.138 119.451  1.00 21.66        AAGL
ATOM    702  O   SER    90      -1.094  31.018 119.792  1.00 18.80        AAGL
ATOM    703  N   ASP    91       0.710  30.249 118.674  1.00 19.99        AAGL
ATOM    704  CA  ASP    91       0.025  29.052 118.188  1.00 21.82        AAGL
ATOM    705  CB  ASP    91      -0.839  29.374 116.961  1.00 26.37        AAGL
ATOM    706  CG  ASP    91      -2.057  30.208 117.305  0.50 27.60        AAGL
ATOM    707  OD1 ASP    91      -2.904  29.743 118.104  0.50 29.99        AAGL
ATOM    708  OD2 ASP    91      -2.168  31.328 116.770  0.50 29.72        AAGL
ATOM    709  C   ASP    91       0.974  27.912 117.816  1.00 19.33        AAGL
ATOM    710  O   ASP    91       1.713  27.997 116.834  1.00 20.80        AAGL
ATOM    711  N   GLN    92       0.945  26.851 118.614  1.00 16.40        AAGL
ATOM    712  CA  GLN    92       1.751  25.653 118.369  1.00 17.43        AAGL
ATOM    713  CB  GLN    92       2.820  25.482 119.449  1.00 16.72        AAGL
ATOM    714  CG  GLN    92       3.897  26.562 119.457  1.00 15.88        AAGL
ATOM    715  CD  GLN    92       4.894  26.427 118.319  1.00 16.69        AAGL
ATOM    716  OE1 GLN    92       5.078  25.345 117.770  1.00 18.84        AAGL
ATOM    717  NE2 GLN    92       5.550  27.524 117.970  1.00 15.00        AAGL
ATOM    718  C   GLN    92       0.782  24.472 118.403  1.00 17.98        AAGL
ATOM    719  O   GLN    92       0.855  23.615 119.284  1.00 18.87        AAGL
ATOM    720  N   THR    93      -0.140  24.444 117.450  1.00 18.32        AAGL
ATOM    721  CA  THR    93      -1.137  23.378 117.396  1.00 19.90        AAGL
ATOM    722  CB  THR    93      -2.303  23.732 116.451  1.00 21.83        AAGL
ATOM    723  OG1 THR    93      -2.845  25.001 116.824  1.00 23.30        AAGL
ATOM    724  CG2 THR    93      -3.415  22.691 116.564  1.00 23.34        AAGL
ATOM    725  C   THR    93      -0.553  22.052 116.946  1.00 19.51        AAGL
```

Fig. 3 cont.

| ATOM | 726 | O   | THR | 93  | 0.000  | 21.935 | 115.856 | 1.00 | 19.99 | AAGL |
|------|-----|-----|-----|-----|--------|--------|---------|------|-------|------|
| ATOM | 727 | N   | THR | 94  | -0.685 | 21.050 | 117.802 | 1.00 | 19.55 | AAGL |
| ATOM | 728 | CA  | THR | 94  | -0.181 | 19.716 | 117.510 | 1.00 | 20.32 | AAGL |
| ATOM | 729 | CB  | THR | 94  | -0.463 | 18.775 | 118.699 | 1.00 | 20.34 | AAGL |
| ATOM | 730 | OG1 | THR | 94  | 0.320  | 19.190 | 119.824 | 1.00 | 20.72 | AAGL |
| ATOM | 731 | CG2 | THR | 94  | -0.141 | 17.334 | 118.348 | 1.00 | 20.41 | AAGL |
| ATOM | 732 | C   | THR | 94  | -0.866 | 19.171 | 116.261 | 1.00 | 19.20 | AAGL |
| ATOM | 733 | O   | THR | 94  | -2.060 | 19.367 | 116.071 | 1.00 | 19.04 | AAGL |
| ATOM | 734 | N   | PRO | 95  | -0.111 | 18.495 | 115.381 | 1.00 | 19.53 | AAGL |
| ATOM | 735 | CD  | PRO | 95  | 1.352  | 18.315 | 115.386 | 1.00 | 17.38 | AAGL |
| ATOM | 736 | CA  | PRO | 95  | -0.703 | 17.937 | 114.160 | 1.00 | 20.73 | AAGL |
| ATOM | 737 | CB  | PRO | 95  | 0.424  | 17.086 | 113.590 | 1.00 | 16.98 | AAGL |
| ATOM | 738 | CG  | PRO | 95  | 1.638  | 17.872 | 113.952 | 1.00 | 20.07 | AAGL |
| ATOM | 739 | C   | PRO | 95  | -1.939 | 17.091 | 114.452 | 1.00 | 22.21 | AAGL |
| ATOM | 740 | O   | PRO | 95  | -2.002 | 16.399 | 115.468 | 1.00 | 19.37 | AAGL |
| ATOM | 741 | N   | SER | 96  | -2.926 | 17.163 | 113.569 | 1.00 | 23.26 | AAGL |
| ATOM | 742 | CA  | SER | 96  | -4.125 | 16.353 | 113.740 | 1.00 | 27.34 | AAGL |
| ATOM | 743 | CB  | SER | 96  | -5.153 | 16.695 | 112.656 | 1.00 | 29.38 | AAGL |
| ATOM | 744 | OG  | SER | 96  | -4.577 | 16.561 | 111.365 | 1.00 | 34.62 | AAGL |
| ATOM | 745 | C   | SER | 96  | -3.635 | 14.911 | 113.590 | 1.00 | 28.07 | AAGL |
| ATOM | 746 | O   | SER | 96  | -2.863 | 14.602 | 112.685 | 1.00 | 29.54 | AAGL |
| ATOM | 747 | N   | GLY | 97  | -4.064 | 14.029 | 114.482 | 1.00 | 28.91 | AAGL |
| ATOM | 748 | CA  | GLY | 97  | -3.607 | 12.655 | 114.390 | 1.00 | 28.58 | AAGL |
| ATOM | 749 | C   | GLY | 97  | -2.478 | 12.365 | 115.365 | 1.00 | 27.25 | AAGL |
| ATOM | 750 | O   | GLY | 97  | -2.214 | 11.202 | 115.679 | 1.00 | 28.56 | AAGL |
| ATOM | 751 | N   | TRP | 98  | -1.786 | 13.408 | 115.819 | 1.00 | 23.62 | AAGL |
| ATOM | 752 | CA  | TRP | 98  | -0.715 | 13.227 | 116.801 | 1.00 | 20.63 | AAGL |
| ATOM | 753 | CB  | TRP | 98  | 0.396  | 14.250 | 116.590 | 1.00 | 20.68 | AAGL |
| ATOM | 754 | CG  | TRP | 98  | 1.253  | 13.995 | 115.382 | 1.00 | 20.26 | AAGL |
| ATOM | 755 | CD2 | TRP | 98  | 2.561  | 14.517 | 115.148 | 1.00 | 19.57 | AAGL |
| ATOM | 756 | CE2 | TRP | 98  | 2.945  | 14.123 | 113.845 | 1.00 | 20.94 | AAGL |
| ATOM | 757 | CE3 | TRP | 98  | 3.449  | 15.288 | 115.913 | 1.00 | 19.61 | AAGL |
| ATOM | 758 | CD1 | TRP | 98  | 0.905  | 13.311 | 114.246 | 1.00 | 21.24 | AAGL |
| ATOM | 759 | NE1 | TRP | 98  | 1.918  | 13.386 | 113.318 | 1.00 | 21.31 | AAGL |
| ATOM | 760 | CZ2 | TRP | 98  | 4.178  | 14.475 | 113.290 | 1.00 | 20.47 | AAGL |
| ATOM | 761 | CZ3 | TRP | 98  | 4.675  | 15.638 | 115.362 | 1.00 | 20.55 | AAGL |
| ATOM | 762 | CH2 | TRP | 98  | 5.028  | 15.230 | 114.058 | 1.00 | 21.24 | AAGL |
| ATOM | 763 | C   | TRP | 98  | -1.348 | 13.397 | 118.190 | 1.00 | 21.31 | AAGL |
| ATOM | 764 | O   | TRP | 98  | -2.422 | 13.973 | 118.312 | 1.00 | 21.68 | AAGL |
| ATOM | 765 | N   | SER | 99  | -0.675 | 12.910 | 119.227 | 1.00 | 22.27 | AAGL |
| ATOM | 766 | CA  | SER | 99  | -1.210 | 12.951 | 120.591 | 1.00 | 20.04 | AAGL |
| ATOM | 767 | CB  | SER | 99  | -0.531 | 11.870 | 121.446 | 1.00 | 21.78 | AAGL |
| ATOM | 768 | OG  | SER | 99  | -1.115 | 11.794 | 122.746 | 1.00 | 19.99 | AAGL |
| ATOM | 769 | C   | SER | 99  | -1.172 | 14.262 | 121.377 | 1.00 | 20.81 | AAGL |
| ATOM | 770 | O   | SER | 99  | -0.174 | 14.974 | 121.391 | 1.00 | 20.17 | AAGL |
| ATOM | 771 | N   | THR | 100 | -2.284 | 14.555 | 122.039 | 1.00 | 21.47 | AAGL |
| ATOM | 772 | CA  | THR | 100 | -2.401 | 15.730 | 122.896 | 1.00 | 22.60 | AAGL |
| ATOM | 773 | CB  | THR | 100 | -3.564 | 16.655 | 122.455 | 1.00 | 22.41 | AAGL |
| ATOM | 774 | OG1 | THR | 100 | -4.759 | 15.882 | 122.308 | 1.00 | 23.06 | AAGL |
| ATOM | 775 | CG2 | THR | 100 | -3.248 | 17.339 | 121.128 | 1.00 | 22.11 | AAGL |
| ATOM | 776 | C   | THR | 100 | -2.706 | 15.190 | 124.294 | 1.00 | 23.80 | AAGL |
| ATOM | 777 | O   | THR | 100 | -3.150 | 15.930 | 125.174 | 1.00 | 23.03 | AAGL |
| ATOM | 778 | N   | THR | 101 | -2.448 | 13.895 | 124.488 | 1.00 | 24.54 | AAGL |
| ATOM | 779 | CA  | THR | 101 | -2.737 | 13.228 | 125.755 | 1.00 | 23.47 | AAGL |
| ATOM | 780 | CB  | THR | 101 | -4.055 | 12.440 | 125.638 | 1.00 | 24.48 | AAGL |
| ATOM | 781 | OG1 | THR | 101 | -3.897 | 11.412 | 124.652 | 1.00 | 25.27 | AAGL |
| ATOM | 782 | CG2 | THR | 101 | -5.198 | 13.356 | 125.213 | 1.00 | 25.93 | AAGL |
| ATOM | 783 | C   | THR | 101 | -1.679 | 12.256 | 126.301 | 1.00 | 25.35 | AAGL |
| ATOM | 784 | O   | THR | 101 | -1.794 | 11.802 | 127.437 | 1.00 | 25.05 | AAGL |
| ATOM | 785 | N   | ASP | 102 | -0.657 | 11.932 | 125.513 | 1.00 | 23.02 | AAGL |
| ATOM | 786 | CA  | ASP | 102 | 0.366  | 10.989 | 125.968 | 1.00 | 24.03 | AAGL |
| ATOM | 787 | CB  | ASP | 102 | 0.013  | 9.579  | 125.488 | 1.00 | 25.87 | AAGL |
| ATOM | 788 | CG  | ASP | 102 | 0.934  | 8.515  | 126.052 | 1.00 | 29.80 | AAGL |
| ATOM | 789 | OD1 | ASP | 102 | 2.163  | 8.600  | 125.864 | 1.00 | 30.75 | AAGL |
| ATOM | 790 | OD2 | ASP | 102 | 0.425  | 7.571  | 126.683 | 1.00 | 35.27 | AAGL |
| ATOM | 791 | C   | ASP | 102 | 1.746  | 11.370 | 125.446 | 1.00 | 24.10 | AAGL |
| ATOM | 792 | O   | ASP | 102 | 2.005  | 11.269 | 124.245 | 1.00 | 24.23 | AAGL |

Fig. 3 cont.

```
ATOM    793  N   LEU   103       2.640  11.791 126.338  1.00 23.33      AAGL
ATOM    794  CA  LEU   103       3.974  12.189 125.898  1.00 23.77      AAGL
ATOM    795  CB  LEU   103       4.801  12.749 127.056  1.00 24.26      AAGL
ATOM    796  CG  LEU   103       6.113  13.383 126.579  1.00 23.41      AAGL
ATOM    797  CD1 LEU   103       5.800  14.627 125.765  1.00 23.25      AAGL
ATOM    798  CD2 LEU   103       7.005  13.729 127.764  1.00 24.01      AAGL
ATOM    799  C   LEU   103       4.744  11.046 125.257  1.00 24.93      AAGL
ATOM    800  O   LEU   103       5.522  11.259 124.326  1.00 22.87      AAGL
ATOM    801  N   GLY   104       4.535   9.837 125.765  1.00 24.55      AAGL
ATOM    802  CA  GLY   104       5.229   8.689 125.213  1.00 25.67      AAGL
ATOM    803  C   GLY   104       4.863   8.514 123.757  1.00 24.34      AAGL
ATOM    804  O   GLY   104       5.727   8.334 122.899  1.00 25.72      AAGL
ATOM    805  N   THR   105       3.571   8.571 123.475  1.00 23.33      AAGL
ATOM    806  CA  THR   105       3.084   8.425 122.115  1.00 24.93      AAGL
ATOM    807  CB  THR   105       1.546   8.360 122.095  1.00 25.14      AAGL
ATOM    808  OG1 THR   105       1.109   7.236 122.870  1.00 28.55      AAGL
ATOM    809  CG2 THR   105       1.029   8.211 120.684  1.00 27.78      AAGL·
ATOM    810  C   THR   105       3.561   9.596 121.260  1.00 23.97      AAGL
ATOM    811  O   THR   105       4.008   9.412 120.132  1.00 24.40      AAGL
ATOM    812  N   LEU   106       3.485  10.802 121.812  1.00 22.92      AAGL
ATOM    813  CA  LEU   106       3.898  12.000 121.085  1.00 21.38      AAGL
ATOM    814  CB  LEU   106       3.568  13.254 121.896  1.00 19.99      AAGL
ATOM    815  CG  LEU   106       3.895  14.579 121.196  1.00 18.13      AAGL
ATOM    816  CD1 LEU   106       3.066  14.714 119.923  1.00 16.54      AAGL
ATOM    817  CD2 LEU   106       3.613  15.735 122.141  1.00 15.43      AAGL
ATOM    818  C   LEU   106       5.382  11.995 120.729  1.00 23.00      AAGL
ATOM    819  O   LEU   106       5.755  12.330 119.601  1.00 22.17      AAGL
ATOM    820  N   LYS   107       6.230  11.627 121.684  1.00 23.39      AAGL
ATOM    821  CA  LYS   107       7.662  11.578 121.420  1.00 24.69      AAGL
ATOM    822  CB  LYS   107       8.446  11.129 122.660  1.00 25.78      AAGL
ATOM    823  CG  LYS   107       8.496  12.144 123.789  1.00 27.94      AAGL
ATOM    824  CD  LYS   107       9.574  11.781 124.801  1.00 31.83      AAGL
ATOM    825  CE  LYS   107       9.360  10.393 125.384  1.00 36.44      AAGL
ATOM    826  NZ  LYS   107      10.431  10.009 126.355  1.00 39.34      AAGL
ATOM    827  C   LYS   107       7.942  10.609 120.278  1.00 24.60      AAGL
ATOM    828  O   LYS   107       8.829  10.852 119.461  1.00 24.29      AAGL
ATOM    829  N   TRP   108       7.183   9.518 120.220  1.00 24.58      AAGL
ATOM    830  CA  TRP   108       7.372   8.526 119.165  1.00 26.57      AAGL
ATOM    831  CB  TRP   108       6.616   7.231 119.487  1.00 30.79      AAGL
ATOM    832  CG  TRP   108       7.429   6.243 120.257  1.00 37.55      AAGL
ATOM    833  CD2 TRP   108       8.617   5.579 119.806  1.00 41.19      AAGL
ATOM    834  CE2 TRP   108       9.055   4.744 120.861  1.00 41.70      AAGL
ATOM    835  CE3 TRP   108       9.356   5.610 118.611  1.00 40.79      AAGL
ATOM    836  CD1 TRP   108       7.199   5.797 121.530  1.00 39.67      AAGL
ATOM    837  NE1 TRP   108       8.173   4.898 121.899  1.00 41.76      AAGL
ATOM    838  CZ2 TRP   108      10.202   3.942 120.760  1.00 42.41      AAGL
ATOM    839  CZ3 TRP   108      10.498   4.814 118.510  1.00 42.96      AAGL
ATOM    840  CH2 TRP   108      10.908   3.992 119.582  1.00 43.14      AAGL
ATOM    841  C   TRP   108       6.925   9.040 117.807  1.00 25.36      AAGL
ATOM    842  O   TRP   108       7.585   8.785 116.801  1.00 25.01      AAGL
ATOM    843  N   GLN   109       5.808   9.763 117.782  1.00 22.63      AAGL
ATOM    844  CA  GLN   109       5.277  10.304 116.539  1.00 22.94      AAGL
ATOM    845  CB  GLN   109       3.884  10.886 116.784  1.00 22.73      AAGL
ATOM    846  CG  GLN   109       2.863   9.838 117.229  1.00 24.36      AAGL
ATOM    847  CD  GLN   109       1.555  10.447 117.706  1.00 25.79      AAGL
ATOM    848  OE1 GLN   109       1.551  11.462 118.410  1.00 25.25      AAGL
ATOM    849  NE2 GLN   109       0.434   9.821 117.340  1.00 24.06      AAGL
ATOM    850  C   GLN   109       6.212  11.362 115.958  1.00 22.81      AAGL
ATOM    851  O   GLN   109       6.416  11.418 114.747  1.00 23.48      AAGL
ATOM    852  N   LEU   110       6.796  12.181 116.826  1.00 23.23      AAGL
ATOM    853  CA  LEU   110       7.716  13.223 116.389  1.00 23.80      AAGL
ATOM    854  CB  LEU   110       8.031  14.188 117.539  1.00 24.37      AAGL
ATOM    855  CG  LEU   110       9.119  15.231 117.255  1.00 22.16      AAGL
ATOM    856  CD1 LEU   110       8.792  15.973 115.960  1.00 22.25      AAGL
ATOM    857  CD2 LEU   110       9.230  16.199 118.420  1.00 23.11      AAGL
ATOM    858  C   LEU   110       9.005  12.596 115.870  1.00 25.82      AAGL
ATOM    859  O   LEU   110       9.523  13.010 114.835  1.00 24.35      AAGL
```

Fig. 3 cont.

| | | | | | | | | | |
|---|---|---|---|---|---|---|---|---|---|
| ATOM | 860 | N | TYR | 111 | 9.524 | 11.608 | 116.594 | 1.00 25.68 | AAGL |
| ATOM | 861 | CA | TYR | 111 | 10.746 | 10.915 | 116.179 | 1.00 24.78 | AAGL |
| ATOM | 862 | CB | TYR | 111 | 11.151 | 9.869 | 117.230 | 1.00 25.83 | AAGL |
| ATOM | 863 | CG | TYR | 111 | 12.199 | 8.874 | 116.767 | 1.00 27.35 | AAGL |
| ATOM | 864 | CD1 | TYR | 111 | 11.848 | 7.774 | 115.986 | 1.00 29.55 | AAGL |
| ATOM | 865 | CE1 | TYR | 111 | 12.810 | 6.866 | 115.544 | 1.00 31.93 | AAGL |
| ATOM | 866 | CD2 | TYR | 111 | 13.541 | 9.043 | 117.099 | 1.00 28.41 | AAGL |
| ATOM | 867 | CE2 | TYR | 111 | 14.514 | 8.143 | 116.661 | 1.00 32.12 | AAGL |
| ATOM | 868 | CZ | TYR | 111 | 14.143 | 7.060 | 115.882 | 1.00 31.55 | AAGL |
| ATOM | 869 | OH | TYR | 111 | 15.104 | 6.183 | 115.423 | 1.00 34.00 | AAGL |
| ATOM | 870 | C | TYR | 111 | 10.505 | 10.246 | 114.832 | 1.00 24.33 | AAGL |
| ATOM | 871 | O | TYR | 111 | 11.307 | 10.383 | 113.901 | 1.00 26.25 | AAGL |
| ATOM | 872 | N | ASN | 112 | 9.398 | 9.521 | 114.731 | 1.00 23.20 | AAGL |
| ATOM | 873 | CA | ASN | 112 | 9.042 | 8.842 | 113.492 | 1.00 24.57 | AAGL |
| ATOM | 874 | CB | ASN | 112 | 7.750 | 8.041 | 113.688 | 1.00 27.15 | AAGL |
| ATOM | 875 | CG | ASN | 112 | 7.963 | 6.757 | 114.473 | 0.50 25.91 | AAGL |
| ATOM | 876 | OD1 | ASN | 112 | 7.010 | 6.023 | 114.752 | 0.50 29.07 | AAGL |
| ATOM | 877 | ND2 | ASN | 112 | 9.209 | 6.475 | 114.825 | 0.50 26.44 | AAGL |
| ATOM | 878 | C | ASN | 112 | 8.865 | 9.865 | 112.364 | 1.00 26.29 | AAGL |
| ATOM | 879 | O | ASN | 112 | 9.227 | 9.607 | 111.211 | 1.00 23.16 | AAGL |
| ATOM | 880 | N | TYR | 113 | 8.317 | 11.028 | 112.702 | 1.00 23.87 | AAGL |
| ATOM | 881 | CA | TYR | 113 | 8.097 | 12.075 | 111.711 | 1.00 23.73 | AAGL |
| ATOM | 882 | CB | TYR | 113 | 7.328 | 13.239 | 112.315 | 1.00 23.08 | AAGL |
| ATOM | 883 | CG | TYR | 113 | 7.148 | 14.387 | 111.341 | 1.00 22.30 | AAGL |
| ATOM | 884 | CD1 | TYR | 113 | 6.290 | 14.271 | 110.243 | 1.00 20.43 | AAGL |
| ATOM | 885 | CE1 | TYR | 113 | 6.134 | 15.327 | 109.335 | 1.00 21.15 | AAGL |
| ATOM | 886 | CD2 | TYR | 113 | 7.847 | 15.584 | 111.510 | 1.00 20.85 | AAGL |
| ATOM | 887 | CE2 | TYR | 113 | 7.699 | 16.642 | 110.612 | 1.00 18.32 | AAGL |
| ATOM | 888 | CZ | TYR | 113 | 6.846 | 16.512 | 109.533 | 1.00 19.02 | AAGL |
| ATOM | 889 | OH | TYR | 113 | 6.706 | 17.562 | 108.654 | 1.00 18.05 | AAGL |
| ATOM | 890 | C | TYR | 113 | 9.391 | 12.613 | 111.111 | 1.00 23.40 | AAGL |
| ATOM | 891 | O | TYR | 113 | 9.561 | 12.611 | 109.891 | 1.00 24.13 | AAGL |
| ATOM | 892 | N | THR | 114 | 10.300 | 13.085 | 111.957 | 1.00 22.35 | AAGL |
| ATOM | 893 | CA | THR | 114 | 11.552 | 13.623 | 111.441 | 1.00 23.52 | AAGL |
| ATOM | 894 | CB | THR | 114 | 12.413 | 14.260 | 112.569 | 1.00 22.78 | AAGL |
| ATOM | 895 | OG1 | THR | 114 | 12.714 | 13.292 | 113.578 | 1.00 23.02 | AAGL |
| ATOM | 896 | CG2 | THR | 114 | 11.662 | 15.433 | 113.210 | 1.00 22.56 | AAGL |
| ATOM | 897 | C | THR | 114 | 12.339 | 12.530 | 110.711 | 1.00 24.38 | AAGL |
| ATOM | 898 | O | THR | 114 | 12.954 | 12.783 | 109.673 | 1.00 23.70 | AAGL |
| ATOM | 899 | N | LEU | 115 | 12.309 | 11.315 | 111.250 | 1.00 26.01 | AAGL |
| ATOM | 900 | CA | LEU | 115 | 12.995 | 10.189 | 110.618 | 1.00 26.48 | AAGL |
| ATOM | 901 | CB | LEU | 115 | 12.785 | 8.909 | 111.443 | 1.00 27.61 | AAGL |
| ATOM | 902 | CG | LEU | 115 | 13.278 | 7.573 | 110.853 | 1.00 28.64 | AAGL |
| ATOM | 903 | CD1 | LEU | 115 | 14.787 | 7.644 | 110.546 | 1.00 29.41 | AAGL |
| ATOM | 904 | CD2 | LEU | 115 | 12.991 | 6.434 | 111.836 | 1.00 31.02 | AAGL |
| ATOM | 905 | C | LEU | 115 | 12.432 | 10.002 | 109.208 | 1.00 27.33 | AAGL |
| ATOM | 906 | O | LEU | 115 | 13.180 | 9.902 | 108.236 | 1.00 29.69 | AAGL |
| ATOM | 907 | N | GLU | 116 | 11.106 | 9.979 | 109.102 | 1.00 27.14 | AAGL |
| ATOM | 908 | CA | GLU | 116 | 10.428 | 9.800 | 107.825 | 1.00 28.85 | AAGL |
| ATOM | 909 | CB | GLU | 116 | 8.919 | 9.674 | 108.057 | 1.00 33.11 | AAGL |
| ATOM | 910 | CG | GLU | 116 | 8.111 | 9.374 | 106.803 | 1.00 40.59 | AAGL |
| ATOM | 911 | CD | GLU | 116 | 8.196 | 7.914 | 106.368 | 1.00 44.26 | AAGL |
| ATOM | 912 | OE1 | GLU | 116 | 7.696 | 7.603 | 105.266 | 1.00 47.23 | AAGL |
| ATOM | 913 | OE2 | GLU | 116 | 8.744 | 7.073 | 107.118 | 1.00 47.05 | AAGL |
| ATOM | 914 | C | GLU | 116 | 10.707 | 10.952 | 106.853 | 1.00 28.50 | AAGL |
| ATOM | 915 | O | GLU | 116 | 10.936 | 10.730 | 105.667 | 1.00 28.60 | AAGL |
| ATOM | 916 | N | VAL | 117 | 10.671 | 12.184 | 107.354 | 1.00 25.75 | AAGL |
| ATOM | 917 | CA | VAL | 117 | 10.933 | 13.345 | 106.507 | 1.00 25.01 | AAGL |
| ATOM | 918 | CB | VAL | 117 | 10.841 | 14.657 | 107.303 | 1.00 25.08 | AAGL |
| ATOM | 919 | CG1 | VAL | 117 | 11.393 | 15.810 | 106.473 | 1.00 24.84 | AAGL |
| ATOM | 920 | CG2 | VAL | 117 | 9.390 | 14.924 | 107.685 | 1.00 25.17 | AAGL |
| ATOM | 921 | C | VAL | 117 | 12.321 | 13.256 | 105.894 | 1.00 25.14 | AAGL |
| ATOM | 922 | O | VAL | 117 | 12.488 | 13.445 | 104.684 | 1.00 26.07 | AAGL |
| ATOM | 923 | N | CYS | 118 | 13.313 | 12.982 | 106.734 | 1.00 22.94 | AAGL |
| ATOM | 924 | CA | CYS | 118 | 14.684 | 12.868 | 106.261 | 1.00 24.56 | AAGL |
| ATOM | 925 | CB | CYS | 118 | 15.644 | 12.710 | 107.446 | 1.00 24.73 | AAGL |
| ATOM | 926 | SG | CYS | 118 | 15.852 | 14.220 | 108.485 | 1.00 26.92 | AAGL |

Fig. 3 cont.

| | | | | | | | | | |
|---|---|---|---|---|---|---|---|---|---|
| ATOM | 927 | C | CYS | 118 | 14.810 | 11.682 | 105.289 | 1.00 25.33 | AAGL |
| ATOM | 928 | O | CYS | 118 | 15.417 | 11.813 | 104.228 | 1.00 25.49 | AAGL |
| ATOM | 929 | N | ASN | 119 | 14.224 | 10.537 | 105.638 | 1.00 25.35 | AAGL |
| ATOM | 930 | CA | ASN | 119 | 14.296 | 9.372 | 104.753 | 1.00 28.13 | AAGL |
| ATOM | 931 | CB | ASN | 119 | 13.618 | 8.156 | 105.382 | 1.00 28.39 | AAGL |
| ATOM | 932 | CG | ASN | 119 | 14.446 | 7.539 | 106.477 | 1.00 28.84 | AAGL |
| ATOM | 933 | OD1 | ASN | 119 | 15.607 | 7.906 | 106.681 | 1.00 28.82 | AAGL |
| ATOM | 934 | ND2 | ASN | 119 | 13.858 | 6.592 | 107.191 | 1.00 31.56 | AAGL |
| ATOM | 935 | C | ASN | 119 | 13.685 | 9.618 | 103.381 | 1.00 28.08 | AAGL |
| ATOM | 936 | O | ASN | 119 | 14.199 | 9.129 | 102.376 | 1.00 31.49 | AAGL |
| ATOM | 937 | N | THR | 120 | 12.594 | 10.372 | 103.326 | 1.00 28.01 | AAGL |
| ATOM | 938 | CA | THR | 120 | 11.952 | 10.641 | 102.046 | 1.00 27.89 | AAGL |
| ATOM | 939 | CB | THR | 120 | 10.596 | 11.321 | 102.231 | 1.00 30.29 | AAGL |
| ATOM | 940 | OG1 | THR | 120 | 9.752 | 10.480 | 103.034 | 1.00 31.43 | AAGL |
| ATOM | 941 | CG2 | THR | 120 | 9.926 | 11.536 | 100.873 | 1.00 30.28 | AAGL |
| ATOM | 942 | C | THR | 120 | 12.838 | 11.495 | 101.147 | 1.00 28.78 | AAGL |
| ATOM | 943 | O | THR | 120 | 12.869 | 11.290 | 99.933 | 1.00 29.09 | AAGL |
| ATOM | 944 | N | PHE | 121 | 13.557 | 12.452 | 101.728 | 1.00 28.45 | AAGL |
| ATOM | 945 | CA | PHE | 121 | 14.463 | 13.269 | 100.930 | 1.00 28.19 | AAGL |
| ATOM | 946 | CB | PHE | 121 | 14.985 | 14.461 | 101.741 | 1.00 29.04 | AAGL |
| ATOM | 947 | CG | PHE | 121 | 14.023 | 15.616 | 101.789 | 1.00 27.88 | AAGL |
| ATOM | 948 | CD1 | PHE | 121 | 12.847 | 15.529 | 102.530 | 1.00 28.91 | AAGL |
| ATOM | 949 | CD2 | PHE | 121 | 14.242 | 16.753 | 101.018 | 1.00 28.77 | AAGL |
| ATOM | 950 | CE1 | PHE | 121 | 11.905 | 16.549 | 102.496 | 1.00 26.83 | AAGL |
| ATOM | 951 | CE2 | PHE | 121 | 13.301 | 17.780 | 100.979 | 1.00 29.21 | AAGL |
| ATOM | 952 | CZ | PHE | 121 | 12.130 | 17.676 | 101.719 | 1.00 29.40 | AAGL |
| ATOM | 953 | C | PHE | 121 | 15.622 | 12.391 | 100.454 | 1.00 28.62 | AAGL |
| ATOM | 954 | O | PHE | 121 | 16.064 | 12.485 | 99.308 | 1.00 29.15 | AAGL |
| ATOM | 955 | N | ALA | 122 | 16.102 | 11.519 | 101.332 | 1.00 28.34 | AAGL |
| ATOM | 956 | CA | ALA | 122 | 17.187 | 10.622 | 100.964 | 1.00 29.64 | AAGL |
| ATOM | 957 | CB | ALA | 122 | 17.599 | 9.768 | 102.158 | 1.00 27.49 | AAGL |
| ATOM | 958 | C | ALA | 122 | 16.748 | 9.731 | 99.795 | 1.00 29.44 | AAGL |
| ATOM | 959 | O | ALA | 122 | 17.538 | 9.447 | 98.890 | 1.00 30.54 | AAGL |
| ATOM | 960 | N | GLU | 123 | 15.492 | 9.295 | 99.801 | 1.00 27.94 | AAGL |
| ATOM | 961 | CA | GLU | 123 | 15.004 | 8.448 | 98.720 | 1.00 28.60 | AAGL |
| ATOM | 962 | CB | GLU | 123 | 13.654 | 7.837 | 99.085 | 1.00 30.65 | AAGL |
| ATOM | 963 | CG | GLU | 123 | 13.693 | 7.161 | 100.439 | 1.00 35.94 | AAGL |
| ATOM | 964 | CD | GLU | 123 | 12.401 | 6.467 | 100.813 | 1.00 38.73 | AAGL |
| ATOM | 965 | OE1 | GLU | 123 | 11.315 | 6.915 | 100.376 | 1.00 39.11 | AAGL |
| ATOM | 966 | OE2 | GLU | 123 | 12.485 | 5.476 | 101.570 | 1.00 39.90 | AAGL |
| ATOM | 967 | C | GLU | 123 | 14.899 | 9.237 | 97.420 | 1.00 28.83 | AAGL |
| ATOM | 968 | O | GLU | 123 | 14.826 | 8.658 | 96.338 | 1.00 25.94 | AAGL |
| ATOM | 969 | N | ASN | 124 | 14.893 | 10.561 | 97.535 | 1.00 27.22 | AAGL |
| ATOM | 970 | CA | ASN | 124 | 14.825 | 11.434 | 96.366 | 1.00 26.84 | AAGL |
| ATOM | 971 | CB | ASN | 124 | 13.786 | 12.537 | 96.579 | 1.00 27.25 | AAGL |
| ATOM | 972 | CG | ASN | 124 | 12.367 | 12.067 | 96.302 | 1.00 28.47 | AAGL |
| ATOM | 973 | OD1 | ASN | 124 | 11.888 | 12.130 | 95.168 | 1.00 28.23 | AAGL |
| ATOM | 974 | ND2 | ASN | 124 | 11.691 | 11.580 | 97.336 | 1.00 30.75 | AAGL |
| ATOM | 975 | C | ASN | 124 | 16.186 | 12.063 | 96.085 | 1.00 26.40 | AAGL |
| ATOM | 976 | O | ASN | 124 | 16.290 | 13.015 | 95.315 | 1.00 25.52 | AAGL |
| ATOM | 977 | N | ASP | 125 | 17.223 | 11.538 | 96.726 | 1.00 26.35 | AAGL |
| ATOM | 978 | CA | ASP | 125 | 18.580 | 12.039 | 96.532 | 1.00 29.66 | AAGL |
| ATOM | 979 | CB | ASP | 125 | 19.066 | 11.654 | 95.131 | 1.00 31.58 | AAGL |
| ATOM | 980 | CG | ASP | 125 | 20.550 | 11.898 | 94.939 | 1.00 34.86 | AAGL |
| ATOM | 981 | OD1 | ASP | 125 | 21.314 | 11.723 | 95.912 | 1.00 36.55 | AAGL |
| ATOM | 982 | OD2 | ASP | 125 | 20.958 | 12.254 | 93.813 | 1.00 35.76 | AAGL |
| ATOM | 983 | C | ASP | 125 | 18.715 | 13.555 | 96.738 | 1.00 30.52 | AAGL |
| ATOM | 984 | O | ASP | 125 | 19.286 | 14.265 | 95.906 | 1.00 28.80 | AAGL |
| ATOM | 985 | N | ILE | 126 | 18.181 | 14.042 | 97.853 | 1.00 30.01 | AAGL |
| ATOM | 986 | CA | ILE | 126 | 18.270 | 15.458 | 98.200 | 1.00 30.54 | AAGL |
| ATOM | 987 | CB | ILE | 126 | 16.886 | 16.127 | 98.234 | 1.00 30.36 | AAGL |
| ATOM | 988 | CG2 | ILE | 126 | 17.014 | 17.532 | 98.817 | 1.00 31.24 | AAGL |
| ATOM | 989 | CG1 | ILE | 126 | 16.294 | 16.182 | 96.823 | 1.00 29.46 | AAGL |
| ATOM | 990 | CD1 | ILE | 126 | 14.803 | 16.480 | 96.798 | 1.00 32.42 | AAGL |
| ATOM | 991 | C | ILE | 126 | 18.894 | 15.566 | 99.590 | 1.00 32.08 | AAGL |
| ATOM | 992 | O | ILE | 126 | 18.381 | 14.988 | 100.550 | 1.00 33.29 | AAGL |
| ATOM | 993 | N | ASP | 127 | 20.004 | 16.292 | 99.689 | 1.00 30.97 | AAGL |

Fig. 3 cont.

| | | | | | | | | | |
|---|---|---|---|---|---|---|---|---|---|
| ATOM | 994 | CA | ASP | 127 | 20.701 | 16.475 | 100.960 | 1.00 32.32 | AAGL |
| ATOM | 995 | CB | ASP | 127 | 22.181 | 16.777 | 100.719 | 1.00 36.39 | AAGL |
| ATOM | 996 | CG | ASP | 127 | 22.849 | 15.758 | 99.822 | 1.00 40.70 | AAGL |
| ATOM | 997 | OD1 | ASP | 127 | 23.019 | 14.591 | 100.244 | 1.00 43.54 | AAGL |
| ATOM | 998 | OD2 | ASP | 127 | 23.201 | 16.126 | 98.680 | 1.00 45.38 | AAGL |
| ATOM | 999 | C | ASP | 127 | 20.082 | 17.655 | 101.687 | 1.00 31.14 | AAGL |
| ATOM | 1000 | O | ASP | 127 | 19.643 | 18.616 | 101.053 | 1.00 30.94 | AAGL |
| ATOM | 1001 | N | ILE | 128 | 20.063 | 17.587 | 103.012 | 1.00 29.03 | AAGL |
| ATOM | 1002 | CA | ILE | 128 | 19.505 | 18.659 | 103.825 | 1.00 27.70 | AAGL |
| ATOM | 1003 | CB | ILE | 128 | 18.442 | 18.112 | 104.806 | 1.00 27.94 | AAGL |
| ATOM | 1004 | CG2 | ILE | 128 | 17.866 | 19.250 | 105.645 | 1.00 25.95 | AAGL |
| ATOM | 1005 | CG1 | ILE | 128 | 17.333 | 17.408 | 104.017 | 1.00 27.55 | AAGL |
| ATOM | 1006 | CD1 | ILE | 128 | 16.289 | 16.716 | 104.883 | 1.00 29.46 | AAGL |
| ATOM | 1007 | C | ILE | 128 | 20.630 | 19.317 | 104.611 | 1.00 25.60 | AAGL |
| ATOM | 1008 | O | ILE | 128 | 21.370 | 18.645 | 105.328 | 1.00 28.07 | AAGL |
| ATOM | 1009 | N | GLU | 129 | 20.766 | 20.632 | 104.465 | 1.00 24.98 | AAGL |
| ATOM | 1010 | CA | GLU | 129 | 21.818 | 21.380 | 105.156 | 1.00 24.49 | AAGL |
| ATOM | 1011 | CB | GLU | 129 | 22.107 | 22.671 | 104.382 | 1.00 27.35 | AAGL |
| ATOM | 1012 | CG | GLU | 129 | 23.218 | 23.552 | 104.946 | 1.00 30.16 | AAGL |
| ATOM | 1013 | CD | GLU | 129 | 24.601 | 22.996 | 104.682 | 1.00 32.15 | AAGL |
| ATOM | 1014 | OE1 | GLU | 129 | 24.720 | 22.097 | 103.821 | 1.00 32.40 | AAGL |
| ATOM | 1015 | OE2 | GLU | 129 | 25.563 | 23.469 | 105.326 | 1.00 31.39 | AAGL |
| ATOM | 1016 | C | GLU | 129 | 21.418 | 21.713 | 106.593 | 1.00 24.14 | AAGL |
| ATOM | 1017 | O | GLU | 129 | 22.210 | 21.561 | 107.531 | 1.00 23.23 | AAGL |
| ATOM | 1018 | N | ILE | 130 | 20.184 | 22.174 | 106.761 | 1.00 22.11 | AAGL |
| ATOM | 1019 | CA | ILE | 130 | 19.696 | 22.535 | 108.083 | 1.00 20.15 | AAGL |
| ATOM | 1020 | CB | ILE | 130 | 19.719 | 24.065 | 108.301 | 1.00 21.07 | AAGL |
| ATOM | 1021 | CG2 | ILE | 130 | 19.096 | 24.406 | 109.636 | 1.00 22.31 | AAGL |
| ATOM | 1022 | CG1 | ILE | 130 | 21.147 | 24.601 | 108.233 | 1.00 20.04 | AAGL |
| ATOM | 1023 | CD1 | ILE | 130 | 21.215 | 26.109 | 108.266 | 1.00 21.74 | AAGL |
| ATOM | 1024 | C | ILE | 130 | 18.256 | 22.091 | 108.265 | 1.00 20.32 | AAGL |
| ATOM | 1025 | O | ILE | 130 | 17.464 | 22.096 | 107.328 | 1.00 18.94 | AAGL |
| ATOM | 1026 | N | ILE | 131 | 17.920 | 21.696 | 109.480 | 1.00 21.44 | AAGL |
| ATOM | 1027 | CA | ILE | 131 | 16.551 | 21.316 | 109.759 | 1.00 22.36 | AAGL |
| ATOM | 1028 | CB | ILE | 131 | 16.324 | 19.791 | 109.544 | 1.00 23.90 | AAGL |
| ATOM | 1029 | CG2 | ILE | 131 | 17.138 | 18.979 | 110.541 | 1.00 28.54 | AAGL |
| ATOM | 1030 | CG1 | ILE | 131 | 14.826 | 19.488 | 109.629 | 1.00 26.48 | AAGL |
| ATOM | 1031 | CD1 | ILE | 131 | 14.427 | 18.156 | 109.005 | 1.00 28.03 | AAGL |
| ATOM | 1032 | C | ILE | 131 | 16.253 | 21.765 | 111.185 | 1.00 21.53 | AAGL |
| ATOM | 1033 | O | ILE | 131 | 16.978 | 21.430 | 112.119 | 1.00 20.84 | AAGL |
| ATOM | 1034 | N | SER | 132 | 15.217 | 22.587 | 111.335 | 1.00 20.93 | AAGL |
| ATOM | 1035 | CA | SER | 132 | 14.859 | 23.089 | 112.654 | 1.00 19.31 | AAGL |
| ATOM | 1036 | CB | SER | 132 | 14.444 | 24.562 | 112.578 | 1.00 18.01 | AAGL |
| ATOM | 1037 | OG | SER | 132 | 13.232 | 24.709 | 111.869 | 1.00 21.72 | AAGL |
| ATOM | 1038 | C | SER | 132 | 13.720 | 22.261 | 113.221 | 1.00 19.27 | AAGL |
| ATOM | 1039 | O | SER | 132 | 12.766 | 21.930 | 112.520 | 1.00 19.32 | AAGL |
| ATOM | 1040 | N | ILE | 133 | 13.842 | 21.901 | 114.491 | 1.00 19.77 | AAGL |
| ATOM | 1041 | CA | ILE | 133 | 12.806 | 21.122 | 115.143 | 1.00 20.58 | AAGL |
| ATOM | 1042 | CB | ILE | 133 | 13.367 | 20.295 | 116.317 | 1.00 21.64 | AAGL |
| ATOM | 1043 | CG2 | ILE | 133 | 12.297 | 19.334 | 116.823 | 1.00 18.97 | AAGL |
| ATOM | 1044 | CG1 | ILE | 133 | 14.644 | 19.559 | 115.890 | 1.00 21.37 | AAGL |
| ATOM | 1045 | CD1 | ILE | 133 | 14.515 | 18.774 | 114.605 | 1.00 25.39 | AAGL |
| ATOM | 1046 | C | ILE | 133 | 11.815 | 22.142 | 115.689 | 1.00 20.75 | AAGL |
| ATOM | 1047 | O | ILE | 133 | 11.890 | 22.529 | 116.850 | 1.00 21.44 | AAGL |
| ATOM | 1048 | N | GLY | 134 | 10.904 | 22.581 | 114.833 | 1.00 19.14 | AAGL |
| ATOM | 1049 | CA | GLY | 134 | 9.919 | 23.560 | 115.241 | 1.00 18.88 | AAGL |
| ATOM | 1050 | C | GLY | 134 | 10.240 | 24.936 | 114.690 | 1.00 18.31 | AAGL |
| ATOM | 1051 | O | GLY | 134 | 11.344 | 25.181 | 114.199 | 1.00 19.16 | AAGL |
| ATOM | 1052 | N | ASN | 135 | 9.268 | 25.835 | 114.769 | 1.00 16.66 | AAGL |
| ATOM | 1053 | CA | ASN | 135 | 9.427 | 27.201 | 114.289 | 1.00 16.54 | AAGL |
| ATOM | 1054 | CB | ASN | 135 | 8.507 | 27.457 | 113.097 | 1.00 15.67 | AAGL |
| ATOM | 1055 | CG | ASN | 135 | 8.666 | 28.854 | 112.532 | 1.00 20.06 | AAGL |
| ATOM | 1056 | OD1 | ASN | 135 | 9.590 | 29.120 | 111.759 | 1.00 19.47 | AAGL |
| ATOM | 1057 | ND2 | ASN | 135 | 7.773 | 29.762 | 112.932 | 1.00 14.55 | AAGL |
| ATOM | 1058 | C | ASN | 135 | 9.044 | 28.146 | 115.420 | 1.00 17.93 | AAGL |
| ATOM | 1059 | O | ASN | 135 | 7.940 | 28.063 | 115.935 | 1.00 16.64 | AAGL |
| ATOM | 1060 | N | GLU | 136 | 9.967 | 29.030 | 115.793 | 1.00 16.85 | AAGL |

Fig. 3 cont.

```
ATOM   1061  CA   GLU  136       9.760  30.001 116.865  1.00 17.43      AAGL
ATOM   1062  CB   GLU  136       8.892  31.169 116.371  1.00 18.10      AAGL
ATOM   1063  CG   GLU  136       9.517  31.970 115.228  1.00 17.17      AAGL
ATOM   1064  CD   GLU  136       8.747  33.240 114.867  1.00 18.85      AAGL
ATOM   1065  OE1  GLU  136       7.592  33.416 115.314  1.00 19.27      AAGL
ATOM   1066  OE2  GLU  136       9.305  34.071 114.120  1.00 18.05      AAGL
ATOM   1067  C    GLU  136       9.116  29.338 118.080  1.00 17.00      AAGL
ATOM   1068  O    GLU  136       8.013  29.697 118.478  1.00 18.88      AAGL
ATOM   1069  N    ILE  137       9.819  28.379 118.674  1.00 16.48      AAGL
ATOM   1070  CA   ILE  137       9.283  27.657 119.828  1.00 16.33      AAGL
ATOM   1071  CB   ILE  137       9.753  26.185 119.830  1.00 17.11      AAGL
ATOM   1072  CG2  ILE  137       9.204  25.457 118.615  1.00 18.25      AAGL
ATOM   1073  CG1  ILE  137      11.276  26.119 119.848  1.00 18.08      AAGL
ATOM   1074  CD1  ILE  137      11.822  24.717 120.029  1.00 19.03      AAGL
ATOM   1075  C    ILE  137       9.600  28.266 121.200  1.00 16.65      AAGL
ATOM   1076  O    ILE  137       9.770  27.540 122.178  1.00 18.23      AAGL
ATOM   1077  N    ARG  138       9.668  29.591 121.271  1.00 15.75      AAGL
ATOM   1078  CA   ARG  138       9.948  30.265 122.537  1.00 19.97      AAGL
ATOM   1079  CB   ARG  138      10.069  31.776 122.327  1.00 21.48      AAGL
ATOM   1080  CG   ARG  138      10.434  32.559 123.586  1.00 23.19      AAGL
ATOM   1081  CD   ARG  138      10.971  33.946 123.230  1.00 25.82      AAGL
ATOM   1082  NE   ARG  138      10.007  34.726 122.454  1.00 29.47      AAGL
ATOM   1083  CZ   ARG  138       8.900  35.263 122.956  1.00 29.69      AAGL
ATOM   1084  NH1  ARG  138       8.610  35.110 124.243  1.00 32.98      AAGL
ATOM   1085  NH2  ARG  138       8.075  35.939 122.168  1.00 29.53      AAGL
ATOM   1086  C    ARG  138       8.852  29.971 123.557  1.00 20.72      AAGL
ATOM   1087  O    ARG  138       9.112  29.926 124.755  1.00 22.83      AAGL
ATOM   1088  N    ALA  139       7.624  29.788 123.081  1.00 19.30      AAGL
ATOM   1089  CA   ALA  139       6.513  29.470 123.969  1.00 19.27      AAGL
ATOM   1090  CB   ALA  139       5.268  30.275 123.586  1.00 21.29      AAGL
ATOM   1091  C    ALA  139       6.227  27.971 123.893  1.00 20.13      AAGL
ATOM   1092  O    ALA  139       5.102  27.517 124.135  1.00 19.76      AAGL
ATOM   1093  N    GLY  140       7.264  27.207 123.565  1.00 16.96      AAGL
ATOM   1094  CA   GLY  140       7.124  25.769 123.465  1.00 17.78      AAGL
ATOM   1095  C    GLY  140       6.640  25.305 122.102  1.00 18.69      AAGL
ATOM   1096  O    GLY  140       6.669  26.058 121.119  1.00 15.87      AAGL
ATOM   1097  N    LEU  141       6.185  24.058 122.051  1.00 18.79      AAGL
ATOM   1098  CA   LEU  141       5.689  23.458 120.815  1.00 18.06      AAGL
ATOM   1099  CB   LEU  141       6.855  22.900 119.999  1.00 17.19      AAGL
ATOM   1100  CG   LEU  141       7.477  21.595 120.523  1.00 18.49      AAGL
ATOM   1101  CD1  LEU  141       8.404  21.018 119.457  1.00 17.04      AAGL
ATOM   1102  CD2  LEU  141       8.231  21.842 121.827  1.00 17.24      AAGL
ATOM   1103  C    LEU  141       4.741  22.310 121.145  1.00 17.11      AAGL
ATOM   1104  O    LEU  141       4.632  21.901 122.295  1.00 19.24      AAGL
ATOM   1105  N    LEU  142       4.063  21.795 120.126  1.00 15.85      AAGL
ATOM   1106  CA   LEU  142       3.162  20.664 120.293  1.00 16.79      AAGL
ATOM   1107  CB   LEU  142       3.981  19.370 120.301  1.00 17.91      AAGL
ATOM   1108  CG   LEU  142       4.783  19.127 119.017  1.00 18.45      AAGL
ATOM   1109  CD1  LEU  142       5.725  17.947 119.195  1.00 16.19      AAGL
ATOM   1110  CD2  LEU  142       3.827  18.888 117.861  1.00 18.62      AAGL
ATOM   1111  C    LEU  142       2.319  20.766 121.562  1.00 18.08      AAGL
ATOM   1112  O    LEU  142       2.374  19.909 122.440  1.00 18.47      AAGL
ATOM   1113  N    TRP  143       1.539  21.830 121.652  1.00 18.54      AAGL
ATOM   1114  CA   TRP  143       0.684  22.038 122.810  1.00 18.96      AAGL
ATOM   1115  CB   TRP  143       0.063  23.431 122.763  1.00 17.05      AAGL
ATOM   1116  CG   TRP  143       1.061  24.544 122.780  1.00 15.57      AAGL
ATOM   1117  CD2  TRP  143       0.807  25.920 122.475  1.00 16.04      AAGL
ATOM   1118  CE2  TRP  143       2.014  26.621 122.675  1.00 15.69      AAGL
ATOM   1119  CE3  TRP  143      -0.324  26.629 122.053  1.00 17.45      AAGL
ATOM   1120  CD1  TRP  143       2.375  24.468 123.139  1.00 15.44      AAGL
ATOM   1121  NE1  TRP  143       2.954  25.711 123.081  1.00 14.73      AAGL
ATOM   1122  CZ2  TRP  143       2.120  27.998 122.467  1.00 18.72      AAGL
ATOM   1123  CZ3  TRP  143      -0.215  28.000 121.848  1.00 20.29      AAGL
ATOM   1124  CH2  TRP  143       0.995  28.666 122.055  1.00 18.09      AAGL
ATOM   1125  C    TRP  143      -0.420  20.989 122.830  1.00 17.60      AAGL
ATOM   1126  O    TRP  143      -0.860  20.526 121.787  1.00 19.46      AAGL
ATOM   1127  N    PRO  144      -0.928  20.646 124.022  1.00 19.35      AAGL
```

Fig. 3 cont.

| ATOM | 1128 | CD  | PRO | 144 | -2.116 | 19.777 | 124.132 | 1.00 | 18.54 | AAGL |
| ATOM | 1129 | CA  | PRO | 144 | -0.549 | 21.167 | 125.340 | 1.00 | 18.49 | AAGL |
| ATOM | 1130 | CB  | PRO | 144 | -1.796 | 20.898 | 126.169 | 1.00 | 18.97 | AAGL |
| ATOM | 1131 | CG  | PRO | 144 | -2.228 | 19.560 | 125.628 | 1.00 | 20.05 | AAGL |
| ATOM | 1132 | C   | PRO | 144 | 0.687  | 20.546 | 125.990 | 1.00 | 17.18 | AAGL |
| ATOM | 1133 | O   | PRO | 144 | 1.303  | 21.162 | 126.855 | 1.00 | 17.80 | AAGL |
| ATOM | 1134 | N   | LEU | 145 | 1.043  | 19.329 | 125.592 | 1.00 | 16.38 | AAGL |
| ATOM | 1135 | CA  | LEU | 145 | 2.184  | 18.655 | 126.206 | 1.00 | 18.03 | AAGL |
| ATOM | 1136 | CB  | LEU | 145 | 2.401  | 17.277 | 125.567 | 1.00 | 19.70 | AAGL |
| ATOM | 1137 | CG  | LEU | 145 | 1.382  | 16.208 | 125.988 | 1.00 | 21.47 | AAGL |
| ATOM | 1138 | CD1 | LEU | 145 | 1.529  | 14.966 | 125.133 | 1.00 | 24.17 | AAGL |
| ATOM | 1139 | CD2 | LEU | 145 | 1.584  | 15.871 | 127.450 | 1.00 | 22.76 | AAGL |
| ATOM | 1140 | C   | LEU | 145 | 3.482  | 19.449 | 126.189 | 1.00 | 18.55 | AAGL |
| ATOM | 1141 | O   | LEU | 145 | 4.291  | 19.335 | 127.113 | 1.00 | 18.42 | AAGL |
| ATOM | 1142 | N   | GLY | 146 | 3.671  | 20.262 | 125.152 | 1.00 | 18.88 | AAGL |
| ATOM | 1143 | CA  | GLY | 146 | 4.884  | 21.050 | 125.045 | 1.00 | 18.53 | AAGL |
| ATOM | 1144 | C   | GLY | 146 | 4.759  | 22.511 | 125.444 | 1.00 | 19.09 | AAGL |
| ATOM | 1145 | O   | GLY | 146 | 5.509  | 23.351 | 124.948 | 1.00 | 17.40 | AAGL |
| ATOM | 1146 | N   | GLU | 147 | 3.811  | 22.827 | 126.326 | 1.00 | 18.92 | AAGL |
| ATOM | 1147 | CA  | GLU | 147 | 3.647  | 24.207 | 126.792 | 1.00 | 18.48 | AAGL |
| ATOM | 1148 | CB  | GLU | 147 | 2.298  | 24.382 | 127.499 | 1.00 | 17.73 | AAGL |
| ATOM | 1149 | CG  | GLU | 147 | 1.111  | 24.296 | 126.565 | 1.00 | 18.17 | AAGL |
| ATOM | 1150 | CD  | GLU | 147 | 0.452  | 25.642 | 126.328 | 1.00 | 21.87 | AAGL |
| ATOM | 1151 | OE1 | GLU | 147 | 1.137  | 26.684 | 126.464 | 1.00 | 24.40 | AAGL |
| ATOM | 1152 | OE2 | GLU | 147 | -0.751 | 25.655 | 125.997 | 1.00 | 22.11 | AAGL |
| ATOM | 1153 | C   | GLU | 147 | 4.789  | 24.512 | 127.759 | 1.00 | 19.00 | AAGL |
| ATOM | 1154 | O   | GLU | 147 | 5.421  | 23.589 | 128.287 | 1.00 | 20.89 | AAGL |
| ATOM | 1155 | N   | THR | 148 | 5.046  | 25.797 | 128.003 | 1.00 | 18.85 | AAGL |
| ATOM | 1156 | CA  | THR | 148 | 6.137  | 26.194 | 128.887 | 1.00 | 21.19 | AAGL |
| ATOM | 1157 | CB  | THR | 148 | 6.486  | 27.705 | 128.746 | 1.00 | 21.41 | AAGL |
| ATOM | 1158 | OG1 | THR | 148 | 5.307  | 28.498 | 128.908 | 1.00 | 23.59 | AAGL |
| ATOM | 1159 | CG2 | THR | 148 | 7.095  | 27.987 | 127.379 | 1.00 | 21.18 | AAGL |
| ATOM | 1160 | C   | THR | 148 | 5.889  | 25.868 | 130.354 | 1.00 | 21.42 | AAGL |
| ATOM | 1161 | O   | THR | 148 | 6.711  | 26.180 | 131.207 | 1.00 | 21.58 | AAGL |
| ATOM | 1162 | N   | SER | 149 | 4.753  | 25.251 | 130.656 | 1.00 | 20.92 | AAGL |
| ATOM | 1163 | CA  | SER | 149 | 4.487  | 24.852 | 132.027 | 1.00 | 22.49 | AAGL |
| ATOM | 1164 | CB  | SER | 149 | 2.990  | 24.593 | 132.228 | 1.00 | 20.24 | AAGL |
| ATOM | 1165 | OG  | SER | 149 | 2.442  | 23.871 | 131.142 | 1.00 | 21.26 | AAGL |
| ATOM | 1166 | C   | SER | 149 | 5.314  | 23.582 | 132.275 | 1.00 | 23.11 | AAGL |
| ATOM | 1167 | O   | SER | 149 | 5.420  | 23.093 | 133.397 | 1.00 | 23.52 | AAGL |
| ATOM | 1168 | N   | SER | 150 | 5.914  | 23.062 | 131.205 | 1.00 | 22.32 | AAGL |
| ATOM | 1169 | CA  | SER | 150 | 6.749  | 21.868 | 131.299 | 1.00 | 22.70 | AAGL |
| ATOM | 1170 | CB  | SER | 150 | 5.925  | 20.609 | 131.003 | 1.00 | 23.28 | AAGL |
| ATOM | 1171 | OG  | SER | 150 | 6.735  | 19.445 | 131.058 | 1.00 | 24.36 | AAGL |
| ATOM | 1172 | C   | SER | 150 | 7.946  | 21.937 | 130.345 | 1.00 | 22.43 | AAGL |
| ATOM | 1173 | O   | SER | 150 | 7.909  | 21.386 | 129.246 | 1.00 | 22.55 | AAGL |
| ATOM | 1174 | N   | TYR | 151 | 9.007  | 22.619 | 130.766 | 1.00 | 22.50 | AAGL |
| ATOM | 1175 | CA  | TYR | 151 | 10.195 | 22.714 | 129.932 | 1.00 | 23.76 | AAGL |
| ATOM | 1176 | CB  | TYR | 151 | 11.192 | 23.730 | 130.511 | 1.00 | 23.66 | AAGL |
| ATOM | 1177 | CG  | TYR | 151 | 10.861 | 25.169 | 130.153 | 1.00 | 25.07 | AAGL |
| ATOM | 1178 | CD1 | TYR | 151 | 10.054 | 25.950 | 130.978 | 1.00 | 22.33 | AAGL |
| ATOM | 1179 | CE1 | TYR | 151 | 9.719  | 27.270 | 130.628 | 1.00 | 22.71 | AAGL |
| ATOM | 1180 | CD2 | TYR | 151 | 11.329 | 25.740 | 128.965 | 1.00 | 24.38 | AAGL |
| ATOM | 1181 | CE2 | TYR | 151 | 10.997 | 27.057 | 128.610 | 1.00 | 23.11 | AAGL |
| ATOM | 1182 | CZ  | TYR | 151 | 10.195 | 27.812 | 129.446 | 1.00 | 22.47 | AAGL |
| ATOM | 1183 | OH  | TYR | 151 | 9.881  | 29.113 | 129.116 | 1.00 | 23.02 | AAGL |
| ATOM | 1184 | C   | TYR | 151 | 10.827 | 21.327 | 129.804 | 1.00 | 24.63 | AAGL |
| ATOM | 1185 | O   | TYR | 151 | 11.627 | 21.070 | 128.903 | 1.00 | 23.36 | AAGL |
| ATOM | 1186 | N   | SER | 152 | 10.441 | 20.427 | 130.703 | 1.00 | 25.50 | AAGL |
| ATOM | 1187 | CA  | SER | 152 | 10.942 | 19.064 | 130.670 | 1.00 | 24.95 | AAGL |
| ATOM | 1188 | CB  | SER | 152 | 10.539 | 18.325 | 131.945 | 1.00 | 25.80 | AAGL |
| ATOM | 1189 | OG  | SER | 152 | 11.051 | 17.010 | 131.928 | 1.00 | 31.90 | AAGL |
| ATOM | 1190 | C   | SER | 152 | 10.364 | 18.358 | 129.442 | 1.00 | 23.88 | AAGL |
| ATOM | 1191 | O   | SER | 152 | 11.081 | 17.695 | 128.696 | 1.00 | 24.71 | AAGL |
| ATOM | 1192 | N   | ASN | 153 | 9.059  | 18.502 | 129.229 | 1.00 | 24.00 | AAGL |
| ATOM | 1193 | CA  | ASN | 153 | 8.414  | 17.885 | 128.075 | 1.00 | 22.02 | AAGL |
| ATOM | 1194 | CB  | ASN | 153 | 6.901  | 18.108 | 128.132 | 1.00 | 21.03 | AAGL |

Fig. 3 cont.

| ATOM | 1195 | CG   | ASN | 153 | 6.225  | 17.239 | 129.168 | 1.00 | 22.68 | AAGL |
| ATOM | 1196 | OD1  | ASN | 153 | 6.888  | 16.579 | 129.971 | 1.00 | 21.72 | AAGL |
| ATOM | 1197 | ND2  | ASN | 153 | 4.897  | 17.235 | 129.159 | 1.00 | 19.51 | AAGL |
| ATOM | 1198 | C    | ASN | 153 | 8.970  | 18.486 | 126.782 | 1.00 | 21.57 | AAGL |
| ATOM | 1199 | O    | ASN | 153 | 9.178  | 17.782 | 125.792 | 1.00 | 19.66 | AAGL |
| ATOM | 1200 | N    | ILE | 154 | 9.192  | 19.797 | 126.798 | 1.00 | 20.58 | AAGL |
| ATOM | 1201 | CA   | ILE | 154 | 9.733  | 20.490 | 125.636 | 1.00 | 21.12 | AAGL |
| ATOM | 1202 | CB   | ILE | 154 | 9.922  | 21.988 | 125.909 | 1.00 | 21.27 | AAGL |
| ATOM | 1203 | CG2  | ILE | 154 | 10.721 | 22.626 | 124.771 | 1.00 | 20.30 | AAGL |
| ATOM | 1204 | CG1  | ILE | 154 | 8.563  | 22.666 | 126.092 | 1.00 | 20.35 | AAGL |
| ATOM | 1205 | CD1  | ILE | 154 | 8.664  | 24.125 | 126.509 | 1.00 | 21.33 | AAGL |
| ATOM | 1206 | C    | ILE | 154 | 11.097 | 19.901 | 125.304 | 1.00 | 22.17 | AAGL |
| ATOM | 1207 | O    | ILE | 154 | 11.395 | 19.610 | 124.147 | 1.00 | 19.83 | AAGL |
| ATOM | 1208 | N    | GLY | 155 | 11.920 | 19.735 | 126.337 | 1.00 | 23.65 | AAGL |
| ATOM | 1209 | CA   | GLY | 155 | 13.246 | 19.181 | 126.147 | 1.00 | 24.02 | AAGL |
| ATOM | 1210 | C    | GLY | 155 | 13.201 | 17.756 | 125.635 | 1.00 | 23.51 | AAGL |
| ATOM | 1211 | O    | GLY | 155 | 13.968 | 17.384 | 124.745 | 1.00 | 23.80 | AAGL |
| ATOM | 1212 | N    | ALA | 156 | 12.300 | 16.952 | 126.191 | 1.00 | 24.34 | AAGL |
| ATOM | 1213 | CA   | ALA | 156 | 12.169 | 15.560 | 125.774 | 1.00 | 23.36 | AAGL |
| ATOM | 1214 | CB   | ALA | 156 | 11.203 | 14.826 | 126.700 | 1.00 | 25.00 | AAGL |
| ATOM | 1215 | C    | ALA | 156 | 11.701 | 15.457 | 124.324 | 1.00 | 23.25 | AAGL |
| ATOM | 1216 | O    | ALA | 156 | 12.121 | 14.571 | 123.589 | 1.00 | 22.33 | AAGL |
| ATOM | 1217 | N    | LEU | 157 | 10.831 | 16.371 | 123.911 | 1.00 | 22.39 | AAGL |
| ATOM | 1218 | CA   | LEU | 157 | 10.340 | 16.376 | 122.538 | 1.00 | 21.31 | AAGL |
| ATOM | 1219 | CB   | LEU | 157 | 9.161  | 17.343 | 122.408 | 1.00 | 20.00 | AAGL |
| ATOM | 1220 | CG   | LEU | 157 | 7.868  | 16.843 | 123.059 | 1.00 | 22.93 | AAGL |
| ATOM | 1221 | CD1  | LEU | 157 | 6.894  | 17.994 | 123.274 | 1.00 | 22.57 | AAGL |
| ATOM | 1222 | CD2  | LEU | 157 | 7.260  | 15.751 | 122.164 | 1.00 | 21.07 | AAGL |
| ATOM | 1223 | C    | LEU | 157 | 11.443 | 16.772 | 121.564 | 1.00 | 21.89 | AAGL |
| ATOM | 1224 | O    | LEU | 157 | 11.616 | 16.146 | 120.518 | 1.00 | 20.81 | AAGL |
| ATOM | 1225 | N    | LEU | 158 | 12.195 | 17.813 | 121.905 | 1.00 | 21.14 | AAGL |
| ATOM | 1226 | CA   | LEU | 158 | 13.267 | 18.257 | 121.021 | 1.00 | 22.43 | AAGL |
| ATOM | 1227 | CB   | LEU | 158 | 13.903 | 19.540 | 121.569 | 1.00 | 22.22 | AAGL |
| ATOM | 1228 | CG   | LEU | 158 | 12.982 | 20.775 | 121.562 | 1.00 | 21.62 | AAGL |
| ATOM | 1229 | CD1  | LEU | 158 | 13.640 | 21.917 | 122.316 | 1.00 | 21.34 | AAGL |
| ATOM | 1230 | CD2  | LEU | 158 | 12.683 | 21.193 | 120.131 | 1.00 | 21.57 | AAGL |
| ATOM | 1231 | C    | LEU | 158 | 14.299 | 17.133 | 120.880 | 1.00 | 24.78 | AAGL |
| ATOM | 1232 | O    | LEU | 158 | 14.807 | 16.880 | 119.794 | 1.00 | 23.68 | AAGL |
| ATOM | 1233 | N    | HIS | 159 | 14.584 | 16.457 | 121.990 | 1.00 | 24.81 | AAGL |
| ATOM | 1234 | CA   | HIS | 159 | 15.518 | 15.332 | 122.009 | 1.00 | 26.46 | AAGL |
| ATOM | 1235 | CB   | HIS | 159 | 15.566 | 14.738 | 123.423 | 1.00 | 27.84 | AAGL |
| ATOM | 1236 | CG   | HIS | 159 | 16.473 | 13.553 | 123.563 | 1.00 | 30.73 | AAGL |
| ATOM | 1237 | CD2  | HIS | 159 | 16.204 | 12.248 | 123.812 | 1.00 | 32.59 | AAGL |
| ATOM | 1238 | ND1  | HIS | 159 | 17.845 | 13.651 | 123.482 | 1.00 | 31.02 | AAGL |
| ATOM | 1239 | CE1  | HIS | 159 | 18.383 | 12.460 | 123.676 | 1.00 | 32.44 | AAGL |
| ATOM | 1240 | NE2  | HIS | 159 | 17.409 | 11.592 | 123.880 | 1.00 | 33.23 | AAGL |
| ATOM | 1241 | C    | HIS | 159 | 15.029 | 14.270 | 121.017 | 1.00 | 26.31 | AAGL |
| ATOM | 1242 | O    | HIS | 159 | 15.796 | 13.772 | 120.190 | 1.00 | 26.14 | AAGL |
| ATOM | 1243 | N    | SER | 160 | 13.749 | 13.922 | 121.110 | 1.00 | 25.57 | AAGL |
| ATOM | 1244 | CA   | SER | 160 | 13.149 | 12.927 | 120.220 | 1.00 | 26.09 | AAGL |
| ATOM | 1245 | CB   | SER | 160 | 11.679 | 12.695 | 120.590 | 1.00 | 26.91 | AAGL |
| ATOM | 1246 | OG   | SER | 160 | 11.555 | 12.082 | 121.857 | 1.00 | 28.98 | AAGL |
| ATOM | 1247 | C    | SER | 160 | 13.225 | 13.333 | 118.745 | 1.00 | 25.22 | AAGL |
| ATOM | 1248 | O    | SER | 160 | 13.564 | 12.516 | 117.885 | 1.00 | 26.49 | AAGL |
| ATOM | 1249 | N    | GLY | 161 | 12.890 | 14.586 | 118.452 | 1.00 | 22.94 | AAGL |
| ATOM | 1250 | CA   | GLY | 161 | 12.934 | 15.051 | 117.078 | 1.00 | 22.94 | AAGL |
| ATOM | 1251 | C    | GLY | 161 | 14.359 | 15.017 | 116.556 | 1.00 | 23.15 | AAGL |
| ATOM | 1252 | O    | GLY | 161 | 14.631 | 14.541 | 115.450 | 1.00 | 23.15 | AAGL |
| ATOM | 1253 | N    | ALA | 162 | 15.277 | 15.519 | 117.368 | 1.00 | 24.30 | AAGL |
| ATOM | 1254 | CA   | ALA | 162 | 16.683 | 15.548 | 117.002 | 1.00 | 26.37 | AAGL |
| ATOM | 1255 | CB   | ALA | 162 | 17.510 | 16.073 | 118.164 | 1.00 | 24.96 | AAGL |
| ATOM | 1256 | C    | ALA | 162 | 17.172 | 14.160 | 116.598 | 1.00 | 27.69 | AAGL |
| ATOM | 1257 | O    | ALA | 162 | 17.801 | 13.995 | 115.546 | 1.00 | 27.54 | AAGL |
| ATOM | 1258 | N    | TRP | 163 | 16.876 | 13.159 | 117.423 | 1.00 | 27.38 | AAGL |
| ATOM | 1259 | CA   | TRP | 163 | 17.320 | 11.806 | 117.124 | 1.00 | 26.93 | AAGL |
| ATOM | 1260 | CB   | TRP | 163 | 17.222 | 10.929 | 118.368 | 1.00 | 28.85 | AAGL |
| ATOM | 1261 | CG   | TRP | 163 | 18.386 | 11.181 | 119.245 | 1.00 | 31.71 | AAGL |

Fig. 3 cont.

```
ATOM   1262  CD2 TRP   163      19.668  10.565 119.134  1.00 32.43      AAGL
ATOM   1263  CE2 TRP   163      20.516  11.194 120.068  1.00 31.66      AAGL
ATOM   1264  CE3 TRP   163      20.185   9.541 118.329  1.00 32.40      AAGL
ATOM   1265  CD1 TRP   163      18.497  12.130 120.217  1.00 31.49      AAGL
ATOM   1266  NE1 TRP   163      19.776  12.149 120.715  1.00 32.86      AAGL
ATOM   1267  CZ2 TRP   163      21.858  10.836 120.223  1.00 32.68      AAGL
ATOM   1268  CZ3 TRP   163      21.522   9.184 118.479  1.00 32.50      AAGL
ATOM   1269  CH2 TRP   163      22.342   9.832 119.421  1.00 32.64      AAGL
ATOM   1270  C   TRP   163      16.636  11.144 115.952  1.00 27.25      AAGL
ATOM   1271  O   TRP   163      17.177  10.205 115.372  1.00 28.73      AAGL
ATOM   1272  N   GLY   164      15.448  11.613 115.598  1.00 25.57      AAGL
ATOM   1273  CA  GLY   164      14.782  11.045 114.445  1.00 24.90      AAGL
ATOM   1274  C   GLY   164      15.651  11.409 113.253  1.00 26.22      AAGL
ATOM   1275  O   GLY   164      15.831  10.618 112.326  1.00 26.72      AAGL
ATOM   1276  N   VAL   165      16.206  12.618 113.290  1.00 25.62      AAGL
ATOM   1277  CA  VAL   165      17.078  13.087 112.219  1.00 26.48      AAGL
ATOM   1278  CB  VAL   165      17.379  14.598 112.356  1.00 26.61      AAGL
ATOM   1279  CG1 VAL   165      18.398  15.026 111.293  1.00 23.67      AAGL
ATOM   1280  CG2 VAL   165      16.090  15.397 112.216  1.00 25.11      AAGL
ATOM   1281  C   VAL   165      18.406  12.328 112.251  1.00 27.69      AAGL
ATOM   1282  O   VAL   165      18.850  11.788 111.233  1.00 29.75      AAGL
ATOM   1283  N   LYS   166      19.037  12.295 113.420  1.00 27.66      AAGL
ATOM   1284  CA  LYS   166      20.313  11.607 113.581  1.00 29.81      AAGL
ATOM   1285  CB  LYS   166      20.770  11.661 115.045  1.00 29.36      AAGL
ATOM   1286  CG  LYS   166      21.062  13.060 115.590  1.00 30.72      AAGL
ATOM   1287  CD  LYS   166      21.442  12.982 117.065  1.00 33.25      AAGL
ATOM   1288  CE  LYS   166      21.674  14.358 117.677  1.00 33.72      AAGL
ATOM   1289  NZ  LYS   166      22.883  15.036 117.122  1.00 33.70      AAGL
ATOM   1290  C   LYS   166      20.229  10.144 113.136  1.00 31.30      AAGL
ATOM   1291  O   LYS   166      21.206   9.594 112.622  1.00 31.56      AAGL
ATOM   1292  N   ASP   167      19.065   9.519 113.319  1.00 30.83      AAGL
ATOM   1293  CA  ASP   167      18.893   8.116 112.944  1.00 32.56      AAGL
ATOM   1294  CB  ASP   167      17.863   7.442 113.854  1.00 31.71      AAGL
ATOM   1295  CG  ASP   167      18.387   7.187 115.245  1.00 33.01      AAGL
ATOM   1296  OD1 ASP   167      19.620   7.148 115.425  1.00 33.60      AAGL
ATOM   1297  OD2 ASP   167      17.558   7.006 116.160  1.00 32.14      AAGL
ATOM   1298  C   ASP   167      18.481   7.858 111.494  1.00 33.63      AAGL
ATOM   1299  O   ASP   167      18.347   6.696 111.082  1.00 32.89      AAGL
ATOM   1300  N   SER   168      18.280   8.925 110.724  1.00 31.74      AAGL
ATOM   1301  CA  SER   168      17.846   8.786 109.341  1.00 31.90      AAGL
ATOM   1302  CB  SER   168      17.279  10.111 108.823  1.00 29.91      AAGL
ATOM   1303  OG  SER   168      18.301  11.074 108.654  1.00 30.10      AAGL
ATOM   1304  C   SER   168      18.922   8.294 108.378  1.00 32.86      AAGL
ATOM   1305  O   SER   168      20.114   8.248 108.704  1.00 31.48      AAGL
ATOM   1306  N   ASN   169      18.470   7.950 107.179  1.00 34.44      AAGL
ATOM   1307  CA  ASN   169      19.328   7.430 106.123  1.00 37.26      AAGL
ATOM   1308  CB  ASN   169      18.493   6.545 105.195  1.00 38.60      AAGL
ATOM   1309  CG  ASN   169      17.848   5.377 105.925  1.00 37.67      AAGL
ATOM   1310  OD1 ASN   169      16.833   4.841 105.482  1.00 40.60      AAGL
ATOM   1311  ND2 ASN   169      18.440   4.971 107.044  1.00 39.67      AAGL
ATOM   1312  C   ASN   169      20.043   8.508 105.308  1.00 38.79      AAGL
ATOM   1313  O   ASN   169      20.725   8.194 104.324  1.00 39.86      AAGL
ATOM   1314  N   LEU   170      19.891   9.773 105.695  1.00 38.43      AAGL
ATOM   1315  CA  LEU   170      20.562  10.849 104.966  1.00 39.07      AAGL
ATOM   1316  CB  LEU   170      20.133  12.222 105.502  1.00 36.50      AAGL
ATOM   1317  CG  LEU   170      18.784  12.783 105.053  1.00 35.65      AAGL
ATOM   1318  CD1 LEU   170      18.533  14.122 105.733  1.00 36.42      AAGL
ATOM   1319  CD2 LEU   170      18.775  12.960 103.548  1.00 35.41      AAGL
ATOM   1320  C   LEU   170      22.068  10.672 105.146  1.00 40.51      AAGL
ATOM   1321  O   LEU   170      22.580  10.787 106.257  1.00 41.18      AAGL
ATOM   1322  N   ALA   171      22.770  10.392 104.050  1.00 43.25      AAGL
ATOM   1323  CA  ALA   171      24.219  10.180 104.078  1.00 44.92      AAGL
ATOM   1324  CB  ALA   171      24.796  10.430 102.700  1.00 45.32      AAGL
ATOM   1325  C   ALA   171      24.913  11.063 105.117  1.00 45.99      AAGL
ATOM   1326  O   ALA   171      25.671  10.568 105.962  1.00 47.05      AAGL
ATOM   1327  N   THR   172      24.668  12.370 105.044  1.00 46.11      AAGL
ATOM   1328  CA  THR   172      25.246  13.316 105.998  1.00 45.78      AAGL
```

Fig. 3 cont.

```
ATOM   1329  CB   THR   172      25.856  14.549 105.320  1.00 46.89      AAGL
ATOM   1330  OG1  THR   172      26.551  14.167 104.132  1.00 48.14      AAGL
ATOM   1331  CG2  THR   172      26.822  15.224 106.269  1.00 46.74      AAGL
ATOM   1332  C    THR   172      24.117  13.844 106.868  1.00 44.10      AAGL
ATOM   1333  O    THR   172      23.086  14.272 106.351  1.00 44.98      AAGL
ATOM   1334  N    THR   173      24.311  13.835 108.179  1.00 42.61      AAGL
ATOM   1335  CA   THR   173      23.283  14.319 109.088  1.00 39.37      AAGL
ATOM   1336  CB   THR   173      23.621  13.926 110.530  1.00 39.69      AAGL
ATOM   1337  OG1  THR   173      23.691  12.497 110.620  1.00 40.97      AAGL
ATOM   1338  CG2  THR   173      22.555  14.436 111.494  1.00 40.31      AAGL
ATOM   1339  C    THR   173      23.140  15.837 108.969  1.00 36.34      AAGL
ATOM   1340  O    THR   173      24.118  16.581 109.083  1.00 35.72      AAGL
ATOM   1341  N    PRO   174      21.916  16.319 108.702  1.00 33.51      AAGL
ATOM   1342  CD   PRO   174      20.709  15.592 108.274  1.00 33.11      AAGL
ATOM   1343  CA   PRO   174      21.728  17.766 108.580  1.00 30.76      AAGL
ATOM   1344  CB   PRO   174      20.252  17.891 108.223  1.00 31.41      AAGL
ATOM   1345  CG   PRO   174      19.989  16.624 107.452  1.00 33.06      AAGL
ATOM   1346  C    PRO   174      22.056  18.475 109.883  1.00 27.61      AAGL
ATOM   1347  O    PRO   174      22.074  17.865 110.945  1.00 26.79      AAGL
ATOM   1348  N    LYS   175      22.332  19.767 109.800  1.00 28.61      AAGL
ATOM   1349  CA   LYS   175      22.614  20.541 111.001  1.00 27.46      AAGL
ATOM   1350  CB   LYS   175      23.167  21.917 110.636  1.00 30.67      AAGL
ATOM   1351  CG   LYS   175      24.679  22.002 110.611  1.00 35.14      AAGL
ATOM   1352  CD   LYS   175      25.286  20.926 109.751  1.00 39.94      AAGL
ATOM   1353  CE   LYS   175      26.804  21.046 109.733  1.00 42.54      AAGL
ATOM   1354  NZ   LYS   175      27.396  20.867 111.091  1.00 43.56      AAGL
ATOM   1355  C    LYS   175      21.267  20.693 111.695  1.00 26.21      AAGL
ATOM   1356  O    LYS   175      20.297  21.096 111.068  1.00 25.54      AAGL
ATOM   1357  N    ILE   176      21.209  20.350 112.975  1.00 24.86      AAGL
ATOM   1358  CA   ILE   176      19.968  20.443 113.728  1.00 24.97      AAGL
ATOM   1359  CB   ILE   176      19.899  19.320 114.779  1.00 25.45      AAGL
ATOM   1360  CG2  ILE   176      18.689  19.515 115.676  1.00 25.15      AAGL
ATOM   1361  CG1  ILE   176      19.847  17.964 114.061  1.00 25.46      AAGL
ATOM   1362  CD1  ILE   176      20.148  16.775 114.941  1.00 26.04      AAGL
ATOM   1363  C    ILE   176      19.866  21.807 114.395  1.00 23.30      AAGL
ATOM   1364  O    ILE   176      20.752  22.208 115.136  1.00 24.10      AAGL
ATOM   1365  N    MET   177      18.769  22.507 114.127  1.00 23.38      AAGL
ATOM   1366  CA   MET   177      18.557  23.847 114.656  1.00 22.20      AAGL
ATOM   1367  CB   MET   177      18.401  24.837 113.488  1.00 20.47      AAGL
ATOM   1368  CG   MET   177      17.934  26.249 113.903  1.00 21.58      AAGL
ATOM   1369  SD   MET   177      17.586  27.336 112.488  1.00 22.93      AAGL
ATOM   1370  CE   MET   177      19.288  27.706 111.969  1.00 22.76      AAGL
ATOM   1371  C    MET   177      17.352  24.013 115.576  1.00 21.82      AAGL
ATOM   1372  O    MET   177      16.343  23.326 115.425  1.00 21.31      AAGL
ATOM   1373  N    ILE   178      17.485  24.927 116.534  1.00 20.60      AAGL
ATOM   1374  CA   ILE   178      16.395  25.294 117.433  1.00 21.53      AAGL
ATOM   1375  CB   ILE   178      16.750  25.134 118.932  1.00 22.17      AAGL
ATOM   1376  CG2  ILE   178      15.678  25.810 119.798  1.00 22.88      AAGL
ATOM   1377  CG1  ILE   178      16.830  23.647 119.286  1.00 23.39      AAGL
ATOM   1378  CD1  ILE   178      17.014  23.363 120.767  1.00 25.76      AAGL
ATOM   1379  C    ILE   178      16.204  26.766 117.088  1.00 19.40      AAGL
ATOM   1380  O    ILE   178      17.156  27.555 117.127  1.00 19.88      AAGL
ATOM   1381  N    HIS   179      14.971  27.125 116.751  1.00 18.62      AAGL
ATOM   1382  CA   HIS   179      14.632  28.475 116.312  1.00 18.14      AAGL
ATOM   1383  CB   HIS   179      14.054  28.356 114.899  1.00 17.60      AAGL
ATOM   1384  CG   HIS   179      13.454  29.617 114.363  1.00 18.42      AAGL
ATOM   1385  CD2  HIS   179      13.731  30.919 114.609  1.00 17.14      AAGL
ATOM   1386  ND1  HIS   179      12.438  29.611 113.432  1.00 18.37      AAGL
ATOM   1387  CE1  HIS   179      12.114  30.855 113.129  1.00 16.27      AAGL
ATOM   1388  NE2  HIS   179      12.883  31.668 113.830  1.00 17.92      AAGL
ATOM   1389  C    HIS   179      13.658  29.235 117.227  1.00 20.10      AAGL
ATOM   1390  O    HIS   179      12.541  28.780 117.470  1.00 20.46      AAGL
ATOM   1391  N    LEU   180      14.090  30.394 117.716  1.00 18.07      AAGL
ATOM   1392  CA   LEU   180      13.258  31.237 118.574  1.00 19.85      AAGL
ATOM   1393  CB   LEU   180      13.930  31.480 119.928  1.00 20.54      AAGL
ATOM   1394  CG   LEU   180      14.253  30.306 120.854  1.00 24.61      AAGL
ATOM   1395  CD1  LEU   180      14.701  30.866 122.208  1.00 23.57      AAGL
```

Fig. 3 cont.

```
ATOM   1396  CD2 LEU   180      13.038  29.405 121.029  1.00 22.59      AAGL
ATOM   1397  C   LEU   180      13.027  32.588 117.905  1.00 20.35      AAGL
ATOM   1398  O   LEU   180      13.838  33.032 117.099  1.00 20.34      AAGL
ATOM   1399  N   ASP   181      11.918  33.237 118.240  1.00 19.30      AAGL
ATOM   1400  CA  ASP   181      11.623  34.548 117.688  1.00 19.90      AAGL
ATOM   1401  CB  ASP   181      10.112  34.796 117.680  1.00 21.15      AAGL
ATOM   1402  CG  ASP   181       9.522  34.825 119.070  1.00 22.95      AAGL
ATOM   1403  OD1 ASP   181       9.910  33.973 119.900  1.00 22.67      AAGL
ATOM   1404  OD2 ASP   181       8.664  35.697 119.336  1.00 25.18      AAGL
ATOM   1405  C   ASP   181      12.315  35.580 118.576  1.00 21.86      AAGL
ATOM   1406  O   ASP   181      13.020  35.218 119.524  1.00 23.76      AAGL
ATOM   1407  N   ASP   182      12.107  36.856 118.271  1.00 22.19      AAGL
ATOM   1408  CA  ASP   182      12.718  37.948 119.034  1.00 22.68      AAGL
ATOM   1409  CB  ASP   182      12.013  38.129 120.381  1.00 24.73      AAGL
ATOM   1410  CG  ASP   182      10.589  38.605 120.234  1.00 26.20      AAGL
ATOM   1411  OD1 ASP   182      10.226  39.052 119.134  1.00 30.46      AAGL
ATOM   1412  OD2 ASP   182       9.829  38.539 121.226  1.00 30.54      AAGL
ATOM   1413  C   ASP   182      14.205  37.719 119.282  1.00 21.94      AAGL
ATOM   1414  O   ASP   182      14.645  37.656 120.432  1.00 22.68      AAGL
ATOM   1415  N   GLY   183      14.975  37.610 118.203  1.00 21.90      AAGL
ATOM   1416  CA  GLY   183      16.403  37.388 118.334  1.00 20.97      AAGL
ATOM   1417  C   GLY   183      17.158  38.524 119.003  1.00 21.01      AAGL
ATOM   1418  O   GLY   183      18.279  38.340 119.478  1.00 24.20      AAGL
ATOM   1419  N   TRP   184      16.550  39.701 119.045  1.00 23.43      AAGL
ATOM   1420  CA  TRP   184      17.191  40.859 119.655  1.00 25.63      AAGL
ATOM   1421  CB  TRP   184      16.514  42.141 119.173  1.00 24.89      AAGL
ATOM   1422  CG  TRP   184      15.045  42.120 119.376  1.00 27.09      AAGL
ATOM   1423  CD2 TRP   184      14.346  42.467 120.576  1.00 28.81      AAGL
ATOM   1424  CE2 TRP   184      12.971  42.248 120.336  1.00 28.20      AAGL
ATOM   1425  CE3 TRP   184      14.750  42.944 121.833  1.00 30.34      AAGL
ATOM   1426  CD1 TRP   184      14.098  41.717 118.481  1.00 27.72      AAGL
ATOM   1427  NE1 TRP   184      12.847  41.792 119.049  1.00 27.27      AAGL
ATOM   1428  CZ2 TRP   184      11.994  42.487 121.308  1.00 32.25      AAGL
ATOM   1429  CZ3 TRP   184      13.776  43.184 122.802  1.00 33.25      AAGL
ATOM   1430  CH2 TRP   184      12.414  42.954 122.533  1.00 30.56      AAGL
ATOM   1431  C   TRP   184      17.155  40.816 121.184  1.00 27.12      AAGL
ATOM   1432  O   TRP   184      17.869  41.563 121.850  1.00 26.68      AAGL
ATOM   1433  N   SER   185      16.332  39.935 121.742  1.00 26.77      AAGL
ATOM   1434  CA  SER   185      16.207  39.846 123.190  1.00 28.56      AAGL
ATOM   1435  CB  SER   185      14.739  39.648 123.558  1.00 28.06      AAGL
ATOM   1436  OG  SER   185      14.594  39.465 124.949  1.00 31.97      AAGL
ATOM   1437  C   SER   185      17.055  38.761 123.858  1.00 27.96      AAGL
ATOM   1438  O   SER   185      16.660  37.600 123.919  1.00 29.29      AAGL
ATOM   1439  N   TRP   186      18.218  39.142 124.374  1.00 27.87      AAGL
ATOM   1440  CA  TRP   186      19.091  38.176 125.032  1.00 27.87      AAGL
ATOM   1441  CB  TRP   186      20.380  38.853 125.511  1.00 29.10      AAGL
ATOM   1442  CG  TRP   186      21.165  38.036 126.509  1.00 27.39      AAGL
ATOM   1443  CD2 TRP   186      21.670  36.705 126.335  1.00 29.36      AAGL
ATOM   1444  CE2 TRP   186      22.338  36.352 127.531  1.00 30.06      AAGL
ATOM   1445  CE3 TRP   186      21.625  35.774 125.285  1.00 30.04      AAGL
ATOM   1446  CD1 TRP   186      21.534  38.422 127.765  1.00 29.38      AAGL
ATOM   1447  NE1 TRP   186      22.239  37.417 128.386  1.00 28.39      AAGL
ATOM   1448  CZ2 TRP   186      22.957  35.108 127.705  1.00 30.53      AAGL
ATOM   1449  CZ3 TRP   186      22.240  34.540 125.459  1.00 30.87      AAGL
ATOM   1450  CH2 TRP   186      22.898  34.218 126.662  1.00 31.05      AAGL
ATOM   1451  C   TRP   186      18.418  37.486 126.217  1.00 28.13      AAGL
ATOM   1452  O   TRP   186      18.620  36.291 126.445  1.00 27.04      AAGL
ATOM   1453  N   ASP   187      17.628  38.232 126.979  1.00 28.09      AAGL
ATOM   1454  CA  ASP   187      16.961  37.643 128.131  1.00 29.42      AAGL
ATOM   1455  CB  ASP   187      16.156  38.704 128.887  1.00 32.15      AAGL
ATOM   1456  CG  ASP   187      17.028  39.817 129.450  1.00 37.52      AAGL
ATOM   1457  OD1 ASP   187      18.255  39.612 129.611  1.00 39.29      AAGL
ATOM   1458  OD2 ASP   187      16.476  40.896 129.748  1.00 41.44      AAGL
ATOM   1459  C   ASP   187      16.035  36.488 127.724  1.00 28.91      AAGL
ATOM   1460  O   ASP   187      16.033  35.431 128.357  1.00 27.77      AAGL
ATOM   1461  N   GLN   188      15.250  36.691 126.668  1.00 27.43      AAGL
ATOM   1462  CA  GLN   188      14.326  35.657 126.215  1.00 27.67      AAGL
```

Fig. 3 cont.

| | | | | | | | | | |
|---|---|---|---|---|---|---|---|---|---|
| ATOM | 1463 | CB | GLN | 188 | 13.357 | 36.220 | 125.170 | 1.00 28.11 | AAGL |
| ATOM | 1464 | CG | GLN | 188 | 12.222 | 37.066 | 125.735 | 1.00 31.74 | AAGL |
| ATOM | 1465 | CD | GLN | 188 | 11.247 | 36.258 | 126.588 | 1.00 36.22 | AAGL |
| ATOM | 1466 | OE1 | GLN | 188 | 10.921 | 35.103 | 126.274 | 1.00 36.68 | AAGL |
| ATOM | 1467 | NE2 | GLN | 188 | 10.760 | 36.867 | 127.660 | 1.00 37.18 | AAGL |
| ATOM | 1468 | C | GLN | 188 | 15.061 | 34.456 | 125.641 | 1.00 26.39 | AAGL |
| ATOM | 1469 | O | GLN | 188 | 14.710 | 33.318 | 125.934 | 1.00 26.19 | AAGL |
| ATOM | 1470 | N | GLN | 189 | 16.086 | 34.712 | 124.829 | 1.00 25.52 | AAGL |
| ATOM | 1471 | CA | GLN | 189 | 16.864 | 33.633 | 124.225 | 1.00 24.65 | AAGL |
| ATOM | 1472 | CB | GLN | 189 | 17.997 | 34.191 | 123.351 | 1.00 24.63 | AAGL |
| ATOM | 1473 | CG | GLN | 189 | 17.576 | 34.991 | 122.126 | 1.00 24.46 | AAGL |
| ATOM | 1474 | CD | GLN | 189 | 16.736 | 34.191 | 121.149 | 1.00 21.93 | AAGL |
| ATOM | 1475 | OE1 | GLN | 189 | 17.097 | 33.084 | 120.760 | 1.00 20.15 | AAGL |
| ATOM | 1476 | NE2 | GLN | 189 | 15.613 | 34.759 | 120.739 | 1.00 23.53 | AAGL |
| ATOM | 1477 | C | GLN | 189 | 17.484 | 32.759 | 125.308 | 1.00 25.42 | AAGL |
| ATOM | 1478 | O | GLN | 189 | 17.314 | 31.544 | 125.324 | 1.00 23.58 | AAGL |
| ATOM | 1479 | N | ASN | 190 | 18.199 | 33.405 | 126.219 | 1.00 25.59 | AAGL |
| ATOM | 1480 | CA | ASN | 190 | 18.892 | 32.725 | 127.293 | 1.00 26.28 | AAGL |
| ATOM | 1481 | CB | ASN | 190 | 19.745 | 33.736 | 128.056 | 1.00 28.08 | AAGL |
| ATOM | 1482 | CG | ASN | 190 | 20.593 | 33.091 | 129.135 | 1.00 29.88 | AAGL |
| ATOM | 1483 | OD1 | ASN | 190 | 21.204 | 32.041 | 128.922 | 1.00 29.87 | AAGL |
| ATOM | 1484 | ND2 | ASN | 190 | 20.649 | 33.727 | 130.295 | 1.00 33.02 | AAGL |
| ATOM | 1485 | C | ASN | 190 | 17.978 | 31.970 | 128.250 | 1.00 26.80 | AAGL |
| ATOM | 1486 | O | ASN | 190 | 18.300 | 30.866 | 128.675 | 1.00 27.29 | AAGL |
| ATOM | 1487 | N | TYR | 191 | 16.838 | 32.554 | 128.590 | 1.00 27.59 | AAGL |
| ATOM | 1488 | CA | TYR | 191 | 15.931 | 31.878 | 129.504 | 1.00 27.82 | AAGL |
| ATOM | 1489 | CB | TYR | 191 | 14.735 | 32.767 | 129.832 | 1.00 28.23 | AAGL |
| ATOM | 1490 | CG | TYR | 191 | 13.815 | 32.132 | 130.844 | 1.00 30.08 | AAGL |
| ATOM | 1491 | CD1 | TYR | 191 | 12.775 | 31.294 | 130.446 | 1.00 32.24 | AAGL |
| ATOM | 1492 | CE1 | TYR | 191 | 11.975 | 30.641 | 131.385 | 1.00 33.28 | AAGL |
| ATOM | 1493 | CD2 | TYR | 191 | 14.032 | 32.308 | 132.210 | 1.00 31.47 | AAGL |
| ATOM | 1494 | CE2 | TYR | 191 | 13.240 | 31.662 | 133.157 | 1.00 31.82 | AAGL |
| ATOM | 1495 | CZ | TYR | 191 | 12.219 | 30.830 | 132.739 | 1.00 34.47 | AAGL |
| ATOM | 1496 | OH | TYR | 191 | 11.458 | 30.168 | 133.679 | 1.00 36.38 | AAGL |
| ATOM | 1497 | C | TYR | 191 | 15.443 | 30.551 | 128.929 | 1.00 27.27 | AAGL |
| ATOM | 1498 | O | TYR | 191 | 15.392 | 29.537 | 129.631 | 1.00 25.68 | AAGL |
| ATOM | 1499 | N | PHE | 192 | 15.079 | 30.557 | 127.651 | 1.00 25.48 | AAGL |
| ATOM | 1500 | CA | PHE | 192 | 14.605 | 29.341 | 127.016 | 1.00 26.24 | AAGL |
| ATOM | 1501 | CB | PHE | 192 | 14.260 | 29.593 | 125.541 | 1.00 24.60 | AAGL |
| ATOM | 1502 | CG | PHE | 192 | 13.854 | 28.351 | 124.799 | 1.00 22.89 | AAGL |
| ATOM | 1503 | CD1 | PHE | 192 | 12.541 | 27.893 | 124.848 | 1.00 23.14 | AAGL |
| ATOM | 1504 | CD2 | PHE | 192 | 14.795 | 27.607 | 124.098 | 1.00 22.70 | AAGL |
| ATOM | 1505 | CE1 | PHE | 192 | 12.169 | 26.706 | 124.208 | 1.00 22.64 | AAGL |
| ATOM | 1506 | CE2 | PHE | 192 | 14.439 | 26.417 | 123.455 | 1.00 22.68 | AAGL |
| ATOM | 1507 | CZ | PHE | 192 | 13.125 | 25.965 | 123.510 | 1.00 23.16 | AAGL |
| ATOM | 1508 | C | PHE | 192 | 15.651 | 28.237 | 127.095 | 1.00 26.50 | AAGL |
| ATOM | 1509 | O | PHE | 192 | 15.386 | 27.154 | 127.612 | 1.00 25.06 | AAGL |
| ATOM | 1510 | N | TYR | 193 | 16.847 | 28.513 | 126.577 | 1.00 26.97 | AAGL |
| ATOM | 1511 | CA | TYR | 193 | 17.898 | 27.510 | 126.570 | 1.00 28.47 | AAGL |
| ATOM | 1512 | CB | TYR | 193 | 19.066 | 27.991 | 125.704 | 1.00 25.93 | AAGL |
| ATOM | 1513 | CG | TYR | 193 | 18.675 | 28.113 | 124.243 | 1.00 26.36 | AAGL |
| ATOM | 1514 | CD1 | TYR | 193 | 18.344 | 26.979 | 123.498 | 1.00 24.37 | AAGL |
| ATOM | 1515 | CE1 | TYR | 193 | 17.905 | 27.084 | 122.178 | 1.00 23.29 | AAGL |
| ATOM | 1516 | CD2 | TYR | 193 | 18.561 | 29.357 | 123.632 | 1.00 26.34 | AAGL |
| ATOM | 1517 | CE2 | TYR | 193 | 18.121 | 29.474 | 122.307 | 1.00 24.57 | AAGL |
| ATOM | 1518 | CZ | TYR | 193 | 17.797 | 28.331 | 121.592 | 1.00 23.44 | AAGL |
| ATOM | 1519 | OH | TYR | 193 | 17.370 | 28.431 | 120.290 | 1.00 24.47 | AAGL |
| ATOM | 1520 | C | TYR | 193 | 18.384 | 27.087 | 127.952 | 1.00 28.72 | AAGL |
| ATOM | 1521 | O | TYR | 193 | 18.542 | 25.892 | 128.212 | 1.00 29.46 | AAGL |
| ATOM | 1522 | N | GLU | 194 | 18.510 | 28.046 | 128.844 | 1.00 30.56 | AAGL |
| ATOM | 1523 | CA | GLU | 194 | 19.081 | 27.684 | 130.177 | 1.00 32.74 | AAGL |
| ATOM | 1524 | CB | GLU | 194 | 19.344 | 28.921 | 131.048 | 1.00 36.66 | AAGL |
| ATOM | 1525 | CG | GLU | 194 | 20.119 | 28.543 | 132.325 | 1.00 42.88 | AAGL |
| ATOM | 1526 | CD | GLU | 194 | 20.271 | 29.668 | 133.327 | 1.00 46.55 | AAGL |
| ATOM | 1527 | OE1 | GLU | 194 | 21.086 | 29.502 | 134.275 | 1.00 48.27 | AAGL |
| ATOM | 1528 | OE2 | GLU | 194 | 19.580 | 30.704 | 133.194 | 1.00 47.67 | AAGL |
| ATOM | 1529 | C | GLU | 194 | 18.056 | 26.802 | 130.875 | 1.00 31.54 | AAGL |

Fig. 3 cont.

```
ATOM   1530  O    GLU  194      18.396  25.764 131.445  1.00 31.58      AAGL
ATOM   1531  N    THR  195      16.795  27.212 130.823  1.00 30.56      AAGL
ATOM   1532  CA   THR  195      15.731  26.453 131.468  1.00 28.40      AAGL
ATOM   1533  CB   THR  195      14.408  27.226 131.402  1.00 27.94      AAGL
ATOM   1534  OG1  THR  195      14.611  28.545 131.929  1.00 25.50      AAGL
ATOM   1535  CG2  THR  195      13.330  26.516 132.211  1.00 26.24      AAGL
ATOM   1536  C    THR  195      15.535  25.054 130.868  1.00 28.06      AAGL
ATOM   1537  O    THR  195      15.427  24.071 131.599  1.00 26.71      AAGL
ATOM   1538  N    VAL  196      15.486  24.961 129.545  1.00 27.08      AAGL
ATOM   1539  CA   VAL  196      15.301  23.666 128.902  1.00 27.16      AAGL
ATOM   1540  CB   VAL  196      15.035  23.838 127.369  1.00 29.10      AAGL
ATOM   1541  CG1  VAL  196      16.227  24.510 126.700  1.00 30.65      AAGL
ATOM   1542  CG2  VAL  196      14.748  22.487 126.727  1.00 31.18      AAGL
ATOM   1543  C    VAL  196      16.502  22.736 129.137  1.00 26.59      AAGL
ATOM   1544  O    VAL  196      16.330  21.563 129.449  1.00 25.06      AAGL
ATOM   1545  N    LEU  197      17.716  23.266 129.015  1.00 26.11      AAGL
ATOM   1546  CA   LEU  197      18.911  22.451 129.214  1.00 28.97      AAGL
ATOM   1547  CB   LEU  197      20.161  23.207 128.735  1.00 29.84      AAGL
ATOM   1548  CG   LEU  197      20.233  23.474 127.220  1.00 30.49      AAGL
ATOM   1549  CD1  LEU  197      21.377  24.445 126.927  1.00 32.56      AAGL
ATOM   1550  CD2  LEU  197      20.413  22.176 126.464  1.00 30.05      AAGL
ATOM   1551  C    LEU  197      19.069  22.032 130.674  1.00 28.89      AAGL
ATOM   1552  O    LEU  197      19.632  20.976 130.971  1.00 30.68      AAGL
ATOM   1553  N    ALA  198      18.550  22.844 131.586  1.00 29.81      AAGL
ATOM   1554  CA   ALA  198      18.646  22.530 133.008  1.00 30.14      AAGL
ATOM   1555  CB   ALA  198      18.110  23.688 133.831  1.00 29.46      AAGL
ATOM   1556  C    ALA  198      17.913  21.237 133.387  1.00 31.06      AAGL
ATOM   1557  O    ALA  198      18.223  20.624 134.411  1.00 30.62      AAGL
ATOM   1558  N    THR  199      16.951  20.814 132.569  1.00 30.12      AAGL
ATOM   1559  CA   THR  199      16.192  19.599 132.868  1.00 29.04      AAGL
ATOM   1560  CB   THR  199      14.831  19.569 132.137  1.00 30.14      AAGL
ATOM   1561  OG1  THR  199      15.051  19.375 130.735  1.00 28.92      AAGL
ATOM   1562  CG2  THR  199      14.058  20.876 132.351  1.00 28.52      AAGL
ATOM   1563  C    THR  199      16.926  18.308 132.497  1.00 30.21      AAGL
ATOM   1564  O    THR  199      16.602  17.237 133.006  1.00 31.94      AAGL
ATOM   1565  N    GLY  200      17.907  18.406 131.613  1.00 29.95      AAGL
ATOM   1566  CA   GLY  200      18.626  17.219 131.194  1.00 30.95      AAGL
ATOM   1567  C    GLY  200      17.868  16.428 130.143  1.00 31.30      AAGL
ATOM   1568  O    GLY  200      18.376  15.436 129.625  1.00 31.90      AAGL
ATOM   1569  N    GLU  201      16.647  16.850 129.823  1.00 31.18      AAGL
ATOM   1570  CA   GLU  201      15.856  16.145 128.813  1.00 30.31      AAGL
ATOM   1571  CB   GLU  201      14.385  16.557 128.881  1.00 29.74      AAGL
ATOM   1572  CG   GLU  201      13.640  16.062 130.110  1.00 32.87      AAGL
ATOM   1573  CD   GLU  201      13.710  14.555 130.285  1.00 33.76      AAGL
ATOM   1574  OE1  GLU  201      13.838  13.833 129.274  1.00 34.18      AAGL
ATOM   1575  OE2  GLU  201      13.617  14.086 131.443  1.00 34.63      AAGL
ATOM   1576  C    GLU  201      16.399  16.440 127.423  1.00 28.94      AAGL
ATOM   1577  O    GLU  201      16.271  15.625 126.511  1.00 27.79      AAGL
ATOM   1578  N    LEU  202      16.988  17.623 127.272  1.00 28.10      AAGL
ATOM   1579  CA   LEU  202      17.587  18.033 126.009  1.00 28.10      AAGL
ATOM   1580  CB   LEU  202      17.029  19.376 125.548  1.00 28.75      AAGL
ATOM   1581  CG   LEU  202      17.766  19.987 124.350  1.00 27.26      AAGL
ATOM   1582  CD1  LEU  202      17.461  19.196 123.090  1.00 27.62      AAGL
ATOM   1583  CD2  LEU  202      17.337  21.430 124.178  1.00 29.02      AAGL
ATOM   1584  C    LEU  202      19.088  18.170 126.240  1.00 28.79      AAGL
ATOM   1585  O    LEU  202      19.518  18.888 127.141  1.00 29.33      AAGL
ATOM   1586  N    LEU  203      19.875  17.473 125.433  1.00 29.74      AAGL
ATOM   1587  CA   LEU  203      21.326  17.524 125.557  1.00 32.35      AAGL
ATOM   1588  CB   LEU  203      21.920  16.146 125.271  1.00 33.32      AAGL
ATOM   1589  CG   LEU  203      21.643  15.084 126.328  1.00 33.68      AAGL
ATOM   1590  CD1  LEU  203      22.436  13.828 125.998  1.00 38.12      AAGL
ATOM   1591  CD2  LEU  203      22.053  15.615 127.694  1.00 37.93      AAGL
ATOM   1592  C    LEU  203      21.934  18.541 124.603  1.00 32.26      AAGL
ATOM   1593  O    LEU  203      21.475  18.694 123.474  1.00 33.19      AAGL
ATOM   1594  N    SER  204      22.975  19.231 125.055  1.00 33.40      AAGL
ATOM   1595  CA   SER  204      23.634  20.215 124.213  1.00 34.27      AAGL
ATOM   1596  CB   SER  204      24.824  20.826 124.947  1.00 34.70      AAGL
```

Fig. 3 cont.

```
ATOM   1597  OG   SER  204      25.380  21.894 124.194  1.00 36.69      AAGL
ATOM   1598  C    SER  204      24.103  19.529 122.934  1.00 34.03      AAGL
ATOM   1599  O    SER  204      24.163  20.145 121.871  1.00 35.28      AAGL
ATOM   1600  N    THR  205      24.438  18.248 123.043  1.00 32.63      AAGL
ATOM   1601  CA   THR  205      24.890  17.491 121.880  1.00 33.11      AAGL
ATOM   1602  CB   THR  205      25.650  16.204 122.302  1.00 33.97      AAGL
ATOM   1603  OG1  THR  205      24.875  15.458 123.256  1.00 35.21      AAGL
ATOM   1604  CG2  THR  205      26.989  16.572 122.919  1.00 34.51      AAGL
ATOM   1605  C    THR  205      23.737  17.111 120.951  1.00 32.07      AAGL
ATOM   1606  O    THR  205      23.960  16.584 119.865  1.00 32.54      AAGL
ATOM   1607  N    ASP  206      22.504  17.389 121.367  1.00 30.83      AAGL
ATOM   1608  CA   ASP  206      21.352  17.054 120.536  1.00 29.51      AAGL
ATOM   1609  CB   ASP  206      20.060  17.033 121.351  1.00 28.56      AAGL
ATOM   1610  CG   ASP  206      19.996  15.871 122.315  1.00 31.99      AAGL
ATOM   1611  OD1  ASP  206      20.539  14.791 121.990  1.00 30.07      AAGL
ATOM   1612  OD2  ASP  206      19.385  16.037 123.390  1.00 30.30      AAGL
ATOM   1613  C    ASP  206      21.151  17.986 119.352  1.00 28.75      AAGL
ATOM   1614  O    ASP  206      20.514  17.597 118.376  1.00 29.56      AAGL
ATOM   1615  N    PHE  207      21.653  19.217 119.437  1.00 27.57      AAGL
ATOM   1616  CA   PHE  207      21.496  20.147 118.321  1.00 27.18      AAGL
ATOM   1617  CB   PHE  207      20.315  21.106 118.567  1.00 24.79      AAGL
ATOM   1618  CG   PHE  207      20.541  22.115 119.651  1.00 24.63      AAGL
ATOM   1619  CD1  PHE  207      20.643  21.728 120.981  1.00 26.07      AAGL
ATOM   1620  CD2  PHE  207      20.613  23.473 119.341  1.00 26.18      AAGL
ATOM   1621  CE1  PHE  207      20.811  22.677 121.986  1.00 23.87      AAGL
ATOM   1622  CE2  PHE  207      20.782  24.433 120.340  1.00 24.35      AAGL
ATOM   1623  CZ   PHE  207      20.880  24.032 121.661  1.00 26.22      AAGL
ATOM   1624  C    PHE  207      22.767  20.917 117.974  1.00 27.60      AAGL
ATOM   1625  O    PHE  207      23.700  20.987 118.772  1.00 28.27      AAGL
ATOM   1626  N    ASP  208      22.784  21.503 116.780  1.00 28.39      AAGL
ATOM   1627  CA   ASP  208      23.958  22.209 116.278  1.00 28.84      AAGL
ATOM   1628  CB   ASP  208      24.329  21.618 114.918  1.00 28.97      AAGL
ATOM   1629  CG   ASP  208      24.337  20.102 114.930  1.00 29.39      AAGL
ATOM   1630  OD1  ASP  208      25.139  19.521 115.686  1.00 30.72      AAGL
ATOM   1631  OD2  ASP  208      23.537  19.494 114.187  1.00 30.15      AAGL
ATOM   1632  C    ASP  208      23.910  23.737 116.143  1.00 28.85      AAGL
ATOM   1633  O    ASP  208      24.866  24.418 116.520  1.00 28.49      AAGL
ATOM   1634  N    TYR  209      22.817  24.263 115.595  1.00 26.19      AAGL
ATOM   1635  CA   TYR  209      22.674  25.704 115.368  1.00 25.08      AAGL
ATOM   1636  CB   TYR  209      22.353  26.001 113.896  1.00 26.01      AAGL
ATOM   1637  CG   TYR  209      23.397  25.677 112.854  1.00 23.51      AAGL
ATOM   1638  CD1  TYR  209      24.728  25.427 113.191  1.00 27.73      AAGL
ATOM   1639  CE1  TYR  209      25.693  25.222 112.194  1.00 27.06      AAGL
ATOM   1640  CD2  TYR  209      23.056  25.705 111.506  1.00 26.41      AAGL
ATOM   1641  CE2  TYR  209      24.007  25.503 110.505  1.00 29.44      AAGL
ATOM   1642  CZ   TYR  209      25.318  25.267 110.856  1.00 25.86      AAGL
ATOM   1643  OH   TYR  209      26.244  25.103 109.853  1.00 26.38      AAGL
ATOM   1644  C    TYR  209      21.578  26.398 116.163  1.00 23.78      AAGL
ATOM   1645  O    TYR  209      20.611  25.774 116.589  1.00 23.59      AAGL
ATOM   1646  N    PHE  210      21.745  27.711 116.315  1.00 25.60      AAGL
ATOM   1647  CA   PHE  210      20.775  28.584 116.969  1.00 24.58      AAGL
ATOM   1648  CB   PHE  210      21.441  29.576 117.918  1.00 25.18      AAGL
ATOM   1649  CG   PHE  210      21.826  29.004 119.234  1.00 26.35      AAGL
ATOM   1650  CD1  PHE  210      20.895  28.309 120.004  1.00 26.01      AAGL
ATOM   1651  CD2  PHE  210      23.104  29.214 119.741  1.00 26.73      AAGL
ATOM   1652  CE1  PHE  210      21.234  27.836 121.269  1.00 28.08      AAGL
ATOM   1653  CE2  PHE  210      23.453  28.746 121.000  1.00 29.00      AAGL
ATOM   1654  CZ   PHE  210      22.519  28.057 121.768  1.00 28.84      AAGL
ATOM   1655  C    PHE  210      20.167  29.402 115.842  1.00 25.37      AAGL
ATOM   1656  O    PHE  210      20.894  29.932 115.005  1.00 26.01      AAGL
ATOM   1657  N    GLY  211      18.845  29.514 115.817  1.00 22.48      AAGL
ATOM   1658  CA   GLY  211      18.214  30.313 114.784  1.00 21.15      AAGL
ATOM   1659  C    GLY  211      17.305  31.333 115.441  1.00 20.32      AAGL
ATOM   1660  O    GLY  211      16.631  31.007 116.412  1.00 22.35      AAGL
ATOM   1661  N    VAL  212      17.285  32.560 114.931  1.00 20.60      AAGL
ATOM   1662  CA   VAL  212      16.428  33.595 115.501  1.00 19.19      AAGL
ATOM   1663  CB   VAL  212      17.206  34.592 116.400  1.00 20.57      AAGL
```

Fig. 3 cont.

```
ATOM   1664  CG1 VAL   212      17.920  33.859 117.512  1.00 21.04           AAGL
ATOM   1665  CG2 VAL   212      18.169  35.419 115.554  1.00 22.31           AAGL
ATOM   1666  C   VAL   212      15.781  34.426 114.410  1.00 19.78           AAGL
ATOM   1667  O   VAL   212      16.358  34.616 113.339  1.00 19.10           AAGL
ATOM   1668  N   SER   213      14.581  34.914 114.692  1.00 18.35           AAGL
ATOM   1669  CA  SER   213      13.869  35.775 113.758  1.00 19.01           AAGL
ATOM   1670  CB  SER   213      12.353  35.630 113.933  1.00 18.11           AAGL
ATOM   1671  OG  SER   213      11.934  34.305 113.696  1.00 17.61           AAGL
ATOM   1672  C   SER   213      14.277  37.187 114.148  1.00 18.11           AAGL
ATOM   1673  O   SER   213      14.506  37.461 115.323  1.00 21.77           AAGL
ATOM   1674  N   TYR   214      14.384  38.081 113.174  1.00 17.30           AAGL
ATOM   1675  CA  TYR   214      14.744  39.458 113.478  1.00 17.43           AAGL
ATOM   1676  CB  TYR   214      16.252  39.688 113.352  1.00 19.55           AAGL
ATOM   1677  CG  TYR   214      16.647  41.122 113.624  1.00 18.83           AAGL
ATOM   1678  CD1 TYR   214      16.558  41.661 114.911  1.00 22.19           AAGL
ATOM   1679  CE1 TYR   214      16.872  43.004 115.158  1.00 22.03           AAGL
ATOM   1680  CD2 TYR   214      17.063  41.959 112.590  1.00 23.69           AAGL
ATOM   1681  CE2 TYR   214      17.381  43.307 112.828  1.00 22.60           AAGL
ATOM   1682  CZ  TYR   214      17.279  43.816 114.113  1.00 22.17           AAGL
ATOM   1683  OH  TYR   214      17.561  45.141 114.346  1.00 24.19           AAGL
ATOM   1684  C   TYR   214      14.013  40.386 112.534  1.00 18.48           AAGL
ATOM   1685  O   TYR   214      14.361  40.488 111.358  1.00 18.33           AAGL
ATOM   1686  N   TYR   215      12.990  41.048 113.067  1.00 18.28           AAGL
ATOM   1687  CA  TYR   215      12.171  41.979 112.311  1.00 16.96           AAGL
ATOM   1688  CB  TYR   215      10.717  41.506 112.321  1.00 16.58           AAGL
ATOM   1689  CG  TYR   215      10.497  40.277 111.465  1.00 16.72           AAGL
ATOM   1690  CD1 TYR   215      10.456  40.377 110.075  1.00 19.62           AAGL
ATOM   1691  CE1 TYR   215      10.264  39.252 109.274  1.00 18.54           AAGL
ATOM   1692  CD2 TYR   215      10.346  39.013 112.038  1.00 16.88           AAGL
ATOM   1693  CE2 TYR   215      10.156  37.875 111.245  1.00 17.19           AAGL
ATOM   1694  CZ  TYR   215      10.111  38.007 109.862  1.00 16.90           AAGL
ATOM   1695  OH  TYR   215       9.868  36.910 109.064  1.00 17.46           AAGL
ATOM   1696  C   TYR   215      12.297  43.374 112.920  1.00 19.56           AAGL
ATOM   1697  O   TYR   215      12.487  43.523 114.124  1.00 19.95           AAGL
ATOM   1698  N   PRO   216      12.184  44.418 112.087  1.00 20.63           AAGL
ATOM   1699  CD  PRO   216      12.160  44.396 110.613  1.00 20.25           AAGL
ATOM   1700  CA  PRO   216      12.308  45.788 112.589  1.00 20.50           AAGL
ATOM   1701  CB  PRO   216      13.033  46.476 111.450  1.00 22.26           AAGL
ATOM   1702  CG  PRO   216      12.318  45.881 110.243  1.00 20.29           AAGL
ATOM   1703  C   PRO   216      11.005  46.503 112.922  1.00 21.80           AAGL
ATOM   1704  O   PRO   216      11.021  47.552 113.569  1.00 23.06           AAGL
ATOM   1705  N   PHE   217       9.885  45.934 112.495  1.00 20.15           AAGL
ATOM   1706  CA  PHE   217       8.599  46.580 112.682  1.00 19.12           AAGL
ATOM   1707  CB  PHE   217       7.940  46.729 111.308  1.00 21.27           AAGL
ATOM   1708  CG  PHE   217       8.166  45.548 110.390  1.00 22.97           AAGL
ATOM   1709  CD1 PHE   217       7.783  44.263 110.773  1.00 22.42           AAGL
ATOM   1710  CD2 PHE   217       8.733  45.730 109.129  1.00 24.02           AAGL
ATOM   1711  CE1 PHE   217       7.953  43.177 109.912  1.00 22.58           AAGL
ATOM   1712  CE2 PHE   217       8.910  44.651 108.260  1.00 22.45           AAGL
ATOM   1713  CZ  PHE   217       8.518  43.372 108.652  1.00 22.51           AAGL
ATOM   1714  C   PHE   217       7.586  46.016 113.671  1.00 20.44           AAGL
ATOM   1715  O   PHE   217       6.391  46.271 113.523  1.00 21.67           AAGL
ATOM   1716  N   TYR   218       8.040  45.270 114.676  1.00 22.47           AAGL
ATOM   1717  CA  TYR   218       7.130  44.715 115.688  1.00 23.80           AAGL
ATOM   1718  CB  TYR   218       7.155  43.177 115.681  1.00 24.44           AAGL
ATOM   1719  CG  TYR   218       6.583  42.525 114.439  1.00 21.12           AAGL
ATOM   1720  CD1 TYR   218       5.331  42.891 113.952  1.00 22.80           AAGL
ATOM   1721  CE1 TYR   218       4.789  42.281 112.815  1.00 25.22           AAGL
ATOM   1722  CD2 TYR   218       7.286  41.528 113.763  1.00 23.62           AAGL
ATOM   1723  CE2 TYR   218       6.753  40.910 112.625  1.00 23.28           AAGL
ATOM   1724  CZ  TYR   218       5.504  41.294 112.159  1.00 24.22           AAGL
ATOM   1725  OH  TYR   218       4.970  40.698 111.038  1.00 24.13           AAGL
ATOM   1726  C   TYR   218       7.493  45.201 117.089  1.00 26.28           AAGL
ATOM   1727  O   TYR   218       6.956  44.707 118.087  1.00 28.68           AAGL
ATOM   1728  N   SER   219       8.407  46.163 117.165  1.00 27.77           AAGL
ATOM   1729  CA  SER   219       8.854  46.712 118.447  1.00 28.32           AAGL
ATOM   1730  CB  SER   219       9.124  45.592 119.457  1.00 29.25           AAGL
```

Fig. 3 cont.

```
ATOM   1731  OG   SER  219       9.908  46.078 120.538  1.00 31.84      AAGL
ATOM   1732  C    SER  219      10.119  47.549 118.303  1.00 28.53      AAGL
ATOM   1733  O    SER  219      11.107  47.110 117.716  1.00 26.20      AAGL
ATOM   1734  N    ALA  220      10.090  48.750 118.870  1.00 29.00      AAGL
ATOM   1735  CA   ALA  220      11.235  49.647 118.816  1.00 28.92      AAGL
ATOM   1736  CB   ALA  220      10.851  51.003 119.371  1.00 28.98      AAGL
ATOM   1737  C    ALA  220      12.440  49.104 119.572  1.00 29.06      AAGL
ATOM   1738  O    ALA  220      13.520  49.683 119.507  1.00 30.49      AAGL
ATOM   1739  N    SER  221      12.260  48.003 120.293  1.00 29.58      AAGL
ATOM   1740  CA   SER  221      13.358  47.404 121.046  1.00 29.31      AAGL
ATOM   1741  CB   SER  221      12.815  46.522 122.169  1.00 29.65      AAGL
ATOM   1742  OG   SER  221      12.148  47.295 123.152  1.00 33.54      AAGL
ATOM   1743  C    SER  221      14.278  46.565 120.160  1.00 27.63      AAGL
ATOM   1744  O    SER  221      15.375  46.201 120.570  1.00 27.79      AAGL
ATOM   1745  N    ALA  222      13.828  46.264 118.948  1.00 26.73      AAGL
ATOM   1746  CA   ALA  222      14.598  45.445 118.017  1.00 25.72      AAGL
ATOM   1747  CB   ALA  222      13.662  44.864 116.953  1.00 24.78      AAGL
ATOM   1748  C    ALA  222      15.764  46.187 117.347  1.00 26.39      AAGL
ATOM   1749  O    ALA  222      15.889  46.189 116.117  1.00 24.72      AAGL
ATOM   1750  N    THR  223      16.619  46.809 118.157  1.00 25.12      AAGL
ATOM   1751  CA   THR  223      17.771  47.536 117.632  1.00 26.47      AAGL
ATOM   1752  CB   THR  223      18.360  48.498 118.678  1.00 26.69      AAGL
ATOM   1753  OG1  THR  223      18.793  47.749 119.822  1.00 28.21      AAGL
ATOM   1754  CG2  THR  223      17.321  49.520 119.104  1.00 25.83      AAGL
ATOM   1755  C    THR  223      18.877  46.573 117.223  1.00 25.83      AAGL
ATOM   1756  O    THR  223      18.982  45.465 117.751  1.00 28.38      AAGL
ATOM   1757  N    LEU  224      19.703  47.000 116.278  1.00 26.34      AAGL
ATOM   1758  CA   LEU  224      20.807  46.177 115.817  1.00 27.64      AAGL
ATOM   1759  CB   LEU  224      21.516  46.857 114.647  1.00 30.65      AAGL
ATOM   1760  CG   LEU  224      20.769  46.842 113.311  1.00 31.90      AAGL
ATOM   1761  CD1  LEU  224      21.565  47.603 112.257  1.00 32.52      AAGL
ATOM   1762  CD2  LEU  224      20.558  45.406 112.873  1.00 32.19      AAGL
ATOM   1763  C    LEU  224      21.781  45.958 116.967  1.00 28.76      AAGL
ATOM   1764  O    LEU  224      22.495  44.956 117.011  1.00 30.90      AAGL
ATOM   1765  N    ALA  225      21.796  46.902 117.903  1.00 29.40      AAGL
ATOM   1766  CA   ALA  225      22.663  46.833 119.070  1.00 29.81      AAGL
ATOM   1767  CB   ALA  225      22.632  48.163 119.812  1.00 31.20      AAGL
ATOM   1768  C    ALA  225      22.252  45.701 120.013  1.00 30.35      AAGL
ATOM   1769  O    ALA  225      23.105  45.003 120.560  1.00 29.58      AAGL
ATOM   1770  N    SER  226      20.948  45.526 120.215  1.00 30.66      AAGL
ATOM   1771  CA   SER  226      20.472  44.454 121.090  1.00 30.00      AAGL
ATOM   1772  CB   SER  226      18.995  44.642 121.423  1.00 30.27      AAGL
ATOM   1773  OG   SER  226      18.851  45.426 122.592  1.00 34.03      AAGL
ATOM   1774  C    SER  226      20.685  43.096 120.437  1.00 27.61      AAGL
ATOM   1775  O    SER  226      21.003  42.114 121.113  1.00 27.38      AAGL
ATOM   1776  N    LEU  227      20.510  43.053 119.119  1.00 26.75      AAGL
ATOM   1777  CA   LEU  227      20.691  41.828 118.359  1.00 27.51      AAGL
ATOM   1778  CB   LEU  227      20.337  42.060 116.884  1.00 25.07      AAGL
ATOM   1779  CG   LEU  227      20.555  40.857 115.967  1.00 24.78      AAGL
ATOM   1780  CD1  LEU  227      19.578  39.755 116.340  1.00 24.45      AAGL
ATOM   1781  CD2  LEU  227      20.374  41.268 114.514  1.00 23.51      AAGL
ATOM   1782  C    LEU  227      22.148  41.407 118.465  1.00 28.41      AAGL
ATOM   1783  O    LEU  227      22.456  40.253 118.726  1.00 28.87      AAGL
ATOM   1784  N    LYS  228      23.037  42.372 118.256  1.00 30.45      AAGL
ATOM   1785  CA   LYS  228      24.474  42.132 118.316  1.00 31.96      AAGL
ATOM   1786  CB   LYS  228      25.201  43.469 118.150  1.00 36.24      AAGL
ATOM   1787  CG   LYS  228      26.700  43.390 117.906  1.00 41.65      AAGL
ATOM   1788  CD   LYS  228      27.242  44.757 117.477  1.00 43.74      AAGL
ATOM   1789  CE   LYS  228      26.876  45.827 118.489  1.00 46.64      AAGL
ATOM   1790  NZ   LYS  228      27.322  47.191 118.075  1.00 47.80      AAGL
ATOM   1791  C    LYS  228      24.820  41.485 119.653  1.00 30.16      AAGL
ATOM   1792  O    LYS  228      25.538  40.484 119.710  1.00 31.36      AAGL
ATOM   1793  N    THR  229      24.299  42.056 120.732  1.00 29.71      AAGL
ATOM   1794  CA   THR  229      24.553  41.532 122.063  1.00 30.66      AAGL
ATOM   1795  CB   THR  229      23.981  42.452 123.142  1.00 31.91      AAGL
ATOM   1796  OG1  THR  229      24.783  43.637 123.232  1.00 35.38      AAGL
ATOM   1797  CG2  THR  229      23.978  41.748 124.483  1.00 34.76      AAGL
```

Fig. 3 cont.

```
ATOM   1798  C    THR  229     23.973  40.145 122.282  1.00 30.52          AAGL
ATOM   1799  O    THR  229     24.615  39.290 122.883  1.00 30.20          AAGL
ATOM   1800  N    SER  230     22.753  39.932 121.795  1.00 29.88          AAGL
ATOM   1801  CA   SER  230     22.077  38.646 121.948  1.00 27.75          AAGL
ATOM   1802  CB   SER  230     20.626  38.766 121.470  1.00 27.43          AAGL
ATOM   1803  OG   SER  230     19.947  37.532 121.612  1.00 28.20          AAGL
ATOM   1804  C    SER  230     22.790  37.534 121.178  1.00 27.11          AAGL
ATOM   1805  O    SER  230     22.994  36.436 121.698  1.00 27.65          AAGL
ATOM   1806  N    LEU  231     23.157  37.814 119.935  1.00 27.30          AAGL
ATOM   1807  CA   LEU  231     23.859  36.829 119.122  1.00 28.25          AAGL
ATOM   1808  CB   LEU  231     24.037  37.341 117.687  1.00 28.04          AAGL
ATOM   1809  CG   LEU  231     22.767  37.430 116.832  1.00 28.82          AAGL
ATOM   1810  CD1  LEU  231     23.091  38.027 115.468  1.00 29.62          AAGL
ATOM   1811  CD2  LEU  231     22.171  36.034 116.670  1.00 25.68          AAGL
ATOM   1812  C    LEU  231     25.228  36.541 119.733  1.00 29.07          AAGL
ATOM   1813  O    LEU  231     25.685  35.399 119.743  1.00 27.21          AAGL
ATOM   1814  N    ALA  232     25.874  37.585 120.244  1.00 30.00          AAGL
ATOM   1815  CA   ALA  232     27.198  37.449 120.849  1.00 31.64          AAGL
ATOM   1816  CB   ALA  232     27.733  38.828 121.257  1.00 30.69          AAGL
ATOM   1817  C    ALA  232     27.142  36.535 122.063  1.00 31.96          AAGL
ATOM   1818  O    ALA  232     27.980  35.645 122.229  1.00 32.99          AAGL
ATOM   1819  N    ASN  233     26.146  36.757 122.913  1.00 31.75          AAGL
ATOM   1820  CA   ASN  233     25.989  35.960 124.118  1.00 33.65          AAGL
ATOM   1821  CB   ASN  233     25.010  36.646 125.071  1.00 33.95          AAGL
ATOM   1822  CG   ASN  233     25.507  38.010 125.528  1.00 37.26          AAGL
ATOM   1823  OD1  ASN  233     26.712  38.267 125.547  1.00 37.11          AAGL
ATOM   1824  ND2  ASN  233     24.582  38.884 125.912  1.00 37.35          AAGL
ATOM   1825  C    ASN  233     25.558  34.513 123.866  1.00 33.38          AAGL
ATOM   1826  O    ASN  233     25.932  33.616 124.621  1.00 34.08          AAGL
ATOM   1827  N    LEU  234     24.780  34.280 122.812  1.00 32.11          AAGL
ATOM   1828  CA   LEU  234     24.331  32.927 122.498  1.00 31.75          AAGL
ATOM   1829  CB   LEU  234     23.387  32.935 121.286  1.00 29.34          AAGL
ATOM   1830  CG   LEU  234     21.875  33.038 121.527  1.00 28.94          AAGL
ATOM   1831  CD1  LEU  234     21.151  33.301 120.209  1.00 28.45          AAGL
ATOM   1832  CD2  LEU  234     21.373  31.739 122.157  1.00 29.20          AAGL
ATOM   1833  C    LEU  234     25.529  32.036 122.200  1.00 31.64          AAGL
ATOM   1834  O    LEU  234     25.651  30.937 122.737  1.00 31.64          AAGL
ATOM   1835  N    GLN  235     26.413  32.530 121.340  1.00 31.31          AAGL
ATOM   1836  CA   GLN  235     27.601  31.797 120.944  1.00 34.83          AAGL
ATOM   1837  CB   GLN  235     28.302  32.560 119.810  1.00 34.48          AAGL
ATOM   1838  CG   GLN  235     29.283  31.756 118.991  1.00 36.34          AAGL
ATOM   1839  CD   GLN  235     30.545  31.410 119.747  1.00 38.22          AAGL
ATOM   1840  OE1  GLN  235     31.065  32.224 120.511  1.00 38.29          AAGL
ATOM   1841  NE2  GLN  235     31.059  30.204 119.521  1.00 38.94          AAGL
ATOM   1842  C    GLN  235     28.557  31.597 122.122  1.00 35.64          AAGL
ATOM   1843  O    GLN  235     29.063  30.500 122.335  1.00 34.97          AAGL
ATOM   1844  N    SER  236     28.776  32.659 122.894  1.00 36.91          AAGL
ATOM   1845  CA   SER  236     29.694  32.626 124.034  1.00 39.04          AAGL
ATOM   1846  CB   SER  236     29.942  34.056 124.552  1.00 39.04          AAGL
ATOM   1847  OG   SER  236     28.764  34.620 125.122  1.00 40.94          AAGL
ATOM   1848  C    SER  236     29.221  31.750 125.191  1.00 39.31          AAGL
ATOM   1849  O    SER  236     30.027  31.118 125.885  1.00 40.12          AAGL
ATOM   1850  N    THR  237     27.913  31.703 125.394  1.00 38.31          AAGL
ATOM   1851  CA   THR  237     27.353  30.930 126.489  1.00 37.56          AAGL
ATOM   1852  CB   THR  237     26.002  31.514 126.918  1.00 36.05          AAGL
ATOM   1853  OG1  THR  237     26.183  32.883 127.291  1.00 35.25          AAGL
ATOM   1854  CG2  THR  237     25.432  30.738 128.101  1.00 36.50          AAGL
ATOM   1855  C    THR  237     27.169  29.459 126.181  1.00 36.88          AAGL
ATOM   1856  O    THR  237     27.503  28.606 127.003  1.00 37.95          AAGL
ATOM   1857  N    TYR  238     26.653  29.158 124.992  1.00 35.86          AAGL
ATOM   1858  CA   TYR  238     26.391  27.777 124.594  1.00 34.18          AAGL
ATOM   1859  CB   TYR  238     24.955  27.684 124.059  1.00 33.21          AAGL
ATOM   1860  CG   TYR  238     23.924  28.178 125.056  1.00 32.37          AAGL
ATOM   1861  CD1  TYR  238     23.513  27.376 126.125  1.00 31.26          AAGL
ATOM   1862  CE1  TYR  238     22.630  27.860 127.093  1.00 32.64          AAGL
ATOM   1863  CD2  TYR  238     23.416  29.473 124.976  1.00 31.04          AAGL
ATOM   1864  CE2  TYR  238     22.531  29.961 125.935  1.00 32.31          AAGL
```

Fig. 3 cont.

```
ATOM   1865  CZ   TYR  238      22.146  29.150 126.992  1.00 32.31      AAGL
ATOM   1866  OH   TYR  238      21.291  29.646 127.951  1.00 34.51      AAGL
ATOM   1867  C    TYR  238      27.377  27.210 123.570  1.00 34.17      AAGL
ATOM   1868  O    TYR  238      27.327  26.023 123.245  1.00 32.44      AAGL
ATOM   1869  N    ASP  239      28.263  28.060 123.060  1.00 34.59      AAGL
ATOM   1870  CA   ASP  239      29.267  27.645 122.080  1.00 35.46      AAGL
ATOM   1871  CB   ASP  239      30.292  26.716 122.754  1.00 38.30      AAGL
ATOM   1872  CG   ASP  239      31.412  26.290 121.819  1.00 39.89      AAGL
ATOM   1873  OD1  ASP  239      31.811  27.088 120.939  1.00 40.54      AAGL
ATOM   1874  OD2  ASP  239      31.911  25.155 121.975  1.00 41.25      AAGL
ATOM   1875  C    ASP  239      28.688  26.982 120.829  1.00 34.34      AAGL
ATOM   1876  O    ASP  239      29.098  25.885 120.451  1.00 34.85      AAGL
ATOM   1877  N    LYS  240      27.735  27.656 120.190  1.00 32.57      AAGL
ATOM   1878  CA   LYS  240      27.121  27.155 118.963  1.00 31.63      AAGL
ATOM   1879  CB   LYS  240      25.746  26.525 119.234  1.00 30.18      AAGL
ATOM   1880  CG   LYS  240      25.764  25.264 120.104  1.00 33.39      AAGL
ATOM   1881  CD   LYS  240      24.367  24.648 120.218  1.00 31.95      AAGL
ATOM   1882  CE   LYS  240      24.318  23.502 121.247  1.00 32.26      AAGL
ATOM   1883  NZ   LYS  240      25.241  22.379 120.930  1.00 29.98      AAGL
ATOM   1884  C    LYS  240      26.953  28.315 117.990  1.00 29.66      AAGL
ATOM   1885  O    LYS  240      26.779  29.460 118.400  1.00 30.38      AAGL
ATOM   1886  N    PRO  241      27.010  28.036 116.679  1.00 29.06      AAGL
ATOM   1887  CD   PRO  241      27.422  26.781 116.028  1.00 29.36      AAGL
ATOM   1888  CA   PRO  241      26.850  29.106 115.691  1.00 27.35      AAGL
ATOM   1889  CB   PRO  241      27.136  28.403 114.371  1.00 27.28      AAGL
ATOM   1890  CG   PRO  241      28.058  27.285 114.768  1.00 29.28      AAGL
ATOM   1891  C    PRO  241      25.434  29.693 115.732  1.00 28.09      AAGL
ATOM   1892  O    PRO  241      24.491  29.048 116.201  1.00 27.43      AAGL
ATOM   1893  N    VAL  242      25.294  30.911 115.225  1.00 27.44      AAGL
ATOM   1894  CA   VAL  242      24.005  31.588 115.192  1.00 27.37      AAGL
ATOM   1895  CB   VAL  242      24.047  32.871 116.015  1.00 24.62      AAGL
ATOM   1896  CG1  VAL  242      24.156  32.531 117.479  1.00 27.77      AAGL
ATOM   1897  CG2  VAL  242      25.242  33.719 115.588  1.00 27.66      AAGL
ATOM   1898  C    VAL  242      23.614  31.929 113.763  1.00 26.08      AAGL
ATOM   1899  O    VAL  242      24.468  32.140 112.903  1.00 27.26      AAGL
ATOM   1900  N    VAL  243      22.313  31.990 113.512  1.00 25.38      AAGL
ATOM   1901  CA   VAL  243      21.806  32.287 112.179  1.00 22.94      AAGL
ATOM   1902  CB   VAL  243      21.431  30.973 111.419  1.00 24.38      AAGL
ATOM   1903  CG1  VAL  243      20.994  31.285 109.996  1.00 23.02      AAGL
ATOM   1904  CG2  VAL  243      22.612  30.009 111.409  1.00 25.53      AAGL
ATOM   1905  C    VAL  243      20.541  33.129 112.289  1.00 22.55      AAGL
ATOM   1906  O    VAL  243      19.691  32.836 113.115  1.00 21.01      AAGL
ATOM   1907  N    VAL  244      20.432  34.188 111.487  1.00 21.40      AAGL
ATOM   1908  CA   VAL  244      19.213  34.995 111.483  1.00 21.25      AAGL
ATOM   1909  CB   VAL  244      19.469  36.463 111.094  1.00 21.49      AAGL
ATOM   1910  CG1  VAL  244      18.139  37.170 110.884  1.00 22.74      AAGL
ATOM   1911  CG2  VAL  244      20.263  37.163 112.188  1.00 20.20      AAGL
ATOM   1912  C    VAL  244      18.414  34.309 110.387  1.00 19.60      AAGL
ATOM   1913  O    VAL  244      18.720  34.446 109.205  1.00 20.42      AAGL
ATOM   1914  N    VAL  245      17.395  33.557 110.780  1.00 17.97      AAGL
ATOM   1915  CA   VAL  245      16.635  32.788 109.807  1.00 17.90      AAGL
ATOM   1916  CB   VAL  245      16.234  31.431 110.413  1.00 18.93      AAGL
ATOM   1917  CG1  VAL  245      17.485  30.699 110.871  1.00 18.12      AAGL
ATOM   1918  CG2  VAL  245      15.274  31.637 111.578  1.00 17.48      AAGL
ATOM   1919  C    VAL  245      15.415  33.450 109.192  1.00 17.32      AAGL
ATOM   1920  O    VAL  245      14.783  32.882 108.308  1.00 17.57      AAGL
ATOM   1921  N    GLU  246      15.085  34.644 109.666  1.00 17.88      AAGL
ATOM   1922  CA   GLU  246      13.949  35.392 109.143  1.00 18.02      AAGL
ATOM   1923  CB   GLU  246      12.657  35.023 109.875  1.00 22.04      AAGL
ATOM   1924  CG   GLU  246      11.917  33.816 109.352  1.00 22.72      AAGL
ATOM   1925  CD   GLU  246      10.611  33.589 110.102  1.00 24.03      AAGL
ATOM   1926  OE1  GLU  246       9.882  34.579 110.340  1.00 20.71      AAGL
ATOM   1927  OE2  GLU  246      10.311  32.422 110.438  1.00 22.70      AAGL
ATOM   1928  C    GLU  246      14.163  36.882 109.327  1.00 18.20      AAGL
ATOM   1929  O    GLU  246      14.547  37.316 110.404  1.00 19.12      AAGL
ATOM   1930  N    THR  247      13.912  37.658 108.281  1.00 17.83      AAGL
ATOM   1931  CA   THR  247      14.024  39.114 108.372  1.00 19.34      AAGL
```

Fig. 3 cont.

```
ATOM   1932  CB   THR  247    15.505  39.584 108.487  1.00 21.29      AAGL
ATOM   1933  OG1  THR  247    15.532  40.968 108.857  1.00 22.65      AAGL
ATOM   1934  CG2  THR  247    16.238  39.409 107.172  1.00 20.07      AAGL
ATOM   1935  C    THR  247    13.356  39.774 107.167  1.00 18.87      AAGL
ATOM   1936  O    THR  247    13.167  39.141 106.134  1.00 19.64      AAGL
ATOM   1937  N    ASN  248    12.980  41.039 107.326  1.00 17.13      AAGL
ATOM   1938  CA   ASN  248    12.312  41.816 106.281  1.00 18.39      AAGL
ATOM   1939  CB   ASN  248    10.793  41.800 106.466  1.00 19.04      AAGL
ATOM   1940  CG   ASN  248    10.095  40.616 105.836  1.00 20.07      AAGL
ATOM   1941  OD1  ASN  248     8.889  40.475 106.007  1.00 23.76      AAGL
ATOM   1942  ND2  ASN  248    10.820  39.775 105.113  1.00 20.10      AAGL
ATOM   1943  C    ASN  248    12.685  43.291 106.427  1.00 18.69      AAGL
ATOM   1944  O    ASN  248    13.135  43.725 107.483  1.00 17.33      AAGL
ATOM   1945  N    TRP  249    12.466  44.046 105.355  1.00 19.91      AAGL
ATOM   1946  CA   TRP  249    12.630  45.503 105.355  1.00 21.18      AAGL
ATOM   1947  CB   TRP  249    14.065  45.981 105.129  1.00 21.42      AAGL
ATOM   1948  CG   TRP  249    14.117  47.491 105.288  1.00 19.99      AAGL
ATOM   1949  CD2  TRP  249    14.261  48.225 106.517  1.00 19.73      AAGL
ATOM   1950  CE2  TRP  249    14.108  49.599 106.208  1.00 19.65      AAGL
ATOM   1951  CE3  TRP  249    14.499  47.853 107.847  1.00 19.37      AAGL
ATOM   1952  CD1  TRP  249    13.895  48.431 104.313  1.00 20.84      AAGL
ATOM   1953  NE1  TRP  249    13.887  49.693 104.861  1.00 19.99      AAGL
ATOM   1954  CZ2  TRP  249    14.185  50.604 107.187  1.00 20.08      AAGL
ATOM   1955  CZ3  TRP  249    14.575  48.853 108.820  1.00 21.35      AAGL
ATOM   1956  CH2  TRP  249    14.418  50.214 108.481  1.00 21.66      AAGL
ATOM   1957  C    TRP  249    11.722  46.003 104.241  1.00 20.70      AAGL
ATOM   1958  O    TRP  249    11.800  45.539 103.102  1.00 22.36      AAGL
ATOM   1959  N    PRO  250    10.838  46.957 104.559  1.00 22.00      AAGL
ATOM   1960  CD   PRO  250    10.686  47.625 105.865  1.00 21.04      AAGL
ATOM   1961  CA   PRO  250     9.894  47.508 103.587  1.00 21.27      AAGL
ATOM   1962  CB   PRO  250     8.876  48.210 104.477  1.00 22.31      AAGL
ATOM   1963  CG   PRO  250     9.744  48.783 105.538  1.00 22.64      AAGL
ATOM   1964  C    PRO  250    10.402  48.435 102.507  1.00 23.33      AAGL
ATOM   1965  O    PRO  250    11.270  49.268 102.743  1.00 21.79      AAGL
ATOM   1966  N    VAL  251     9.844  48.282 101.311  1.00 23.27      AAGL
ATOM   1967  CA   VAL  251    10.185  49.165 100.212  1.00 24.85      AAGL
ATOM   1968  CB   VAL  251    10.171  48.437  98.854  1.00 24.44      AAGL
ATOM   1969  CG1  VAL  251    11.335  47.476  98.787  1.00 24.31      AAGL
ATOM   1970  CG2  VAL  251     8.865  47.699  98.657  1.00 28.76      AAGL
ATOM   1971  C    VAL  251     9.095  50.227 100.278  1.00 26.42      AAGL
ATOM   1972  O    VAL  251     9.177  51.281  99.646  1.00 24.68      AAGL
ATOM   1973  N    SER  252     8.075  49.934 101.083  1.00 27.57      AAGL
ATOM   1974  CA   SER  252     6.962  50.851 101.298  1.00 27.22      AAGL
ATOM   1975  CB   SER  252     5.942  50.722 100.164  1.00 28.72      AAGL
ATOM   1976  OG   SER  252     4.895  51.662 100.327  1.00 28.82      AAGL
ATOM   1977  C    SER  252     6.289  50.558 102.642  1.00 28.31      AAGL
ATOM   1978  O    SER  252     5.858  49.434 102.886  1.00 26.39      AAGL
ATOM   1979  N    CYS  253     6.232  51.559 103.518  1.00 27.82      AAGL
ATOM   1980  CA   CYS  253     5.594  51.413 104.824  1.00 27.19      AAGL
ATOM   1981  C    CYS  253     4.932  52.738 105.201  1.00 28.86      AAGL
ATOM   1982  O    CYS  253     5.411  53.436 106.091  1.00 27.40      AAGL
ATOM   1983  CB   CYS  253     6.611  51.031 105.913  1.00 27.78      AAGL
ATOM   1984  SG   CYS  253     5.803  50.369 107.406  1.00 28.15      AAGL
ATOM   1985  N    PRO  254     3.812  53.089 104.528  1.00 30.47      AAGL
ATOM   1986  CD   PRO  254     3.166  52.222 103.525  1.00 30.66      AAGL
ATOM   1987  CA   PRO  254     3.022  54.314 104.725  1.00 32.44      AAGL
ATOM   1988  CB   PRO  254     1.739  54.023 103.951  1.00 32.43      AAGL
ATOM   1989  CG   PRO  254     2.206  53.171 102.837  1.00 33.11      AAGL
ATOM   1990  C    PRO  254     2.739  54.660 106.181  1.00 34.76      AAGL
ATOM   1991  O    PRO  254     2.780  55.828 106.570  1.00 35.87      AAGL
ATOM   1992  N    ASN  255     2.429  53.653 106.987  1.00 35.37      AAGL
ATOM   1993  CA   ASN  255     2.161  53.912 108.392  1.00 36.89      AAGL
ATOM   1994  CB   ASN  255     0.755  54.457 108.575  1.00 37.41      AAGL
ATOM   1995  CG   ASN  255     0.410  54.682 110.030  1.00 38.46      AAGL
ATOM   1996  OD1  ASN  255     1.254  55.124 110.832  1.00 35.39      AAGL
ATOM   1997  ND2  ASN  255    -0.833  54.389 110.387  1.00 34.81      AAGL
ATOM   1998  C    ASN  255     2.354  52.691 109.263  1.00 35.87      AAGL
```

Fig. 3 cont.

```
ATOM  1999  O    ASN  255      1.471  51.841 109.375  1.00 36.70      AAGL
ATOM  2000  N    PRO  256      3.520  52.601 109.910  1.00 35.76      AAGL
ATOM  2001  CD   PRO  256      4.640  53.550 109.780  1.00 35.85      AAGL
ATOM  2002  CA   PRO  256      3.878  51.493 110.791  1.00 34.93      AAGL
ATOM  2003  CB   PRO  256      5.387  51.654 110.927  1.00 35.60      AAGL
ATOM  2004  CG   PRO  256      5.558  53.122 110.901  1.00 36.37      AAGL
ATOM  2005  C    PRO  256      3.158  51.543 112.140  1.00 34.50      AAGL
ATOM  2006  O    PRO  256      3.041  52.604 112.752  1.00 33.71      AAGL
ATOM  2007  N    ALA  257      2.683  50.393 112.603  1.00 32.93      AAGL
ATOM  2008  CA   ALA  257      1.988  50.327 113.880  1.00 31.85      AAGL
ATOM  2009  CB   ALA  257      1.371  48.946 114.079  1.00 31.01      AAGL
ATOM  2010  C    ALA  257      2.970  50.621 115.000  1.00 32.12      AAGL
ATOM  2011  O    ALA  257      2.591  51.139 116.046  1.00 31.82      AAGL
ATOM  2012  N    TYR  258      4.237  50.291 114.771  1.00 31.15      AAGL
ATOM  2013  CA   TYR  258      5.279  50.504 115.761  1.00 32.72      AAGL
ATOM  2014  CB   TYR  258      5.892  49.168 116.169  1.00 35.88      AAGL
ATOM  2015  CG   TYR  258      4.954  48.226 116.880  1.00 38.05      AAGL
ATOM  2016  CD1  TYR  258      4.136  47.341 116.170  1.00 37.62      AAGL
ATOM  2017  CE1  TYR  258      3.276  46.468 116.840  1.00 40.53      AAGL
ATOM  2018  CD2  TYR  258      4.889  48.216 118.267  1.00 39.82      AAGL
ATOM  2019  CE2  TYR  258      4.039  47.357 118.943  1.00 41.64      AAGL
ATOM  2020  CZ   TYR  258      3.236  46.489 118.232  1.00 42.48      AAGL
ATOM  2021  OH   TYR  258      2.386  45.659 118.934  1.00 45.83      AAGL
ATOM  2022  C    TYR  258      6.414  51.411 115.293  1.00 32.44      AAGL
ATOM  2023  O    TYR  258      6.736  51.468 114.108  1.00 31.27      AAGL
ATOM  2024  N    ALA  259      7.021  52.121 116.237  1.00 30.79      AAGL
ATOM  2025  CA   ALA  259      8.147  52.983 115.919  1.00 31.35      AAGL
ATOM  2026  CB   ALA  259      8.479  53.864 117.118  1.00 33.39      AAGL
ATOM  2027  C    ALA  259      9.315  52.046 115.607  1.00 29.93      AAGL
ATOM  2028  O    ALA  259      9.458  51.004 116.242  1.00 29.16      AAGL
ATOM  2029  N    PHE  260     10.137  52.392 114.623  1.00 29.81      AAGL
ATOM  2030  CA   PHE  260     11.281  51.548 114.285  1.00 29.03      AAGL
ATOM  2031  CB   PHE  260     11.772  51.871 112.867  1.00 28.71      AAGL
ATOM  2032  CG   PHE  260     11.007  51.157 111.776  1.00 29.00      AAGL
ATOM  2033  CD1  PHE  260      9.622  51.242 111.704  1.00 29.61      AAGL
ATOM  2034  CD2  PHE  260     11.676  50.379 110.840  1.00 28.02      AAGL
ATOM  2035  CE1  PHE  260      8.915  50.558 110.720  1.00 30.59      AAGL
ATOM  2036  CE2  PHE  260     10.979  49.694 109.854  1.00 29.46      AAGL
ATOM  2037  CZ   PHE  260      9.594  49.783 109.796  1.00 29.30      AAGL
ATOM  2038  C    PHE  260     12.409  51.765 115.300  1.00 29.23      AAGL
ATOM  2039  O    PHE  260     12.464  52.806 115.957  1.00 29.38      AAGL
ATOM  2040  N    PRO  261     13.302  50.771 115.466  1.00 29.34      AAGL
ATOM  2041  CD   PRO  261     13.247  49.414 114.891  1.00 29.47      AAGL
ATOM  2042  CA   PRO  261     14.418  50.891 116.409  1.00 29.63      AAGL
ATOM  2043  CB   PRO  261     15.194  49.599 116.186  1.00 28.18      AAGL
ATOM  2044  CG   PRO  261     14.096  48.617 115.852  1.00 28.51      AAGL
ATOM  2045  C    PRO  261     15.240  52.137 116.063  1.00 29.95      AAGL
ATOM  2046  O    PRO  261     15.312  52.539 114.897  1.00 30.37      AAGL
ATOM  2047  N    SER  262     15.846  52.736 117.082  1.00 32.41      AAGL
ATOM  2048  CA   SER  262     16.637  53.951 116.922  1.00 31.88      AAGL
ATOM  2049  CB   SER  262     17.167  54.396 118.291  1.00 33.67      AAGL
ATOM  2050  OG   SER  262     17.708  53.295 119.003  1.00 37.49      AAGL
ATOM  2051  C    SER  262     17.785  53.858 115.918  1.00 32.30      AAGL
ATOM  2052  O    SER  262     17.967  54.773 115.107  1.00 32.95      AAGL
ATOM  2053  N    ASP  263     18.565  52.778 115.955  1.00 31.17      AAGL
ATOM  2054  CA   ASP  263     19.660  52.663 115.000  1.00 31.60      AAGL
ATOM  2055  CB   ASP  263     20.768  51.724 115.512  1.00 31.48      AAGL
ATOM  2056  CG   ASP  263     20.241  50.418 116.090  1.00 31.74      AAGL
ATOM  2057  OD1  ASP  263     19.111  49.994 115.748  1.00 30.33      AAGL
ATOM  2058  OD2  ASP  263     20.987  49.796 116.887  1.00 30.41      AAGL
ATOM  2059  C    ASP  263     19.210  52.227 113.604  1.00 31.45      AAGL
ATOM  2060  O    ASP  263     20.036  51.858 112.768  1.00 32.04      AAGL
ATOM  2061  N    LEU  264     17.905  52.296 113.344  1.00 30.59      AAGL
ATOM  2062  CA   LEU  264     17.363  51.920 112.038  1.00 28.75      AAGL
ATOM  2063  CB   LEU  264     16.621  50.575 112.123  1.00 27.83      AAGL
ATOM  2064  CG   LEU  264     17.375  49.323 112.570  1.00 24.26      AAGL
ATOM  2065  CD1  LEU  264     16.389  48.179 112.752  1.00 25.96      AAGL
```

Fig. 3 cont.

```
ATOM  2066  CD2  LEU  264  18.429  48.955  111.552  1.00  27.53      AAGL
ATOM  2067  C    LEU  264  16.391  52.971  111.512  1.00  28.95      AAGL
ATOM  2068  O    LEU  264  15.941  52.893  110.374  1.00  27.43      AAGL
ATOM  2069  N    SER  265  16.074  53.965  112.331  1.00  30.75      AAGL
ATOM  2070  CA   SER  265  15.120  54.986  111.925  1.00  32.24      AAGL
ATOM  2071  CB   SER  265  14.662  55.779  113.154  1.00  33.67      AAGL
ATOM  2072  OG   SER  265  15.763  56.287  113.892  1.00  34.70      AAGL
ATOM  2073  C    SER  265  15.572  55.941  110.815  1.00  33.25      AAGL
ATOM  2074  O    SER  265  14.776  56.742  110.328  1.00  34.94      AAGL
ATOM  2075  N    SER  266  16.832  55.859  110.399  1.00  33.96      AAGL
ATOM  2076  CA   SER  266  17.305  56.745  109.339  1.00  33.28      AAGL
ATOM  2077  CB   SER  266  18.765  57.133  109.576  1.00  34.74      AAGL
ATOM  2078  OG   SER  266  19.652  56.107  109.142  1.00  40.32      AAGL
ATOM  2079  C    SER  266  17.176  56.085  107.964  1.00  31.87      AAGL
ATOM  2080  O    SER  266  17.236  56.754  106.931  1.00  30.82      AAGL
ATOM  2081  N    ILE  267  16.982  54.773  107.956  1.00  28.10      AAGL
ATOM  2082  CA   ILE  267  16.874  54.025  106.713  1.00  26.55      AAGL
ATOM  2083  CB   ILE  267  17.067  52.523  106.983  1.00  25.69      AAGL
ATOM  2084  CG2  ILE  267  17.120  51.757  105.666  1.00  26.74      AAGL
ATOM  2085  CG1  ILE  267  18.349  52.323  107.801  1.00  28.70      AAGL
ATOM  2086  CD1  ILE  267  18.606  50.889  108.250  1.00  27.91      AAGL
ATOM  2087  C    ILE  267  15.537  54.267  106.024  1.00  25.54      AAGL
ATOM  2088  O    ILE  267  14.482  54.060  106.604  1.00  24.26      AAGL
ATOM  2089  N    PRO  268  15.567  54.734  104.767  1.00  25.09      AAGL
ATOM  2090  CD   PRO  268  16.725  55.097  103.932  1.00  26.35      AAGL
ATOM  2091  CA   PRO  268  14.312  54.986  104.058  1.00  25.07      AAGL
ATOM  2092  CB   PRO  268  14.767  55.792  102.844  1.00  26.89      AAGL
ATOM  2093  CG   PRO  268  16.108  55.205  102.560  1.00  26.87      AAGL
ATOM  2094  C    PRO  268  13.602  53.694  103.662  1.00  24.21      AAGL
ATOM  2095  O    PRO  268  14.208  52.622  103.644  1.00  23.10      AAGL
ATOM  2096  N    PHE  269  12.313  53.806  103.362  1.00  23.20      AAGL
ATOM  2097  CA   PHE  269  11.525  52.664  102.931  1.00  23.46      AAGL
ATOM  2098  CB   PHE  269  10.091  52.765  103.446  1.00  24.32      AAGL
ATOM  2099  CG   PHE  269   9.994  52.861  104.942  1.00  24.64      AAGL
ATOM  2100  CD1  PHE  269  10.819  52.093  105.758  1.00  25.88      AAGL
ATOM  2101  CD2  PHE  269   9.070  53.706  105.535  1.00  25.95      AAGL
ATOM  2102  CE1  PHE  269  10.722  52.168  107.151  1.00  26.08      AAGL
ATOM  2103  CE2  PHE  269   8.965  53.788  106.925  1.00  23.79      AAGL
ATOM  2104  CZ   PHE  269   9.793  53.016  107.732  1.00  23.02      AAGL
ATOM  2105  C    PHE  269  11.548  52.698  101.413  1.00  23.22      AAGL
ATOM  2106  O    PHE  269  10.778  53.420  100.774  1.00  23.95      AAGL
ATOM  2107  N    SER  270  12.462  51.916  100.848  1.00  23.29      AAGL
ATOM  2108  CA   SER  270  12.649  51.848   99.410  1.00  24.41      AAGL
ATOM  2109  CB   SER  270  13.282  53.140   98.924  1.00  24.90      AAGL
ATOM  2110  OG   SER  270  14.547  53.300   99.540  1.00  25.23      AAGL
ATOM  2111  C    SER  270  13.596  50.702   99.125  1.00  22.81      AAGL
ATOM  2112  O    SER  270  14.147  50.105  100.055  1.00  25.01      AAGL
ATOM  2113  N    VAL  271  13.791  50.392   97.845  1.00  23.71      AAGL
ATOM  2114  CA   VAL  271  14.702  49.316   97.477  1.00  22.85      AAGL
ATOM  2115  CB   VAL  271  14.846  49.170   95.948  1.00  24.85      AAGL
ATOM  2116  CG1  VAL  271  15.953  48.172   95.630  1.00  23.46      AAGL
ATOM  2117  CG2  VAL  271  13.534  48.698   95.338  1.00  22.67      AAGL
ATOM  2118  C    VAL  271  16.065  49.649   98.056  1.00  24.60      AAGL
ATOM  2119  O    VAL  271  16.744  48.787   98.613  1.00  24.45      AAGL
ATOM  2120  N    ALA  272  16.453  50.914   97.932  1.00  25.33      AAGL
ATOM  2121  CA   ALA  272  17.740  51.373   98.442  1.00  24.59      AAGL
ATOM  2122  CB   ALA  272  17.946  52.858   98.104  1.00  26.33      AAGL
ATOM  2123  C    ALA  272  17.814  51.162   99.951  1.00  21.83      AAGL
ATOM  2124  O    ALA  272  18.839  50.732  100.479  1.00  21.37      AAGL
ATOM  2125  N    GLY  273  16.722  51.463  100.646  1.00  22.29      AAGL
ATOM  2126  CA   GLY  273  16.710  51.284  102.086  1.00  22.02      AAGL
ATOM  2127  C    GLY  273  16.808  49.814  102.448  1.00  21.98      AAGL
ATOM  2128  O    GLY  273  17.427  49.442  103.443  1.00  22.94      AAGL
ATOM  2129  N    GLN  274  16.192  48.973  101.623  1.00  23.13      AAGL
ATOM  2130  CA   GLN  274  16.210  47.534  101.837  1.00  23.82      AAGL
ATOM  2131  CB   GLN  274  15.354  46.862  100.770  1.00  26.47      AAGL
ATOM  2132  CG   GLN  274  14.976  45.429  101.049  1.00  28.49      AAGL
```

Fig. 3 cont.

| | | | | | | | | |
|---|---|---|---|---|---|---|---|---|
| ATOM | 2133 | CD | GLN | 274 | 13.969 | 44.926 | 100.034 | 1.00 29.11 | AAGL |
| ATOM | 2134 | OE1 | GLN | 274 | 14.273 | 44.819 | 98.846 | 1.00 26.58 | AAGL |
| ATOM | 2135 | NE2 | GLN | 274 | 12.760 | 44.630 | 100.491 | 1.00 22.87 | AAGL |
| ATOM | 2136 | C | GLN | 274 | 17.655 | 47.047 | 101.741 | 1.00 24.42 | AAGL |
| ATOM | 2137 | O | GLN | 274 | 18.090 | 46.184 | 102.500 | 1.00 23.54 | AAGL |
| ATOM | 2138 | N | GLN | 275 | 18.405 | 47.621 | 100.807 | 1.00 22.92 | AAGL |
| ATOM | 2139 | CA | GLN | 275 | 19.802 | 47.240 | 100.627 | 1.00 22.23 | AAGL |
| ATOM | 2140 | CB | GLN | 275 | 20.347 | 47.863 | 99.349 | 1.00 25.17 | AAGL |
| ATOM | 2141 | CG | GLN | 275 | 19.668 | 47.370 | 98.089 | 1.00 25.16 | AAGL |
| ATOM | 2142 | CD | GLN | 275 | 20.162 | 48.099 | 96.862 | 1.00 29.65 | AAGL |
| ATOM | 2143 | OE1 | GLN | 275 | 19.879 | 49.283 | 96.677 | 1.00 33.06 | AAGL |
| ATOM | 2144 | NE2 | GLN | 275 | 20.915 | 47.403 | 96.021 | 1.00 30.34 | AAGL |
| ATOM | 2145 | C | GLN | 275 | 20.658 | 47.679 | 101.807 | 1.00 22.46 | AAGL |
| ATOM | 2146 | O | GLN | 275 | 21.492 | 46.924 | 102.289 | 1.00 23.14 | AAGL |
| ATOM | 2147 | N | GLU | 276 | 20.444 | 48.906 | 102.268 | 1.00 23.39 | AAGL |
| ATOM | 2148 | CA | GLU | 276 | 21.203 | 49.448 | 103.386 | 1.00 22.93 | AAGL |
| ATOM | 2149 | CB | GLU | 276 | 20.821 | 50.917 | 103.615 | 1.00 26.77 | AAGL |
| ATOM | 2150 | CG | GLU | 276 | 21.393 | 51.518 | 104.891 | 1.00 31.09 | AAGL |
| ATOM | 2151 | CD | GLU | 276 | 21.007 | 52.982 | 105.081 | 1.00 33.52 | AAGL |
| ATOM | 2152 | OE1 | GLU | 276 | 19.968 | 53.402 | 104.533 | 1.00 35.95 | AAGL |
| ATOM | 2153 | OE2 | GLU | 276 | 21.734 | 53.704 | 105.791 | 1.00 34.45 | AAGL |
| ATOM | 2154 | C | GLU | 276 | 20.948 | 48.620 | 104.643 | 1.00 23.86 | AAGL |
| ATOM | 2155 | O | GLU | 276 | 21.870 | 48.302 | 105.385 | 1.00 22.86 | AAGL |
| ATOM | 2156 | N | PHE | 277 | 19.692 | 48.261 | 104.876 | 1.00 22.41 | AAGL |
| ATOM | 2157 | CA | PHE | 277 | 19.355 | 47.458 | 106.042 | 1.00 21.05 | AAGL |
| ATOM | 2158 | CB | PHE | 277 | 17.844 | 47.222 | 106.120 | 1.00 20.89 | AAGL |
| ATOM | 2159 | CG | PHE | 277 | 17.447 | 46.219 | 107.171 | 1.00 19.02 | AAGL |
| ATOM | 2160 | CD1 | PHE | 277 | 17.541 | 46.533 | 108.518 | 1.00 21.55 | AAGL |
| ATOM | 2161 | CD2 | PHE | 277 | 17.003 | 44.946 | 106.805 | 1.00 22.72 | AAGL |
| ATOM | 2162 | CE1 | PHE | 277 | 17.200 | 45.594 | 109.498 | 1.00 23.87 | AAGL |
| ATOM | 2163 | CE2 | PHE | 277 | 16.660 | 43.998 | 107.781 | 1.00 21.01 | AAGL |
| ATOM | 2164 | CZ | PHE | 277 | 16.759 | 44.323 | 109.122 | 1.00 22.10 | AAGL |
| ATOM | 2165 | C | PHE | 277 | 20.051 | 46.102 | 105.989 | 1.00 20.46 | AAGL |
| ATOM | 2166 | O | PHE | 277 | 20.676 | 45.674 | 106.952 | 1.00 20.12 | AAGL |
| ATOM | 2167 | N | LEU | 278 | 19.928 | 45.421 | 104.856 | 1.00 20.92 | AAGL |
| ATOM | 2168 | CA | LEU | 278 | 20.541 | 44.107 | 104.716 | 1.00 23.04 | AAGL |
| ATOM | 2169 | CB | LEU | 278 | 20.225 | 43.512 | 103.340 | 1.00 24.67 | AAGL |
| ATOM | 2170 | CG | LEU | 278 | 18.764 | 43.076 | 103.160 | 1.00 24.46 | AAGL |
| ATOM | 2171 | CD1 | LEU | 278 | 18.548 | 42.589 | 101.741 | 1.00 26.14 | AAGL |
| ATOM | 2172 | CD2 | LEU | 278 | 18.427 | 41.964 | 104.161 | 1.00 26.55 | AAGL |
| ATOM | 2173 | C | LEU | 278 | 22.040 | 44.144 | 104.947 | 1.00 23.23 | AAGL |
| ATOM | 2174 | O | LEU | 278 | 22.593 | 43.273 | 105.615 | 1.00 20.93 | AAGL |
| ATOM | 2175 | N | GLU | 279 | 22.707 | 45.155 | 104.404 | 1.00 24.22 | AAGL |
| ATOM | 2176 | CA | GLU | 279 | 24.141 | 45.244 | 104.601 | 1.00 25.09 | AAGL |
| ATOM | 2177 | CB | GLU | 279 | 24.735 | 46.309 | 103.682 | 1.00 26.59 | AAGL |
| ATOM | 2178 | CG | GLU | 279 | 24.418 | 46.045 | 102.213 | 1.00 32.07 | AAGL |
| ATOM | 2179 | CD | GLU | 279 | 25.419 | 46.691 | 101.274 | 1.00 37.00 | AAGL |
| ATOM | 2180 | OE1 | GLU | 279 | 25.859 | 47.815 | 101.576 | 1.00 39.68 | AAGL |
| ATOM | 2181 | OE2 | GLU | 279 | 25.756 | 46.078 | 100.235 | 1.00 40.09 | AAGL |
| ATOM | 2182 | C | GLU | 279 | 24.460 | 45.537 | 106.062 | 1.00 23.19 | AAGL |
| ATOM | 2183 | O | GLU | 279 | 25.409 | 44.984 | 106.614 | 1.00 23.97 | AAGL |
| ATOM | 2184 | N | LYS | 280 | 23.669 | 46.391 | 106.701 | 1.00 24.51 | AAGL |
| ATOM | 2185 | CA | LYS | 280 | 23.922 | 46.688 | 108.105 | 1.00 24.24 | AAGL |
| ATOM | 2186 | CB | LYS | 280 | 23.076 | 47.879 | 108.566 | 1.00 25.42 | AAGL |
| ATOM | 2187 | CG | LYS | 280 | 23.535 | 49.186 | 107.912 | 1.00 30.50 | AAGL |
| ATOM | 2188 | CD | LYS | 280 | 22.847 | 50.429 | 108.463 | 1.00 35.06 | AAGL |
| ATOM | 2189 | CE | LYS | 280 | 23.561 | 51.683 | 107.932 | 1.00 38.33 | AAGL |
| ATOM | 2190 | NZ | LYS | 280 | 23.003 | 52.962 | 108.460 | 1.00 39.58 | AAGL |
| ATOM | 2191 | C | LYS | 280 | 23.665 | 45.458 | 108.975 | 1.00 24.77 | AAGL |
| ATOM | 2192 | O | LYS | 280 | 24.382 | 45.219 | 109.949 | 1.00 21.68 | AAGL |
| ATOM | 2193 | N | LEU | 281 | 22.655 | 44.669 | 108.614 | 1.00 23.74 | AAGL |
| ATOM | 2194 | CA | LEU | 281 | 22.351 | 43.449 | 109.365 | 1.00 23.71 | AAGL |
| ATOM | 2195 | CB | LEU | 281 | 21.023 | 42.844 | 108.891 | 1.00 21.53 | AAGL |
| ATOM | 2196 | CG | LEU | 281 | 20.603 | 41.484 | 109.478 | 1.00 21.28 | AAGL |
| ATOM | 2197 | CD1 | LEU | 281 | 20.583 | 41.533 | 110.996 | 1.00 19.24 | AAGL |
| ATOM | 2198 | CD2 | LEU | 281 | 19.226 | 41.109 | 108.937 | 1.00 19.79 | AAGL |
| ATOM | 2199 | C | LEU | 281 | 23.482 | 42.429 | 109.172 | 1.00 22.36 | AAGL |

Fig. 3 cont.

```
ATOM   2200  O    LEU  281      23.940  41.803 110.125  1.00 24.16      AAGL
ATOM   2201  N    ALA  282      23.921  42.267 107.928  1.00 23.73      AAGL
ATOM   2202  CA   ALA  282      24.998  41.339 107.611  1.00 23.94      AAGL
ATOM   2203  CB   ALA  282      25.272  41.356 106.120  1.00 23.77      AAGL
ATOM   2204  C    ALA  282      26.264  41.713 108.382  1.00 24.05      AAGL
ATOM   2205  O    ALA  282      27.060  40.848 108.741  1.00 25.21      AAGL
ATOM   2206  N    ALA  283      26.441  43.005 108.643  1.00 25.21      AAGL
ATOM   2207  CA   ALA  283      27.614  43.477 109.372  1.00 25.75      AAGL
ATOM   2208  CB   ALA  283      27.616  45.005 109.424  1.00 26.48      AAGL
ATOM   2209  C    ALA  283      27.635  42.898 110.786  1.00 26.18      AAGL
ATOM   2210  O    ALA  283      28.658  42.387 111.248  1.00 25.57      AAGL
ATOM   2211  N    VAL  284      26.493  42.963 111.466  1.00 25.74      AAGL
ATOM   2212  CA   VAL  284      26.383  42.438 112.824  1.00 25.11      AAGL
ATOM   2213  CB   VAL  284      24.972  42.711 113.414  1.00 24.63      AAGL
ATOM   2214  CG1  VAL  284      24.806  41.992 114.744  1.00 24.88      AAGL
ATOM   2215  CG2  VAL  284      24.779  44.220 113.606  1.00 27.53      AAGL
ATOM   2216  C    VAL  284      26.658  40.941 112.857  1.00 23.65      AAGL
ATOM   2217  O    VAL  284      27.416  40.456 113.694  1.00 23.12      AAGL
ATOM   2218  N    VAL  285      26.052  40.209 111.930  1.00 25.11      AAGL
ATOM   2219  CA   VAL  285      26.236  38.769 111.881  1.00 23.69      AAGL
ATOM   2220  CB   VAL  285      25.302  38.135 110.839  1.00 24.54      AAGL
ATOM   2221  CG1  VAL  285      25.490  36.626 110.822  1.00 25.86      AAGL
ATOM   2222  CG2  VAL  285      23.855  38.490 111.171  1.00 26.53      AAGL
ATOM   2223  C    VAL  285      27.679  38.406 111.559  1.00 26.05      AAGL
ATOM   2224  O    VAL  285      28.256  37.514 112.179  1.00 25.09      AAGL
ATOM   2225  N    GLU  286      28.259  39.101 110.587  1.00 24.87      AAGL
ATOM   2226  CA   GLU  286      29.639  38.847 110.201  1.00 26.91      AAGL
ATOM   2227  CB   GLU  286      30.041  39.737 109.025  1.00 29.06      AAGL
ATOM   2228  CG   GLU  286      31.518  39.586 108.629  1.00 32.60      AAGL
ATOM   2229  CD   GLU  286      31.812  38.250 107.971  1.00 35.44      AAGL
ATOM   2230  OE1  GLU  286      31.578  38.120 106.751  1.00 36.64      AAGL
ATOM   2231  OE2  GLU  286      32.264  37.322 108.672  1.00 35.13      AAGL
ATOM   2232  C    GLU  286      30.587  39.110 111.367  1.00 26.68      AAGL
ATOM   2233  O    GLU  286      31.528  38.354 111.590  1.00 27.24      AAGL
ATOM   2234  N    ALA  287      30.343  40.181 112.111  1.00 25.24      AAGL
ATOM   2235  CA   ALA  287      31.211  40.522 113.230  1.00 27.43      AAGL
ATOM   2236  CB   ALA  287      31.032  41.990 113.600  1.00 27.81      AAGL
ATOM   2237  C    ALA  287      31.003  39.650 114.465  1.00 29.71      AAGL
ATOM   2238  O    ALA  287      31.726  39.795 115.451  1.00 31.32      AAGL
ATOM   2239  N    THR  288      30.024  38.749 114.415  1.00 28.83      AAGL
ATOM   2240  CA   THR  288      29.744  37.871 115.549  1.00 29.55      AAGL
ATOM   2241  CB   THR  288      28.242  37.499 115.618  1.00 28.36      AAGL
ATOM   2242  OG1  THR  288      27.444  38.680 115.459  1.00 29.45      AAGL
ATOM   2243  CG2  THR  288      27.921  36.854 116.962  1.00 31.36      AAGL
ATOM   2244  C    THR  288      30.533  36.577 115.393  1.00 27.55      AAGL
ATOM   2245  O    THR  288      30.708  36.094 114.280  1.00 27.21      AAGL
ATOM   2246  N    THR  289      31.006  36.015 116.504  1.00 30.08      AAGL
ATOM   2247  CA   THR  289      31.757  34.770 116.437  1.00 31.68      AAGL
ATOM   2248  CB   THR  289      32.352  34.384 117.806  1.00 34.06      AAGL
ATOM   2249  OG1  THR  289      33.186  35.449 118.291  1.00 35.86      AAGL
ATOM   2250  CG2  THR  289      33.186  33.128 117.673  1.00 34.89      AAGL
ATOM   2251  C    THR  289      30.817  33.659 115.964  1.00 33.04      AAGL
ATOM   2252  O    THR  289      29.842  33.332 116.632  1.00 34.14      AAGL
ATOM   2253  N    ASP  290      31.120  33.085 114.807  1.00 33.28      AAGL
ATOM   2254  CA   ASP  290      30.298  32.030 114.211  1.00 32.82      AAGL
ATOM   2255  CB   ASP  290      30.183  30.812 115.137  1.00 33.97      AAGL
ATOM   2256  CG   ASP  290      31.397  29.900 115.054  1.00 38.26      AAGL
ATOM   2257  OD1  ASP  290      32.093  29.921 114.006  1.00 38.79      AAGL
ATOM   2258  OD2  ASP  290      31.651  29.152 116.024  1.00 38.34      AAGL
ATOM   2259  C    ASP  290      28.903  32.495 113.793  1.00 30.86      AAGL
ATOM   2260  O    ASP  290      27.909  31.781 113.979  1.00 31.04      AAGL
ATOM   2261  N    GLY  291      28.841  33.705 113.246  1.00 30.92      AAGL
ATOM   2262  CA   GLY  291      27.590  34.240 112.740  1.00 28.36      AAGL
ATOM   2263  C    GLY  291      27.579  33.689 111.331  1.00 28.69      AAGL
ATOM   2264  O    GLY  291      28.358  34.133 110.487  1.00 29.95      AAGL
ATOM   2265  N    LEU  292      26.702  32.726 111.065  1.00 25.52      AAGL
ATOM   2266  CA   LEU  292      26.662  32.072 109.767  1.00 25.89      AAGL
```

Fig. 3 cont.

```
ATOM   2267  CB   LEU   292      26.184  30.632 109.940  1.00 25.46      AAGL
ATOM   2268  CG   LEU   292      27.072  29.798 110.858  1.00 26.52      AAGL
ATOM   2269  CD1  LEU   292      26.632  28.354 110.807  1.00 26.92      AAGL
ATOM   2270  CD2  LEU   292      28.526  29.929 110.418  1.00 27.08      AAGL
ATOM   2271  C    LEU   292      25.908  32.700 108.613  1.00 25.35      AAGL
ATOM   2272  O    LEU   292      26.298  32.528 107.459  1.00 25.52      AAGL
ATOM   2273  N    GLY   293      24.824  33.413 108.887  1.00 25.75      AAGL
ATOM   2274  CA   GLY   293      24.118  33.990 107.769  1.00 22.89      AAGL
ATOM   2275  C    GLY   293      22.785  34.642 108.043  1.00 23.42      AAGL
ATOM   2276  O    GLY   293      22.366  34.828 109.187  1.00 21.61      AAGL
ATOM   2277  N    VAL   294      22.123  34.984 106.950  1.00 21.14      AAGL
ATOM   2278  CA   VAL   294      20.841  35.647 107.003  1.00 22.60      AAGL
ATOM   2279  CB   VAL   294      21.013  37.164 106.775  1.00 24.33      AAGL
ATOM   2280  CG1  VAL   294      19.657  37.818 106.538  1.00 25.68      AAGL
ATOM   2281  CG2  VAL   294      21.719  37.789 107.969  1.00 23.35      AAGL
ATOM   2282  C    VAL   294      19.926  35.094 105.932  1.00 23.50      AAGL
ATOM   2283  O    VAL   294      20.351  34.867 104.799  1.00 22.80      AAGL
ATOM   2284  N    TYR   295      18.668  34.871 106.293  1.00 21.62      AAGL
ATOM   2285  CA   TYR   295      17.684  34.387 105.338  1.00 20.32      AAGL
ATOM   2286  CB   TYR   295      17.105  33.035 105.761  1.00 20.96      AAGL
ATOM   2287  CG   TYR   295      18.040  31.862 105.606  1.00 21.66      AAGL
ATOM   2288  CD1  TYR   295      19.124  31.692 106.461  1.00 20.77      AAGL
ATOM   2289  CE1  TYR   295      19.974  30.584 106.337  1.00 22.52      AAGL
ATOM   2290  CD2  TYR   295      17.820  30.904 104.617  1.00 21.20      AAGL
ATOM   2291  CE2  TYR   295      18.658  29.798 104.481  1.00 22.01      AAGL
ATOM   2292  CZ   TYR   295      19.732  29.640 105.341  1.00 22.76      AAGL
ATOM   2293  OH   TYR   295      20.564  28.543 105.211  1.00 23.00      AAGL
ATOM   2294  C    TYR   295      16.554  35.399 105.295  1.00 21.79      AAGL
ATOM   2295  O    TYR   295      15.933  35.672 106.325  1.00 20.79      AAGL
ATOM   2296  N    TYR   296      16.296  35.966 104.118  1.00 20.08      AAGL
ATOM   2297  CA   TYR   296      15.212  36.927 103.975  1.00 19.64      AAGL
ATOM   2298  CB   TYR   296      15.328  37.704 102.666  1.00 20.69      AAGL
ATOM   2299  CG   TYR   296      14.503  38.972 102.656  1.00 19.70      AAGL
ATOM   2300  CD1  TYR   296      15.005  40.152 103.194  1.00 21.48      AAGL
ATOM   2301  CE1  TYR   296      14.236  41.310 103.232  1.00 21.48      AAGL
ATOM   2302  CD2  TYR   296      13.203  38.980 102.147  1.00 19.37      AAGL
ATOM   2303  CE2  TYR   296      12.423  40.138 102.182  1.00 21.23      AAGL
ATOM   2304  CZ   TYR   296      12.948  41.295 102.729  1.00 20.28      AAGL
ATOM   2305  OH   TYR   296      12.177  42.427 102.797  1.00 19.16      AAGL
ATOM   2306  C    TYR   296      13.947  36.090 103.939  1.00 20.23      AAGL
ATOM   2307  O    TYR   296      13.945  35.010 103.359  1.00 22.11      AAGL
ATOM   2308  N    TRP   297      12.868  36.578 104.538  1.00 17.43      AAGL
ATOM   2309  CA   TRP   297      11.641  35.795 104.553  1.00 17.69      AAGL
ATOM   2310  CB   TRP   297      10.942  35.894 105.920  1.00 19.08      AAGL
ATOM   2311  CG   TRP   297       9.854  34.864 106.075  1.00 19.30      AAGL
ATOM   2312  CD2  TRP   297       8.440  35.098 106.104  1.00 19.62      AAGL
ATOM   2313  CE2  TRP   297       7.808  33.837 106.201  1.00 20.98      AAGL
ATOM   2314  CE3  TRP   297       7.644  36.250 106.057  1.00 21.65      AAGL
ATOM   2315  CD1  TRP   297      10.018  33.511 106.155  1.00 21.34      AAGL
ATOM   2316  NE1  TRP   297       8.793  32.885 106.231  1.00 21.42      AAGL
ATOM   2317  CZ2  TRP   297       6.418  33.696 106.251  1.00 19.44      AAGL
ATOM   2318  CZ3  TRP   297       6.257  36.109 106.106  1.00 24.11      AAGL
ATOM   2319  CH2  TRP   297       5.661  34.836 106.201  1.00 22.67      AAGL
ATOM   2320  C    TRP   297      10.647  36.175 103.464  1.00 18.74      AAGL
ATOM   2321  O    TRP   297      10.158  37.305 103.428  1.00 17.76      AAGL
ATOM   2322  N    GLU   298      10.357  35.214 102.584  1.00 18.51      AAGL
ATOM   2323  CA   GLU   298       9.391  35.390 101.505  1.00 18.03      AAGL
ATOM   2324  CB   GLU   298       7.976  35.340 102.084  1.00 19.76      AAGL
ATOM   2325  CG   GLU   298       7.562  33.964 102.582  1.00 19.56      AAGL
ATOM   2326  CD   GLU   298       7.283  32.996 101.447  1.00 20.53      AAGL
ATOM   2327  OE1  GLU   298       7.320  33.422 100.274  1.00 21.41      AAGL
ATOM   2328  OE2  GLU   298       7.016  31.811 101.733  1.00 22.59      AAGL
ATOM   2329  C    GLU   298       9.553  36.664 100.668  1.00 20.54      AAGL
ATOM   2330  O    GLU   298       8.636  37.482 100.569  1.00 21.31      AAGL
ATOM   2331  N    PRO   299      10.715  36.832 100.025  1.00 21.16      AAGL
ATOM   2332  CD   PRO   299      11.893  35.949 100.046  1.00 20.70      AAGL
ATOM   2333  CA   PRO   299      10.964  38.022  99.203  1.00 21.46      AAGL
```

Fig. 3 cont.

| | | | | | | | | | |
|---|---|---|---|---|---|---|---|---|---|
| ATOM | 2334 | CB | PRO | 299 | 12.455 | 37.913 | 98.897 | 1.00 22.49 | AAGL |
| ATOM | 2335 | CG | PRO | 299 | 12.658 | 36.429 | 98.826 | 1.00 23.37 | AAGL |
| ATOM | 2336 | C | PRO | 299 | 10.133 | 38.131 | 97.924 | 1.00 21.34 | AAGL |
| ATOM | 2337 | O | PRO | 299 | 10.051 | 39.203 | 97.329 | 1.00 25.08 | AAGL |
| ATOM | 2338 | N | ALA | 300 | 9.515 | 37.031 | 97.507 | 1.00 21.73 | AAGL |
| ATOM | 2339 | CA | ALA | 300 | 8.751 | 37.021 | 96.264 | 1.00 23.94 | AAGL |
| ATOM | 2340 | CB | ALA | 300 | 9.418 | 36.071 | 95.272 | 1.00 23.80 | AAGL |
| ATOM | 2341 | C | ALA | 300 | 7.280 | 36.663 | 96.386 | 1.00 23.97 | AAGL |
| ATOM | 2342 | O | ALA | 300 | 6.663 | 36.277 | 95.394 | 1.00 24.57 | AAGL |
| ATOM | 2343 | N | TRP | 301 | 6.707 | 36.802 | 97.579 | 1.00 25.04 | AAGL |
| ATOM | 2344 | CA | TRP | 301 | 5.301 | 36.454 | 97.775 | 1.00 24.04 | AAGL |
| ATOM | 2345 | CB | TRP | 301 | 5.007 | 36.244 | 99.266 | 1.00 25.15 | AAGL |
| ATOM | 2346 | CG | TRP | 301 | 3.744 | 35.459 | 99.531 | 1.00 23.59 | AAGL |
| ATOM | 2347 | CD2 | TRP | 301 | 3.394 | 34.781 | 100.744 | 1.00 23.73 | AAGL |
| ATOM | 2348 | CE2 | TRP | 301 | 2.119 | 34.200 | 100.548 | 1.00 23.63 | AAGL |
| ATOM | 2349 | CE3 | TRP | 301 | 4.033 | 34.607 | 101.980 | 1.00 24.03 | AAGL |
| ATOM | 2350 | CD1 | TRP | 301 | 2.697 | 35.267 | 98.673 | 1.00 23.60 | AAGL |
| ATOM | 2351 | NE1 | TRP | 301 | 1.717 | 34.513 | 99.278 | 1.00 24.88 | AAGL |
| ATOM | 2352 | CZ2 | TRP | 301 | 1.470 | 33.458 | 101.544 | 1.00 22.63 | AAGL |
| ATOM | 2353 | CZ3 | TRP | 301 | 3.387 | 33.871 | 102.969 | 1.00 22.92 | AAGL |
| ATOM | 2354 | CH2 | TRP | 301 | 2.119 | 33.306 | 102.741 | 1.00 21.62 | AAGL |
| ATOM | 2355 | C | TRP | 301 | 4.322 | 37.485 | 97.213 | 1.00 25.72 | AAGL |
| ATOM | 2356 | O | TRP | 301 | 3.682 | 38.220 | 97.968 | 1.00 24.12 | AAGL |
| ATOM | 2357 | N | ILE | 302 | 4.192 | 37.532 | 95.889 | 1.00 26.27 | AAGL |
| ATOM | 2358 | CA | ILE | 302 | 3.273 | 38.475 | 95.256 | 1.00 26.33 | AAGL |
| ATOM | 2359 | CB | ILE | 302 | 3.257 | 38.317 | 93.722 | 1.00 28.94 | AAGL |
| ATOM | 2360 | CG2 | ILE | 302 | 2.804 | 39.615 | 93.081 | 1.00 30.12 | AAGL |
| ATOM | 2361 | CG1 | ILE | 302 | 4.653 | 37.963 | 93.215 | 1.00 32.05 | AAGL |
| ATOM | 2362 | CD1 | ILE | 302 | 5.671 | 39.038 | 93.462 | 1.00 33.22 | AAGL |
| ATOM | 2363 | C | ILE | 302 | 1.872 | 38.180 | 95.770 | 1.00 24.91 | AAGL |
| ATOM | 2364 | O | ILE | 302 | 1.467 | 37.017 | 95.840 | 1.00 26.39 | AAGL |
| ATOM | 2365 | N | GLY | 303 | 1.134 | 39.223 | 96.133 | 1.00 25.25 | AAGL |
| ATOM | 2366 | CA | GLY | 303 | -0.210 | 39.018 | 96.646 | 1.00 27.25 | AAGL |
| ATOM | 2367 | C | GLY | 303 | -0.298 | 39.086 | 98.159 | 1.00 26.83 | AAGL |
| ATOM | 2368 | O | GLY | 303 | -1.394 | 39.110 | 98.728 | 1.00 27.53 | AAGL |
| ATOM | 2369 | N | ASN | 304 | 0.861 | 39.090 | 98.812 | 1.00 25.82 | AAGL |
| ATOM | 2370 | CA | ASN | 304 | 0.958 | 39.182 | 100.267 | 1.00 23.80 | AAGL |
| ATOM | 2371 | CB | ASN | 304 | 1.113 | 37.783 | 100.887 | 1.00 22.97 | AAGL |
| ATOM | 2372 | CG | ASN | 304 | 1.131 | 37.811 | 102.413 | 1.00 23.62 | AAGL |
| ATOM | 2373 | OD1 | ASN | 304 | 0.494 | 38.663 | 103.038 | 1.00 25.26 | AAGL |
| ATOM | 2374 | ND2 | ASN | 304 | 1.841 | 36.864 | 103.017 | 1.00 20.66 | AAGL |
| ATOM | 2375 | C | ASN | 304 | 2.200 | 40.031 | 100.539 | 1.00 22.75 | AAGL |
| ATOM | 2376 | O | ASN | 304 | 3.030 | 39.704 | 101.382 | 1.00 21.47 | AAGL |
| ATOM | 2377 | N | ALA | 305 | 2.306 | 41.139 | 99.812 | 1.00 23.77 | AAGL |
| ATOM | 2378 | CA | ALA | 305 | 3.454 | 42.028 | 99.926 | 1.00 23.13 | AAGL |
| ATOM | 2379 | CB | ALA | 305 | 3.281 | 43.211 | 98.980 | 1.00 25.11 | AAGL |
| ATOM | 2380 | C | ALA | 305 | 3.770 | 42.520 | 101.335 | 1.00 22.70 | AAGL |
| ATOM | 2381 | O | ALA | 305 | 4.928 | 42.784 | 101.650 | 1.00 23.39 | AAGL |
| ATOM | 2382 | N | GLY | 306 | 2.753 | 42.632 | 102.182 | 1.00 23.04 | AAGL |
| ATOM | 2383 | CA | GLY | 306 | 2.970 | 43.093 | 103.543 | 1.00 21.61 | AAGL |
| ATOM | 2384 | C | GLY | 306 | 3.592 | 42.023 | 104.421 | 1.00 20.83 | AAGL |
| ATOM | 2385 | O | GLY | 306 | 4.185 | 42.323 | 105.461 | 1.00 20.31 | AAGL |
| ATOM | 2386 | N | LEU | 307 | 3.445 | 40.771 | 103.997 | 1.00 20.88 | AAGL |
| ATOM | 2387 | CA | LEU | 307 | 3.980 | 39.615 | 104.710 | 1.00 19.63 | AAGL |
| ATOM | 2388 | CB | LEU | 307 | 5.511 | 39.575 | 104.599 | 1.00 19.26 | AAGL |
| ATOM | 2389 | CG | LEU | 307 | 6.089 | 39.333 | 103.198 | 1.00 17.07 | AAGL |
| ATOM | 2390 | CD1 | LEU | 307 | 7.602 | 39.293 | 103.292 | 1.00 21.74 | AAGL |
| ATOM | 2391 | CD2 | LEU | 307 | 5.568 | 38.012 | 102.625 | 1.00 18.50 | AAGL |
| ATOM | 2392 | C | LEU | 307 | 3.580 | 39.543 | 106.178 | 1.00 20.69 | AAGL |
| ATOM | 2393 | O | LEU | 307 | 4.377 | 39.131 | 107.018 | 1.00 20.88 | AAGL |
| ATOM | 2394 | N | GLY | 308 | 2.352 | 39.955 | 106.484 | 1.00 19.76 | AAGL |
| ATOM | 2395 | CA | GLY | 308 | 1.870 | 39.898 | 107.854 | 1.00 22.38 | AAGL |
| ATOM | 2396 | C | GLY | 308 | 2.188 | 41.068 | 108.769 | 1.00 23.64 | AAGL |
| ATOM | 2397 | O | GLY | 308 | 1.785 | 41.072 | 109.938 | 1.00 23.65 | AAGL |
| ATOM | 2398 | N | SER | 309 | 2.907 | 42.060 | 108.252 | 1.00 23.88 | AAGL |
| ATOM | 2399 | CA | SER | 309 | 3.275 | 43.227 | 109.045 | 1.00 22.50 | AAGL |
| ATOM | 2400 | CB | SER | 309 | 4.693 | 43.684 | 108.695 | 1.00 22.00 | AAGL |

Fig. 3 cont.

| | | | | | | | | | |
|---|---|---|---|---|---|---|---|---|---|
| ATOM | 2401 | OG | SER | 309 | 4.719 | 44.264 | 107.407 | 1.00 20.09 | AAGL |
| ATOM | 2402 | C | SER | 309 | 2.312 | 44.385 | 108.790 | 1.00 23.02 | AAGL |
| ATOM | 2403 | O | SER | 309 | 1.388 | 44.271 | 107.983 | 1.00 23.42 | AAGL |
| ATOM | 2404 | N | SER | 310 | 2.539 | 45.494 | 109.486 | 1.00 20.79 | AAGL |
| ATOM | 2405 | CA | SER | 310 | 1.707 | 46.684 | 109.316 | 1.00 23.22 | AAGL |
| ATOM | 2406 | CB | SER | 310 | 1.715 | 47.535 | 110.592 | 1.00 22.59 | AAGL |
| ATOM | 2407 | OG | SER | 310 | 3.022 | 48.003 | 110.903 | 1.00 24.03 | AAGL |
| ATOM | 2408 | C | SER | 310 | 2.234 | 47.512 | 108.138 | 1.00 23.44 | AAGL |
| ATOM | 2409 | O | SER | 310 | 1.658 | 48.545 | 107.773 | 1.00 23.68 | AAGL |
| ATOM | 2410 | N | CYS | 311 | 3.340 | 47.069 | 107.548 | 1.00 21.68 | AAGL |
| ATOM | 2411 | CA | CYS | 311 | 3.892 | 47.788 | 106.413 | 1.00 23.63 | AAGL |
| ATOM | 2412 | C | CYS | 311 | 3.210 | 47.381 | 105.123 | 1.00 24.17 | AAGL |
| ATOM | 2413 | O | CYS | 311 | 2.591 | 46.321 | 105.044 | 1.00 26.98 | AAGL |
| ATOM | 2414 | CB | CYS | 311 | 5.387 | 47.545 | 106.289 | 1.00 25.30 | AAGL |
| ATOM | 2415 | SG | CYS | 311 | 6.407 | 48.425 | 107.501 | 1.00 27.01 | AAGL |
| ATOM | 2416 | N | ALA | 312 | 3.343 | 48.219 | 104.104 | 1.00 23.57 | AAGL |
| ATOM | 2417 | CA | ALA | 312 | 2.707 | 47.954 | 102.821 | 1.00 25.20 | AAGL |
| ATOM | 2418 | CB | ALA | 312 | 2.516 | 49.266 | 102.053 | 1.00 25.76 | AAGL |
| ATOM | 2419 | C | ALA | 312 | 3.400 | 46.950 | 101.919 | 1.00 25.50 | AAGL |
| ATOM | 2420 | O | ALA | 312 | 2.741 | 46.128 | 101.288 | 1.00 24.61 | AAGL |
| ATOM | 2421 | N | ASP | 313 | 4.726 | 47.003 | 101.858 | 1.00 25.50 | AAGL |
| ATOM | 2422 | CA | ASP | 313 | 5.444 | 46.122 | 100.949 | 1.00 25.55 | AAGL |
| ATOM | 2423 | CB | ASP | 313 | 5.560 | 46.827 | 99.596 | 1.00 28.83 | AAGL |
| ATOM | 2424 | CG | ASP | 313 | 5.870 | 45.886 | 98.471 | 1.00 31.63 | AAGL |
| ATOM | 2425 | OD1 | ASP | 313 | 6.652 | 44.940 | 98.680 | 1.00 29.42 | AAGL |
| ATOM | 2426 | OD2 | ASP | 313 | 5.337 | 46.107 | 97.358 | 1.00 37.09 | AAGL |
| ATOM | 2427 | C | ASP | 313 | 6.836 | 45.752 | 101.440 | 1.00 25.26 | AAGL |
| ATOM | 2428 | O | ASP | 313 | 7.698 | 46.620 | 101.575 | 1.00 25.34 | AAGL |
| ATOM | 2429 | N | ASN | 314 | 7.049 | 44.460 | 101.685 | 1.00 22.30 | AAGL |
| ATOM | 2430 | CA | ASN | 314 | 8.335 | 43.956 | 102.157 | 1.00 21.78 | AAGL |
| ATOM | 2431 | CB | ASN | 314 | 8.156 | 43.167 | 103.458 | 1.00 23.69 | AAGL |
| ATOM | 2432 | CG | ASN | 314 | 7.832 | 44.056 | 104.640 | 1.00 25.29 | AAGL |
| ATOM | 2433 | OD1 | ASN | 314 | 8.520 | 45.039 | 104.883 | 1.00 28.43 | AAGL |
| ATOM | 2434 | ND2 | ASN | 314 | 6.787 | 43.710 | 105.382 | 1.00 24.92 | AAGL |
| ATOM | 2435 | C | ASN | 314 | 8.999 | 43.053 | 101.127 | 1.00 22.83 | AAGL |
| ATOM | 2436 | O | ASN | 314 | 10.043 | 42.469 | 101.393 | 1.00 21.72 | AAGL |
| ATOM | 2437 | N | LEU | 315 | 8.388 | 42.942 | 99.955 | 1.00 22.78 | AAGL |
| ATOM | 2438 | CA | LEU | 315 | 8.919 | 42.086 | 98.907 | 1.00 22.99 | AAGL |
| ATOM | 2439 | CB | LEU | 315 | 7.879 | 41.913 | 97.796 | 1.00 22.49 | AAGL |
| ATOM | 2440 | CG | LEU | 315 | 6.491 | 41.421 | 98.219 | 1.00 22.62 | AAGL |
| ATOM | 2441 | CD1 | LEU | 315 | 5.599 | 41.214 | 96.991 | 1.00 25.48 | AAGL |
| ATOM | 2442 | CD2 | LEU | 315 | 6.638 | 40.117 | 98.978 | 1.00 23.90 | AAGL |
| ATOM | 2443 | C | LEU | 315 | 10.219 | 42.604 | 98.310 | 1.00 24.65 | AAGL |
| ATOM | 2444 | O | LEU | 315 | 10.608 | 43.756 | 98.523 | 1.00 24.23 | AAGL |
| ATOM | 2445 | N | MET | 316 | 10.898 | 41.728 | 97.576 | 1.00 25.62 | AAGL |
| ATOM | 2446 | CA | MET | 316 | 12.135 | 42.088 | 96.901 | 1.00 28.28 | AAGL |
| ATOM | 2447 | CB | MET | 316 | 13.280 | 41.159 | 97.321 | 1.00 26.81 | AAGL |
| ATOM | 2448 | CG | MET | 316 | 13.718 | 41.299 | 98.777 | 1.00 27.89 | AAGL |
| ATOM | 2449 | SD | MET | 316 | 15.182 | 40.302 | 99.187 | 1.00 29.46 | AAGL |
| ATOM | 2450 | CE | MET | 316 | 16.470 | 41.485 | 98.890 | 1.00 29.41 | AAGL |
| ATOM | 2451 | C | MET | 316 | 11.889 | 41.977 | 95.393 | 1.00 29.33 | AAGL |
| ATOM | 2452 | O | MET | 316 | 12.824 | 41.939 | 94.599 | 1.00 29.21 | AAGL |
| ATOM | 2453 | N | VAL | 317 | 10.616 | 41.910 | 95.015 | 1.00 30.78 | AAGL |
| ATOM | 2454 | CA | VAL | 317 | 10.217 | 41.820 | 93.614 | 1.00 32.20 | AAGL |
| ATOM | 2455 | CB | VAL | 317 | 9.681 | 40.416 | 93.263 | 1.00 31.88 | AAGL |
| ATOM | 2456 | CG1 | VAL | 317 | 10.763 | 39.374 | 93.477 | 1.00 33.90 | AAGL |
| ATOM | 2457 | CG2 | VAL | 317 | 8.479 | 40.100 | 94.128 | 1.00 36.43 | AAGL |
| ATOM | 2458 | C | VAL | 317 | 9.113 | 42.836 | 93.346 | 1.00 33.46 | AAGL |
| ATOM | 2459 | O | VAL | 317 | 8.342 | 43.169 | 94.246 | 1.00 30.98 | AAGL |
| ATOM | 2460 | N | ASP | 318 | 9.041 | 43.333 | 92.113 | 1.00 33.99 | AAGL |
| ATOM | 2461 | CA | ASP | 318 | 8.015 | 44.309 | 91.760 | 1.00 38.16 | AAGL |
| ATOM | 2462 | CB | ASP | 318 | 8.405 | 45.073 | 90.493 | 1.00 39.54 | AAGL |
| ATOM | 2463 | CG | ASP | 318 | 7.502 | 46.252 | 90.240 | 1.00 38.96 | AAGL |
| ATOM | 2464 | OD1 | ASP | 318 | 6.267 | 46.066 | 90.216 | 1.00 40.93 | AAGL |
| ATOM | 2465 | OD2 | ASP | 318 | 8.022 | 47.370 | 90.058 | 1.00 42.03 | AAGL |
| ATOM | 2466 | C | ASP | 318 | 6.671 | 43.621 | 91.547 | 1.00 41.03 | AAGL |
| ATOM | 2467 | O | ASP | 318 | 6.512 | 42.800 | 90.642 | 1.00 41.02 | AAGL |

Fig. 3 cont.

```
ATOM   2468  N    TYR   319       5.695  43.985  92.373  1.00  43.91      AAGL
ATOM   2469  CA   TYR   319       4.370  43.388  92.312  1.00  46.99      AAGL
ATOM   2470  CB   TYR   319       3.555  43.811  93.548  1.00  48.59      AAGL
ATOM   2471  CG   TYR   319       3.003  45.224  93.516  1.00  48.66      AAGL
ATOM   2472  CD1  TYR   319       1.702  45.475  93.080  1.00  49.01      AAGL
ATOM   2473  CE1  TYR   319       1.180  46.778  93.066  1.00  49.49      AAGL
ATOM   2474  CD2  TYR   319       3.772  46.305  93.937  1.00  49.12      AAGL
ATOM   2475  CE2  TYR   319       3.264  47.610  93.929  1.00  49.13      AAGL
ATOM   2476  CZ   TYR   319       1.967  47.836  93.493  1.00  49.15      AAGL
ATOM   2477  OH   TYR   319       1.457  49.115  93.495  1.00  48.83      AAGL
ATOM   2478  C    TYR   319       3.602  43.705  91.034  1.00  49.01      AAGL
ATOM   2479  O    TYR   319       2.479  43.221  90.840  1.00  51.46      AAGL
ATOM   2480  N    THR   320       4.178  44.522  90.158  1.00  48.98      AAGL
ATOM   2481  CA   THR   320       3.491  44.827  88.909  1.00  48.98      AAGL
ATOM   2482  CB   THR   320       3.383  46.349  88.642  1.00  48.87      AAGL
ATOM   2483  OG1  THR   320       4.681  46.899  88.371  1.00  48.24      AAGL
ATOM   2484  CG2  THR   320       2.770  47.054  89.829  1.00  48.99      AAGL
ATOM   2485  C    THR   320       4.206  44.184  87.730  1.00  49.75      AAGL
ATOM   2486  O    THR   320       3.572  43.536  86.896  1.00  50.61      AAGL
ATOM   2487  N    THR   321       5.524  44.349  87.671  1.00  49.77      AAGL
ATOM   2488  CA   THR   321       6.316  43.798  86.575  1.00  50.22      AAGL
ATOM   2489  CB   THR   321       7.561  44.673  86.297  1.00  50.80      AAGL
ATOM   2490  OG1  THR   321       8.505  44.522  87.368  1.00  51.66      AAGL
ATOM   2491  CG2  THR   321       7.168  46.144  86.193  1.00  51.57      AAGL
ATOM   2492  C    THR   321       6.805  42.371  86.807  1.00  50.00      AAGL
ATOM   2493  O    THR   321       7.360  41.743  85.905  1.00  50.77      AAGL
ATOM   2494  N    ASP   322       6.617  41.859  88.016  1.00  49.25      AAGL
ATOM   2495  CA   ASP   322       7.082  40.515  88.345  1.00  47.20      AAGL
ATOM   2496  CB   ASP   322       6.534  39.471  87.354  1.00  50.64      AAGL
ATOM   2497  CG   ASP   322       5.010  39.462  87.262  1.00  52.01      AAGL
ATOM   2498  OD1  ASP   322       4.313  39.445  88.309  1.00  52.82      AAGL
ATOM   2499  OD2  ASP   322       4.502  39.442  86.113  1.00  55.12      AAGL
ATOM   2500  C    ASP   322       8.616  40.486  88.288  1.00  44.47      AAGL
ATOM   2501  O    ASP   322       9.231  39.416  88.385  1.00  44.83      AAGL
ATOM   2502  N    GLU   323       9.236  41.652  88.124  1.00  41.39      AAGL
ATOM   2503  CA   GLU   323      10.696  41.745  88.049  1.00  39.30      AAGL
ATOM   2504  CB   GLU   323      11.093  42.894  87.127  1.00  41.31      AAGL
ATOM   2505  CG   GLU   323      12.586  43.108  86.977  1.00  44.75      AAGL
ATOM   2506  CD   GLU   323      12.911  44.040  85.812  1.00  47.16      AAGL
ATOM   2507  OE1  GLU   323      14.099  44.371  85.612  1.00  47.71      AAGL
ATOM   2508  OE2  GLU   323      11.971  44.438  85.091  1.00  47.99      AAGL
ATOM   2509  C    GLU   323      11.346  41.939  89.420  1.00  36.82      AAGL
ATOM   2510  O    GLU   323      10.898  42.761  90.220  1.00  35.46      AAGL
ATOM   2511  N    VAL   324      12.410  41.182  89.675  1.00  35.31      AAGL
ATOM   2512  CA   VAL   324      13.120  41.257  90.948  1.00  32.93      AAGL
ATOM   2513  CB   VAL   324      14.154  40.103  91.099  1.00  33.31      AAGL
ATOM   2514  CG1  VAL   324      13.487  38.770  90.827  1.00  32.75      AAGL
ATOM   2515  CG2  VAL   324      15.341  40.316  90.153  1.00  32.38      AAGL
ATOM   2516  C    VAL   324      13.864  42.573  91.090  1.00  33.56      AAGL
ATOM   2517  O    VAL   324      14.329  43.153  90.093  1.00  33.29      AAGL
ATOM   2518  N    TYR   325      13.974  43.045  92.328  1.00  30.85      AAGL
ATOM   2519  CA   TYR   325      14.683  44.282  92.608  1.00  31.59      AAGL
ATOM   2520  CB   TYR   325      14.228  44.910  93.929  1.00  30.31      AAGL
ATOM   2521  CG   TYR   325      12.794  45.387  93.972  1.00  31.58      AAGL
ATOM   2522  CD1  TYR   325      12.225  46.079  92.901  1.00  31.55      AAGL
ATOM   2523  CE1  TYR   325      10.908  46.548  92.970  1.00  33.68      AAGL
ATOM   2524  CD2  TYR   325      12.015  45.177  95.112  1.00  30.63      AAGL
ATOM   2525  CE2  TYR   325      10.714  45.639  95.192  1.00  30.81      AAGL
ATOM   2526  CZ   TYR   325      10.164  46.323  94.127  1.00  33.10      AAGL
ATOM   2527  OH   TYR   325       8.878  46.780  94.231  1.00  32.89      AAGL
ATOM   2528  C    TYR   325      16.169  44.003  92.714  1.00  31.02      AAGL
ATOM   2529  O    TYR   325      16.602  42.859  92.908  1.00  28.70      AAGL
ATOM   2530  N    GLU   326      16.946  45.070  92.599  1.00  31.64      AAGL
ATOM   2531  CA   GLU   326      18.398  45.010  92.684  1.00  31.11      AAGL
ATOM   2532  CB   GLU   326      18.949  46.406  92.388  1.00  34.73      AAGL
ATOM   2533  CG   GLU   326      20.432  46.588  92.571  1.00  39.05      AAGL
ATOM   2534  CD   GLU   326      20.851  47.994  92.209  1.00  41.46      AAGL
```

Fig. 3 cont.

```
ATOM   2535  OE1 GLU  326      20.682  48.359  91.021  1.00 42.66      AAGL
ATOM   2536  OE2 GLU  326      21.334  48.731  93.106  1.00 40.82      AAGL
ATOM   2537  C   GLU  326      18.848  44.538  94.065  1.00 29.10      AAGL
ATOM   2538  O   GLU  326      19.996  44.136  94.253  1.00 27.19      AAGL
ATOM   2539  N   SER  327      17.939  44.581  95.035  1.00 27.41      AAGL
ATOM   2540  CA  SER  327      18.265  44.147  96.387  1.00 25.31      AAGL
ATOM   2541  CB  SER  327      17.127  44.519  97.347  1.00 23.59      AAGL
ATOM   2542  OG  SER  327      15.870  44.218  96.776  1.00 25.25      AAGL
ATOM   2543  C   SER  327      18.574  42.650  96.458  1.00 24.17      AAGL
ATOM   2544  O   SER  327      19.243  42.195  97.383  1.00 25.88      AAGL
ATOM   2545  N   ILE  328      18.107  41.880  95.479  1.00 27.45      AAGL
ATOM   2546  CA  ILE  328      18.395  40.446  95.466  1.00 28.86      AAGL
ATOM   2547  CB  ILE  328      17.692  39.728  94.295  1.00 31.12      AAGL
ATOM   2548  CG2 ILE  328      18.120  38.277  94.250  1.00 35.58      AAGL
ATOM   2549  CG1 ILE  328      16.175  39.823  94.448  1.00 33.48      AAGL
ATOM   2550  CD1 ILE  328      15.647  39.194  95.727  1.00 36.80      AAGL
ATOM   2551  C   ILE  328      19.904  40.248  95.317  1.00 29.16      AAGL
ATOM   2552  O   ILE  328      20.486  39.324  95.897  1.00 27.50      AAGL
ATOM   2553  N   GLU  329      20.536  41.124  94.538  1.00 30.01      AAGL
ATOM   2554  CA  GLU  329      21.978  41.045  94.328  1.00 30.96      AAGL
ATOM   2555  CB  GLU  329      22.435  42.017  93.229  1.00 33.99      AAGL
ATOM   2556  CG  GLU  329      21.773  41.813  91.866  1.00 37.96      AAGL
ATOM   2557  CD  GLU  329      22.520  42.542  90.746  1.00 42.17      AAGL
ATOM   2558  OE1 GLU  329      22.731  43.773  90.863  1.00 42.73      AAGL
ATOM   2559  OE2 GLU  329      22.898  41.883  89.746  1.00 42.99      AAGL
ATOM   2560  C   GLU  329      22.682  41.386  95.627  1.00 29.64      AAGL
ATOM   2561  O   GLU  329      23.693  40.771  95.988  1.00 29.09      AAGL
ATOM   2562  N   THR  330      22.142  42.368  96.340  1.00 28.03      AAGL
ATOM   2563  CA  THR  330      22.720  42.776  97.611  1.00 26.58      AAGL
ATOM   2564  CB  THR  330      21.958  43.986  98.200  1.00 27.90      AAGL
ATOM   2565  OG1 THR  330      22.099  45.110  97.323  1.00 26.78      AAGL
ATOM   2566  CG2 THR  330      22.495  44.345  99.574  1.00 27.91      AAGL
ATOM   2567  C   THR  330      22.671  41.608  98.606  1.00 26.92      AAGL
ATOM   2568  O   THR  330      23.654  41.325  99.301  1.00 25.31      AAGL
ATOM   2569  N   LEU  331      21.529  40.930  98.667  1.00 25.72      AAGL
ATOM   2570  CA  LEU  331      21.368  39.791  99.571  1.00 24.97      AAGL
ATOM   2571  CB  LEU  331      19.923  39.282  99.532  1.00 24.19      AAGL
ATOM   2572  CG  LEU  331      19.567  37.968 100.247  1.00 23.31      AAGL
ATOM   2573  CD1 LEU  331      19.873  38.051 101.736  1.00 25.91      AAGL
ATOM   2574  CD2 LEU  331      18.082  37.674 100.034  1.00 23.20      AAGL
ATOM   2575  C   LEU  331      22.319  38.674  99.158  1.00 25.90      AAGL
ATOM   2576  O   LEU  331      22.971  38.054 100.001  1.00 25.54      AAGL
ATOM   2577  N   GLY  332      22.390  38.427  97.853  1.00 26.10      AAGL
ATOM   2578  CA  GLY  332      23.262  37.386  97.337  1.00 28.89      AAGL
ATOM   2579  C   GLY  332      24.738  37.631  97.594  1.00 31.12      AAGL
ATOM   2580  O   GLY  332      25.526  36.682  97.614  1.00 30.65      AAGL
ATOM   2581  N   GLU  333      25.120  38.890  97.805  1.00 31.60      AAGL
ATOM   2582  CA  GLU  333      26.524  39.229  98.044  1.00 33.74      AAGL
ATOM   2583  CB  GLU  333      26.949  40.400  97.148  1.00 34.97      AAGL
ATOM   2584  CG  GLU  333      26.639  40.205  95.673  1.00 37.79      AAGL
ATOM   2585  CD  GLU  333      26.846  41.471  94.846  1.00 41.19      AAGL
ATOM   2586  OE1 GLU  333      26.164  41.621  93.807  1.00 40.67      AAGL
ATOM   2587  OE2 GLU  333      27.694  42.309  95.225  1.00 44.05      AAGL
ATOM   2588  C   GLU  333      26.844  39.586  99.490  1.00 35.01      AAGL
ATOM   2589  O   GLU  333      27.924  40.109  99.776  1.00 33.69      AAGL
ATOM   2590  N   LEU  334      25.925  39.319 100.410  1.00 34.35      AAGL
ATOM   2591  CA  LEU  334      26.193  39.655 101.805  1.00 33.87      AAGL
ATOM   2592  CB  LEU  334      24.963  39.371 102.672  1.00 33.01      AAGL
ATOM   2593  CG  LEU  334      23.721  40.228 102.407  1.00 32.82      AAGL
ATOM   2594  CD1 LEU  334      22.611  39.797 103.347  1.00 28.38      AAGL
ATOM   2595  CD2 LEU  334      24.044  41.711 102.607  1.00 30.26      AAGL
ATOM   2596  C   LEU  334      27.396  38.881 102.344  1.00 35.69      AAGL
ATOM   2597  O   LEU  334      27.475  37.650 102.129  1.00 36.26      AAGL
ATOM   2598  OXT LEU  334      28.249  39.520 102.989  1.00 35.77      AAGL
END
```

Fig. 3 cont.

| HEADER | | | | | | | | | BLGL | |
|---|---|---|---|---|---|---|---|---|---|---|
| ATOM | 1 | C | GLY | 11 | 35.975 | 14.251 | 23.684 | 1.00 | 48.49 | BLGL |
| ATOM | 2 | O | GLY | 11 | 36.590 | 13.193 | 23.517 | 1.00 | 48.50 | BLGL |
| ATOM | 3 | N | GLY | 11 | 36.372 | 16.222 | 25.216 | 1.00 | 48.08 | BLGL |
| ATOM | 4 | CA | GLY | 11 | 36.733 | 15.548 | 23.933 | 1.00 | 47.57 | BLGL |
| ATOM | 5 | N | LEU | 12 | 34.642 | 14.326 | 23.653 | 1.00 | 48.44 | BLGL |
| ATOM | 6 | CA | LEU | 12 | 33.796 | 13.147 | 23.416 | 1.00 | 45.49 | BLGL |
| ATOM | 7 | CB | LEU | 12 | 32.592 | 13.139 | 24.371 | 1.00 | 43.64 | BLGL |
| ATOM | 8 | CG | LEU | 12 | 31.626 | 11.961 | 24.199 | 1.00 | 41.45 | BLGL |
| ATOM | 9 | CD1 | LEU | 12 | 32.074 | 10.803 | 25.085 | 1.00 | 36.51 | BLGL |
| ATOM | 10 | CD2 | LEU | 12 | 30.203 | 12.400 | 24.550 | 1.00 | 41.11 | BLGL |
| ATOM | 11 | C | LEU | 12 | 33.272 | 13.109 | 21.979 | 1.00 | 44.11 | BLGL |
| ATOM | 12 | O | LEU | 12 | 32.688 | 14.086 | 21.502 | 1.00 | 45.18 | BLGL |
| ATOM | 13 | N | TYR | 13 | 33.487 | 11.986 | 21.295 | 1.00 | 42.63 | BLGL |
| ATOM | 14 | CA | TYR | 13 | 33.004 | 11.817 | 19.928 | 1.00 | 41.19 | BLGL |
| ATOM | 15 | CB | TYR | 13 | 34.083 | 11.206 | 19.042 | 1.00 | 45.36 | BLGL |
| ATOM | 16 | CG | TYR | 13 | 33.594 | 10.996 | 17.624 | 1.00 | 52.03 | BLGL |
| ATOM | 17 | CD1 | TYR | 13 | 33.232 | 9.727 | 17.167 | 1.00 | 53.91 | BLGL |
| ATOM | 18 | CE1 | TYR | 13 | 32.703 | 9.545 | 15.872 | 1.00 | 55.69 | BLGL |
| ATOM | 19 | CD2 | TYR | 13 | 33.420 | 12.083 | 16.756 | 1.00 | 53.77 | BLGL |
| ATOM | 20 | CE2 | TYR | 13 | 32.890 | 11.914 | 15.466 | 1.00 | 54.66 | BLGL |
| ATOM | 21 | CZ | TYR | 13 | 32.534 | 10.644 | 15.031 | 1.00 | 56.09 | BLGL |
| ATOM | 22 | OH | TYR | 13 | 32.009 | 10.473 | 13.764 | 1.00 | 56.62 | BLGL |
| ATOM | 23 | C | TYR | 13 | 31.755 | 10.932 | 19.837 | 1.00 | 38.22 | BLGL |
| ATOM | 24 | O | TYR | 13 | 31.686 | 9.887 | 20.471 | 1.00 | 38.74 | BLGL |
| ATOM | 25 | N | VAL | 14 | 30.776 | 11.355 | 19.039 | 1.00 | 34.88 | BLGL |
| ATOM | 26 | CA | VAL | 14 | 29.537 | 10.604 | 18.845 | 1.00 | 31.50 | BLGL |
| ATOM | 27 | CB | VAL | 14 | 28.418 | 11.094 | 19.777 | 1.00 | 30.78 | BLGL |
| ATOM | 28 | CG1 | VAL | 14 | 27.102 | 10.405 | 19.427 | 1.00 | 30.71 | BLGL |
| ATOM | 29 | CG2 | VAL | 14 | 28.790 | 10.812 | 21.203 | 1.00 | 30.70 | BLGL |
| ATOM | 30 | C | VAL | 14 | 29.069 | 10.798 | 17.420 | 1.00 | 30.74 | BLGL |
| ATOM | 31 | O | VAL | 14 | 28.776 | 11.917 | 17.007 | 1.00 | 31.52 | BLGL |
| ATOM | 32 | N | GLU | 15 | 28.994 | 9.710 | 16.669 | 1.00 | 30.21 | BLGL |
| ATOM | 33 | CA | GLU | 15 | 28.555 | 9.788 | 15.288 | 1.00 | 30.31 | BLGL |
| ATOM | 34 | CB | GLU | 15 | 29.002 | 8.546 | 14.534 | 1.00 | 33.96 | BLGL |
| ATOM | 35 | CG | GLU | 15 | 28.509 | 8.486 | 13.113 | 1.00 | 43.05 | BLGL |
| ATOM | 36 | CD | GLU | 15 | 28.927 | 7.202 | 12.424 | 1.00 | 49.32 | BLGL |
| ATOM | 37 | OE1 | GLU | 15 | 28.886 | 6.140 | 13.087 | 1.00 | 51.29 | BLGL |
| ATOM | 38 | OE2 | GLU | 15 | 29.285 | 7.251 | 11.223 | 1.00 | 54.28 | BLGL |
| ATOM | 39 | C | GLU | 15 | 27.045 | 9.931 | 15.206 | 1.00 | 28.83 | BLGL |
| ATOM | 40 | O | GLU | 15 | 26.303 | 9.161 | 15.816 | 1.00 | 26.88 | BLGL |
| ATOM | 41 | N | LYS | 16 | 26.596 | 10.923 | 14.445 | 1.00 | 29.24 | BLGL |
| ATOM | 42 | CA | LYS | 16 | 25.173 | 11.173 | 14.280 | 1.00 | 30.57 | BLGL |
| ATOM | 43 | CB | LYS | 16 | 24.933 | 12.207 | 13.174 | 1.00 | 32.52 | BLGL |
| ATOM | 44 | CG | LYS | 16 | 23.454 | 12.496 | 12.948 | 1.00 | 38.94 | BLGL |
| ATOM | 45 | CD | LYS | 16 | 23.141 | 12.889 | 11.510 | 1.00 | 43.38 | BLGL |
| ATOM | 46 | CE | LYS | 16 | 23.632 | 14.282 | 11.176 | 1.00 | 46.85 | BLGL |
| ATOM | 47 | NZ | LYS | 16 | 23.276 | 14.648 | 9.776 | 1.00 | 50.40 | BLGL |
| ATOM | 48 | C | LYS | 16 | 24.399 | 9.902 | 13.938 | 1.00 | 29.87 | BLGL |
| ATOM | 49 | O | LYS | 16 | 24.836 | 9.090 | 13.121 | 1.00 | 28.75 | BLGL |
| ATOM | 50 | N | VAL | 17 | 23.249 | 9.733 | 14.575 | 1.00 | 29.36 | BLGL |
| ATOM | 51 | CA | VAL | 17 | 22.394 | 8.591 | 14.306 | 1.00 | 29.25 | BLGL |
| ATOM | 52 | CB | VAL | 17 | 21.437 | 8.328 | 15.476 | 1.00 | 28.63 | BLGL |
| ATOM | 53 | CG1 | VAL | 17 | 20.469 | 7.201 | 15.127 | 1.00 | 28.74 | BLGL |
| ATOM | 54 | CG2 | VAL | 17 | 22.236 | 7.982 | 16.702 | 1.00 | 30.70 | BLGL |
| ATOM | 55 | C | VAL | 17 | 21.582 | 8.940 | 13.064 | 1.00 | 30.63 | BLGL |
| ATOM | 56 | O | VAL | 17 | 20.794 | 9.891 | 13.064 | 1.00 | 30.98 | BLGL |
| ATOM | 57 | N | SER | 18 | 21.782 | 8.172 | 12.005 | 1.00 | 30.58 | BLGL |
| ATOM | 58 | CA | SER | 18 | 21.083 | 8.422 | 10.758 | 1.00 | 33.73 | BLGL |
| ATOM | 59 | CB | SER | 18 | 21.787 | 7.675 | 9.628 | 1.00 | 36.18 | BLGL |
| ATOM | 60 | OG | SER | 18 | 21.984 | 6.324 | 9.990 | 1.00 | 38.96 | BLGL |
| ATOM | 61 | C | SER | 18 | 19.611 | 8.032 | 10.800 | 1.00 | 32.04 | BLGL |
| ATOM | 62 | O | SER | 18 | 19.264 | 6.933 | 11.231 | 1.00 | 31.91 | BLGL |
| ATOM | 63 | N | GLY | 19 | 18.755 | 8.950 | 10.359 | 1.00 | 31.92 | BLGL |
| ATOM | 64 | CA | GLY | 19 | 17.328 | 8.697 | 10.327 | 1.00 | 30.75 | BLGL |
| ATOM | 65 | C | GLY | 19 | 16.601 | 8.894 | 11.638 | 1.00 | 30.09 | BLGL |

Fig. 4

| | | | | | | | | | |
|---|---|---|---|---|---|---|---|---|---|
| ATOM | 66 | O | GLY | 19 | 15.395 | 8.684 | 11.705 | 1.00 32.49 | BLGL |
| ATOM | 67 | N | LEU | 20 | 17.314 | 9.295 | 12.681 | 1.00 28.46 | BLGL |
| ATOM | 68 | CA | LEU | 20 | 16.672 | 9.498 | 13.967 | 1.00 28.28 | BLGL |
| ATOM | 69 | CB | LEU | 20 | 17.706 | 9.910 | 15.013 | 1.00 29.28 | BLGL |
| ATOM | 70 | CG | LEU | 20 | 17.141 | 9.983 | 16.436 | 1.00 29.10 | BLGL |
| ATOM | 71 | CD1 | LEU | 20 | 16.756 | 8.586 | 16.904 | 1.00 27.36 | BLGL |
| ATOM | 72 | CD2 | LEU | 20 | 18.165 | 10.598 | 17.359 | 1.00 29.58 | BLGL |
| ATOM | 73 | C | LEU | 20 | 15.565 | 10.548 | 13.890 | 1.00 25.87 | BLGL |
| ATOM | 74 | O | LEU | 20 | 15.821 | 11.686 | 13.535 | 1.00 24.28 | BLGL |
| ATOM | 75 | N | ARG | 21 | 14.342 | 10.147 | 14.226 | 1.00 28.07 | BLGL |
| ATOM | 76 | CA | ARG | 21 | 13.176 | 11.030 | 14.213 | 1.00 30.64 | BLGL |
| ATOM | 77 | CB | ARG | 21 | 11.912 | 10.211 | 14.476 | 1.00 31.64 | BLGL |
| ATOM | 78 | CG | ARG | 21 | 11.955 | 9.430 | 15.792 | 1.00 35.81 | BLGL |
| ATOM | 79 | CD | ARG | 21 | 10.892 | 8.339 | 15.840 | 1.00 36.79 | BLGL |
| ATOM | 80 | NE | ARG | 21 | 9.536 | 8.877 | 15.850 | 1.00 37.50 | BLGL |
| ATOM | 81 | CZ | ARG | 21 | 8.445 | 8.133 | 15.699 | 1.00 38.47 | BLGL |
| ATOM | 82 | NH1 | ARG | 21 | 8.567 | 6.826 | 15.525 | 1.00 37.04 | BLGL |
| ATOM | 83 | NH2 | ARG | 21 | 7.235 | 8.688 | 15.731 | 1.00 39.56 | BLGL |
| ATOM | 84 | C | ARG | 21 | 13.316 | 12.114 | 15.277 | 1.00 32.05 | BLGL |
| ATOM | 85 | O | ARG | 21 | 13.840 | 11.862 | 16.354 | 1.00 31.41 | BLGL |
| ATOM | 86 | N | LYS | 22 | 12.832 | 13.315 | 14.978 | 1.00 35.57 | BLGL |
| ATOM | 87 | CA | LYS | 22 | 12.927 | 14.428 | 15.916 | 1.00 37.84 | BLGL |
| ATOM | 88 | CB | LYS | 22 | 12.378 | 15.713 | 15.291 | 1.00 42.04 | BLGL |
| ATOM | 89 | CG | LYS | 22 | 13.278 | 16.381 | 14.265 | 1.00 47.84 | BLGL |
| ATOM | 90 | CD | LYS | 22 | 12.908 | 17.872 | 14.150 | 1.00 51.73 | BLGL |
| ATOM | 91 | CE | LYS | 22 | 13.460 | 18.518 | 12.882 | 1.00 52.80 | BLGL |
| ATOM | 92 | NZ | LYS | 22 | 12.732 | 18.062 | 11.661 | 1.00 52.64 | BLGL |
| ATOM | 93 | C | LYS | 22 | 12.225 | 14.227 | 17.253 | 1.00 36.42 | BLGL |
| ATOM | 94 | O | LYS | 22 | 12.672 | 14.762 | 18.264 | 1.00 37.54 | BLGL |
| ATOM | 95 | N | ASP | 23 | 11.128 | 13.476 | 17.262 | 1.00 34.94 | BLGL |
| ATOM | 96 | CA | ASP | 23 | 10.370 | 13.264 | 18.495 | 1.00 33.91 | BLGL |
| ATOM | 97 | CB | ASP | 23 | 8.869 | 13.257 | 18.181 | 1.00 34.54 | BLGL |
| ATOM | 98 | CG | ASP | 23 | 8.465 | 12.096 | 17.303 | 1.00 34.79 | BLGL |
| ATOM | 99 | OD1 | ASP | 23 | 9.242 | 11.739 | 16.392 | 1.00 33.67 | BLGL |
| ATOM | 100 | OD2 | ASP | 23 | 7.365 | 11.547 | 17.521 | 1.00 39.44 | BLGL |
| ATOM | 101 | C | ASP | 23 | 10.754 | 11.989 | 19.238 | 1.00 31.78 | BLGL |
| ATOM | 102 | O | ASP | 23 | 10.001 | 11.495 | 20.083 | 1.00 31.40 | BLGL |
| ATOM | 103 | N | PHE | 24 | 11.932 | 11.467 | 18.921 | 1.00 28.21 | BLGL |
| ATOM | 104 | CA | PHE | 24 | 12.423 | 10.256 | 19.551 | 1.00 25.65 | BLGL |
| ATOM | 105 | CB | PHE | 24 | 13.788 | 9.904 | 18.967 | 1.00 25.73 | BLGL |
| ATOM | 106 | CG | PHE | 24 | 14.281 | 8.538 | 19.337 | 1.00 25.81 | BLGL |
| ATOM | 107 | CD1 | PHE | 24 | 15.134 | 8.359 | 20.422 | 1.00 25.77 | BLGL |
| ATOM | 108 | CD2 | PHE | 24 | 13.930 | 7.431 | 18.573 | 1.00 25.98 | BLGL |
| ATOM | 109 | CE1 | PHE | 24 | 15.642 | 7.093 | 20.739 | 1.00 25.74 | BLGL |
| ATOM | 110 | CE2 | PHE | 24 | 14.431 | 6.161 | 18.881 | 1.00 27.08 | BLGL |
| ATOM | 111 | CZ | PHE | 24 | 15.292 | 5.992 | 19.967 | 1.00 24.69 | BLGL |
| ATOM | 112 | C | PHE | 24 | 12.517 | 10.473 | 21.055 | 1.00 22.99 | BLGL |
| ATOM | 113 | O | PHE | 24 | 12.961 | 11.520 | 21.519 | 1.00 23.30 | BLGL |
| ATOM | 114 | N | ILE | 25 | 12.077 | 9.474 | 21.804 | 1.00 19.49 | BLGL |
| ATOM | 115 | CA | ILE | 25 | 12.096 | 9.514 | 23.254 | 1.00 17.47 | BLGL |
| ATOM | 116 | CB | ILE | 25 | 11.137 | 8.465 | 23.820 | 1.00 15.37 | BLGL |
| ATOM | 117 | CG2 | ILE | 25 | 11.388 | 8.253 | 25.306 | 1.00 13.70 | BLGL |
| ATOM | 118 | CG1 | ILE | 25 | 9.706 | 8.883 | 23.524 | 1.00 13.77 | BLGL |
| ATOM | 119 | CD1 | ILE | 25 | 8.696 | 7.834 | 23.915 | 1.00 18.01 | BLGL |
| ATOM | 120 | C | ILE | 25 | 13.487 | 9.227 | 23.799 | 1.00 17.49 | BLGL |
| ATOM | 121 | O | ILE | 25 | 14.091 | 8.211 | 23.465 | 1.00 16.53 | BLGL |
| ATOM | 122 | N | LYS | 26 | 13.985 | 10.128 | 24.637 | 1.00 16.78 | BLGL |
| ATOM | 123 | CA | LYS | 26 | 15.294 | 9.962 | 25.259 | 1.00 18.11 | BLGL |
| ATOM | 124 | CB | LYS | 26 | 16.213 | 11.096 | 24.825 | 1.00 19.07 | BLGL |
| ATOM | 125 | CG | LYS | 26 | 16.276 | 11.237 | 23.314 | 1.00 21.25 | BLGL |
| ATOM | 126 | CD | LYS | 26 | 16.943 | 12.520 | 22.899 | 1.00 23.74 | BLGL |
| ATOM | 127 | CE | LYS | 26 | 16.949 | 12.669 | 21.387 | 1.00 24.53 | BLGL |
| ATOM | 128 | NZ | LYS | 26 | 17.505 | 13.994 | 20.995 | 1.00 26.16 | BLGL |
| ATOM | 129 | C | LYS | 26 | 15.032 | 10.015 | 26.754 | 1.00 17.62 | BLGL |
| ATOM | 130 | O | LYS | 26 | 14.990 | 11.089 | 27.340 | 1.00 18.88 | BLGL |
| ATOM | 131 | N | GLY | 27 | 14.845 | 8.850 | 27.367 | 1.00 15.97 | BLGL |

Fig. 4 cont.

| | | | | | | | | | |
|---|---|---|---|---|---|---|---|---|---|
| ATOM | 132 | CA | GLY | 27 | 14.540 | 8.822 | 28.783 | 1.00 14.87 | BLGL |
| ATOM | 133 | C | GLY | 27 | 15.553 | 8.183 | 29.706 | 1.00 15.36 | BLGL |
| ATOM | 134 | O | GLY | 27 | 16.490 | 7.523 | 29.278 | 1.00 14.26 | BLGL |
| ATOM | 135 | N | VAL | 28 | 15.364 | 8.413 | 30.997 | 1.00 15.73 | BLGL |
| ATOM | 136 | CA | VAL | 28 | 16.233 | 7.847 | 32.002 | 1.00 15.81 | BLGL |
| ATOM | 137 | CB | VAL | 28 | 17.285 | 8.866 | 32.505 | 1.00 15.33 | BLGL |
| ATOM | 138 | CG1 | VAL | 28 | 18.189 | 9.289 | 31.359 | 1.00 15.90 | BLGL |
| ATOM | 139 | CG2 | VAL | 28 | 16.604 | 10.073 | 33.113 | 1.00 15.60 | BLGL |
| ATOM | 140 | C | VAL | 28 | 15.367 | 7.411 | 33.164 | 1.00 17.23 | BLGL |
| ATOM | 141 | O | VAL | 28 | 14.294 | 7.967 | 33.405 | 1.00 16.45 | BLGL |
| ATOM | 142 | N | ASP | 29 | 15.817 | 6.380 | 33.860 | 1.00 17.41 | BLGL |
| ATOM | 143 | CA | ASP | 29 | 15.098 | 5.902 | 35.023 | 1.00 18.06 | BLGL |
| ATOM | 144 | CB | ASP | 29 | 14.855 | 4.391 | 34.925 | 1.00 16.28 | BLGL |
| ATOM | 145 | CG | ASP | 29 | 14.123 | 3.832 | 36.138 | 1.00 18.27 | BLGL |
| ATOM | 146 | OD1 | ASP | 29 | 13.426 | 2.801 | 35.978 | 1.00 15.84 | BLGL |
| ATOM | 147 | OD2 | ASP | 29 | 14.258 | 4.409 | 37.246 | 1.00 14.09 | BLGL |
| ATOM | 148 | C | ASP | 29 | 16.006 | 6.248 | 36.201 | 1.00 17.72 | BLGL |
| ATOM | 149 | O | ASP | 29 | 17.075 | 5.670 | 36.362 | 1.00 18.18 | BLGL |
| ATOM | 150 | N | VAL | 30 | 15.592 | 7.228 | 36.994 | 1.00 17.06 | BLGL |
| ATOM | 151 | CA | VAL | 30 | 16.360 | 7.653 | 38.158 | 1.00 14.73 | BLGL |
| ATOM | 152 | CB | VAL | 30 | 16.740 | 9.151 | 38.051 | 1.00 13.70 | BLGL |
| ATOM | 153 | CG1 | VAL | 30 | 17.688 | 9.354 | 36.880 | 1.00 12.16 | BLGL |
| ATOM | 154 | CG2 | VAL | 30 | 15.485 | 10.017 | 37.872 | 1.00 9.08 | BLGL |
| ATOM | 155 | C | VAL | 30 | 15.551 | 7.422 | 39.426 | 1.00 14.73 | BLGL |
| ATOM | 156 | O | VAL | 30 | 15.491 | 8.275 | 40.302 | 1.00 16.61 | BLGL |
| ATOM | 157 | N | SER | 31 | 14.931 | 6.252 | 39.515 | 1.00 16.06 | BLGL |
| ATOM | 158 | CA | SER | 31 | 14.090 | 5.899 | 40.660 | 1.00 19.01 | BLGL |
| ATOM | 159 | CB | SER | 31 | 13.540 | 4.481 | 40.481 | 1.00 17.38 | BLGL |
| ATOM | 160 | OG | SER | 31 | 12.719 | 4.395 | 39.331 | 1.00 19.20 | BLGL |
| ATOM | 161 | C | SER | 31 | 14.769 | 6.007 | 42.030 | 1.00 19.31 | BLGL |
| ATOM | 162 | O | SER | 31 | 14.120 | 6.282 | 43.041 | 1.00 19.82 | BLGL |
| ATOM | 163 | N | SER | 32 | 16.075 | 5.797 | 42.059 | 1.00 18.54 | BLGL |
| ATOM | 164 | CA | SER | 32 | 16.826 | 5.845 | 43.301 | 1.00 19.36 | BLGL |
| ATOM | 165 | CB | SER | 32 | 18.121 | 5.055 | 43.133 | 1.00 18.42 | BLGL |
| ATOM | 166 | OG | SER | 32 | 18.909 | 5.611 | 42.088 | 1.00 16.54 | BLGL |
| ATOM | 167 | C | SER | 32 | 17.161 | 7.259 | 43.775 | 1.00 21.13 | BLGL |
| ATOM | 168 | O | SER | 32 | 17.612 | 7.442 | 44.902 | 1.00 20.54 | BLGL |
| ATOM | 169 | N | ILE | 33 | 16.931 | 8.256 | 42.925 | 1.00 21.96 | BLGL |
| ATOM | 170 | CA | ILE | 33 | 17.256 | 9.644 | 43.263 | 1.00 22.33 | BLGL |
| ATOM | 171 | CB | ILE | 33 | 16.752 | 10.622 | 42.161 | 1.00 21.13 | BLGL |
| ATOM | 172 | CG2 | ILE | 33 | 15.234 | 10.621 | 42.095 | 1.00 19.56 | BLGL |
| ATOM | 173 | CG1 | ILE | 33 | 17.283 | 12.027 | 42.439 | 1.00 20.03 | BLGL |
| ATOM | 174 | CD1 | ILE | 33 | 18.794 | 12.117 | 42.425 | 1.00 17.45 | BLGL |
| ATOM | 175 | C | ILE | 33 | 16.796 | 10.152 | 44.636 | 1.00 23.71 | BLGL |
| ATOM | 176 | O | ILE | 33 | 17.549 | 10.858 | 45.309 | 1.00 25.43 | BLGL |
| ATOM | 177 | N | ILE | 34 | 15.581 | 9.797 | 45.059 | 1.00 24.35 | BLGL |
| ATOM | 178 | CA | ILE | 34 | 15.066 | 10.235 | 46.362 | 1.00 23.98 | BLGL |
| ATOM | 179 | CB | ILE | 34 | 13.539 | 9.951 | 46.486 | 1.00 23.20 | BLGL |
| ATOM | 180 | CG2 | ILE | 34 | 13.170 | 9.637 | 47.922 | 1.00 24.75 | BLGL |
| ATOM | 181 | CG1 | ILE | 34 | 12.735 | 11.183 | 46.063 | 1.00 20.84 | BLGL |
| ATOM | 182 | CD1 | ILE | 34 | 13.078 | 11.696 | 44.729 | 1.00 21.81 | BLGL |
| ATOM | 183 | C | ILE | 34 | 15.815 | 9.598 | 47.550 | 1.00 24.38 | BLGL |
| ATOM | 184 | O | ILE | 34 | 16.186 | 10.290 | 48.502 | 1.00 25.31 | BLGL |
| ATOM | 185 | N | ALA | 35 | 16.041 | 8.290 | 47.500 | 1.00 22.66 | BLGL |
| ATOM | 186 | CA | ALA | 35 | 16.761 | 7.622 | 48.579 | 1.00 22.83 | BLGL |
| ATOM | 187 | CB | ALA | 35 | 16.803 | 6.117 | 48.344 | 1.00 20.64 | BLGL |
| ATOM | 188 | C | ALA | 35 | 18.178 | 8.165 | 48.681 | 1.00 23.42 | BLGL |
| ATOM | 189 | O | ALA | 35 | 18.687 | 8.377 | 49.776 | 1.00 25.98 | BLGL |
| ATOM | 190 | N | LEU | 36 | 18.813 | 8.382 | 47.536 | 1.00 23.28 | BLGL |
| ATOM | 191 | CA | LEU | 36 | 20.173 | 8.900 | 47.508 | 1.00 25.90 | BLGL |
| ATOM | 192 | CB | LEU | 36 | 20.726 | 8.908 | 46.073 | 1.00 26.42 | BLGL |
| ATOM | 193 | CG | LEU | 36 | 21.093 | 7.571 | 45.421 | 1.00 25.94 | BLGL |
| ATOM | 194 | CD1 | LEU | 36 | 21.783 | 7.836 | 44.105 | 1.00 29.58 | BLGL |
| ATOM | 195 | CD2 | LEU | 36 | 22.017 | 6.778 | 46.323 | 1.00 28.67 | BLGL |
| ATOM | 196 | C | LEU | 36 | 20.237 | 10.308 | 48.089 | 1.00 26.59 | BLGL |
| ATOM | 197 | O | LEU | 36 | 21.140 | 10.637 | 48.863 | 1.00 25.84 | BLGL |

Fig. 4 cont.

| | | | | | | | | | |
|---|---|---|---|---|---|---|---|---|---|
| ATOM | 198 | N | GLU | 37 | 19.282 | 11.144 | 47.708 | 1.00 26.12 | BLGL |
| ATOM | 199 | CA | GLU | 37 | 19.259 | 12.501 | 48.214 | 1.00 28.35 | BLGL |
| ATOM | 200 | CB | GLU | 37 | 18.092 | 13.264 | 47.594 | 1.00 26.08 | BLGL |
| ATOM | 201 | CG | GLU | 37 | 18.409 | 13.814 | 46.220 | 1.00 29.12 | BLGL |
| ATOM | 202 | CD | GLU | 37 | 17.238 | 14.542 | 45.612 | 1.00 30.50 | BLGL |
| ATOM | 203 | OE1 | GLU | 37 | 17.422 | 15.243 | 44.593 | 1.00 26.60 | BLGL |
| ATOM | 204 | OE2 | GLU | 37 | 16.128 | 14.400 | 46.163 | 1.00 35.60 | BLGL |
| ATOM | 205 | C | GLU | 37 | 19.170 | 12.526 | 49.739 | 1.00 28.90 | BLGL |
| ATOM | 206 | O | GLU | 37 | 19.828 | 13.334 | 50.393 | 1.00 30.03 | BLGL |
| ATOM | 207 | N | GLU | 38 | 18.366 | 11.633 | 50.301 | 1.00 29.70 | BLGL |
| ATOM | 208 | CA | GLU | 38 | 18.212 | 11.570 | 51.746 | 1.00 31.72 | BLGL |
| ATOM | 209 | CB | GLU | 38 | 17.037 | 10.677 | 52.125 | 1.00 31.95 | BLGL |
| ATOM | 210 | CG | GLU | 38 | 15.752 | 11.052 | 51.450 | 1.00 37.83 | BLGL |
| ATOM | 211 | CD | GLU | 38 | 14.562 | 10.379 | 52.094 | 1.00 40.58 | BLGL |
| ATOM | 212 | OE1 | GLU | 38 | 14.609 | 9.150 | 52.302 | 1.00 39.84 | BLGL |
| ATOM | 213 | OE2 | GLU | 38 | 13.578 | 11.086 | 52.390 | 1.00 45.75 | BLGL |
| ATOM | 214 | C | GLU | 38 | 19.467 | 11.026 | 52.415 | 1.00 32.56 | BLGL |
| ATOM | 215 | O | GLU | 38 | 19.641 | 11.156 | 53.627 | 1.00 36.26 | BLGL |
| ATOM | 216 | N | SER | 39 | 20.335 | 10.402 | 51.632 | 1.00 30.07 | BLGL |
| ATOM | 217 | CA | SER | 39 | 21.553 | 9.842 | 52.176 | 1.00 27.49 | BLGL |
| ATOM | 218 | CB | SER | 39 | 21.939 | 8.602 | 51.379 | 1.00 29.09 | BLGL |
| ATOM | 219 | OG | SER | 39 | 20.872 | 7.667 | 51.376 | 1.00 24.83 | BLGL |
| ATOM | 220 | C | SER | 39 | 22.660 | 10.882 | 52.133 | 1.00 28.20 | BLGL |
| ATOM | 221 | O | SER | 39 | 23.791 | 10.624 | 52.547 | 1.00 29.82 | BLGL |
| ATOM | 222 | N | GLY | 40 | 22.327 | 12.063 | 51.626 | 1.00 28.31 | BLGL |
| ATOM | 223 | CA | GLY | 40 | 23.303 | 13.135 | 51.558 | 1.00 29.30 | BLGL |
| ATOM | 224 | C | GLY | 40 | 23.975 | 13.332 | 50.214 | 1.00 29.65 | BLGL |
| ATOM | 225 | O | GLY | 40 | 24.717 | 14.296 | 50.031 | 1.00 31.52 | BLGL |
| ATOM | 226 | N | VAL | 41 | 23.730 | 12.428 | 49.272 | 1.00 28.29 | BLGL |
| ATOM | 227 | CA | VAL | 41 | 24.333 | 12.540 | 47.948 | 1.00 27.33 | BLGL |
| ATOM | 228 | CB | VAL | 41 | 24.014 | 11.299 | 47.075 | 1.00 26.80 | BLGL |
| ATOM | 229 | CG1 | VAL | 41 | 24.634 | 11.458 | 45.699 | 1.00 24.11 | BLGL |
| ATOM | 230 | CG2 | VAL | 41 | 24.531 | 10.034 | 47.754 | 1.00 25.53 | BLGL |
| ATOM | 231 | C | VAL | 41 | 23.816 | 13.788 | 47.242 | 1.00 27.51 | BLGL |
| ATOM | 232 | O | VAL | 41 | 22.630 | 14.107 | 47.315 | 1.00 27.71 | BLGL |
| ATOM | 233 | N | ALA | 42 | 24.716 | 14.496 | 46.568 | 1.00 28.05 | BLGL |
| ATOM | 234 | CA | ALA | 42 | 24.364 | 15.713 | 45.840 | 1.00 27.62 | BLGL |
| ATOM | 235 | CB | ALA | 42 | 24.952 | 16.935 | 46.538 | 1.00 26.85 | BLGL |
| ATOM | 236 | C | ALA | 42 | 24.898 | 15.624 | 44.415 | 1.00 28.00 | BLGL |
| ATOM | 237 | O | ALA | 42 | 25.918 | 14.986 | 44.158 | 1.00 29.09 | BLGL |
| ATOM | 238 | N | PHE | 43 | 24.205 | 16.267 | 43.489 | 1.00 27.56 | BLGL |
| ATOM | 239 | CA | PHE | 43 | 24.625 | 16.244 | 42.101 | 1.00 30.30 | BLGL |
| ATOM | 240 | CB | PHE | 43 | 23.529 | 15.626 | 41.223 | 1.00 29.43 | BLGL |
| ATOM | 241 | CG | PHE | 43 | 23.281 | 14.176 | 41.513 | 1.00 29.78 | BLGL |
| ATOM | 242 | CD1 | PHE | 43 | 22.538 | 13.791 | 42.630 | 1.00 26.98 | BLGL |
| ATOM | 243 | CD2 | PHE | 43 | 23.855 | 13.188 | 40.714 | 1.00 28.78 | BLGL |
| ATOM | 244 | CE1 | PHE | 43 | 22.373 | 12.442 | 42.957 | 1.00 25.96 | BLGL |
| ATOM | 245 | CE2 | PHE | 43 | 23.698 | 11.835 | 41.031 | 1.00 28.67 | BLGL |
| ATOM | 246 | CZ | PHE | 43 | 22.954 | 11.461 | 42.160 | 1.00 26.33 | BLGL |
| ATOM | 247 | C | PHE | 43 | 24.954 | 17.651 | 41.632 | 1.00 32.38 | BLGL |
| ATOM | 248 | O | PHE | 43 | 24.351 | 18.622 | 42.096 | 1.00 33.12 | BLGL |
| ATOM | 249 | N | TYR | 44 | 25.915 | 17.759 | 40.719 | 1.00 32.89 | BLGL |
| ATOM | 250 | CA | TYR | 44 | 26.326 | 19.054 | 40.203 | 1.00 34.23 | BLGL |
| ATOM | 251 | CB | TYR | 44 | 27.807 | 19.289 | 40.482 | 1.00 33.04 | BLGL |
| ATOM | 252 | CG | TYR | 44 | 28.165 | 19.083 | 41.926 | 1.00 33.71 | BLGL |
| ATOM | 253 | CD1 | TYR | 44 | 28.177 | 17.809 | 42.481 | 1.00 32.43 | BLGL |
| ATOM | 254 | CE1 | TYR | 44 | 28.453 | 17.617 | 43.820 | 1.00 35.78 | BLGL |
| ATOM | 255 | CD2 | TYR | 44 | 28.444 | 20.167 | 42.752 | 1.00 34.36 | BLGL |
| ATOM | 256 | CE2 | TYR | 44 | 28.721 | 19.986 | 44.099 | 1.00 34.85 | BLGL |
| ATOM | 257 | CZ | TYR | 44 | 28.722 | 18.708 | 44.627 | 1.00 35.70 | BLGL |
| ATOM | 258 | OH | TYR | 44 | 28.974 | 18.515 | 45.966 | 1.00 37.37 | BLGL |
| ATOM | 259 | C | TYR | 44 | 26.085 | 19.114 | 38.717 | 1.00 35.88 | BLGL |
| ATOM | 260 | O | TYR | 44 | 25.531 | 18.189 | 38.134 | 1.00 36.33 | BLGL |
| ATOM | 261 | N | ASN | 45 | 26.509 | 20.211 | 38.106 | 1.00 39.58 | BLGL |
| ATOM | 262 | CA | ASN | 45 | 26.350 | 20.391 | 36.672 | 1.00 43.09 | BLGL |
| ATOM | 263 | CB | ASN | 45 | 25.429 | 21.581 | 36.391 | 1.00 45.50 | BLGL |

Fig. 4 cont.

```
ATOM    264  CG  ASN    45      26.156  22.912  36.452  1.00 47.10      BLGL
ATOM    265  OD1 ASN    45      26.932  23.180  37.373  1.00 44.32      BLGL
ATOM    266  ND2 ASN    45      25.897  23.760  35.464  1.00 49.84      BLGL
ATOM    267  C   ASN    45      27.721  20.618  36.038  1.00 43.53      BLGL
ATOM    268  O   ASN    45      28.746  20.564  36.718  1.00 41.75      BLGL
ATOM    269  N   GLU    46      27.733  20.861  34.735  1.00 47.02      BLGL
ATOM    270  CA  GLU    46      28.979  21.090  34.011  1.00 51.61      BLGL
ATOM    271  CB  GLU    46      28.673  21.715  32.656  1.00 55.53      BLGL
ATOM    272  CG  GLU    46      27.635  20.976  31.820  1.00 59.75      BLGL
ATOM    273  CD  GLU    46      28.162  19.673  31.261  1.00 62.26      BLGL
ATOM    274  OE1 GLU    46      29.304  19.665  30.749  1.00 62.58      BLGL
ATOM    275  OE2 GLU    46      27.429  18.665  31.320  1.00 63.83      BLGL
ATOM    276  C   GLU    46      29.917  22.027  34.782  1.00 52.77      BLGL
ATOM    277  O   GLU    46      31.035  21.648  35.144  1.00 52.27      BLGL
ATOM    278  N   SER    47      29.440  23.248  35.029  1.00 53.78      BLGL
ATOM    279  CA  SER    47      30.197  24.288  35.723  1.00 54.29      BLGL
ATOM    280  CB  SER    47      29.312  25.518  35.940  1.00 56.24      BLGL
ATOM    281  OG  SER    47      28.822  26.029  34.707  1.00 57.54      BLGL
ATOM    282  C   SER    47      30.779  23.857  37.058  1.00 54.34      BLGL
ATOM    283  O   SER    47      31.720  24.477  37.552  1.00 56.28      BLGL
ATOM    284  N   GLY    48      30.215  22.812  37.651  1.00 53.12      BLGL
ATOM    285  CA  GLY    48      30.724  22.344  38.926  1.00 52.44      BLGL
ATOM    286  C   GLY    48      29.883  22.783  40.109  1.00 52.32      BLGL
ATOM    287  O   GLY    48      30.200  22.455  41.258  1.00 51.88      BLGL
ATOM    288  N   LYS    49      28.807  23.518  39.832  1.00 51.68      BLGL
ATOM    289  CA  LYS    49      27.919  24.009  40.882  1.00 50.92      BLGL
ATOM    290  CB  LYS    49      27.338  25.368  40.477  1.00 52.51      BLGL
ATOM    291  CG  LYS    49      26.440  25.314  39.255  1.00 54.74      BLGL
ATOM    292  CD  LYS    49      26.139  26.704  38.706  1.00 58.30      BLGL
ATOM    293  CE  LYS    49      25.326  27.551  39.672  1.00 59.50      BLGL
ATOM    294  NZ  LYS    49      25.039  28.909  39.112  1.00 61.13      BLGL
ATOM    295  C   LYS    49      26.779  23.039  41.204  1.00 49.26      BLGL
ATOM    296  O   LYS    49      26.215  22.391  40.320  1.00 50.56      BLGL
ATOM    297  N   LYS    50      26.444  22.953  42.483  1.00 46.67      BLGL
ATOM    298  CA  LYS    50      25.377  22.082  42.955  1.00 44.89      BLGL
ATOM    299  CB  LYS    50      25.229  22.272  44.465  1.00 44.47      BLGL
ATOM    300  CG  LYS    50      24.483  21.182  45.190  1.00 47.37      BLGL
ATOM    301  CD  LYS    50      24.732  21.290  46.692  1.00 50.81      BLGL
ATOM    302  CE  LYS    50      23.926  20.260  47.478  1.00 53.40      BLGL
ATOM    303  NZ  LYS    50      24.326  20.203  48.917  1.00 55.24      BLGL
ATOM    304  C   LYS    50      24.088  22.473  42.221  1.00 43.33      BLGL
ATOM    305  O   LYS    50      23.726  23.647  42.187  1.00 43.90      BLGL
ATOM    306  N   GLN    51      23.400  21.497  41.631  1.00 41.68      BLGL
ATOM    307  CA  GLN    51      22.167  21.765  40.884  1.00 38.41      BLGL
ATOM    308  CB  GLN    51      22.531  22.164  39.449  1.00 38.23      BLGL
ATOM    309  CG  GLN    51      21.352  22.358  38.507  1.00 38.66      BLGL
ATOM    310  CD  GLN    51      21.797  22.731  37.099  1.00 38.67      BLGL
ATOM    311  OE1 GLN    51      22.206  23.862  36.846  1.00 38.64      BLGL
ATOM    312  NE2 GLN    51      21.730  21.771  36.181  1.00 38.86      BLGL
ATOM    313  C   GLN    51      21.241  20.548  40.867  1.00 35.96      BLGL
ATOM    314  O   GLN    51      21.714  19.417  40.893  1.00 35.98      BLGL
ATOM    315  N   ASP    52      19.928  20.778  40.827  1.00 34.78      BLGL
ATOM    316  CA  ASP    52      18.955  19.677  40.797  1.00 34.16      BLGL
ATOM    317  CB  ASP    52      17.522  20.215  40.657  1.00 35.75      BLGL
ATOM    318  CG  ASP    52      16.475  19.100  40.603  1.00 36.25      BLGL
ATOM    319  OD1 ASP    52      15.271  19.396  40.465  1.00 35.18      BLGL
ATOM    320  OD2 ASP    52      16.857  17.919  40.703  1.00 41.59      BLGL
ATOM    321  C   ASP    52      19.269  18.760  39.610  1.00 33.33      BLGL
ATOM    322  O   ASP    52      19.475  19.231  38.483  1.00 33.59      BLGL
ATOM    323  N   ILE    53      19.294  17.454  39.856  1.00 29.47      BLGL
ATOM    324  CA  ILE    53      19.620  16.512  38.797  1.00 26.79      BLGL
ATOM    325  CB  ILE    53      19.692  15.059  39.336  1.00 25.32      BLGL
ATOM    326  CG2 ILE    53      18.304  14.567  39.715  1.00 24.80      BLGL
ATOM    327  CG1 ILE    53      20.326  14.147  38.277  1.00 25.86      BLGL
ATOM    328  CD1 ILE    53      20.638  12.753  38.777  1.00 25.81      BLGL
ATOM    329  C   ILE    53      18.644  16.588  37.631  1.00 25.41      BLGL
```

Fig. 4 cont.

| ATOM | 330 | O   | ILE | 53 | 19.042 | 16.436 | 36.475 | 1.00 | 23.70 | BLGL |
| ATOM | 331 | N   | PHE | 54 | 17.372 | 16.836 | 37.926 | 1.00 | 23.59 | BLGL |
| ATOM | 332 | CA  | PHE | 54 | 16.380 | 16.930 | 36.868 | 1.00 | 25.83 | BLGL |
| ATOM | 333 | CB  | PHE | 54 | 14.972 | 17.002 | 37.456 | 1.00 | 23.83 | BLGL |
| ATOM | 334 | CG  | PHE | 54 | 14.526 | 15.723 | 38.072 | 1.00 | 22.74 | BLGL |
| ATOM | 335 | CD1 | PHE | 54 | 14.799 | 15.449 | 39.402 | 1.00 | 25.01 | BLGL |
| ATOM | 336 | CD2 | PHE | 54 | 13.885 | 14.760 | 37.306 | 1.00 | 21.32 | BLGL |
| ATOM | 337 | CE1 | PHE | 54 | 14.443 | 14.229 | 39.961 | 1.00 | 27.14 | BLGL |
| ATOM | 338 | CE2 | PHE | 54 | 13.525 | 13.537 | 37.856 | 1.00 | 23.72 | BLGL |
| ATOM | 339 | CZ  | PHE | 54 | 13.803 | 13.268 | 39.184 | 1.00 | 24.12 | BLGL |
| ATOM | 340 | C   | PHE | 54 | 16.641 | 18.121 | 35.953 | 1.00 | 27.75 | BLGL |
| ATOM | 341 | O   | PHE | 54 | 16.378 | 18.064 | 34.753 | 1.00 | 27.66 | BLGL |
| ATOM | 342 | N   | ASN | 55 | 17.167 | 19.197 | 36.522 | 1.00 | 30.60 | BLGL |
| ATOM | 343 | CA  | ASN | 55 | 17.485 | 20.385 | 35.740 | 1.00 | 32.40 | BLGL |
| ATOM | 344 | CB  | ASN | 55 | 17.927 | 21.528 | 36.665 | 1.00 | 38.72 | BLGL |
| ATOM | 345 | CG  | ASN | 55 | 18.157 | 22.835 | 35.919 | 1.00 | 43.16 | BLGL |
| ATOM | 346 | OD1 | ASN | 55 | 18.775 | 23.767 | 36.444 | 1.00 | 46.30 | BLGL |
| ATOM | 347 | ND2 | ASN | 55 | 17.657 | 22.912 | 34.692 | 1.00 | 47.38 | BLGL |
| ATOM | 348 | C   | ASN | 55 | 18.631 | 19.996 | 34.808 | 1.00 | 30.86 | BLGL |
| ATOM | 349 | O   | ASN | 55 | 18.624 | 20.327 | 33.623 | 1.00 | 29.18 | BLGL |
| ATOM | 350 | N   | THR | 56 | 19.608 | 19.281 | 35.363 | 1.00 | 28.42 | BLGL |
| ATOM | 351 | CA  | THR | 56 | 20.765 | 18.824 | 34.606 | 1.00 | 26.82 | BLGL |
| ATOM | 352 | CB  | THR | 56 | 21.769 | 18.101 | 35.514 | 1.00 | 27.58 | BLGL |
| ATOM | 353 | OG1 | THR | 56 | 22.198 | 18.988 | 36.558 | 1.00 | 29.47 | BLGL |
| ATOM | 354 | CG2 | THR | 56 | 22.969 | 17.642 | 34.714 | 1.00 | 22.45 | BLGL |
| ATOM | 355 | C   | THR | 56 | 20.353 | 17.870 | 33.489 | 1.00 | 27.22 | BLGL |
| ATOM | 356 | O   | THR | 56 | 20.851 | 17.952 | 32.366 | 1.00 | 27.23 | BLGL |
| ATOM | 357 | N   | LEU | 57 | 19.441 | 16.961 | 33.805 | 1.00 | 27.52 | BLGL |
| ATOM | 358 | CA  | LEU | 57 | 18.950 | 15.997 | 32.830 | 1.00 | 27.42 | BLGL |
| ATOM | 359 | CB  | LEU | 57 | 17.978 | 15.033 | 33.508 | 1.00 | 26.87 | BLGL |
| ATOM | 360 | CG  | LEU | 57 | 18.453 | 13.617 | 33.847 | 1.00 | 26.41 | BLGL |
| ATOM | 361 | CD1 | LEU | 57 | 19.941 | 13.572 | 34.078 | 1.00 | 23.65 | BLGL |
| ATOM | 362 | CD2 | LEU | 57 | 17.691 | 13.138 | 35.074 | 1.00 | 25.32 | BLGL |
| ATOM | 363 | C   | LEU | 57 | 18.257 | 16.686 | 31.662 | 1.00 | 28.88 | BLGL |
| ATOM | 364 | O   | LEU | 57 | 18.430 | 16.288 | 30.515 | 1.00 | 29.93 | BLGL |
| ATOM | 365 | N   | LYS | 58 | 17.474 | 17.718 | 31.959 | 1.00 | 30.47 | BLGL |
| ATOM | 366 | CA  | LYS | 58 | 16.757 | 18.455 | 30.926 | 1.00 | 30.56 | BLGL |
| ATOM | 367 | CB  | LYS | 58 | 15.836 | 19.507 | 31.561 | 1.00 | 32.82 | BLGL |
| ATOM | 368 | CG  | LYS | 58 | 15.038 | 20.330 | 30.551 | 1.00 | 33.72 | BLGL |
| ATOM | 369 | CD  | LYS | 58 | 14.129 | 19.438 | 29.710 | 1.00 | 36.45 | BLGL |
| ATOM | 370 | CE  | LYS | 58 | 13.279 | 20.253 | 28.732 | 1.00 | 38.35 | BLGL |
| ATOM | 371 | NZ  | LYS | 58 | 12.233 | 19.436 | 28.049 | 1.00 | 36.51 | BLGL |
| ATOM | 372 | C   | LYS | 58 | 17.726 | 19.135 | 29.969 | 1.00 | 30.23 | BLGL |
| ATOM | 373 | O   | LYS | 58 | 17.564 | 19.064 | 28.753 | 1.00 | 31.14 | BLGL |
| ATOM | 374 | N   | GLU | 59 | 18.734 | 19.793 | 30.522 | 1.00 | 30.65 | BLGL |
| ATOM | 375 | CA  | GLU | 59 | 19.722 | 20.483 | 29.709 | 1.00 | 31.60 | BLGL |
| ATOM | 376 | CB  | GLU | 59 | 20.668 | 21.275 | 30.610 | 1.00 | 35.74 | BLGL |
| ATOM | 377 | CG  | GLU | 59 | 19.971 | 22.381 | 31.397 | 1.00 | 42.93 | BLGL |
| ATOM | 378 | CD  | GLU | 59 | 20.839 | 22.960 | 32.511 | 1.00 | 48.75 | BLGL |
| ATOM | 379 | OE1 | GLU | 59 | 20.327 | 23.818 | 33.264 | 1.00 | 51.01 | BLGL |
| ATOM | 380 | OE2 | GLU | 59 | 22.026 | 22.558 | 32.638 | 1.00 | 51.49 | BLGL |
| ATOM | 381 | C   | GLU | 59 | 20.511 | 19.493 | 28.862 | 1.00 | 30.47 | BLGL |
| ATOM | 382 | O   | GLU | 59 | 21.086 | 19.859 | 27.838 | 1.00 | 30.17 | BLGL |
| ATOM | 383 | N   | ALA | 60 | 20.531 | 18.235 | 29.293 | 1.00 | 29.36 | BLGL |
| ATOM | 384 | CA  | ALA | 60 | 21.253 | 17.186 | 28.582 | 1.00 | 28.02 | BLGL |
| ATOM | 385 | CB  | ALA | 60 | 21.611 | 16.065 | 29.543 | 1.00 | 29.83 | BLGL |
| ATOM | 386 | C   | ALA | 60 | 20.461 | 16.623 | 27.406 | 1.00 | 27.47 | BLGL |
| ATOM | 387 | O   | ALA | 60 | 20.975 | 15.807 | 26.643 | 1.00 | 26.82 | BLGL |
| ATOM | 388 | N   | GLY | 61 | 19.208 | 17.048 | 27.269 | 1.00 | 27.12 | BLGL |
| ATOM | 389 | CA  | GLY | 61 | 18.387 | 16.574 | 26.167 | 1.00 | 25.98 | BLGL |
| ATOM | 390 | C   | GLY | 61 | 17.379 | 15.484 | 26.500 | 1.00 | 24.46 | BLGL |
| ATOM | 391 | O   | GLY | 61 | 16.678 | 14.995 | 25.613 | 1.00 | 22.97 | BLGL |
| ATOM | 392 | N   | VAL | 62 | 17.307 | 15.101 | 27.773 | 1.00 | 23.85 | BLGL |
| ATOM | 393 | CA  | VAL | 62 | 16.373 | 14.075 | 28.223 | 1.00 | 22.41 | BLGL |
| ATOM | 394 | CB  | VAL | 62 | 16.738 | 13.577 | 29.651 | 1.00 | 22.60 | BLGL |
| ATOM | 395 | CG1 | VAL | 62 | 15.754 | 12.514 | 30.107 | 1.00 | 22.01 | BLGL |

Fig. 4 cont.

```
ATOM    396  CG2 VAL    62      18.146  13.018  29.664  1.00 20.65      BLGL
ATOM    397  C   VAL    62      14.958  14.658  28.230  1.00 22.28      BLGL
ATOM    398  O   VAL    62      14.743  15.783  28.686  1.00 24.37      BLGL
ATOM    399  N   ASN    63      13.997  13.896  27.721  1.00 20.64      BLGL
ATOM    400  CA  ASN    63      12.615  14.356  27.660  1.00 21.22      BLGL
ATOM    401  CB  ASN    63      12.203  14.546  26.204  1.00 20.41      BLGL
ATOM    402  CG  ASN    63      12.528  13.337  25.349  1.00 20.90      BLGL
ATOM    403  OD1 ASN    63      12.248  12.195  25.723  1.00 22.33      BLGL
ATOM    404  ND2 ASN    63      13.112  13.581  24.189  1.00 20.98      BLGL
ATOM    405  C   ASN    63      11.641  13.396  28.330  1.00 21.56      BLGL
ATOM    406  O   ASN    63      10.426  13.606  28.304  1.00 24.89      BLGL
ATOM    407  N   TYR    64      12.171  12.346  28.939  1.00 19.85      BLGL
ATOM    408  CA  TYR    64      11.323  11.360  29.578  1.00 18.37      BLGL
ATOM    409  CB  TYR    64      11.054  10.226  28.590  1.00 18.15      BLGL
ATOM    410  CG  TYR    64       9.601  10.025  28.244  1.00 18.02      BLGL
ATOM    411  CD1 TYR    64       8.724   9.446  29.155  1.00 16.59      BLGL
ATOM    412  CE1 TYR    64       7.397   9.210  28.821  1.00 17.75      BLGL
ATOM    413  CD2 TYR    64       9.109  10.375  26.985  1.00 20.14      BLGL
ATOM    414  CE2 TYR    64       7.781  10.145  26.640  1.00 17.07      BLGL
ATOM    415  CZ  TYR    64       6.935   9.560  27.562  1.00 18.10      BLGL
ATOM    416  OH  TYR    64       5.634   9.301  27.223  1.00 19.97      BLGL
ATOM    417  C   TYR    64      11.963  10.804  30.839  1.00 17.64      BLGL
ATOM    418  O   TYR    64      13.181  10.683  30.927  1.00 17.84      BLGL
ATOM    419  N   VAL    65      11.137  10.470  31.819  1.00 15.63      BLGL
ATOM    420  CA  VAL    65      11.644   9.905  33.050  1.00 16.50      BLGL
ATOM    421  CB  VAL    65      11.567  10.909  34.215  1.00 15.92      BLGL
ATOM    422  CG1 VAL    65      11.909  10.207  35.522  1.00 14.90      BLGL
ATOM    423  CG2 VAL    65      12.536  12.055  33.975  1.00 14.25      BLGL
ATOM    424  C   VAL    65      10.847   8.668  33.414  1.00 15.70      BLGL
ATOM    425  O   VAL    65       9.621   8.691  33.388  1.00 16.30      BLGL
ATOM    426  N   ARG    66      11.548   7.587  33.740  1.00 15.28      BLGL
ATOM    427  CA  ARG    66      10.898   6.343  34.126  1.00 14.69      BLGL
ATOM    428  CB  ARG    66      11.520   5.145  33.396  1.00 12.92      BLGL
ATOM    429  CG  ARG    66      10.676   3.897  33.521  1.00 16.36      BLGL
ATOM    430  CD  ARG    66      11.131   2.751  32.621  1.00 17.95      BLGL
ATOM    431  NE  ARG    66      11.997   1.835  33.347  1.00 21.82      BLGL
ATOM    432  CZ  ARG    66      11.882   0.514  33.336  1.00 20.23      BLGL
ATOM    433  NH1 ARG    66      10.933  -0.072  32.628  1.00 20.47      BLGL
ATOM    434  NH2 ARG    66      12.720  -0.218  34.050  1.00 22.65      BLGL
ATOM    435  C   ARG    66      11.049   6.155  35.627  1.00 15.52      BLGL
ATOM    436  O   ARG    66      12.097   6.461  36.194  1.00 19.23      BLGL
ATOM    437  N   VAL    67      10.003   5.663  36.277  1.00 14.45      BLGL
ATOM    438  CA  VAL    67      10.065   5.437  37.709  1.00 14.29      BLGL
ATOM    439  CB  VAL    67       9.387   6.591  38.500  1.00 14.34      BLGL
ATOM    440  CG1 VAL    67       8.010   6.866  37.946  1.00 15.07      BLGL
ATOM    441  CG2 VAL    67       9.279   6.226  39.974  1.00 14.76      BLGL
ATOM    442  C   VAL    67       9.380   4.134  38.050  1.00 13.80      BLGL
ATOM    443  O   VAL    67       8.243   3.902  37.652  1.00 16.06      BLGL
ATOM    444  N   ARG    68      10.084   3.274  38.772  1.00 12.24      BLGL
ATOM    445  CA  ARG    68       9.512   2.007  39.170  1.00 13.36      BLGL
ATOM    446  CB  ARG    68      10.613   0.987  39.505  1.00 15.94      BLGL
ATOM    447  CG  ARG    68      11.653   1.445  40.530  1.00 16.59      BLGL
ATOM    448  CD  ARG    68      12.582   0.299  40.946  1.00 17.71      BLGL
ATOM    449  NE  ARG    68      13.727   0.787  41.717  1.00 20.66      BLGL
ATOM    450  CZ  ARG    68      14.806   1.365  41.187  1.00 19.69      BLGL
ATOM    451  NH1 ARG    68      15.791   1.788  41.964  1.00 18.60      BLGL
ATOM    452  NH2 ARG    68      14.912   1.502  39.876  1.00 19.53      BLGL
ATOM    453  C   ARG    68       8.621   2.250  40.383  1.00 16.28      BLGL
ATOM    454  O   ARG    68       8.875   3.152  41.185  1.00 13.92      BLGL
ATOM    455  N   ILE    69       7.567   1.449  40.506  1.00 16.59      BLGL
ATOM    456  CA  ILE    69       6.649   1.582  41.619  1.00 17.08      BLGL
ATOM    457  CB  ILE    69       5.331   2.254  41.176  1.00 17.80      BLGL
ATOM    458  CG2 ILE    69       4.442   2.505  42.392  1.00 16.20      BLGL
ATOM    459  CG1 ILE    69       5.634   3.577  40.463  1.00 18.54      BLGL
ATOM    460  CD1 ILE    69       4.420   4.258  39.861  1.00 16.60      BLGL
ATOM    461  C   ILE    69       6.326   0.224  42.227  1.00 19.49      BLGL
```

Fig. 4 cont.

| | | | | | | | | | | |
|---|---|---|---|---|---|---|---|---|---|---|
| ATOM | 462 | O | ILE | 69 | 5.851 | -0.684 | 41.537 | 1.00 | 21.07 | BLGL |
| ATOM | 463 | N | TRP | 70 | 6.613 | 0.088 | 43.518 | 1.00 | 19.80 | BLGL |
| ATOM | 464 | CA | TRP | 70 | 6.329 | -1.132 | 44.261 | 1.00 | 20.02 | BLGL |
| ATOM | 465 | CB | TRP | 70 | 7.534 | -1.548 | 45.108 | 1.00 | 20.03 | BLGL |
| ATOM | 466 | CG | TRP | 70 | 8.693 | -2.052 | 44.299 | 1.00 | 20.74 | BLGL |
| ATOM | 467 | CD2 | TRP | 70 | 10.078 | -1.707 | 44.460 | 1.00 | 20.58 | BLGL |
| ATOM | 468 | CE2 | TRP | 70 | 10.807 | -2.445 | 43.496 | 1.00 | 20.35 | BLGL |
| ATOM | 469 | CE3 | TRP | 70 | 10.774 | -0.847 | 45.322 | 1.00 | 19.46 | BLGL |
| ATOM | 470 | CD1 | TRP | 70 | 8.643 | -2.958 | 43.278 | 1.00 | 20.51 | BLGL |
| ATOM | 471 | NE1 | TRP | 70 | 9.906 | -3.198 | 42.791 | 1.00 | 18.08 | BLGL |
| ATOM | 472 | CZ2 | TRP | 70 | 12.200 | -2.350 | 43.372 | 1.00 | 17.40 | BLGL |
| ATOM | 473 | CZ3 | TRP | 70 | 12.162 | -0.752 | 45.197 | 1.00 | 18.53 | BLGL |
| ATOM | 474 | CH2 | TRP | 70 | 12.856 | -1.501 | 44.227 | 1.00 | 17.88 | BLGL |
| ATOM | 475 | C | TRP | 70 | 5.145 | -0.805 | 45.164 | 1.00 | 21.18 | BLGL |
| ATOM | 476 | O | TRP | 70 | 5.010 | 0.328 | 45.626 | 1.00 | 20.39 | BLGL |
| ATOM | 477 | N | ASN | 71 | 4.279 | -1.782 | 45.405 | 1.00 | 21.89 | BLGL |
| ATOM | 478 | CA | ASN | 71 | 3.105 | -1.553 | 46.238 | 1.00 | 23.11 | BLGL |
| ATOM | 479 | CB | ASN | 71 | 2.204 | -2.787 | 46.234 | 1.00 | 21.89 | BLGL |
| ATOM | 480 | CG | ASN | 71 | 1.600 | -3.059 | 44.875 | 1.00 | 24.42 | BLGL |
| ATOM | 481 | OD1 | ASN | 71 | 2.312 | -3.325 | 43.907 | 1.00 | 24.93 | BLGL |
| ATOM | 482 | ND2 | ASN | 71 | 0.277 | -2.986 | 44.792 | 1.00 | 24.52 | BLGL |
| ATOM | 483 | C | ASN | 71 | 3.454 | -1.182 | 47.673 | 1.00 | 23.89 | BLGL |
| ATOM | 484 | O | ASN | 71 | 3.114 | -0.093 | 48.150 | 1.00 | 23.65 | BLGL |
| ATOM | 485 | N | ASP | 72 | 4.139 | -2.094 | 48.356 | 1.00 | 25.19 | BLGL |
| ATOM | 486 | CA | ASP | 72 | 4.531 | -1.888 | 49.747 | 1.00 | 24.90 | BLGL |
| ATOM | 487 | CB | ASP | 72 | 3.576 | -2.642 | 50.669 | 1.00 | 24.77 | BLGL |
| ATOM | 488 | CG | ASP | 72 | 3.706 | -2.214 | 52.105 | 1.00 | 25.24 | BLGL |
| ATOM | 489 | OD1 | ASP | 72 | 3.494 | -3.063 | 52.990 | 1.00 | 26.84 | BLGL |
| ATOM | 490 | OD2 | ASP | 72 | 4.006 | -1.026 | 52.346 | 1.00 | 24.35 | BLGL |
| ATOM | 491 | C | ASP | 72 | 5.953 | -2.384 | 49.997 | 1.00 | 24.58 | BLGL |
| ATOM | 492 | O | ASP | 72 | 6.151 | -3.472 | 50.538 | 1.00 | 25.47 | BLGL |
| ATOM | 493 | N | PRO | 73 | 6.962 | -1.586 | 49.619 | 1.00 | 24.27 | BLGL |
| ATOM | 494 | CD | PRO | 73 | 6.856 | -0.281 | 48.940 | 1.00 | 23.33 | BLGL |
| ATOM | 495 | CA | PRO | 73 | 8.366 | -1.962 | 49.805 | 1.00 | 24.32 | BLGL |
| ATOM | 496 | CB | PRO | 73 | 9.091 | -1.009 | 48.866 | 1.00 | 24.01 | BLGL |
| ATOM | 497 | CG | PRO | 73 | 8.272 | 0.237 | 49.001 | 1.00 | 23.40 | BLGL |
| ATOM | 498 | C | PRO | 73 | 8.863 | -1.840 | 51.248 | 1.00 | 27.14 | BLGL |
| ATOM | 499 | O | PRO | 73 | 9.987 | -1.395 | 51.491 | 1.00 | 28.54 | BLGL |
| ATOM | 500 | N | TYR | 74 | 8.033 | -2.233 | 52.208 | 1.00 | 27.12 | BLGL |
| ATOM | 501 | CA | TYR | 74 | 8.429 | -2.147 | 53.609 | 1.00 | 26.57 | BLGL |
| ATOM | 502 | CB | TYR | 74 | 7.838 | -0.889 | 54.256 | 1.00 | 25.70 | BLGL |
| ATOM | 503 | CG | TYR | 74 | 8.022 | 0.386 | 53.463 | 1.00 | 21.92 | BLGL |
| ATOM | 504 | CD1 | TYR | 74 | 7.148 | 0.721 | 52.427 | 1.00 | 22.26 | BLGL |
| ATOM | 505 | CE1 | TYR | 74 | 7.304 | 1.909 | 51.707 | 1.00 | 21.83 | BLGL |
| ATOM | 506 | CD2 | TYR | 74 | 9.057 | 1.265 | 53.758 | 1.00 | 18.92 | BLGL |
| ATOM | 507 | CE2 | TYR | 74 | 9.223 | 2.448 | 53.049 | 1.00 | 19.47 | BLGL |
| ATOM | 508 | CZ | TYR | 74 | 8.345 | 2.766 | 52.026 | 1.00 | 21.06 | BLGL |
| ATOM | 509 | OH | TYR | 74 | 8.503 | 3.939 | 51.323 | 1.00 | 21.16 | BLGL |
| ATOM | 510 | C | TYR | 74 | 7.970 | -3.371 | 54.395 | 1.00 | 26.69 | BLGL |
| ATOM | 511 | O | TYR | 74 | 7.119 | -4.131 | 53.928 | 1.00 | 26.70 | BLGL |
| ATOM | 512 | N | ASP | 75 | 8.547 | -3.568 | 55.579 | 1.00 | 25.47 | BLGL |
| ATOM | 513 | CA | ASP | 75 | 8.151 | -4.687 | 56.422 | 1.00 | 25.66 | BLGL |
| ATOM | 514 | CB | ASP | 75 | 9.348 | -5.260 | 57.201 | 1.00 | 26.96 | BLGL |
| ATOM | 515 | CG | ASP | 75 | 9.948 | -4.282 | 58.207 | 1.00 | 26.69 | BLGL |
| ATOM | 516 | OD1 | ASP | 75 | 10.931 | -4.668 | 58.867 | 1.00 | 25.84 | BLGL |
| ATOM | 517 | OD2 | ASP | 75 | 9.455 | -3.146 | 58.350 | 1.00 | 28.52 | BLGL |
| ATOM | 518 | C | ASP | 75 | 7.060 | -4.208 | 57.367 | 1.00 | 26.20 | BLGL |
| ATOM | 519 | O | ASP | 75 | 6.634 | -3.063 | 57.286 | 1.00 | 27.42 | BLGL |
| ATOM | 520 | N | ALA | 76 | 6.602 | -5.078 | 58.255 | 1.00 | 27.05 | BLGL |
| ATOM | 521 | CA | ALA | 76 | 5.535 | -4.722 | 59.184 | 1.00 | 28.91 | BLGL |
| ATOM | 522 | CB | ALA | 76 | 5.304 | -5.869 | 60.153 | 1.00 | 29.44 | BLGL |
| ATOM | 523 | C | ALA | 76 | 5.793 | -3.438 | 59.964 | 1.00 | 29.89 | BLGL |
| ATOM | 524 | O | ALA | 76 | 4.873 | -2.666 | 60.241 | 1.00 | 31.61 | BLGL |
| ATOM | 525 | N | ASN | 77 | 7.051 | -3.213 | 60.307 | 1.00 | 29.94 | BLGL |
| ATOM | 526 | CA | ASN | 77 | 7.445 | -2.059 | 61.091 | 1.00 | 30.08 | BLGL |
| ATOM | 527 | CB | ASN | 77 | 8.619 | -2.460 | 61.970 | 1.00 | 30.88 | BLGL |

Fig. 4 cont.

| | | | | | | | | | |
|---|---|---|---|---|---|---|---|---|---|
| ATOM | 528 | CG | ASN | 77 | 8.337 | -3.728 | 62.740 | 1.00 31.46 | BLGL |
| ATOM | 529 | OD1 | ASN | 77 | 9.085 | -4.700 | 62.659 | 1.00 35.40 | BLGL |
| ATOM | 530 | ND2 | ASN | 77 | 7.241 | -3.729 | 63.485 | 1.00 29.08 | BLGL |
| ATOM | 531 | C | ASN | 77 | 7.768 | -0.802 | 60.294 | 1.00 30.14 | BLGL |
| ATOM | 532 | O | ASN | 77 | 8.048 | 0.249 | 60.874 | 1.00 31.47 | BLGL |
| ATOM | 533 | N | GLY | 78 | 7.742 | -0.906 | 58.971 | 1.00 29.60 | BLGL |
| ATOM | 534 | CA | GLY | 78 | 7.998 | 0.260 | 58.146 | 1.00 30.47 | BLGL |
| ATOM | 535 | C | GLY | 78 | 9.422 | 0.434 | 57.665 | 1.00 30.69 | BLGL |
| ATOM | 536 | O | GLY | 78 | 9.803 | 1.524 | 57.243 | 1.00 31.23 | BLGL |
| ATOM | 537 | N | ASN | 79 | 10.212 | -0.631 | 57.735 | 1.00 30.64 | BLGL |
| ATOM | 538 | CA | ASN | 79 | 11.599 | -0.586 | 57.285 | 1.00 31.66 | BLGL |
| ATOM | 539 | CB | ASN | 79 | 12.437 | -1.618 | 58.043 | 1.00 32.77 | BLGL |
| ATOM | 540 | CG | ASN | 79 | 12.478 | -1.356 | 59.539 | 1.00 32.28 | BLGL |
| ATOM | 541 | OD1 | ASN | 79 | 12.875 | -0.277 | 59.981 | 1.00 31.97 | BLGL |
| ATOM | 542 | ND2 | ASN | 79 | 12.074 | -2.346 | 60.325 | 1.00 29.86 | BLGL |
| ATOM | 543 | C | ASN | 79 | 11.652 | -0.888 | 55.788 | 1.00 31.40 | BLGL |
| ATOM | 544 | O | ASN | 79 | 11.253 | -1.971 | 55.352 | 1.00 31.55 | BLGL |
| ATOM | 545 | N | GLY | 80 | 12.146 | 0.072 | 55.013 | 1.00 30.48 | BLGL |
| ATOM | 546 | CA | GLY | 80 | 12.224 | -0.092 | 53.573 | 1.00 28.01 | BLGL |
| ATOM | 547 | C | GLY | 80 | 13.066 | -1.265 | 53.132 | 1.00 26.92 | BLGL |
| ATOM | 548 | O | GLY | 80 | 14.104 | -1.544 | 53.737 | 1.00 28.09 | BLGL |
| ATOM | 549 | N | TYR | 81 | 12.611 | -1.958 | 52.089 | 1.00 25.24 | BLGL |
| ATOM | 550 | CA | TYR | 81 | 13.330 | -3.110 | 51.539 | 1.00 24.70 | BLGL |
| ATOM | 551 | CB | TYR | 81 | 12.446 | -3.891 | 50.559 | 1.00 26.19 | BLGL |
| ATOM | 552 | CG | TYR | 81 | 11.309 | -4.704 | 51.155 | 1.00 28.51 | BLGL |
| ATOM | 553 | CD1 | TYR | 81 | 10.337 | -5.264 | 50.324 | 1.00 30.98 | BLGL |
| ATOM | 554 | CE1 | TYR | 81 | 9.285 | -6.014 | 50.836 | 1.00 33.39 | BLGL |
| ATOM | 555 | CD2 | TYR | 81 | 11.202 | -4.919 | 52.525 | 1.00 27.25 | BLGL |
| ATOM | 556 | CE2 | TYR | 81 | 10.151 | -5.673 | 53.053 | 1.00 30.71 | BLGL |
| ATOM | 557 | CZ | TYR | 81 | 9.191 | -6.218 | 52.201 | 1.00 32.59 | BLGL |
| ATOM | 558 | OH | TYR | 81 | 8.134 | -6.955 | 52.701 | 1.00 29.32 | BLGL |
| ATOM | 559 | C | TYR | 81 | 14.581 | -2.643 | 50.791 | 1.00 23.17 | BLGL |
| ATOM | 560 | O | TYR | 81 | 15.424 | -3.449 | 50.411 | 1.00 22.30 | BLGL |
| ATOM | 561 | N | GLY | 82 | 14.692 | -1.337 | 50.575 | 1.00 22.25 | BLGL |
| ATOM | 562 | CA | GLY | 82 | 15.840 | -0.812 | 49.863 | 1.00 22.06 | BLGL |
| ATOM | 563 | C | GLY | 82 | 15.544 | -0.631 | 48.388 | 1.00 23.07 | BLGL |
| ATOM | 564 | O | GLY | 82 | 14.392 | -0.466 | 47.994 | 1.00 22.83 | BLGL |
| ATOM | 565 | N | GLY | 83 | 16.582 | -0.660 | 47.561 | 1.00 23.84 | BLGL |
| ATOM | 566 | CA | GLY | 83 | 16.384 | -0.485 | 46.133 | 1.00 23.31 | BLGL |
| ATOM | 567 | C | GLY | 83 | 15.731 | 0.843 | 45.796 | 1.00 23.19 | BLGL |
| ATOM | 568 | O | GLY | 83 | 15.219 | 1.024 | 44.693 | 1.00 23.86 | BLGL |
| ATOM | 569 | N | GLY | 84 | 15.740 | 1.772 | 46.748 | 1.00 22.55 | BLGL |
| ATOM | 570 | CA | GLY | 84 | 15.142 | 3.075 | 46.514 | 1.00 18.60 | BLGL |
| ATOM | 571 | C | GLY | 84 | 13.832 | 3.262 | 47.243 | 1.00 18.25 | BLGL |
| ATOM | 572 | O | GLY | 84 | 13.282 | 4.354 | 47.254 | 1.00 19.59 | BLGL |
| ATOM | 573 | N | ASN | 85 | 13.339 | 2.199 | 47.867 | 1.00 18.82 | BLGL |
| ATOM | 574 | CA | ASN | 85 | 12.070 | 2.246 | 48.591 | 1.00 22.71 | BLGL |
| ATOM | 575 | CB | ASN | 85 | 12.217 | 3.011 | 49.914 | 1.00 22.20 | BLGL |
| ATOM | 576 | CG | ASN | 85 | 13.143 | 2.319 | 50.902 | 1.00 24.42 | BLGL |
| ATOM | 577 | OD1 | ASN | 85 | 13.320 | 1.102 | 50.869 | 1.00 25.77 | BLGL |
| ATOM | 578 | ND2 | ASN | 85 | 13.721 | 3.098 | 51.806 | 1.00 25.80 | BLGL |
| ATOM | 579 | C | ASN | 85 | 11.004 | 2.929 | 47.729 | 1.00 23.49 | BLGL |
| ATOM | 580 | O | ASN | 85 | 10.235 | 3.761 | 48.214 | 1.00 23.21 | BLGL |
| ATOM | 581 | N | ASN | 86 | 10.950 | 2.566 | 46.452 | 1.00 23.70 | BLGL |
| ATOM | 582 | CA | ASN | 86 | 10.001 | 3.196 | 45.546 | 1.00 24.44 | BLGL |
| ATOM | 583 | CB | ASN | 86 | 10.447 | 3.008 | 44.106 | 1.00 21.35 | BLGL |
| ATOM | 584 | CG | ASN | 86 | 11.781 | 3.627 | 43.847 | 1.00 21.48 | BLGL |
| ATOM | 585 | OD1 | ASN | 86 | 12.811 | 2.972 | 43.976 | 1.00 22.65 | BLGL |
| ATOM | 586 | ND2 | ASN | 86 | 11.781 | 4.908 | 43.500 | 1.00 20.47 | BLGL |
| ATOM | 587 | C | ASN | 86 | 8.546 | 2.785 | 45.679 | 1.00 25.13 | BLGL |
| ATOM | 588 | O | ASN | 86 | 8.159 | 1.666 | 45.357 | 1.00 23.77 | BLGL |
| ATOM | 589 | N | ASP | 87 | 7.742 | 3.723 | 46.155 | 1.00 25.52 | BLGL |
| ATOM | 590 | CA | ASP | 87 | 6.323 | 3.500 | 46.323 | 1.00 26.02 | BLGL |
| ATOM | 591 | CB | ASP | 87 | 5.954 | 3.547 | 47.803 | 1.00 25.67 | BLGL |
| ATOM | 592 | CG | ASP | 87 | 6.584 | 4.724 | 48.524 | 1.00 30.07 | BLGL |
| ATOM | 593 | OD1 | ASP | 87 | 6.994 | 5.705 | 47.851 | 1.00 29.90 | BLGL |

Fig. 4 cont.

| | | | | | | | | | |
|---|---|---|---|---|---|---|---|---|---|
| ATOM | 594 | OD2 | ASP | 87 | 6.656 | 4.668 | 49.771 | 1.00 31.21 | BLGL |
| ATOM | 595 | C | ASP | 87 | 5.625 | 4.613 | 45.566 | 1.00 25.13 | BLGL |
| ATOM | 596 | O | ASP | 87 | 6.276 | 5.396 | 44.877 | 1.00 25.07 | BLGL |
| ATOM | 597 | N | LEU | 88 | 4.307 | 4.693 | 45.694 | 1.00 25.05 | BLGL |
| ATOM | 598 | CA | LEU | 88 | 3.566 | 5.732 | 44.996 | 1.00 27.31 | BLGL |
| ATOM | 599 | CB | LEU | 88 | 2.059 | 5.528 | 45.183 | 1.00 25.49 | BLGL |
| ATOM | 600 | CG | LEU | 88 | 1.163 | 6.603 | 44.564 | 1.00 23.47 | BLGL |
| ATOM | 601 | CD1 | LEU | 88 | 1.378 | 6.668 | 43.059 | 1.00 23.31 | BLGL |
| ATOM | 602 | CD2 | LEU | 88 | -0.283 | 6.294 | 44.880 | 1.00 23.48 | BLGL |
| ATOM | 603 | C | LEU | 88 | 3.956 | 7.146 | 45.440 | 1.00 28.05 | BLGL |
| ATOM | 604 | O | LEU | 88 | 3.942 | 8.072 | 44.633 | 1.00 28.88 | BLGL |
| ATOM | 605 | N | GLU | 89 | 4.310 | 7.312 | 46.713 | 1.00 28.47 | BLGL |
| ATOM | 606 | CA | GLU | 89 | 4.679 | 8.627 | 47.223 | 1.00 31.19 | BLGL |
| ATOM | 607 | CB | GLU | 89 | 4.884 | 8.596 | 48.743 | 1.00 38.35 | BLGL |
| ATOM | 608 | CG | GLU | 89 | 4.732 | 7.224 | 49.404 | 1.00 49.47 | BLGL |
| ATOM | 609 | CD | GLU | 89 | 3.309 | 6.673 | 49.355 | 1.00 54.88 | BLGL |
| ATOM | 610 | OE1 | GLU | 89 | 3.095 | 5.617 | 48.709 | 1.00 55.88 | BLGL |
| ATOM | 611 | OE2 | GLU | 89 | 2.413 | 7.297 | 49.968 | 1.00 58.86 | BLGL |
| ATOM | 612 | C | GLU | 89 | 5.931 | 9.157 | 46.547 | 1.00 28.83 | BLGL |
| ATOM | 613 | O | GLU | 89 | 5.958 | 10.293 | 46.083 | 1.00 29.30 | BLGL |
| ATOM | 614 | N | LYS | 90 | 6.970 | 8.337 | 46.486 | 1.00 27.00 | BLGL |
| ATOM | 615 | CA | LYS | 90 | 8.202 | 8.758 | 45.833 | 1.00 25.31 | BLGL |
| ATOM | 616 | CB | LYS | 90 | 9.308 | 7.731 | 46.074 | 1.00 24.21 | BLGL |
| ATOM | 617 | CG | LYS | 90 | 9.730 | 7.618 | 47.526 | 1.00 23.42 | BLGL |
| ATOM | 618 | CD | LYS | 90 | 11.003 | 6.815 | 47.664 | 1.00 23.39 | BLGL |
| ATOM | 619 | CE | LYS | 90 | 11.521 | 6.845 | 49.092 | 1.00 22.77 | BLGL |
| ATOM | 620 | NZ | LYS | 90 | 10.589 | 6.181 | 50.039 | 1.00 24.27 | BLGL |
| ATOM | 621 | C | LYS | 90 | 7.966 | 8.940 | 44.333 | 1.00 24.86 | BLGL |
| ATOM | 622 | O | LYS | 90 | 8.604 | 9.779 | 43.696 | 1.00 23.88 | BLGL |
| ATOM | 623 | N | ALA | 91 | 7.043 | 8.157 | 43.776 | 1.00 22.89 | BLGL |
| ATOM | 624 | CA | ALA | 91 | 6.727 | 8.252 | 42.362 | 1.00 23.29 | BLGL |
| ATOM | 625 | CB | ALA | 91 | 5.709 | 7.175 | 41.972 | 1.00 21.21 | BLGL |
| ATOM | 626 | C | ALA | 91 | 6.172 | 9.644 | 42.060 | 1.00 23.82 | BLGL |
| ATOM | 627 | O | ALA | 91 | 6.501 | 10.244 | 41.042 | 1.00 24.10 | BLGL |
| ATOM | 628 | N | ILE | 92 | 5.335 | 10.154 | 42.956 | 1.00 24.44 | BLGL |
| ATOM | 629 | CA | ILE | 92 | 4.743 | 11.471 | 42.782 | 1.00 25.65 | BLGL |
| ATOM | 630 | CB | ILE | 92 | 3.549 | 11.651 | 43.748 | 1.00 26.69 | BLGL |
| ATOM | 631 | CG2 | ILE | 92 | 2.943 | 13.041 | 43.600 | 1.00 25.04 | BLGL |
| ATOM | 632 | CG1 | ILE | 92 | 2.484 | 10.602 | 43.418 | 1.00 27.42 | BLGL |
| ATOM | 633 | CD1 | ILE | 92 | 1.341 | 10.553 | 44.385 | 1.00 25.99 | BLGL |
| ATOM | 634 | C | ILE | 92 | 5.794 | 12.568 | 42.992 | 1.00 25.95 | BLGL |
| ATOM | 635 | O | ILE | 92 | 5.800 | 13.575 | 42.286 | 1.00 26.66 | BLGL |
| ATOM | 636 | N | GLN | 93 | 6.687 | 12.367 | 43.956 | 1.00 25.21 | BLGL |
| ATOM | 637 | CA | GLN | 93 | 7.746 | 13.332 | 44.206 | 1.00 25.19 | BLGL |
| ATOM | 638 | CB | GLN | 93 | 8.623 | 12.886 | 45.369 | 1.00 27.76 | BLGL |
| ATOM | 639 | CG | GLN | 93 | 8.285 | 13.505 | 46.705 | 1.00 33.90 | BLGL |
| ATOM | 640 | CD | GLN | 93 | 9.215 | 13.020 | 47.818 | 1.00 38.24 | BLGL |
| ATOM | 641 | OE1 | GLN | 93 | 9.088 | 11.890 | 48.303 | 1.00 35.85 | BLGL |
| ATOM | 642 | NE2 | GLN | 93 | 10.165 | 13.873 | 48.216 | 1.00 40.86 | BLGL |
| ATOM | 643 | C | GLN | 93 | 8.595 | 13.427 | 42.949 | 1.00 24.82 | BLGL |
| ATOM | 644 | O | GLN | 93 | 8.870 | 14.514 | 42.454 | 1.00 27.29 | BLGL |
| ATOM | 645 | N | ILE | 94 | 9.008 | 12.276 | 42.434 | 1.00 23.84 | BLGL |
| ATOM | 646 | CA | ILE | 94 | 9.818 | 12.225 | 41.223 | 1.00 21.73 | BLGL |
| ATOM | 647 | CB | ILE | 94 | 10.263 | 10.772 | 40.929 | 1.00 20.65 | BLGL |
| ATOM | 648 | CG2 | ILE | 94 | 10.936 | 10.687 | 39.568 | 1.00 19.77 | BLGL |
| ATOM | 649 | CG1 | ILE | 94 | 11.202 | 10.293 | 42.043 | 1.00 18.55 | BLGL |
| ATOM | 650 | CD1 | ILE | 94 | 11.644 | 8.866 | 41.914 | 1.00 12.93 | BLGL |
| ATOM | 651 | C | ILE | 94 | 9.027 | 12.770 | 40.038 | 1.00 21.61 | BLGL |
| ATOM | 652 | O | ILE | 94 | 9.545 | 13.553 | 39.232 | 1.00 19.49 | BLGL |
| ATOM | 653 | N | GLY | 95 | 7.764 | 12.362 | 39.955 | 1.00 22.02 | BLGL |
| ATOM | 654 | CA | GLY | 95 | 6.897 | 12.798 | 38.876 | 1.00 23.64 | BLGL |
| ATOM | 655 | C | GLY | 95 | 6.787 | 14.302 | 38.771 | 1.00 24.52 | BLGL |
| ATOM | 656 | O | GLY | 95 | 6.932 | 14.870 | 37.683 | 1.00 24.81 | BLGL |
| ATOM | 657 | N | LYS | 96 | 6.526 | 14.947 | 39.907 | 1.00 26.80 | BLGL |
| ATOM | 658 | CA | LYS | 96 | 6.401 | 16.403 | 39.971 | 1.00 26.56 | BLGL |
| ATOM | 659 | CB | LYS | 96 | 6.095 | 16.844 | 41.401 | 1.00 26.83 | BLGL |

Fig. 4 cont.

```
ATOM    660  CG   LYS   96       4.653   16.630   41.818  1.00 30.58      BLGL
ATOM    661  CD   LYS   96       4.413   17.224   43.192  1.00 34.86      BLGL
ATOM    662  CE   LYS   96       2.939   17.256   43.541  1.00 38.91      BLGL
ATOM    663  NZ   LYS   96       2.712   17.810   44.909  1.00 42.19      BLGL
ATOM    664  C    LYS   96       7.663   17.106   39.474  1.00 26.13      BLGL
ATOM    665  O    LYS   96       7.592   18.041   38.676  1.00 25.77      BLGL
ATOM    666  N    ARG   97       8.818   16.649   39.946  1.00 26.45      BLGL
ATOM    667  CA   ARG   97      10.089   17.232   39.533  1.00 25.62      BLGL
ATOM    668  CB   ARG   97      11.229   16.598   40.335  1.00 26.14      BLGL
ATOM    669  CG   ARG   97      11.105   16.909   41.824  1.00 28.26      BLGL
ATOM    670  CD   ARG   97      12.157   16.228   42.687  1.00 28.70      BLGL
ATOM    671  NE   ARG   97      13.514   16.674   42.385  1.00 30.96      BLGL
ATOM    672  CZ   ARG   97      14.593   16.211   43.007  1.00 29.36      BLGL
ATOM    673  NH1  ARG   97      14.460   15.297   43.959  1.00 26.96      BLGL
ATOM    674  NH2  ARG   97      15.799   16.650   42.671  1.00 26.20      BLGL
ATOM    675  C    ARG   97      10.310   17.060   38.032  1.00 24.94      BLGL
ATOM    676  O    ARG   97      10.778   17.973   37.354  1.00 24.07      BLGL
ATOM    677  N    ALA   98       9.959   15.890   37.510  1.00 24.88      BLGL
ATOM    678  CA   ALA   98      10.104   15.626   36.084  1.00 24.73      BLGL
ATOM    679  CB   ALA   98       9.673   14.198   35.771  1.00 26.89      BLGL
ATOM    680  C    ALA   98       9.265   16.620   35.277  1.00 24.32      BLGL
ATOM    681  O    ALA   98       9.715   17.145   34.256  1.00 21.35      BLGL
ATOM    682  N    ASN   99       8.041   16.875   35.727  1.00 25.11      BLGL
ATOM    683  CA   ASN   99       7.196   17.830   35.019  1.00 27.26      BLGL
ATOM    684  CB   ASN   99       5.802   17.871   35.601  1.00 29.92      BLGL
ATOM    685  CG   ASN   99       5.039   16.631   35.330  1.00 36.77      BLGL
ATOM    686  OD1  ASN   99       3.817   16.649   35.364  1.00 43.97      BLGL
ATOM    687  ND2  ASN   99       5.743   15.529   35.063  1.00 38.67      BLGL
ATOM    688  C    ASN   99       7.766   19.229   35.096  1.00 26.84      BLGL
ATOM    689  O    ASN   99       7.850   19.919   34.090  1.00 29.38      BLGL
ATOM    690  N    ALA  100       8.143   19.652   36.298  1.00 23.90      BLGL
ATOM    691  CA   ALA  100       8.689   20.982   36.481  1.00 23.21      BLGL
ATOM    692  CB   ALA  100       9.214   21.137   37.894  1.00 20.39      BLGL
ATOM    693  C    ALA  100       9.800   21.244   35.470  1.00 25.29      BLGL
ATOM    694  O    ALA  100      10.088   22.394   35.141  1.00 26.23      BLGL
ATOM    695  N    ASN  101      10.409   20.174   34.963  1.00 25.14      BLGL
ATOM    696  CA   ASN  101      11.492   20.307   33.998  1.00 25.17      BLGL
ATOM    697  CB   ASN  101      12.696   19.515   34.483  1.00 24.95      BLGL
ATOM    698  CG   ASN  101      13.280   20.091   35.747  1.00 25.85      BLGL
ATOM    699  OD1  ASN  101      13.914   21.145   35.719  1.00 29.40      BLGL
ATOM    700  ND2  ASN  101      13.054   19.422   36.868  1.00 24.97      BLGL
ATOM    701  C    ASN  101      11.118   19.898   32.582  1.00 25.90      BLGL
ATOM    702  O    ASN  101      11.978   19.563   31.772  1.00 27.14      BLGL
ATOM    703  N    GLY  102       9.824   19.932   32.290  1.00 25.80      BLGL
ATOM    704  CA   GLY  102       9.345   19.598   30.962  1.00 24.78      BLGL
ATOM    705  C    GLY  102       9.671   18.215   30.447  1.00 25.83      BLGL
ATOM    706  O    GLY  102      10.048   18.061   29.289  1.00 27.54      BLGL
ATOM    707  N    MET  103       9.525   17.205   31.297  1.00 26.80      BLGL
ATOM    708  CA   MET  103       9.793   15.827   30.899  1.00 26.04      BLGL
ATOM    709  CB   MET  103      11.006   15.283   31.662  1.00 26.48      BLGL
ATOM    710  CG   MET  103      12.265   16.110   31.451  1.00 29.27      BLGL
ATOM    711  SD   MET  103      13.767   15.380   32.124  1.00 31.74      BLGL
ATOM    712  CE   MET  103      13.716   16.017   33.804  1.00 31.73      BLGL
ATOM    713  C    MET  103       8.559   14.978   31.191  1.00 25.31      BLGL
ATOM    714  O    MET  103       7.892   15.179   32.206  1.00 24.54      BLGL
ATOM    715  N    LYS  104       8.243   14.044   30.294  1.00 24.62      BLGL
ATOM    716  CA   LYS  104       7.082   13.174   30.484  1.00 24.42      BLGL
ATOM    717  CB   LYS  104       6.668   12.527   29.167  1.00 28.12      BLGL
ATOM    718  CG   LYS  104       6.265   13.483   28.062  1.00 32.81      BLGL
ATOM    719  CD   LYS  104       4.800   13.820   28.149  1.00 35.64      BLGL
ATOM    720  CE   LYS  104       4.294   14.402   26.843  1.00 37.37      BLGL
ATOM    721  NZ   LYS  104       2.807   14.485   26.870  1.00 40.79      BLGL
ATOM    722  C    LYS  104       7.452   12.075   31.466  1.00 22.98      BLGL
ATOM    723  O    LYS  104       8.632   11.840   31.720  1.00 23.51      BLGL
ATOM    724  N    LEU  105       6.450   11.398   32.014  1.00 21.49      BLGL
ATOM    725  CA   LEU  105       6.705   10.313   32.955  1.00 19.77      BLGL
```

Fig. 4 cont.

```
ATOM    726  CB   LEU   105       5.975  10.559  34.279  1.00 18.76      BLGL
ATOM    727  CG   LEU   105       6.334   9.548  35.381  1.00 19.18      BLGL
ATOM    728  CD1  LEU   105       7.586  10.007  36.100  1.00 16.56      BLGL
ATOM    729  CD2  LEU   105       5.195   9.412  36.364  1.00 21.13      BLGL
ATOM    730  C    LEU   105       6.280   8.941  32.418  1.00 19.86      BLGL
ATOM    731  O    LEU   105       5.285   8.812  31.701  1.00 16.96      BLGL
ATOM    732  N    LEU   106       7.059   7.920  32.758  1.00 19.88      BLGL
ATOM    733  CA   LEU   106       6.738   6.551  32.381  1.00 19.92      BLGL
ATOM    734  CB   LEU   106       7.889   5.878  31.637  1.00 17.61      BLGL
ATOM    735  CG   LEU   106       7.550   4.607  30.838  1.00 21.29      BLGL
ATOM    736  CD1  LEU   106       8.845   3.872  30.511  1.00 18.25      BLGL
ATOM    737  CD2  LEU   106       6.627   3.689  31.604  1.00 17.96      BLGL
ATOM    738  C    LEU   106       6.567   5.877  33.730  1.00 19.81      BLGL
ATOM    739  O    LEU   106       7.546   5.660  34.437  1.00 19.58      BLGL
ATOM    740  N    ALA   107       5.327   5.581  34.102  1.00 20.44      BLGL
ATOM    741  CA   ALA   107       5.052   4.922  35.373  1.00 20.99      BLGL
ATOM    742  CB   ALA   107       3.634   5.240  35.826  1.00 21.52      BLGL
ATOM    743  C    ALA   107       5.224   3.418  35.177  1.00 21.97      BLGL
ATOM    744  O    ALA   107       4.493   2.796  34.406  1.00 23.04      BLGL
ATOM    745  N    ASP   108       6.192   2.828  35.867  1.00 21.22      BLGL
ATOM    746  CA   ASP   108       6.438   1.400  35.726  1.00 20.00      BLGL
ATOM    747  CB   ASP   108       7.932   1.175  35.463  1.00 17.66      BLGL
ATOM    748  CG   ASP   108       8.327  -0.289  35.455  1.00 17.79      BLGL
ATOM    749  OD1  ASP   108       7.448  -1.173  35.519  1.00 16.92      BLGL
ATOM    750  OD2  ASP   108       9.542  -0.562  35.385  1.00 18.27      BLGL
ATOM    751  C    ASP   108       5.966   0.625  36.953  1.00 21.24      BLGL
ATOM    752  O    ASP   108       6.635   0.614  37.984  1.00 25.51      BLGL
ATOM    753  N    PHE   109       4.801  -0.010  36.840  1.00 19.98      BLGL
ATOM    754  CA   PHE   109       4.256  -0.792  37.939  1.00 20.05      BLGL
ATOM    755  CB   PHE   109       2.739  -0.903  37.850  1.00 20.06      BLGL
ATOM    756  CG   PHE   109       2.033   0.386  38.066  1.00 21.36      BLGL
ATOM    757  CD1  PHE   109       1.751   1.225  36.995  1.00 21.28      BLGL
ATOM    758  CD2  PHE   109       1.665   0.777  39.349  1.00 21.79      BLGL
ATOM    759  CE1  PHE   109       1.110   2.442  37.194  1.00 24.40      BLGL
ATOM    760  CE2  PHE   109       1.026   1.989  39.564  1.00 23.03      BLGL
ATOM    761  CZ   PHE   109       0.745   2.828  38.482  1.00 23.74      BLGL
ATOM    762  C    PHE   109       4.822  -2.190  37.949  1.00 19.77      BLGL
ATOM    763  O    PHE   109       4.680  -2.932  36.978  1.00 18.81      BLGL
ATOM    764  N    HIS   110       5.464  -2.547  39.054  1.00 19.76      BLGL
ATOM    765  CA   HIS   110       6.023  -3.875  39.188  1.00 20.72      BLGL
ATOM    766  CB   HIS   110       7.207  -3.876  40.157  1.00 20.31      BLGL
ATOM    767  CG   HIS   110       8.497  -3.439  39.540  1.00 20.23      BLGL
ATOM    768  CD2  HIS   110       8.779  -2.456  38.653  1.00 19.83      BLGL
ATOM    769  ND1  HIS   110       9.703  -4.034  39.845  1.00 21.63      BLGL
ATOM    770  CE1  HIS   110      10.671  -3.437  39.174  1.00 20.13      BLGL
ATOM    771  NE2  HIS   110      10.137  -2.475  38.442  1.00 20.13      BLGL
ATOM    772  C    HIS   110       4.948  -4.823  39.695  1.00 20.55      BLGL
ATOM    773  O    HIS   110       5.056  -6.036  39.536  1.00 20.58      BLGL
ATOM    774  N    TYR   111       3.900  -4.267  40.291  1.00 21.08      BLGL
ATOM    775  CA   TYR   111       2.827  -5.093  40.830  1.00 23.38      BLGL
ATOM    776  CB   TYR   111       2.039  -5.759  39.695  1.00 22.62      BLGL
ATOM    777  CG   TYR   111       1.274  -4.758  38.858  1.00 23.84      BLGL
ATOM    778  CD1  TYR   111       1.551  -4.593  37.501  1.00 22.76      BLGL
ATOM    779  CE1  TYR   111       0.878  -3.641  36.742  1.00 23.56      BLGL
ATOM    780  CD2  TYR   111       0.297  -3.945  39.437  1.00 24.23      BLGL
ATOM    781  CE2  TYR   111      -0.378  -2.991  38.688  1.00 23.70      BLGL
ATOM    782  CZ   TYR   111      -0.082  -2.844  37.344  1.00 23.27      BLGL
ATOM    783  OH   TYR   111      -0.738  -1.887  36.609  1.00 24.35      BLGL
ATOM    784  C    TYR   111       3.439  -6.137  41.754  1.00 22.90      BLGL
ATOM    785  O    TYR   111       3.094  -7.317  41.718  1.00 22.52      BLGL
ATOM    786  N    SER   112       4.372  -5.668  42.574  1.00 22.56      BLGL
ATOM    787  CA   SER   112       5.071  -6.493  43.544  1.00 22.63      BLGL
ATOM    788  CB   SER   112       6.249  -7.201  42.892  1.00 22.37      BLGL
ATOM    789  OG   SER   112       7.002  -7.894  43.866  1.00 23.73      BLGL
ATOM    790  C    SER   112       5.585  -5.542  44.601  1.00 23.27      BLGL
ATOM    791  O    SER   112       5.631  -4.333  44.368  1.00 24.65      BLGL
```

Fig. 4 cont.

| | | | | | | | | | |
|---|---|---|---|---|---|---|---|---|---|
| ATOM | 792 | N | ASP | 113 | 5.968 | -6.069 | 45.760 | 1.00 22.31 | BLGL |
| ATOM | 793 | CA | ASP | 113 | 6.486 | -5.208 | 46.815 | 1.00 22.28 | BLGL |
| ATOM | 794 | CB | ASP | 113 | 6.202 | -5.795 | 48.199 | 1.00 22.82 | BLGL |
| ATOM | 795 | CG | ASP | 113 | 4.732 | -5.719 | 48.577 | 1.00 25.54 | BLGL |
| ATOM | 796 | OD1 | ASP | 113 | 4.032 | -4.825 | 48.056 | 1.00 23.47 | BLGL |
| ATOM | 797 | OD2 | ASP | 113 | 4.281 | -6.544 | 49.406 | 1.00 24.91 | BLGL |
| ATOM | 798 | C | ASP | 113 | 7.982 | -4.969 | 46.651 | 1.00 21.86 | BLGL |
| ATOM | 799 | O | ASP | 113 | 8.548 | -4.101 | 47.309 | 1.00 21.62 | BLGL |
| ATOM | 800 | N | PHE | 114 | 8.622 | -5.738 | 45.775 | 1.00 20.23 | BLGL |
| ATOM | 801 | CA | PHE | 114 | 10.046 | -5.563 | 45.547 | 1.00 20.78 | BLGL |
| ATOM | 802 | CB | PHE | 114 | 10.853 | -6.387 | 46.549 | 1.00 21.28 | BLGL |
| ATOM | 803 | CG | PHE | 114 | 12.221 | -5.822 | 46.838 | 1.00 24.03 | BLGL |
| ATOM | 804 | CD1 | PHE | 114 | 12.420 | -4.441 | 46.919 | 1.00 24.35 | BLGL |
| ATOM | 805 | CD2 | PHE | 114 | 13.308 | -6.666 | 47.064 | 1.00 24.49 | BLGL |
| ATOM | 806 | CE1 | PHE | 114 | 13.684 | -3.909 | 47.224 | 1.00 22.80 | BLGL |
| ATOM | 807 | CE2 | PHE | 114 | 14.575 | -6.144 | 47.372 | 1.00 20.26 | BLGL |
| ATOM | 808 | CZ | PHE | 114 | 14.761 | -4.767 | 47.451 | 1.00 20.45 | BLGL |
| ATOM | 809 | C | PHE | 114 | 10.392 | -5.952 | 44.122 | 1.00 21.41 | BLGL |
| ATOM | 810 | O | PHE | 114 | 9.507 | -6.328 | 43.361 | 1.00 21.59 | BLGL |
| ATOM | 811 | N | TRP | 115 | 11.675 | -5.856 | 43.768 | 1.00 20.29 | BLGL |
| ATOM | 812 | CA | TRP | 115 | 12.152 | -6.160 | 42.418 | 1.00 19.28 | BLGL |
| ATOM | 813 | CB | TRP | 115 | 13.634 | -6.577 | 42.445 | 1.00 20.57 | BLGL |
| ATOM | 814 | CG | TRP | 115 | 14.575 | -5.534 | 42.963 | 1.00 21.03 | BLGL |
| ATOM | 815 | CD2 | TRP | 115 | 14.942 | -4.315 | 42.311 | 1.00 20.71 | BLGL |
| ATOM | 816 | CE2 | TRP | 115 | 15.786 | -3.607 | 43.198 | 1.00 21.97 | BLGL |
| ATOM | 817 | CE3 | TRP | 115 | 14.637 | -3.747 | 41.066 | 1.00 20.82 | BLGL |
| ATOM | 818 | CD1 | TRP | 115 | 15.202 | -5.523 | 44.177 | 1.00 19.55 | BLGL |
| ATOM | 819 | NE1 | TRP | 115 | 15.929 | -4.371 | 44.328 | 1.00 18.99 | BLGL |
| ATOM | 820 | CZ2 | TRP | 115 | 16.329 | -2.350 | 42.878 | 1.00 22.16 | BLGL |
| ATOM | 821 | CZ3 | TRP | 115 | 15.177 | -2.499 | 40.746 | 1.00 21.59 | BLGL |
| ATOM | 822 | CH2 | TRP | 115 | 16.013 | -1.815 | 41.653 | 1.00 22.47 | BLGL |
| ATOM | 823 | C | TRP | 115 | 11.361 | -7.231 | 41.665 | 1.00 18.82 | BLGL |
| ATOM | 824 | O | TRP | 115 | 11.090 | -8.308 | 42.193 | 1.00 17.18 | BLGL |
| ATOM | 825 | N | ALA | 116 | 10.995 | -6.925 | 40.426 | 1.00 17.42 | BLGL |
| ATOM | 826 | CA | ALA | 116 | 10.277 | -7.874 | 39.589 | 1.00 19.55 | BLGL |
| ATOM | 827 | CB | ALA | 116 | 8.914 | -7.326 | 39.223 | 1.00 18.74 | BLGL |
| ATOM | 828 | C | ALA | 116 | 11.110 | -8.105 | 38.331 | 1.00 22.25 | BLGL |
| ATOM | 829 | O | ALA | 116 | 11.457 | -7.157 | 37.631 | 1.00 25.39 | BLGL |
| ATOM | 830 | N | ASP | 117 | 11.450 | -9.358 | 38.051 | 1.00 21.71 | BLGL |
| ATOM | 831 | CA | ASP | 117 | 12.243 | -9.672 | 36.872 | 1.00 22.29 | BLGL |
| ATOM | 832 | CB | ASP | 117 | 13.736 | -9.620 | 37.209 | 1.00 22.60 | BLGL |
| ATOM | 833 | CG | ASP | 117 | 14.124 | -10.578 | 38.309 | 1.00 26.69 | BLGL |
| ATOM | 834 | OD1 | ASP | 117 | 13.662 | -11.738 | 38.294 | 1.00 29.56 | BLGL |
| ATOM | 835 | OD2 | ASP | 117 | 14.907 | -10.171 | 39.190 | 1.00 30.52 | BLGL |
| ATOM | 836 | C | ASP | 117 | 11.843 | -11.045 | 36.346 | 1.00 22.91 | BLGL |
| ATOM | 837 | O | ASP | 117 | 10.840 | -11.601 | 36.784 | 1.00 24.06 | BLGL |
| ATOM | 838 | N | PRO | 118 | 12.617 | -11.619 | 35.409 | 1.00 22.06 | BLGL |
| ATOM | 839 | CD | PRO | 118 | 13.734 | -11.056 | 34.639 | 1.00 20.93 | BLGL |
| ATOM | 840 | CA | PRO | 118 | 12.252 | -12.935 | 34.880 | 1.00 24.27 | BLGL |
| ATOM | 841 | CB | PRO | 118 | 13.301 | -13.176 | 33.802 | 1.00 22.87 | BLGL |
| ATOM | 842 | CG | PRO | 118 | 13.629 | -11.821 | 33.353 | 1.00 24.48 | BLGL |
| ATOM | 843 | C | PRO | 118 | 12.202 | -14.077 | 35.884 | 1.00 26.00 | BLGL |
| ATOM | 844 | O | PRO | 118 | 11.667 | -15.140 | 35.580 | 1.00 29.05 | BLGL |
| ATOM | 845 | N | ALA | 119 | 12.755 | -13.868 | 37.071 | 1.00 28.00 | BLGL |
| ATOM | 846 | CA | ALA | 119 | 12.762 | -14.917 | 38.086 | 1.00 28.48 | BLGL |
| ATOM | 847 | CB | ALA | 119 | 14.186 | -15.188 | 38.543 | 1.00 27.97 | BLGL |
| ATOM | 848 | C | ALA | 119 | 11.899 | -14.568 | 39.283 | 1.00 28.36 | BLGL |
| ATOM | 849 | O | ALA | 119 | 11.407 | -15.447 | 39.981 | 1.00 30.80 | BLGL |
| ATOM | 850 | N | LYS | 120 | 11.719 | -13.279 | 39.524 | 1.00 29.14 | BLGL |
| ATOM | 851 | CA | LYS | 120 | 10.920 | -12.842 | 40.654 | 1.00 29.76 | BLGL |
| ATOM | 852 | CB | LYS | 120 | 11.793 | -12.032 | 41.617 | 1.00 31.32 | BLGL |
| ATOM | 853 | CG | LYS | 120 | 12.940 | -12.838 | 42.213 | 1.00 38.25 | BLGL |
| ATOM | 854 | CD | LYS | 120 | 13.897 | -12.000 | 43.074 | 1.00 40.66 | BLGL |
| ATOM | 855 | CE | LYS | 120 | 14.801 | -11.115 | 42.222 | 1.00 44.93 | BLGL |
| ATOM | 856 | NZ | LYS | 120 | 15.827 | -10.373 | 43.027 | 1.00 46.70 | BLGL |
| ATOM | 857 | C | LYS | 120 | 9.708 | -12.020 | 40.224 | 1.00 28.61 | BLGL |

Fig. 4 cont.

| | | | | | | | | | |
|---|---|---|---|---|---|---|---|---|---|
| ATOM | 858 | O | LYS | 120 | 9.841 | -10.912 | 39.702 | 1.00 28.45 | BLGL |
| ATOM | 859 | N | GLN | 121 | 8.525 | -12.589 | 40.425 | 1.00 26.27 | BLGL |
| ATOM | 860 | CA | GLN | 121 | 7.273 | -11.913 | 40.108 | 1.00 25.49 | BLGL |
| ATOM | 861 | CB | GLN | 121 | 6.673 | -12.457 | 38.805 | 1.00 24.33 | BLGL |
| ATOM | 862 | CG | GLN | 121 | 7.392 | -12.034 | 37.525 | 1.00 20.53 | BLGL |
| ATOM | 863 | CD | GLN | 121 | 7.376 | -10.528 | 37.291 | 1.00 18.36 | BLGL |
| ATOM | 864 | OE1 | GLN | 121 | 6.425 | -9.838 | 37.659 | 1.00 15.80 | BLGL |
| ATOM | 865 | NE2 | GLN | 121 | 8.424 | -10.017 | 36.655 | 1.00 17.37 | BLGL |
| ATOM | 866 | C | GLN | 121 | 6.328 | -12.176 | 41.281 | 1.00 25.36 | BLGL |
| ATOM | 867 | O | GLN | 121 | 5.176 | -12.571 | 41.099 | 1.00 26.22 | BLGL |
| ATOM | 868 | N | LYS | 122 | 6.843 | -11.970 | 42.489 | 1.00 25.47 | BLGL |
| ATOM | 869 | CA | LYS | 122 | 6.091 | -12.188 | 43.716 | 1.00 25.96 | BLGL |
| ATOM | 870 | CB | LYS | 122 | 7.031 | -12.079 | 44.924 | 1.00 27.22 | BLGL |
| ATOM | 871 | CG | LYS | 122 | 6.394 | -12.412 | 46.260 | 1.00 29.39 | BLGL |
| ATOM | 872 | CD | LYS | 122 | 6.870 | -13.759 | 46.785 | 1.00 32.32 | BLGL |
| ATOM | 873 | CE | LYS | 122 | 7.832 | -13.609 | 47.961 | 1.00 31.56 | BLGL |
| ATOM | 874 | NZ | LYS | 122 | 7.187 | -12.997 | 49.160 | 1.00 32.62 | BLGL |
| ATOM | 875 | C | LYS | 122 | 4.968 | -11.162 | 43.833 | 1.00 26.53 | BLGL |
| ATOM | 876 | O | LYS | 122 | 5.151 | -9.988 | 43.504 | 1.00 28.15 | BLGL |
| ATOM | 877 | N | ALA | 123 | 3.804 | -11.603 | 44.298 | 1.00 25.34 | BLGL |
| ATOM | 878 | CA | ALA | 123 | 2.669 | -10.700 | 44.449 | 1.00 24.78 | BLGL |
| ATOM | 879 | CB | ALA | 123 | 1.377 | -11.491 | 44.559 | 1.00 24.09 | BLGL |
| ATOM | 880 | C | ALA | 123 | 2.830 | -9.820 | 45.675 | 1.00 23.46 | BLGL |
| ATOM | 881 | O | ALA | 123 | 3.519 | -10.177 | 46.622 | 1.00 23.28 | BLGL |
| ATOM | 882 | N | PRO | 124 | 2.212 | -8.636 | 45.660 | 1.00 23.79 | BLGL |
| ATOM | 883 | CD | PRO | 124 | 1.484 | -7.998 | 44.548 | 1.00 21.21 | BLGL |
| ATOM | 884 | CA | PRO | 124 | 2.310 | -7.738 | 46.811 | 1.00 22.77 | BLGL |
| ATOM | 885 | CB | PRO | 124 | 1.392 | -6.588 | 46.419 | 1.00 21.28 | BLGL |
| ATOM | 886 | CG | PRO | 124 | 1.521 | -6.547 | 44.927 | 1.00 19.51 | BLGL |
| ATOM | 887 | C | PRO | 124 | 1.791 | -8.491 | 48.037 | 1.00 23.09 | BLGL |
| ATOM | 888 | O | PRO | 124 | 0.883 | -9.312 | 47.922 | 1.00 22.17 | BLGL |
| ATOM | 889 | N | LYS | 125 | 2.360 | -8.228 | 49.205 | 1.00 25.24 | BLGL |
| ATOM | 890 | CA | LYS | 125 | 1.910 | -8.916 | 50.411 | 1.00 25.84 | BLGL |
| ATOM | 891 | CB | LYS | 125 | 2.612 | -8.350 | 51.656 | 1.00 23.65 | BLGL |
| ATOM | 892 | CG | LYS | 125 | 4.109 | -8.642 | 51.733 | 1.00 21.46 | BLGL |
| ATOM | 893 | CD | LYS | 125 | 4.750 | -8.067 | 52.990 | 1.00 15.25 | BLGL |
| ATOM | 894 | CE | LYS | 125 | 4.683 | -6.554 | 53.029 | 1.00 20.47 | BLGL |
| ATOM | 895 | NZ | LYS | 125 | 5.440 | -5.911 | 51.912 | 1.00 22.44 | BLGL |
| ATOM | 896 | C | LYS | 125 | 0.391 | -8.807 | 50.570 | 1.00 27.21 | BLGL |
| ATOM | 897 | O | LYS | 125 | -0.264 | -9.763 | 50.976 | 1.00 27.46 | BLGL |
| ATOM | 898 | N | ALA | 126 | -0.170 | -7.651 | 50.232 | 1.00 27.45 | BLGL |
| ATOM | 899 | CA | ALA | 126 | -1.608 | -7.438 | 50.360 | 1.00 28.44 | BLGL |
| ATOM | 900 | CB | ALA | 126 | -1.942 | -5.996 | 50.042 | 1.00 27.50 | BLGL |
| ATOM | 901 | C | ALA | 126 | -2.445 | -8.367 | 49.487 | 1.00 30.46 | BLGL |
| ATOM | 902 | O | ALA | 126 | -3.578 | -8.700 | 49.835 | 1.00 32.72 | BLGL |
| ATOM | 903 | N | TRP | 127 | -1.893 | -8.780 | 48.352 | 1.00 31.67 | BLGL |
| ATOM | 904 | CA | TRP | 127 | -2.608 | -9.663 | 47.436 | 1.00 32.34 | BLGL |
| ATOM | 905 | CB | TRP | 127 | -2.274 | -9.301 | 45.983 | 1.00 29.98 | BLGL |
| ATOM | 906 | CG | TRP | 127 | -2.525 | -7.864 | 45.623 | 1.00 26.78 | BLGL |
| ATOM | 907 | CD2 | TRP | 127 | -2.176 | -7.215 | 44.392 | 1.00 25.87 | BLGL |
| ATOM | 908 | CE2 | TRP | 127 | -2.582 | -5.869 | 44.499 | 1.00 24.64 | BLGL |
| ATOM | 909 | CE3 | TRP | 127 | -1.558 | -7.643 | 43.207 | 1.00 25.70 | BLGL |
| ATOM | 910 | CD1 | TRP | 127 | -3.116 | -6.913 | 46.400 | 1.00 25.22 | BLGL |
| ATOM | 911 | NE1 | TRP | 127 | -3.153 | -5.712 | 45.735 | 1.00 25.00 | BLGL |
| ATOM | 912 | CZ2 | TRP | 127 | -2.390 | -4.942 | 43.469 | 1.00 23.42 | BLGL |
| ATOM | 913 | CZ3 | TRP | 127 | -1.367 | -6.723 | 42.183 | 1.00 24.22 | BLGL |
| ATOM | 914 | CH2 | TRP | 127 | -1.781 | -5.387 | 42.323 | 1.00 24.78 | BLGL |
| ATOM | 915 | C | TRP | 127 | -2.220 | -11.113 | 47.694 | 1.00 34.48 | BLGL |
| ATOM | 916 | O | TRP | 127 | -2.786 | -12.039 | 47.101 | 1.00 34.45 | BLGL |
| ATOM | 917 | N | ALA | 128 | -1.244 | -11.284 | 48.585 | 1.00 37.15 | BLGL |
| ATOM | 918 | CA | ALA | 128 | -0.704 | -12.589 | 48.971 | 1.00 38.47 | BLGL |
| ATOM | 919 | CB | ALA | 128 | -0.198 | -12.528 | 50.396 | 1.00 40.00 | BLGL |
| ATOM | 920 | C | ALA | 128 | -1.663 | -13.759 | 48.817 | 1.00 39.10 | BLGL |
| ATOM | 921 | O | ALA | 128 | -1.406 | -14.671 | 48.032 | 1.00 38.72 | BLGL |
| ATOM | 922 | N | ASN | 129 | -2.754 | -13.751 | 49.574 | 1.00 40.50 | BLGL |
| ATOM | 923 | CA | ASN | 129 | -3.716 | -14.836 | 49.473 | 1.00 44.45 | BLGL |

Fig. 4 cont.

```
ATOM    924  CB  ASN   129      -3.794 -15.632  50.788  1.00 47.42      BLGL
ATOM    925  CG  ASN   129      -3.746 -14.751  52.018  1.00 50.55      BLGL
ATOM    926  OD1 ASN   129      -3.975 -13.545  51.941  1.00 54.24      BLGL
ATOM    927  ND2 ASN   129      -3.460 -15.356  53.168  1.00 50.85      BLGL
ATOM    928  C   ASN   129      -5.107 -14.380  49.047  1.00 44.76      BLGL
ATOM    929  O   ASN   129      -6.070 -14.460  49.813  1.00 45.16      BLGL
ATOM    930  N   LEU   130      -5.194 -13.901  47.810  1.00 44.30      BLGL
ATOM    931  CA  LEU   130      -6.452 -13.456  47.230  1.00 43.76      BLGL
ATOM    932  CB  LEU   130      -6.341 -12.018  46.731  1.00 44.19      BLGL
ATOM    933  CG  LEU   130      -6.396 -10.901  47.767  1.00 44.74      BLGL
ATOM    934  CD1 LEU   130      -6.258  -9.564  47.071  1.00 45.24      BLGL
ATOM    935  CD2 LEU   130      -7.712 -10.970  48.515  1.00 45.37      BLGL
ATOM    936  C   LEU   130      -6.727 -14.363  46.049  1.00 43.61      BLGL
ATOM    937  O   LEU   130      -5.801 -14.769  45.351  1.00 43.36      BLGL
ATOM    938  N   ASN   131      -7.991 -14.695  45.823  1.00 44.12      BLGL
ATOM    939  CA  ASN   131      -8.318 -15.549  44.690  1.00 44.97      BLGL
ATOM    940  CB  ASN   131      -9.757 -16.078  44.801  1.00 47.76      BLGL
ATOM    941  CG  ASN   131     -10.794 -14.976  44.772  1.00 51.05      BLGL
ATOM    942  OD1 ASN   131     -10.669 -13.968  45.465  1.00 55.52      BLGL
ATOM    943  ND2 ASN   131     -11.835 -15.170  43.977  1.00 52.37      BLGL
ATOM    944  C   ASN   131      -8.133 -14.706  43.436  1.00 43.17      BLGL
ATOM    945  O   ASN   131      -8.381 -13.502  43.451  1.00 42.05      BLGL
ATOM    946  N   PHE   132      -7.682 -15.338  42.360  1.00 42.47      BLGL
ATOM    947  CA  PHE   132      -7.440 -14.638  41.107  1.00 42.04      BLGL
ATOM    948  CB  PHE   132      -7.430 -15.619  39.940  1.00 42.05      BLGL
ATOM    949  CG  PHE   132      -7.126 -14.971  38.633  1.00 42.75      BLGL
ATOM    950  CD1 PHE   132      -5.870 -14.426  38.396  1.00 42.49      BLGL
ATOM    951  CD2 PHE   132      -8.103 -14.855  37.656  1.00 43.76      BLGL
ATOM    952  CE1 PHE   132      -5.594 -13.769  37.204  1.00 42.79      BLGL
ATOM    953  CE2 PHE   132      -7.834 -14.197  36.455  1.00 44.60      BLGL
ATOM    954  CZ  PHE   132      -6.579 -13.655  36.232  1.00 43.31      BLGL
ATOM    955  C   PHE   132      -8.439 -13.523  40.808  1.00 41.68      BLGL
ATOM    956  O   PHE   132      -8.050 -12.415  40.445  1.00 41.50      BLGL
ATOM    957  N   GLU   133      -9.725 -13.815  40.951  1.00 42.52      BLGL
ATOM    958  CA  GLU   133     -10.759 -12.821  40.691  1.00 42.35      BLGL
ATOM    959  CB  GLU   133     -12.138 -13.409  40.985  1.00 46.23      BLGL
ATOM    960  CG  GLU   133     -12.591 -14.433  39.967  1.00 53.21      BLGL
ATOM    961  CD  GLU   133     -12.550 -13.879  38.553  1.00 57.33      BLGL
ATOM    962  OE1 GLU   133     -13.059 -12.757  38.347  1.00 58.31      BLGL
ATOM    963  OE2 GLU   133     -12.015 -14.564  37.652  1.00 61.34      BLGL
ATOM    964  C   GLU   133     -10.573 -11.542  41.500  1.00 40.12      BLGL
ATOM    965  O   GLU   133     -10.654 -10.443  40.951  1.00 38.25      BLGL
ATOM    966  N   ASP   134     -10.326 -11.691  42.800  1.00 38.18      BLGL
ATOM    967  CA  ASP   134     -10.133 -10.547  43.684  1.00 37.03      BLGL
ATOM    968  CB  ASP   134     -10.203 -10.994  45.142  1.00 39.68      BLGL
ATOM    969  CG  ASP   134     -11.625 -11.128  45.640  1.00 40.58      BLGL
ATOM    970  OD1 ASP   134     -11.816 -11.683  46.744  1.00 40.76      BLGL
ATOM    971  OD2 ASP   134     -12.546 -10.666  44.930  1.00 42.41      BLGL
ATOM    972  C   ASP   134      -8.816  -9.822  43.434  1.00 34.44      BLGL
ATOM    973  O   ASP   134      -8.710  -8.611  43.633  1.00 33.65      BLGL
ATOM    974  N   LYS   135      -7.810 -10.570  43.003  1.00 32.43      BLGL
ATOM    975  CA  LYS   135      -6.510  -9.989  42.717  1.00 30.17      BLGL
ATOM    976  CB  LYS   135      -5.468 -11.092  42.537  1.00 28.01      BLGL
ATOM    977  CG  LYS   135      -4.058 -10.568  42.377  1.00 25.79      BLGL
ATOM    978  CD  LYS   135      -3.090 -11.647  41.928  1.00 24.80      BLGL
ATOM    979  CE  LYS   135      -2.994 -12.773  42.922  1.00 24.10      BLGL
ATOM    980  NZ  LYS   135      -1.961 -13.742  42.491  1.00 24.21      BLGL
ATOM    981  C   LYS   135      -6.615  -9.147  41.443  1.00 29.06      BLGL
ATOM    982  O   LYS   135      -6.092  -8.032  41.384  1.00 29.12      BLGL
ATOM    983  N   LYS   136      -7.303  -9.682  40.436  1.00 28.19      BLGL
ATOM    984  CA  LYS   136      -7.492  -8.986  39.166  1.00 26.63      BLGL
ATOM    985  CB  LYS   136      -8.364  -9.819  38.220  1.00 28.55      BLGL
ATOM    986  CG  LYS   136      -8.455  -9.248  36.811  1.00 33.70      BLGL
ATOM    987  CD  LYS   136      -9.739  -9.661  36.093  1.00 40.26      BLGL
ATOM    988  CE  LYS   136      -9.825 -11.171  35.873  1.00 44.05      BLGL
ATOM    989  NZ  LYS   136     -11.113 -11.590  35.228  1.00 44.46      BLGL
```

Fig. 4 cont.

| | | | | | | | | | |
|---|---|---|---|---|---|---|---|---|---|
| ATOM | 990 | C | LYS | 136 | -8.149 | -7.627 | 39.408 | 1.00 24.62 | BLGL |
| ATOM | 991 | O | LYS | 136 | -7.714 | -6.611 | 38.868 | 1.00 24.91 | BLGL |
| ATOM | 992 | N | THR | 137 | -9.197 | -7.607 | 40.221 | 1.00 23.73 | BLGL |
| ATOM | 993 | CA | THR | 137 | -9.874 | -6.356 | 40.519 | 1.00 24.53 | BLGL |
| ATOM | 994 | CB | THR | 137 | -11.262 | -6.603 | 41.168 | 1.00 26.21 | BLGL |
| ATOM | 995 | OG1 | THR | 137 | -11.679 | -5.422 | 41.855 | 1.00 28.27 | BLGL |
| ATOM | 996 | CG2 | THR | 137 | -11.220 | -7.759 | 42.134 | 1.00 27.71 | BLGL |
| ATOM | 997 | C | THR | 137 | -9.017 | -5.451 | 41.412 | 1.00 24.00 | BLGL |
| ATOM | 998 | O | THR | 137 | -9.108 | -4.221 | 41.334 | 1.00 23.13 | BLGL |
| ATOM | 999 | N | ALA | 138 | -8.174 | -6.054 | 42.248 | 1.00 22.08 | BLGL |
| ATOM | 1000 | CA | ALA | 138 | -7.289 | -5.277 | 43.115 | 1.00 23.30 | BLGL |
| ATOM | 1001 | CB | ALA | 138 | -6.612 | -6.182 | 44.128 | 1.00 19.73 | BLGL |
| ATOM | 1002 | C | ALA | 138 | -6.228 | -4.570 | 42.265 | 1.00 23.73 | BLGL |
| ATOM | 1003 | O | ALA | 138 | -5.896 | -3.401 | 42.497 | 1.00 23.84 | BLGL |
| ATOM | 1004 | N | LEU | 139 | -5.700 | -5.288 | 41.280 | 1.00 21.33 | BLGL |
| ATOM | 1005 | CA | LEU | 139 | -4.690 | -4.729 | 40.402 | 1.00 22.61 | BLGL |
| ATOM | 1006 | CB | LEU | 139 | -4.144 | -5.806 | 39.460 | 1.00 21.44 | BLGL |
| ATOM | 1007 | CG | LEU | 139 | -2.895 | -5.411 | 38.656 | 1.00 21.68 | BLGL |
| ATOM | 1008 | CD1 | LEU | 139 | -2.111 | -6.664 | 38.340 | 1.00 22.58 | BLGL |
| ATOM | 1009 | CD2 | LEU | 139 | -3.265 | -4.658 | 37.383 | 1.00 17.55 | BLGL |
| ATOM | 1010 | C | LEU | 139 | -5.280 | -3.576 | 39.603 | 1.00 23.36 | BLGL |
| ATOM | 1011 | O | LEU | 139 | -4.629 | -2.550 | 39.401 | 1.00 23.02 | BLGL |
| ATOM | 1012 | N | TYR | 140 | -6.513 | -3.747 | 39.141 | 1.00 24.62 | BLGL |
| ATOM | 1013 | CA | TYR | 140 | -7.176 | -2.697 | 38.381 | 1.00 25.60 | BLGL |
| ATOM | 1014 | CB | TYR | 140 | -8.514 | -3.206 | 37.833 | 1.00 23.98 | BLGL |
| ATOM | 1015 | CG | TYR | 140 | -9.494 | -2.109 | 37.498 | 1.00 22.17 | BLGL |
| ATOM | 1016 | CD1 | TYR | 140 | -10.389 | -1.634 | 38.452 | 1.00 25.15 | BLGL |
| ATOM | 1017 | CE1 | TYR | 140 | -11.259 | -0.580 | 38.167 | 1.00 25.77 | BLGL |
| ATOM | 1018 | CD2 | TYR | 140 | -9.492 | -1.508 | 36.247 | 1.00 22.26 | BLGL |
| ATOM | 1019 | CE2 | TYR | 140 | -10.353 | -0.457 | 35.950 | 1.00 24.44 | BLGL |
| ATOM | 1020 | CZ | TYR | 140 | -11.235 | 0.003 | 36.911 | 1.00 25.75 | BLGL |
| ATOM | 1021 | OH | TYR | 140 | -12.096 | 1.036 | 36.615 | 1.00 25.22 | BLGL |
| ATOM | 1022 | C | TYR | 140 | -7.393 | -1.468 | 39.272 | 1.00 27.76 | BLGL |
| ATOM | 1023 | O | TYR | 140 | -7.167 | -0.335 | 38.845 | 1.00 26.59 | BLGL |
| ATOM | 1024 | N | GLN | 141 | -7.828 | -1.698 | 40.508 | 1.00 29.36 | BLGL |
| ATOM | 1025 | CA | GLN | 141 | -8.061 | -0.605 | 41.446 | 1.00 31.47 | BLGL |
| ATOM | 1026 | CB | GLN | 141 | -8.645 | -1.134 | 42.758 | 1.00 34.45 | BLGL |
| ATOM | 1027 | CG | GLN | 141 | -10.105 | -1.525 | 42.664 | 1.00 44.36 | BLGL |
| ATOM | 1028 | CD | GLN | 141 | -11.015 | -0.331 | 42.408 | 1.00 49.85 | BLGL |
| ATOM | 1029 | OE1 | GLN | 141 | -12.161 | -0.487 | 41.957 | 1.00 52.06 | BLGL |
| ATOM | 1030 | NE2 | GLN | 141 | -10.515 | 0.870 | 42.707 | 1.00 49.83 | BLGL |
| ATOM | 1031 | C | GLN | 141 | -6.782 | 0.154 | 41.751 | 1.00 29.93 | BLGL |
| ATOM | 1032 | O | GLN | 141 | -6.751 | 1.387 | 41.698 | 1.00 28.20 | BLGL |
| ATOM | 1033 | N | TYR | 142 | -5.730 | -0.593 | 42.079 | 1.00 27.46 | BLGL |
| ATOM | 1034 | CA | TYR | 142 | -4.445 | -0.002 | 42.413 | 1.00 25.44 | BLGL |
| ATOM | 1035 | CB | TYR | 142 | -3.426 | -1.105 | 42.694 | 1.00 26.98 | BLGL |
| ATOM | 1036 | CG | TYR | 142 | -2.025 | -0.585 | 42.928 | 1.00 26.89 | BLGL |
| ATOM | 1037 | CD1 | TYR | 142 | -1.752 | 0.281 | 43.979 | 1.00 25.19 | BLGL |
| ATOM | 1038 | CE1 | TYR | 142 | -0.473 | 0.768 | 44.189 | 1.00 28.95 | BLGL |
| ATOM | 1039 | CD2 | TYR | 142 | -0.979 | -0.950 | 42.088 | 1.00 27.59 | BLGL |
| ATOM | 1040 | CE2 | TYR | 142 | 0.305 | -0.468 | 42.287 | 1.00 29.43 | BLGL |
| ATOM | 1041 | CZ | TYR | 142 | 0.553 | 0.390 | 43.341 | 1.00 30.68 | BLGL |
| ATOM | 1042 | OH | TYR | 142 | 1.829 | 0.862 | 43.554 | 1.00 32.86 | BLGL |
| ATOM | 1043 | C | TYR | 142 | -3.922 | 0.912 | 41.311 | 1.00 24.17 | BLGL |
| ATOM | 1044 | O | TYR | 142 | -3.466 | 2.026 | 41.572 | 1.00 22.37 | BLGL |
| ATOM | 1045 | N | THR | 143 | -3.988 | 0.432 | 40.076 | 1.00 23.95 | BLGL |
| ATOM | 1046 | CA | THR | 143 | -3.518 | 1.205 | 38.941 | 1.00 24.20 | BLGL |
| ATOM | 1047 | CB | THR | 143 | -3.626 | 0.397 | 37.649 | 1.00 22.46 | BLGL |
| ATOM | 1048 | OG1 | THR | 143 | -3.000 | -0.875 | 37.838 | 1.00 19.33 | BLGL |
| ATOM | 1049 | CG2 | THR | 143 | -2.948 | 1.129 | 36.508 | 1.00 20.23 | BLGL |
| ATOM | 1050 | C | THR | 143 | -4.361 | 2.459 | 38.803 | 1.00 25.95 | BLGL |
| ATOM | 1051 | O | THR | 143 | -3.836 | 3.568 | 38.689 | 1.00 27.54 | BLGL |
| ATOM | 1052 | N | LYS | 144 | -5.673 | 2.263 | 38.821 | 1.00 27.01 | BLGL |
| ATOM | 1053 | CA | LYS | 144 | -6.636 | 3.346 | 38.690 | 1.00 28.79 | BLGL |
| ATOM | 1054 | CB | LYS | 144 | -8.053 | 2.779 | 38.818 | 1.00 30.43 | BLGL |
| ATOM | 1055 | CG | LYS | 144 | -9.167 | 3.787 | 38.626 | 1.00 32.32 | BLGL |

Fig. 4 cont.

```
ATOM   1056  CD   LYS   144      -9.391   4.123  37.167  1.00 35.17      BLGL
ATOM   1057  CE   LYS   144     -10.603   5.033  37.010  1.00 36.95      BLGL
ATOM   1058  NZ   LYS   144     -11.835   4.435  37.605  1.00 37.88      BLGL
ATOM   1059  C    LYS   144      -6.401   4.421  39.748  1.00 28.67      BLGL
ATOM   1060  O    LYS   144      -6.322   5.606  39.433  1.00 29.09      BLGL
ATOM   1061  N    GLN   145      -6.287   4.010  41.004  1.00 28.65      BLGL
ATOM   1062  CA   GLN   145      -6.062   4.969  42.075  1.00 31.28      BLGL
ATOM   1063  CB   GLN   145      -6.116   4.281  43.440  1.00 35.75      BLGL
ATOM   1064  CG   GLN   145      -7.463   3.632  43.756  1.00 45.00      BLGL
ATOM   1065  CD   GLN   145      -8.638   4.586  43.565  1.00 50.27      BLGL
ATOM   1066  OE1  GLN   145      -8.697   5.651  44.189  1.00 53.13      BLGL
ATOM   1067  NE2  GLN   145      -9.580   4.206  42.699  1.00 51.05      BLGL
ATOM   1068  C    GLN   145      -4.720   5.666  41.905  1.00 30.73      BLGL
ATOM   1069  O    GLN   145      -4.653   6.895  41.883  1.00 31.69      BLGL
ATOM   1070  N    SER   146      -3.655   4.880  41.778  1.00 28.68      BLGL
ATOM   1071  CA   SER   146      -2.315   5.429  41.614  1.00 27.00      BLGL
ATOM   1072  CB   SER   146      -1.326   4.319  41.276  1.00 26.10      BLGL
ATOM   1073  OG   SER   146      -1.175   3.432  42.363  1.00 25.05      BLGL
ATOM   1074  C    SER   146      -2.258   6.485  40.529  1.00 26.20      BLGL
ATOM   1075  O    SER   146      -1.733   7.576  40.739  1.00 24.18      BLGL
ATOM   1076  N    LEU   147      -2.793   6.148  39.363  1.00 26.95      BLGL
ATOM   1077  CA   LEU   147      -2.798   7.069  38.240  1.00 28.50      BLGL
ATOM   1078  CB   LEU   147      -3.399   6.386  37.004  1.00 29.76      BLGL
ATOM   1079  CG   LEU   147      -2.403   5.891  35.949  1.00 29.50      BLGL
ATOM   1080  CD1  LEU   147      -1.214   5.237  36.616  1.00 31.84      BLGL
ATOM   1081  CD2  LEU   147      -3.098   4.918  35.010  1.00 31.26      BLGL
ATOM   1082  C    LEU   147      -3.554   8.352  38.563  1.00 28.49      BLGL
ATOM   1083  O    LEU   147      -3.059   9.448  38.291  1.00 26.93      BLGL
ATOM   1084  N    LYS   148      -4.740   8.227  39.156  1.00 29.43      BLGL
ATOM   1085  CA   LYS   148      -5.520   9.412  39.485  1.00 32.08      BLGL
ATOM   1086  CB   LYS   148      -6.897   9.041  40.039  1.00 35.85      BLGL
ATOM   1087  CG   LYS   148      -7.879  10.208  39.955  1.00 44.89      BLGL
ATOM   1088  CD   LYS   148      -9.276   9.854  40.430  1.00 48.80      BLGL
ATOM   1089  CE   LYS   148      -9.319   9.641  41.939  1.00 53.72      BLGL
ATOM   1090  NZ   LYS   148      -8.537   8.451  42.388  1.00 55.41      BLGL
ATOM   1091  C    LYS   148      -4.772  10.277  40.488  1.00 30.09      BLGL
ATOM   1092  O    LYS   148      -4.833  11.502  40.419  1.00 30.55      BLGL
ATOM   1093  N    ALA   149      -4.063   9.636  41.412  1.00 27.72      BLGL
ATOM   1094  CA   ALA   149      -3.279  10.352  42.411  1.00 27.90      BLGL
ATOM   1095  CB   ALA   149      -2.623   9.367  43.368  1.00 26.54      BLGL
ATOM   1096  C    ALA   149      -2.208  11.196  41.720  1.00 28.02      BLGL
ATOM   1097  O    ALA   149      -1.981  12.357  42.075  1.00 27.39      BLGL
ATOM   1098  N    MET   150      -1.547  10.607  40.729  1.00 27.66      BLGL
ATOM   1099  CA   MET   150      -0.511  11.319  39.996  1.00 28.87      BLGL
ATOM   1100  CB   MET   150       0.228  10.357  39.063  1.00 28.84      BLGL
ATOM   1101  CG   MET   150       1.084   9.358  39.828  1.00 31.73      BLGL
ATOM   1102  SD   MET   150       2.122   8.307  38.803  1.00 34.53      BLGL
ATOM   1103  CE   MET   150       1.218   6.808  38.827  1.00 36.46      BLGL
ATOM   1104  C    MET   150      -1.101  12.491  39.219  1.00 28.60      BLGL
ATOM   1105  O    MET   150      -0.518  13.575  39.167  1.00 25.71      BLGL
ATOM   1106  N    LYS   151      -2.269  12.274  38.626  1.00 30.33      BLGL
ATOM   1107  CA   LYS   151      -2.939  13.327  37.871  1.00 31.72      BLGL
ATOM   1108  CB   LYS   151      -4.229  12.793  37.254  1.00 32.47      BLGL
ATOM   1109  CG   LYS   151      -4.036  12.005  35.980  1.00 35.00      BLGL
ATOM   1110  CD   LYS   151      -3.833  12.927  34.789  1.00 38.64      BLGL
ATOM   1111  CE   LYS   151      -3.939  12.159  33.477  1.00 40.97      BLGL
ATOM   1112  NZ   LYS   151      -3.816  13.050  32.295  1.00 40.80      BLGL
ATOM   1113  C    LYS   151      -3.261  14.501  38.787  1.00 31.68      BLGL
ATOM   1114  O    LYS   151      -3.008  15.655  38.442  1.00 32.97      BLGL
ATOM   1115  N    ALA   152      -3.823  14.199  39.953  1.00 31.23      BLGL
ATOM   1116  CA   ALA   152      -4.176  15.228  40.921  1.00 30.30      BLGL
ATOM   1117  CB   ALA   152      -4.759  14.590  42.185  1.00 29.61      BLGL
ATOM   1118  C    ALA   152      -2.952  16.057  41.273  1.00 29.37      BLGL
ATOM   1119  O    ALA   152      -3.066  17.247  41.544  1.00 30.53      BLGL
ATOM   1120  N    ALA   153      -1.783  15.425  41.272  1.00 29.04      BLGL
ATOM   1121  CA   ALA   153      -0.543  16.124  41.596  1.00 29.10      BLGL
```

Fig. 4 cont.

| ATOM | 1122 | CB  | ALA | 153 | 0.517  | 15.134 | 42.032 | 1.00 | 30.13 | BLGL |
|------|------|-----|-----|-----|--------|--------|--------|------|-------|------|
| ATOM | 1123 | C   | ALA | 153 | -0.056 | 16.910 | 40.391 | 1.00 | 29.10 | BLGL |
| ATOM | 1124 | O   | ALA | 153 | 0.990  | 17.561 | 40.435 | 1.00 | 29.45 | BLGL |
| ATOM | 1125 | N   | GLY | 154 | -0.824 | 16.835 | 39.310 | 1.00 | 28.65 | BLGL |
| ATOM | 1126 | CA  | GLY | 154 | -0.482 | 17.557 | 38.101 | 1.00 | 26.76 | BLGL |
| ATOM | 1127 | C   | GLY | 154 | 0.711  | 17.017 | 37.340 | 1.00 | 26.93 | BLGL |
| ATOM | 1128 | O   | GLY | 154 | 1.406  | 17.770 | 36.661 | 1.00 | 25.28 | BLGL |
| ATOM | 1129 | N   | ILE | 155 | 0.948  | 15.713 | 37.444 | 1.00 | 27.10 | BLGL |
| ATOM | 1130 | CA  | ILE | 155 | 2.064  | 15.080 | 36.745 | 1.00 | 25.61 | BLGL |
| ATOM | 1131 | CB  | ILE | 155 | 2.532  | 13.809 | 37.496 | 1.00 | 24.73 | BLGL |
| ATOM | 1132 | CG2 | ILE | 155 | 3.661  | 13.118 | 36.724 | 1.00 | 23.73 | BLGL |
| ATOM | 1133 | CG1 | ILE | 155 | 2.985  | 14.196 | 38.907 | 1.00 | 22.31 | BLGL |
| ATOM | 1134 | CD1 | ILE | 155 | 3.188  | 13.018 | 39.842 | 1.00 | 21.74 | BLGL |
| ATOM | 1135 | C   | ILE | 155 | 1.672  | 14.723 | 35.306 | 1.00 | 24.09 | BLGL |
| ATOM | 1136 | O   | ILE | 155 | 0.568  | 14.240 | 35.056 | 1.00 | 25.01 | BLGL |
| ATOM | 1137 | N   | ASP | 156 | 2.581  | 14.975 | 34.369 | 1.00 | 21.70 | BLGL |
| ATOM | 1138 | CA  | ASP | 156 | 2.354  | 14.695 | 32.959 | 1.00 | 23.92 | BLGL |
| ATOM | 1139 | CB  | ASP | 156 | 3.172  | 15.657 | 32.089 | 1.00 | 26.46 | BLGL |
| ATOM | 1140 | CG  | ASP | 156 | 2.889  | 15.486 | 30.602 | 1.00 | 30.77 | BLGL |
| ATOM | 1141 | OD1 | ASP | 156 | 3.579  | 16.140 | 29.792 | 1.00 | 33.81 | BLGL |
| ATOM | 1142 | OD2 | ASP | 156 | 1.976  | 14.706 | 30.239 | 1.00 | 32.30 | BLGL |
| ATOM | 1143 | C   | ASP | 156 | 2.757  | 13.261 | 32.644 | 1.00 | 23.58 | BLGL |
| ATOM | 1144 | O   | ASP | 156 | 3.904  | 12.986 | 32.319 | 1.00 | 26.10 | BLGL |
| ATOM | 1145 | N   | ILE | 157 | 1.805  | 12.348 | 32.750 | 1.00 | 22.55 | BLGL |
| ATOM | 1146 | CA  | ILE | 157 | 2.062  | 10.945 | 32.484 | 1.00 | 21.98 | BLGL |
| ATOM | 1147 | CB  | ILE | 157 | 1.070  | 10.058 | 33.254 | 1.00 | 22.84 | BLGL |
| ATOM | 1148 | CG2 | ILE | 157 | 1.368  | 8.595  | 32.990 | 1.00 | 18.93 | BLGL |
| ATOM | 1149 | CG1 | ILE | 157 | 1.137  | 10.385 | 34.744 | 1.00 | 23.81 | BLGL |
| ATOM | 1150 | CD1 | ILE | 157 | -0.082 | 9.922  | 35.514 | 1.00 | 26.52 | BLGL |
| ATOM | 1151 | C   | ILE | 157 | 1.894  | 10.675 | 30.997 | 1.00 | 20.48 | BLGL |
| ATOM | 1152 | O   | ILE | 157 | 0.819  | 10.885 | 30.443 | 1.00 | 22.51 | BLGL |
| ATOM | 1153 | N   | GLY | 158 | 2.950  | 10.207 | 30.349 | 1.00 | 18.57 | BLGL |
| ATOM | 1154 | CA  | GLY | 158 | 2.847  | 9.927  | 28.935 | 1.00 | 16.55 | BLGL |
| ATOM | 1155 | C   | GLY | 158 | 2.758  | 8.445  | 28.632 | 1.00 | 17.26 | BLGL |
| ATOM | 1156 | O   | GLY | 158 | 2.227  | 8.042  | 27.599 | 1.00 | 17.93 | BLGL |
| ATOM | 1157 | N   | MET | 159 | 3.245  | 7.622  | 29.550 | 1.00 | 18.71 | BLGL |
| ATOM | 1158 | CA  | MET | 159 | 3.260  | 6.186  | 29.322 | 1.00 | 19.00 | BLGL |
| ATOM | 1159 | CB  | MET | 159 | 4.559  | 5.834  | 28.588 | 1.00 | 17.91 | BLGL |
| ATOM | 1160 | CG  | MET | 159 | 4.563  | 4.506  | 27.872 | 1.00 | 24.08 | BLGL |
| ATOM | 1161 | SD  | MET | 159 | 6.139  | 4.187  | 27.000 | 1.00 | 30.17 | BLGL |
| ATOM | 1162 | CE  | MET | 159 | 6.095  | 5.442  | 25.740 | 1.00 | 26.74 | BLGL |
| ATOM | 1163 | C   | MET | 159 | 3.156  | 5.395  | 30.630 | 1.00 | 19.17 | BLGL |
| ATOM | 1164 | O   | MET | 159 | 3.573  | 5.855  | 31.696 | 1.00 | 16.99 | BLGL |
| ATOM | 1165 | N   | VAL | 160 | 2.579  | 4.204  | 30.543 | 1.00 | 18.21 | BLGL |
| ATOM | 1166 | CA  | VAL | 160 | 2.450  | 3.345  | 31.707 | 1.00 | 17.42 | BLGL |
| ATOM | 1167 | CB  | VAL | 160 | 1.002  | 3.285  | 32.245 | 1.00 | 17.75 | BLGL |
| ATOM | 1168 | CG1 | VAL | 160 | 0.920  | 2.287  | 33.384 | 1.00 | 16.21 | BLGL |
| ATOM | 1169 | CG2 | VAL | 160 | 0.570  | 4.654  | 32.739 | 1.00 | 18.60 | BLGL |
| ATOM | 1170 | C   | VAL | 160 | 2.891  | 1.944  | 31.332 | 1.00 | 17.12 | BLGL |
| ATOM | 1171 | O   | VAL | 160 | 2.516  | 1.406  | 30.292 | 1.00 | 17.78 | BLGL |
| ATOM | 1172 | N   | GLN | 161 | 3.704  | 1.360  | 32.192 | 1.00 | 17.31 | BLGL |
| ATOM | 1173 | CA  | GLN | 161 | 4.211  | 0.028  | 31.963 | 1.00 | 17.58 | BLGL |
| ATOM | 1174 | CB  | GLN | 161 | 5.709  | 0.018  | 32.272 | 1.00 | 17.55 | BLGL |
| ATOM | 1175 | CG  | GLN | 161 | 6.446  | -1.213 | 31.826 | 1.00 | 16.31 | BLGL |
| ATOM | 1176 | CD  | GLN | 161 | 7.935  | -1.106 | 32.056 | 1.00 | 16.53 | BLGL |
| ATOM | 1177 | OE1 | GLN | 161 | 8.570  | -0.132 | 31.641 | 1.00 | 17.05 | BLGL |
| ATOM | 1178 | NE2 | GLN | 161 | 8.508  | -2.114 | 32.707 | 1.00 | 12.70 | BLGL |
| ATOM | 1179 | C   | GLN | 161 | 3.439  | -0.903 | 32.893 | 1.00 | 16.74 | BLGL |
| ATOM | 1180 | O   | GLN | 161 | 3.455  | -0.719 | 34.106 | 1.00 | 17.03 | BLGL |
| ATOM | 1181 | N   | VAL | 162 | 2.736  | -1.882 | 32.330 | 1.00 | 14.93 | BLGL |
| ATOM | 1182 | CA  | VAL | 162 | 1.975  | -2.818 | 33.153 | 1.00 | 14.33 | BLGL |
| ATOM | 1183 | CB  | VAL | 162 | 0.648  | -3.209 | 32.455 | 1.00 | 14.98 | BLGL |
| ATOM | 1184 | CG1 | VAL | 162 | -0.143 | -4.195 | 33.304 | 1.00 | 12.90 | BLGL |
| ATOM | 1185 | CG2 | VAL | 162 | -0.176 | -1.964 | 32.213 | 1.00 | 12.73 | BLGL |
| ATOM | 1186 | C   | VAL | 162 | 2.840  | -4.051 | 33.411 | 1.00 | 15.01 | BLGL |
| ATOM | 1187 | O   | VAL | 162 | 2.763  | -5.046 | 32.691 | 1.00 | 15.57 | BLGL |

Fig. 4 cont.

| | | | | | | | | | |
|---|---|---|---|---|---|---|---|---|---|
| ATOM | 1188 | N | GLY | 163 | 3.674 | -3.965 | 34.444 | 1.00 13.93 | BLGL |
| ATOM | 1189 | CA | GLY | 163 | 4.568 | -5.062 | 34.765 | 1.00 16.33 | BLGL |
| ATOM | 1190 | C | GLY | 163 | 6.001 | -4.755 | 34.350 | 1.00 17.03 | BLGL |
| ATOM | 1191 | O | GLY | 163 | 6.239 | -3.875 | 33.521 | 1.00 17.31 | BLGL |
| ATOM | 1192 | N | ASN | 164 | 6.958 | -5.485 | 34.917 | 1.00 17.42 | BLGL |
| ATOM | 1193 | CA | ASN | 164 | 8.374 | -5.274 | 34.628 | 1.00 16.23 | BLGL |
| ATOM | 1194 | CB | ASN | 164 | 9.035 | -4.629 | 35.845 | 1.00 13.47 | BLGL |
| ATOM | 1195 | CG | ASN | 164 | 10.413 | -4.117 | 35.556 | 1.00 11.45 | BLGL |
| ATOM | 1196 | OD1 | ASN | 164 | 10.581 | -3.019 | 35.026 | 1.00 13.59 | BLGL |
| ATOM | 1197 | ND2 | ASN | 164 | 11.416 | -4.912 | 35.889 | 1.00 11.01 | BLGL |
| ATOM | 1198 | C | ASN | 164 | 9.051 | -6.614 | 34.315 | 1.00 17.48 | BLGL |
| ATOM | 1199 | O | ASN | 164 | 9.131 | -7.490 | 35.175 | 1.00 19.59 | BLGL |
| ATOM | 1200 | N | GLU | 165 | 9.537 | -6.765 | 33.085 | 1.00 17.58 | BLGL |
| ATOM | 1201 | CA | GLU | 165 | 10.197 | -7.998 | 32.643 | 1.00 17.54 | BLGL |
| ATOM | 1202 | CB | GLU | 165 | 11.605 | -8.093 | 33.244 | 1.00 16.33 | BLGL |
| ATOM | 1203 | CG | GLU | 165 | 12.467 | -6.875 | 32.940 | 1.00 17.40 | BLGL |
| ATOM | 1204 | CD | GLU | 165 | 13.938 | -7.095 | 33.223 | 1.00 17.97 | BLGL |
| ATOM | 1205 | OE1 | GLU | 165 | 14.260 | -7.739 | 34.236 | 1.00 20.07 | BLGL |
| ATOM | 1206 | OE2 | GLU | 165 | 14.783 | -6.613 | 32.442 | 1.00 15.79 | BLGL |
| ATOM | 1207 | C | GLU | 165 | 9.372 | -9.248 | 32.982 | 1.00 16.57 | BLGL |
| ATOM | 1208 | O | GLU | 165 | 9.875 | -10.221 | 33.534 | 1.00 14.22 | BLGL |
| ATOM | 1209 | N | THR | 166 | 8.094 | -9.196 | 32.618 | 1.00 16.92 | BLGL |
| ATOM | 1210 | CA | THR | 166 | 7.146 | -10.267 | 32.860 | 1.00 15.12 | BLGL |
| ATOM | 1211 | CB | THR | 166 | 5.723 | -9.713 | 32.782 | 1.00 17.38 | BLGL |
| ATOM | 1212 | OG1 | THR | 166 | 5.514 | -9.130 | 31.490 | 1.00 16.95 | BLGL |
| ATOM | 1213 | CG2 | THR | 166 | 5.511 | -8.629 | 33.850 | 1.00 17.63 | BLGL |
| ATOM | 1214 | C | THR | 166 | 7.304 | -11.411 | 31.860 | 1.00 15.92 | BLGL |
| ATOM | 1215 | O | THR | 166 | 6.380 | -11.741 | 31.131 | 1.00 13.18 | BLGL |
| ATOM | 1216 | N | ASN | 167 | 8.488 | -12.013 | 31.835 | 1.00 18.90 | BLGL |
| ATOM | 1217 | CA | ASN | 167 | 8.775 | -13.122 | 30.933 | 1.00 19.84 | BLGL |
| ATOM | 1218 | CB | ASN | 167 | 10.277 | -13.399 | 30.885 | 1.00 19.56 | BLGL |
| ATOM | 1219 | CG | ASN | 167 | 11.014 | -12.455 | 29.974 | 1.00 19.68 | BLGL |
| ATOM | 1220 | OD1 | ASN | 167 | 10.597 | -11.320 | 29.774 | 1.00 21.70 | BLGL |
| ATOM | 1221 | ND2 | ASN | 167 | 12.132 | -12.912 | 29.429 | 1.00 19.90 | BLGL |
| ATOM | 1222 | C | ASN | 167 | 8.074 | -14.397 | 31.343 | 1.00 20.80 | BLGL |
| ATOM | 1223 | O | ASN | 167 | 7.670 | -15.175 | 30.489 | 1.00 22.87 | BLGL |
| ATOM | 1224 | N | GLY | 168 | 7.936 | -14.615 | 32.647 | 1.00 22.03 | BLGL |
| ATOM | 1225 | CA | GLY | 168 | 7.302 | -15.833 | 33.114 | 1.00 24.61 | BLGL |
| ATOM | 1226 | C | GLY | 168 | 6.216 | -15.699 | 34.164 | 1.00 26.99 | BLGL |
| ATOM | 1227 | O | GLY | 168 | 5.663 | -16.702 | 34.620 | 1.00 28.98 | BLGL |
| ATOM | 1228 | N | GLY | 169 | 5.898 | -14.478 | 34.562 | 1.00 26.63 | BLGL |
| ATOM | 1229 | CA | GLY | 169 | 4.865 | -14.319 | 35.558 | 1.00 25.86 | BLGL |
| ATOM | 1230 | C | GLY | 169 | 4.516 | -12.878 | 35.831 | 1.00 27.02 | BLGL |
| ATOM | 1231 | O | GLY | 169 | 5.166 | -11.959 | 35.334 | 1.00 28.44 | BLGL |
| ATOM | 1232 | N | LEU | 170 | 3.467 | -12.691 | 36.622 | 1.00 26.37 | BLGL |
| ATOM | 1233 | CA | LEU | 170 | 2.996 | -11.371 | 37.005 | 1.00 23.73 | BLGL |
| ATOM | 1234 | CB | LEU | 170 | 2.164 | -10.751 | 35.875 | 1.00 20.57 | BLGL |
| ATOM | 1235 | CG | LEU | 170 | 1.474 | -9.415 | 36.185 | 1.00 21.09 | BLGL |
| ATOM | 1236 | CD1 | LEU | 170 | 2.470 | -8.395 | 36.723 | 1.00 21.42 | BLGL |
| ATOM | 1237 | CD2 | LEU | 170 | 0.811 | -8.894 | 34.934 | 1.00 20.49 | BLGL |
| ATOM | 1238 | C | LEU | 170 | 2.158 | -11.504 | 38.272 | 1.00 23.90 | BLGL |
| ATOM | 1239 | O | LEU | 170 | 1.222 | -12.305 | 38.326 | 1.00 22.71 | BLGL |
| ATOM | 1240 | N | ALA | 171 | 2.522 | -10.731 | 39.292 | 1.00 23.01 | BLGL |
| ATOM | 1241 | CA | ALA | 171 | 1.816 | -10.724 | 40.567 | 1.00 22.14 | BLGL |
| ATOM | 1242 | CB | ALA | 171 | 0.544 | -9.911 | 40.433 | 1.00 22.04 | BLGL |
| ATOM | 1243 | C | ALA | 171 | 1.488 | -12.114 | 41.109 | 1.00 23.55 | BLGL |
| ATOM | 1244 | O | ALA | 171 | 0.354 | -12.382 | 41.512 | 1.00 23.66 | BLGL |
| ATOM | 1245 | N | GLY | 172 | 2.479 | -12.996 | 41.122 | 1.00 22.96 | BLGL |
| ATOM | 1246 | CA | GLY | 172 | 2.259 | -14.337 | 41.632 | 1.00 25.97 | BLGL |
| ATOM | 1247 | C | GLY | 172 | 1.592 | -15.299 | 40.666 | 1.00 27.36 | BLGL |
| ATOM | 1248 | O | GLY | 172 | 1.412 | -16.474 | 40.980 | 1.00 27.94 | BLGL |
| ATOM | 1249 | N | GLU | 173 | 1.225 | -14.808 | 39.490 | 1.00 28.30 | BLGL |
| ATOM | 1250 | CA | GLU | 173 | 0.584 | -15.643 | 38.487 | 1.00 29.90 | BLGL |
| ATOM | 1251 | CB | GLU | 173 | -0.540 | -14.858 | 37.815 | 1.00 30.87 | BLGL |
| ATOM | 1252 | CG | GLU | 173 | -1.888 | -15.557 | 37.824 | 1.00 33.63 | BLGL |
| ATOM | 1253 | CD | GLU | 173 | -2.308 | -16.014 | 39.208 | 1.00 34.41 | BLGL |

Fig. 4 cont.

| | | | | | | | | | |
|---|---|---|---|---|---|---|---|---|---|
| ATOM | 1254 | OE1 | GLU | 173 | -2.334 | -15.181 | 40.139 | 1.00 34.20 | BLGL |
| ATOM | 1255 | OE2 | GLU | 173 | -2.618 | -17.214 | 39.359 | 1.00 34.57 | BLGL |
| ATOM | 1256 | C | GLU | 173 | 1.619 | -16.084 | 37.450 | 1.00 30.77 | BLGL |
| ATOM | 1257 | O | GLU | 173 | 2.481 | -15.302 | 37.053 | 1.00 31.69 | BLGL |
| ATOM | 1258 | N | THR | 174 | 1.539 | -17.338 | 37.017 | 1.00 30.71 | BLGL |
| ATOM | 1259 | CA | THR | 174 | 2.484 | -17.864 | 36.038 | 1.00 30.81 | BLGL |
| ATOM | 1260 | CB | THR | 174 | 3.366 | -18.975 | 36.661 | 1.00 30.70 | BLGL |
| ATOM | 1261 | OG1 | THR | 174 | 2.533 | -20.027 | 37.167 | 1.00 33.92 | BLGL |
| ATOM | 1262 | CG2 | THR | 174 | 4.201 | -18.416 | 37.792 | 1.00 29.44 | BLGL |
| ATOM | 1263 | C | THR | 174 | 1.801 | -18.426 | 34.792 | 1.00 31.23 | BLGL |
| ATOM | 1264 | O | THR | 174 | 2.470 | -18.868 | 33.857 | 1.00 31.14 | BLGL |
| ATOM | 1265 | N | ASP | 175 | 0.473 | -18.409 | 34.779 | 1.00 31.31 | BLGL |
| ATOM | 1266 | CA | ASP | 175 | -0.276 | -18.923 | 33.640 | 1.00 31.53 | BLGL |
| ATOM | 1267 | CB | ASP | 175 | -1.565 | -19.589 | 34.120 | 1.00 35.17 | BLGL |
| ATOM | 1268 | CG | ASP | 175 | -2.447 | -20.030 | 32.972 | 1.00 38.71 | BLGL |
| ATOM | 1269 | OD1 | ASP | 175 | -1.925 | -20.654 | 32.023 | 1.00 39.79 | BLGL |
| ATOM | 1270 | OD2 | ASP | 175 | -3.665 | -19.758 | 33.022 | 1.00 42.47 | BLGL |
| ATOM | 1271 | C | ASP | 175 | -0.605 | -17.796 | 32.674 | 1.00 30.63 | BLGL |
| ATOM | 1272 | O | ASP | 175 | -1.363 | -16.890 | 33.016 | 1.00 30.64 | BLGL |
| ATOM | 1273 | N | TRP | 176 | -0.055 | -17.861 | 31.463 | 1.00 27.62 | BLGL |
| ATOM | 1274 | CA | TRP | 176 | -0.281 | -16.806 | 30.480 | 1.00 27.93 | BLGL |
| ATOM | 1275 | CB | TRP | 176 | 0.403 | -17.147 | 29.157 | 1.00 24.63 | BLGL |
| ATOM | 1276 | CG | TRP | 176 | 1.882 | -16.910 | 29.193 | 1.00 26.55 | BLGL |
| ATOM | 1277 | CD2 | TRP | 176 | 2.557 | -15.666 | 28.966 | 1.00 27.36 | BLGL |
| ATOM | 1278 | CE2 | TRP | 176 | 3.940 | -15.900 | 29.148 | 1.00 27.27 | BLGL |
| ATOM | 1279 | CE3 | TRP | 176 | 2.128 | -14.375 | 28.625 | 1.00 27.01 | BLGL |
| ATOM | 1280 | CD1 | TRP | 176 | 2.855 | -17.820 | 29.498 | 1.00 26.56 | BLGL |
| ATOM | 1281 | NE1 | TRP | 176 | 4.094 | -17.222 | 29.473 | 1.00 26.37 | BLGL |
| ATOM | 1282 | CZ2 | TRP | 176 | 4.899 | -14.887 | 29.004 | 1.00 25.56 | BLGL |
| ATOM | 1283 | CZ3 | TRP | 176 | 3.085 | -13.365 | 28.482 | 1.00 25.94 | BLGL |
| ATOM | 1284 | CH2 | TRP | 176 | 4.453 | -13.631 | 28.671 | 1.00 25.57 | BLGL |
| ATOM | 1285 | C | TRP | 176 | -1.739 | -16.427 | 30.234 | 1.00 29.80 | BLGL |
| ATOM | 1286 | O | TRP | 176 | -2.033 | -15.289 | 29.857 | 1.00 30.42 | BLGL |
| ATOM | 1287 | N | ALA | 177 | -2.656 | -17.368 | 30.441 | 1.00 31.37 | BLGL |
| ATOM | 1288 | CA | ALA | 177 | -4.073 | -17.077 | 30.249 | 1.00 30.31 | BLGL |
| ATOM | 1289 | CB | ALA | 177 | -4.889 | -18.354 | 30.339 | 1.00 30.40 | BLGL |
| ATOM | 1290 | C | ALA | 177 | -4.500 | -16.104 | 31.342 | 1.00 31.32 | BLGL |
| ATOM | 1291 | O | ALA | 177 | -5.199 | -15.124 | 31.085 | 1.00 31.10 | BLGL |
| ATOM | 1292 | N | LYS | 178 | -4.070 | -16.379 | 32.569 | 1.00 30.35 | BLGL |
| ATOM | 1293 | CA | LYS | 178 | -4.401 | -15.507 | 33.680 | 1.00 31.58 | BLGL |
| ATOM | 1294 | CB | LYS | 178 | -4.181 | -16.235 | 35.008 | 1.00 33.69 | BLGL |
| ATOM | 1295 | CG | LYS | 178 | -5.114 | -17.410 | 35.234 | 1.00 37.35 | BLGL |
| ATOM | 1296 | CD | LYS | 178 | -4.994 | -17.911 | 36.664 | 1.00 43.39 | BLGL |
| ATOM | 1297 | CE | LYS | 178 | -5.780 | -19.196 | 36.897 | 1.00 45.38 | BLGL |
| ATOM | 1298 | NZ | LYS | 178 | -5.125 | -20.370 | 36.252 | 1.00 47.94 | BLGL |
| ATOM | 1299 | C | LYS | 178 | -3.568 | -14.217 | 33.637 | 1.00 30.97 | BLGL |
| ATOM | 1300 | O | LYS | 178 | -4.040 | -13.153 | 34.043 | 1.00 31.65 | BLGL |
| ATOM | 1301 | N | MET | 179 | -2.333 | -14.306 | 33.149 | 1.00 29.06 | BLGL |
| ATOM | 1302 | CA | MET | 179 | -1.485 | -13.126 | 33.062 | 1.00 26.50 | BLGL |
| ATOM | 1303 | CB | MET | 179 | -0.110 | -13.481 | 32.521 | 1.00 27.08 | BLGL |
| ATOM | 1304 | CG | MET | 179 | 0.789 | -14.179 | 33.507 | 1.00 29.22 | BLGL |
| ATOM | 1305 | SD | MET | 179 | 2.433 | -14.378 | 32.801 | 1.00 32.04 | BLGL |
| ATOM | 1306 | CE | MET | 179 | 2.432 | -16.100 | 32.529 | 1.00 37.19 | BLGL |
| ATOM | 1307 | C | MET | 179 | -2.122 | -12.106 | 32.141 | 1.00 25.11 | BLGL |
| ATOM | 1308 | O | MET | 179 | -2.206 | -10.924 | 32.478 | 1.00 24.38 | BLGL |
| ATOM | 1309 | N | SER | 180 | -2.566 | -12.572 | 30.977 | 1.00 23.38 | BLGL |
| ATOM | 1310 | CA | SER | 180 | -3.199 | -11.707 | 29.985 | 1.00 23.70 | BLGL |
| ATOM | 1311 | CB | SER | 180 | -3.725 | -12.533 | 28.812 | 1.00 23.12 | BLGL |
| ATOM | 1312 | OG | SER | 180 | -2.691 | -13.297 | 28.223 | 1.00 23.86 | BLGL |
| ATOM | 1313 | C | SER | 180 | -4.348 | -10.933 | 30.605 | 1.00 24.08 | BLGL |
| ATOM | 1314 | O | SER | 180 | -4.552 | -9.756 | 30.313 | 1.00 23.86 | BLGL |
| ATOM | 1315 | N | GLN | 181 | -5.101 | -11.601 | 31.467 | 1.00 25.04 | BLGL |
| ATOM | 1316 | CA | GLN | 181 | -6.226 | -10.965 | 32.129 | 1.00 27.04 | BLGL |
| ATOM | 1317 | CB | GLN | 181 | -7.064 | -12.009 | 32.864 | 1.00 29.17 | BLGL |
| ATOM | 1318 | CG | GLN | 181 | -7.820 | -12.940 | 31.932 | 1.00 33.08 | BLGL |
| ATOM | 1319 | CD | GLN | 181 | -8.761 | -13.860 | 32.675 | 1.00 35.97 | BLGL |

Fig. 4 cont.

```
ATOM   1320  OE1 GLN   181      -8.558 -15.077  32.724  1.00 36.76      BLGL
ATOM   1321  NE2 GLN   181      -9.801 -13.280  33.269  1.00 37.03      BLGL
ATOM   1322  C   GLN   181      -5.774  -9.874  33.091  1.00 27.11      BLGL
ATOM   1323  O   GLN   181      -6.459  -8.864  33.252  1.00 28.46      BLGL
ATOM   1324  N   LEU   182      -4.628 -10.080  33.737  1.00 26.80      BLGL
ATOM   1325  CA  LEU   182      -4.086  -9.081  34.655  1.00 25.48      BLGL
ATOM   1326  CB  LEU   182      -2.932  -9.665  35.472  1.00 25.40      BLGL
ATOM   1327  CG  LEU   182      -3.296 -10.736  36.504  1.00 27.62      BLGL
ATOM   1328  CD1 LEU   182      -2.035 -11.268  37.156  1.00 27.60      BLGL
ATOM   1329  CD2 LEU   182      -4.229 -10.149  37.556  1.00 26.92      BLGL
ATOM   1330  C   LEU   182      -3.591  -7.899  33.823  1.00 24.10      BLGL
ATOM   1331  O   LEU   182      -3.739  -6.740  34.211  1.00 23.49      BLGL
ATOM   1332  N   PHE   183      -3.000  -8.211  32.675  1.00 21.91      BLGL
ATOM   1333  CA  PHE   183      -2.512  -7.187  31.770  1.00 22.28      BLGL
ATOM   1334  CB  PHE   183      -1.888  -7.826  30.528  1.00 21.38      BLGL
ATOM   1335  CG  PHE   183      -0.500  -8.347  30.737  1.00 20.19      BLGL
ATOM   1336  CD1 PHE   183      -0.064  -9.469  30.042  1.00 20.38      BLGL
ATOM   1337  CD2 PHE   183       0.385  -7.704  31.597  1.00 22.77      BLGL
ATOM   1338  CE1 PHE   183       1.236  -9.953  30.192  1.00 20.30      BLGL
ATOM   1339  CE2 PHE   183       1.693  -8.174  31.761  1.00 24.59      BLGL
ATOM   1340  CZ  PHE   183       2.120  -9.305  31.054  1.00 23.28      BLGL
ATOM   1341  C   PHE   183      -3.668  -6.283  31.348  1.00 22.44      BLGL
ATOM   1342  O   PHE   183      -3.548  -5.059  31.384  1.00 22.23      BLGL
ATOM   1343  N   ASN   184      -4.792  -6.881  30.954  1.00 22.00      BLGL
ATOM   1344  CA  ASN   184      -5.939  -6.087  30.533  1.00 20.53      BLGL
ATOM   1345  CB  ASN   184      -7.012  -6.964  29.895  1.00 20.92      BLGL
ATOM   1346  CG  ASN   184      -6.677  -7.345  28.474  1.00 21.95      BLGL
ATOM   1347  OD1 ASN   184      -6.162  -6.535  27.708  1.00 24.93      BLGL
ATOM   1348  ND2 ASN   184      -6.983  -8.579  28.108  1.00 26.02      BLGL
ATOM   1349  C   ASN   184      -6.538  -5.293  31.679  1.00 17.99      BLGL
ATOM   1350  O   ASN   184      -7.053  -4.199  31.474  1.00 18.30      BLGL
ATOM   1351  N   ALA   185      -6.458  -5.841  32.884  1.00 16.83      BLGL
ATOM   1352  CA  ALA   185      -6.976  -5.163  34.066  1.00 18.27      BLGL
ATOM   1353  CB  ALA   185      -6.815  -6.048  35.294  1.00 16.14      BLGL
ATOM   1354  C   ALA   185      -6.215  -3.857  34.261  1.00 18.87      BLGL
ATOM   1355  O   ALA   185      -6.812  -2.795  34.422  1.00 17.89      BLGL
ATOM   1356  N   GLY   186      -4.888  -3.945  34.244  1.00 20.07      BLGL
ATOM   1357  CA  GLY   186      -4.073  -2.756  34.409  1.00 19.75      BLGL
ATOM   1358  C   GLY   186      -4.273  -1.834  33.226  1.00 19.07      BLGL
ATOM   1359  O   GLY   186      -4.367  -0.620  33.373  1.00 20.22      BLGL
ATOM   1360  N   SER   187      -4.345  -2.424  32.042  1.00 18.72      BLGL
ATOM   1361  CA  SER   187      -4.534  -1.664  30.819  1.00 18.78      BLGL
ATOM   1362  CB  SER   187      -4.570  -2.618  29.627  1.00 19.99      BLGL
ATOM   1363  OG  SER   187      -4.606  -1.903  28.409  1.00 22.89      BLGL
ATOM   1364  C   SER   187      -5.840  -0.877  30.897  1.00 20.30      BLGL
ATOM   1365  O   SER   187      -5.879   0.311  30.582  1.00 20.23      BLGL
ATOM   1366  N   GLN   188      -6.903  -1.554  31.325  1.00 19.43      BLGL
ATOM   1367  CA  GLN   188      -8.233  -0.960  31.465  1.00 20.10      BLGL
ATOM   1368  CB  GLN   188      -9.192  -1.990  32.093  1.00 21.27      BLGL
ATOM   1369  CG  GLN   188     -10.592  -1.480  32.439  1.00 24.00      BLGL
ATOM   1370  CD  GLN   188     -11.358  -0.973  31.228  1.00 29.54      BLGL
ATOM   1371  OE1 GLN   188     -11.546  -1.695  30.242  1.00 33.67      BLGL
ATOM   1372  NE2 GLN   188     -11.808   0.274  31.295  1.00 28.21      BLGL
ATOM   1373  C   GLN   188      -8.191   0.303  32.322  1.00 20.12      BLGL
ATOM   1374  O   GLN   188      -8.779   1.322  31.984  1.00 19.92      BLGL
ATOM   1375  N   ALA   189      -7.493   0.227  33.442  1.00 20.06      BLGL
ATOM   1376  CA  ALA   189      -7.383   1.366  34.329  1.00 19.56      BLGL
ATOM   1377  CB  ALA   189      -6.587   0.982  35.563  1.00 18.86      BLGL
ATOM   1378  C   ALA   189      -6.728   2.546  33.626  1.00 19.66      BLGL
ATOM   1379  O   ALA   189      -7.150   3.681  33.805  1.00 20.48      BLGL
ATOM   1380  N   VAL   190      -5.697   2.273  32.831  1.00 19.85      BLGL
ATOM   1381  CA  VAL   190      -4.984   3.324  32.108  1.00 21.68      BLGL
ATOM   1382  CB  VAL   190      -3.717   2.755  31.378  1.00 21.13      BLGL
ATOM   1383  CG1 VAL   190      -2.955   3.875  30.675  1.00 17.97      BLGL
ATOM   1384  CG2 VAL   190      -2.809   2.069  32.376  1.00 18.02      BLGL
ATOM   1385  C   VAL   190      -5.922   3.966  31.087  1.00 22.56      BLGL
```

Fig. 4 cont.

```
ATOM   1386  O    VAL   190      -6.041   5.190  31.007  1.00 21.59           BLGL
ATOM   1387  N    ARG   191      -6.590   3.122  30.311  1.00 24.93           BLGL
ATOM   1388  CA   ARG   191      -7.528   3.577  29.297  1.00 24.90           BLGL
ATOM   1389  CB   ARG   191      -8.199   2.375  28.640  1.00 22.96           BLGL
ATOM   1390  CG   ARG   191      -7.687   2.059  27.236  1.00 25.30           BLGL
ATOM   1391  CD   ARG   191      -6.416   1.230  27.171  1.00 24.11           BLGL
ATOM   1392  NE   ARG   191      -5.369   1.936  26.503  1.00 24.46           BLGL
ATOM   1393  CZ   ARG   191      -4.581   1.653  25.474  1.00 21.34           BLGL
ATOM   1394  NH1  ARG   191      -3.733   2.613  25.208  1.00 22.37           BLGL
ATOM   1395  NH2  ARG   191      -4.584   0.551  24.731  1.00 21.45           BLGL
ATOM   1396  C    ARG   191      -8.590   4.492  29.892  1.00 25.14           BLGL
ATOM   1397  O    ARG   191      -8.904   5.535  29.334  1.00 27.85           BLGL
ATOM   1398  N    GLU   192      -9.145   4.098  31.026  1.00 25.90           BLGL
ATOM   1399  CA   GLU   192     -10.170   4.895  31.683  1.00 28.14           BLGL
ATOM   1400  CB   GLU   192     -10.761   4.129  32.865  1.00 28.90           BLGL
ATOM   1401  CG   GLU   192     -11.776   3.079  32.494  1.00 31.91           BLGL
ATOM   1402  CD   GLU   192     -12.200   2.266  33.697  1.00 32.43           BLGL
ATOM   1403  OE1  GLU   192     -12.359   2.874  34.772  1.00 28.80           BLGL
ATOM   1404  OE2  GLU   192     -12.378   1.033  33.569  1.00 34.08           BLGL
ATOM   1405  C    GLU   192      -9.630   6.223  32.190  1.00 28.73           BLGL
ATOM   1406  O    GLU   192     -10.352   7.219  32.278  1.00 31.92           BLGL
ATOM   1407  N    THR   193      -8.355   6.237  32.541  1.00 27.87           BLGL
ATOM   1408  CA   THR   193      -7.741   7.445  33.064  1.00 26.29           BLGL
ATOM   1409  CB   THR   193      -6.416   7.098  33.780  1.00 25.98           BLGL
ATOM   1410  OG1  THR   193      -6.697   6.231  34.884  1.00 27.07           BLGL
ATOM   1411  CG2  THR   193      -5.725   8.350  34.296  1.00 24.23           BLGL
ATOM   1412  C    THR   193      -7.488   8.500  31.990  1.00 25.40           BLGL
ATOM   1413  O    THR   193      -7.827   9.666  32.160  1.00 22.00           BLGL
ATOM   1414  N    ASP   194      -6.909   8.084  30.872  1.00 27.05           BLGL
ATOM   1415  CA   ASP   194      -6.585   9.020  29.810  1.00 27.87           BLGL
ATOM   1416  CB   ASP   194      -5.396   9.870  30.271  1.00 29.53           BLGL
ATOM   1417  CG   ASP   194      -4.956  10.881  29.243  1.00 32.75           BLGL
ATOM   1418  OD1  ASP   194      -4.131  11.746  29.606  1.00 34.57           BLGL
ATOM   1419  OD2  ASP   194      -5.418  10.816  28.081  1.00 35.03           BLGL
ATOM   1420  C    ASP   194      -6.245   8.249  28.546  1.00 27.55           BLGL
ATOM   1421  O    ASP   194      -5.389   7.368  28.565  1.00 29.57           BLGL
ATOM   1422  N    SER   195      -6.917   8.580  27.449  1.00 27.67           BLGL
ATOM   1423  CA   SER   195      -6.690   7.903  26.169  1.00 30.14           BLGL
ATOM   1424  CB   SER   195      -7.748   8.333  25.154  1.00 31.04           BLGL
ATOM   1425  OG   SER   195      -9.041   7.986  25.608  1.00 38.90           BLGL
ATOM   1426  C    SER   195      -5.314   8.137  25.553  1.00 29.28           BLGL
ATOM   1427  O    SER   195      -4.830   7.319  24.773  1.00 26.29           BLGL
ATOM   1428  N    ASN   196      -4.690   9.255  25.903  1.00 30.46           BLGL
ATOM   1429  CA   ASN   196      -3.387   9.600  25.358  1.00 32.52           BLGL
ATOM   1430  CB   ASN   196      -3.147  11.097  25.514  1.00 38.65           BLGL
ATOM   1431  CG   ASN   196      -4.246  11.919  24.892  1.00 45.74           BLGL
ATOM   1432  OD1  ASN   196      -4.436  11.902  23.672  1.00 47.81           BLGL
ATOM   1433  ND2  ASN   196      -4.996  12.637  25.729  1.00 49.19           BLGL
ATOM   1434  C    ASN   196      -2.232   8.838  25.981  1.00 30.86           BLGL
ATOM   1435  O    ASN   196      -1.141   8.779  25.411  1.00 31.65           BLGL
ATOM   1436  N    ILE   197      -2.459   8.260  27.153  1.00 28.33           BLGL
ATOM   1437  CA   ILE   197      -1.403   7.517  27.816  1.00 25.33           BLGL
ATOM   1438  CB   ILE   197      -1.771   7.224  29.282  1.00 24.62           BLGL
ATOM   1439  CG2  ILE   197      -0.720   6.335  29.919  1.00 24.24           BLGL
ATOM   1440  CG1  ILE   197      -1.873   8.542  30.053  1.00 24.08           BLGL
ATOM   1441  CD1  ILE   197      -2.239   8.380  31.513  1.00 24.86           BLGL
ATOM   1442  C    ILE   197      -1.149   6.222  27.064  1.00 23.64           BLGL
ATOM   1443  O    ILE   197      -2.081   5.487  26.748  1.00 23.83           BLGL
ATOM   1444  N    LEU   198       0.116   5.962  26.754  1.00 21.57           BLGL
ATOM   1445  CA   LEU   198       0.483   4.751  26.039  1.00 21.61           BLGL
ATOM   1446  CB   LEU   198       1.787   4.962  25.271  1.00 21.02           BLGL
ATOM   1447  CG   LEU   198       1.683   5.885  24.055  1.00 22.44           BLGL
ATOM   1448  CD1  LEU   198       3.062   6.252  23.554  1.00 22.29           BLGL
ATOM   1449  CD2  LEU   198       0.881   5.188  22.967  1.00 23.53           BLGL
ATOM   1450  C    LEU   198       0.653   3.605  27.013  1.00 21.75           BLGL
ATOM   1451  O    LEU   198       1.250   3.776  28.073  1.00 23.44           BLGL
```

Fig. 4 cont.

| | | | | | | | | | |
|---|---|---|---|---|---|---|---|---|---|
| ATOM | 1452 | N | VAL | 199 | 0.114 | 2.441 | 26.666 | 1.00 20.49 | BLGL |
| ATOM | 1453 | CA | VAL | 199 | 0.244 | 1.266 | 27.516 | 1.00 19.26 | BLGL |
| ATOM | 1454 | CB | VAL | 199 | -1.040 | 0.450 | 27.555 | 1.00 19.98 | BLGL |
| ATOM | 1455 | CG1 | VAL | 199 | -0.816 | -0.815 | 28.364 | 1.00 19.20 | BLGL |
| ATOM | 1456 | CG2 | VAL | 199 | -2.148 | 1.282 | 28.149 | 1.00 21.20 | BLGL |
| ATOM | 1457 | C | VAL | 199 | 1.352 | 0.376 | 26.979 | 1.00 18.65 | BLGL |
| ATOM | 1458 | O | VAL | 199 | 1.329 | -0.029 | 25.818 | 1.00 16.57 | BLGL |
| ATOM | 1459 | N | ALA | 200 | 2.314 | 0.061 | 27.839 | 1.00 17.36 | BLGL |
| ATOM | 1460 | CA | ALA | 200 | 3.436 | -0.760 | 27.432 | 1.00 17.13 | BLGL |
| ATOM | 1461 | CB | ALA | 200 | 4.701 | 0.087 | 27.427 | 1.00 15.68 | BLGL |
| ATOM | 1462 | C | ALA | 200 | 3.645 | -1.991 | 28.299 | 1.00 16.72 | BLGL |
| ATOM | 1463 | O | ALA | 200 | 3.403 | -1.960 | 29.501 | 1.00 15.94 | BLGL |
| ATOM | 1464 | N | LEU | 201 | 4.079 | -3.077 | 27.661 | 1.00 17.11 | BLGL |
| ATOM | 1465 | CA | LEU | 201 | 4.390 | -4.332 | 28.339 | 1.00 17.16 | BLGL |
| ATOM | 1466 | CB | LEU | 201 | 3.638 | -5.502 | 27.706 | 1.00 17.16 | BLGL |
| ATOM | 1467 | CG | LEU | 201 | 2.114 | -5.388 | 27.753 | 1.00 17.50 | BLGL |
| ATOM | 1468 | CD1 | LEU | 201 | 1.497 | -6.671 | 27.236 | 1.00 20.85 | BLGL |
| ATOM | 1469 | CD2 | LEU | 201 | 1.654 | -5.132 | 29.172 | 1.00 19.12 | BLGL |
| ATOM | 1470 | C | LEU | 201 | 5.907 | -4.497 | 28.186 | 1.00 17.78 | BLGL |
| ATOM | 1471 | O | LEU | 201 | 6.465 | -4.279 | 27.111 | 1.00 17.49 | BLGL |
| ATOM | 1472 | N | HIS | 202 | 6.568 | -4.874 | 29.272 | 1.00 18.05 | BLGL |
| ATOM | 1473 | CA | HIS | 202 | 8.018 | -4.981 | 29.294 | 1.00 17.54 | BLGL |
| ATOM | 1474 | CB | HIS | 202 | 8.519 | -4.129 | 30.460 | 1.00 17.68 | BLGL |
| ATOM | 1475 | CG | HIS | 202 | 10.002 | -4.110 | 30.616 | 1.00 19.94 | BLGL |
| ATOM | 1476 | CD2 | HIS | 202 | 10.998 | -4.372 | 29.741 | 1.00 20.39 | BLGL |
| ATOM | 1477 | ND1 | HIS | 202 | 10.613 | -3.773 | 31.805 | 1.00 21.65 | BLGL |
| ATOM | 1478 | CE1 | HIS | 202 | 11.922 | -3.831 | 31.655 | 1.00 22.99 | BLGL |
| ATOM | 1479 | NE2 | HIS | 202 | 12.183 | -4.193 | 30.411 | 1.00 23.44 | BLGL |
| ATOM | 1480 | C | HIS | 202 | 8.569 | -6.400 | 29.402 | 1.00 18.30 | BLGL |
| ATOM | 1481 | O | HIS | 202 | 8.272 | -7.122 | 30.354 | 1.00 18.51 | BLGL |
| ATOM | 1482 | N | PHE | 203 | 9.386 | -6.790 | 28.429 | 1.00 16.01 | BLGL |
| ATOM | 1483 | CA | PHE | 203 | 9.989 | -8.114 | 28.431 | 1.00 16.62 | BLGL |
| ATOM | 1484 | CB | PHE | 203 | 9.398 | -8.963 | 27.316 | 1.00 13.11 | BLGL |
| ATOM | 1485 | CG | PHE | 203 | 7.912 | -9.055 | 27.375 | 1.00 17.34 | BLGL |
| ATOM | 1486 | CD1 | PHE | 203 | 7.116 | -8.119 | 26.724 | 1.00 17.15 | BLGL |
| ATOM | 1487 | CD2 | PHE | 203 | 7.299 | -10.037 | 28.144 | 1.00 15.95 | BLGL |
| ATOM | 1488 | CE1 | PHE | 203 | 5.738 | -8.158 | 26.840 | 1.00 16.32 | BLGL |
| ATOM | 1489 | CE2 | PHE | 203 | 5.925 | -10.083 | 28.266 | 1.00 16.04 | BLGL |
| ATOM | 1490 | CZ | PHE | 203 | 5.141 | -9.140 | 27.612 | 1.00 18.54 | BLGL |
| ATOM | 1491 | C | PHE | 203 | 11.504 | -8.033 | 28.274 | 1.00 19.65 | BLGL |
| ATOM | 1492 | O | PHE | 203 | 12.051 | -6.987 | 27.910 | 1.00 21.99 | BLGL |
| ATOM | 1493 | N | THR | 204 | 12.188 | -9.135 | 28.552 | 1.00 17.81 | BLGL |
| ATOM | 1494 | CA | THR | 204 | 13.634 | -9.133 | 28.426 | 1.00 18.21 | BLGL |
| ATOM | 1495 | CB | THR | 204 | 14.314 | -8.849 | 29.798 | 1.00 17.19 | BLGL |
| ATOM | 1496 | OG1 | THR | 204 | 15.726 | -8.736 | 29.611 | 1.00 14.37 | BLGL |
| ATOM | 1497 | CG2 | THR | 204 | 14.006 | -9.951 | 30.809 | 1.00 13.65 | BLGL |
| ATOM | 1498 | C | THR | 204 | 14.161 | -10.428 | 27.809 | 1.00 18.61 | BLGL |
| ATOM | 1499 | O | THR | 204 | 13.394 | -11.352 | 27.534 | 1.00 16.21 | BLGL |
| ATOM | 1500 | N | ASN | 205 | 15.469 | -10.473 | 27.580 | 1.00 17.26 | BLGL |
| ATOM | 1501 | CA | ASN | 205 | 16.112 | -11.622 | 26.964 | 1.00 17.80 | BLGL |
| ATOM | 1502 | CB | ASN | 205 | 15.814 | -12.907 | 27.728 | 1.00 18.45 | BLGL |
| ATOM | 1503 | CG | ASN | 205 | 16.601 | -13.000 | 29.001 | 1.00 18.12 | BLGL |
| ATOM | 1504 | OD1 | ASN | 205 | 16.070 | -12.811 | 30.094 | 1.00 20.78 | BLGL |
| ATOM | 1505 | ND2 | ASN | 205 | 17.890 | -13.266 | 28.868 | 1.00 18.03 | BLGL |
| ATOM | 1506 | C | ASN | 205 | 15.701 | -11.784 | 25.520 | 1.00 17.89 | BLGL |
| ATOM | 1507 | O | ASN | 205 | 15.129 | -12.800 | 25.135 | 1.00 18.21 | BLGL |
| ATOM | 1508 | N | PRO | 206 | 15.988 | -10.771 | 24.697 | 1.00 18.39 | BLGL |
| ATOM | 1509 | CD | PRO | 206 | 16.580 | -9.480 | 25.080 | 1.00 15.66 | BLGL |
| ATOM | 1510 | CA | PRO | 206 | 15.657 | -10.778 | 23.273 | 1.00 19.70 | BLGL |
| ATOM | 1511 | CB | PRO | 206 | 15.903 | -9.334 | 22.867 | 1.00 19.33 | BLGL |
| ATOM | 1512 | CG | PRO | 206 | 17.029 | -8.939 | 23.756 | 1.00 16.74 | BLGL |
| ATOM | 1513 | C | PRO | 206 | 16.500 | -11.748 | 22.459 | 1.00 21.36 | BLGL |
| ATOM | 1514 | O | PRO | 206 | 16.158 | -12.055 | 21.318 | 1.00 22.70 | BLGL |
| ATOM | 1515 | N | GLU | 207 | 17.601 | -12.224 | 23.034 | 1.00 23.27 | BLGL |
| ATOM | 1516 | CA | GLU | 207 | 18.478 | -13.154 | 22.324 | 1.00 25.47 | BLGL |
| ATOM | 1517 | CB | GLU | 207 | 19.871 | -13.210 | 22.959 | 1.00 26.18 | BLGL |

Fig. 4 cont.

```
ATOM   1518  CG  GLU  207     20.021 -12.502  24.288  1.00 30.25      BLGL
ATOM   1519  CD  GLU  207     19.242 -13.139  25.413  1.00 29.52      BLGL
ATOM   1520  OE1 GLU  207     19.387 -14.353  25.643  1.00 33.25      BLGL
ATOM   1521  OE2 GLU  207     18.495 -12.413  26.081  1.00 29.56      BLGL
ATOM   1522  C   GLU  207     17.924 -14.561  22.258  1.00 26.20      BLGL
ATOM   1523  O   GLU  207     18.354 -15.357  21.426  1.00 29.50      BLGL
ATOM   1524  N   THR  208     16.982 -14.873  23.139  1.00 25.50      BLGL
ATOM   1525  CA  THR  208     16.384 -16.196  23.151  1.00 25.38      BLGL
ATOM   1526  CB  THR  208     15.419 -16.349  24.314  1.00 25.02      BLGL
ATOM   1527  OG1 THR  208     16.108 -16.063  25.532  1.00 24.40      BLGL
ATOM   1528  CG2 THR  208     14.871 -17.765  24.361  1.00 24.75      BLGL
ATOM   1529  C   THR  208     15.628 -16.435  21.853  1.00 24.66      BLGL
ATOM   1530  O   THR  208     14.689 -15.711  21.531  1.00 23.66      BLGL
ATOM   1531  N   SER  209     16.047 -17.455  21.114  1.00 24.67      BLGL
ATOM   1532  CA  SER  209     15.424 -17.791  19.842  1.00 25.56      BLGL
ATOM   1533  CB  SER  209     15.971 -19.120  19.334  1.00 23.59      BLGL
ATOM   1534  OG  SER  209     15.290 -19.524  18.166  1.00 26.21      BLGL
ATOM   1535  C   SER  209     13.896 -17.862  19.885  1.00 26.32      BLGL
ATOM   1536  O   SER  209     13.321 -18.668  20.632  1.00 23.52      BLGL
ATOM   1537  N   GLY  210     13.257 -17.004  19.083  1.00 26.00      BLGL
ATOM   1538  CA  GLY  210     11.803 -16.966  18.977  1.00 25.41      BLGL
ATOM   1539  C   GLY  210     10.990 -16.593  20.204  1.00 26.60      BLGL
ATOM   1540  O   GLY  210      9.768 -16.755  20.215  1.00 26.52      BLGL
ATOM   1541  N   ARG  211     11.659 -16.080  21.231  1.00 27.83      BLGL
ATOM   1542  CA  ARG  211     11.004 -15.692  22.478  1.00 25.31      BLGL
ATOM   1543  CB  ARG  211     12.046 -15.244  23.496  1.00 26.05      BLGL
ATOM   1544  CG  ARG  211     11.487 -15.024  24.881  1.00 26.98      BLGL
ATOM   1545  CD  ARG  211     12.479 -14.289  25.747  1.00 28.49      BLGL
ATOM   1546  NE  ARG  211     12.362 -14.719  27.125  1.00 32.45      BLGL
ATOM   1547  CZ  ARG  211     13.043 -15.727  27.655  1.00 34.26      BLGL
ATOM   1548  NH1 ARG  211     13.903 -16.408  26.920  1.00 33.07      BLGL
ATOM   1549  NH2 ARG  211     12.850 -16.067  28.924  1.00 40.91      BLGL
ATOM   1550  C   ARG  211      9.977 -14.580  22.294  1.00 24.24      BLGL
ATOM   1551  O   ARG  211      8.806 -14.744  22.634  1.00 24.47      BLGL
ATOM   1552  N   TYR  212     10.413 -13.440  21.768  1.00 22.57      BLGL
ATOM   1553  CA  TYR  212      9.499 -12.323  21.558  1.00 20.27      BLGL
ATOM   1554  CB  TYR  212     10.262 -11.080  21.093  1.00 18.26      BLGL
ATOM   1555  CG  TYR  212     11.063 -10.409  22.188  1.00 20.40      BLGL
ATOM   1556  CD1 TYR  212     11.669  -9.170  21.972  1.00 19.09      BLGL
ATOM   1557  CE1 TYR  212     12.387  -8.538  22.982  1.00 16.98      BLGL
ATOM   1558  CD2 TYR  212     11.204 -11.001  23.445  1.00 17.87      BLGL
ATOM   1559  CE2 TYR  212     11.919 -10.377  24.457  1.00 15.68      BLGL
ATOM   1560  CZ  TYR  212     12.505  -9.147  24.225  1.00 16.21      BLGL
ATOM   1561  OH  TYR  212     13.200  -8.514  25.235  1.00 15.74      BLGL
ATOM   1562  C   TYR  212      8.398 -12.670  20.559  1.00 20.87      BLGL
ATOM   1563  O   TYR  212      7.259 -12.237  20.712  1.00 20.22      BLGL
ATOM   1564  N   ALA  213      8.734 -13.449  19.537  1.00 19.68      BLGL
ATOM   1565  CA  ALA  213      7.742 -13.847  18.547  1.00 19.79      BLGL
ATOM   1566  CB  ALA  213      8.399 -14.687  17.454  1.00 17.89      BLGL
ATOM   1567  C   ALA  213      6.629 -14.642  19.231  1.00 19.99      BLGL
ATOM   1568  O   ALA  213      5.451 -14.479  18.911  1.00 19.71      BLGL
ATOM   1569  N   TRP  214      7.009 -15.496  20.176  1.00 20.09      BLGL
ATOM   1570  CA  TRP  214      6.039 -16.309  20.900  1.00 21.30      BLGL
ATOM   1571  CB  TRP  214      6.753 -17.375  21.732  1.00 22.71      BLGL
ATOM   1572  CG  TRP  214      5.815 -18.281  22.468  1.00 24.60      BLGL
ATOM   1573  CD2 TRP  214      5.308 -18.094  23.795  1.00 24.97      BLGL
ATOM   1574  CE2 TRP  214      4.449 -19.183  24.074  1.00 24.59      BLGL
ATOM   1575  CE3 TRP  214      5.496 -17.112  24.775  1.00 25.69      BLGL
ATOM   1576  CD1 TRP  214      5.256 -19.440  22.005  1.00 24.97      BLGL
ATOM   1577  NE1 TRP  214      4.436 -19.989  22.966  1.00 25.84      BLGL
ATOM   1578  CZ2 TRP  214      3.780 -19.319  25.294  1.00 22.78      BLGL
ATOM   1579  CZ3 TRP  214      4.829 -17.248  25.991  1.00 27.53      BLGL
ATOM   1580  CH2 TRP  214      3.981 -18.345  26.238  1.00 24.84      BLGL
ATOM   1581  C   TRP  214      5.167 -15.453  21.816  1.00 21.83      BLGL
ATOM   1582  O   TRP  214      3.948 -15.630  21.857  1.00 20.77      BLGL
ATOM   1583  N   ILE  215      5.793 -14.531  22.550  1.00 21.49      BLGL
```

Fig. 4 cont.

```
ATOM   1584  CA   ILE   215      5.067  -13.654  23.469  1.00 19.18        BLGL
ATOM   1585  CB   ILE   215      6.038  -12.771  24.300  1.00 19.85        BLGL
ATOM   1586  CG2  ILE   215      5.257  -11.811  25.198  1.00 15.32        BLGL
ATOM   1587  CG1  ILE   215      6.930  -13.651  25.170  1.00 18.25        BLGL
ATOM   1588  CD1  ILE   215      7.930  -12.876  25.975  1.00 15.25        BLGL
ATOM   1589  C    ILE   215      4.104  -12.740  22.725  1.00 19.79        BLGL
ATOM   1590  O    ILE   215      2.964  -12.550  23.146  1.00 18.73        BLGL
ATOM   1591  N    ALA   216      4.565  -12.163  21.621  1.00 19.35        BLGL
ATOM   1592  CA   ALA   216      3.723  -11.275  20.840  1.00 18.57        BLGL
ATOM   1593  CB   ALA   216      4.492  -10.751  19.650  1.00 18.16        BLGL
ATOM   1594  C    ALA   216      2.472  -12.020  20.378  1.00 20.55        BLGL
ATOM   1595  O    ALA   216      1.359  -11.501  20.466  1.00 16.58        BLGL
ATOM   1596  N    GLU   217      2.669  -13.242  19.890  1.00 22.90        BLGL
ATOM   1597  CA   GLU   217      1.569  -14.077  19.419  1.00 24.77        BLGL
ATOM   1598  CB   GLU   217      2.122  -15.338  18.747  1.00 28.27        BLGL
ATOM   1599  CG   GLU   217      1.063  -16.371  18.379  1.00 33.34        BLGL
ATOM   1600  CD   GLU   217     -0.002  -15.823  17.449  1.00 35.08        BLGL
ATOM   1601  OE1  GLU   217     -1.049  -16.485  17.288  1.00 39.18        BLGL
ATOM   1602  OE2  GLU   217      0.208  -14.737  16.875  1.00 35.59        BLGL
ATOM   1603  C    GLU   217      0.623  -14.468  20.560  1.00 24.16        BLGL
ATOM   1604  O    GLU   217     -0.596  -14.464  20.395  1.00 22.67        BLGL
ATOM   1605  N    THR   218      1.195  -14.805  21.713  1.00 24.08        BLGL
ATOM   1606  CA   THR   218      0.412  -15.191  22.878  1.00 23.79        BLGL
ATOM   1607  CB   THR   218      1.334  -15.684  24.027  1.00 25.12        BLGL
ATOM   1608  OG1  THR   218      1.985  -16.896  23.630  1.00 26.14        BLGL
ATOM   1609  CG2  THR   218      0.537  -15.942  25.298  1.00 23.98        BLGL
ATOM   1610  C    THR   218     -0.429  -14.014  23.362  1.00 22.94        BLGL
ATOM   1611  O    THR   218     -1.600  -14.179  23.692  1.00 24.35        BLGL
ATOM   1612  N    LEU   219      0.160  -12.825  23.401  1.00 21.92        BLGL
ATOM   1613  CA   LEU   219     -0.578  -11.644  23.846  1.00 23.28        BLGL
ATOM   1614  CB   LEU   219      0.333  -10.410  23.863  1.00 21.92        BLGL
ATOM   1615  CG   LEU   219      1.462  -10.359  24.893  1.00 18.90        BLGL
ATOM   1616  CD1  LEU   219      2.386   -9.209  24.570  1.00 14.80        BLGL
ATOM   1617  CD2  LEU   219      0.879  -10.220  26.289  1.00 16.33        BLGL
ATOM   1618  C    LEU   219     -1.753  -11.394  22.903  1.00 24.55        BLGL
ATOM   1619  O    LEU   219     -2.850  -11.031  23.322  1.00 25.23        BLGL
ATOM   1620  N    HIS   220     -1.512  -11.603  21.619  1.00 25.34        BLGL
ATOM   1621  CA   HIS   220     -2.539  -11.401  20.622  1.00 25.88        BLGL
ATOM   1622  CB   HIS   220     -1.904  -11.450  19.236  1.00 27.15        BLGL
ATOM   1623  CG   HIS   220     -2.888  -11.366  18.116  1.00 31.81        BLGL
ATOM   1624  CD2  HIS   220     -3.485  -10.300  17.529  1.00 31.02        BLGL
ATOM   1625  ND1  HIS   220     -3.388  -12.486  17.483  1.00 33.38        BLGL
ATOM   1626  CE1  HIS   220     -4.250  -12.111  16.554  1.00 33.29        BLGL
ATOM   1627  NE2  HIS   220     -4.326  -10.791  16.562  1.00 32.86        BLGL
ATOM   1628  C    HIS   220     -3.665  -12.423  20.743  1.00 26.70        BLGL
ATOM   1629  O    HIS   220     -4.839  -12.076  20.617  1.00 25.81        BLGL
ATOM   1630  N    ARG   221     -3.312  -13.679  20.993  1.00 28.18        BLGL
ATOM   1631  CA   ARG   221     -4.314  -14.730  21.133  1.00 30.04        BLGL
ATOM   1632  CB   ARG   221     -3.648  -16.090  21.361  1.00 33.95        BLGL
ATOM   1633  CG   ARG   221     -3.038  -16.680  20.095  1.00 40.22        BLGL
ATOM   1634  CD   ARG   221     -2.052  -17.802  20.368  1.00 47.28        BLGL
ATOM   1635  NE   ARG   221     -2.419  -19.012  19.696  1.00 52.72        BLGL
ATOM   1636  CZ   ARG   221     -1.881  -19.711  18.699  1.00 54.00        BLGL
ATOM   1637  NH1  ARG   221     -2.572  -20.786  18.387  1.00 56.27        BLGL
ATOM   1638  NH2  ARG   221     -0.762  -19.439  18.032  1.00 52.22        BLGL
ATOM   1639  C    ARG   221     -5.263  -14.440  22.276  1.00 29.71        BLGL
ATOM   1640  O    ARG   221     -6.441  -14.790  22.204  1.00 30.75        BLGL
ATOM   1641  N    HIS   222     -4.757  -13.803  23.331  1.00 27.89        BLGL
ATOM   1642  CA   HIS   222     -5.599  -13.482  24.477  1.00 27.09        BLGL
ATOM   1643  CB   HIS   222     -4.844  -13.728  25.782  1.00 26.93        BLGL
ATOM   1644  CG   HIS   222     -4.530  -15.168  26.023  1.00 28.56        BLGL
ATOM   1645  CD2  HIS   222     -5.196  -16.121  26.716  1.00 30.01        BLGL
ATOM   1646  ND1  HIS   222     -3.441  -15.797  25.459  1.00 31.08        BLGL
ATOM   1647  CE1  HIS   222     -3.448  -17.076  25.792  1.00 30.75        BLGL
ATOM   1648  NE2  HIS   222     -4.504  -17.298  26.554  1.00 33.11        BLGL
ATOM   1649  C    HIS   222     -6.159  -12.064  24.456  1.00 26.57        BLGL
```

Fig. 4 cont.

```
ATOM   1650  O   HIS  222    -6.646 -11.564  25.469  1.00 25.69      BLGL
ATOM   1651  N   HIS  223    -6.084 -11.418  23.300  1.00 25.18      BLGL
ATOM   1652  CA  HIS  223    -6.627 -10.082  23.151  1.00 26.33      BLGL
ATOM   1653  CB  HIS  223    -8.147 -10.149  23.214  1.00 30.76      BLGL
ATOM   1654  CG  HIS  223    -8.739 -11.182  22.309  1.00 38.88      BLGL
ATOM   1655  CD2 HIS  223    -9.524 -12.253  22.570  1.00 41.07      BLGL
ATOM   1656  ND1 HIS  223    -8.531 -11.182  20.945  1.00 43.14      BLGL
ATOM   1657  CE1 HIS  223    -9.161 -12.210  20.405  1.00 43.27      BLGL
ATOM   1658  NE2 HIS  223    -9.771 -12.876  21.370  1.00 45.48      BLGL
ATOM   1659  C   HIS  223    -6.149  -9.081  24.186  1.00 26.02      BLGL
ATOM   1660  O   HIS  223    -6.961  -8.345  24.750  1.00 27.73      BLGL
ATOM   1661  N   VAL  224    -4.846  -9.044  24.446  1.00 22.81      BLGL
ATOM   1662  CA  VAL  224    -4.316  -8.096  25.413  1.00 18.14      BLGL
ATOM   1663  CB  VAL  224    -2.912  -8.499  25.895  1.00 16.94      BLGL
ATOM   1664  CG1 VAL  224    -2.312  -7.399  26.758  1.00 12.94      BLGL
ATOM   1665  CG2 VAL  224    -2.998  -9.783  26.676  1.00 15.42      BLGL
ATOM   1666  C   VAL  224    -4.241  -6.742  24.734  1.00 17.57      BLGL
ATOM   1667  O   VAL  224    -3.683  -6.610  23.646  1.00 16.83      BLGL
ATOM   1668  N   ASP  225    -4.808  -5.738  25.386  1.00 16.35      BLGL
ATOM   1669  CA  ASP  225    -4.820  -4.393  24.849  1.00 17.47      BLGL
ATOM   1670  CB  ASP  225    -6.123  -3.707  25.254  1.00 17.33      BLGL
ATOM   1671  CG  ASP  225    -6.172  -2.260  24.843  1.00 19.19      BLGL
ATOM   1672  OD1 ASP  225    -5.722  -1.945  23.717  1.00 21.14      BLGL
ATOM   1673  OD2 ASP  225    -6.672  -1.444  25.643  1.00 19.74      BLGL
ATOM   1674  C   ASP  225    -3.626  -3.562  25.306  1.00 18.47      BLGL
ATOM   1675  O   ASP  225    -3.609  -3.073  26.433  1.00 19.94      BLGL
ATOM   1676  N   TYR  226    -2.626  -3.415  24.440  1.00 17.31      BLGL
ATOM   1677  CA  TYR  226    -1.441  -2.610  24.762  1.00 19.05      BLGL
ATOM   1678  CB  TYR  226    -0.315  -3.483  25.359  1.00 17.31      BLGL
ATOM   1679  CG  TYR  226     0.380  -4.417  24.386  1.00 17.91      BLGL
ATOM   1680  CD1 TYR  226    -0.315  -5.469  23.780  1.00 17.20      BLGL
ATOM   1681  CE1 TYR  226     0.317  -6.338  22.891  1.00 14.85      BLGL
ATOM   1682  CD2 TYR  226     1.737  -4.253  24.076  1.00 15.96      BLGL
ATOM   1683  CE2 TYR  226     2.380  -5.117  23.184  1.00 15.01      BLGL
ATOM   1684  CZ  TYR  226     1.661  -6.156  22.598  1.00 16.47      BLGL
ATOM   1685  OH  TYR  226     2.279  -7.019  21.725  1.00 13.64      BLGL
ATOM   1686  C   TYR  226    -0.944  -1.877  23.513  1.00 17.95      BLGL
ATOM   1687  O   TYR  226    -1.285  -2.251  22.398  1.00 17.24      BLGL
ATOM   1688  N   ASP  227    -0.141  -0.836  23.697  1.00 18.09      BLGL
ATOM   1689  CA  ASP  227     0.361  -0.075  22.557  1.00 20.63      BLGL
ATOM   1690  CB  ASP  227     0.126   1.424  22.760  1.00 23.61      BLGL
ATOM   1691  CG  ASP  227    -1.247   1.736  23.282  1.00 24.31      BLGL
ATOM   1692  OD1 ASP  227    -2.242   1.427  22.597  1.00 26.42      BLGL
ATOM   1693  OD2 ASP  227    -1.327   2.298  24.388  1.00 29.59      BLGL
ATOM   1694  C   ASP  227     1.846  -0.263  22.289  1.00 21.20      BLGL
ATOM   1695  O   ASP  227     2.283  -0.241  21.141  1.00 21.63      BLGL
ATOM   1696  N   VAL  228     2.626  -0.432  23.350  1.00 21.33      BLGL
ATOM   1697  CA  VAL  228     4.069  -0.571  23.205  1.00 18.22      BLGL
ATOM   1698  CB  VAL  228     4.822   0.572  23.961  1.00 16.56      BLGL
ATOM   1699  CG1 VAL  228     6.307   0.511  23.669  1.00 16.51      BLGL
ATOM   1700  CG2 VAL  228     4.268   1.921  23.569  1.00 16.96      BLGL
ATOM   1701  C   VAL  228     4.631  -1.892  23.700  1.00 16.80      BLGL
ATOM   1702  O   VAL  228     4.338  -2.338  24.811  1.00 16.77      BLGL
ATOM   1703  N   PHE  229     5.444  -2.510  22.858  1.00 15.66      BLGL
ATOM   1704  CA  PHE  229     6.115  -3.747  23.213  1.00 16.03      BLGL
ATOM   1705  CB  PHE  229     6.177  -4.694  22.007  1.00 15.71      BLGL
ATOM   1706  CG  PHE  229     6.773  -6.038  22.323  1.00 18.72      BLGL
ATOM   1707  CD1 PHE  229     8.148  -6.193  22.458  1.00 20.15      BLGL
ATOM   1708  CD2 PHE  229     5.957  -7.141  22.537  1.00 19.69      BLGL
ATOM   1709  CE1 PHE  229     8.698  -7.424  22.805  1.00 20.33      BLGL
ATOM   1710  CE2 PHE  229     6.502  -8.376  22.885  1.00 19.99      BLGL
ATOM   1711  CZ  PHE  229     7.873  -8.516  23.020  1.00 20.18      BLGL
ATOM   1712  C   PHE  229     7.517  -3.278  23.608  1.00 15.51      BLGL
ATOM   1713  O   PHE  229     8.336  -2.965  22.747  1.00 16.80      BLGL
ATOM   1714  N   ALA  230     7.781  -3.205  24.909  1.00 14.48      BLGL
ATOM   1715  CA  ALA  230     9.076  -2.740  25.392  1.00 16.32      BLGL
```

Fig. 4 cont.

| | | | | | | | | | |
|---|---|---|---|---|---|---|---|---|---|
| ATOM | 1716 | CB | ALA | 230 | 8.892 | -1.878 | 26.632 | 1.00 15.48 | BLGL |
| ATOM | 1717 | C | ALA | 230 | 10.040 | -3.878 | 25.691 | 1.00 17.75 | BLGL |
| ATOM | 1718 | O | ALA | 230 | 9.624 | -4.990 | 26.019 | 1.00 19.06 | BLGL |
| ATOM | 1719 | N | SER | 231 | 11.334 | -3.588 | 25.580 | 1.00 15.44 | BLGL |
| ATOM | 1720 | CA | SER | 231 | 12.363 | -4.583 | 25.829 | 1.00 15.19 | BLGL |
| ATOM | 1721 | CB | SER | 231 | 12.863 | -5.165 | 24.498 | 1.00 12.54 | BLGL |
| ATOM | 1722 | OG | SER | 231 | 13.966 | -6.035 | 24.696 | 1.00 9.34 | BLGL |
| ATOM | 1723 | C | SER | 231 | 13.554 | -4.024 | 26.601 | 1.00 16.12 | BLGL |
| ATOM | 1724 | O | SER | 231 | 13.915 | -2.852 | 26.463 | 1.00 17.19 | BLGL |
| ATOM | 1725 | N | SER | 232 | 14.152 | -4.865 | 27.434 | 1.00 14.04 | BLGL |
| ATOM | 1726 | CA | SER | 232 | 15.341 | -4.463 | 28.159 | 1.00 15.04 | BLGL |
| ATOM | 1727 | CB | SER | 232 | 15.505 | -5.272 | 29.447 | 1.00 14.50 | BLGL |
| ATOM | 1728 | OG | SER | 232 | 14.733 | -4.727 | 30.499 | 1.00 17.36 | BLGL |
| ATOM | 1729 | C | SER | 232 | 16.485 | -4.810 | 27.216 | 1.00 15.02 | BLGL |
| ATOM | 1730 | O | SER | 232 | 16.354 | -5.696 | 26.374 | 1.00 14.13 | BLGL |
| ATOM | 1731 | N | TYR | 233 | 17.591 | -4.094 | 27.326 | 1.00 14.36 | BLGL |
| ATOM | 1732 | CA | TYR | 233 | 18.738 | -4.410 | 26.506 | 1.00 16.28 | BLGL |
| ATOM | 1733 | CB | TYR | 233 | 18.721 | -3.697 | 25.152 | 1.00 15.72 | BLGL |
| ATOM | 1734 | CG | TYR | 233 | 19.901 | -4.146 | 24.318 | 1.00 18.38 | BLGL |
| ATOM | 1735 | CD1 | TYR | 233 | 19.935 | -5.428 | 23.762 | 1.00 17.95 | BLGL |
| ATOM | 1736 | CE1 | TYR | 233 | 21.072 | -5.905 | 23.102 | 1.00 17.74 | BLGL |
| ATOM | 1737 | CD2 | TYR | 233 | 21.038 | -3.342 | 24.185 | 1.00 19.16 | BLGL |
| ATOM | 1738 | CE2 | TYR | 233 | 22.181 | -3.809 | 23.528 | 1.00 18.72 | BLGL |
| ATOM | 1739 | CZ | TYR | 233 | 22.188 | -5.090 | 22.991 | 1.00 20.19 | BLGL |
| ATOM | 1740 | OH | TYR | 233 | 23.305 | -5.552 | 22.339 | 1.00 21.28 | BLGL |
| ATOM | 1741 | C | TYR | 233 | 20.051 | -4.096 | 27.204 | 1.00 18.26 | BLGL |
| ATOM | 1742 | O | TYR | 233 | 20.488 | -2.941 | 27.282 | 1.00 19.11 | BLGL |
| ATOM | 1743 | N | TYR | 234 | 20.672 | -5.148 | 27.715 | 1.00 18.61 | BLGL |
| ATOM | 1744 | CA | TYR | 234 | 21.951 | -5.047 | 28.382 | 1.00 20.22 | BLGL |
| ATOM | 1745 | CB | TYR | 234 | 21.838 | -5.594 | 29.794 | 1.00 18.03 | BLGL |
| ATOM | 1746 | CG | TYR | 234 | 21.020 | -4.689 | 30.678 | 1.00 19.42 | BLGL |
| ATOM | 1747 | CD1 | TYR | 234 | 21.536 | -3.473 | 31.130 | 1.00 17.03 | BLGL |
| ATOM | 1748 | CE1 | TYR | 234 | 20.778 | -2.628 | 31.935 | 1.00 15.84 | BLGL |
| ATOM | 1749 | CD2 | TYR | 234 | 19.718 | -5.035 | 31.051 | 1.00 20.59 | BLGL |
| ATOM | 1750 | CE2 | TYR | 234 | 18.950 | -4.194 | 31.854 | 1.00 18.88 | BLGL |
| ATOM | 1751 | CZ | TYR | 234 | 19.489 | -2.995 | 32.294 | 1.00 17.70 | BLGL |
| ATOM | 1752 | OH | TYR | 234 | 18.745 | -2.180 | 33.108 | 1.00 17.67 | BLGL |
| ATOM | 1753 | C | TYR | 234 | 22.896 | -5.875 | 27.538 | 1.00 20.87 | BLGL |
| ATOM | 1754 | O | TYR | 234 | 22.858 | -7.104 | 27.570 | 1.00 23.14 | BLGL |
| ATOM | 1755 | N | PRO | 235 | 23.749 | -5.201 | 26.756 | 1.00 21.55 | BLGL |
| ATOM | 1756 | CD | PRO | 235 | 23.983 | -3.751 | 26.857 | 1.00 21.91 | BLGL |
| ATOM | 1757 | CA | PRO | 235 | 24.728 | -5.825 | 25.864 | 1.00 22.81 | BLGL |
| ATOM | 1758 | CB | PRO | 235 | 25.551 | -4.639 | 25.367 | 1.00 22.48 | BLGL |
| ATOM | 1759 | CG | PRO | 235 | 25.422 | -3.640 | 26.471 | 1.00 21.97 | BLGL |
| ATOM | 1760 | C | PRO | 235 | 25.575 | -6.912 | 26.508 | 1.00 23.83 | BLGL |
| ATOM | 1761 | O | PRO | 235 | 26.118 | -7.762 | 25.812 | 1.00 26.44 | BLGL |
| ATOM | 1762 | N | PHE | 236 | 25.673 | -6.894 | 27.834 | 1.00 24.38 | BLGL |
| ATOM | 1763 | CA | PHE | 236 | 26.451 | -7.894 | 28.556 | 1.00 23.56 | BLGL |
| ATOM | 1764 | CB | PHE | 236 | 26.439 | -7.613 | 30.069 | 1.00 22.41 | BLGL |
| ATOM | 1765 | CG | PHE | 236 | 26.751 | -6.190 | 30.432 | 1.00 20.97 | BLGL |
| ATOM | 1766 | CD1 | PHE | 236 | 25.769 | -5.363 | 30.960 | 1.00 22.30 | BLGL |
| ATOM | 1767 | CD2 | PHE | 236 | 28.018 | -5.666 | 30.224 | 1.00 21.90 | BLGL |
| ATOM | 1768 | CE1 | PHE | 236 | 26.043 | -4.031 | 31.274 | 1.00 20.76 | BLGL |
| ATOM | 1769 | CE2 | PHE | 236 | 28.304 | -4.335 | 30.534 | 1.00 22.34 | BLGL |
| ATOM | 1770 | CZ | PHE | 236 | 27.310 | -3.518 | 31.060 | 1.00 22.41 | BLGL |
| ATOM | 1771 | C | PHE | 236 | 25.901 | -9.297 | 28.322 | 1.00 24.55 | BLGL |
| ATOM | 1772 | O | PHE | 236 | 26.664 | -10.252 | 28.209 | 1.00 26.43 | BLGL |
| ATOM | 1773 | N | TRP | 237 | 24.581 | -9.425 | 28.226 | 1.00 25.33 | BLGL |
| ATOM | 1774 | CA | TRP | 237 | 23.971 | -10.745 | 28.067 | 1.00 26.98 | BLGL |
| ATOM | 1775 | CB | TRP | 237 | 23.270 | -11.144 | 29.367 | 1.00 27.82 | BLGL |
| ATOM | 1776 | CG | TRP | 237 | 23.960 | -10.698 | 30.606 | 1.00 30.90 | BLGL |
| ATOM | 1777 | CD2 | TRP | 237 | 23.562 | -9.632 | 31.466 | 1.00 31.06 | BLGL |
| ATOM | 1778 | CE2 | TRP | 237 | 24.489 | -9.585 | 32.535 | 1.00 31.99 | BLGL |
| ATOM | 1779 | CE3 | TRP | 237 | 22.511 | -8.711 | 31.443 | 1.00 32.34 | BLGL |
| ATOM | 1780 | CD1 | TRP | 237 | 25.084 | -11.238 | 31.162 | 1.00 33.44 | BLGL |
| ATOM | 1781 | NE1 | TRP | 237 | 25.408 | -10.577 | 32.324 | 1.00 32.26 | BLGL |

Fig. 4 cont.

| | | | | | | | | | |
|---|---|---|---|---|---|---|---|---|---|
| ATOM | 1782 | CZ2 | TRP | 237 | 24.396 | -8.652 | 33.570 | 1.00 32.74 | BLGL |
| ATOM | 1783 | CZ3 | TRP | 237 | 22.417 | -7.780 | 32.477 | 1.00 34.34 | BLGL |
| ATOM | 1784 | CH2 | TRP | 237 | 23.357 | -7.761 | 33.526 | 1.00 33.93 | BLGL |
| ATOM | 1785 | C | TRP | 237 | 22.938 | -10.894 | 26.960 | 1.00 26.05 | BLGL |
| ATOM | 1786 | O | TRP | 237 | 22.632 | -12.011 | 26.543 | 1.00 25.25 | BLGL |
| ATOM | 1787 | N | HIS | 238 | 22.401 | -9.778 | 26.487 | 1.00 24.70 | BLGL |
| ATOM | 1788 | CA | HIS | 238 | 21.333 | -9.824 | 25.504 | 1.00 20.96 | BLGL |
| ATOM | 1789 | CB | HIS | 238 | 20.358 | -8.703 | 25.824 | 1.00 19.05 | BLGL |
| ATOM | 1790 | CG | HIS | 238 | 19.772 | -8.821 | 27.192 | 1.00 17.38 | BLGL |
| ATOM | 1791 | CD2 | HIS | 238 | 19.601 | -9.900 | 27.990 | 1.00 16.73 | BLGL |
| ATOM | 1792 | ND1 | HIS | 238 | 19.291 | -7.743 | 27.896 | 1.00 20.29 | BLGL |
| ATOM | 1793 | CE1 | HIS | 238 | 18.850 | -8.151 | 29.073 | 1.00 20.03 | BLGL |
| ATOM | 1794 | NE2 | HIS | 238 | 19.026 | -9.456 | 29.154 | 1.00 19.52 | BLGL |
| ATOM | 1795 | C | HIS | 238 | 21.628 | -9.863 | 24.019 | 1.00 20.65 | BLGL |
| ATOM | 1796 | O | HIS | 238 | 20.854 | -9.354 | 23.217 | 1.00 22.38 | BLGL |
| ATOM | 1797 | N | GLY | 239 | 22.730 | -10.489 | 23.643 | 1.00 19.61 | BLGL |
| ATOM | 1798 | CA | GLY | 239 | 23.037 | -10.607 | 22.234 | 1.00 19.09 | BLGL |
| ATOM | 1799 | C | GLY | 239 | 23.345 | -9.338 | 21.474 | 1.00 18.09 | BLGL |
| ATOM | 1800 | O | GLY | 239 | 23.535 | -8.271 | 22.046 | 1.00 17.84 | BLGL |
| ATOM | 1801 | N | THR | 240 | 23.369 | -9.476 | 20.158 | 1.00 17.37 | BLGL |
| ATOM | 1802 | CA | THR | 240 | 23.697 | -8.387 | 19.258 | 1.00 18.95 | BLGL |
| ATOM | 1803 | CB | THR | 240 | 24.139 | -8.949 | 17.896 | 1.00 18.49 | BLGL |
| ATOM | 1804 | OG1 | THR | 240 | 23.028 | -9.589 | 17.262 | 1.00 18.33 | BLGL |
| ATOM | 1805 | CG2 | THR | 240 | 25.239 | -9.964 | 18.076 | 1.00 14.06 | BLGL |
| ATOM | 1806 | C | THR | 240 | 22.610 | -7.348 | 19.003 | 1.00 20.98 | BLGL |
| ATOM | 1807 | O | THR | 240 | 21.418 | -7.604 | 19.169 | 1.00 19.90 | BLGL |
| ATOM | 1808 | N | LEU | 241 | 23.043 | -6.165 | 18.581 | 1.00 21.55 | BLGL |
| ATOM | 1809 | CA | LEU | 241 | 22.115 | -5.094 | 18.277 | 1.00 21.65 | BLGL |
| ATOM | 1810 | CB | LEU | 241 | 22.874 | -3.780 | 18.086 | 1.00 20.04 | BLGL |
| ATOM | 1811 | CG | LEU | 241 | 23.464 | -3.205 | 19.381 | 1.00 21.24 | BLGL |
| ATOM | 1812 | CD1 | LEU | 241 | 24.455 | -2.105 | 19.074 | 1.00 18.53 | BLGL |
| ATOM | 1813 | CD2 | LEU | 241 | 22.339 | -2.689 | 20.259 | 1.00 19.54 | BLGL |
| ATOM | 1814 | C | LEU | 241 | 21.350 | -5.458 | 17.011 | 1.00 22.88 | BLGL |
| ATOM | 1815 | O | LEU | 241 | 20.213 | -5.043 | 16.827 | 1.00 23.81 | BLGL |
| ATOM | 1816 | N | LYS | 242 | 21.971 | -6.248 | 16.143 | 1.00 23.90 | BLGL |
| ATOM | 1817 | CA | LYS | 242 | 21.322 | -6.659 | 14.902 | 1.00 25.71 | BLGL |
| ATOM | 1818 | CB | LYS | 242 | 22.314 | -7.426 | 14.025 | 1.00 30.56 | BLGL |
| ATOM | 1819 | CG | LYS | 242 | 21.771 | -7.855 | 12.670 | 1.00 36.92 | BLGL |
| ATOM | 1820 | CD | LYS | 242 | 22.735 | -8.821 | 11.983 | 1.00 43.60 | BLGL |
| ATOM | 1821 | CE | LYS | 242 | 22.175 | -9.333 | 10.664 | 1.00 48.93 | BLGL |
| ATOM | 1822 | NZ | LYS | 242 | 21.895 | -8.217 | 9.709 | 1.00 51.96 | BLGL |
| ATOM | 1823 | C | LYS | 242 | 20.108 | -7.537 | 15.208 | 1.00 24.37 | BLGL |
| ATOM | 1824 | O | LYS | 242 | 19.070 | -7.444 | 14.551 | 1.00 23.45 | BLGL |
| ATOM | 1825 | N | ASN | 243 | 20.248 | -8.384 | 16.219 | 1.00 23.09 | BLGL |
| ATOM | 1826 | CA | ASN | 243 | 19.178 | -9.279 | 16.637 | 1.00 21.13 | BLGL |
| ATOM | 1827 | CB | ASN | 243 | 19.716 | -10.285 | 17.653 | 1.00 20.66 | BLGL |
| ATOM | 1828 | CG | ASN | 243 | 18.639 | -11.196 | 18.185 | 1.00 22.04 | BLGL |
| ATOM | 1829 | OD1 | ASN | 243 | 18.181 | -12.102 | 17.495 | 1.00 21.37 | BLGL |
| ATOM | 1830 | ND2 | ASN | 243 | 18.215 | -10.951 | 19.415 | 1.00 21.96 | BLGL |
| ATOM | 1831 | C | ASN | 243 | 18.041 | -8.477 | 17.264 | 1.00 21.16 | BLGL |
| ATOM | 1832 | O | ASN | 243 | 16.861 | -8.684 | 16.957 | 1.00 18.33 | BLGL |
| ATOM | 1833 | N | LEU | 244 | 18.408 | -7.557 | 18.151 | 1.00 20.72 | BLGL |
| ATOM | 1834 | CA | LEU | 244 | 17.429 | -6.712 | 18.821 | 1.00 19.78 | BLGL |
| ATOM | 1835 | CB | LEU | 244 | 18.131 | -5.667 | 19.695 | 1.00 18.01 | BLGL |
| ATOM | 1836 | CG | LEU | 244 | 17.188 | -4.669 | 20.372 | 1.00 16.83 | BLGL |
| ATOM | 1837 | CD1 | LEU | 244 | 16.393 | -5.385 | 21.463 | 1.00 13.98 | BLGL |
| ATOM | 1838 | CD2 | LEU | 244 | 17.995 | -3.515 | 20.950 | 1.00 16.04 | BLGL |
| ATOM | 1839 | C | LEU | 244 | 16.565 | -6.000 | 17.792 | 1.00 19.53 | BLGL |
| ATOM | 1840 | O | LEU | 244 | 15.341 | -6.054 | 17.853 | 1.00 20.39 | BLGL |
| ATOM | 1841 | N | THR | 245 | 17.214 | -5.332 | 16.846 | 1.00 18.73 | BLGL |
| ATOM | 1842 | CA | THR | 245 | 16.505 | -4.606 | 15.810 | 1.00 18.66 | BLGL |
| ATOM | 1843 | CB | THR | 245 | 17.474 | -3.996 | 14.785 | 1.00 19.64 | BLGL |
| ATOM | 1844 | OG1 | THR | 245 | 18.318 | -3.037 | 15.430 | 1.00 21.51 | BLGL |
| ATOM | 1845 | CG2 | THR | 245 | 16.697 | -3.311 | 13.664 | 1.00 17.47 | BLGL |
| ATOM | 1846 | C | THR | 245 | 15.574 | -5.531 | 15.062 | 1.00 19.92 | BLGL |
| ATOM | 1847 | O | THR | 245 | 14.410 | -5.219 | 14.834 | 1.00 21.53 | BLGL |

Fig. 4 cont.

```
ATOM   1848  N    SER  246     16.109   -6.678  14.678  1.00 20.39      BLGL
ATOM   1849  CA   SER  246     15.361   -7.661  13.927  1.00 19.04      BLGL
ATOM   1850  CB   SER  246     16.303   -8.792  13.538  1.00 18.29      BLGL
ATOM   1851  OG   SER  246     15.593   -9.911  13.053  1.00 23.84      BLGL
ATOM   1852  C    SER  246     14.164   -8.205  14.695  1.00 20.89      BLGL
ATOM   1853  O    SER  246     13.034   -8.169  14.214  1.00 22.76      BLGL
ATOM   1854  N    VAL  247     14.411   -8.703  15.899  1.00 21.65      BLGL
ATOM   1855  CA   VAL  247     13.343   -9.280  16.701  1.00 21.83      BLGL
ATOM   1856  CB   VAL  247     13.923   -9.883  18.005  1.00 20.50      BLGL
ATOM   1857  CG1  VAL  247     14.342   -8.786  18.962  1.00 20.71      BLGL
ATOM   1858  CG2  VAL  247     12.912  -10.800  18.636  1.00 23.56      BLGL
ATOM   1859  C    VAL  247     12.215   -8.275  17.006  1.00 22.43      BLGL
ATOM   1860  O    VAL  247     11.031   -8.631  17.000  1.00 22.15      BLGL
ATOM   1861  N    LEU  248     12.578   -7.020  17.255  1.00 22.41      BLGL
ATOM   1862  CA   LEU  248     11.584   -5.990  17.538  1.00 22.55      BLGL
ATOM   1863  CB   LEU  248     12.251   -4.734  18.125  1.00 20.88      BLGL
ATOM   1864  CG   LEU  248     12.778   -4.816  19.563  1.00 19.44      BLGL
ATOM   1865  CD1  LEU  248     13.426   -3.498  19.954  1.00 17.12      BLGL
ATOM   1866  CD2  LEU  248     11.639   -5.143  20.505  1.00 15.29      BLGL
ATOM   1867  C    LEU  248     10.805   -5.617  16.270  1.00 23.02      BLGL
ATOM   1868  O    LEU  248      9.597   -5.381  16.318  1.00 22.01      BLGL
ATOM   1869  N    THR  249     11.496   -5.570  15.136  1.00 20.49      BLGL
ATOM   1870  CA   THR  249     10.844   -5.220  13.890  1.00 21.29      BLGL
ATOM   1871  CB   THR  249     11.836   -5.197  12.722  1.00 22.20      BLGL
ATOM   1872  OG1  THR  249     12.872   -4.246  12.994  1.00 24.83      BLGL
ATOM   1873  CG2  THR  249     11.128   -4.808  11.440  1.00 20.47      BLGL
ATOM   1874  C    THR  249      9.739   -6.214  13.573  1.00 22.84      BLGL
ATOM   1875  O    THR  249      8.706   -5.842  13.020  1.00 20.69      BLGL
ATOM   1876  N    SER  250      9.956   -7.481  13.920  1.00 23.97      BLGL
ATOM   1877  CA   SER  250      8.945   -8.509  13.667  1.00 25.77      BLGL
ATOM   1878  CB   SER  250      9.451   -9.889  14.076  1.00 27.18      BLGL
ATOM   1879  OG   SER  250     10.487  -10.310  13.213  1.00 34.71      BLGL
ATOM   1880  C    SER  250      7.686   -8.196  14.446  1.00 24.53      BLGL
ATOM   1881  O    SER  250      6.590   -8.207  13.892  1.00 24.89      BLGL
ATOM   1882  N    VAL  251      7.850   -7.919  15.736  1.00 22.02      BLGL
ATOM   1883  CA   VAL  251      6.713   -7.592  16.581  1.00 20.32      BLGL
ATOM   1884  CB   VAL  251      7.156   -7.246  18.022  1.00 19.00      BLGL
ATOM   1885  CG1  VAL  251      5.972   -6.733  18.822  1.00 19.03      BLGL
ATOM   1886  CG2  VAL  251      7.736   -8.475  18.693  1.00 17.23      BLGL
ATOM   1887  C    VAL  251      5.968   -6.401  15.984  1.00 20.70      BLGL
ATOM   1888  O    VAL  251      4.741   -6.399  15.912  1.00 20.26      BLGL
ATOM   1889  N    ALA  252      6.717   -5.396  15.546  1.00 20.84      BLGL
ATOM   1890  CA   ALA  252      6.123   -4.198  14.965  1.00 21.97      BLGL
ATOM   1891  CB   ALA  252      7.203   -3.175  14.663  1.00 21.24      BLGL
ATOM   1892  C    ALA  252      5.330   -4.497  13.701  1.00 22.61      BLGL
ATOM   1893  O    ALA  252      4.137   -4.219  13.629  1.00 23.36      BLGL
ATOM   1894  N    ASP  253      5.999   -5.069  12.711  1.00 22.58      BLGL
ATOM   1895  CA   ASP  253      5.366   -5.386  11.440  1.00 23.48      BLGL
ATOM   1896  CB   ASP  253      6.394   -5.968  10.472  1.00 23.27      BLGL
ATOM   1897  CG   ASP  253      7.403   -4.946  10.019  1.00 25.67      BLGL
ATOM   1898  OD1  ASP  253      8.372   -5.346   9.337  1.00 26.60      BLGL
ATOM   1899  OD2  ASP  253      7.224   -3.744  10.344  1.00 27.47      BLGL
ATOM   1900  C    ASP  253      4.203   -6.352  11.556  1.00 24.77      BLGL
ATOM   1901  O    ASP  253      3.174   -6.174  10.904  1.00 25.85      BLGL
ATOM   1902  N    THR  254      4.359   -7.371  12.389  1.00 24.09      BLGL
ATOM   1903  CA   THR  254      3.317   -8.374  12.537  1.00 22.38      BLGL
ATOM   1904  CB   THR  254      3.892   -9.679  13.094  1.00 21.12      BLGL
ATOM   1905  OG1  THR  254      5.000  -10.096  12.287  1.00 22.06      BLGL
ATOM   1906  CG2  THR  254      2.836  -10.765  13.073  1.00 20.31      BLGL
ATOM   1907  C    THR  254      2.123   -7.977  13.395  1.00 23.11      BLGL
ATOM   1908  O    THR  254      0.995   -8.366  13.102  1.00 26.89      BLGL
ATOM   1909  N    TYR  255      2.345   -7.201  14.444  1.00 21.45      BLGL
ATOM   1910  CA   TYR  255      1.231   -6.835  15.307  1.00 20.15      BLGL
ATOM   1911  CB   TYR  255      1.488   -7.377  16.709  1.00 20.87      BLGL
ATOM   1912  CG   TYR  255      1.670   -8.876  16.701  1.00 22.40      BLGL
ATOM   1913  CD1  TYR  255      0.568   -9.728  16.568  1.00 21.45      BLGL
```

Fig. 4 cont.

```
ATOM   1914  CE1  TYR  255    0.731  -11.107  16.494  1.00  21.01      BLGL
ATOM   1915  CD2  TYR  255    2.943   -9.443  16.761  1.00  19.96      BLGL
ATOM   1916  CE2  TYR  255    3.117  -10.822  16.686  1.00  20.59      BLGL
ATOM   1917  CZ   TYR  255    2.008  -11.647  16.554  1.00  21.17      BLGL
ATOM   1918  OH   TYR  255    2.179  -13.009  16.495  1.00  21.44      BLGL
ATOM   1919  C    TYR  255    0.927   -5.357  15.360  1.00  19.29      BLGL
ATOM   1920  O    TYR  255    0.056   -4.923  16.104  1.00  19.71      BLGL
ATOM   1921  N    GLY  256    1.649   -4.585  14.562  1.00  20.06      BLGL
ATOM   1922  CA   GLY  256    1.421   -3.155  14.516  1.00  21.23      BLGL
ATOM   1923  C    GLY  256    1.582   -2.454  15.847  1.00  21.40      BLGL
ATOM   1924  O    GLY  256    0.788   -1.593  16.212  1.00  22.35      BLGL
ATOM   1925  N    LYS  257    2.619   -2.815  16.581  1.00  20.19      BLGL
ATOM   1926  CA   LYS  257    2.845   -2.182  17.861  1.00  21.01      BLGL
ATOM   1927  CB   LYS  257    3.032   -3.244  18.949  1.00  20.86      BLGL
ATOM   1928  CG   LYS  257    1.863   -4.191  19.122  1.00  18.58      BLGL
ATOM   1929  CD   LYS  257    0.615   -3.458  19.566  1.00  17.81      BLGL
ATOM   1930  CE   LYS  257   -0.524   -4.428  19.765  1.00  16.84      BLGL
ATOM   1931  NZ   LYS  257   -1.801   -3.739  20.053  1.00  19.74      BLGL
ATOM   1932  C    LYS  257    4.082   -1.300  17.792  1.00  20.95      BLGL
ATOM   1933  O    LYS  257    4.934   -1.474  16.918  1.00  19.83      BLGL
ATOM   1934  N    LYS  258    4.161   -0.333  18.699  1.00  19.92      BLGL
ATOM   1935  CA   LYS  258    5.329    0.526  18.771  1.00  21.02      BLGL
ATOM   1936  CB   LYS  258    5.037    1.785  19.581  1.00  24.26      BLGL
ATOM   1937  CG   LYS  258    3.850    2.601  19.139  1.00  27.83      BLGL
ATOM   1938  CD   LYS  258    4.143    3.387  17.887  1.00  33.22      BLGL
ATOM   1939  CE   LYS  258    3.297    4.652  17.862  1.00  36.49      BLGL
ATOM   1940  NZ   LYS  258    1.845    4.362  18.036  1.00  38.07      BLGL
ATOM   1941  C    LYS  258    6.322   -0.326  19.559  1.00  21.33      BLGL
ATOM   1942  O    LYS  258    5.923   -1.248  20.276  1.00  21.62      BLGL
ATOM   1943  N    VAL  259    7.607   -0.037  19.430  1.00  18.75      BLGL
ATOM   1944  CA   VAL  259    8.604   -0.786  20.176  1.00  17.87      BLGL
ATOM   1945  CB   VAL  259    9.391   -1.762  19.271  1.00  17.66      BLGL
ATOM   1946  CG1  VAL  259    8.447   -2.789  18.686  1.00  16.47      BLGL
ATOM   1947  CG2  VAL  259   10.118   -0.997  18.171  1.00  16.36      BLGL
ATOM   1948  C    VAL  259    9.572    0.190  20.816  1.00  18.60      BLGL
ATOM   1949  O    VAL  259    9.628    1.362  20.443  1.00  19.89      BLGL
ATOM   1950  N    MET  260   10.328   -0.280  21.794  1.00  18.23      BLGL
ATOM   1951  CA   MET  260   11.295    0.583  22.452  1.00  18.93      BLGL
ATOM   1952  CB   MET  260   10.594    1.741  23.179  1.00  17.82      BLGL
ATOM   1953  CG   MET  260    9.861    1.335  24.450  1.00  18.62      BLGL
ATOM   1954  SD   MET  260    9.338    2.760  25.444  1.00  20.82      BLGL
ATOM   1955  CE   MET  260    9.092    1.989  27.061  1.00  14.70      BLGL
ATOM   1956  C    MET  260   12.109   -0.200  23.461  1.00  18.97      BLGL
ATOM   1957  O    MET  260   11.757   -1.326  23.827  1.00  18.84      BLGL
ATOM   1958  N    VAL  261   13.207    0.401  23.900  1.00  18.49      BLGL
ATOM   1959  CA   VAL  261   14.049   -0.215  24.907  1.00  19.01      BLGL
ATOM   1960  CB   VAL  261   15.545   -0.063  24.567  1.00  18.88      BLGL
ATOM   1961  CG1  VAL  261   16.399   -0.549  25.728  1.00  19.31      BLGL
ATOM   1962  CG2  VAL  261   15.867   -0.867  23.326  1.00  17.95      BLGL
ATOM   1963  C    VAL  261   13.713    0.493  26.218  1.00  17.97      BLGL
ATOM   1964  O    VAL  261   13.854    1.712  26.343  1.00  14.60      BLGL
ATOM   1965  N    ALA  262   13.228   -0.280  27.180  1.00  18.80      BLGL
ATOM   1966  CA   ALA  262   12.846    0.269  28.473  1.00  21.56      BLGL
ATOM   1967  CB   ALA  262   11.777   -0.617  29.107  1.00  20.01      BLGL
ATOM   1968  C    ALA  262   14.047    0.409  29.412  1.00  21.77      BLGL
ATOM   1969  O    ALA  262   14.079    1.297  30.262  1.00  22.42      BLGL
ATOM   1970  N    GLU  263   15.036   -0.464  29.247  1.00  20.47      BLGL
ATOM   1971  CA   GLU  263   16.214   -0.433  30.091  1.00  19.18      BLGL
ATOM   1972  CB   GLU  263   16.099   -1.464  31.211  1.00  18.99      BLGL
ATOM   1973  CG   GLU  263   15.178   -1.102  32.358  1.00  21.05      BLGL
ATOM   1974  CD   GLU  263   15.151   -2.191  33.417  1.00  19.91      BLGL
ATOM   1975  OE1  GLU  263   16.207   -2.819  33.642  1.00  20.67      BLGL
ATOM   1976  OE2  GLU  263   14.087   -2.422  34.029  1.00  22.21      BLGL
ATOM   1977  C    GLU  263   17.483   -0.729  29.319  1.00  19.96      BLGL
ATOM   1978  O    GLU  263   17.497   -1.587  28.440  1.00  20.56      BLGL
ATOM   1979  N    THR  264   18.547   -0.013  29.661  1.00  17.62      BLGL
```

Fig. 4 cont.

```
ATOM   1980  CA   THR  264      19.844   -0.219   29.042  1.00 15.98       BLGL
ATOM   1981  CB   THR  264      19.874    0.247   27.573  1.00 16.21       BLGL
ATOM   1982  OG1  THR  264      20.989   -0.366   26.907  1.00 15.60       BLGL
ATOM   1983  CG2  THR  264      20.036    1.771   27.494  1.00 13.52       BLGL
ATOM   1984  C    THR  264      20.872    0.578   29.820  1.00 15.21       BLGL
ATOM   1985  O    THR  264      20.532    1.477   30.579  1.00 14.74       BLGL
ATOM   1986  N    SER  265      22.136    0.240   29.621  1.00 15.34       BLGL
ATOM   1987  CA   SER  265      23.229    0.936   30.280  1.00 16.34       BLGL
ATOM   1988  CB   SER  265      23.113    0.819   31.802  1.00 16.26       BLGL
ATOM   1989  OG   SER  265      23.293   -0.517   32.249  1.00 16.64       BLGL
ATOM   1990  C    SER  265      24.531    0.312   29.826  1.00 17.34       BLGL
ATOM   1991  O    SER  265      24.543   -0.607   29.005  1.00 18.70       BLGL
ATOM   1992  N    TYR  266      25.629    0.836   30.349  1.00 18.17       BLGL
ATOM   1993  CA   TYR  266      26.939    0.307   30.039  1.00 17.93       BLGL
ATOM   1994  CB   TYR  266      27.397    0.699   28.640  1.00 15.84       BLGL
ATOM   1995  CG   TYR  266      28.485   -0.218   28.131  1.00 17.82       BLGL
ATOM   1996  CD1  TYR  266      28.192   -1.527   27.774  1.00 18.54       BLGL
ATOM   1997  CE1  TYR  266      29.186   -2.396   27.329  1.00 19.26       BLGL
ATOM   1998  CD2  TYR  266      29.816    0.210   28.035  1.00 20.22       BLGL
ATOM   1999  CE2  TYR  266      30.826   -0.656   27.591  1.00 19.11       BLGL
ATOM   2000  CZ   TYR  266      30.499   -1.962   27.238  1.00 19.47       BLGL
ATOM   2001  OH   TYR  266      31.472   -2.836   26.784  1.00 18.36       BLGL
ATOM   2002  C    TYR  266      27.911    0.846   31.064  1.00 18.90       BLGL
ATOM   2003  O    TYR  266      27.681    1.895   31.665  1.00 18.09       BLGL
ATOM   2004  N    THR  267      28.995    0.105   31.259  1.00 20.38       BLGL
ATOM   2005  CA   THR  267      30.037    0.462   32.210  1.00 21.04       BLGL
ATOM   2006  CB   THR  267      30.852   -0.773   32.580  1.00 20.00       BLGL
ATOM   2007  OG1  THR  267      31.305   -1.402   31.373  1.00 19.78       BLGL
ATOM   2008  CG2  THR  267      30.017   -1.752   33.366  1.00 19.30       BLGL
ATOM   2009  C    THR  267      31.000    1.482   31.619  1.00 21.49       BLGL
ATOM   2010  O    THR  267      31.455    1.315   30.488  1.00 24.81       BLGL
ATOM   2011  N    TYR  268      31.320    2.525   32.384  1.00 20.55       BLGL
ATOM   2012  CA   TYR  268      32.268    3.546   31.933  1.00 20.98       BLGL
ATOM   2013  CB   TYR  268      31.724    4.958   32.205  1.00 21.01       BLGL
ATOM   2014  CG   TYR  268      31.844    5.439   33.639  1.00 19.32       BLGL
ATOM   2015  CD1  TYR  268      33.019    6.027   34.105  1.00 20.87       BLGL
ATOM   2016  CE1  TYR  268      33.129    6.471   35.426  1.00 20.17       BLGL
ATOM   2017  CD2  TYR  268      30.778    5.302   34.532  1.00 21.37       BLGL
ATOM   2018  CE2  TYR  268      30.873    5.739   35.853  1.00 19.23       BLGL
ATOM   2019  CZ   TYR  268      32.049    6.322   36.295  1.00 21.74       BLGL
ATOM   2020  OH   TYR  268      32.137    6.753   37.604  1.00 22.30       BLGL
ATOM   2021  C    TYR  268      33.597    3.364   32.664  1.00 21.83       BLGL
ATOM   2022  O    TYR  268      34.590    4.013   32.344  1.00 18.94       BLGL
ATOM   2023  N    THR  269      33.600    2.479   33.657  1.00 22.82       BLGL
ATOM   2024  CA   THR  269      34.795    2.213   34.451  1.00 23.10       BLGL
ATOM   2025  CB   THR  269      34.970    3.271   35.573  1.00 20.44       BLGL
ATOM   2026  OG1  THR  269      36.161    2.989   36.311  1.00 20.91       BLGL
ATOM   2027  CG2  THR  269      33.791    3.250   36.524  1.00 18.84       BLGL
ATOM   2028  C    THR  269      34.693    0.834   35.083  1.00 23.00       BLGL
ATOM   2029  O    THR  269      33.607    0.376   35.403  1.00 25.15       BLGL
ATOM   2030  N    ALA  270      35.826    0.170   35.259  1.00 24.31       BLGL
ATOM   2031  CA   ALA  270      35.825   -1.158   35.853  1.00 24.71       BLGL
ATOM   2032  CB   ALA  270      37.058   -1.933   35.409  1.00 21.17       BLGL
ATOM   2033  C    ALA  270      35.810   -1.019   37.361  1.00 25.78       BLGL
ATOM   2034  O    ALA  270      35.538   -1.970   38.080  1.00 29.18       BLGL
ATOM   2035  N    GLU  271      36.083    0.185   37.836  1.00 27.12       BLGL
ATOM   2036  CA   GLU  271      36.133    0.448   39.263  1.00 29.78       BLGL
ATOM   2037  CB   GLU  271      36.914    1.742   39.495  1.00 32.08       BLGL
ATOM   2038  CG   GLU  271      36.864    2.261   40.920  1.00 35.54       BLGL
ATOM   2039  CD   GLU  271      37.750    3.466   41.110  1.00 36.58       BLGL
ATOM   2040  OE1  GLU  271      38.022    4.167   40.108  1.00 36.10       BLGL
ATOM   2041  OE2  GLU  271      38.160    3.714   42.262  1.00 38.61       BLGL
ATOM   2042  C    GLU  271      34.783    0.527   39.977  1.00 30.16       BLGL
ATOM   2043  O    GLU  271      33.776    0.938   39.405  1.00 31.60       BLGL
ATOM   2044  N    ASP  272      34.782    0.125   41.242  1.00 30.13       BLGL
ATOM   2045  CA   ASP  272      33.590    0.169   42.081  1.00 30.63       BLGL
```

Fig. 4 cont.

```
ATOM   2046  CB   ASP  272      33.333   -1.190   42.722  1.00 29.68      BLGL
ATOM   2047  CG   ASP  272      32.488   -1.081   43.968  1.00 29.93      BLGL
ATOM   2048  OD1  ASP  272      31.427   -0.428   43.896  1.00 29.02      BLGL
ATOM   2049  OD2  ASP  272      32.884   -1.640   45.014  1.00 30.80      BLGL
ATOM   2050  C    ASP  272      33.865    1.188   43.178  1.00 31.65      BLGL
ATOM   2051  O    ASP  272      34.705    0.946   44.045  1.00 33.92      BLGL
ATOM   2052  N    GLY  273      33.163    2.318   43.157  1.00 31.58      BLGL
ATOM   2053  CA   GLY  273      33.420    3.340   44.158  1.00 32.18      BLGL
ATOM   2054  C    GLY  273      32.476    3.304   45.333  1.00 31.14      BLGL
ATOM   2055  O    GLY  273      32.407    4.250   46.116  1.00 32.09      BLGL
ATOM   2056  N    ASP  274      31.786    2.184   45.472  1.00 30.99      BLGL
ATOM   2057  CA   ASP  274      30.790    2.002   46.511  1.00 30.40      BLGL
ATOM   2058  CB   ASP  274      29.550    1.377   45.871  1.00 31.29      BLGL
ATOM   2059  CG   ASP  274      28.304    1.620   46.659  1.00 32.35      BLGL
ATOM   2060  OD1  ASP  274      27.319    0.902   46.433  1.00 34.84      BLGL
ATOM   2061  OD2  ASP  274      28.299    2.539   47.495  1.00 38.43      BLGL
ATOM   2062  C    ASP  274      31.264    1.104   47.649  1.00 30.15      BLGL
ATOM   2063  O    ASP  274      31.075    1.408   48.827  1.00 28.39      BLGL
ATOM   2064  N    GLY  275      31.867   -0.017   47.283  1.00 28.33      BLGL
ATOM   2065  CA   GLY  275      32.311   -0.956   48.283  1.00 29.05      BLGL
ATOM   2066  C    GLY  275      31.486   -2.210   48.099  1.00 28.72      BLGL
ATOM   2067  O    GLY  275      31.881   -3.298   48.519  1.00 31.31      BLGL
ATOM   2068  N    HIS  276      30.325   -2.046   47.472  1.00 26.86      BLGL
ATOM   2069  CA   HIS  276      29.431   -3.164   47.191  1.00 24.43      BLGL
ATOM   2070  CB   HIS  276      27.974   -2.726   47.336  1.00 23.89      BLGL
ATOM   2071  CG   HIS  276      26.986   -3.842   47.172  1.00 26.16      BLGL
ATOM   2072  CD2  HIS  276      26.329   -4.297   46.078  1.00 24.85      BLGL
ATOM   2073  ND1  HIS  276      26.595   -4.652   48.217  1.00 24.36      BLGL
ATOM   2074  CE1  HIS  276      25.741   -5.557   47.776  1.00 24.78      BLGL
ATOM   2075  NE2  HIS  276      25.562   -5.363   46.481  1.00 25.01      BLGL
ATOM   2076  C    HIS  276      29.691   -3.597   45.748  1.00 24.24      BLGL
ATOM   2077  O    HIS  276      29.512   -2.808   44.822  1.00 23.66      BLGL
ATOM   2078  N    GLY  277      30.108   -4.844   45.562  1.00 23.41      BLGL
ATOM   2079  CA   GLY  277      30.397   -5.343   44.225  1.00 23.85      BLGL
ATOM   2080  C    GLY  277      29.405   -4.987   43.130  1.00 24.88      BLGL
ATOM   2081  O    GLY  277      28.185   -5.064   43.320  1.00 25.03      BLGL
ATOM   2082  N    ASN  278      29.935   -4.616   41.966  1.00 24.25      BLGL
ATOM   2083  CA   ASN  278      29.114   -4.238   40.822  1.00 22.79      BLGL
ATOM   2084  CB   ASN  278      29.827   -3.150   40.027  1.00 21.96      BLGL
ATOM   2085  CG   ASN  278      29.928   -1.844   40.797  1.00 23.90      BLGL
ATOM   2086  ND2  ASN  278      30.661   -0.934   40.410  1.00 26.25      BLGL
ATOM   2087  OD1  ASN  278      29.177   -1.742   41.889  1.00 21.34      BLGL
ATOM   2088  C    ASN  278      28.748   -5.407   39.910  1.00 23.33      BLGL
ATOM   2089  O    ASN  278      29.408   -6.443   39.898  1.00 22.97      BLGL
ATOM   2090  N    THR  279      27.675   -5.226   39.152  1.00 23.75      BLGL
ATOM   2091  CA   THR  279      27.188   -6.247   38.241  1.00 24.46      BLGL
ATOM   2092  CB   THR  279      25.821   -5.857   37.666  1.00 25.31      BLGL
ATOM   2093  OG1  THR  279      24.874   -5.729   38.728  1.00 27.04      BLGL
ATOM   2094  CG2  THR  279      25.331   -6.910   36.701  1.00 28.22      BLGL
ATOM   2095  C    THR  279      28.137   -6.482   37.078  1.00 24.01      BLGL
ATOM   2096  O    THR  279      28.356   -7.613   36.659  1.00 24.35      BLGL
ATOM   2097  N    ALA  280      28.687   -5.401   36.547  1.00 24.16      BLGL
ATOM   2098  CA   ALA  280      29.599   -5.495   35.422  1.00 24.11      BLGL
ATOM   2099  CB   ALA  280      28.857   -5.182   34.137  1.00 21.63      BLGL
ATOM   2100  C    ALA  280      30.749   -4.522   35.616  1.00 25.17      BLGL
ATOM   2101  O    ALA  280      30.638   -3.565   36.379  1.00 26.21      BLGL
ATOM   2102  N    PRO  281      31.881   -4.766   34.942  1.00 25.93      BLGL
ATOM   2103  CD   PRO  281      32.977   -3.790   34.829  1.00 26.64      BLGL
ATOM   2104  CA   PRO  281      32.106   -5.896   34.037  1.00 27.75      BLGL
ATOM   2105  CB   PRO  281      33.155   -5.353   33.084  1.00 27.25      BLGL
ATOM   2106  CG   PRO  281      34.001   -4.545   33.998  1.00 28.42      BLGL
ATOM   2107  C    PRO  281      32.590   -7.142   34.773  1.00 29.21      BLGL
ATOM   2108  O    PRO  281      33.055   -7.071   35.902  1.00 31.08      BLGL
ATOM   2109  N    LYS  282      32.468   -8.287   34.123  1.00 31.67      BLGL
ATOM   2110  CA   LYS  282      32.902   -9.546   34.705  1.00 35.33      BLGL
ATOM   2111  CB   LYS  282      31.788  -10.169   35.537  1.00 34.90      BLGL
```

Fig. 4 cont.

```
ATOM   2112  CG   LYS  282     31.527   -9.495   36.861  1.00  37.13       BLGL
ATOM   2113  CD   LYS  282     30.496  -10.301   37.636  1.00  38.88       BLGL
ATOM   2114  CE   LYS  282     30.386   -9.846   39.077  1.00  40.27       BLGL
ATOM   2115  NZ   LYS  282     29.540  -10.796   39.851  1.00  42.22       BLGL
ATOM   2116  C    LYS  282     33.270  -10.495   33.583  1.00  38.11       BLGL
ATOM   2117  O    LYS  282     32.931  -10.251   32.429  1.00  39.52       BLGL
ATOM   2118  N    ASN  283     33.967  -11.575   33.920  1.00  42.82       BLGL
ATOM   2119  CA   ASN  283     34.355  -12.558   32.914  1.00  46.20       BLGL
ATOM   2120  CB   ASN  283     35.290  -13.614   33.512  1.00  50.82       BLGL
ATOM   2121  CG   ASN  283     36.534  -13.010   34.122  1.00  56.85       BLGL
ATOM   2122  OD1  ASN  283     36.474  -12.369   35.175  1.00  61.22       BLGL
ATOM   2123  ND2  ASN  283     37.672  -13.200   33.461  1.00  58.97       BLGL
ATOM   2124  C    ASN  283     33.100  -13.246   32.382  1.00  45.60       BLGL
ATOM   2125  O    ASN  283     32.163  -13.532   33.138  1.00  44.14       BLGL
ATOM   2126  N    GLY  284     33.081  -13.507   31.080  1.00  44.05       BLGL
ATOM   2127  CA   GLY  284     31.927  -14.166   30.499  1.00  42.01       BLGL
ATOM   2128  C    GLY  284     30.920  -13.195   29.918  1.00  40.47       BLGL
ATOM   2129  O    GLY  284     30.072  -13.590   29.114  1.00  41.73       BLGL
ATOM   2130  N    GLN  285     30.997  -11.929   30.321  1.00  36.97       BLGL
ATOM   2131  CA   GLN  285     30.081  -10.934   29.794  1.00  32.62       BLGL
ATOM   2132  CB   GLN  285     29.904   -9.781   30.771  1.00  31.11       BLGL
ATOM   2133  CG   GLN  285     29.440  -10.187   32.149  1.00  29.26       BLGL
ATOM   2134  CD   GLN  285     29.234   -8.985   33.046  1.00  27.08       BLGL
ATOM   2135  OE1  GLN  285     29.922   -7.973   32.910  1.00  26.10       BLGL
ATOM   2136  NE2  GLN  285     28.296   -9.091   33.974  1.00  25.79       BLGL
ATOM   2137  C    GLN  285     30.634  -10.397   28.487  1.00  30.85       BLGL
ATOM   2138  O    GLN  285     31.844  -10.301   28.302  1.00  31.43       BLGL
ATOM   2139  N    THR  286     29.735  -10.047   27.581  1.00  29.00       BLGL
ATOM   2140  CA   THR  286     30.119   -9.516   26.292  1.00  26.23       BLGL
ATOM   2141  CB   THR  286     29.000   -9.741   25.280  1.00  26.60       BLGL
ATOM   2142  OG1  THR  286     28.755  -11.147   25.159  1.00  26.51       BLGL
ATOM   2143  CG2  THR  286     29.370   -9.150   23.928  1.00  26.18       BLGL
ATOM   2144  C    THR  286     30.401   -8.030   26.413  1.00  25.38       BLGL
ATOM   2145  O    THR  286     29.553   -7.266   26.859  1.00  25.73       BLGL
ATOM   2146  N    LEU  287     31.596   -7.619   26.016  1.00  25.58       BLGL
ATOM   2147  CA   LEU  287     31.957   -6.219   26.098  1.00  25.95       BLGL
ATOM   2148  CB   LEU  287     33.036   -6.034   27.159  1.00  23.53       BLGL
ATOM   2149  CG   LEU  287     32.593   -6.516   28.539  1.00  22.29       BLGL
ATOM   2150  CD1  LEU  287     33.742   -6.413   29.523  1.00  21.57       BLGL
ATOM   2151  CD2  LEU  287     31.409   -5.692   28.998  1.00  20.26       BLGL
ATOM   2152  C    LEU  287     32.446   -5.739   24.748  1.00  28.08       BLGL
ATOM   2153  O    LEU  287     33.648   -5.666   24.503  1.00  29.85       BLGL
ATOM   2154  N    ASN  288     31.508   -5.406   23.870  1.00  29.45       BLGL
ATOM   2155  CA   ASN  288     31.869   -4.949   22.537  1.00  31.56       BLGL
ATOM   2156  CB   ASN  288     30.641   -4.928   21.632  1.00  35.67       BLGL
ATOM   2157  CG   ASN  288     30.039   -6.306   21.456  1.00  41.56       BLGL
ATOM   2158  OD1  ASN  288     30.766   -7.298   21.320  1.00  42.80       BLGL
ATOM   2159  ND2  ASN  288     28.707   -6.380   21.449  1.00  43.66       BLGL
ATOM   2160  C    ASN  288     32.533   -3.590   22.523  1.00  30.88       BLGL
ATOM   2161  O    ASN  288     33.295   -3.281   21.615  1.00  32.37       BLGL
ATOM   2162  N    ASN  289     32.242   -2.767   23.520  1.00  30.69       BLGL
ATOM   2163  CA   ASN  289     32.849   -1.447   23.583  1.00  29.17       BLGL
ATOM   2164  CB   ASN  289     31.778   -0.364   23.737  1.00  29.80       BLGL
ATOM   2165  CG   ASN  289     31.108   -0.018   22.420  1.00  34.65       BLGL
ATOM   2166  OD1  ASN  289     31.733    0.562   21.529  1.00  36.80       BLGL
ATOM   2167  ND2  ASN  289     29.834   -0.382   22.285  1.00  34.27       BLGL
ATOM   2168  C    ASN  289     33.818   -1.386   24.746  1.00  28.28       BLGL
ATOM   2169  O    ASN  289     33.698   -2.144   25.718  1.00  26.00       BLGL
ATOM   2170  N    PRO  290     34.815   -0.497   24.654  1.00  26.69       BLGL
ATOM   2171  CD   PRO  290     35.116    0.459   23.576  1.00  25.39       BLGL
ATOM   2172  CA   PRO  290     35.783   -0.375   25.740  1.00  24.60       BLGL
ATOM   2173  CB   PRO  290     36.796    0.616   25.184  1.00  23.11       BLGL
ATOM   2174  CG   PRO  290     35.977    1.470   24.294  1.00  24.06       BLGL
ATOM   2175  C    PRO  290     35.098    0.132   27.006  1.00  25.03       BLGL
ATOM   2176  O    PRO  290     34.140    0.916   26.951  1.00  24.16       BLGL
ATOM   2177  N    VAL  291     35.582   -0.334   28.149  1.00  23.84       BLGL
```

Fig. 4 cont.

```
ATOM   2178  CA  VAL   291      35.019   0.083  29.420  1.00 21.28      BLGL
ATOM   2179  CB  VAL   291      35.340  -0.945  30.520  1.00 21.94      BLGL
ATOM   2180  CG1 VAL   291      34.752  -0.488  31.852  1.00 20.42      BLGL
ATOM   2181  CG2 VAL   291      34.775  -2.309  30.114  1.00 17.11      BLGL
ATOM   2182  C   VAL   291      35.607   1.448  29.760  1.00 20.16      BLGL
ATOM   2183  O   VAL   291      36.504   1.574  30.588  1.00 19.20      BLGL
ATOM   2184  N   THR   292      35.100   2.464  29.070  1.00 19.49      BLGL
ATOM   2185  CA  THR   292      35.532   3.842  29.250  1.00 18.74      BLGL
ATOM   2186  CB  THR   292      36.660   4.228  28.251  1.00 18.53      BLGL
ATOM   2187  OG1 THR   292      36.111   4.400  26.939  1.00 17.67      BLGL
ATOM   2188  CG2 THR   292      37.716   3.148  28.196  1.00 17.15      BLGL
ATOM   2189  C   THR   292      34.335   4.759  28.994  1.00 19.39      BLGL
ATOM   2190  O   THR   292      33.275   4.308  28.568  1.00 19.27      BLGL
ATOM   2191  N   VAL   293      34.514   6.048  29.252  1.00 20.06      BLGL
ATOM   2192  CA  VAL   293      33.446   7.005  29.039  1.00 20.55      BLGL
ATOM   2193  CB  VAL   293      33.865   8.406  29.544  1.00 20.16      BLGL
ATOM   2194  CG1 VAL   293      32.857   9.451  29.100  1.00 20.66      BLGL
ATOM   2195  CG2 VAL   293      33.936   8.390  31.074  1.00 16.78      BLGL
ATOM   2196  C   VAL   293      33.051   7.044  27.562  1.00 20.97      BLGL
ATOM   2197  O   VAL   293      31.864   7.124  27.234  1.00 21.53      BLGL
ATOM   2198  N   GLN   294      34.039   6.962  26.674  1.00 20.45      BLGL
ATOM   2199  CA  GLN   294      33.770   6.956  25.238  1.00 21.64      BLGL
ATOM   2200  CB  GLN   294      35.066   7.058  24.431  1.00 25.60      BLGL
ATOM   2201  CG  GLN   294      35.192   8.341  23.619  1.00 29.52      BLGL
ATOM   2202  CD  GLN   294      34.031   8.562  22.666  1.00 29.94      BLGL
ATOM   2203  OE1 GLN   294      33.739   9.696  22.296  1.00 34.05      BLGL
ATOM   2204  NE2 GLN   294      33.371   7.485  22.260  1.00 28.56      BLGL
ATOM   2205  C   GLN   294      33.058   5.672  24.834  1.00 22.39      BLGL
ATOM   2206  O   GLN   294      32.199   5.677  23.950  1.00 19.94      BLGL
ATOM   2207  N   GLY   295      33.444   4.566  25.468  1.00 22.59      BLGL
ATOM   2208  CA  GLY   295      32.814   3.295  25.173  1.00 20.59      BLGL
ATOM   2209  C   GLY   295      31.349   3.362  25.564  1.00 22.43      BLGL
ATOM   2210  O   GLY   295      30.464   3.047  24.767  1.00 23.22      BLGL
ATOM   2211  N   GLN   296      31.099   3.787  26.798  1.00 19.02      BLGL
ATOM   2212  CA  GLN   296      29.750   3.905  27.313  1.00 19.21      BLGL
ATOM   2213  CB  GLN   296      29.789   4.581  28.683  1.00 19.90      BLGL
ATOM   2214  CG  GLN   296      28.467   4.668  29.419  1.00 18.48      BLGL
ATOM   2215  CD  GLN   296      28.572   5.536  30.669  1.00 17.80      BLGL
ATOM   2216  OE1 GLN   296      29.027   6.679  30.595  1.00 16.03      BLGL
ATOM   2217  NE2 GLN   296      28.152   4.999  31.818  1.00 15.03      BLGL
ATOM   2218  C   GLN   296      28.906   4.719  26.336  1.00 19.79      BLGL
ATOM   2219  O   GLN   296      27.777   4.347  26.016  1.00 20.36      BLGL
ATOM   2220  N   ALA   297      29.458   5.825  25.851  1.00 18.99      BLGL
ATOM   2221  CA  ALA   297      28.733   6.669  24.905  1.00 18.45      BLGL
ATOM   2222  CB  ALA   297      29.546   7.916  24.578  1.00 14.36      BLGL
ATOM   2223  C   ALA   297      28.416   5.895  23.630  1.00 19.50      BLGL
ATOM   2224  O   ALA   297      27.301   5.978  23.104  1.00 20.34      BLGL
ATOM   2225  N   ASN   298      29.395   5.142  23.135  1.00 19.83      BLGL
ATOM   2226  CA  ASN   298      29.196   4.352  21.926  1.00 21.45      BLGL
ATOM   2227  CB  ASN   298      30.442   3.524  21.592  1.00 24.97      BLGL
ATOM   2228  CG  ASN   298      31.563   4.358  20.999  1.00 26.63      BLGL
ATOM   2229  OD1 ASN   298      31.329   5.440  20.459  1.00 25.65      BLGL
ATOM   2230  ND2 ASN   298      32.791   3.843  21.078  1.00 27.74      BLGL
ATOM   2231  C   ASN   298      28.027   3.405  22.133  1.00 21.39      BLGL
ATOM   2232  O   ASN   298      27.130   3.306  21.297  1.00 21.38      BLGL
ATOM   2233  N   ALA   299      28.061   2.713  23.266  1.00 19.25      BLGL
ATOM   2234  CA  ALA   299      27.038   1.754  23.633  1.00 17.97      BLGL
ATOM   2235  CB  ALA   299      27.294   1.264  25.030  1.00 16.35      BLGL
ATOM   2236  C   ALA   299      25.638   2.339  23.537  1.00 19.35      BLGL
ATOM   2237  O   ALA   299      24.763   1.771  22.881  1.00 17.73      BLGL
ATOM   2238  N   VAL   300      25.432   3.474  24.201  1.00 20.77      BLGL
ATOM   2239  CA  VAL   300      24.134   4.146  24.202  1.00 20.54      BLGL
ATOM   2240  CB  VAL   300      24.141   5.382  25.141  1.00 19.20      BLGL
ATOM   2241  CG1 VAL   300      22.786   6.081  25.108  1.00 16.54      BLGL
ATOM   2242  CG2 VAL   300      24.467   4.948  26.556  1.00 16.81      BLGL
ATOM   2243  C   VAL   300      23.761   4.597  22.795  1.00 20.62      BLGL
```

Fig. 4 cont.

| ATOM | 2244 | O   | VAL | 300 | 22.643 | 4.383  | 22.332 | 1.00 | 22.02 | BLGL |
| ATOM | 2245 | N   | ARG | 301 | 24.711 | 5.220  | 22.117 | 1.00 | 19.80 | BLGL |
| ATOM | 2246 | CA  | ARG | 301 | 24.485 | 5.699  | 20.770 | 1.00 | 20.87 | BLGL |
| ATOM | 2247 | CB  | ARG | 301 | 25.764 | 6.370  | 20.273 | 1.00 | 20.72 | BLGL |
| ATOM | 2248 | CG  | ARG | 301 | 25.697 | 6.960  | 18.884 | 1.00 | 19.75 | BLGL |
| ATOM | 2249 | CD  | ARG | 301 | 25.963 | 5.909  | 17.841 | 1.00 | 20.20 | BLGL |
| ATOM | 2250 | NE  | ARG | 301 | 25.950 | 6.479  | 16.502 | 1.00 | 21.66 | BLGL |
| ATOM | 2251 | CZ  | ARG | 301 | 25.770 | 5.763  | 15.400 | 1.00 | 21.05 | BLGL |
| ATOM | 2252 | NH1 | ARG | 301 | 25.593 | 4.453  | 15.484 | 1.00 | 23.39 | BLGL |
| ATOM | 2253 | NH2 | ARG | 301 | 25.741 | 6.359  | 14.223 | 1.00 | 19.98 | BLGL |
| ATOM | 2254 | C   | ARG | 301 | 24.050 | 4.575  | 19.824 | 1.00 | 21.51 | BLGL |
| ATOM | 2255 | O   | ARG | 301 | 23.190 | 4.774  | 18.967 | 1.00 | 23.05 | BLGL |
| ATOM | 2256 | N   | ASP | 302 | 24.633 | 3.394  | 19.989 | 1.00 | 20.34 | BLGL |
| ATOM | 2257 | CA  | ASP | 302 | 24.306 | 2.262  | 19.138 | 1.00 | 19.74 | BLGL |
| ATOM | 2258 | CB  | ASP | 302 | 25.378 | 1.190  | 19.260 | 1.00 | 22.07 | BLGL |
| ATOM | 2259 | CG  | ASP | 302 | 26.659 | 1.571  | 18.548 | 1.00 | 26.74 | BLGL |
| ATOM | 2260 | OD1 | ASP | 302 | 27.647 | 0.818  | 18.676 | 1.00 | 31.70 | BLGL |
| ATOM | 2261 | OD2 | ASP | 302 | 26.686 | 2.618  | 17.857 | 1.00 | 28.72 | BLGL |
| ATOM | 2262 | C   | ASP | 302 | 22.947 | 1.648  | 19.408 | 1.00 | 20.74 | BLGL |
| ATOM | 2263 | O   | ASP | 302 | 22.329 | 1.083  | 18.509 | 1.00 | 23.13 | BLGL |
| ATOM | 2264 | N   | VAL | 303 | 22.482 | 1.740  | 20.644 | 1.00 | 18.00 | BLGL |
| ATOM | 2265 | CA  | VAL | 303 | 21.182 | 1.189  | 20.971 | 1.00 | 18.00 | BLGL |
| ATOM | 2266 | CB  | VAL | 303 | 20.971 | 1.110  | 22.503 | 1.00 | 17.67 | BLGL |
| ATOM | 2267 | CG1 | VAL | 303 | 19.626 | 0.483  | 22.813 | 1.00 | 17.30 | BLGL |
| ATOM | 2268 | CG2 | VAL | 303 | 22.075 | 0.299  | 23.132 | 1.00 | 20.13 | BLGL |
| ATOM | 2269 | C   | VAL | 303 | 20.126 | 2.099  | 20.346 | 1.00 | 18.76 | BLGL |
| ATOM | 2270 | O   | VAL | 303 | 19.099 | 1.638  | 19.854 | 1.00 | 16.54 | BLGL |
| ATOM | 2271 | N   | ILE | 304 | 20.392 | 3.401  | 20.367 | 1.00 | 19.37 | BLGL |
| ATOM | 2272 | CA  | ILE | 304 | 19.471 | 4.371  | 19.793 | 1.00 | 20.60 | BLGL |
| ATOM | 2273 | CB  | ILE | 304 | 19.955 | 5.820  | 20.067 | 1.00 | 21.68 | BLGL |
| ATOM | 2274 | CG2 | ILE | 304 | 19.113 | 6.835  | 19.293 | 1.00 | 19.25 | BLGL |
| ATOM | 2275 | CG1 | ILE | 304 | 19.853 | 6.108  | 21.567 | 1.00 | 21.33 | BLGL |
| ATOM | 2276 | CD1 | ILE | 304 | 20.334 | 7.482  | 21.961 | 1.00 | 21.10 | BLGL |
| ATOM | 2277 | C   | ILE | 304 | 19.387 | 4.102  | 18.294 | 1.00 | 21.62 | BLGL |
| ATOM | 2278 | O   | ILE | 304 | 18.316 | 4.130  | 17.695 | 1.00 | 22.05 | BLGL |
| ATOM | 2279 | N   | GLN | 305 | 20.531 | 3.820  | 17.694 | 1.00 | 21.95 | BLGL |
| ATOM | 2280 | CA  | GLN | 305 | 20.579 | 3.523  | 16.279 | 1.00 | 22.70 | BLGL |
| ATOM | 2281 | CB  | GLN | 305 | 22.031 | 3.274  | 15.855 | 1.00 | 25.34 | BLGL |
| ATOM | 2282 | CG  | GLN | 305 | 22.203 | 2.958  | 14.381 | 1.00 | 28.30 | BLGL |
| ATOM | 2283 | CD  | GLN | 305 | 22.031 | 4.178  | 13.505 | 1.00 | 30.27 | BLGL |
| ATOM | 2284 | OE1 | GLN | 305 | 22.915 | 5.030  | 13.430 | 1.00 | 30.12 | BLGL |
| ATOM | 2285 | NE2 | GLN | 305 | 20.884 | 4.273  | 12.841 | 1.00 | 32.34 | BLGL |
| ATOM | 2286 | C   | GLN | 305 | 19.736 | 2.278  | 16.006 | 1.00 | 22.92 | BLGL |
| ATOM | 2287 | O   | GLN | 305 | 18.925 | 2.258  | 15.080 | 1.00 | 23.46 | BLGL |
| ATOM | 2288 | N   | ALA | 306 | 19.931 | 1.247  | 16.831 | 1.00 | 22.84 | BLGL |
| ATOM | 2289 | CA  | ALA | 306 | 19.221 | -0.031 | 16.693 | 1.00 | 21.78 | BLGL |
| ATOM | 2290 | CB  | ALA | 306 | 19.708 | -1.019 | 17.743 | 1.00 | 18.27 | BLGL |
| ATOM | 2291 | C   | ALA | 306 | 17.704 | 0.090  | 16.773 | 1.00 | 22.33 | BLGL |
| ATOM | 2292 | O   | ALA | 306 | 16.987 | -0.569 | 16.018 | 1.00 | 23.37 | BLGL |
| ATOM | 2293 | N   | VAL | 307 | 17.219 | 0.919  | 17.691 | 1.00 | 20.00 | BLGL |
| ATOM | 2294 | CA  | VAL | 307 | 15.788 | 1.112  | 17.844 | 1.00 | 20.55 | BLGL |
| ATOM | 2295 | CB  | VAL | 307 | 15.450 | 1.823  | 19.169 | 1.00 | 20.50 | BLGL |
| ATOM | 2296 | CG1 | VAL | 307 | 13.959 | 2.106  | 19.248 | 1.00 | 17.36 | BLGL |
| ATOM | 2297 | CG2 | VAL | 307 | 15.878 | 0.960  | 20.337 | 1.00 | 19.55 | BLGL |
| ATOM | 2298 | C   | VAL | 307 | 15.274 | 1.959  | 16.696 | 1.00 | 21.97 | BLGL |
| ATOM | 2299 | O   | VAL | 307 | 14.164 | 1.750  | 16.195 | 1.00 | 22.69 | BLGL |
| ATOM | 2300 | N   | SER | 308 | 16.097 | 2.916  | 16.283 | 1.00 | 21.64 | BLGL |
| ATOM | 2301 | CA  | SER | 308 | 15.750 | 3.818  | 15.197 | 1.00 | 21.48 | BLGL |
| ATOM | 2302 | CB  | SER | 308 | 16.809 | 4.916  | 15.073 | 1.00 | 22.23 | BLGL |
| ATOM | 2303 | OG  | SER | 308 | 16.510 | 5.812  | 14.018 | 1.00 | 26.06 | BLGL |
| ATOM | 2304 | C   | SER | 308 | 15.633 | 3.059  | 13.885 | 1.00 | 20.97 | BLGL |
| ATOM | 2305 | O   | SER | 308 | 14.781 | 3.372  | 13.054 | 1.00 | 17.14 | BLGL |
| ATOM | 2306 | N   | ASP | 309 | 16.490 | 2.057  | 13.709 | 1.00 | 21.61 | BLGL |
| ATOM | 2307 | CA  | ASP | 309 | 16.480 | 1.252  | 12.494 | 1.00 | 23.50 | BLGL |
| ATOM | 2308 | CB  | ASP | 309 | 17.698 | 0.332  | 12.434 | 1.00 | 25.27 | BLGL |
| ATOM | 2309 | CG  | ASP | 309 | 18.971 | 1.069  | 12.064 | 1.00 | 29.05 | BLGL |

Fig. 4 cont.

| | | | | | | | | | |
|---|---|---|---|---|---|---|---|---|---|
| ATOM | 2310 | OD1 | ASP | 309 | 18.874 | 2.130 | 11.401 | 1.00 26.38 | BLGL |
| ATOM | 2311 | OD2 | ASP | 309 | 20.066 | 0.576 | 12.423 | 1.00 30.01 | BLGL |
| ATOM | 2312 | C | ASP | 309 | 15.225 | 0.412 | 12.339 | 1.00 24.33 | BLGL |
| ATOM | 2313 | O | ASP | 309 | 14.972 | -0.124 | 11.265 | 1.00 26.71 | BLGL |
| ATOM | 2314 | N | VAL | 310 | 14.450 | 0.280 | 13.409 | 1.00 24.29 | BLGL |
| ATOM | 2315 | CA | VAL | 310 | 13.219 | -0.490 | 13.344 | 1.00 23.62 | BLGL |
| ATOM | 2316 | CB | VAL | 310 | 12.582 | -0.647 | 14.730 | 1.00 23.06 | BLGL |
| ATOM | 2317 | CG1 | VAL | 310 | 11.232 | -1.336 | 14.606 | 1.00 21.23 | BLGL |
| ATOM | 2318 | CG2 | VAL | 310 | 13.509 | -1.443 | 15.632 | 1.00 21.91 | BLGL |
| ATOM | 2319 | C | VAL | 310 | 12.248 | 0.247 | 12.440 | 1.00 23.63 | BLGL |
| ATOM | 2320 | O | VAL | 310 | 11.360 | -0.352 | 11.834 | 1.00 25.38 | BLGL |
| ATOM | 2321 | N | GLY | 311 | 12.438 | 1.555 | 12.343 | 1.00 23.71 | BLGL |
| ATOM | 2322 | CA | GLY | 311 | 11.573 | 2.373 | 11.519 | 1.00 23.98 | BLGL |
| ATOM | 2323 | C | GLY | 311 | 10.628 | 3.201 | 12.366 | 1.00 27.47 | BLGL |
| ATOM | 2324 | O | GLY | 311 | 10.919 | 3.565 | 13.514 | 1.00 28.40 | BLGL |
| ATOM | 2325 | N | GLU | 312 | 9.469 | 3.474 | 11.783 | 1.00 27.49 | BLGL |
| ATOM | 2326 | CA | GLU | 312 | 8.438 | 4.262 | 12.419 | 1.00 27.36 | BLGL |
| ATOM | 2327 | CB | GLU | 312 | 7.210 | 4.291 | 11.514 | 1.00 32.86 | BLGL |
| ATOM | 2328 | CG | GLU | 312 | 6.318 | 5.503 | 11.705 | 1.00 43.92 | BLGL |
| ATOM | 2329 | CD | GLU | 312 | 4.950 | 5.314 | 11.071 | 1.00 50.44 | BLGL |
| ATOM | 2330 | OE1 | GLU | 312 | 4.889 | 4.793 | 9.930 | 1.00 51.60 | BLGL |
| ATOM | 2331 | OE2 | GLU | 312 | 3.939 | 5.694 | 11.713 | 1.00 53.86 | BLGL |
| ATOM | 2332 | C | GLU | 312 | 8.039 | 3.746 | 13.805 | 1.00 25.87 | BLGL |
| ATOM | 2333 | O | GLU | 312 | 7.717 | 4.537 | 14.683 | 1.00 27.15 | BLGL |
| ATOM | 2334 | N | ALA | 313 | 8.067 | 2.431 | 14.003 | 1.00 22.50 | BLGL |
| ATOM | 2335 | CA | ALA | 313 | 7.671 | 1.814 | 15.273 | 1.00 19.75 | BLGL |
| ATOM | 2336 | CB | ALA | 313 | 7.480 | 0.315 | 15.077 | 1.00 19.28 | BLGL |
| ATOM | 2337 | C | ALA | 313 | 8.608 | 2.054 | 16.454 | 1.00 18.86 | BLGL |
| ATOM | 2338 | O | ALA | 313 | 8.167 | 2.049 | 17.602 | 1.00 15.56 | BLGL |
| ATOM | 2339 | N | GLY | 314 | 9.897 | 2.238 | 16.173 | 1.00 19.40 | BLGL |
| ATOM | 2340 | CA | GLY | 314 | 10.868 | 2.476 | 17.232 | 1.00 21.12 | BLGL |
| ATOM | 2341 | C | GLY | 314 | 10.667 | 3.878 | 17.787 | 1.00 22.30 | BLGL |
| ATOM | 2342 | O | GLY | 314 | 11.016 | 4.865 | 17.135 | 1.00 23.19 | BLGL |
| ATOM | 2343 | N | ILE | 315 | 10.122 | 3.973 | 18.997 | 1.00 19.98 | BLGL |
| ATOM | 2344 | CA | ILE | 315 | 9.841 | 5.267 | 19.580 | 1.00 18.06 | BLGL |
| ATOM | 2345 | CB | ILE | 315 | 8.457 | 5.265 | 20.248 | 1.00 17.92 | BLGL |
| ATOM | 2346 | CG2 | ILE | 315 | 7.402 | 4.928 | 19.221 | 1.00 16.03 | BLGL |
| ATOM | 2347 | CG1 | ILE | 315 | 8.417 | 4.242 | 21.378 | 1.00 17.81 | BLGL |
| ATOM | 2348 | CD1 | ILE | 315 | 7.113 | 4.236 | 22.116 | 1.00 16.57 | BLGL |
| ATOM | 2349 | C | ILE | 315 | 10.852 | 5.818 | 20.563 | 1.00 18.49 | BLGL |
| ATOM | 2350 | O | ILE | 315 | 10.851 | 7.012 | 20.836 | 1.00 19.85 | BLGL |
| ATOM | 2351 | N | GLY | 316 | 11.719 | 4.974 | 21.101 | 1.00 18.64 | BLGL |
| ATOM | 2352 | CA | GLY | 316 | 12.692 | 5.492 | 22.042 | 1.00 17.78 | BLGL |
| ATOM | 2353 | C | GLY | 316 | 13.562 | 4.510 | 22.803 | 1.00 18.38 | BLGL |
| ATOM | 2354 | O | GLY | 316 | 13.500 | 3.290 | 22.618 | 1.00 17.99 | BLGL |
| ATOM | 2355 | N | VAL | 317 | 14.381 | 5.081 | 23.680 | 1.00 17.69 | BLGL |
| ATOM | 2356 | CA | VAL | 317 | 15.312 | 4.328 | 24.512 | 1.00 17.45 | BLGL |
| ATOM | 2357 | CB | VAL | 317 | 16.727 | 4.367 | 23.916 | 1.00 17.12 | BLGL |
| ATOM | 2358 | CG1 | VAL | 317 | 17.710 | 3.738 | 24.882 | 1.00 16.69 | BLGL |
| ATOM | 2359 | CG2 | VAL | 317 | 16.753 | 3.642 | 22.586 | 1.00 16.13 | BLGL |
| ATOM | 2360 | C | VAL | 317 | 15.385 | 4.902 | 25.921 | 1.00 17.08 | BLGL |
| ATOM | 2361 | O | VAL | 317 | 15.386 | 6.116 | 26.101 | 1.00 19.09 | BLGL |
| ATOM | 2362 | N | PHE | 318 | 15.441 | 4.032 | 26.920 | 1.00 17.11 | BLGL |
| ATOM | 2363 | CA | PHE | 318 | 15.547 | 4.488 | 28.298 | 1.00 16.85 | BLGL |
| ATOM | 2364 | CB | PHE | 318 | 14.389 | 3.976 | 29.146 | 1.00 17.66 | BLGL |
| ATOM | 2365 | CG | PHE | 318 | 13.154 | 4.821 | 29.068 | 1.00 19.59 | BLGL |
| ATOM | 2366 | CD1 | PHE | 318 | 12.208 | 4.615 | 28.063 | 1.00 17.88 | BLGL |
| ATOM | 2367 | CD2 | PHE | 318 | 12.922 | 5.811 | 30.017 | 1.00 18.14 | BLGL |
| ATOM | 2368 | CE1 | PHE | 318 | 11.041 | 5.383 | 28.007 | 1.00 15.40 | BLGL |
| ATOM | 2369 | CE2 | PHE | 318 | 11.760 | 6.585 | 29.968 | 1.00 20.01 | BLGL |
| ATOM | 2370 | CZ | PHE | 318 | 10.815 | 6.367 | 28.960 | 1.00 16.53 | BLGL |
| ATOM | 2371 | C | PHE | 318 | 16.839 | 3.996 | 28.914 | 1.00 17.63 | BLGL |
| ATOM | 2372 | O | PHE | 318 | 17.132 | 2.802 | 28.878 | 1.00 19.56 | BLGL |
| ATOM | 2373 | N | TYR | 319 | 17.619 | 4.914 | 29.471 | 1.00 17.12 | BLGL |
| ATOM | 2374 | CA | TYR | 319 | 18.859 | 4.531 | 30.127 | 1.00 17.31 | BLGL |
| ATOM | 2375 | CB | TYR | 319 | 19.876 | 5.676 | 30.103 | 1.00 15.56 | BLGL |

Fig. 4 cont.

| ATOM | 2376 | CG  | TYR | 319 | 21.255 | 5.211  | 30.495 | 1.00 | 17.60 | BLGL |
|------|------|-----|-----|-----|--------|--------|--------|------|-------|------|
| ATOM | 2377 | CD1 | TYR | 319 | 22.257 | 5.060  | 29.541 | 1.00 | 16.51 | BLGL |
| ATOM | 2378 | CE1 | TYR | 319 | 23.503 | 4.568  | 29.886 | 1.00 | 17.94 | BLGL |
| ATOM | 2379 | CD2 | TYR | 319 | 21.541 | 4.860  | 31.815 | 1.00 | 17.35 | BLGL |
| ATOM | 2380 | CE2 | TYR | 319 | 22.781 | 4.366  | 32.174 | 1.00 | 18.20 | BLGL |
| ATOM | 2381 | CZ  | TYR | 319 | 23.761 | 4.220  | 31.207 | 1.00 | 18.82 | BLGL |
| ATOM | 2382 | OH  | TYR | 319 | 24.993 | 3.717  | 31.560 | 1.00 | 17.43 | BLGL |
| ATOM | 2383 | C   | TYR | 319 | 18.465 | 4.214  | 31.568 | 1.00 | 15.84 | BLGL |
| ATOM | 2384 | O   | TYR | 319 | 17.852 | 5.040  | 32.231 | 1.00 | 17.43 | BLGL |
| ATOM | 2385 | N   | TRP | 320 | 18.811 | 3.024  | 32.050 | 1.00 | 15.86 | BLGL |
| ATOM | 2386 | CA  | TRP | 320 | 18.448 | 2.622  | 33.408 | 1.00 | 14.37 | BLGL |
| ATOM | 2387 | CB  | TRP | 320 | 18.286 | 1.099  | 33.489 | 1.00 | 13.03 | BLGL |
| ATOM | 2388 | CG  | TRP | 320 | 17.673 | 0.644  | 34.786 | 1.00 | 13.67 | BLGL |
| ATOM | 2389 | CD2 | TRP | 320 | 18.348 | -0.001 | 35.873 | 1.00 | 13.63 | BLGL |
| ATOM | 2390 | CE2 | TRP | 320 | 17.408 | -0.123 | 36.930 | 1.00 | 16.14 | BLGL |
| ATOM | 2391 | CE3 | TRP | 320 | 19.654 | -0.480 | 36.063 | 1.00 | 12.95 | BLGL |
| ATOM | 2392 | CD1 | TRP | 320 | 16.388 | 0.865  | 35.210 | 1.00 | 10.20 | BLGL |
| ATOM | 2393 | NE1 | TRP | 320 | 16.225 | 0.413  | 36.491 | 1.00 | 11.94 | BLGL |
| ATOM | 2394 | CZ2 | TRP | 320 | 17.736 | -0.706 | 38.171 | 1.00 | 14.00 | BLGL |
| ATOM | 2395 | CZ3 | TRP | 320 | 19.984 | -1.057 | 37.292 | 1.00 | 14.81 | BLGL |
| ATOM | 2396 | CH2 | TRP | 320 | 19.023 | -1.163 | 38.332 | 1.00 | 15.77 | BLGL |
| ATOM | 2397 | C   | TRP | 320 | 19.428 | 3.071  | 34.484 | 1.00 | 14.79 | BLGL |
| ATOM | 2398 | O   | TRP | 320 | 20.624 | 2.786  | 34.403 | 1.00 | 13.40 | BLGL |
| ATOM | 2399 | N   | GLU | 321 | 18.898 | 3.770  | 35.487 | 1.00 | 14.52 | BLGL |
| ATOM | 2400 | CA  | GLU | 321 | 19.671 | 4.261  | 36.630 | 1.00 | 16.07 | BLGL |
| ATOM | 2401 | CB  | GLU | 321 | 19.878 | 3.117  | 37.634 | 1.00 | 16.50 | BLGL |
| ATOM | 2402 | CG  | GLU | 321 | 18.605 | 2.675  | 38.362 | 1.00 | 15.22 | BLGL |
| ATOM | 2403 | CD  | GLU | 321 | 18.179 | 3.653  | 39.439 | 1.00 | 15.33 | BLGL |
| ATOM | 2404 | OE1 | GLU | 321 | 17.190 | 3.375  | 40.156 | 1.00 | 13.74 | BLGL |
| ATOM | 2405 | OE2 | GLU | 321 | 18.840 | 4.703  | 39.573 | 1.00 | 17.28 | BLGL |
| ATOM | 2406 | C   | GLU | 321 | 21.015 | 4.890  | 36.267 | 1.00 | 16.30 | BLGL |
| ATOM | 2407 | O   | GLU | 321 | 22.078 | 4.321  | 36.533 | 1.00 | 19.88 | BLGL |
| ATOM | 2408 | N   | PRO | 322 | 20.985 | 6.085  | 35.664 | 1.00 | 13.95 | BLGL |
| ATOM | 2409 | CD  | PRO | 322 | 19.800 | 6.807  | 35.166 | 1.00 | 13.71 | BLGL |
| ATOM | 2410 | CA  | PRO | 322 | 22.207 | 6.776  | 35.269 | 1.00 | 13.32 | BLGL |
| ATOM | 2411 | CB  | PRO | 322 | 21.727 | 7.665  | 34.136 | 1.00 | 13.68 | BLGL |
| ATOM | 2412 | CG  | PRO | 322 | 20.397 | 8.108  | 34.648 | 1.00 | 11.78 | BLGL |
| ATOM | 2413 | C   | PRO | 322 | 22.826 | 7.588  | 36.391 | 1.00 | 14.16 | BLGL |
| ATOM | 2414 | O   | PRO | 322 | 23.849 | 8.235  | 36.191 | 1.00 | 17.47 | BLGL |
| ATOM | 2415 | N   | ALA | 323 | 22.215 | 7.564  | 37.568 | 1.00 | 12.38 | BLGL |
| ATOM | 2416 | CA  | ALA | 323 | 22.742 | 8.345  | 38.676 | 1.00 | 11.98 | BLGL |
| ATOM | 2417 | CB  | ALA | 323 | 21.979 | 9.660  | 38.786 | 1.00 | 8.04  | BLGL |
| ATOM | 2418 | C   | ALA | 323 | 22.736 | 7.619  | 40.012 | 1.00 | 12.24 | BLGL |
| ATOM | 2419 | O   | ALA | 323 | 22.580 | 8.245  | 41.060 | 1.00 | 10.55 | BLGL |
| ATOM | 2420 | N   | TRP | 324 | 22.910 | 6.300  | 39.980 | 1.00 | 14.35 | BLGL |
| ATOM | 2421 | CA  | TRP | 324 | 22.933 | 5.515  | 41.215 | 1.00 | 15.62 | BLGL |
| ATOM | 2422 | CB  | TRP | 324 | 22.422 | 4.094  | 40.973 | 1.00 | 15.22 | BLGL |
| ATOM | 2423 | CG  | TRP | 324 | 21.843 | 3.473  | 42.201 | 1.00 | 16.28 | BLGL |
| ATOM | 2424 | CD2 | TRP | 324 | 20.827 | 2.465  | 42.257 | 1.00 | 18.02 | BLGL |
| ATOM | 2425 | CE2 | TRP | 324 | 20.595 | 2.181  | 43.622 | 1.00 | 18.70 | BLGL |
| ATOM | 2426 | CE3 | TRP | 324 | 20.086 | 1.776  | 41.287 | 1.00 | 16.37 | BLGL |
| ATOM | 2427 | CD1 | TRP | 324 | 22.178 | 3.748  | 43.494 | 1.00 | 17.37 | BLGL |
| ATOM | 2428 | NE1 | TRP | 324 | 21.434 | 2.978  | 44.354 | 1.00 | 19.41 | BLGL |
| ATOM | 2429 | CZ2 | TRP | 324 | 19.655 | 1.231  | 44.044 | 1.00 | 19.78 | BLGL |
| ATOM | 2430 | CZ3 | TRP | 324 | 19.154 | 0.834  | 41.703 | 1.00 | 16.22 | BLGL |
| ATOM | 2431 | CH2 | TRP | 324 | 18.944 | 0.570  | 43.071 | 1.00 | 18.68 | BLGL |
| ATOM | 2432 | C   | TRP | 324 | 24.378 | 5.467  | 41.707 | 1.00 | 16.46 | BLGL |
| ATOM | 2433 | O   | TRP | 324 | 24.986 | 4.405  | 41.823 | 1.00 | 13.25 | BLGL |
| ATOM | 2434 | N   | ILE | 325 | 24.916 | 6.645  | 41.994 | 1.00 | 18.45 | BLGL |
| ATOM | 2435 | CA  | ILE | 325 | 26.284 | 6.781  | 42.453 | 1.00 | 20.02 | BLGL |
| ATOM | 2436 | CB  | ILE | 325 | 26.796 | 8.203  | 42.189 | 1.00 | 19.48 | BLGL |
| ATOM | 2437 | CG2 | ILE | 325 | 26.652 | 8.518  | 40.706 | 1.00 | 18.33 | BLGL |
| ATOM | 2438 | CG1 | ILE | 325 | 26.021 | 9.212  | 43.032 | 1.00 | 17.13 | BLGL |
| ATOM | 2439 | CD1 | ILE | 325 | 26.493 | 10.630 | 42.843 | 1.00 | 14.92 | BLGL |
| ATOM | 2440 | C   | ILE | 325 | 26.448 | 6.429  | 43.926 | 1.00 | 21.37 | BLGL |
| ATOM | 2441 | O   | ILE | 325 | 25.473 | 6.373  | 44.675 | 1.00 | 20.25 | BLGL |

Fig. 4 cont.

| ATOM | 2442 | N | PRO | 326 | 27.697 | 6.188 | 44.358 | 1.00 | 22.85 | BLGL |
|------|------|------|------|-----|--------|-------|--------|------|-------|------|
| ATOM | 2443 | CD | PRO | 326 | 28.935 | 6.258 | 43.557 | 1.00 | 21.92 | BLGL |
| ATOM | 2444 | CA | PRO | 326 | 27.988 | 5.827 | 45.750 | 1.00 | 23.11 | BLGL |
| ATOM | 2445 | CB | PRO | 326 | 29.488 | 5.535 | 45.724 | 1.00 | 21.79 | BLGL |
| ATOM | 2446 | CG | PRO | 326 | 29.992 | 6.401 | 44.613 | 1.00 | 23.00 | BLGL |
| ATOM | 2447 | C | PRO | 326 | 27.604 | 6.851 | 46.806 | 1.00 | 22.87 | BLGL |
| ATOM | 2448 | O | PRO | 326 | 27.666 | 8.055 | 46.564 | 1.00 | 22.51 | BLGL |
| ATOM | 2449 | N | VAL | 327 | 27.189 | 6.360 | 47.975 | 1.00 | 22.78 | BLGL |
| ATOM | 2450 | CA | VAL | 327 | 26.812 | 7.236 | 49.083 | 1.00 | 24.67 | BLGL |
| ATOM | 2451 | CB | VAL | 327 | 25.918 | 6.519 | 50.133 | 1.00 | 26.26 | BLGL |
| ATOM | 2452 | CG1 | VAL | 327 | 24.651 | 5.996 | 49.478 | 1.00 | 27.07 | BLGL |
| ATOM | 2453 | CG2 | VAL | 327 | 26.691 | 5.393 | 50.805 | 1.00 | 23.81 | BLGL |
| ATOM | 2454 | C | VAL | 327 | 28.072 | 7.697 | 49.798 | 1.00 | 25.35 | BLGL |
| ATOM | 2455 | O | VAL | 327 | 28.036 | 8.643 | 50.582 | 1.00 | 25.02 | BLGL |
| ATOM | 2456 | N | GLY | 328 | 29.176 | 7.007 | 49.516 | 1.00 | 26.68 | BLGL |
| ATOM | 2457 | CA | GLY | 328 | 30.459 | 7.315 | 50.120 | 1.00 | 27.54 | BLGL |
| ATOM | 2458 | C | GLY | 328 | 31.540 | 6.412 | 49.551 | 1.00 | 29.31 | BLGL |
| ATOM | 2459 | O | GLY | 328 | 31.219 | 5.392 | 48.938 | 1.00 | 29.16 | BLGL |
| ATOM | 2460 | N | PRO | 329 | 32.830 | 6.751 | 49.743 | 1.00 | 30.18 | BLGL |
| ATOM | 2461 | CD | PRO | 329 | 33.277 | 7.948 | 50.477 | 1.00 | 30.73 | BLGL |
| ATOM | 2462 | CA | PRO | 329 | 33.989 | 5.994 | 49.255 | 1.00 | 30.09 | BLGL |
| ATOM | 2463 | CB | PRO | 329 | 35.166 | 6.722 | 49.891 | 1.00 | 30.88 | BLGL |
| ATOM | 2464 | CG | PRO | 329 | 34.685 | 8.128 | 49.959 | 1.00 | 31.43 | BLGL |
| ATOM | 2465 | C | PRO | 329 | 33.966 | 4.520 | 49.614 | 1.00 | 29.93 | BLGL |
| ATOM | 2466 | O | PRO | 329 | 33.416 | 4.132 | 50.639 | 1.00 | 30.03 | BLGL |
| ATOM | 2467 | N | ALA | 330 | 34.582 | 3.706 | 48.768 | 1.00 | 29.86 | BLGL |
| ATOM | 2468 | CA | ALA | 330 | 34.614 | 2.272 | 48.987 | 1.00 | 32.93 | BLGL |
| ATOM | 2469 | CB | ALA | 330 | 35.343 | 1.585 | 47.833 | 1.00 | 31.50 | BLGL |
| ATOM | 2470 | C | ALA | 330 | 35.265 | 1.911 | 50.313 | 1.00 | 35.35 | BLGL |
| ATOM | 2471 | O | ALA | 330 | 34.894 | 0.916 | 50.940 | 1.00 | 35.56 | BLGL |
| ATOM | 2472 | N | HIS | 331 | 36.228 | 2.721 | 50.749 | 1.00 | 37.94 | BLGL |
| ATOM | 2473 | CA | HIS | 331 | 36.922 | 2.440 | 52.001 | 1.00 | 40.82 | BLGL |
| ATOM | 2474 | CB | HIS | 331 | 38.282 | 3.143 | 52.049 | 1.00 | 41.19 | BLGL |
| ATOM | 2475 | CG | HIS | 331 | 38.195 | 4.632 | 52.171 | 1.00 | 42.83 | BLGL |
| ATOM | 2476 | CD2 | HIS | 331 | 38.170 | 5.436 | 53.261 | 1.00 | 42.69 | BLGL |
| ATOM | 2477 | ND1 | HIS | 331 | 38.130 | 5.469 | 51.077 | 1.00 | 43.41 | BLGL |
| ATOM | 2478 | CE1 | HIS | 331 | 38.073 | 6.725 | 51.488 | 1.00 | 42.26 | BLGL |
| ATOM | 2479 | NE2 | HIS | 331 | 38.096 | 6.732 | 52.809 | 1.00 | 42.43 | BLGL |
| ATOM | 2480 | C | HIS | 331 | 36.130 | 2.805 | 53.254 | 1.00 | 42.32 | BLGL |
| ATOM | 2481 | O | HIS | 331 | 36.674 | 2.788 | 54.354 | 1.00 | 43.73 | BLGL |
| ATOM | 2482 | N | ARG | 332 | 34.857 | 3.149 | 53.105 | 1.00 | 43.54 | BLGL |
| ATOM | 2483 | CA | ARG | 332 | 34.041 | 3.478 | 54.264 | 1.00 | 43.67 | BLGL |
| ATOM | 2484 | CB | ARG | 332 | 33.446 | 4.878 | 54.152 | 1.00 | 46.16 | BLGL |
| ATOM | 2485 | CG | ARG | 332 | 34.428 | 6.031 | 54.232 | 1.00 | 51.93 | BLGL |
| ATOM | 2486 | CD | ARG | 332 | 33.693 | 7.258 | 54.754 | 1.00 | 55.92 | BLGL |
| ATOM | 2487 | NE | ARG | 332 | 32.323 | 7.299 | 54.240 | 1.00 | 62.04 | BLGL |
| ATOM | 2488 | CZ | ARG | 332 | 31.376 | 8.138 | 54.664 | 1.00 | 64.85 | BLGL |
| ATOM | 2489 | NH1 | ARG | 332 | 30.154 | 8.095 | 54.132 | 1.00 | 64.81 | BLGL |
| ATOM | 2490 | NH2 | ARG | 332 | 31.640 | 9.023 | 55.622 | 1.00 | 65.83 | BLGL |
| ATOM | 2491 | C | ARG | 332 | 32.899 | 2.482 | 54.368 | 1.00 | 43.46 | BLGL |
| ATOM | 2492 | O | ARG | 332 | 31.882 | 2.766 | 54.999 | 1.00 | 42.10 | BLGL |
| ATOM | 2493 | N | LEU | 333 | 33.077 | 1.318 | 53.748 | 1.00 | 43.54 | BLGL |
| ATOM | 2494 | CA | LEU | 333 | 32.058 | 0.277 | 53.739 | 1.00 | 44.90 | BLGL |
| ATOM | 2495 | CB | LEU | 333 | 32.700 | -1.104 | 53.605 | 1.00 | 44.71 | BLGL |
| ATOM | 2496 | CG | LEU | 333 | 32.076 | -1.981 | 52.511 | 1.00 | 47.14 | BLGL |
| ATOM | 2497 | CD1 | LEU | 333 | 32.702 | -3.370 | 52.561 | 1.00 | 47.53 | BLGL |
| ATOM | 2498 | CD2 | LEU | 333 | 30.561 | -2.068 | 52.691 | 1.00 | 46.62 | BLGL |
| ATOM | 2499 | C | LEU | 333 | 31.154 | 0.282 | 54.959 | 1.00 | 46.15 | BLGL |
| ATOM | 2500 | O | LEU | 333 | 29.931 | 0.378 | 54.833 | 1.00 | 47.20 | BLGL |
| ATOM | 2501 | N | GLU | 334 | 31.755 | 0.183 | 56.139 | 1.00 | 47.86 | BLGL |
| ATOM | 2502 | CA | GLU | 334 | 30.989 | 0.159 | 57.384 | 1.00 | 48.83 | BLGL |
| ATOM | 2503 | CB | GLU | 334 | 31.934 | 0.012 | 58.584 | 1.00 | 51.92 | BLGL |
| ATOM | 2504 | CG | GLU | 334 | 32.639 | -1.345 | 58.641 | 1.00 | 58.71 | BLGL |
| ATOM | 2505 | CD | GLU | 334 | 31.663 | -2.521 | 58.588 | 1.00 | 61.85 | BLGL |
| ATOM | 2506 | OE1 | GLU | 334 | 30.824 | -2.642 | 59.510 | 1.00 | 62.23 | BLGL |
| ATOM | 2507 | OE2 | GLU | 334 | 31.734 | -3.319 | 57.622 | 1.00 | 63.86 | BLGL |

Fig. 4 cont.

| | | | | | | | | | |
|---|---|---|---|---|---|---|---|---|---|
| ATOM | 2508 | C | GLU | 334 | 30.083 | 1.374 | 57.584 | 1.00 46.21 | BLGL |
| ATOM | 2509 | O | GLU | 334 | 28.939 | 1.246 | 58.030 | 1.00 45.37 | BLGL |
| ATOM | 2510 | N | LYS | 335 | 30.583 | 2.552 | 57.251 | 1.00 44.31 | BLGL |
| ATOM | 2511 | CA | LYS | 335 | 29.783 | 3.752 | 57.415 | 1.00 43.94 | BLGL |
| ATOM | 2512 | CB | LYS | 335 | 30.687 | 4.980 | 57.370 | 1.00 48.35 | BLGL |
| ATOM | 2513 | CG | LYS | 335 | 30.158 | 6.168 | 58.168 | 1.00 51.85 | BLGL |
| ATOM | 2514 | CD | LYS | 335 | 29.958 | 5.809 | 59.653 | 1.00 56.01 | BLGL |
| ATOM | 2515 | CE | LYS | 335 | 31.207 | 5.161 | 60.270 | 1.00 57.13 | BLGL |
| ATOM | 2516 | NZ | LYS | 335 | 32.440 | 5.982 | 60.078 | 1.00 58.45 | BLGL |
| ATOM | 2517 | C | LYS | 335 | 28.717 | 3.843 | 56.318 | 1.00 42.75 | BLGL |
| ATOM | 2518 | O | LYS | 335 | 27.664 | 4.458 | 56.508 | 1.00 40.92 | BLGL |
| ATOM | 2519 | N | ASN | 336 | 28.999 | 3.229 | 55.169 | 1.00 40.89 | BLGL |
| ATOM | 2520 | CA | ASN | 336 | 28.068 | 3.233 | 54.050 | 1.00 36.25 | BLGL |
| ATOM | 2521 | CB | ASN | 336 | 28.758 | 2.764 | 52.774 | 1.00 34.22 | BLGL |
| ATOM | 2522 | CG | ASN | 336 | 29.754 | 3.770 | 52.252 | 1.00 33.73 | BLGL |
| ATOM | 2523 | OD1 | ASN | 336 | 29.698 | 4.949 | 52.593 | 1.00 33.95 | BLGL |
| ATOM | 2524 | ND2 | ASN | 336 | 30.661 | 3.316 | 51.401 | 1.00 34.13 | BLGL |
| ATOM | 2525 | C | ASN | 336 | 26.883 | 2.332 | 54.333 | 1.00 35.83 | BLGL |
| ATOM | 2526 | O | ASN | 336 | 25.742 | 2.702 | 54.050 | 1.00 35.07 | BLGL |
| ATOM | 2527 | N | LYS | 337 | 27.161 | 1.147 | 54.882 | 1.00 34.86 | BLGL |
| ATOM | 2528 | CA | LYS | 337 | 26.116 | 0.171 | 55.209 | 1.00 33.18 | BLGL |
| ATOM | 2529 | CB | LYS | 337 | 26.712 | -1.023 | 55.953 | 1.00 31.58 | BLGL |
| ATOM | 2530 | CG | LYS | 337 | 27.594 | -1.901 | 55.095 | 1.00 32.46 | BLGL |
| ATOM | 2531 | CD | LYS | 337 | 28.112 | -3.095 | 55.881 | 1.00 33.49 | BLGL |
| ATOM | 2532 | CE | LYS | 337 | 28.869 | -4.046 | 54.967 | 1.00 38.20 | BLGL |
| ATOM | 2533 | NZ | LYS | 337 | 29.366 | -5.262 | 55.679 | 1.00 41.08 | BLGL |
| ATOM | 2534 | C | LYS | 337 | 25.042 | 0.812 | 56.069 | 1.00 32.37 | BLGL |
| ATOM | 2535 | O | LYS | 337 | 23.866 | 0.477 | 55.971 | 1.00 30.10 | BLGL |
| ATOM | 2536 | N | ALA | 338 | 25.466 | 1.738 | 56.917 | 1.00 32.27 | BLGL |
| ATOM | 2537 | CA | ALA | 338 | 24.543 | 2.434 | 57.793 | 1.00 32.10 | BLGL |
| ATOM | 2538 | CB | ALA | 338 | 25.313 | 3.383 | 58.712 | 1.00 30.46 | BLGL |
| ATOM | 2539 | C | ALA | 338 | 23.533 | 3.211 | 56.951 | 1.00 31.53 | BLGL |
| ATOM | 2540 | O | ALA | 338 | 22.332 | 3.174 | 57.217 | 1.00 32.87 | BLGL |
| ATOM | 2541 | N | LEU | 339 | 24.025 | 3.915 | 55.937 | 1.00 29.75 | BLGL |
| ATOM | 2542 | CA | LEU | 339 | 23.165 | 4.703 | 55.064 | 1.00 28.75 | BLGL |
| ATOM | 2543 | CB | LEU | 339 | 24.019 | 5.580 | 54.149 | 1.00 29.58 | BLGL |
| ATOM | 2544 | CG | LEU | 339 | 24.839 | 6.671 | 54.842 | 1.00 29.29 | BLGL |
| ATOM | 2545 | CD1 | LEU | 339 | 25.763 | 7.358 | 53.858 | 1.00 30.28 | BLGL |
| ATOM | 2546 | CD2 | LEU | 339 | 23.889 | 7.674 | 55.457 | 1.00 30.12 | BLGL |
| ATOM | 2547 | C | LEU | 339 | 22.246 | 3.824 | 54.217 | 1.00 28.58 | BLGL |
| ATOM | 2548 | O | LEU | 339 | 21.035 | 4.049 | 54.154 | 1.00 28.13 | BLGL |
| ATOM | 2549 | N | TRP | 340 | 22.828 | 2.828 | 53.557 | 1.00 27.39 | BLGL |
| ATOM | 2550 | CA | TRP | 340 | 22.052 | 1.925 | 52.719 | 1.00 26.49 | BLGL |
| ATOM | 2551 | CB | TRP | 340 | 22.900 | 0.746 | 52.236 | 1.00 23.72 | BLGL |
| ATOM | 2552 | CG | TRP | 340 | 24.091 | 1.114 | 51.444 | 1.00 22.86 | BLGL |
| ATOM | 2553 | CD2 | TRP | 340 | 25.305 | 0.366 | 51.336 | 1.00 23.48 | BLGL |
| ATOM | 2554 | CE2 | TRP | 340 | 26.154 | 1.077 | 50.458 | 1.00 23.45 | BLGL |
| ATOM | 2555 | CE3 | TRP | 340 | 25.760 | -0.839 | 51.895 | 1.00 23.20 | BLGL |
| ATOM | 2556 | CD1 | TRP | 340 | 24.243 | 2.214 | 50.651 | 1.00 22.87 | BLGL |
| ATOM | 2557 | NE1 | TRP | 340 | 25.480 | 2.200 | 50.056 | 1.00 22.68 | BLGL |
| ATOM | 2558 | CZ2 | TRP | 340 | 27.437 | 0.626 | 50.123 | 1.00 23.93 | BLGL |
| ATOM | 2559 | CZ3 | TRP | 340 | 27.036 | -1.288 | 51.561 | 1.00 24.91 | BLGL |
| ATOM | 2560 | CH2 | TRP | 340 | 27.859 | -0.553 | 50.682 | 1.00 23.29 | BLGL |
| ATOM | 2561 | C | TRP | 340 | 20.891 | 1.359 | 53.505 | 1.00 26.35 | BLGL |
| ATOM | 2562 | O | TRP | 340 | 19.777 | 1.252 | 53.005 | 1.00 26.95 | BLGL |
| ATOM | 2563 | N | GLU | 341 | 21.179 | 0.990 | 54.743 | 1.00 27.03 | BLGL |
| ATOM | 2564 | CA | GLU | 341 | 20.206 | 0.383 | 55.629 | 1.00 27.61 | BLGL |
| ATOM | 2565 | CB | GLU | 341 | 20.939 | -0.239 | 56.818 | 1.00 29.81 | BLGL |
| ATOM | 2566 | CG | GLU | 341 | 20.338 | -1.534 | 57.345 | 1.00 32.17 | BLGL |
| ATOM | 2567 | CD | GLU | 341 | 20.490 | -2.693 | 56.384 | 1.00 34.50 | BLGL |
| ATOM | 2568 | OE1 | GLU | 341 | 20.087 | -3.811 | 56.756 | 1.00 38.21 | BLGL |
| ATOM | 2569 | OE2 | GLU | 341 | 21.003 | -2.503 | 55.261 | 1.00 35.23 | BLGL |
| ATOM | 2570 | C | GLU | 341 | 19.150 | 1.366 | 56.112 | 1.00 27.16 | BLGL |
| ATOM | 2571 | O | GLU | 341 | 17.967 | 1.044 | 56.169 | 1.00 27.02 | BLGL |
| ATOM | 2572 | N | THR | 342 | 19.569 | 2.572 | 56.452 | 1.00 27.11 | BLGL |
| ATOM | 2573 | CA | THR | 342 | 18.624 | 3.562 | 56.940 | 1.00 27.99 | BLGL |

Fig. 4 cont.

| | | | | | | | | | |
|---|---|---|---|---|---|---|---|---|---|
| ATOM | 2574 | CB | THR | 342 | 19.356 | 4.706 | 57.658 | 1.00 27.99 | BLGL |
| ATOM | 2575 | OG1 | THR | 342 | 20.097 | 4.174 | 58.759 | 1.00 29.52 | BLGL |
| ATOM | 2576 | CG2 | THR | 342 | 18.365 | 5.731 | 58.173 | 1.00 28.27 | BLGL |
| ATOM | 2577 | C | THR | 342 | 17.732 | 4.169 | 55.860 | 1.00 27.72 | BLGL |
| ATOM | 2578 | O | THR | 342 | 16.527 | 4.283 | 56.047 | 1.00 27.61 | BLGL |
| ATOM | 2579 | N | TYR | 343 | 18.319 | 4.554 | 54.732 | 1.00 28.64 | BLGL |
| ATOM | 2580 | CA | TYR | 343 | 17.544 | 5.185 | 53.675 | 1.00 29.90 | BLGL |
| ATOM | 2581 | CB | TYR | 343 | 18.260 | 6.448 | 53.209 | 1.00 31.83 | BLGL |
| ATOM | 2582 | CG | TYR | 343 | 18.573 | 7.381 | 54.350 | 1.00 35.78 | BLGL |
| ATOM | 2583 | CD1 | TYR | 343 | 19.798 | 7.313 | 55.013 | 1.00 36.95 | BLGL |
| ATOM | 2584 | CE1 | TYR | 343 | 20.078 | 8.151 | 56.085 | 1.00 38.42 | BLGL |
| ATOM | 2585 | CD2 | TYR | 343 | 17.631 | 8.313 | 54.792 | 1.00 35.14 | BLGL |
| ATOM | 2586 | CE2 | TYR | 343 | 17.901 | 9.153 | 55.864 | 1.00 36.75 | BLGL |
| ATOM | 2587 | CZ | TYR | 343 | 19.128 | 9.067 | 56.503 | 1.00 38.36 | BLGL |
| ATOM | 2588 | OH | TYR | 343 | 19.417 | 9.904 | 57.554 | 1.00 40.88 | BLGL |
| ATOM | 2589 | C | TYR | 343 | 17.202 | 4.327 | 52.469 | 1.00 28.69 | BLGL |
| ATOM | 2590 | O | TYR | 343 | 16.524 | 4.788 | 51.554 | 1.00 28.30 | BLGL |
| ATOM | 2591 | N | GLY | 344 | 17.652 | 3.081 | 52.470 | 1.00 28.37 | BLGL |
| ATOM | 2592 | CA | GLY | 344 | 17.375 | 2.204 | 51.347 | 1.00 29.03 | BLGL |
| ATOM | 2593 | C | GLY | 344 | 18.001 | 2.730 | 50.068 | 1.00 28.56 | BLGL |
| ATOM | 2594 | O | GLY | 344 | 17.425 | 2.603 | 48.987 | 1.00 27.04 | BLGL |
| ATOM | 2595 | N | SER | 345 | 19.187 | 3.320 | 50.199 | 1.00 27.20 | BLGL |
| ATOM | 2596 | CA | SER | 345 | 19.903 | 3.888 | 49.067 | 1.00 25.65 | BLGL |
| ATOM | 2597 | CB | SER | 345 | 20.754 | 5.061 | 49.530 | 1.00 25.43 | BLGL |
| ATOM | 2598 | OG | SER | 345 | 21.600 | 4.654 | 50.582 | 1.00 31.71 | BLGL |
| ATOM | 2599 | C | SER | 345 | 20.780 | 2.853 | 48.380 | 1.00 25.28 | BLGL |
| ATOM | 2600 | O | SER | 345 | 21.554 | 3.183 | 47.479 | 1.00 24.47 | BLGL |
| ATOM | 2601 | N | GLY | 346 | 20.662 | 1.604 | 48.823 | 1.00 24.37 | BLGL |
| ATOM | 2602 | CA | GLY | 346 | 21.414 | 0.518 | 48.220 | 1.00 21.46 | BLGL |
| ATOM | 2603 | C | GLY | 346 | 20.430 | -0.252 | 47.360 | 1.00 20.92 | BLGL |
| ATOM | 2604 | O | GLY | 346 | 19.286 | 0.183 | 47.216 | 1.00 21.35 | BLGL |
| ATOM | 2605 | N | TRP | 347 | 20.834 | -1.385 | 46.795 | 1.00 18.57 | BLGL |
| ATOM | 2606 | CA | TRP | 347 | 19.915 | -2.145 | 45.959 | 1.00 18.47 | BLGL |
| ATOM | 2607 | CB | TRP | 347 | 20.677 | -3.115 | 45.057 | 1.00 19.55 | BLGL |
| ATOM | 2608 | CG | TRP | 347 | 20.976 | -4.426 | 45.700 | 1.00 24.39 | BLGL |
| ATOM | 2609 | CD2 | TRP | 347 | 20.205 | -5.626 | 45.576 | 1.00 26.03 | BLGL |
| ATOM | 2610 | CE2 | TRP | 347 | 20.843 | -6.616 | 46.361 | 1.00 27.34 | BLGL |
| ATOM | 2611 | CE3 | TRP | 347 | 19.035 | -5.963 | 44.878 | 1.00 25.88 | BLGL |
| ATOM | 2612 | CD1 | TRP | 347 | 22.023 | -4.725 | 46.533 | 1.00 24.43 | BLGL |
| ATOM | 2613 | NE1 | TRP | 347 | 21.950 | -6.039 | 46.931 | 1.00 24.87 | BLGL |
| ATOM | 2614 | CZ2 | TRP | 347 | 20.344 | -7.926 | 46.467 | 1.00 27.61 | BLGL |
| ATOM | 2615 | CZ3 | TRP | 347 | 18.541 | -7.268 | 44.982 | 1.00 26.42 | BLGL |
| ATOM | 2616 | CH2 | TRP | 347 | 19.195 | -8.229 | 45.770 | 1.00 25.85 | BLGL |
| ATOM | 2617 | C | TRP | 347 | 18.910 | -2.916 | 46.807 | 1.00 17.94 | BLGL |
| ATOM | 2618 | O | TRP | 347 | 17.820 | -3.255 | 46.347 | 1.00 16.07 | BLGL |
| ATOM | 2619 | N | ALA | 348 | 19.296 | -3.197 | 48.047 | 1.00 19.28 | BLGL |
| ATOM | 2620 | CA | ALA | 348 | 18.444 | -3.918 | 48.984 | 1.00 21.94 | BLGL |
| ATOM | 2621 | CB | ALA | 348 | 18.387 | -5.394 | 48.607 | 1.00 20.51 | BLGL |
| ATOM | 2622 | C | ALA | 348 | 18.948 | -3.767 | 50.422 | 1.00 24.22 | BLGL |
| ATOM | 2623 | O | ALA | 348 | 20.138 | -3.549 | 50.659 | 1.00 25.24 | BLGL |
| ATOM | 2624 | N | THR | 349 | 18.030 | -3.870 | 51.379 | 1.00 25.44 | BLGL |
| ATOM | 2625 | CA | THR | 349 | 18.378 | -3.774 | 52.789 | 1.00 25.50 | BLGL |
| ATOM | 2626 | CB | THR | 349 | 17.509 | -2.738 | 53.553 | 1.00 26.44 | BLGL |
| ATOM | 2627 | OG1 | THR | 349 | 16.167 | -3.228 | 53.679 | 1.00 25.28 | BLGL |
| ATOM | 2628 | CG2 | THR | 349 | 17.500 | -1.400 | 52.823 | 1.00 24.16 | BLGL |
| ATOM | 2629 | C | THR | 349 | 18.102 | -5.139 | 53.383 | 1.00 26.30 | BLGL |
| ATOM | 2630 | O | THR | 349 | 17.382 | -5.942 | 52.791 | 1.00 26.26 | BLGL |
| ATOM | 2631 | N | SER | 350 | 18.671 | -5.403 | 54.551 | 1.00 27.06 | BLGL |
| ATOM | 2632 | CA | SER | 350 | 18.463 | -6.685 | 55.208 | 1.00 26.38 | BLGL |
| ATOM | 2633 | CB | SER | 350 | 19.252 | -6.738 | 56.514 | 1.00 23.71 | BLGL |
| ATOM | 2634 | OG | SER | 350 | 18.812 | -5.726 | 57.400 | 1.00 21.01 | BLGL |
| ATOM | 2635 | C | SER | 350 | 16.975 | -6.911 | 55.490 | 1.00 26.83 | BLGL |
| ATOM | 2636 | O | SER | 350 | 16.509 | -8.046 | 55.520 | 1.00 26.17 | BLGL |
| ATOM | 2637 | N | TYR | 351 | 16.225 | -5.830 | 55.683 | 1.00 28.04 | BLGL |
| ATOM | 2638 | CA | TYR | 351 | 14.796 | -5.946 | 55.965 | 1.00 30.41 | BLGL |
| ATOM | 2639 | CB | TYR | 351 | 14.208 | -4.566 | 56.244 | 1.00 32.17 | BLGL |

Fig. 4 cont.

```
ATOM   2640  CG   TYR  351     14.911   -3.829  57.352  1.00 33.63      BLGL
ATOM   2641  CD1  TYR  351     15.961   -2.951  57.083  1.00 35.43      BLGL
ATOM   2642  CE1  TYR  351     16.623   -2.279  58.114  1.00 35.75      BLGL
ATOM   2643  CD2  TYR  351     14.539   -4.020  58.677  1.00 35.69      BLGL
ATOM   2644  CE2  TYR  351     15.193   -3.355  59.717  1.00 36.21      BLGL
ATOM   2645  CZ   TYR  351     16.231   -2.488  59.427  1.00 35.60      BLGL
ATOM   2646  OH   TYR  351     16.865   -1.828  60.451  1.00 36.59      BLGL
ATOM   2647  C    TYR  351     14.012   -6.626  54.836  1.00 30.90      BLGL
ATOM   2648  O    TYR  351     12.921   -7.159  55.055  1.00 30.86      BLGL
ATOM   2649  N    ALA  352     14.572   -6.604  53.633  1.00 30.77      BLGL
ATOM   2650  CA   ALA  352     13.936   -7.220  52.476  1.00 31.75      BLGL
ATOM   2651  CB   ALA  352     14.611   -6.744  51.202  1.00 30.75      BLGL
ATOM   2652  C    ALA  352     13.989   -8.745  52.545  1.00 33.29      BLGL
ATOM   2653  O    ALA  352     13.411   -9.434  51.700  1.00 33.71      BLGL
ATOM   2654  N    ALA  353     14.680   -9.273  53.549  1.00 33.30      BLGL
ATOM   2655  CA   ALA  353     14.804  -10.718  53.706  1.00 33.02      BLGL
ATOM   2656  CB   ALA  353     15.687  -11.033  54.908  1.00 34.24      BLGL
ATOM   2657  C    ALA  353     13.449  -11.409  53.856  1.00 32.34      BLGL
ATOM   2658  O    ALA  353     13.270  -12.545  53.422  1.00 30.15      BLGL
ATOM   2659  N    GLU  354     12.496  -10.716  54.466  1.00 33.65      BLGL
ATOM   2660  CA   GLU  354     11.176  -11.284  54.668  1.00 35.34      BLGL
ATOM   2661  CB   GLU  354     10.345  -10.375  55.578  1.00 35.98      BLGL
ATOM   2662  CG   GLU  354      9.744   -9.163  54.894  1.00 37.66      BLGL
ATOM   2663  CD   GLU  354      8.831   -8.378  55.818  1.00 40.92      BLGL
ATOM   2664  OE1  GLU  354      8.010   -7.584  55.310  1.00 42.14      BLGL
ATOM   2665  OE2  GLU  354      8.935   -8.548  57.055  1.00 41.70      BLGL
ATOM   2666  C    GLU  354     10.437  -11.503  53.343  1.00 36.54      BLGL
ATOM   2667  O    GLU  354      9.614  -12.416  53.228  1.00 36.40      BLGL
ATOM   2668  N    TYR  355     10.735  -10.673  52.345  1.00 36.32      BLGL
ATOM   2669  CA   TYR  355     10.072  -10.778  51.046  1.00 35.27      BLGL
ATOM   2670  CB   TYR  355      9.800   -9.381  50.496  1.00 32.38      BLGL
ATOM   2671  CG   TYR  355      8.715   -9.339  49.445  1.00 32.93      BLGL
ATOM   2672  CD1  TYR  355      9.022   -9.211  48.087  1.00 31.94      BLGL
ATOM   2673  CE1  TYR  355      8.014   -9.141  47.126  1.00 30.60      BLGL
ATOM   2674  CD2  TYR  355      7.372   -9.403  49.812  1.00 31.34      BLGL
ATOM   2675  CE2  TYR  355      6.364   -9.333  48.864  1.00 31.48      BLGL
ATOM   2676  CZ   TYR  355      6.688   -9.198  47.524  1.00 32.10      BLGL
ATOM   2677  OH   TYR  355      5.679   -9.084  46.593  1.00 32.53      BLGL
ATOM   2678  C    TYR  355     10.873  -11.590  50.034  1.00 36.46      BLGL
ATOM   2679  O    TYR  355     10.306  -12.262  49.177  1.00 33.16      BLGL
ATOM   2680  N    ASP  356     12.196  -11.513  50.133  1.00 39.53      BLGL
ATOM   2681  CA   ASP  356     13.079  -12.251  49.241  1.00 42.86      BLGL
ATOM   2682  CB   ASP  356     13.568  -11.355  48.096  1.00 43.64      BLGL
ATOM   2683  CG   ASP  356     14.568  -12.064  47.182  1.00 44.35      BLGL
ATOM   2684  OD1  ASP  356     15.202  -11.382  46.349  1.00 42.98      BLGL
ATOM   2685  OD2  ASP  356     14.715  -13.303  47.293  1.00 45.31      BLGL
ATOM   2686  C    ASP  356     14.278  -12.741  50.045  1.00 45.45      BLGL
ATOM   2687  O    ASP  356     15.302  -12.058  50.133  1.00 47.13      BLGL
ATOM   2688  N    PRO  357     14.165  -13.931  50.650  1.00 46.19      BLGL
ATOM   2689  CD   PRO  357     12.983  -14.810  50.688  1.00 45.78      BLGL
ATOM   2690  CA   PRO  357     15.260  -14.493  51.447  1.00 46.80      BLGL
ATOM   2691  CB   PRO  357     14.578  -15.627  52.196  1.00 46.98      BLGL
ATOM   2692  CG   PRO  357     13.567  -16.109  51.196  1.00 46.25      BLGL
ATOM   2693  C    PRO  357     16.412  -14.990  50.581  1.00 48.11      BLGL
ATOM   2694  O    PRO  357     17.562  -15.006  51.007  1.00 48.32      BLGL
ATOM   2695  N    GLU  358     16.075  -15.381  49.358  1.00 49.36      BLGL
ATOM   2696  CA   GLU  358     17.019  -15.911  48.385  1.00 51.27      BLGL
ATOM   2697  CB   GLU  358     16.257  -16.304  47.125  1.00 53.72      BLGL
ATOM   2698  CG   GLU  358     15.040  -17.170  47.389  1.00 58.04      BLGL
ATOM   2699  CD   GLU  358     15.414  -18.587  47.774  1.00 62.05      BLGL
ATOM   2700  OE1  GLU  358     15.886  -19.331  46.886  1.00 63.62      BLGL
ATOM   2701  OE2  GLU  358     15.244  -18.955  48.961  1.00 64.62      BLGL
ATOM   2702  C    GLU  358     18.142  -14.958  47.995  1.00 52.75      BLGL
ATOM   2703  O    GLU  358     19.319  -15.232  48.240  1.00 53.92      BLGL
ATOM   2704  N    ASP  359     17.768  -13.850  47.366  1.00 53.56      BLGL
ATOM   2705  CA   ASP  359     18.717  -12.847  46.902  1.00 53.46      BLGL
```

Fig. 4 cont.

| | | | | | | | | | |
|---|---|---|---|---|---|---|---|---|---|
| ATOM | 2706 | CB | ASP | 359 | 18.203 | -12.213 | 45.609 | 1.00 56.56 | BLGL |
| ATOM | 2707 | CG | ASP | 359 | 18.748 | -12.887 | 44.366 | 1.00 58.60 | BLGL |
| ATOM | 2708 | OD1 | ASP | 359 | 18.654 | -14.130 | 44.268 | 1.00 60.63 | BLGL |
| ATOM | 2709 | OD2 | ASP | 359 | 19.268 | -12.166 | 43.485 | 1.00 59.51 | BLGL |
| ATOM | 2710 | C | ASP | 359 | 18.959 | -11.751 | 47.928 | 1.00 51.60 | BLGL |
| ATOM | 2711 | O | ASP | 359 | 19.876 | -11.837 | 48.742 | 1.00 50.90 | BLGL |
| ATOM | 2712 | N | ALA | 360 | 18.132 | -10.713 | 47.865 | 1.00 51.06 | BLGL |
| ATOM | 2713 | CA | ALA | 360 | 18.226 | -9.578 | 48.768 | 1.00 50.62 | BLGL |
| ATOM | 2714 | CB | ALA | 360 | 16.945 | -8.767 | 48.697 | 1.00 49.16 | BLGL |
| ATOM | 2715 | C | ALA | 360 | 18.471 | -10.058 | 50.193 | 1.00 50.90 | BLGL |
| ATOM | 2716 | O | ALA | 360 | 19.164 | -9.403 | 50.973 | 1.00 49.67 | BLGL |
| ATOM | 2717 | N | GLY | 361 | 17.896 | -11.214 | 50.515 | 1.00 52.39 | BLGL |
| ATOM | 2718 | CA | GLY | 361 | 18.042 | -11.794 | 51.837 | 1.00 52.85 | BLGL |
| ATOM | 2719 | C | GLY | 361 | 19.481 | -11.858 | 52.312 | 1.00 53.39 | BLGL |
| ATOM | 2720 | O | GLY | 361 | 19.809 | -11.331 | 53.378 | 1.00 54.42 | BLGL |
| ATOM | 2721 | N | LYS | 362 | 20.351 | -12.496 | 51.540 | 1.00 53.32 | BLGL |
| ATOM | 2722 | CA | LYS | 362 | 21.737 | -12.588 | 51.954 | 1.00 54.47 | BLGL |
| ATOM | 2723 | CB | LYS | 362 | 22.081 | -14.037 | 52.329 | 1.00 57.86 | BLGL |
| ATOM | 2724 | CG | LYS | 362 | 21.401 | -15.120 | 51.495 | 1.00 59.76 | BLGL |
| ATOM | 2725 | CD | LYS | 362 | 22.199 | -15.482 | 50.251 | 1.00 61.95 | BLGL |
| ATOM | 2726 | CE | LYS | 362 | 21.745 | -16.833 | 49.698 | 1.00 63.37 | BLGL |
| ATOM | 2727 | NZ | LYS | 362 | 22.557 | -17.264 | 48.522 | 1.00 62.07 | BLGL |
| ATOM | 2728 | C | LYS | 362 | 22.741 | -12.034 | 50.953 | 1.00 53.61 | BLGL |
| ATOM | 2729 | O | LYS | 362 | 23.823 | -12.595 | 50.770 | 1.00 54.78 | BLGL |
| ATOM | 2730 | N | TRP | 363 | 22.376 | -10.921 | 50.323 | 1.00 52.09 | BLGL |
| ATOM | 2731 | CA | TRP | 363 | 23.236 | -10.246 | 49.357 | 1.00 49.55 | BLGL |
| ATOM | 2732 | CB | TRP | 363 | 23.048 | -10.816 | 47.948 | 1.00 53.13 | BLGL |
| ATOM | 2733 | CG | TRP | 363 | 23.559 | -12.215 | 47.792 | 1.00 58.47 | BLGL |
| ATOM | 2734 | CD2 | TRP | 363 | 24.840 | -12.716 | 48.201 | 1.00 61.21 | BLGL |
| ATOM | 2735 | CE2 | TRP | 363 | 24.867 | -14.096 | 47.894 | 1.00 62.60 | BLGL |
| ATOM | 2736 | CE3 | TRP | 363 | 25.966 | -12.135 | 48.802 | 1.00 63.42 | BLGL |
| ATOM | 2737 | CD1 | TRP | 363 | 22.885 | -13.277 | 47.262 | 1.00 60.70 | BLGL |
| ATOM | 2738 | NE1 | TRP | 363 | 23.663 | -14.412 | 47.320 | 1.00 62.38 | BLGL |
| ATOM | 2739 | CZ2 | TRP | 363 | 25.981 | -14.907 | 48.168 | 1.00 63.65 | BLGL |
| ATOM | 2740 | CZ3 | TRP | 363 | 27.076 | -12.945 | 49.076 | 1.00 64.57 | BLGL |
| ATOM | 2741 | CH2 | TRP | 363 | 27.071 | -14.315 | 48.757 | 1.00 63.75 | BLGL |
| ATOM | 2742 | C | TRP | 363 | 22.900 | -8.765 | 49.354 | 1.00 45.74 | BLGL |
| ATOM | 2743 | O | TRP | 363 | 23.315 | -8.031 | 48.460 | 1.00 46.95 | BLGL |
| ATOM | 2744 | N | PHE | 364 | 22.143 | -8.333 | 50.357 | 1.00 40.08 | BLGL |
| ATOM | 2745 | CA | PHE | 364 | 21.748 | -6.939 | 50.478 | 1.00 36.02 | BLGL |
| ATOM | 2746 | CB | PHE | 364 | 20.798 | -6.763 | 51.664 | 1.00 35.97 | BLGL |
| ATOM | 2747 | CG | PHE | 364 | 21.393 | -7.163 | 52.989 | 1.00 35.49 | BLGL |
| ATOM | 2748 | CD1 | PHE | 364 | 22.170 | -6.264 | 53.723 | 1.00 34.51 | BLGL |
| ATOM | 2749 | CD2 | PHE | 364 | 21.194 | -8.448 | 53.493 | 1.00 34.67 | BLGL |
| ATOM | 2750 | CE1 | PHE | 364 | 22.739 | -6.637 | 54.937 | 1.00 33.03 | BLGL |
| ATOM | 2751 | CE2 | PHE | 364 | 21.759 | -8.834 | 54.705 | 1.00 33.39 | BLGL |
| ATOM | 2752 | CZ | PHE | 364 | 22.534 | -7.927 | 55.429 | 1.00 33.77 | BLGL |
| ATOM | 2753 | C | PHE | 364 | 22.978 | -6.061 | 50.655 | 1.00 33.99 | BLGL |
| ATOM | 2754 | O | PHE | 364 | 23.998 | -6.506 | 51.181 | 1.00 34.27 | BLGL |
| ATOM | 2755 | N | GLY | 365 | 22.881 | -4.816 | 50.208 | 1.00 30.67 | BLGL |
| ATOM | 2756 | CA | GLY | 365 | 24.008 | -3.915 | 50.322 | 1.00 28.90 | BLGL |
| ATOM | 2757 | C | GLY | 365 | 23.806 | -2.610 | 49.581 | 1.00 27.08 | BLGL |
| ATOM | 2758 | O | GLY | 365 | 22.708 | -2.058 | 49.571 | 1.00 27.26 | BLGL |
| ATOM | 2759 | N | GLY | 366 | 24.863 | -2.122 | 48.943 | 1.00 26.06 | BLGL |
| ATOM | 2760 | CA | GLY | 366 | 24.777 | -0.860 | 48.230 | 1.00 22.87 | BLGL |
| ATOM | 2761 | C | GLY | 366 | 24.434 | -0.934 | 46.757 | 1.00 22.45 | BLGL |
| ATOM | 2762 | O | GLY | 366 | 23.680 | -1.800 | 46.312 | 1.00 20.99 | BLGL |
| ATOM | 2763 | N | SER | 367 | 24.996 | 0.004 | 46.002 | 1.00 22.77 | BLGL |
| ATOM | 2764 | CA | SER | 367 | 24.779 | 0.098 | 44.566 | 1.00 21.36 | BLGL |
| ATOM | 2765 | CB | SER | 367 | 25.081 | 1.511 | 44.079 | 1.00 19.13 | BLGL |
| ATOM | 2766 | OG | SER | 367 | 25.081 | 1.539 | 42.665 | 1.00 20.78 | BLGL |
| ATOM | 2767 | C | SER | 367 | 25.649 | -0.877 | 43.802 | 1.00 20.92 | BLGL |
| ATOM | 2768 | O | SER | 367 | 26.828 | -1.040 | 44.111 | 1.00 22.00 | BLGL |
| ATOM | 2769 | N | ALA | 368 | 25.072 | -1.518 | 42.794 | 1.00 19.58 | BLGL |
| ATOM | 2770 | CA | ALA | 368 | 25.823 | -2.474 | 41.992 | 1.00 19.49 | BLGL |
| ATOM | 2771 | CB | ALA | 368 | 25.069 | -3.792 | 41.921 | 1.00 18.00 | BLGL |

Fig. 4 cont.

```
ATOM   2772  C    ALA  368      26.058   -1.928  40.595  1.00 19.35      BLGL
ATOM   2773  O    ALA  368      26.610   -2.612  39.735  1.00 19.98      BLGL
ATOM   2774  N    VAL  369      25.656   -0.679  40.387  1.00 19.26      BLGL
ATOM   2775  CA   VAL  369      25.775   -0.041  39.080  1.00 19.71      BLGL
ATOM   2776  CB   VAL  369      24.391    0.041  38.379  1.00 16.72      BLGL
ATOM   2777  CG1  VAL  369      23.863   -1.349  38.093  1.00 13.08      BLGL
ATOM   2778  CG2  VAL  369      23.411    0.804  39.265  1.00 10.69      BLGL
ATOM   2779  C    VAL  369      26.357    1.366  39.124  1.00 20.80      BLGL
ATOM   2780  O    VAL  369      26.139    2.156  38.201  1.00 21.48      BLGL
ATOM   2781  N    ASP  370      27.083    1.693  40.187  1.00 21.01      BLGL
ATOM   2782  CA   ASP  370      27.680    3.024  40.269  1.00 21.96      BLGL
ATOM   2783  CB   ASP  370      28.401    3.226  41.617  1.00 20.78      BLGL
ATOM   2784  CG   ASP  370      29.224    2.016  42.042  1.00 26.31      BLGL
ATOM   2785  OD1  ASP  370      28.640    1.027  42.529  1.00 27.68      BLGL
ATOM   2786  OD2  ASP  370      30.466    2.045  41.893  1.00 31.81      BLGL
ATOM   2787  C    ASP  370      28.649    3.264  39.098  1.00 21.03      BLGL
ATOM   2788  O    ASP  370      28.886    4.405  38.695  1.00 16.48      BLGL
ATOM   2789  N    ASN  371      29.188    2.181  38.542  1.00 20.75      BLGL
ATOM   2790  CA   ASN  371      30.126    2.291  37.431  1.00 21.39      BLGL
ATOM   2791  CB   ASN  371      31.159    1.161  37.506  1.00 19.36      BLGL
ATOM   2792  CG   ASN  371      30.554   -0.202  37.257  1.00 17.69      BLGL
ATOM   2793  OD1  ASN  371      29.412   -0.471  37.631  1.00 16.68      BLGL
ATOM   2794  ND2  ASN  371      31.329   -1.081  36.635  1.00 15.28      BLGL
ATOM   2795  C    ASN  371      29.435    2.298  36.062  1.00 22.85      BLGL
ATOM   2796  O    ASN  371      30.088    2.203  35.018  1.00 21.45      BLGL
ATOM   2797  N    GLN  372      28.109    2.405  36.074  1.00 21.57      BLGL
ATOM   2798  CA   GLN  372      27.355    2.458  34.837  1.00 21.91      BLGL
ATOM   2799  CB   GLN  372      26.432    1.248  34.702  1.00 19.34      BLGL
ATOM   2800  CG   GLN  372      27.186   -0.043  34.541  1.00 19.05      BLGL
ATOM   2801  CD   GLN  372      26.332   -1.154  33.981  1.00 18.53      BLGL
ATOM   2802  OE1  GLN  372      25.802   -1.043  32.881  1.00 16.76      BLGL
ATOM   2803  NE2  GLN  372      26.199   -2.240  34.732  1.00 19.99      BLGL
ATOM   2804  C    GLN  372      26.550    3.750  34.783  1.00 22.49      BLGL
ATOM   2805  O    GLN  372      25.693    3.927  33.920  1.00 24.48      BLGL
ATOM   2806  N    ALA  373      26.842    4.658  35.705  1.00 21.34      BLGL
ATOM   2807  CA   ALA  373      26.155    5.940  35.755  1.00 21.66      BLGL
ATOM   2808  CB   ALA  373      26.301    6.544  37.148  1.00 20.20      BLGL
ATOM   2809  C    ALA  373      26.702    6.914  34.705  1.00 22.35      BLGL
ATOM   2810  O    ALA  373      27.707    6.638  34.038  1.00 21.94      BLGL
ATOM   2811  N    LEU  374      26.025    8.048  34.555  1.00 21.60      BLGL
ATOM   2812  CA   LEU  374      26.454    9.080  33.617  1.00 21.79      BLGL
ATOM   2813  CB   LEU  374      25.273    9.548  32.763  1.00 19.88      BLGL
ATOM   2814  CG   LEU  374      24.631    8.408  31.962  1.00 19.67      BLGL
ATOM   2815  CD1  LEU  374      23.430    8.928  31.196  1.00 19.92      BLGL
ATOM   2816  CD2  LEU  374      25.650    7.809  31.011  1.00 17.34      BLGL
ATOM   2817  C    LEU  374      27.040   10.236  34.431  1.00 22.87      BLGL
ATOM   2818  O    LEU  374      27.314   11.319  33.905  1.00 21.82      BLGL
ATOM   2819  N    PHE  375      27.214    9.981  35.728  1.00 21.81      BLGL
ATOM   2820  CA   PHE  375      27.800   10.937  36.664  1.00 23.69      BLGL
ATOM   2821  CB   PHE  375      26.780   11.387  37.722  1.00 22.43      BLGL
ATOM   2822  CG   PHE  375      25.641   12.195  37.169  1.00 24.54      BLGL
ATOM   2823  CD1  PHE  375      24.652   11.592  36.389  1.00 24.54      BLGL
ATOM   2824  CD2  PHE  375      25.563   13.566  37.407  1.00 22.99      BLGL
ATOM   2825  CE1  PHE  375      23.606   12.343  35.856  1.00 21.26      BLGL
ATOM   2826  CE2  PHE  375      24.521   14.324  36.877  1.00 20.60      BLGL
ATOM   2827  CZ   PHE  375      23.543   13.712  36.101  1.00 22.10      BLGL
ATOM   2828  C    PHE  375      28.928   10.184  37.356  1.00 24.96      BLGL
ATOM   2829  O    PHE  375      28.849    8.963  37.505  1.00 26.41      BLGL
ATOM   2830  N    ASP  376      29.975   10.890  37.771  1.00 24.80      BLGL
ATOM   2831  CA   ASP  376      31.070   10.217  38.449  1.00 24.64      BLGL
ATOM   2832  CB   ASP  376      32.369   11.030  38.382  1.00 25.91      BLGL
ATOM   2833  CG   ASP  376      32.243   12.411  39.007  1.00 26.81      BLGL
ATOM   2834  OD1  ASP  376      31.528   12.566  40.022  1.00 26.23      BLGL
ATOM   2835  OD2  ASP  376      32.885   13.343  38.484  1.00 27.73      BLGL
ATOM   2836  C    ASP  376      30.698    9.969  39.899  1.00 24.00      BLGL
ATOM   2837  O    ASP  376      29.621   10.349  40.344  1.00 22.18      BLGL
```

Fig. 4 cont.

| | | | | | | | | | |
|---|---|---|---|---|---|---|---|---|---|
| ATOM | 2838 | N | PHE | 377 | 31.610 | 9.333 | 40.625 | 1.00 24.93 | BLGL |
| ATOM | 2839 | CA | PHE | 377 | 31.421 | 9.000 | 42.030 | 1.00 26.87 | BLGL |
| ATOM | 2840 | CB | PHE | 377 | 32.652 | 8.256 | 42.530 | 1.00 24.91 | BLGL |
| ATOM | 2841 | CG | PHE | 377 | 32.915 | 6.967 | 41.811 | 1.00 26.64 | BLGL |
| ATOM | 2842 | CD1 | PHE | 377 | 34.185 | 6.394 | 41.837 | 1.00 27.20 | BLGL |
| ATOM | 2843 | CD2 | PHE | 377 | 31.891 | 6.298 | 41.141 | 1.00 27.03 | BLGL |
| ATOM | 2844 | CE1 | PHE | 377 | 34.434 | 5.168 | 41.209 | 1.00 27.98 | BLGL |
| ATOM | 2845 | CE2 | PHE | 377 | 32.127 | 5.073 | 40.511 | 1.00 27.70 | BLGL |
| ATOM | 2846 | CZ | PHE | 377 | 33.402 | 4.505 | 40.546 | 1.00 28.28 | BLGL |
| ATOM | 2847 | C | PHE | 377 | 31.162 | 10.214 | 42.919 | 1.00 28.76 | BLGL |
| ATOM | 2848 | O | PHE | 377 | 30.660 | 10.084 | 44.041 | 1.00 29.47 | BLGL |
| ATOM | 2849 | N | LYS | 378 | 31.500 | 11.393 | 42.410 | 1.00 30.92 | BLGL |
| ATOM | 2850 | CA | LYS | 378 | 31.322 | 12.634 | 43.155 | 1.00 32.99 | BLGL |
| ATOM | 2851 | CB | LYS | 378 | 32.533 | 13.546 | 42.927 | 1.00 36.98 | BLGL |
| ATOM | 2852 | CG | LYS | 378 | 33.889 | 12.924 | 43.274 | 1.00 39.50 | BLGL |
| ATOM | 2853 | CD | LYS | 378 | 34.230 | 13.053 | 44.759 | 1.00 43.64 | BLGL |
| ATOM | 2854 | CE | LYS | 378 | 33.249 | 12.300 | 45.651 | 1.00 45.28 | BLGL |
| ATOM | 2855 | NZ | LYS | 378 | 33.467 | 12.607 | 47.092 | 1.00 46.72 | BLGL |
| ATOM | 2856 | C | LYS | 378 | 30.040 | 13.391 | 42.800 | 1.00 32.50 | BLGL |
| ATOM | 2857 | O | LYS | 378 | 29.803 | 14.487 | 43.309 | 1.00 31.66 | BLGL |
| ATOM | 2858 | N | GLY | 379 | 29.224 | 12.816 | 41.919 | 1.00 32.04 | BLGL |
| ATOM | 2859 | CA | GLY | 379 | 27.975 | 13.453 | 41.544 | 1.00 32.10 | BLGL |
| ATOM | 2860 | C | GLY | 379 | 28.092 | 14.430 | 40.397 | 1.00 33.14 | BLGL |
| ATOM | 2861 | O | GLY | 379 | 27.146 | 15.159 | 40.085 | 1.00 32.60 | BLGL |
| ATOM | 2862 | N | ARG | 380 | 29.261 | 14.451 | 39.771 | 1.00 35.05 | BLGL |
| ATOM | 2863 | CA | ARG | 380 | 29.507 | 15.342 | 38.647 | 1.00 35.69 | BLGL |
| ATOM | 2864 | CB | ARG | 380 | 30.958 | 15.817 | 38.660 | 1.00 40.31 | BLGL |
| ATOM | 2865 | CG | ARG | 380 | 31.123 | 17.323 | 38.592 | 1.00 48.35 | BLGL |
| ATOM | 2866 | CD | ARG | 380 | 32.569 | 17.728 | 38.876 | 1.00 55.04 | BLGL |
| ATOM | 2867 | NE | ARG | 380 | 33.058 | 17.213 | 40.164 | 1.00 61.15 | BLGL |
| ATOM | 2868 | CZ | ARG | 380 | 33.782 | 16.100 | 40.318 | 1.00 61.98 | BLGL |
| ATOM | 2869 | NH1 | ARG | 380 | 34.117 | 15.362 | 39.267 | 1.00 62.74 | BLGL |
| ATOM | 2870 | NH2 | ARG | 380 | 34.178 | 15.720 | 41.529 | 1.00 60.75 | BLGL |
| ATOM | 2871 | C | ARG | 380 | 29.216 | 14.587 | 37.354 | 1.00 34.09 | BLGL |
| ATOM | 2872 | O | ARG | 380 | 29.551 | 13.404 | 37.213 | 1.00 34.62 | BLGL |
| ATOM | 2873 | N | PRO | 381 | 28.590 | 15.265 | 36.386 | 1.00 30.20 | BLGL |
| ATOM | 2874 | CD | PRO | 381 | 28.201 | 16.683 | 36.407 | 1.00 27.18 | BLGL |
| ATOM | 2875 | CA | PRO | 381 | 28.250 | 14.653 | 35.101 | 1.00 28.29 | BLGL |
| ATOM | 2876 | CB | PRO | 381 | 27.395 | 15.723 | 34.438 | 1.00 27.26 | BLGL |
| ATOM | 2877 | CG | PRO | 381 | 28.018 | 16.980 | 34.941 | 1.00 26.31 | BLGL |
| ATOM | 2878 | C | PRO | 381 | 29.453 | 14.278 | 34.260 | 1.00 26.53 | BLGL |
| ATOM | 2879 | O | PRO | 381 | 30.436 | 15.014 | 34.221 | 1.00 27.34 | BLGL |
| ATOM | 2880 | N | LEU | 382 | 29.370 | 13.122 | 33.601 | 1.00 26.02 | BLGL |
| ATOM | 2881 | CA | LEU | 382 | 30.439 | 12.645 | 32.721 | 1.00 24.03 | BLGL |
| ATOM | 2882 | CB | LEU | 382 | 30.475 | 11.116 | 32.656 | 1.00 21.52 | BLGL |
| ATOM | 2883 | CG | LEU | 382 | 30.769 | 10.338 | 33.934 | 1.00 22.08 | BLGL |
| ATOM | 2884 | CD1 | LEU | 382 | 30.549 | 8.867 | 33.678 | 1.00 21.34 | BLGL |
| ATOM | 2885 | CD2 | LEU | 382 | 32.190 | 10.608 | 34.390 | 1.00 21.32 | BLGL |
| ATOM | 2886 | C | LEU | 382 | 30.128 | 13.174 | 31.336 | 1.00 23.10 | BLGL |
| ATOM | 2887 | O | LEU | 382 | 28.964 | 13.412 | 30.996 | 1.00 22.81 | BLGL |
| ATOM | 2888 | N | PRO | 383 | 31.160 | 13.364 | 30.511 | 1.00 22.83 | BLGL |
| ATOM | 2889 | CD | PRO | 383 | 32.593 | 13.134 | 30.744 | 1.00 21.59 | BLGL |
| ATOM | 2890 | CA | PRO | 383 | 30.919 | 13.873 | 29.159 | 1.00 22.58 | BLGL |
| ATOM | 2891 | CB | PRO | 383 | 32.327 | 13.950 | 28.559 | 1.00 22.02 | BLGL |
| ATOM | 2892 | CG | PRO | 383 | 33.101 | 12.953 | 29.345 | 1.00 23.42 | BLGL |
| ATOM | 2893 | C | PRO | 383 | 29.959 | 13.008 | 28.340 | 1.00 22.29 | BLGL |
| ATOM | 2894 | O | PRO | 383 | 29.346 | 13.491 | 27.395 | 1.00 23.29 | BLGL |
| ATOM | 2895 | N | SER | 384 | 29.815 | 11.739 | 28.718 | 1.00 23.07 | BLGL |
| ATOM | 2896 | CA | SER | 384 | 28.918 | 10.830 | 28.014 | 1.00 23.32 | BLGL |
| ATOM | 2897 | CB | SER | 384 | 29.189 | 9.387 | 28.438 | 1.00 23.43 | BLGL |
| ATOM | 2898 | OG | SER | 384 | 28.997 | 9.221 | 29.827 | 1.00 22.72 | BLGL |
| ATOM | 2899 | C | SER | 384 | 27.441 | 11.166 | 28.253 | 1.00 24.76 | BLGL |
| ATOM | 2900 | O | SER | 384 | 26.556 | 10.584 | 27.629 | 1.00 25.96 | BLGL |
| ATOM | 2901 | N | LEU | 385 | 27.166 | 12.094 | 29.160 | 1.00 23.88 | BLGL |
| ATOM | 2902 | CA | LEU | 385 | 25.792 | 12.474 | 29.419 | 1.00 24.72 | BLGL |
| ATOM | 2903 | CB | LEU | 385 | 25.721 | 13.380 | 30.644 | 1.00 22.46 | BLGL |

Fig. 4 cont.

| | | | | | | | | |
|---|---|---|---|---|---|---|---|---|
| ATOM | 2904 | CG | LEU | 385 | 24.332 | 13.873 | 31.055 | 1.00 23.33 | BLGL |
| ATOM | 2905 | CD1 | LEU | 385 | 23.424 | 12.687 | 31.367 | 1.00 22.86 | BLGL |
| ATOM | 2906 | CD2 | LEU | 385 | 24.458 | 14.778 | 32.268 | 1.00 20.09 | BLGL |
| ATOM | 2907 | C | LEU | 385 | 25.250 | 13.207 | 28.193 | 1.00 26.26 | BLGL |
| ATOM | 2908 | O | LEU | 385 | 24.041 | 13.255 | 27.958 | 1.00 25.15 | BLGL |
| ATOM | 2909 | N | HIS | 386 | 26.161 | 13.763 | 27.404 | 1.00 28.46 | BLGL |
| ATOM | 2910 | CA | HIS | 386 | 25.789 | 14.512 | 26.213 | 1.00 32.60 | BLGL |
| ATOM | 2911 | CB | HIS | 386 | 26.937 | 15.437 | 25.816 | 1.00 37.77 | BLGL |
| ATOM | 2912 | CG | HIS | 386 | 27.172 | 16.539 | 26.799 | 1.00 45.65 | BLGL |
| ATOM | 2913 | CD2 | HIS | 386 | 26.393 | 17.016 | 27.801 | 1.00 45.94 | BLGL |
| ATOM | 2914 | ND1 | HIS | 386 | 28.330 | 17.291 | 26.820 | 1.00 48.26 | BLGL |
| ATOM | 2915 | CE1 | HIS | 386 | 28.254 | 18.180 | 27.795 | 1.00 49.16 | BLGL |
| ATOM | 2916 | NE2 | HIS | 386 | 27.089 | 18.033 | 28.405 | 1.00 49.07 | BLGL |
| ATOM | 2917 | C | HIS | 386 | 25.392 | 13.656 | 25.025 | 1.00 32.02 | BLGL |
| ATOM | 2918 | O | HIS | 386 | 25.011 | 14.184 | 23.979 | 1.00 34.90 | BLGL |
| ATOM | 2919 | N | VAL | 387 | 25.467 | 12.341 | 25.177 | 1.00 29.53 | BLGL |
| ATOM | 2920 | CA | VAL | 387 | 25.117 | 11.461 | 24.075 | 1.00 27.58 | BLGL |
| ATOM | 2921 | CB | VAL | 387 | 25.236 | 9.974 | 24.496 | 1.00 27.23 | BLGL |
| ATOM | 2922 | CG1 | VAL | 387 | 24.191 | 9.637 | 25.547 | 1.00 25.13 | BLGL |
| ATOM | 2923 | CG2 | VAL | 387 | 25.114 | 9.072 | 23.276 | 1.00 23.77 | BLGL |
| ATOM | 2924 | C | VAL | 387 | 23.701 | 11.760 | 23.572 | 1.00 26.94 | BLGL |
| ATOM | 2925 | O | VAL | 387 | 23.450 | 11.750 | 22.369 | 1.00 26.81 | BLGL |
| ATOM | 2926 | N | PHE | 388 | 22.788 | 12.060 | 24.491 | 1.00 25.61 | BLGL |
| ATOM | 2927 | CA | PHE | 388 | 21.403 | 12.339 | 24.136 | 1.00 26.79 | BLGL |
| ATOM | 2928 | CB | PHE | 388 | 20.586 | 12.619 | 25.390 | 1.00 25.81 | BLGL |
| ATOM | 2929 | CG | PHE | 388 | 20.433 | 11.432 | 26.272 | 1.00 26.19 | BLGL |
| ATOM | 2930 | CD1 | PHE | 388 | 21.003 | 11.412 | 27.536 | 1.00 27.32 | BLGL |
| ATOM | 2931 | CD2 | PHE | 388 | 19.728 | 10.317 | 25.834 | 1.00 25.78 | BLGL |
| ATOM | 2932 | CE1 | PHE | 388 | 20.873 | 10.300 | 28.355 | 1.00 27.00 | BLGL |
| ATOM | 2933 | CE2 | PHE | 388 | 19.592 | 9.198 | 26.647 | 1.00 26.04 | BLGL |
| ATOM | 2934 | CZ | PHE | 388 | 20.166 | 9.189 | 27.909 | 1.00 26.12 | BLGL |
| ATOM | 2935 | C | PHE | 388 | 21.188 | 13.470 | 23.141 | 1.00 29.70 | BLGL |
| ATOM | 2936 | O | PHE | 388 | 20.176 | 13.496 | 22.424 | 1.00 29.14 | BLGL |
| ATOM | 2937 | N | GLN | 389 | 22.125 | 14.412 | 23.102 | 1.00 31.10 | BLGL |
| ATOM | 2938 | CA | GLN | 389 | 22.022 | 15.532 | 22.174 | 1.00 32.46 | BLGL |
| ATOM | 2939 | CB | GLN | 389 | 22.603 | 16.797 | 22.793 | 1.00 35.41 | BLGL |
| ATOM | 2940 | CG | GLN | 389 | 22.086 | 17.088 | 24.177 | 1.00 44.69 | BLGL |
| ATOM | 2941 | CD | GLN | 389 | 22.807 | 18.261 | 24.818 | 1.00 50.70 | BLGL |
| ATOM | 2942 | OE1 | GLN | 389 | 22.674 | 19.401 | 24.372 | 1.00 52.70 | BLGL |
| ATOM | 2943 | NE2 | GLN | 389 | 23.588 | 17.985 | 25.866 | 1.00 53.54 | BLGL |
| ATOM | 2944 | C | GLN | 389 | 22.779 | 15.221 | 20.893 | 1.00 30.30 | BLGL |
| ATOM | 2945 | O | GLN | 389 | 22.270 | 15.416 | 19.790 | 1.00 31.42 | BLGL |
| ATOM | 2946 | N | TYR | 390 | 23.993 | 14.715 | 21.051 | 1.00 28.80 | BLGL |
| ATOM | 2947 | CA | TYR | 390 | 24.851 | 14.403 | 19.917 | 1.00 30.88 | BLGL |
| ATOM | 2948 | CB | TYR | 390 | 26.204 | 13.911 | 20.427 | 1.00 35.50 | BLGL |
| ATOM | 2949 | CG | TYR | 390 | 26.963 | 14.956 | 21.217 | 1.00 41.72 | BLGL |
| ATOM | 2950 | CD1 | TYR | 390 | 28.151 | 14.632 | 21.871 | 1.00 45.09 | BLGL |
| ATOM | 2951 | CE1 | TYR | 390 | 28.861 | 15.595 | 22.603 | 1.00 47.24 | BLGL |
| ATOM | 2952 | CD2 | TYR | 390 | 26.496 | 16.273 | 21.313 | 1.00 42.36 | BLGL |
| ATOM | 2953 | CE2 | TYR | 390 | 27.192 | 17.240 | 22.043 | 1.00 45.40 | BLGL |
| ATOM | 2954 | CZ | TYR | 390 | 28.376 | 16.894 | 22.686 | 1.00 47.41 | BLGL |
| ATOM | 2955 | OH | TYR | 390 | 29.078 | 17.841 | 23.406 | 1.00 46.59 | BLGL |
| ATOM | 2956 | C | TYR | 390 | 24.298 | 13.425 | 18.889 | 1.00 29.06 | BLGL |
| ATOM | 2957 | O | TYR | 390 | 24.591 | 13.553 | 17.704 | 1.00 29.24 | BLGL |
| ATOM | 2958 | N | VAL | 391 | 23.508 | 12.450 | 19.324 | 1.00 27.33 | BLGL |
| ATOM | 2959 | CA | VAL | 391 | 22.943 | 11.488 | 18.381 | 1.00 25.21 | BLGL |
| ATOM | 2960 | CB | VAL | 391 | 22.008 | 10.476 | 19.087 | 1.00 23.42 | BLGL |
| ATOM | 2961 | CG1 | VAL | 391 | 22.803 | 9.635 | 20.061 | 1.00 19.38 | BLGL |
| ATOM | 2962 | CG2 | VAL | 391 | 20.886 | 11.202 | 19.805 | 1.00 21.53 | BLGL |
| ATOM | 2963 | C | VAL | 391 | 22.154 | 12.226 | 17.299 | 1.00 26.03 | BLGL |
| ATOM | 2964 | O | VAL | 391 | 22.028 | 11.749 | 16.175 | 1.00 23.37 | BLGL |
| ATOM | 2965 | N | ASP | 392 | 21.635 | 13.400 | 17.647 | 1.00 27.71 | BLGL |
| ATOM | 2966 | CA | ASP | 392 | 20.862 | 14.200 | 16.710 | 1.00 30.77 | BLGL |
| ATOM | 2967 | CB | ASP | 392 | 20.134 | 15.323 | 17.448 | 1.00 32.83 | BLGL |
| ATOM | 2968 | CG | ASP | 392 | 18.986 | 14.820 | 18.302 | 1.00 34.68 | BLGL |
| ATOM | 2969 | OD1 | ASP | 392 | 18.444 | 15.617 | 19.103 | 1.00 35.32 | BLGL |

Fig. 4 cont.

```
ATOM   2970  OD2  ASP   392     18.618  13.636  18.167  1.00 35.22        BLGL
ATOM   2971  C    ASP   392     21.731  14.818  15.621  1.00 33.35        BLGL
ATOM   2972  O    ASP   392     21.467  14.650  14.430  1.00 35.61        BLGL
ATOM   2973  N    THR   393     22.777  15.526  16.035  1.00 34.96        BLGL
ATOM   2974  CA   THR   393     23.664  16.215  15.105  1.00 34.87        BLGL
ATOM   2975  CB   THR   393     23.998  17.626  15.602  1.00 35.87        BLGL
ATOM   2976  OG1  THR   393     24.820  17.526  16.774  1.00 37.14        BLGL
ATOM   2977  CG2  THR   393     22.726  18.392  15.952  1.00 35.93        BLGL
ATOM   2978  C    THR   393     24.991  15.518  14.908  1.00 36.53        BLGL
ATOM   2979  O    THR   393     25.462  15.358  13.787  1.00 36.72        BLGL
ATOM   2980  N    GLY   394     25.596  15.115  16.014  1.00 38.00        BLGL
ATOM   2981  CA   GLY   394     26.896  14.481  15.961  1.00 38.77        BLGL
ATOM   2982  C    GLY   394     27.828  15.442  16.679  1.00 40.97        BLGL
ATOM   2983  O    GLY   394     27.389  16.494  17.143  1.00 40.87        BLGL
ATOM   2984  N    THR   395     29.105  15.107  16.787  1.00 43.10        BLGL
ATOM   2985  CA   THR   395     30.043  15.990  17.461  1.00 45.02        BLGL
ATOM   2986  CB   THR   395     30.967  15.197  18.393  1.00 43.84        BLGL
ATOM   2987  OG1  THR   395     31.206  13.896  17.840  1.00 43.18        BLGL
ATOM   2988  CG2  THR   395     30.340  15.054  19.753  1.00 41.53        BLGL
ATOM   2989  C    THR   395     30.883  16.752  16.443  1.00 48.88        BLGL
ATOM   2990  O    THR   395     31.470  16.155  15.536  1.00 49.70        BLGL
ATOM   2991  N    PRO   396     30.941  18.089  16.578  1.00 52.29        BLGL
ATOM   2992  CD   PRO   396     30.225  18.889  17.594  1.00 52.46        BLGL
ATOM   2993  CA   PRO   396     31.712  18.955  15.672  1.00 52.98        BLGL
ATOM   2994  CB   PRO   396     31.537  20.343  16.291  1.00 53.36        BLGL
ATOM   2995  CG   PRO   396     30.173  20.256  16.948  1.00 52.73        BLGL
ATOM   2996  C    PRO   396     33.188  18.543  15.578  1.00 53.94        BLGL
ATOM   2997  O    PRO   396     33.678  18.369  14.436  1.00 54.55        BLGL
END
```

Fig. 4 cont.

```
                                 9          19         29         39
----------  ----------  -ALTYRGVDW SSVVVEERAG VSYKNTNGNA QPLENILAAN  39 MT
----------  ----------  -ALQYKGVDW SSVMVEERAG VRYKNVNGQE KPLEYILAEN  39 HI
----------  ----------  -ALTYRGADI SSLLLLEDEG YSYKNLNGQT QALETILADA  39 AA
AHRDSGTAKS  GLYVEKVSGL  RKDFIKGVDV SSIIALEESG VAFYNESGKK QDIFNTLKEA  60 BL
    10          20         30         40         50         60

49          54         61         71         81         91
GVNTVRQRVW  VNPAD-----  ---GNYNLDY NIAIAKRAKA AGLGVYIDFH YSDTWADPAH  91
GVNMVRQRVW  VNPWD-----  ---GNYNLDY NIQLARRAKA AGLGLYINFH YSDTWADPAH  91
GINSIRQRVW  VNPSD-----  ---GSYDLDY NLELAKRVKA AGMSLYLDLH LSDTWADPSD  91
GVNYVRVRIW  NDPYDANGNG  YGGGNNDLEK AIQIGKRANA NGMKLLADFH YSDFWADPAK 120
    70          80         90        100        110        120

100         110        120        130        140        150
QTMPAGWP-S  DIDNLSWKLY  NYTLDAANKL QNAGIQPTIV SIGNEIRAGL LWPTGRTENW 150
QTTPAGWP-S  DINNLAWKLY  NYTLDSMNRF ADAGIQVDIV SIGNEITQGL LWPLGKTNNW 150
QTTPSGWSTT  DLGTLKWQLY  NYTLEVCNTF AENDIDIEII SIGNEIRAGL LWPLGETSSY 151
QKAPKAWANL  NFEDKKTALY  QYTKQSLKAM KAAGIDIGMV QVGNETNGGL A----GETDW 176
   130         140        150        160        170        176

160         170        180        190        200        210
ANIARLLHSA  AWGIKDSSLS  PKPKIMIHLD NGWDWGTQNW WYTNVLKQGT LELSDFDMMG 210
YNIARLLHSA  AWGVKDSRLN  PKPKIMVHLD NGWNWDTQNW WYTNVLSQGP FEMSDFDMMG 210
SNIGALLHSG  AWGVKDSNLA  TTPKIMIHLD DGWSWDQQNY FYETVLATGE LLSTDFDYFG 211
AKMSQLFNAG  SQAVRETD--  SNILVALHFT NPETSGRYAW IAETLHRH-- --HVDYDVFA 230
   186                     204        214                   230

220         230        240        250        255        265
VSFYPFYSSS  ATLSALKSSL  DNMAKTWNKE IAVVETNWPI SC-----PNP RYSFPSDVKN 265
VSFYPFYSAS  ATLDSLRRSL  NNMVSRWGKE VAVVETNWPT SC-----PYP RYQFPADVRN 265
VSYYPFYSAS  ATLASLKTSL  ANLQSTYDKP VVVVETNWPV SC-----PNP AYAFPSDLSS 266
SSYYPFW--H  GTLKNLTSVL  TSVADTYGKK VMVAETSYTY TAEDGDGHGN TAPKNGQTLN 288
   238         248        258        268        278        288

275         285        294
IPFSPEGQTT  FITNVANIVS  SVS-RGVGLF YWEPAWIH-- ---------- ---------- 302
VPFSAAGQTQ  YIQSVANVVS  SVS-KGVGLF YWEPAWIH-- ---------- ---------- 302
IPFSVAGQQE  FLEKLAAVVE  ATT-DGLGVY YWEPAWIG-- ---------- ---------- 303
NPVTVQGQAN  AVRDVIQAVS  DVGEAGIGVF YWEPAWIPVG PAHRLEKNKA LWETYGSGWA 348
                                     298        308        318        328        338        348

309        318        328
----------  ---NANLGSS  CADNTMFSQ- SGQALSSLSV FQRI------ --  332
----------  ---NANLGSS  CADNTMFTP- SGQALSSLSV FHRI------ --  332
----------  ---NAGLGSS  CADNLMVDYT TDEVYESIET LGEL------ --  334
TSYAAEYDPE  DAGKWFGGSA  VDNQALFDF- KGRPLPSLHV FQYVDTGTPF KN  399
   358         368        377        387        397
```

Fig. 5

```
                                    9         19         29         39
---------- ----------  -ALTYRGVDW SSVVVEERAG VSYKNTNGNA QPLENILAAN  39 MT
---------- ----------  -ALQYKGVDW SSVMVEERAG VRYKNVNGQE KPLEYILAEN  39 HI
---------- ----------  -ALTYRGADI SSLLLLEDEG YSYKNLNGQT QALETILADA  39 AA
AHRDSGTAKS GLYVEKVSGL  RKDFIKGVDV SSIIALEESG VAFYNESGKK QDIFNTLKEA  60 BL
---------- ----------  -ALTYRGADI SSLLIEEDAG ISYKNLNGET QALEDILVNN  39 AT
---------- ---------M  NKDFIKGADV SSVIALENSG VTFYNTNGKR QDIFTTLKQA  41 BS
---------- ----NTGVAD  NTPFYVGADL SYVNEMESCG ATYRD-QGKK VDPFQLFADK  45 PF
                6          16         26         35         45

49         54         61         71         81         91
GVNTVRQRVW VNPAD----- ---GNYNLDY NIAIAKRAKA AGLGVYIDFH YSDTWADPAH  91
GVNMVRQRVW VNPWD----- ---GNYNLDY NIQLARRAKA AGLGLYINFH YSDTWADPAH  91
GINSIRQRVW VNPSD----- ---GSYDLDY NLELAKRVKA AGMSLYLDLH LSDTWADPSD  91
GVNYVRVRIW NDPYDANGNG YGGGNNDLEK AIQIGKRANA NGMKLLADFH YSDFWADPAK 120
GVNSIRQRVW VDPSD----- ---GSYDLDY NLKLAKRVQA AGMSIYLDLH LSDTWADPSD  91
GVNYVRVRIW NHPYDSNGNG YGGGNNDVQK AIEIGKRATA NGMKVLADFH YSDFWADPAK 101
GADLVRVRLW HNATWT---- ---KYSDLKD VSKTLKRAKN AGMKTLLDFH YSDTWTDPEK  98
    55         61         68         78         88         98

99         109        119        129        139        145
QTMPAGWP-- SDIDNLSWKL YNYTLDAANK LQNAGIQPTI VSIGNEIRAG LLWPTG---- 145
QTTPAGWP-- SDINNLAWKL YNYTLDSMNR FADAGIQVDI VSIGNEITQG LLWPLG---- 145
QTTPSGWST- TDLGTLKWQL YNYTLEVCNT FAENDIDIEI ISIGNEIRAG LLWPLG---- 146
QKAPKAWAN- LNFEDKKTAL YQYTKQSLKA MKAAGIDIGM VQVGNETNGG LA-------- 171
QTTPTGWST- TDIDTLTWQL YNYTLEVCNT FAENDIDVEI VSIGNEISSG LLWPLG---- 146
QKVPKAWAN- LSFEAKKAKL YEYTKQSLQK MIKEGVDIGM VQVGNETTGG FA-------- 152
QFIPKAWAHI TDTKELAKAL YDYTTDTLAS LDQQQLLPNL VQVGNETNIE ILQAEDTLVH 158
    109        118        128        138        148        158

155        165        175        185        195        205
RTENWANIAR LLHSAAWGIK DSSLSPKPKI MIHLDNGWDW GTQNWWYTNV LKQGTLELSD 205.
KTNNWYNIAR LLHSAAWGVK DSRLNPKPKI MVHLDNGWNW DTQNWWYTNV LSQGPFEMSD 205
ETSSYSNIGA LLHSGAWGVK DSNLATPKI MIHLDDGWSW DQQNYFYETV LATGELLSTD 206
GETDWAKMSQ LFNAGSQAVR ETD--SNILV ALHFTNPETS GRYAWIAETL HRH----HVD 225
KTSNYDNIAK LLHSGAWGVK DSDLTTTPKI MIHLDNGWDW DEQEYFYKTV LATGSLLSTD 206
GETDWTKMCQ LFNEGSRAVR ETN--SNILV ALHFTNPETA GRYSFIAETL SKN----KVD 206
GIPNWQRNAT LLNSGVNAVR DYSKKTGKPI QVVLHIAQPE NALWWFKQAK ENG----VID 214
    168        178        188        198        208        214

215        225        235        245        252        260
FDMMGVSFYP FYSSSATLSA LKSSLDNMAK TWNKEIAVVE TNWPISC--- --PNPRYSFP 260
FDMMGVSFYP FYSASATLDS LRRSLNNMVS RWGKEVAVVE TNWPTSC--- --PYPRYQFP 260
FDYFGVSYYP FYSASATLAS LKTSLANLQS TYDKPVVVE TNWPVSC--- --PNPAYAFP 261
YDVFASSYYP FW--HGTLKN LTSVLTSVAD TYGKVMVAE TSYTYTAEDG DGHGNTAPKN 283
FDLMGVSYYP FYSSEATLSS LKTSLTNMQS NYDKPVVVE TNWPVSC--- --PDPEYSFP 261
YDVFASSYYP FW--HGTLQN LTSVLKAVAN TYGKVMVAE TSYTYTAEDG DGHGNTAPKS 264
YDVIGLSYYP QWS-EYSLPQ LPDAIAELQN TYHKPVMIVE TAYPWTLHNF DQAGNVLGEK 273
    224        233        243        253        263        273

270        280        289        299
SDVKNIPFSP EGQTTFITNV ANIVSSVS-R GVGLFYWEPA WIH------- ---------- 302
ADVRNVPFSA AGQTQYIQSV ANVVSSVS-K GVGLFYWEPA WIH------- ---------- 302
SDLSSIPFSV AGQQEFLEKL AAVVEATT-D GLGVYYWEPA WIG------- ---------- 303
GQTLNNPVTV QGQANAVRDV IQAVSDVGEA GIGVFYWEPA WIPVGPAHRL EKNKALWETY 333
SDLTSIPFSA AGQEEFLEKL AEVVEGVT-D GLGIYYWEPA WID------- ---------- 303
GQTLPYPISV QGQATAVRDV MEAVANTGKA GLGVFYWEPA WIPVGPKTQI EKNKVLWETY 314
AVQPEFPASP RGQLTYLLTL TQLVKSAG-- GMGVIYWEPA WVSTRCR--- ---------- 318
    283        293        301        311
```

Fig. 6

```
                                  314        322        332
---------- --------NA NLGSSCADNT MFSQ--SGQA LSSLSVFQRI --------  332
---------- --------NA NLGSSCADNT MFTP--SGQA LSSLSVFHRI --------  332
---------- --------NA GLGSSCADNL MVDYT-TDEV YESIETLGEL --------  334
GSGWATSYAA EYDPEDAGKW FGGSAVDNQA LFDF--KGRP LPSLHVFQYV DTGTPFKN  399
---------- --------NA GLGSSCADNL MVDVN-TDEV LESVTVFEDL --------  334
GSGWASSYAA EYDPEDAGKW YGGSAVDNQA LFDF--NGHP LPSLQVFQYA --------  372
---------- -------TLW GKGSHWENAS FFDATRKNNA LPAFLFFKAD YQASAQAE  359
                  321        331        341        351
```

GALACTANASE VARIANTS

CROSS-REFERENCE TO RELATED APPLICATIONS

This application is a 35 U.S.C. 371 national application of PCT/DK2003/000851 filed Dec. 11, 2003. which claims priority or the benefit under 35 U.S.C. 119 of Danish application nos. PA 2002 01968 and PA 2003 00537 filed Dec. 20, 2002 and Apr. 8, 2003, respectively, and U.S. provisional application Nos. 60/437,615 and 60/461,230 filed Jan. 2, 2003 and Apr. 8, 2003, respectively, the contents of which are fully incorporated herein by reference.

FIELD OF THE INVENTION

The present invention relates to variants of galactanases of Glycoside Hydrolase Family 53, their production, and their use within the dairy industry.

BACKGROUND OF THE INVENTION

Background Art

The crystallization and preliminary X-ray studies of the galactanase from *Aspergillus aculeatus* is described by Ryttersgaard et al in Acta. Cryst. (1999), D55, 929-930.

SUMMARY OF THE INVENTION

The invention provides variants of a parent Glycoside Hydrolase Family 53 galactanase, comprising an alteration in at least one of the following positions: −6, −4, −2, 1, 3, 4, 5, 6, 7, 8, 9, 10, 11, 12, 13, 14, 15, 16, 18, 20, 22, 24, 25, 26, 29, 30, 31, 32, 36, 39, 40, 41, 43, 44, 45, 46, 47, 48, 49, 50, 51, 52, 53, 54, 54a, 54e, 54f, 54g, 54h, 55, 56, 57, 58, 61, 62, 65, 69, 77, 79, 80, 81, 82, 83, 84, 85, 86, 87, 88, 89, 90, 91, 92, 93, 94, 95, 96, 97, 101, 106, 107, 110, 113, 114, 126, 131, 132, 133, 134, 135, 136, 137, 138, 139, 140, 141, 142, 144, 145, 146, 147, 150, 153, 157, 159, 163, 169, 171, 172, 176, 177, 178, 179, 180, 181, 182, 183, 184, 185, 186, 187, 188, 189, 191, 192, 194, 198, 200, 203, 204, 209, 210, 211, 212, 213, 214, 215, 216, 217, 218, 219, 220, 221, 222, 223, 224, 225, 226, 227, 228, 229, 230, 231, 232, 233, 234, 241, 242, 243, 244, 245, 246, 247, 248, 249, 250, 252, 252d, 252e, 253, 254, 255, 256, 257, 258, 259, 260, 261, 262, 263, 264, 265, 266, 273, 274, 276, 277, 280, 283, 284, 286, 288, 288a, 289, 292, 293, 294, 295, 296, 297, 298, 299, 300, 301, 302, 302a, 302d, 302j, 302k, 302m, 302n, 302o, 302q, 302r, 302s, 302t, 302u, 302v, 302x, 302y, 302z, 302aa, 302bb, 302cc, 302dd, 302ee, 302ff, 302gg, 302hh, 302ii, 302jj, 303, 304, 305, 306, 307, 308, 309, 310, 311, 312, 313, 314, 315, 316, 317, 318, 319, 320, 321, 322, 323, 324, 325, 326, 327, 328, 329, and 330; wherein (a) the alteration(s) are independently (i) an insertion of an amino acid immediately down-stream of the position, (ii) a deletion of the amino acid which occupies the position, and/or (iii) a substitution of the amino acid which occupies the position; and (b) the variant has galactanase activity.

BRIEF DESCRIPTION OF DRAWINGS

FIG. 1 shows the coordinates for the 3D structure of a GH Family 53 galactanase from *Myceliophthora thermophila* having SEQ ID NO: 1;

FIG. 2 shows the coordinates for the 3D structure of a GH Family 53 galactanase from *Humicola insolens* having SEQ ID NO: 2;

FIG. 3 shows the coordinates for the 3D structure of a GH Family 53 galactanase from *Aspergillus aculeatus* having SEQ ID NO: 3;

FIG. 4 shows the coordinates for the 3D structure of a GH Family 53 galactanase from *Bacillus licheniformis* having SEQ ID NO: 4;

FIG. 5 shows a multiple alignment of SEQ ID NOs: 1-4; and

FIG. 6 shows the alignment of FIG. 5 with three additional galactanase sequences added (SEQ ID NO: 7-9).

DETAILED DESCRIPTION OF THE INVENTION

3D-Structure Determination

The crystallization and preliminary X-ray studies of the galactanase from *Aspergillus aculeatus* (AAGAL) is described by Ryttersgaard et al in Acta. Cryst. (1999), D55, 929-930. The galactanases from *Myceliophthora thermophila* (MTGAL) and *Humicola insolens* (HIGAL) (WO 97/32014), and the galactanase from *Bacillus licheniformis* (BLGAL) (WO 00/47711) were crystallized using similar principles.

The 3D-structures were solved in accordance with the principles for X-ray crystallographic methods as given, for example, in X-Ray Structure Determination, Stout, G. K. and Jensen, L. H., John Wiley & Sons, Inc. NY, 1989. The structural coordinates for the crystal structure of the *Aspergillus aculeatus* galactanase (AAGAL), as determined by multiple isomorphous replacement to 1.8 Å resolution at 100 K are given in FIG. 1 in standard PDB format (Protein Data Bank, Brookhaven National Laboratory, Brookhaven, Conn.).

The structures of the other three galactanases were solved by Molecular Replacement, using the AAGAL293 structure (to 2.3 Å resolution at 293K) as a search model. Data from 20-2.55 Å, 18-2.14 Å, and 19.67-2.60 Å were used for HIGAL, MTGAL and BLGAL, respectively, within AMoRe (J. Navaza: AMoRe: an Automated package for Molecular Replacement. Acta Crystallogr., A50:157-163, 1994). The respective coordinates are given in FIGS. 2-4 in standard PDB format.

Variant

The term "galactanase variant," or simply "variant," refers to a galactanase comprising one or more alteration(s), such as substitution(s), insertion(s), deletion(s), and/or truncation(s) of one or more specific amino acid residue(s) in one or more specific position(s) in a parent galactanase.

The total number of such alterations is typically not more than thirty, e.g. one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, or thirty of said alterations. In addition, the variant of the invention may include other modifications of the parent enzyme, typically not more than 10, e.g. not more than 5 such modifications.

Nomenclature and Conventions for Designation of Variants

A substitution in a variant is indicated as "original amino acid-position-substituted amino acid." The one letter code is preferably used, but it can of course be translated into the three letter code as desired. The codes X (or Xaa) may be used to indicate any amino acid residue. Accordingly, the notation "D182N" or means, that the variant comprises a substitution of aspartic acid with asparagine acid in the variant amino acid position corresponding to the amino acid in position 182 in MTGAL, when the two are aligned as indicated in FIG. 5.

Where the original amino acid residue may be any amino acid residue, a short hand notation may at times be used indicating only the position, and the substituted amino acid, for example: "Position-substituted amino acid", or "182N". This notation is particular relevant in connection with modification(s) in a series of homologous polypeptides, such as the galactanases of GH Family 53. Similarly when the identity of the substituting amino acid residue(s) is immaterial: "Original amino acid-position;" or "D182".

When both the original amino acid(s) and substituted amino acid(s) may be any amino acid, then only the position is indicated, e.g. "182".

When the original amino acid(s) and/or substituted amino acid(s) may comprise more than one, but not all amino acid(s), then the amino acids are listed, separated by commas: "Original amino acid-position no.-substituted amino acid"; e.g. "H91D,L,N".

A number of examples of this nomenclature are listed below:

The substitution of aspartic acid for asparagine in position 182 is designated as D182N.

The substitution of any amino acid residue for serine in position 131 is designated as S131X, or S131.

The substitution of proline for any amino acid residue in position 29 would thus be designated X29P, or 29P.

For a modification where the original amino acid(s) and/or substituted amino acid(s) may comprise more than one, but not all amino acid(s), the substitution of aspartic acid, leucine, or asparagine for histidine in position 91 would be indicated by H91D,L,N; which indicates the specific variants H91D, H91L, or H91N.

A deletion of glutamic acid in position 288a will be indicated by E288a*. Correspondingly, the deletion of more than one amino acid residue, such as the deletion of glutamic acid and aspartic acid in positions 252a and 252b will be designated "E252a*+D252b*"

A truncation means an N- or C-terminal shortening of the complete amino acid sequence, i.e. a deletion of one, or usually more, amino acids and the N- or C-terminal end of the peptide. As regards the designation of truncated variants, the general rule for deletions may be used.

The insertion of an additional amino acid residue such as e.g. a valine after F216 is indicated by "F216FV"; or, when more than one amino acid residue is inserted, such as e.g. a valine, alanine, serine, threonine and a glycine after F216 this will be indicated as:"F216FVASTG".

In such cases the inserted amino acid residue(s) are numbered by the addition of lower case letters to the position number of the amino acid residue preceding the inserted amino acid residue(s). In the above example the sequences would thus be:

| Parent: | | Variant: | | | | | |
|---|---|---|---|---|---|---|---|
| 216 | 216 | 216a | 216b | 216c | 216d | 216e | 217 |
| F | F | V | A | S | T | G | Y |

Once all lower case letters from a to z (a,b,c,d,e,f,g,h,i,j,k,l,m,n,o,p,q,r,s,t,u,v,x,y,z) have been used for this purpose, double letters aa, bb, cc etc. onto zz are used, see e.g. the alignment of FIG. 5, between positions 302 and 303.

In cases where an amino acid residue identical to the existing amino acid residue is inserted, it is clear that degeneracy in the nomenclature arises. If for example a phenylalanine would be inserted after the phenylalanine in the above example this would be indicated by "F216FF".

Given that a proline is present in position 215, the same actual change could just as well be indicated as "P215PF":

| | Parent: | | Variant: | | |
|---|---|---|---|---|---|
| Numbering I: | 215 | 216 | 215 | 216 | 216a |
| Sequence: | P | F | P | F | F |
| Numbering II: | | | 215 | 215a | 216 |

Such instances will be apparent to the skilled person, and the indication "F216FF" and corresponding indications for this type of insertions is thus meant to comprise such equivalent degenerate indications.

By analogy, if amino acid sequence segments are repeated in the parent galactanase and/or in the variant, it will be apparent to the skilled person that equivalent degenerate indications are comprised, also when other alterations than insertions are listed such as deletions and/or substitutions. For instance, the deletion of two consecutive amino acids "DG" in the sequence "DGDG" from position 252b-252e, may be written as "D252b*+G252c*" or "D252d*+G252e*" or "G252c*+D252d":

| | Parent: | | | | Variant: | |
|---|---|---|---|---|---|---|
| Numbering I: | 252b | 252c | 252d | 252e | 252b | 252c |
| Sequence: | D | G | D | G | D | G |
| Numbering II: | | | | | 252d | 252e |
| Numbering III: | | | | | 252b | 252e |

Variants comprising multiple modifications are separated by pluses, e.g. "A90S+H91D"

representing modifications in positions 90 and 91 substituting tyrosine and glutamic acid for arginine and glycine, respectively. Thus, "A90S+H91D,N,L" designates the following variants: A90S+H91D, A90S+H91N, and A90S+H91L. Likewise, N303D,H+N305D,H,P designates the following variants: N303D+N305D; N303D+N305H; N303D+N305P; N303H+N305D; N303H+N305H, and N303H+N305P.

This nomenclature is particular relevant relating to modifications aimed at substituting, inserting or deleting amino acid residues having specific common properties, such modifications are referred to as conservative amino acid modification(s). Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the in reverse.

For the present purposes, the sequence of MTGAL (SEQ ID NO:1) has been selected as the frame of reference, meaning that all variants will be defined on the basis of the amino acid sequence of MTGAL. In particular, each amino acid residue in a galactanase sequence is assigned a number, a position, or a position number, by reference to FIG. 5 herein, viz. the number of the corresponding amino acid residue in the *Myceliophthora thermophila* galactanase backbone (MT; the uppermost line of the alignment of FIG. 5). In this context, the term "corresponding" refers to the amino acid which, according to the alignment, is in the same column as the amino acid residue in question, but in the first row designated "MT".

For example, the variant of the galactanase from *Bacillus licheniformis* (BL) which by reference to SEQ ID NO: 4 may be designated S39C will, for the present purposes, be designated S18C, because S39 of BL corresponds to A18 of MT. As another example, the variant of the galactanase from *Aspergillus aculeatus* which by reference to SEQ ID NO: 3 may be designated D182N will, for the present purposes, be designated D181N, because D182 of M corresponds to N181 of MT. As a still further example, variant K16P of BL may be designated *–6P, because K16P of BL corresponds to a missing or deleted amino acid in position –6 of MT, still by strict formal reference to FIG. 5.

However, if desired, the variants of the invention may also be defined by reference to their respective "own" backbone, e.g. with reference to SEQ ID NO:1, SEQ ID NO:2, SEQ ID NO: 3, or SEQ ID NO: 4. The corresponding position numbers are easily deduced, in the same way as described above, from FIGS. 5-6 or, for additional galactanase sequences, from a figure which can be prepared according to the principles described herein.

Molecular Dynamics (MD)

Molecular Dynamics (MD) simulations are indicative of the mobility of the amino acids in a protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at, e.g., different temperatures, the temperature related mobility of residues is simulated. Regions having the highest mobility or flexibility (here isotropic fluctuations) may be suggested for random mutagenesis. It is here understood that the high mobility found in certain areas of the protein, may be thermally improved by substituting these residues.

Variants of Amended Properties

Based on the 3D-structure of the galactanase from *Myceliophthora thermophila* of SEQ ID NO:1, the following variants are contemplated, in which at least one of the below-mentioned residues have been amended and/or at least one of the below-mentioned alterations have been introduced:

i) variants of an amended specific activity, within 10 Å from the active site: Y4, G6, V7, D8, W9, S10, R45, Q46, R47, W49, Y77, D79, F80, H81, Y82, W86, A87, D88, P89, A90, H91, Q92, T93, S131, I132, G133, N134, E135, I136, R137, A138, G139, L140, L141, W142, G145, R146, T147, I153, L157, M176, I177, H178, L179, D180, N181, G182, W183, T187, Q188, W191, Y192, M209, G210, V211, S212, F213, Y214, P215, F216, Y217, A221, L226, I241, A242, V243, V244, E245, T246, N247, W248, F276, I277, V280, V284, G292, L293, F294, Y295, W296, E297, P298, W300, L306, G307, F329;

ii) variants of an amended activity on lactose, within 10 Å from the active site: Y214S,N+N247Y+L306Q; Y214A; F216FVASTGY217; P89W+W86N;

iii) variants of an amended pH-activity profile: H91N,L,D; N313D; N303D,H; N305D,H; A90S+H91D;

iv) variants of an amended thermostability, by insertion of prolines: Y22P, N24P, T25P, A29P, A53P, N56P, T93P, D101P, W142P, T147P, Q198P, L203P, S204P, S219P, S258P, S288P, A304P, A311P, Q318P, A322P, S324P, S325P, S327P;

v) variants of an amended thermostability, by increasing surface hydrophobicity: W107S,H;

vi) variants of an amended thermostability, by amending the surface electrostatic potential: Q126E;

vii) variants of an amended thermostability, by disulfide bridges (double mutations to cysteines): V20C+G320C, N39C+L326C, Y110C+G163C, W150C+N194C, T274C+V328C, I301C+F316C viii) variants of amended thermostability, by improved side-chain packing: 9F,Y,W; 12V, 80F, 82Y, 191Y,W; 213F; 9W+12V; 80F+82Y.

Based on the 3D-structure of the galactanase from *Humicola insolens*, the following variants are contemplated, in which at least one of the below-mentioned residues have been amended and/or at least one of the below-mentioned alterations have been introduced:

i) variants of an amended thermostability, by insertion of prolines: V20P, V25P, E29P, V41P, V50P, W53P, N56P, T94P, A96P, W142P, L169P, W185P, Q198P, M203P, A219P, A221P, T222P, Q258P, A261P, D262P, S288P, N305P, A311P, A322P, S324P, S325P.

ii) variants of an amended thermostability, by disulfide bridges (double mutations to cysteines): T113C+G163C, W185C+S229C, S218C+A221C, R227C+V283C.

Based on the 3D-structure of the galactanase from *Aspergillus aculeatus*, the following variants are contemplated, in which at least one of the below-mentioned residues have been amended and/or at least one of the below-mentioned alterations have been introduced::

i) variants of an amended pH-activity profile: D181N;

ii) variants of an amended thermostability, by insertion of prolines: T3P, Y20P, N24P, L25P, T29P, A31P, V50P, S53P, S56P, T93P, T94P, S96P, W142P, L144P, E146P, T147P, T172P, E200P, S203P, A219P, A256P, A258P, S261P, S264P, I266P, T288P, I301P, A304P, Y318P, E324P;

iii) variants of an amended thermostability, by disulfide bridges (double mutations to cysteines): L13C+L65C, N24C+Q30C, S218C+A221C, A304C+Y318C.

Based on the 3D-structure of the galactanase from *Bacillus licheniformis*, the following variants are contemplated, in which at least one of the below-mentioned residues have been amended and/or at least one of the below-mentioned alterations have been introduced::

i) variants of an amended thermostability, by insertion of prolines: K-6P, S-4P, L-2P, K1P, V20P, S26P, K29P, D31P, A54aP, G54eP, N57P, K93P, A97P, N101P, S171P, S185P, T256P, N260P, N266P, D286P, E288aP, A289P, A302dP, S302yP, Y302zP, A302bbP, E302ccP, E302ggP, F305P, D311P, F318P;

ii) variants of an amended thermostability, by disulfide bridges (double mutations to cysteines): S18C+Y302qC, G40C+Q330C, V44C+A69C, I48C+A62C, N50C+D84C, G54gC+T302xC, N56C+G302rC, A62C+G146C, K106C+A159C, K114C+A163C, E183C+G221C, T227C+A283C, A234C+V241C, Y250C+Q273C, A302aaC+A302iiC.

Additional variants of the invention which may exhibit amended properties as regards substrate binding and/or substrate specificity are listed below.

According to "Nomenclature for sugar-binding subsites in glycosyl hydrolases", G. J. Davis, K. S. Wilson and B. Henrissart, Biochemical Journal, Volume 321, pages 557 to 559 (1997), so-called subsites may be determined. Such subsites may be labelled from –N to +N (where N is an integer). –N represents the non reducing end and +N the reducing end of the polysaccharide. The cleaveage is taking place between the −1 and +1 subsites. The principal constituent of a sugar binding subsite is also called an aromatic platform. That is an aromatic residue, i.e. one of the following: W, H, Y or F.

Based on FIGS. 1-4 the inventors identified subsites as follows:

For MTGAL, HIGAI and AAGAL the following subsites were identified, reference being here had to the position numbering of SEQ ID NOs 1, 2, and 3, respectively (not to the corresponding residue in SEQ ID NO: 1):

Subsite −4: MTGAL none; HIGAL W53; AAGAL none.
Subsite −2: MTGAL W86, W300; HIGAL W86, W300; AAGAL W86, W301.
Subsite −1: MTGAL W296; HIGAL W296; AAGAL W297.
Subsite +1: MTGAL Y217, Y214; HIGAL Y217, Y214; AAGAL Y218, Y215.
Subsite +2: MT W183; HIGAL W183; AAGAL W184.

For BLGAL the following subsites were identified, reference being here had to the position numbering of SEQ ID NO: 4 (not to the corresponding residue in SEQ ID NO: 1):

Subsite −4: W363.
Subsite −3: W347.
Subsite −2: W115.
Subsite −1: W320.
Subsite +1: W237, Y234.

Also the residues in the near vicinity (5 Å) of the above residues may be altered and provide an amended substrate specificity and/or substrate binding. These residues are the following, reference being here had to the position numbering of SEQ ID NOs 1, 2, 3, and 4, respectively (not to the corresponding residue in SEQ ID NO: 1):

MTGAL (SEQ ID NO: 1): G6, V7, D8, W9, S10, S11, V12, V13, V14, E15, E16, A18, V20, Y22, L32, L36, T43, V44, R45, Q46, R47, V48, W49, V50, N51, P52, D54, N56, Y57, Y61, Y77, D79, F80, H81, Y82, S83, D84, T85, W86, A87, D88, P89, A90, H91, Q92, T93, M94, P95, G133, N134, E135, I136, R137, G139, L140, L141, W142, H178, L179, D180, N181, G182, W183, D184, W185, G186, T187, Q188, N189, G210, V211, S212, F213, Y214, P215, F216, Y217, S218, S219, S220, A221, T222, L223, S224, A225, L226, K227, S228, S229, L230, D231, N232, M233, I241, A242, V243, V244, E245, T246, N247, W248, P249, I250, C252, P255, R256, Y257, S258, F259, P260, D262, V263, Q273, F276, I277, V280, I283, L293, F294, Y295, W296, E297, P298, A299, W300, I301, H302, N303, A304, N305, L306, G307, S308, S309, C310, A311, D312, N313, T314, M315, F316, S317, Q318, S319, G320, Q321, L326, F329.

HIGAL (SEQ ID NO: 2): G6, V7, D8, W9, S10, S11, V12, M13, V14, E15, E16, A18, V20, Y22, L32, L36, M43, V44, R45, Q46, R47, V48, W49, V50, N51, P52, W53, D54, G55, N56, Y57, N58, Y61, Y77, N79, F80, H81, Y82, S83, D84, T85, W86, A87, D88, P89, A90, H91, Q92, T93, T94, A96, G133, N134, E135, I136, T137, G139, L141, W142, H178, L179, D180, N181, G182, W183, N184, W185, D186, T187, Q188, N189, G210, V211, S212, F213, Y214, P215, F216, Y217, S218, A219, S220, A221, T222, L223, D224, S225, L226, R227, R228, S229, L230, N231, N232, M233, V241, A242, V243, V244, E245, T246, N247, W248, P249, C252, P255, R256, Y257, Q258, F259, P260, D262, V263, Q273, Y276, I277, V280, V283, L293, F294, Y295, W296, E297, P298, A299, W300, I301, H302, N303, A304, N305, L306, G307, S308, S309, C310, A311, D312, N313, T314, M315, F316, T317, P318, S319, G320, Q321, L326, F329.

AAGAL (SEQ ID NO: 3): R5, G6, A7, D8, I9, S10, S11, L12, L13, L14, L15, E16, E18, Y20, Y22, L32, L36, S43, I44, R45, Q46, R47, V48, W49, V50, N51, P52, D54, S56, Y57, Y61, Y77, D79, L80, H81, L82, S83, D84, T85, W86, A87, D88, P89, S90, D91, Q92, T93, T94, P95, G134, N135, E136, I137, R138, G140, L142, W143, H179, L180, D181, D182, G183, W184, S185, W186, D187, Q188, Q189, N190, G211, V212, S213, Y214, Y215, P216, F217, Y218, S219, A220, S221, A222, T223, L224, A225, S226, L227, K228, T229, S230, L231, A232, N233, L234, V243, V244, V245, E246, T247, N248, W249, P250, C253, P256, A257, Y258, A259, F260, P261, D263, L264, Q274, F277, L278, L281, V284, V294, Y295, Y296, W297, E298, P299, A300, W301, I302, G303, N304, A305, G306, L307, G308, S309, S310, C311, A312, D313, N314, L315, M316, V317, D318, Y319, T320, D322, V324, Y325, I328, L331.

BLGAL (SEQ ID NO: 4): K26, G27, V28, D29, V30, S31, S32, A35, L36, Y64, V65, R66, V67, R68, I69, W70, N71, D72, P73, Y74, G80, Y81, G82, G83, G84, N85, N86, L106, D108, F109, H110, Y111, S112, D113, F114, W115, A116, D117, P118, A119, K120, Q121, K122, A123, P124, Q161, G163, N164, E165, T166, G169, A171, G172, H202, F203, T204, N205, P206, E207, T208, R211, Y212, S231, S232, Y233, Y234, P235, F236, W237, H238, G239, T240, L241, N243, L244, V261, A262, E263, T264, S265, Y266, T267, D274, G275, H276, G277, N278, T279, A280, P281, K282, N283, G284, Q285, T286, L287, N288, Q296, A299, V300, V303, V317, F318, Y319, W320, E321, P322, A323, W324, I325, V327, N336, K337, L339, W340, E341, Y343, G344, S345, G346, W347, A348, T349, S350, Y351, A352, A353, Y355, D356, P357, E358, D359, A360, G361, K362, W363, F364, G365, G366, S367, A368, V369, D370, N371, Q372, A373, L374, F375, F388.

The above amino acids may be substituted with any other amino acid, e.g. any of the remaining 19 natural amino acids. In the variants of the invention, at least one of the above-mentioned residues have been amended to introduce either of the other nineteen amino acid residues. The above variants are also included in dependent claims, however in the claims they have been renumbered according to the principles outlined above, each position being assigned the number of the corresponding amino acid residue in SEQ ID NO: 1.

Alignments

The program ClustalW (CLUSTAL W: improving the sensitivity of progressive multiple sequence alignment through sequence weighting, position specific gap penalties and weight matrix choice." Julie D. Thompson, Desmond G. Higgins, and Toby J. Gibson, Nucleic Acids Research, 22(22): 4673-4680 (1994)) is used for the purposes of the present invention for pairwise protein sequence alignments, multiple protein sequence alignments and protein profile alignments (version 1.82, default parameters).

For pairwise sequence comparison and calculation of percentage identity, the pairwise alignment parameters were: Slow/Accurate; Gap Open Penalty=10.00; Gap Extension Penalty=0.10; Protein weight matrix=Gonnet series; DNA weight matrix=IUB.

The consensus length is calculated automatically by the program. The number of identical residues (identified with an asterisk) is counted. The percentage of sequence identity is calculated as follows: the number of identical residues is divided by the consensus length and multiplied by 100.

The multiple alignment of FIG. 5 is based on a multiple alignment of the four sequences using Clustalw, but, importantly, it is combined with information derived from the 3D-structures, each position in each backbone being carefully evaluated, and the alignment modified by the present inventors. In other words, the multiple alignment of FIG. 5 is not a simple ClustalW multiple alignment reflecting only sequence homologies, it also reflects structural similarities.

The alignment of FIG. 5. can therefore be used to deduce corresponding variants in other backbones, and these variants are likely to also exhibit the amended property in question. For example, the above-mentioned variant A90S+H91D of MT is transferable to the other backbones or parent galactanases shown in FIG. 5 as follows: According to the FIG. 5 alignment, this variant would correspond to: A90S+H91D of HI; and A90S+K91D of BL. Because AA already has the sequence of S90D91, this variant is not relevant for AA. Another example is variant T288P of AA, which, using the alignment of FIG. 5, translates into S288P in MT and HI, and G288P in BL.

Other galactanase backbones of Glycoside Family 53 are known (see below under parents), and these can be added to the alignment of FIG. 5 as described below, and thereby corresponding variants can be deduced also for these backbones, as just described above.

For aligning a new sequence to the multiple alignment of FIG. 5, the Clustalw option called profile alignment is used as follows: The FIG. 5 multiple alignment is used as profile 1, and then the new sequence as profile 2. Then the program is asked to "Align sequence to 1st. profile," using the following parameters:

Multiple alignment parameters=Slow/Accurate; Gap Open Penalty=10.00; Gap Extension Penalty=0.20; Delay divergent sequences=30%; DNA Transitions Weight:0.50; Protein weight matrix=Gonnet series; DNA weight matrix=IUB; Use negative matrix=OFF;

Protein Gap Parameters: Toggle Residue-Specific Penalties=ON; Toggle Hydrophilic Penalties=ON; Hydrophilic Residues=GPSNDQEKR; Gap Separation Distance=4; Toggle End Gap Separation=OFF.

In FIG. 6, as an example, three new galactanase sequences have been added to the FIG. 5 alignment. The new galactanases are added at the bottom of the alignment, as rows nos. 5, 6 and 7. The galactanases are: AT (the galactanase of *Aspergillus tubigensis*, (SEQ ID NO: 7)); BS (the galactanase of *Bacillus subtilis* (SEQ ID NO: 8)); and PF (the galactanase of *Pseudomonas fluorescens* (SEQ ID NO: 9)). Thus, using FIG. 6, the above-mentioned variant A90S+H91D of MT translates into A90S+K91D of BS, and E90S+K91D of PF. Because AT already has the sequence of S90D91, this variant is not relevant for AT. Another example is variant T288P of AA, which, using the alignment of FIG. 6, translates into variants T288P of AT, G288P of BS, and G288P of PF.

In the alternative, alignments of sequences and calculation of degree %-identity may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Parent

The term "parent galactanase," or simply "parent," refers to the galactanase on which the variant was based, and also to the galactanase with which the variant is compared and aligned.

The parent may be a naturally occurring (wildtype) galactanase, or it may in turn even be a variant thereof, prepared by any suitable means. For instance, the parent galactanase may be a variant of a naturally occurring galactanase which has been modified or altered in the amino acid sequence. A parent may also be an allelic variant which is any of two or more alternative forms of a gene occupying the same chromosomal locus. Allelic variation arises naturally through mutation, and may result in polymorphism within populations as is well-described in the art. An allelic variant of a polypeptide is a polypeptide encoded by the corresponding allelic variant of a gene.

Galactanase

This section is applicable to the parent galactanases, as well as the variant galactanases of the invention.

Galactanases catalyze the endohydrolysis of 1,4-beta-D-galactosidic linkages in arabinogalactans of type I and/or galactans (see the structure of rhamnogalacturonan I as described in Carpita et al. in Plant J:, 3:1-30, 1993).

In the present context, a galactanase is a polypeptide having galactanase activity. Galactanase activity can be measured using a substrate including 1,4-beta-D-galactosidic linkages. Examples of galactanase substrates are arabinogalactans of type I and galactans. Particularly suitable substrates are i) lupin galactan, and potato galactan (commercially available from, e.g., MegaZyme, Australia); as well as ii) AZCL-galactan substrates such as AZCL-potato-galactan, and AZCL-lupin-galactan (also commercially available from MegaZyme, Australia). For the substrates mentioned under i) above, galactanase activity may be measured as release of reducing sugars, whereas for the AZCL-substrates, the galactanase activity is measured spectrophotometrically (formation of a blue colour). In a particular embodiment, the galactanase assay is based on the substrate lupin AZCL galactan.

The person skilled in the art will know how to adapt assay-pH and assay-temperature to the galactanase in question. Examples of assay-pH-values are pH 2, 3, 4, 5, 6, 7, 8, 9, 10, or 11. Examples of assay-temperatures are 20, 25, 30, 35, 37, 40, 45, 50, 55, 60, 65, 70, 75, 80, or 90° C.

A preferred galactanase assay is described in Example 2 herein.

In a particular embodiment, the galactanase is an enzyme classified as EC 3.2.1.89, the official name of which is arabinogalactan-endo-1,4-beta-galactosidase. Alternative names are endo-1,4-beta-galactanase, galactanase, or arabinogalactanase. EC refers to Enzyme Class as described at a) www.chem.qmul.ac.uk/iubmb/enzyme/, and/or in b) Enzyme Nomenclature 1992 from NC-IUBMB, Academic Press, San Diego, Calif., published by Academic Press for IUBMB in 1992 (ISBN 0-12-227164-5), as regularly supplemented and updated. For supplements and updates, please consult www.chem.qmul.ac.uk/iubmb/enzyme/supplements/, giving details regarding the following supplements: Supplement 1 (1993) (Eur. J. Biochem., 1994 223, 1-5); Supplement 2 (1994) (Eur. J. Biochem., 1995 232, 1-6); Supplement 3 (1995) (Eur. J. Biochem., 1996 237, 1-5); Supplement 4 (1997) (Eur. J. Biochem., 1997, 250, 1-6); Supplement 5 (1999) (Eur. J. Biochem., 1999, 264, 610-650): Supplement 6 (2000); Supplement 7 (2001); and Supplement 8 (2002).

Glycoside Hydrolase (GH) Family 53

The EC-classification referred to above is mainly based on substrate specificity of the enzymes, and does therefore not reflect the structural features of these enzymes. A classification of glycoside hydrolases in families based on amino acid sequence similarities has been proposed a few years ago; see the CAZy(ModO) site at the internet:

Coutinho, P. M. & Henrissat, B. (1999) Carbohydrate-Active Enzymes server at URL: amfb.cnrs-mrs.fr/~cazy/CAZY/index.html; and/or Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of celluloses and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23; Henrissat B., A classification of glycosyl hydrolases based on amino-acid sequence similarities. Biochem. J. 280:309-316 (1991); Henrissat B., Bairoch A. New families in the classification of glycosyl hydrolases based on amino- acid sequence similarities. Biochem. J. 293:781-788 (1993); Henrissat B., Bairoch A. Updating the sequence-based classification of glycosyl hydrolases. Biochem. J. 316:695-696 (1996); and/or Davies G., Henrissat B. Structures and mechanisms of glycosyl hydrolases. Structure 3:853-859(1995).

Glycoside Hydrolase Family 53 is found under the entry relating to Glycosidases and Transglycosidases (or Glycoside Hydrolases).

These are particular embodiments of the GH Family 53 galactanase,
 i) it is an endo-1,4-beta-galactanase (EC 3.2.1.89);
 ii) it has a retaining catalytic mechanism;
 iii) it has Glu as a catalytic nucleophile or base;
 iv) it has Glu as a catalytic proton donor;
 v) its 3D Structure has a fold (beta/alpha)$_8$; and/or
 vi) it belongs to GH Clan GH-A.

For the purposes of the present invention, the below glycoside hydrolases of Family 53 are non-limiting examples of a parent galactanase:

| Protein | Organism | GenBank | GenPept | SwissProt | Publication |
|---|---|---|---|---|---|
| galactanase 1 | *Aspergillus aculeatus* | L34599 | AAA32692.1 | P48842 | Christgau et al, Curr. Genet. 27: 135–141(1995) |
| endo-1,4-beta-galactanase (GalA) | *Aspergillus niger* | AJ305303 | CAC83735.1 | Q8X168 | — |
| galactanase GalA | *Aspergillus-tubingensis* | AJ012316 | CAB40555.1 | Q9Y7F8 | Van der Vlugt Bergmans et al, Biotechnol. Tech. 13: 87–92(1999) |
| ORF 1 | *Bacillus circulans* | L03425 | AAA22259.1 | P48843 | SEQ ID NO: 10 of WO 00/47711 |
| ORF BH2023 | *Bacillus halodurans* | AP001514 NC_002570 | BAB05742.1 NP_242889.1 | Q9KBA5 | Takami et al, Extremophiles 3 (1), 21–28 (1999) |
| ORF yvfO | *Bacillus subtilis* | Z94043 Z99121 | CAB08009.1 CAB15417.1 | O07013 O07013 O32260 | SEQ ID NO: 14 of WO 00/47711 |
| YvfO | *Bifidobacterium longum* | AE014643 NC_004307 | AAN24099.1 NP_695463.1 | | Schell et al, Proc. Natl. Acad. Sci. U.S.A. 99 (22), 14422–14427 (2002) |
| galactanase | *Cellvibrio japonicus* (*Pseudomonas cellulosa*) | X91885 | CAA62990.1 | P48841 | Braithwaite et al, Biochemistry 36: 15489–15500 (1997) |
| ORF CAC2570 | *Clostridium acetobutylicum* | AE007755 | AAK80519.1 | Q97G04 | Nolling et al, J. Bacteriol. 183 (16), 4823–4838 (2001) |
| ORF TM1201 | *Thermotoga maritima* | AE001777 NC_000853 | AAD36276.1 NP_229006.1 | Q9XOS8 | Nelson et al, Nature 399: 323–329(1999) |
| Sequence 2 from patent U.S. Pat. No. 6242237 | *Myceliophthora thermophila* | AAE73520 | AAE73520.1 | | U.S. Pat. No. 6242237 |
| Sequence 4 from patant U.S. Pat. No. 6242237 | *Humicola insolens* | AAE73521 | AAE73521.1 | | U.S. Pat. No. 6242237 |
| ORF GalA | *Xanthomonas axonopodis* pv. *citri* | AE011762 NC_003919 | AAM36180.1 NP_641644.1 | | da Silva et al, Nature 417 (6887), 459–463 (2002) |
| ORF XAC0575 | *Xanthomonas axonopodis* pv. *citri* | AE011684 NC_003919 | AAM35464.1 NP_640928.1 | | da Silva et al, Nature 417 (6887), 459–463 (2002) |
| ORF GalA | *Xanthomonas campestris* pv. *campestris* | AE012224 NC_003902 | AAM40555.1 NP_636631.1 | | da Silva et al, Nature 417 (6887), 459–463 (2002) |
| ORF GalA | *Xanthomonas campestris* pv. *campestris* | AE012483 NC_003902 | AAM42894.1 NP_638970.1 | | da Silva et al, Nature 417 (6887), 459–463 (2002) |
| ORF YPO0853 | *Yersinia pestis* | AJ414145 NC_003143 | CAC89700.1 NP_404474.1 | Q8ZHN7 | Parkhill et al, Nature 413: 523–527(2001) |

| Protein | Organism | GenBank | GenPept | SwissProt | Publication |
|---|---|---|---|---|---|
| ORF Y3238 | *Yersinia pestis* | AE013925<br>NC_004088 | AAM86788.1<br>NP_670537.1 | | Deng et al J.<br>Bacteriol. 184 (16),<br>4601–4611 (2002) |

Additional examples of a parent galactanase of the invention are the galactanases derived from *Meripilus giganteus* (SEQ ID NO: 2 of WO 97/32013), *Pseudomonas fluorescens, Bacillus agaradhaerens* (SEQ ID NO: 12 of WO 00/47711), and *Bacillus licheniformis* (SEQ ID NO: 8 of WO 00/47711).

The present invention specifically includes variants of each and every of the above specific parent galactanases of GH Family 53 corresponding to the claimed variants of MTGAL, HIGAL, AAGAL and BLGAL, such variants being derivable by adding the parent galactanase sequence in question to the FIG. 5 alignment as described above for the construction of FIG. 6, and translating each MTGAL, HIGAL, AAGAL, or BLGAL variant into the parent galactanase in question, using the concept of corresponding amino acid residue as defined above.

In a first embodiment, the parent GH Family 53 galactanase is a fungal galactanase. The fungal galactanase may be derived from a yeast, or from a filamentous fungus. The yeast galactanase may be derived from *Yersinia*, e.g. from *Yersinia pestis*. The filamentous fungal galactanase may be derived from a strain of *Aspergillus, Humicola, Meripilus, Myceliophthora,* or *Thermomyces*. Examples of these strains are *Aspergillus aculeatus, Aspergillus niger, Aspergillus tubingensis, Humicola insolens, Meripilus giganteus,* and *Myceliophthora thermophila*.

In a second embodiment, the parent GH Family 53 galactanase is a bacterial galactanase. The bacterial galactanase may be derived from a strain of *Bacillus, Bifidobacterium, Cellvibrio, Clostridium, Pseudomonas, Thermotoga,* or *Xanthomonas*. Examples of such strains are *Bacillus agaradhaerens, Bacillus circulans, Bacillus halodurans, Bacillus licheniformis, Bacillus subtilis, Bifidobacterium longum, Cellvibrio japonicus, Clostridium acetobutylicum, Pseudomonas fluorescens, Pseudomonas cellulosa, Thermotoga maritime, Xanthomonas axonopodis* pv. *citri,* and *Xanthomonas campestris* pv. *campestris*.

Particularly preferred parent galactanases are those with the above-mentioned GenBank, GenPept, or SwissProt accession numbers, and those with the above-mentioned SEQ ID NO's.

Further particularly preferred GH Family 53 parent galactanases are the following:

| Strain of origin | Sequence<br>Number (herein) | Abbreviations<br>used herein |
|---|---|---|
| *Myceliophthora thermophila* | SEQ ID NO: 1 | MTGAL, or MT |
| *Humicola insolens* | SEQ ID NO: 2 | HIGAL, or HI |
| *Aspergillus aculeatus* | SEQ ID NO: 3 | AAGAL, or AA |
| *Bacillus licheniformis* | SEQ ID NO: 4 | BLGAL, or BL |

Preferred subgroups of the above are a) MTGAL, HIGAL, AAGAL; b) MTGAL, HIGAL, BLGAL; and c) MTGAL, HIGAL.

In a third embodiment, the parent galactanase has a percentage identity to SEQ ID NO: 1 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In a fourth embodiment, the galactanase variant has a percentage identity to SEQ ID NO: 1 of at least 50%, using the program ClustalW and the settings referred to above. In further particular embodiments, the percentage identity is at least 55, 60, 65, 70, 75, 80, 85, 90, 95, 97, or at least 99%.

In a fifth embodiment, the parent galactanase has a percentage identity to SEQ ID NO: 2 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In a sixth embodiment, the galactanase variant has a percentage identity to SEQ ID NO: 2 of at least 50%, using the program ClustalW and the settings referred to above. In further particular embodiments, the percentage identity is at least 55, 60, 65, 70, 75, 80, 85, 90, 95, 97, or at least 99%.

In a seventh embodiment, the parent galactanase has a percentage identity to SEQ ID NO: 3 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In an eighth embodiment, the galactanase variant has a percentage identity to SEQ ID NO: 3 of at least 50%, using the program ClustalW and the settings referred to above. In further particular embodiments, the percentage identity is at least 55, 60, 65, 70, 75, 80, 85, 90, 95, 97, or at least 99%.

In a ninth embodiment, the parent galactanase has a percentage identity to SEQ ID NO: 4 of at least 25%, using the program ClustalW and the settings referred to above. In further particular embodiments, the percentage identity is at least 30, 35, 40, 45, 50, 55, 60, 65, 70, 75, 80, 85, 90, or at least 95%.

In a tenth embodiment, the galactanase variant has a percentage identity to SEQ ID NO: 4 of at least 50%, using the program ClustalW and the settings referred to above. In further particular embodiments, the percentage identity is at least 55, 60, 65, 70, 75, 80, 85, 90, 95, 97, or at least 99%.

In further particular embodiments of each of the above first to tenth embodiments, the alignment is a full Smith-Waterman alignment with the settings referred to above, preferably made with the FASTA package also referred to above.

It is to be understood that also variants of galactanases are contemplated as the parent enzyme.

Preparation of Galactanase Variants

The galactanase variants may be prepared by any method known in the art, see e.g. Example 1 herein. Typically, a galactanase variant library is prepared. The term "randomized library", "variant library", or simply "library" refers to such library of galactanase variants. Diversity in the variant library can be generated via mutagenesis of the genes encoding the variants at the DNA triplet level, such that individual codons are variegated e.g. by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29 (Novozymes A/S). They also include the use of DNA shuffling techniques to create a library of full length genes, wherein several gene segments are combined, and wherein each segment may be diversified e.g. by spiked mutagenesis (Stemmer, Nature 370, pp. 389-391, 1994 and U.S. Pat. Nos. 5,811,238; 5,605,793; and 5,830,721). One can use a gene encoding a galactanase "backbone" (wildtype parent galactanase) as a template polynucleotide, and combine this with one or more single or double-stranded oligonucleotides as described in WO 98/41623 and in WO 98/41622 (Novozymes A/S). The single-stranded oligonucleotides could be partially randomized during synthesis. The double-stranded oligonucleotides could be PCR products incorporating diversity in a specific region. In both cases, one can dilute the diversity with corresponding segments encoding the sequence of the backbone galactanase in order to limit the average number of changes that are introduced.

Methods have also been established for designing the ratios of nucleotide mixtures (A; C; T; G) to be inserted in specific codon positions during oligo- or polynucleotide synthesis, so as to introduce a bias in order to approximate a desired frequency distribution towards a set of one or more desired amino acids that will be encoded by the particular codons. It may be of interest to produce a variant library that comprises permutations of a number of known amino acid modifications in different locations in the primary sequence of the polypeptide. These could be introduced post-translationally or by chemical modification sites, or they could be introduced through mutations in the encoding genes. The modifications by themselves may previously have been proven beneficial for one reason or another (e.g. decreasing antigenicity, or improving specific activity, performance, stability, or other characteristics). In such instances, it may be desirable first to create a library of diverse combinations of known sequences. For example, if twelve individual mutations are known, one could combine (at least) twelve segments of the parent protein encoding gene, wherein each segment is present in two forms: one with, and one without the desired mutation. By varying the relative amounts of those segments, one could design a library (of size 212) for which the average number of mutations per gene can be predicted. This can be a useful way of combining mutations, that by themselves give some, but not sufficient effect, without resorting to very large libraries, as is often the case when using 'spiked mutagenesis'. Another way to combine these 'known mutations' could be by using family shuffling of oligomeric DNA encoding the known mutations with fragments of the full length wild type sequence.

The mutated DNA can be expressed by any method known in the art, see e.g. Example 1. Generally, the host cell may be a unicellular microorganism, e.g., a prokaryote, or a non-unicellular microorganism, e.g., a eukaryote.

Useful unicellular cells are bacteria such as *Bacillus, Streptomyces, E. coli, Pseudomonas* sp., *Lactococcus, Lactobacillus, Leuconostoc, Streptococcus, Pediococcus*, and *Enterococcus*.

Examples of eukaryote cells are non-human animal cells, insect cells, plant cells, or fungal cells. Examples of fungal cells are *Candida, Hansenula, Kluyveromyces, Pichia, Saccharomyces, Schizosaccharomyces, Yarrowia, Acremonium, Aspergillus, Fusarium, Humicola, Mucor, Myceliophthora, Neurospora, Penicillium, Thielavia, Tolypocladium*, and *Trichoderma*.

Applications

The galactanase variants of the invention are useful in animal feed, see e.g. WO 97/16982. Non-limiting examples of desirable characteristics of galactanase variants for feed applications are: High temperature stability, acid-stability and high specific activity.

The galactanase variants of the invention, e.g., but not exclusively, those of claims 1-4, may also be used to prepare galacto-oligo-saccharides and for hydrolysis of lactose, both of which are relevant for, e.g., the dairy industry. For example, the method of Example 5 can be used for screening of galactanase variants for improved activity on lactose, in particular for improved transglycosylation and/or hydrolytic activity on lactose.

The transglycosylation reactions observed with ONPG (Example 4) can be used for screening of galactanase variants for suitable acceptor affinities. The screening may be a high-through-put screening. This provides valuable knowledge of the affinities of the individual subsites (such as subsites +1, +2, +3, +4) for various acceptors, e.g. galactose (Gal), β-1,4-galactobiose (Gal2) (Megazyme), β-1,4-galactotriose (Gal3), β-1,4-galactotetraose (Gal4), glucose (Glu), arabinose (Ara), galacturonic acid (Gala), maltose (Mal) or maltotriose (Mal3).

The results of Example 3 provides knowledge of individual subsites for galactose (−3 to +3), as well as knowledge of the tendencies to transglycosylate instead of hydrolyse substrates. This knowledge is useful for the designing of galactanase variants of desired properties.

Various references are cited herein, the disclosures of which are incorporated by reference in their entireties.

EXAMPLES

Example 1

Preparation of Galactanase Variants

The D181N mutation was introduced in the AAGAL encoding gene by the use of the mutagenic oligonucleotide 5'-CAT TTG GAC AAC GGC TGG AGC-3' (SEQ ID NO: 5) and the mega-priming method described by Sarkar, G., and Sommer, S. S., 1990. The "Megaprimer" Method of Site-Directed Mutagenesis. BioTechniques, 8: 404-407. The mutations D181N+S90A+D91H were introduced in a similar way.

The resulting variant genes were cloned into plasmid pHD464 as described in Dalbøge H., Heldt-Hansen H. 1994. A novel method for efficient expression cloning of fungal enzyme genes. Mol. Gen. Genet. 243: 253-260, and the correct introduction of the mutations were verified by DNA sequencing.

The A90S+H91D double mutation was introduced in the MTGAL encoding gene essentially as described above by the use of the mutageneic oligonucleotode 5'-GCC GAT CCT TCT GAT CAG ACC ATG CC-3' (SEQ ID NO: 6).

Proteins were expressed in, and secreted from *Aspergillus oryzae* essentially as described in Christensen, T., Wöldike, H., Boel, E., Mortensen, S. B., Hjortshøj, K., Thim, L., Hansen, M. T., 1988. High level expression of recombinant genes in *Aspergillus oryzae*. Bio/Technology 6, 1419-1422.

Example 2

Purification and Characterization of Galactanase Variants

Purification of *Aspergillus aculeatus* Galactanase Variants

The culture supernatant from a fermentation of the *Aspergillus oryzae* strain expressing the site-directed recombinant *Aspergillus aculeatus* galactanase variant D181N (described in Example 1) was filtered through a 0.22 μm filter to remove the mycelia. 1200 ml filtrate was added ammonium sulphate to a concentration of 1.6 M, loaded onto a 50 ml butyl column equilibrated with 25 mM sodium acetate, 1.6 M ammonium sulphate pH 5.0 and eluted using a linear ammonium sulphate decreasing from 1.6 M to 0 M over 10 column volumes. Galactanase activity was measured by mixing 40 μl of fractions with 200 μl 10 mg/ml lupin AZCL-galactan (Megazyme, Australia) in 0.5 M MES pH 6.5 After about 30 min incubation at room temperature, insoluble substrate was removed by centrifugation, and absorbance of supernatant measured at 590 nm. Fractions containing galactanase activity eluted around 1 M ammonium sulphate were pooled and dialysed against 10 mM sodium citrate pH 3.5. Dialysate (400 ml) was diluted to 2000 ml with water and loaded onto a 50 ml S-Sepharose column equilibrated with 10 mM sodium citrate pH 3.5. Galactanase activity did not bind to this column and was concentrated, to 80 ml on an Amicon ultrafiltration device with a 10 kDa cut off filter. The concentrate was at least 95% pure estimated from SDS-PAGE.

The culture supernatant from a fermentation of the *Aspergillus oryzae* strain expressing the site-directed recombinant *Aspergillus aculeatus* galactanase variant D181N+S90A+D91H was filtered as described above. 900 ml filtrate was added ammonium sulphate to a concentration of 1.6 M, and eluted from a 50 ml butyl column as described above. Galactanase activity was measured as described above. Fractions containing galactanase activity eluted around 0.35 M ammonium sulphate and were pooled and dialysed against 25 mM sodium acetate pH 5.5. Dialysate (200 ml) was diluted to 275 ml with water, loaded onto a 50 ml Q-Sepharose column equilibrated with 25 mM sodium acetate pH 5.5, and eluted with a linear gradient from 0 to 1 M NaCl over 10 column volumes. Fractions containing galactanase activity (around 0.8 M NaCl) were pooled and concentrated to 10 ml on an Amicon ultrafiltration device with a 10 kDa cut off filter. The concentrate was at least 95% pure estimated from SDS-PAGE.

Purification of *Myceliophthora thermophila* Galactanase Variants

The culture supernatant from a fermentation of the *Aspergillus oryzae* strain expressing the site-directed recombinant *Myceliophthora thermophila* galactanase variant A90S+H91D (described in Example 1) was filtered through a 0.22 μm filter to remove the mycelia. 1200 ml filtrate was added ammonium sulphate to a concentration of 1.6 M, loaded onto a 50 ml butyl column equilibrated with 25 mM sodium acetate, 1.6 M ammonium sulphate pH 5.0 and eluted using a linear ammonium sulphate decreasing from 1.6 M to 0 M over 10 column volumes. Galactanase activity was measured by mixing 40 μl of fractions with 200 μl 10 mg/ml lupin AZCL-galactan (Megazyme, Australia) in 0.5 M MES pH 6.5 After about 30 min incubation at room temperature, insoluble substrate was removed by centrifugation, and absorbance of supernatant measured at 590 nm. Fractions containing galactanase activity eluted around 1 M ammonium sulphate were pooled and dialysed against 10 mM sodium citrate pH 3.5. Dialysate (400 ml) was diluted to 2000 ml with water and loaded onto a 50 ml S-Sepharose column equilibrated with 10 mM sodium citrate pH 3.5. Galactanase activity did not bind to this column and was concentrated to 80 ml on an Amicon ultrafiltration device with a 10 kDa cut off filter. The concentrate was at least 95% pure estimated from SDS-PAGE.

Characterization of the Purified Variants

The pH profiles of the purified variants described above were established as follows: Galactanase activity at various pH was measured by mixing 500 μl 4 mg/ml lupin AZCL-galactan (Megazyme, Australia) in water with 500 μl buffer (50 mM sodium acetate, 50 mM potassium dihydrogenphosphate, 50 mM boric acid, 1 mM $CaCl_2$, 0.01% Triton X-100 adjusted to pH 2.5, 3.5, 4.5, 5.5, 6.5, 7.5, 8.5 or 9.5 with HCl/NaOH) and 25 μl purified enzyme diluted to about 0.5-2 μg/ml in water. The mixture was incubated 15 min at 37° C., insoluble material was removed by centrifugation, and absorbance in the supernatant was measured at 590 nm.

From the results shown in Table 1 below, it appears that the pH profiles have changed (the profile of the AAGAL variants D181N, and D181N+S90A+D91H have been shifted to the alkaline side; and the pH profile of the MTGAL variant A90S+H91D has been shifted to the acidic side, as compared to the wild types).

TABLE 1

| Galactanase | pH | | | | | | | |
|---|---|---|---|---|---|---|---|---|
| | 2.5 | 3.5 | 4.5 | 5.5 | 6.5 | 7.5 | 8.5 | 9.5 |
| AAGAL | 73 | 100 | 83 | 47 | 32 | 0 | 2 | 0 |
| AAGAL D181N | 74 | 99 | 100 | 87 | 74 | 35 | 7 | 0 |
| AAGAL D181N + S90A + D91H | 55 | 59 | 71 | 83 | 100 | 90 | 21 | 0 |
| MTGAL | 0 | 12 | 41 | 63 | 90 | 100 | 54 | 7 |
| MTGAL A90S + H91D | 0 | 8 | 51 | 75 | 100 | 95 | 35 | 4 |

Example 3

Activity on Galactooligosaccharides

Preparation of galactotriose (Gal3), galactotetraose (Gal4), methyl-galactotrioside (MeGal3) and methyl-galactotetraoside (MeGal4)

Galactan (lupin) was purchased from Megazyme. All solvents, reagents and TLC-plates (Silica gel 60 $F_{254}$) were purchased from Merck. $^1$H NMR spectra were recorded on a Varian Mercury 400 MHz at 30° C. As reference values $CHCl_3$ in $CDCl_3$ (7.27 ppm) and HDO in $D_2O$ (4.67 ppm) were used. Flash chromatography was accomplished using a FLASH 40i chromatography module from Biotage.

Undeca-O-acetyl galactotriose: Arabinofuranosidase treated lupin galactan (0.50 g) was dissolved in 10 mM Bis-Tris buffer pH 6.5 (50 mL) by stirring for 1 h at 37° C. BLGAL was added (250 GalU/mL) and the solution stirred for 3 h at 37° C. and then 5 min at 100° C. TLC (eluent: propanol/ethanol/$H_2O$ (7:1:2)) showed a major (Gal3) and a minor product (Gal4) both eluting below commercial galactobiose. After cooling, the solution was concentrated, dried and acetylated and worked up by standard procedures ($Ac_2O$/pyridine, 48 h at room temperature (rt)). The crude product was purified by flash chromatography (eluent:EtOAc/heptane 5:2) to give 0.20 g of pure Gal3 peracetate (mixture of alpha- and beta-anomer (1:2)). $^1$H NMR (selected data, CDCl$_3$): 6.29 ppm (d, $J_{1,2}$=3.5 Hz, H-1alpha), 5.63 ppm (d, $J_{1,2}$=8.4 Hz, H-1β).

Galactotriose (Gal3): Deacetylation of the acetylated triose was accomplished by stirring overnight in methanol/NaOCH$_3$ (1 mL 1M NaOCH$_3$ in 3 mL methanol) and then neutralized by addition of Dowex 50 W×8. Water (2 mL) was added and the resin removed by filtration. The clear solution was concentrated (freeze-drying) to give 0.10 g of solid G3. MS (MALDI-TOF): 527 (M+23, Na). $^1$H NMR (selected data, D$_2$O): 5.20 ppm (d, J=3.6 Hz, H-1alpha), 4.5-4.6 (3×d, H-1β, H-1', H-1").

Methyl deca-O-acetyl galactotrioside: The acetylated galactotriose (0.24 g) was converted into the bromide by treatment (5 h) with 30% HBr in acetic acid (2.5 mL) and CH$_2$Cl$_2$ (2 mL) at 0° C.→ rt. The reaction was worked up by standard procedures and concentrated to give a yellowish syrup (194 mg) of the alpha-bromo compound, which was used without further purification. $^1$H NMR (selected data, CDCl$_3$): 6.57 ppm (d, 1H, $J_{1,2}$=3.8 Hz, H-1). The bromoglycoside (0.19 g, 0.20 mmol) was converted into the methyl glycoside by overnight treatment with Ag$_2$CO$_3$ (60 mg, 22 mmol) in dry methanol (10 mL) (under nitrogen). After work up, the methyl glycoside was purified by flash chromatography (eluent:EtOAc/heptane (3:1)) to give 30 mg of pure compound (colorless oil). $^1$H NMR (selected data, CDCl$_3$): 4.48 ppm, 4.39 ppm and 4.35 ppm (3×d, 3H, $J_{1,2}$=8.0 Hz, H-1, H-1' and H-1"), 3.47 ppm (3H, s, OCH$_3$).

Methyl galactotrioside (MeGal3): The acetylated methyl glycoside (30 mg) was deacetylated as described above to give 10 mg of syrupy material.

Galactotetraose (Gal4): This was prepared as described for Gal3 using 100 GalU/mL. Yield of final deacetylated product: 17 mg.

Methyl galactotetraoside (MeGal4): This compound was prepared in analogy with MeGal3 and 41 mg of MeGal4 was obtained from 1 g of galactan. MS (MALDI-TOF): 704 (M+23, Na).

Activity of HIGAL, MTGAL, AAGAL and BLGAL on Galactooligosaccharides

The activity on the galacto-oligosaccharide substrates prepared as described above and on the commercially available galactobiose (Gal2, Megazyme) was studied for the four purified galactanases HIGAL, MTGAL, AAGAL and BLGAL. The buffers and temperatures used were: 25 mM sodium acetate, 0.5 mM CaCl$_2$, 0.005% Triton X-100, pH 6.5 at 37° C. for HIGAL and MTGAL, 50 mM sodium acetate, 1 mM CaCl$_2$, pH 4 at 30° C. for AAGAL and 50 mM Mes, 1 mM CaCl$_2$, pH 6.5 at 30° C. for BLGAL. Enzyme concentrations used were 0.8 µg/ml for HIGAL, 0.2 µg/ml for MTGAL, and 10 µg/ml for AAGAL and BLGAL. With HIGAL and MTGAL substrate concentrations were all 0.25 mg/ml, whereas 0.34 mg/ml Gal2, 0.050 mg/ml Gal3 and 0.067 mg/ml Gal4 were used for AAGAL and BLGAL. Enzyme activity in samples withdrawn after various incubation times was inactivated by heating to 95° C. for 10 min. Compositions of reaction products were analysed using HPAE-PAD (Dionex) applying a PA-100 column and a linear gradient of sodium acetate (0-0.18 M) in 0.15 M NaOH. Response factors of the individual carbohydrates were estimated from reference runs with MeGal3, MeGal4, Gal, Gal2, Gal3 and Gal4. Selected results are shown in Tables 2-8 below (the figures indicating weight percentage of glactooligosaccharides).

Neither of the enzymes HIGAL, MTGAL, AAGAL or BLGAL had any detectable activity on Gal2 in 24 hours. HIGAL, MTGAL and AAGAL degraded Gal3 to Gal2 and Gal, whereas BLGAL had no visible activity on Gal3 after 24 hours. Incubation of HIGAL and MTGAL with MeGal3 (See Tables 2 and 3) gave much higher release of MeGal than MeGal2, indicating that Gal is released from the reducing end of Gal3 with both enzymes. HIGAL and MTGAL degraded Gal4 (also containing about 40% Gal3) (Tables 4 and 5) mainly to Gal and Gal2, whereas Gal3 did not accumulate. Results for HIGAL and MTGAL with MeGal4 (Tables 6 and 7) gave initial release mainly of MeGal, MeGal2 and Gal3 and some Gal2 but little Gal, again indicating that Gal is released mainly from the reducing end of Gal4. The production of Gal from MeGal4 in the later stages of the hydrolysis may be mainly due to hydrolysis of transglycosylation products with no methyl group at the reducing end. BLGAL degrades galactotetraose mainly to galactose and galactotriose. With MeGal4 the main products from BLGAL were MeGal and Gal3, indicating that Gal is released from reducing end of Gal4. With AAGAL the initial products from galactotetraose are about equimolar amounts of galactose, galactobiose and galactotriose, but subsequently the galactotriose is degraded to galactobiose and galactose.

TABLE 2

Degradation of MeGal3 with HIGAL

| | Incubation time (hours) | | | | |
|---|---|---|---|---|---|
| | 0.0 | 0.5 | 2.2 | 5.0 | 72.0 |
| Gal | 0.0 | 0.0 | 2.3 | 3.0 | 17.1 |
| Gal2 | 0.0 | 3.9 | 12.5 | 20.2 | 36.2 |
| Gal3 | 0.0 | 1.2 | 3.3 | 10.6 | 8.0 |
| MeGal | 0.0 | 11.4 | 18.4 | 36.8 | 34.6 |
| MeGal2 | 0.0 | 3.3 | 3.7 | 5.2 | 4.2 |
| MeGal3 | 100.0 | 80.3 | 59.7 | 24.2 | 0.0 |

TABLE 3

Degradation of MeGal3 with MTGAL

| | Incubation time (hours) | | | | |
|---|---|---|---|---|---|
| | 0.0 | 0.5 | 2.2 | 5.0 | 72.0 |
| Gal | 0.0 | 0.0 | 14.1 | 2.2 | 6.5 |
| Gal2 | 0.0 | 0.0 | 8.5 | 10.9 | 37.2 |
| Gal3 | 0.0 | 0.0 | 0.4 | 15.7 | 23.2 |
| MeGal | 0.0 | 10.1 | 27.6 | 17.4 | 28.3 |
| MeGal2 | 0.0 | 2.7 | 1.9 | 3.2 | 3.5 |
| MeGal3 | 100.0 | 87.2 | 47.5 | 50.6 | 1.3 |

TABLE 4

Degradation of Gal4 with HIGAL

| | Incubation time (hours) | | | | |
|---|---|---|---|---|---|
| | 0.0 | 0.5 | 2.2 | 5.0 | 72.0 |
| Gal | 0.0 | 5.8 | 16.7 | 35.6 | 65.2 |
| Gal2 | 0.0 | 8.1 | 21.9 | 34.8 | 33.6 |
| Gal3 | 42.0 | 43.2 | 39.8 | 23.9 | 0.9 |
| Gal4 | 58.0 | 42.9 | 21.6 | 5.7 | 0.2 |

TABLE 5

Degradation of Gal4 with MTGAL

| | Incubation time (hours) | | | | |
|---|---|---|---|---|---|
| | 0.0 | 0.5 | 2.2 | 5.0 | 72.0 |
| Gal | 0.0 | 11.6 | 14.9 | 29.2 | 54.9 |
| Gal2 | 0.0 | 9.9 | 17.4 | 29.1 | 43.5 |
| Gal3 | 42.0 | 27.7 | 45.5 | 29.5 | 1.5 |
| Gal4 | 58.0 | 50.8 | 22.3 | 12.1 | 0.0 |

TABLE 6

Degradation of MeGal4 with HIGAL

| | Incubation time (hours) | | | | |
|---|---|---|---|---|---|
| | 0.0 | 0.5 | 2.0 | 5.0 | 24.0 |
| Gal | 0.0 | 2.3 | 1.6 | 7.4 | 26.4 |
| Gal2 | 0.0 | 6.3 | 5.0 | 13.8 | 25.3 |
| Gal3 | 0.0 | 20.6 | 16.0 | 19.7 | 9.1 |
| Gal4 | 0.0 | 3.3 | 3.2 | 3.2 | 1.7 |
| MeGal | 1.6 | 12.1 | 10.5 | 16.6 | 19.1 |
| MeGal2 | 4.7 | 12.6 | 13.2 | 16.1 | 13.4 |
| MeGal3 | 14.8 | 17.2 | 18.4 | 15.5 | 5.0 |
| MeGal4 | 79.0 | 25.5 | 32.1 | 7.6 | 0.0 |

TABLE 7

Degradation of MeGal4 with MTGAL

| | Incubation time (hours) | | | | |
|---|---|---|---|---|---|
| | 0.0 | 0.5 | 2.0 | 5.0 | 24.0 |
| Gal | 0.0 | 0.9 | 4.8 | 12.4 | 24.2 |
| Gal2 | 0.0 | 3.3 | 10.9 | 20.1 | 32.7 |
| Gal3 | 0.0 | 13.7 | 23.9 | 17.9 | 3.4 |
| Gal4 | 0.0 | 2.5 | 3.7 | 2.9 | 1.1 |
| MeGal | 1.6 | 8.9 | 16.2 | 19.3 | 20.1 |
| MeGal2 | 4.7 | 9.6 | 13.6 | 13.9 | 13.3 |
| MeGal3 | 14.8 | 17.1 | 16.0 | 9.9 | 2.3 |
| MeGal4 | 79.0 | 43.9 | 10.9 | 3.5 | 2.9 |

Example 4

Activity with o-nitrophenyl-β-D-galactopyranoside (ONPG)

The activity of HIGAL and MTGAL with ONPG was tested by mixing 200 μl (normally 5.5 mg/ml) ONPG in 50 mM sodium acetate, 1 mM $CaCl_2$, 0.01% Triton X-100, pH 6.5 with 25 μl galactanase (normally 1 mg/ml) in the well of a microtiter plate. Release of o-nitrophenol (ONP) was measured at room temperature at 405 nm every 10 seconds normally for 30 min on a SpectraMaxPlus (Molecular Devices). Effects on the observed release of ONP was studied with varied enzyme concentration, ONPG concentration and with addition of galactose (Gal), β-1,4-galactobiose (Gal2) (Megazyme), β-1,4-galactotriose (Gal3), β-1,4-galactotetraose (Gal4), glucose (Glu), arabinose (Ara), galacturonic acid (Gala), maltose (Mal) or maltotriose (Mal3).

In Tables 8-11 below, incubation times required to increase the observed absorbance at 405 nm by given amounts are listed. Cells marked 'n.r.' indicate that the increase in absorbance was not reached in the experiment. In general, the initial increase in absorbance at 405 nm was very slow, but after a lag phase the rate of ONP release often increased drastically—often approximately exponentially. The most likely explanation for the observed kinetics is that ONPG reacts with the enzyme to give an enzyme-galactosyl intermediate which hydrolyses very slowly. Instead, the Gal of the intermediate is released by transglycosylation, initially with ONPG or added sugar as acceptor. In cases where the rate of ONP release increases, these transglycosylation products are even better acceptors than the initial ones. As seen in Table 8, the rate of ONP release is about proportional to the amount of added enzyme. HIGAL releases ONP faster than MTGAL at identical enzyme dosage. Addition of Gal (5 mg/ml) is seen to slow the ONP release by about a factor of two for MTGAL and a factor of three for HIGAL. Probably, Gal does not significantly slow formation of the enzyme-galactosyl intermediate, which would accumulate even if Gal had high affinity for the −1 or +1 subsite. More likely, Gal inhibits the subsequent transglycosylation, which requires binding of ONPG to the +1 and +2 subsites, e.g. by binding to the +2 subsite. With 50 mg/ml Gal added (results not shown) release of ONP was even slower with only insignificant increase of absorbance at 405 nm in 30 min.

The results in Table 9 show that rate of ONP release is similar with 5 and 10 mg/ml ONPG but slower at 2.5 and especially 1.25 mg/ml ONPG. This indicates that the rate-limiting transglycosylation reaction with ONPG as acceptor has a Km of about 3 mg/ml.

In Table 10 effects of adding 0.5 or 0.05 mg/ml Gal2, Gal3 or Gal4 are given. Contrary to Gal each of these three galactooligosaccharides increases the rate of ONP release. The initial ONP release rates indicate that Gal4 is more efficient than Gal3 as acceptor, and that Gal3 is more efficient than Gal2. With Gal2 and Gal3, ONP release rate increases significantly with incubation time, indicating that transglycosylation products (initially Gal3 and Gal4, respectively) are more efficient acceptors than the added sugars, whereas the release rate is relatively constant with Gal4. These results indicate that HIGAL possesses four significant subsites (+1,+2,+3,+4) on the reducing side of the cleaved bond.

In Table 11 results upon addition of Glu, Ara, Mal, Mal3 and Gala are given. As experiments were run on three different days, and ONP release rate even in identical experiments had been seen to vary slightly (possible due to variants in temperature), results with only ONPG and HIGAL added rub in the same three times slower ONP release 5 mg/ml Glu also has slight inhibitory effect, whereas 50 mg/ml Glu (results not shown) resulted in very little ONP release (<0.02) in 30 min. As with Gal, this indicates binding of these sugars to subsites in the enzyme-galactosyl intermediate, which presents ONPG to act as acceptor and where the sugars themselves also has little or no acceptor function. With 5 mg/ml Mal and Mal3 no significant effects on ONP release are observed. 5 mg/ml Gala has weak inhibitory effect, whereas 50 mg/ml Gala shows ONP release by about a factor two. From these results ranking of the inhibitory effect of the tested sugars is: Gal~Ara>Glu>Gala>Mal=Mal3=0.

Using HPAE-PAD chromatography) Dionex LC-500 System, PA-100 column, linear gradient of 0-0.6 M sodium acetate in 100 mM NaOH), the production of larger oligosaccharides from transglycosylation upon incubation of HIGAL (110 μg/ml) at room temperature (0.5 to 14 min followed by heat activation for 10 min at 95° C. resulting in $A_{405}$: 0.15-0.67) in 50 mM sodium acetate, 1 mM $CaCl_2$, 0.01% Triton X-100, pH 6.5 with ONPG )5 mg/ml) with and without Gal2 (0.05mg/ml) or Gal3 (0.05 mg/ml) as acceptor was verified.

TABLE 8

Rate of ONP release, MTGAL and HIGAL in varying dosages, and +/− sugar

| | | Enzyme: µg/ml | | | | | | | | | |
|---|---|---|---|---|---|---|---|---|---|---|---|
| | | MTGAL 110 | MTGAL 55 | MTGAL 28 | MTGAL 110 | MTGAL 55 | HIGAL 110 | HIGAL 55 | HIGAL 28 | HIGAL 110 | HIGAL 55 |
| ONPG (5 mg/ml) | | | | | | | | | | | |
| Sugar: mg/ml | | | | | Gal: 5 | Gal: 5 | | | | Gal: 5 | Gal: 5 |
| Time (min) | 0.025 | 14.0 | 29.9 | 40.4 | 26.9 | 40.2 | 9.0 | 20.4 | 41.4 | 32.0 | 57.0 |
| to increase | 0.05 | 20.5 | 42.5 | n.r. | 44.5 | n.r. | 10.3 | 22.9 | 46.5 | 35.7 | n.r. |
| A405 by: | 0.1 | 26.4 | 54.5 | n.r. | n.r. | n.r. | 11.5 | 25.4 | 51.0 | 41.5 | n.r. |
| | 0.2 | 31.4 | n.r. | n.r. | n.r. | n.r. | 12.7 | 28.0 | 56.5 | 46.7 | n.r. |
| | 0.4 | 34.5 | n.r. | n.r. | n.r. | n.r. | 13.8 | 30.9 | n.r. | 52.7 | n.r. |
| | 0.8 | 39.2 | n.r. | n.r. | n.r. | n.r. | 15.0 | 32.0 | n.r. | 59.0 | n.r. |
| | 1.6 | 43.9 | n.r. | n.r. | n.r. | n.r. | 15.0 | 35.0 | n.r. | n.r. | n.r. |
| | 3.2 | 46.7 | n.r. | n.r. | n.r. | n.r. | 17.7 | 37.9 | n.r. | n.r. | n.r. |

TABLE 9

Rate of ONP release at varying ONPG concentrations

| | | Enzyme: µg/ml | | | | | | | |
|---|---|---|---|---|---|---|---|---|---|
| | | HIGAL: 110 | HIGAL: 110 | HIGAL: 110 | HIGAL: 110 | HIGAL: 110 | HIGAL: 110 | HIGAL: 110 | HIGAL: 110 |
| ONPG (mg/ml) | | 10 | 5 | 2.5 | 1.25 | | | | |
| Sugar: mg/ml | | | | | | | | | |
| Time (min) | 0.025 | 6.3 | 6.0 | 9.7 | 28.7 | | | | |
| to increase | 0.05 | 7.7 | 8.0 | 11.3 | n.r. | | | | |
| A405 by: | 0.1 | 8.8 | 9.2 | 12.7 | n.r. | | | | |
| | 0.2 | 10.0 | 10.2 | 14.0 | n.r. | | | | |
| | 0.4 | 11.2 | 11.3 | 15.5 | n.r. | | | | |
| | 0.8 | 12.3 | 12.5 | 17.3 | n.r. | | | | |
| | 1.6 | 13.5 | 13.8 | 19.5 | n.r. | | | | |
| | 3.2 | 14.7 | 15.3 | 22.8 | n.r. | | | | |

TABLE 10

Rate of ONP release, addition of various amounts of various galactooligosaccharides

| | | Enzyme: µg/ml | | | | | | |
|---|---|---|---|---|---|---|---|---|
| | | HIGAL: 110 | HIGAL: 110 | HIGAL: 110 | HIGAL: 110 | HIGAL: 110 | HIGAL: 110 | HIGAL: 110 |
| ONPG (mg/ml) | | 5 | 5 | 5 | 5 | 5 | 5 | 5 |
| Sugar: mg/ml | | | Gal2: 0.5 | Gal2: 0.05 | Gal3: 0.5 | Gal3: 0.05 | Gal4: 0.5 | Gal4: 0.05 |
| Initial rate (mOD/min) | | 0.9 | 6 | 2 | 200 | 40 | 700 | 80 |
| Time (min) | 0.025 | 10.0 | 2.7 | 5.5 | 0.0 | 0.5 | 0.0 | 0.2 |
| to increase | 0.05 | 11.3 | 3.5 | 6.8 | 0.2 | 1.0 | 0.0 | 0.5 |
| A405 by: | 0.1 | 12.8 | 4.8 | 8.2 | 0.3 | 1.7 | 0.0 | 0.8 |
| | 0.2 | 14.2 | 6.0 | 9.5 | 0.5 | 2.3 | 0.2 | 1.5 |
| | 0.4 | 15.7 | 7.2 | 10.7 | 0.8 | 3.3 | 0.5 | 2.5 |
| | 0.8 | 17.0 | 8.3 | 11.8 | 1.5 | 4.8 | 1.0 | 3.7 |
| | 1.6 | 18.5 | 9.7 | 13.3 | 2.5 | 6.3 | 2.2 | 5.2 |
| | 3.2 | 20.0 | 11.0 | 15.2 | 3.8 | 7.7 | 5.3 | 7.5 |

TABLE 11

Rate of ONP release, inhibition by sugars

| | | Enzyme: µg/ml | | | | | | | | |
|---|---|---|---|---|---|---|---|---|---|---|
| | | HIGAL: 110 | HIGAL: 110 | HIGAL: 110 | HIGAL: 110 | HIGAL: 110 | HIGAL: 110 | HIGAL: 110 | HIGAL: 110 | HIGAL: 110 |
| ONPG (mg/ml) | | 5 | 5 | 5 | 5 | 5 | 5 | 5 | 5 | 5 |
| Sugar: mg/ml | | | Glu: 5 | Ara: 5 | | Mal: 5 | Mal3: 5 | | GalA: 50 | GalA: 5 |
| Time (min) | 0.025 | 8.5 | 12.8 | 26.5 | 11.0 | 11.5 | 11.0 | 8.7 | 13.7 | 9.5 |
| to increase | 0.05 | 9.5 | 14.8 | n.r. | 12.5 | 13.0 | 12.3 | 9.8 | 16.7 | 11.2 |
| A405 by: | 0.1 | 10.8 | 17.0 | n.r. | 13.8 | 14.3 | 13.8 | 11.0 | 20.0 | 12.7 |
| | 0.2 | 12.0 | 19.3 | n.r. | 15.2 | 15.7 | 15.2 | 12.2 | 23.3 | 14.3 |

TABLE 11-continued

Rate of ONP release, inhibition by sugars

Enzyme: µg/ml

| | HIGAL: 110 | HIGAL: 110 | HIGAL: 110 | HIGAL: 110 | HIGAL: 110 | HIGAL: 110 | HIGAL: 110 | HIGAL: 110 | HIGAL: 110 |
|---|---|---|---|---|---|---|---|---|---|
| 0.4 | 13.3 | 21.8 | n.r. | 16.5 | 17.2 | 16.5 | 13.3 | 26.8 | 15.8 |
| 0.8 | 14.5 | 24.3 | n.r. | 18.0 | 18.7 | 18.0 | 14.7 | n.r. | 17.5 |
| 1.6 | 15.8 | 27.0 | n.r. | 19.5 | 20.2 | 19.3 | 16.0 | n.r. | 19.3 |
| 3.2 | 17.3 | n.r. | n.r. | 21.3 | 22.0 | 21.3 | 17.3 | n.r. | 22.5 |

Example 5

Activity on Lactose

HIGAL (60 µg/ml) and MTGAL (750 µg/ml) were incubated at 50° C. with lactose (Lac) (100 mg/ml) at pH 4.8 (25 mM sodium citrate), 6.45 (25 mM sodium acetate, 0.5 mM CaCl$_2$, 0.005% Triton X-100) and 8.6 (50 mM Tris, 0.01% Brij 35). 20 µl samples were withdrawn after 2, 23 and 120 hours, 980 water added and enzyme inactivated by heating to 95° C. for 10 min. After a further 20 time dilution with water, samples were analysed using HPAE-PAD (Dionex LC-500 system, PA-100 column, 0-3 min: 150 mM NaOH, 3-19 min: linear gradient 0-0.18 M sodium acetate in 150 mM NaOH). Response factors for the individual peaks were estimated from standards of Gal, Glu, Lac, Gal2, Gal3 and Gal4.

Under these conditions only MTGAL at pH 4.5 and 6.5 gave significant conversion of Lac. In Tables 12 and 13 weight fractions of the analysed products with MTGAL at pH 4.5 and 6.45 are given. The figures indicate weight % of the products resulting from the incubation. The term DP3 indicates transglycosylation product consisting of three sugar units, and the term DP4+ transglycosylation products consisting of four or more sugar units. Unfortunately, the analysis method used was not able to separate Glu and Gal.

With transglycosylation occurring according to the reaction:

$$2Lac \rightarrow DP3(=Gal_2Glu)+Glu$$

the weight fraction of DP3 should be about three times higher than the weight of the monomer. After 2 hours the ratio is about 1.5 at both pH's indicating that this is not the only reaction taking place. The production of larger oligosaccharides (DP4+) is a result of the initial transglycosylation product functioning as acceptor for further transglycosylation:

$$Lac+DP3 \rightarrow DP4+Glu$$

Also, from the increasing amount of Gal/Glu without corresponding increase in transglycosylation products (DP3 and DP4+) after 23 and 120 hours, it is evident that hydrolysis of transglycosylation products takes place. These hydrolysis reactions seem to be slower at pH 6.45 than at pH 4.5.

TABLE 12

Activity of MTGAL on lactose (pH 4.5)

| | Incubation time (hours) | | |
|---|---|---|---|
| | 2 | 23 | 120 |
| Glu/Gal | 1.4 | 12.5 | 38.8 |
| Lac/Gal2 | 96.0 | 78.7 | 51.2 |

TABLE 12-continued

Activity of MTGAL on lactose (pH 4.5)

| | Incubation time (hours) | | |
|---|---|---|---|
| | 2 | 23 | 120 |
| DP3 | 2.0 | 7.0 | 8.9 |
| DP4+ | 0.5 | 1.8 | 1.1 |

TABLE 13

Activity of MTGAL on lactose (pH 6.45)

| | Incubation time (hours) | | |
|---|---|---|---|
| | 2 | 23 | 120 |
| Glu/Gal | 1.0 | 6.5 | 21.0 |
| Lac/Gal2 | 95.7 | 85.3 | 62.6 |
| DP3 | 1.4 | 6.3 | 11.7 |
| DP4+ | 1.9 | 1.9 | 4.7 |

Example 6

Activity on Galactan

Lupin galactan (Megazyme) was incubated with BLGAL (0.1-10 µg/ml) at pH 6.5 (50 mM MES, 1 mM CaCl2) and with AAGAL (0.1-10 µg/ml) at pH 4.0 (50 mM sodium acetate, 1 mM CaCl2) at 30° C. Samples were withdrawn after 45 min to 24 hours and enzyme inactivated by heating to 95° C. for 10 min. Reaction products were analysed using HPAEC-PAD on a Dionex chromatographic system using a CarboPac PA-100 column and a linear gradient 0 to 0.3 M sodium acetate in 0.15 M NaOH. Purified galacto-oligosaccharides were used to identify products.

With BLGAL the initial main product is galactotetraose with both smaller and larger oligomers also present. Upon longer incubation the fractions of galactose, galactobiose and galactotriose increase and after prolonged incubation only these three oligomers are seen in molar ratios of about 1:0.4:0.9.

AAGAL initially produces a more homogeneous mixture of galactooligomers. Further degradation yields mainly galactose, galactobiose and galactotriose, and finally almost exclusively galactose and galactobiose are seen in a molar ratio of about 2:1. Small peaks probably corresponding to galactobioses and galactotrioses resulting from transglycosylation reactions with glucosidic bonds different from β-1,4 are also present.

The invention claimed is:

1. A variant of a parent Glycoside Hydrolase Family 53 galactanase, comprising an alteration in at least one of the following positions:
90, 91, 181, 303, 305, and 313,
wherein
 (a) the parent Glycoside Hydrolase Family 53 galactanase comprises an amino acid sequence which is at least 80% identical to SEQ ID NO: 1;
 (b) the variant comprises an amino acid sequence which is at least 80% identical to SEQ ID NO: 1; wherein the variant is not SEQ ID NO: 1;
 (c) each position is the number of the corresponding amino acid residue in SEQ ID NO: 1;
 (d) the alteration(s) are independently
   (i) an insertion of an amino acid immediately downstream of the position,
   (ii) a deletion of the amino acid which occupies the position, and/or
   (iii) a substitution of the amino acid which occupies the position with a different amino acid; and
 (e) the variant has galactanase activity.

2. The variant of claim 1, wherein the alteration(s) are substitutions.

3. The variant of claim 1, wherein the parent Glycoside Hydrolase Family 53 galactanase comprises an amino acid sequence which is at least 85% identical to SEQ ID NO: 1.

4. The variant of claim 1, wherein the parent Glycoside Hydrolase Family 53 galactanase comprises an amino acid sequence which is at least 90% identical to SEQ ID NO: 1.

5. The variant of claim 1, wherein the parent Glycoside Hydrolase Family 53 galactanase comprises an amino acid sequence which is at least 95% identical to SEQ ID NO: 1.

6. The variant of claim 1, wherein the variant comprises an amino acid sequence which is at least 85% identical to SEQ ID NO: 1.

7. The variant of claim 1, wherein the variant comprises an amino acid sequence which is at least 90% identical to SEQ ID NO: 1.

8. The variant of claim 1, wherein the variant comprises an amino acid sequence which is at least 95% identical to SEQ ID NO: 1.

9. The variant of claim 1, which comprises an alteration at position 90.

10. The variant of claim 9, wherein the variant comprises: 90A,C,D,E,F,G,H,I,K,L,M,N,P,Q,R,S,T,V,W,Y.

11. The variant of claim 10, wherein the variant comprises: 90A,C,D,E,F,G,H,I,K,L,M,N,P,Q,R,T,V,W,Y.

12. The variant of claim 1, which comprises an alteration at position 91.

13. The variant of claim 12, wherein the variant comprises: 91A,C,D,E,F,G,H,I,K,L,M,N,P,Q,R,S,T,V,W,Y.

14. The variant of claim 1, which comprises an alteration at position 181.

15. The variant of claim 14, wherein the variant comprises: 181A,C,D,E,F,G,H,I,K,L,M,N,P,Q,R,S,T,V,W,Y.

16. The variant of claim 1, which comprises an alteration at position 303.

17. The variant of claim 16, wherein the variant comprises: 303A,C,D,E,F,G,H,I,K,L,M,N,P,Q,R,S,T,V,W,Y.

18. The variant of claim 1, which comprises an alteration at position 305.

19. The variant of claim 18, wherein the variant comprises: 305A,C,D,E,F,G,H,I,K,L,M,N,P,Q,R,S,T,V,W,Y.

20. The variant of claim 1, which comprises an alteration at position 313.

21. The variant of claim 20, wherein the variant comprises: 313A,C,D,E,F,G,H,I,K,L,M,N,P,Q,R,S,T,V,W,Y.

22. The variant of claim 1, wherein the variant comprises at least one of the following substitutions:
 (a) Y214N,S+N247Y+L306Q; Y214A; F216FVASTG; and/or P89W+W86N;
 (b) A90S+H91D; H91N,L,D; N313D; N303D,H; and/or N305D,H; and/or N305D,H;
 (c) Y22P, N24P, T25P, A29P, A53P, N56P, T93P, D101P, W142P, T147P, Q198P, L203P, S204P, S219P, S258P, S288P, A304P, A311P, Q318P, A322P, S324P, S325P, and/or S327P;
 (d) W107S,H;
 (e) Q126E;
 (f) N39C+L326C; V20C+G320C; Y110C+G163C; W150C+N194C; T274C+V328C; and/or I301C+F316C; and/or
 (g) A90C,D,E,F,G,H,I,K,L,M,N,P,Q,R,S,T,V,W,Y; H91A,C,D,E,F,G,I,K,L,M,N,P,Q,R,S,T,V,W,Y; N181A,C,D,E,F,G,H,I,K,L,M,P,Q,R,S,T,V,W,Y; N303A,C,D,E,F,G, H,I,K,L,M,P,Q,R,S,T,V,W,Y; N305A,C,D,E,F,G,H,I,K, L,M,P,Q,R,S,T,V,W,Y; and/or N313A,C,D,E,F,G,H,I, K,L,M,P,Q,R,S,T,V,W,Y.

23. The variant of claim 22, which is a variant of a *Myceliophthora thermophila* galactanase.

24. The variant of claim 1, wherein the variant comprises at least one of the following substitutions:
   (a) V20P, V25P, E29P, V41P, V50P, W53P, N56P, T94P, A96P, W142P, L169P, W185P, Q198P, M203P, A219P, A221P, T222P, Q258P, A261P, D262P, S288P, N305P, A311P, A322P, S324P, and/or S325P;
   (b) T113C+G163C, W185C+S229C, S218C+A221C, R227C+V283C; and/or
   (c) A90C,D,E,F,G,H,I,J,K,L,M,N,P,Q,R,S,T,V,W,Y; H91A,C,D,E,F,G,I,J,K,L,M,N,P,Q,R,S,T,V,W,Y; N181A,C,D,E,F,G,H,I,J,K,L,M,P,Q,R,S,T,V,W,Y; N303A,C,D,E,F,G,H,I,J,K,L,M,P,Q,R,S,T,V,W,Y; N305A,C,D,E,F,G,H,I,J,K,L,M,P,Q,R,S,T,V,W,Y; and/or N313A,C,D,E,F,G,H,I,J,K,L,M,P,Q,R,S,T,V,W,Y.

25. The variant of claim 24, which is a variant of a *Humicola insolens* galactanase.

26. The variant of claim 1, wherein the variant comprises at least one of the following substitutions:
   (a) D181N, D181N+S90A+D91H;
   (b) T3P, Y20P, N24P, L25P, T29P, A31P, V50P, S53P, S56P, T93P, T94P, S96P, W142P, L144P, E146P, T147P, T172P, E200P, S203P, A219P, A256P, A258P, S261P, S264P, I266P, T288P, I301P, A304P, Y318P, and/or E324P;
   (c) L13C+L65C, N24C+Q30C, S218C+A221C, A304C+Y318C; and/or
   (d) S90A,C,D,E,F,G,H,I,K,L,M,N,P,Q,R,T,V,W,Y; D91A, C,E,F,G,H,I,K,L,M,N,P,Q,R,S,T,V,W,Y; D181A,C,E,F, G,H,I,K,L,M,N,P,Q,R,S,T,V,W,Y; N303A,C,D,E,F,G, H,I,K,L,M,P,Q,R,S,T,V,W,Y; G305A,C,D,E,F,H,I,K,L, M,N,P,Q,R,S,T,V,W,Y; and/or N313A,C,D,E,F,G,H,I, K,L,M,P,Q,R,S,T,V,W,Y; and/or
   (e) 19F,Y,W; L12V; L80F; L82Y; F191Y,W; Y213F; I9W+L12V; L82Y+L80F.

27. The variant of claim 26, which is a variant of an *Aspergillus aculeatus* galactanase.

28. The variant of claim 1, wherein the variant comprises at least one of the following substitutions:
   (a) K-6P, S-4P, L-2P, K1P, V20P, S26P, K29P, D31P, A54aP, G54eP, N57P, K93P, A97P, N101P, S171P, S185P, T256P, N260P, N266P, D286P, E288aP, A289P, A302dP, S302yP, Y302zP, A302bbP, E302ccP, E302ggP, F305P, D311P, F318P;
   (b) S18C+Y302qC, G40C+Q330C, V44C+A69C, I48C+A62C, N50D84C, G54gC+T302xC, N56C+G302rC, A62C+G146C, K106C+A159C, K114C+A163C, E183C+G221C, T227C+A283C, A234C+V241C, Y250C+Q273C, A302aaC+A302iiC; and/or
   (c) A90C,D,E,F,G,H,I,K,L,M,N,P,Q,R,S,T,V,W,Y; K91A, C,D,E,F,G,H,I,L,M,N,P,Q,R,S,T,V,W,Y; N181A,C,D, E,F,G,H,I,K,L,M,P,Q,R,S,T,V,W,Y; K303A,C,D,E,F,G, H,I,L,M,N,P,Q,R,S,T,V,W,Y; F305A,C,D,E,G,H,I,K,L, M,N,P,Q,R,S,T,V,W,Y; and/or Q313A,C,D,E,F,G,H,I, K,L,M,N,P,R,S,T,V,W,Y.

29. The variant of claim 28, which is a variant of a *Bacillus licheniformis* galactanase.

30. The variant of claim 1, wherein the parent galactanase is obtained from a strain of *Aspergillus, Bacillus, Bifidobacterium, Cellvibrio, Clostridium, Humicola, Meripilus, Myceliophthora, Pseudomonas, Thermomyces, Thermotoga, Xanthomonas,* or *Yersinia.*

31. An animal feed composition, comprising a variant of claim 1.

32. A method for hydrolyzing lactose, comprising treating the lactose with a galactanase variant of claim 1.

* * * * *

UNITED STATES PATENT AND TRADEMARK OFFICE
CERTIFICATE OF CORRECTION

PATENT NO. : 7,537,921 B2  
APPLICATION NO. : 10/537746  
DATED : May 26, 2009  
INVENTOR(S) : De Maria et al.

Page 1 of 1

It is certified that error appears in the above-identified patent and that said Letters Patent is hereby corrected as shown below:

On the Title page, in the Inventors section, please delete "Ryttersgaard" and insert --Ryttergaard--.

In claim 28, phrase (b), at column 44, line 15, please delete "N50D84C" and insert --N50C+D84C--.

Signed and Sealed this

Fourteenth Day of July, 2009

JOHN DOLL  
*Acting Director of the United States Patent and Trademark Office*

SEQUENCE LISTING

<160> NUMBER OF SEQ ID NOS: 9

<210> SEQ ID NO 1
<211> LENGTH: 332
<212> TYPE: PRT
<213> ORGANISM: Myceliophthora thermophila
<220> FEATURE:
<221> NAME/KEY: mat_peptide
<222> LOCATION: (1)..()

<400> SEQUENCE: 1

```
Ala Leu Thr Tyr Arg Gly Val Asp Trp Ser Val Val Glu Glu
1               5                   10                  15

Arg Ala Gly Val Ser Tyr Lys Asn Thr Asn Gly Asn Ala Gln Pro Leu
            20                  25                  30

Glu Asn Ile Leu Ala Ala Asn Gly Val Asn Thr Val Arg Gln Arg Val
            35                  40                  45

Trp Val Asn Pro Ala Asp Gly Asn Tyr Asn Leu Asp Tyr Asn Ile Ala
        50                  55                  60

Ile Ala Lys Arg Ala Lys Ala Ala Gly Leu Gly Val Tyr Ile Asp Phe
65                  70                  75                  80

His Tyr Ser Asp Thr Trp Ala Asp Pro Ala His Gln Thr Met Pro Ala
                85                  90                  95

Gly Trp Pro Ser Asp Ile Asp Asn Leu Ser Trp Lys Leu Tyr Asn Tyr
            100                 105                 110

Thr Leu Asp Ala Ala Asn Lys Leu Gln Asn Ala Gly Ile Gln Pro Thr
        115                 120                 125

Ile Val Ser Ile Gly Asn Glu Ile Arg Ala Gly Leu Leu Trp Pro Thr
130                 135                 140

Gly Arg Thr Glu Asn Trp Ala Asn Ile Ala Arg Leu Leu His Ser Ala
145                 150                 155                 160

Ala Trp Gly Ile Lys Asp Ser Ser Leu Ser Pro Lys Pro Lys Ile Met
                165                 170                 175

Ile His Leu Asp Asn Gly Trp Asp Trp Gly Thr Gln Asn Trp Trp Tyr
            180                 185                 190

Thr Asn Val Leu Lys Gln Gly Thr Leu Glu Leu Ser Asp Phe Asp Met
        195                 200                 205

Met Gly Val Ser Phe Tyr Pro Phe Tyr Ser Ser Ala Thr Leu Ser
210                 215                 220

Ala Leu Lys Ser Ser Leu Asp Asn Met Ala Lys Thr Trp Asn Lys Glu
225                 230                 235                 240

Ile Ala Val Val Glu Thr Asn Trp Pro Ile Ser Cys Pro Asn Pro Arg
                245                 250                 255

Tyr Ser Phe Pro Ser Asp Val Lys Asn Ile Pro Phe Ser Pro Glu Gly
            260                 265                 270

Gln Thr Thr Phe Ile Thr Asn Val Ala Asn Ile Val Ser Ser Val Ser
        275                 280                 285

Arg Gly Val Gly Leu Phe Tyr Trp Glu Pro Ala Trp Ile His Asn Ala
        290                 295                 300

Asn Leu Gly Ser Ser Cys Ala Asp Asn Thr Met Phe Ser Gln Ser Gly
305                 310                 315                 320

Gln Ala Leu Ser Ser Leu Ser Val Phe Gln Arg Ile
                325                 330
```

```
<210> SEQ ID NO 2
<211> LENGTH: 332
<212> TYPE: PRT
<213> ORGANISM: Humicola insolens
<220> FEATURE:
<221> NAME/KEY: mat_peptide
<222> LOCATION: (1)..()

<400> SEQUENCE: 2

Ala Leu Gln Tyr Lys Gly Val Asp Trp Ser Val Met Val Glu Glu
 1               5                  10                  15

Arg Ala Gly Val Arg Tyr Lys Asn Val Asn Gly Gln Glu Lys Pro Leu
                20                  25                  30

Glu Tyr Ile Leu Ala Glu Asn Gly Val Asn Met Val Arg Gln Arg Val
                35                  40                  45

Trp Val Asn Pro Trp Asp Gly Asn Tyr Asn Leu Asp Tyr Asn Ile Gln
        50                  55                  60

Leu Ala Arg Arg Ala Lys Ala Ala Gly Leu Gly Leu Tyr Ile Asn Phe
65                  70                  75                  80

His Tyr Ser Asp Thr Trp Ala Asp Pro Ala His Gln Thr Thr Pro Ala
                85                  90                  95

Gly Trp Pro Ser Asp Ile Asn Asn Leu Ala Trp Lys Leu Tyr Asn Tyr
                100                 105                 110

Thr Leu Asp Ser Met Asn Arg Phe Ala Asp Ala Gly Ile Gln Val Asp
                115                 120                 125

Ile Val Ser Ile Gly Asn Glu Ile Thr Gln Gly Leu Leu Trp Pro Leu
        130                 135                 140

Gly Lys Thr Asn Asn Trp Tyr Asn Ile Ala Arg Leu Leu His Ser Ala
145                 150                 155                 160

Ala Trp Gly Val Lys Asp Ser Arg Leu Asn Pro Lys Pro Lys Ile Met
                165                 170                 175

Val His Leu Asp Asn Gly Trp Asn Trp Asp Thr Gln Asn Trp Trp Tyr
                180                 185                 190

Thr Asn Val Leu Ser Gln Gly Pro Phe Glu Met Ser Asp Phe Asp Met
                195                 200                 205

Met Gly Val Ser Phe Tyr Pro Phe Tyr Ser Ala Ser Ala Thr Leu Asp
        210                 215                 220

Ser Leu Arg Arg Ser Leu Asn Asn Met Val Ser Arg Trp Gly Lys Glu
225                 230                 235                 240

Val Ala Val Val Glu Thr Asn Trp Pro Thr Ser Cys Pro Tyr Pro Arg
                245                 250                 255

Tyr Gln Phe Pro Ala Asp Val Arg Asn Val Pro Phe Ser Ala Ala Gly
                260                 265                 270

Gln Thr Gln Tyr Ile Gln Ser Val Ala Asn Val Val Ser Ser Val Ser
                275                 280                 285

Lys Gly Val Gly Leu Phe Tyr Trp Glu Pro Ala Trp Ile His Asn Ala
        290                 295                 300

Asn Leu Gly Ser Ser Cys Ala Asp Asn Thr Met Phe Thr Pro Ser Gly
305                 310                 315                 320

Gln Ala Leu Ser Ser Leu Ser Val Phe His Arg Ile
                325                 330

<210> SEQ ID NO 3
<211> LENGTH: 334
<212> TYPE: PRT
<213> ORGANISM: Aspergillus aculeatus
<220> FEATURE:
```

```
<221> NAME/KEY: mat_peptide
<222> LOCATION: (1)..()

<400> SEQUENCE: 3

Ala Leu Thr Tyr Arg Gly Ala Asp Ile Ser Ser Leu Leu Leu Leu Glu
1               5                   10                  15

Asp Glu Gly Tyr Ser Tyr Lys Asn Leu Asn Gly Gln Thr Gln Ala Leu
            20                  25                  30

Glu Thr Ile Leu Ala Asp Ala Gly Ile Asn Ser Ile Arg Gln Arg Val
        35                  40                  45

Trp Val Asn Pro Ser Asp Gly Ser Tyr Asp Leu Asp Tyr Asn Leu Glu
    50                  55                  60

Leu Ala Lys Arg Val Lys Ala Ala Gly Met Ser Leu Tyr Leu Asp Leu
65                  70                  75                  80

His Leu Ser Asp Thr Trp Ala Asp Pro Ser Asp Gln Thr Thr Pro Ser
                85                  90                  95

Gly Trp Ser Thr Thr Asp Leu Gly Thr Leu Lys Trp Gln Leu Tyr Asn
            100                 105                 110

Tyr Thr Leu Glu Val Cys Asn Thr Phe Ala Glu Asn Asp Ile Asp Ile
        115                 120                 125

Glu Ile Ile Ser Ile Gly Asn Glu Ile Arg Ala Gly Leu Leu Trp Pro
    130                 135                 140

Leu Gly Glu Thr Ser Ser Tyr Ser Asn Ile Gly Ala Leu Leu His Ser
145                 150                 155                 160

Gly Ala Trp Gly Val Lys Asp Ser Asn Leu Ala Thr Thr Pro Lys Ile
                165                 170                 175

Met Ile His Leu Asp Asp Gly Trp Ser Trp Asp Gln Gln Asn Tyr Phe
            180                 185                 190

Tyr Glu Thr Val Leu Ala Thr Gly Glu Leu Leu Ser Thr Asp Phe Asp
        195                 200                 205

Tyr Phe Gly Val Ser Tyr Tyr Pro Phe Tyr Ser Ser Ala Thr Leu
    210                 215                 220

Ala Ser Leu Lys Thr Ser Leu Ala Asn Leu Gln Ser Thr Tyr Asp Lys
225                 230                 235                 240

Pro Val Val Val Glu Thr Asn Trp Pro Val Ser Cys Pro Asn Pro
                245                 250                 255

Ala Tyr Ala Phe Pro Ser Asp Leu Ser Ser Ile Pro Phe Ser Val Ala
            260                 265                 270

Gly Gln Gln Glu Phe Leu Glu Lys Leu Ala Ala Val Glu Ala Thr
        275                 280                 285

Thr Asp Gly Leu Gly Val Tyr Tyr Trp Glu Pro Ala Trp Ile Gly Asn
    290                 295                 300

Ala Gly Leu Gly Ser Ser Cys Ala Asp Asn Leu Met Val Asp Tyr Thr
305                 310                 315                 320

Thr Asp Glu Val Tyr Glu Ser Ile Glu Thr Leu Gly Glu Leu
                325                 330

<210> SEQ ID NO 4
<211> LENGTH: 399
<212> TYPE: PRT
<213> ORGANISM: Bacillus licheniformis

<400> SEQUENCE: 4

Ala His Arg Asp Ser Gly Thr Ala Lys Ser Gly Leu Tyr Val Glu Lys
1               5                   10                  15
```

Val Ser Gly Leu Arg Lys Asp Phe Ile Lys Gly Val Asp Val Ser Ser
            20                  25                  30

Ile Ile Ala Leu Glu Glu Ser Gly Val Ala Phe Tyr Asn Glu Ser Gly
        35                  40                  45

Lys Lys Gln Asp Ile Phe Asn Thr Leu Lys Glu Ala Gly Val Asn Tyr
    50                  55                  60

Val Arg Val Arg Ile Trp Asn Asp Pro Tyr Asp Ala Asn Gly Asn Gly
65                  70                  75                  80

Tyr Gly Gly Gly Asn Asn Asp Leu Glu Lys Ala Ile Gln Ile Gly Lys
                85                  90                  95

Arg Ala Asn Ala Asn Gly Met Lys Leu Leu Ala Asp Phe His Tyr Ser
            100                 105                 110

Asp Phe Trp Ala Asp Pro Ala Lys Gln Lys Ala Pro Lys Ala Trp Ala
        115                 120                 125

Asn Leu Asn Phe Glu Asp Lys Lys Thr Ala Leu Tyr Gln Tyr Thr Lys
    130                 135                 140

Gln Ser Leu Lys Ala Met Lys Ala Ala Gly Ile Asp Ile Gly Met Val
145                 150                 155                 160

Gln Val Gly Asn Glu Thr Asn Gly Gly Leu Ala Gly Glu Thr Asp Trp
                165                 170                 175

Ala Lys Met Ser Gln Leu Phe Asn Ala Gly Ser Gln Ala Val Arg Glu
            180                 185                 190

Thr Asp Ser Asn Ile Leu Val Ala Leu His Phe Thr Asn Pro Glu Thr
        195                 200                 205

Ser Gly Arg Tyr Ala Trp Ile Ala Glu Thr Leu His Arg His His Val
    210                 215                 220

Asp Tyr Asp Val Phe Ala Ser Ser Tyr Tyr Pro Phe Trp His Gly Thr
225                 230                 235                 240

Leu Lys Asn Leu Thr Ser Val Leu Thr Ser Val Ala Asp Thr Tyr Gly
                245                 250                 255

Lys Lys Val Met Val Ala Glu Thr Ser Tyr Thr Tyr Thr Ala Glu Asp
            260                 265                 270

Gly Asp Gly His Gly Asn Thr Ala Pro Lys Asn Gly Gln Thr Leu Asn
        275                 280                 285

Asn Pro Val Thr Val Gln Gly Gln Ala Asn Ala Val Arg Asp Val Ile
    290                 295                 300

Gln Ala Val Ser Asp Val Gly Glu Ala Gly Ile Gly Val Phe Tyr Trp
305                 310                 315                 320

Glu Pro Ala Trp Ile Pro Val Gly Pro Ala His Arg Leu Glu Lys Asn
                325                 330                 335

Lys Ala Leu Trp Glu Thr Tyr Gly Ser Gly Trp Ala Thr Ser Tyr Ala
            340                 345                 350

Ala Glu Tyr Asp Pro Glu Asp Ala Gly Lys Trp Phe Gly Gly Ser Ala
        355                 360                 365

Val Asp Asn Gln Ala Leu Phe Asp Phe Lys Gly Arg Pro Leu Pro Ser
    370                 375                 380

Leu His Val Phe Gln Tyr Val Asp Thr Gly Thr Pro Phe Lys Asn
385                 390                 395

<210> SEQ ID NO 5
<211> LENGTH: 21
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<223> OTHER INFORMATION: Primer

<400> SEQUENCE: 5
catttggaca acggctggag c                                           21

<210> SEQ ID NO 6
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 6
gccgatcctt ctgatcagac catgcc                                      26

<210> SEQ ID NO 7
<211> LENGTH: 334
<212> TYPE: PRT
<213> ORGANISM: Aspergillus tubingensis
<220> FEATURE:
<221> NAME/KEY: mat_peptide
<222> LOCATION: (1)..()

<400> SEQUENCE: 7

Ala Leu Thr Tyr Arg Gly Ala Asp Ile Ser Ser Leu Leu Ile Glu Glu
1               5                   10                  15

Asp Ala Gly Ile Ser Tyr Lys Asn Leu Asn Gly Glu Thr Gln Ala Leu
            20                  25                  30

Glu Asp Ile Leu Val Asn Asn Gly Val Asn Ser Ile Arg Gln Arg Val
        35                  40                  45

Trp Val Asp Pro Ser Asp Gly Ser Tyr Asp Leu Asp Tyr Asn Leu Lys
    50                  55                  60

Leu Ala Lys Arg Val Gln Ala Ala Gly Met Ser Ile Tyr Leu Asp Leu
65                  70                  75                  80

His Leu Ser Asp Thr Trp Ala Asp Pro Ser Asp Gln Thr Thr Pro Thr
                85                  90                  95

Gly Trp Ser Thr Thr Asp Ile Asp Thr Leu Thr Trp Gln Leu Tyr Asn
            100                 105                 110

Tyr Thr Leu Glu Val Cys Asn Thr Phe Ala Glu Asn Asp Ile Asp Val
        115                 120                 125

Glu Ile Val Ser Ile Gly Asn Glu Ile Ser Ser Gly Leu Leu Trp Pro
    130                 135                 140

Leu Gly Lys Thr Ser Asn Tyr Asp Asn Ile Ala Lys Leu Leu His Ser
145                 150                 155                 160

Gly Ala Trp Gly Val Lys Asp Ser Asp Leu Thr Thr Pro Lys Ile
                165                 170                 175

Met Ile His Leu Asp Asn Gly Trp Asp Trp Asp Glu Gln Tyr Phe
            180                 185                 190

Tyr Lys Thr Val Leu Ala Thr Gly Ser Leu Leu Ser Thr Asp Phe Asp
        195                 200                 205

Leu Met Gly Val Ser Tyr Tyr Pro Phe Tyr Ser Ser Glu Ala Thr Leu
    210                 215                 220

Ser Ser Leu Lys Thr Ser Leu Thr Asn Met Gln Ser Asn Tyr Asp Lys
225                 230                 235                 240
```

```
Pro Val Val Val Glu Thr Asn Trp Pro Val Ser Cys Pro Asp Pro
                245                 250                 255

Glu Tyr Ser Phe Pro Ser Asp Leu Thr Ser Ile Pro Phe Ser Ala Ala
            260                 265                 270

Gly Gln Glu Glu Phe Leu Glu Lys Leu Ala Glu Val Val Glu Gly Val
        275                 280                 285

Thr Asp Gly Leu Gly Ile Tyr Tyr Trp Glu Pro Ala Trp Ile Asp Asn
    290                 295                 300

Ala Gly Leu Gly Ser Ser Cys Ala Asp Asn Leu Met Val Asp Val Asn
305                 310                 315                 320

Thr Asp Glu Val Leu Glu Ser Val Thr Val Phe Glu Asp Leu
                325                 330
```

```
<210> SEQ ID NO 8
<211> LENGTH: 372
<212> TYPE: PRT
<213> ORGANISM: Bacillus subtilis
<220> FEATURE:
<221> NAME/KEY: mat_peptide
<222> LOCATION: (1)..()

<400> SEQUENCE: 8
```

```
Met Asn Lys Asp Phe Ile Lys Gly Ala Asp Val Ser Ser Val Ile Ala
1               5                   10                  15

Leu Glu Asn Ser Gly Val Thr Phe Tyr Asn Thr Asn Gly Lys Arg Gln
                20                  25                  30

Asp Ile Phe Thr Thr Leu Lys Gln Ala Gly Val Asn Tyr Val Arg Val
            35                  40                  45

Arg Ile Trp Asn His Pro Tyr Asp Ser Asn Gly Asn Gly Tyr Gly Gly
    50                  55                  60

Gly Asn Asn Asp Val Gln Lys Ala Ile Glu Ile Gly Lys Arg Ala Thr
65                  70                  75                  80

Ala Asn Gly Met Lys Val Leu Ala Asp Phe His Tyr Ser Asp Phe Trp
                85                  90                  95

Ala Asp Pro Ala Lys Gln Lys Val Pro Lys Ala Trp Ala Asn Leu Ser
            100                 105                 110

Phe Glu Ala Lys Lys Ala Lys Leu Tyr Glu Tyr Thr Lys Gln Ser Leu
        115                 120                 125

Gln Lys Met Ile Lys Glu Gly Val Asp Ile Gly Met Val Gln Val Gly
    130                 135                 140

Asn Glu Thr Thr Gly Gly Phe Ala Gly Glu Thr Asp Trp Thr Lys Met
145                 150                 155                 160

Cys Gln Leu Phe Asn Glu Gly Ser Arg Ala Val Arg Glu Thr Asn Ser
                165                 170                 175

Asn Ile Leu Val Ala Leu His Phe Thr Asn Pro Glu Thr Ala Gly Arg
            180                 185                 190

Tyr Ser Phe Ile Ala Glu Thr Leu Ser Lys Asn Lys Val Asp Tyr Asp
        195                 200                 205

Val Phe Ala Ser Ser Tyr Tyr Pro Phe Trp His Gly Thr Leu Gln Asn
    210                 215                 220

Leu Thr Ser Val Leu Lys Ala Val Ala Asn Thr Tyr Gly Lys Lys Val
225                 230                 235                 240

Met Val Ala Glu Thr Ser Tyr Thr Tyr Thr Ala Glu Asp Gly Asp Gly
                245                 250                 255

His Gly Asn Thr Ala Pro Lys Ser Gly Gln Thr Leu Pro Tyr Pro Ile
            260                 265                 270
```

```
Ser Val Gln Gly Gln Ala Thr Ala Val Arg Asp Val Met Glu Ala Val
            275                 280                 285
Ala Asn Thr Gly Lys Ala Gly Leu Gly Val Phe Tyr Trp Glu Pro Ala
        290                 295                 300
Trp Ile Pro Val Gly Pro Lys Thr Gln Ile Glu Lys Asn Lys Val Leu
305                 310                 315                 320
Trp Glu Thr Tyr Gly Ser Gly Trp Ala Ser Ser Tyr Ala Ala Glu Tyr
                325                 330                 335
Asp Pro Glu Asp Ala Gly Lys Trp Tyr Gly Gly Ser Ala Val Asp Asn
            340                 345                 350
Gln Ala Leu Phe Asp Phe Asn Gly His Pro Leu Pro Ser Leu Gln Val
        355                 360                 365
Phe Gln Tyr Ala
    370

<210> SEQ ID NO 9
<211> LENGTH: 359
<212> TYPE: PRT
<213> ORGANISM: Pseudomonas fluorscens
<220> FEATURE:
<221> NAME/KEY: mat_peptide
<222> LOCATION: (1)..()

<400> SEQUENCE: 9

Asn Thr Gly Val Ala Asp Asn Thr Pro Phe Tyr Val Gly Ala Asp Leu
1               5                   10                  15
Ser Tyr Val Asn Glu Met Glu Ser Cys Gly Ala Thr Tyr Arg Asp Gln
            20                  25                  30
Gly Lys Lys Val Asp Pro Phe Gln Leu Phe Ala Asp Lys Gly Ala Asp
        35                  40                  45
Leu Val Arg Val Arg Leu Trp His Asn Ala Thr Trp Thr Lys Tyr Ser
    50                  55                  60
Asp Leu Lys Asp Val Ser Lys Thr Leu Lys Arg Ala Lys Asn Ala Gly
65                  70                  75                  80
Met Lys Thr Leu Leu Asp Phe His Tyr Ser Asp Thr Trp Thr Asp Pro
                85                  90                  95
Glu Lys Gln Phe Ile Pro Lys Ala Trp Ala His Ile Thr Asp Thr Lys
            100                 105                 110
Glu Leu Ala Lys Ala Leu Tyr Asp Tyr Thr Thr Asp Thr Leu Ala Ser
        115                 120                 125
Leu Asp Gln Gln Gln Leu Leu Pro Asn Leu Val Gln Val Gly Asn Glu
    130                 135                 140
Thr Asn Ile Glu Ile Leu Gln Ala Glu Asp Thr Leu Val His Gly Ile
145                 150                 155                 160
Pro Asn Trp Gln Arg Asn Ala Thr Leu Leu Asn Ser Gly Val Asn Ala
                165                 170                 175
Val Arg Asp Tyr Ser Lys Lys Thr Gly Lys Pro Ile Gln Val Val Leu
            180                 185                 190
His Ile Ala Gln Pro Glu Asn Ala Leu Trp Trp Phe Lys Gln Ala Lys
        195                 200                 205
Glu Asn Gly Val Ile Asp Tyr Asp Val Ile Gly Leu Ser Tyr Tyr Pro
    210                 215                 220
Gln Trp Ser Glu Tyr Ser Leu Pro Gln Leu Pro Asp Ala Ile Ala Glu
225                 230                 235                 240
Leu Gln Asn Thr Tyr His Lys Pro Val Met Ile Val Glu Thr Ala Tyr
```

```
                        245                 250                 255
    Pro Trp Thr Leu His Asn Phe Asp Gln Ala Gly Asn Val Leu Gly Glu
                260                 265                 270

Lys Ala Val Gln Pro Glu Phe Pro Ala Ser Pro Arg Gly Gln Leu Thr
                275                 280                 285

Tyr Leu Leu Thr Leu Thr Gln Leu Val Lys Ser Ala Gly Gly Met Gly
                290                 295                 300

Val Ile Tyr Trp Glu Pro Ala Trp Val Ser Thr Arg Cys Arg Thr Leu
    305                 310                 315                 320

Trp Gly Lys Gly Ser His Trp Glu Asn Ala Ser Phe Phe Asp Ala Thr
                    325                 330                 335

Arg Lys Asn Asn Ala Leu Pro Ala Phe Leu Phe Phe Lys Ala Asp Tyr
                    340                 345                 350

Gln Ala Ser Ala Gln Ala Glu
                    355
```